US012649783B2

(12) United States Patent
Rothstein et al.

(10) Patent No.: US 12,649,783 B2
(45) Date of Patent: Jun. 9, 2026

(54) ANTI-MCT1 ANTIBODIES AND USES THEREOF

(71) Applicants: IMMUNEXT INC., Lebanon, NH (US); AMGEN INC., Thousand Oaks, CA (US)

(72) Inventors: Jay L. Rothstein, Norwich, VT (US); Grace Ki Jeong Lee, Simi Valley, CA (US); Kimberly P. Shigenaka, Seattle, WA (US); Marcia Gordon, Seattle, WA (US); Kim Quon, Seattle, WA (US); Philipe Gobeil, Toronto (CA); Catherine Carriere, Lebanon, NH (US); Sergey Seregin, Lebanon, NH (US)

(73) Assignee: IMMUNOMETABOLISM DEVELOPMENT CO., LLC, Lebanon, NH (US)

( * ) Notice: Subject to any disclaimer, the term of this patent is extended or adjusted under 35 U.S.C. 154(b) by 293 days.

(21) Appl. No.: 16/240,499

(22) Filed: Jan. 4, 2019

(65) Prior Publication Data

US 2019/0263931 A1     Aug. 29, 2019

Related U.S. Application Data

(60) Provisional application No. 62/614,081, filed on Jan. 5, 2018, provisional application No. 62/703,223, filed on Jul. 25, 2018, provisional application No. 62/717,289, filed on Aug. 10, 2018, provisional application No. 62/719,364, filed on Aug. 17, 2018.

(51) Int. Cl.
| | |
|---|---|
| *C07K 16/28* | (2006.01) |
| *A61K 47/68* | (2017.01) |
| *A61P 3/10* | (2006.01) |
| *A61P 37/06* | (2006.01) |
| *C07K 16/40* | (2006.01) |
| *G01N 33/50* | (2006.01) |
| *A61K 39/00* | (2006.01) |
| *A61K 45/06* | (2006.01) |

(52) U.S. Cl.
CPC .............. *C07K 16/28* (2013.01); *A61K 47/68* (2017.08); *A61P 3/10* (2018.01); *A61P 37/06* (2018.01); *C07K 16/40* (2013.01); *G01N 33/5011* (2013.01); *A61K 2039/505* (2013.01); *A61K 45/06* (2013.01); *C07K 2317/24* (2013.01); *C07K 2317/33* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2004/0132813 A1 | 7/2004 | Brooks |
| 2005/0118567 A1 | 6/2005 | Merril et al. |
| 2005/0142133 A1 | 6/2005 | Lazar et al. |
| 2007/0154479 A1 | 7/2007 | Kim et al. |
| 2008/0206239 A1 | 8/2008 | Jones et al. |
| 2010/0260773 A1 | 10/2010 | Gozzard et al. |
| 2011/0020369 A1 | 1/2011 | De Waal Malefyt |
| 2014/0193436 A1 | 7/2014 | Prudent |
| 2017/0088613 A1 | 3/2017 | Grogan et al. |
| 2017/0355987 A1 | 12/2017 | Mauro et al. |

FOREIGN PATENT DOCUMENTS

| | | |
|---|---|---|
| WO | 2016/039321 A1 | 3/2016 |
| WO | 2023/044325 A1 | 3/2023 |

OTHER PUBLICATIONS

Wu, Nie, Huse, and WATKINS. Humanization of a murine monoclonal antibody by simultaneous optimization of framework and CDR residues. Journal of Molecular Biology, 1999. Vol. 294, pp. 151-162. (Year: 1999).*
Vajdos, Adams, Breece, Presta, De Vos, and SIDHU. Comprehensive functional maps of the antigen-binding site of an anti-ErbB2 antibody obtained with shotgun scanning mutagenesis. Journal of Molecular Biology, 2002. Vol. 320, pp. 415-428. (Year: 2002).*
Maccallum et al. (1996) J. Mol. Biol. 262: 732-745. (Year: 1996).*

(Continued)

*Primary Examiner* — Michael D Pak
(74) *Attorney, Agent, or Firm* — Robin L. Teskin; Baker, Donelson, Bearman, Caldwell & Berkowitz PC

(57)     ABSTRACT

This invention generally pertains to antibodies and antigen-binding fragments thereof, e.g., humanized, chimeric, and human antibodies and antigen-binding fragments thereof, and fusion proteins, compositions containing such antibodies and antigen-binding fragments thereof and fusion proteins, wherein such antibodies and antigen-binding fragments thereof and fusion proteins specifically bind to MCT1, e.g., human or non-human MCT1 and antagonize, inhibit or block one or more MCT1-associated functions in vitro and/or in vivo. The invention also relates to therapeutic and diagnostic uses of these anti-MCT1 antibodies, antigen-binding fragments, fusion proteins and compositions containing optionally wherein these anti-MCT1 antibodies, antigen-binding fragments, fusion proteins and compositions containing are used in therapeutic regimens that further include the administration of other therapeutic agents, e.g., mitochondrial inhibitors and/or biguanides or small molecule MCT1 inhibitors.

5 Claims, 59 Drawing Sheets

Specification includes a Sequence Listing.

(56)                    References Cited

OTHER PUBLICATIONS

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. Vol. 307, pp. 198-205. (Year: 2003).*

SKOLNICK and FETROW. From genes to protein structure and function: novel applications of computational approaches in the genomic era. Trends in Biotechnology, 2000. Vol. 18, page (Year: 2000).*

Wilson, et al. "Studies On the Dids-Binding Site of Monocarboxylate Transporter 1 Suggests a Homology Model of the Open Conformation and a Plausible Translocation Cycle" J Biol Chem. Jul. 24, 2009. vol. 284, No. 30, pp. 20011-20021.

Document from WIPO Examination of relation application: "Written Opinion of the International Search Authority," Date of completion of this opinion as per Form PCT/ISA/210: Date of the actual completion of the International search Jun. 28, 2019, Date of mailing of the international search report: Jul. 19, 2019.

\* cited by examiner

| Sample Name | Name |
|---|---|
| human stimed PBMC MCT1 | Lymphocytes |
| human resting PBMC MCT1 | Lymphocytes |
| human PBMC contrl | Lymphocytes |

| Sample Name | Name |
|---|---|
| Cyno stimed CD25 MCT1 | live |
| Cyno resting CD25 MCT1 | live |
| Cyno PBMC control | live |

| Sample Name | Name |
|---|---|
| Rabbit stimed CD25-MCT1 | live |
| Rabbit resting CD25-MCT1 | live |
| Rabbit PBMC only | live |

| Sample Name | Name |
|---|---|
| Rat stimed PBMC MCT1 | live |
| Rat resting PBMC MCT1 | live |
| Rat PBMC control | live |

V$_H$ CDR3

FIG 22:Redundant paths avoid tox outside lymph system

| Organ | Lactate/PyruvateTransporter | | | | | |
|---|---|---|---|---|---|---|
| | MCT1 | MCT2 | MCT3 | MCT4 | SMCT1 | SMCT2 |
| Sole Transport Pathway Enables Efficacy in Lymphoid System | | | | | | |
| B cells & T cells | | | | | | |
| Redundant Pathways Avoid Tox Elsewhere | | | | | | |
| Innate immune | | | | | | |
| Liver | | | | | | |
| Muscle | | | | | | |
| Heart | | | | | | |
| Lung | | | | | | |
| Gut | | | | | | |
| Brain | | | | | | |
| Kidney | | | | | | |
| Retina | | | | | | |

Expressed

Expressed but non essential for efficacy

Not expressed

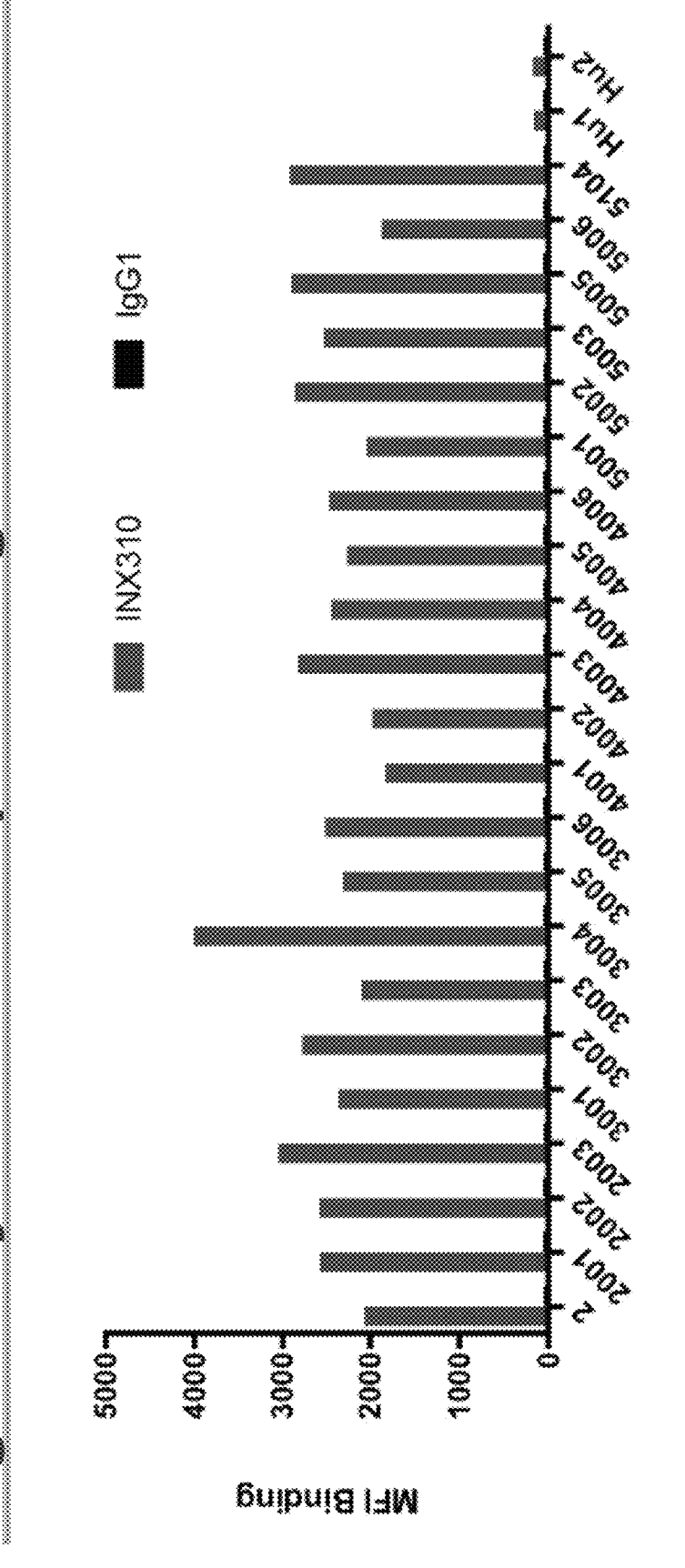
Fig 23: Cyno RBCs express high levels of MCT1
- Expression on cyno RBCs raises two questions:
  - Will cynos tolerate the drug?
  - Will sufficient drug exposure be feasible in cynos?

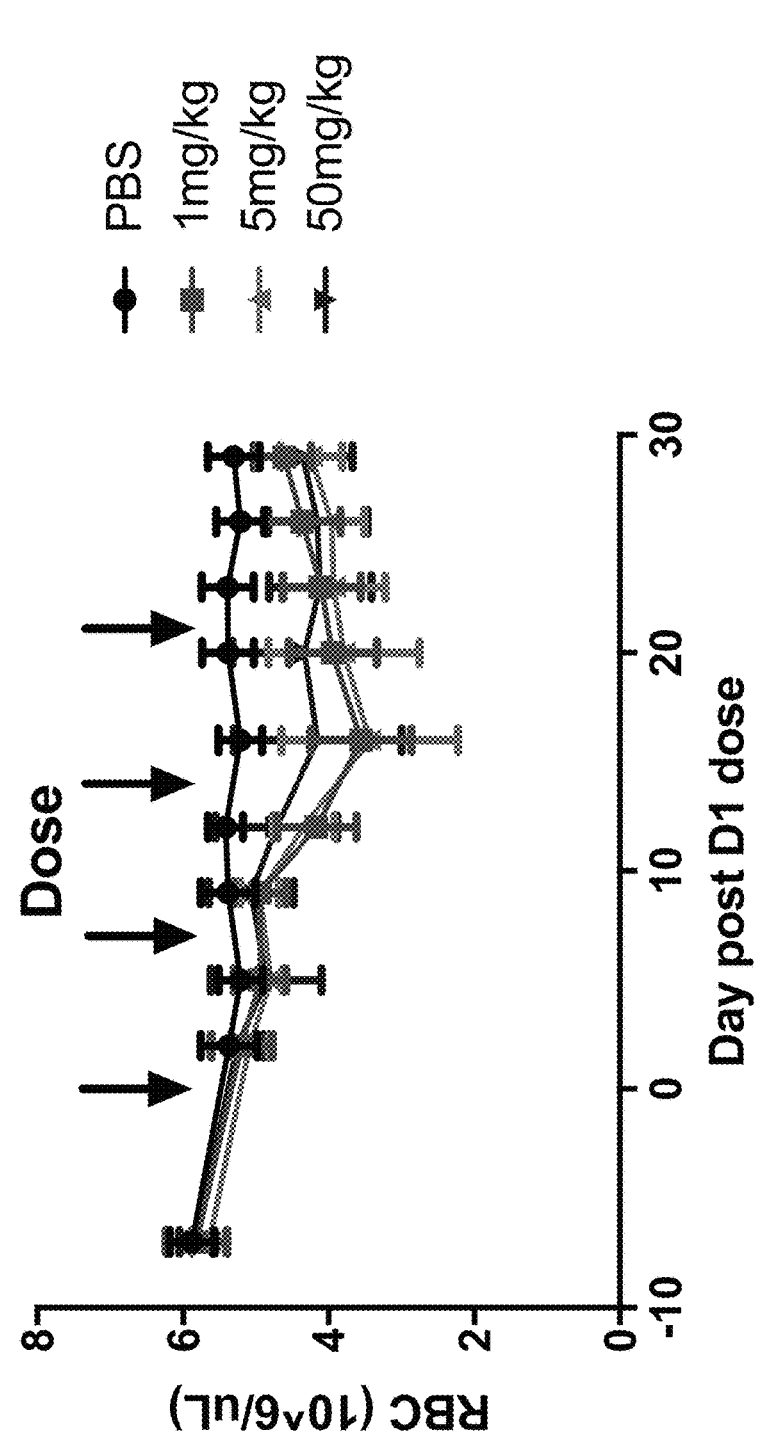
Fig. 24: Cynos tolerate repeated dosing of Ab1 at 50mpk
Reduction of RBC mass resolves
2 of 18 animals on drug holiday

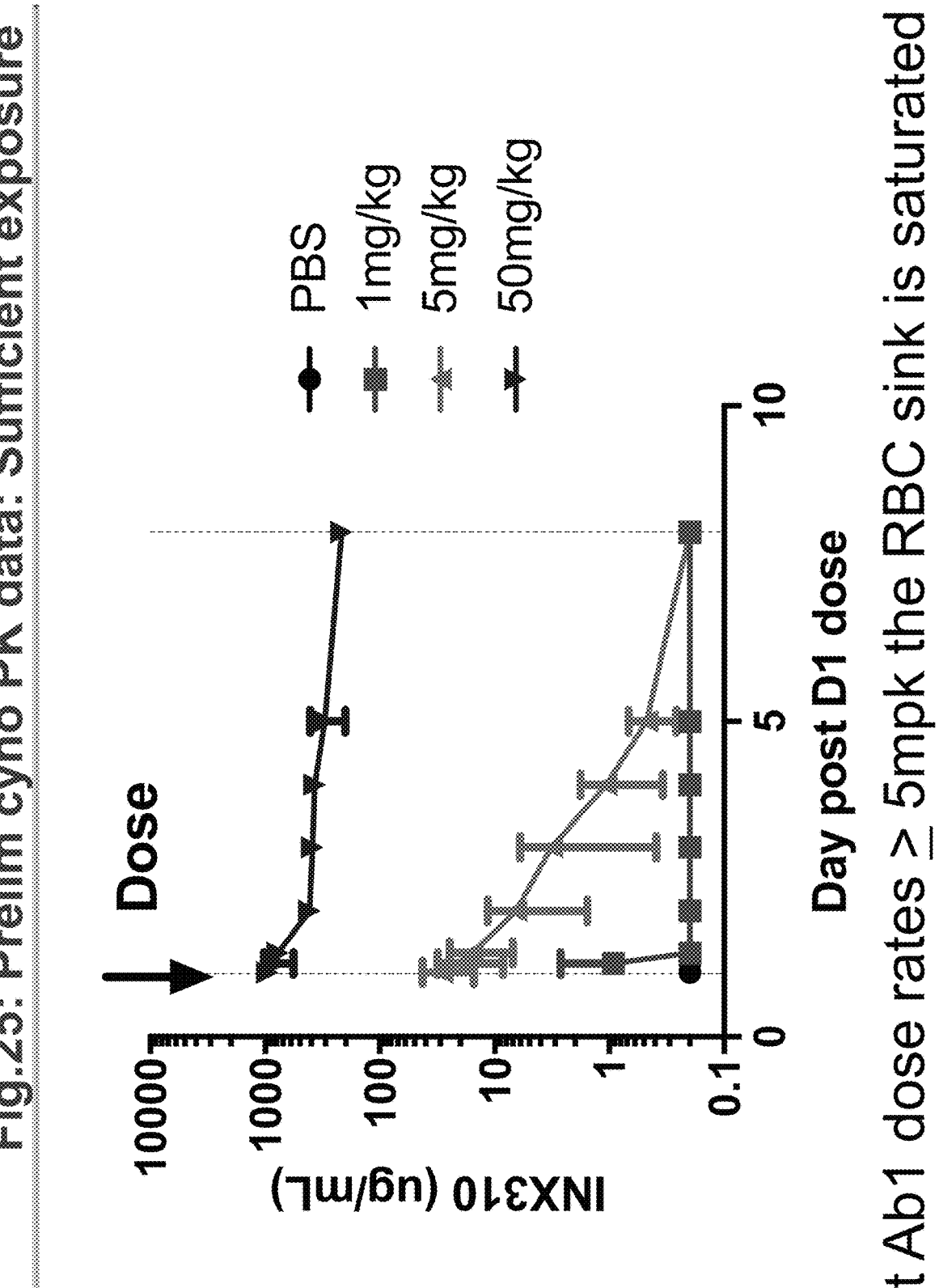
Fig.25: Prelim cyno PK data: Sufficient exposure
At Ab1 dose rates ≥ 5mpk the RBC sink is saturated

Fig. 26 Evaluating target tissues in the tamoxifen-inducible MCT-1 knockout mouse

- 4 male mice per group
  - 4 MCT-1 fl/fl, Cre -/- (WT)
  - 4 MCT-1 fl/fl, Cre +/+ (KO)
- 4 months old at tamoxifen dosing
- 8 months old at necropsy
  - Histopathology of select tissues identified in liability assessments
    - Eyes with optic nerve, testes, heart, skeletal muscles (extensor digitorum longus, soleus, psoas, diaphragm)
  - Clinical chemistry of select parameters implicated in liability assessment
    - ALT, AST, ALP, Na, K, Ca, phosphorus, Cl, total protein, albumin, albumin/globulin ratio (calculated), globulin (calculated), glucose, BUN, creatinine, total bilirubin, GGT, $CO_2$, cholesterol, triglycerides

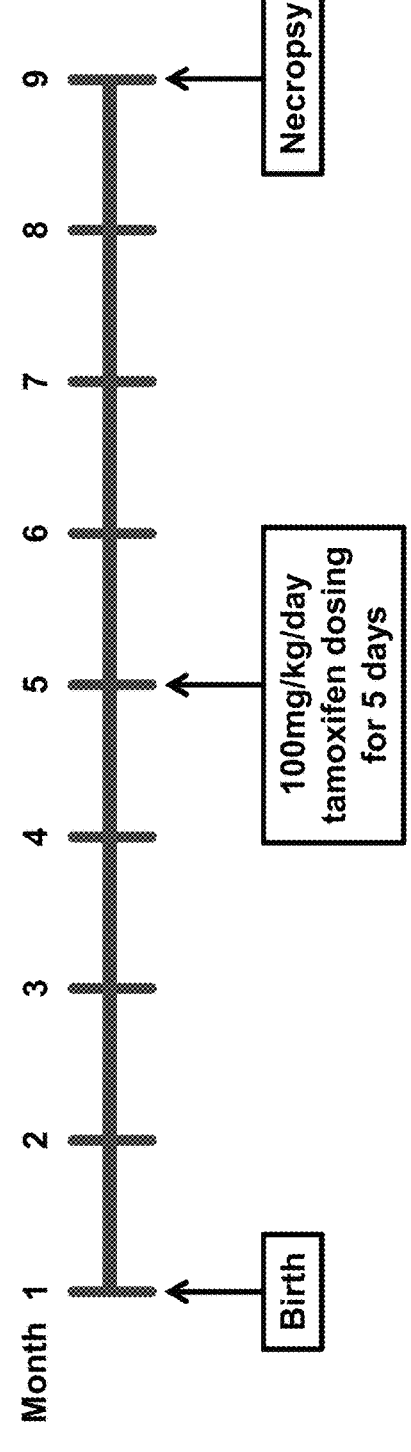

Figure 27:
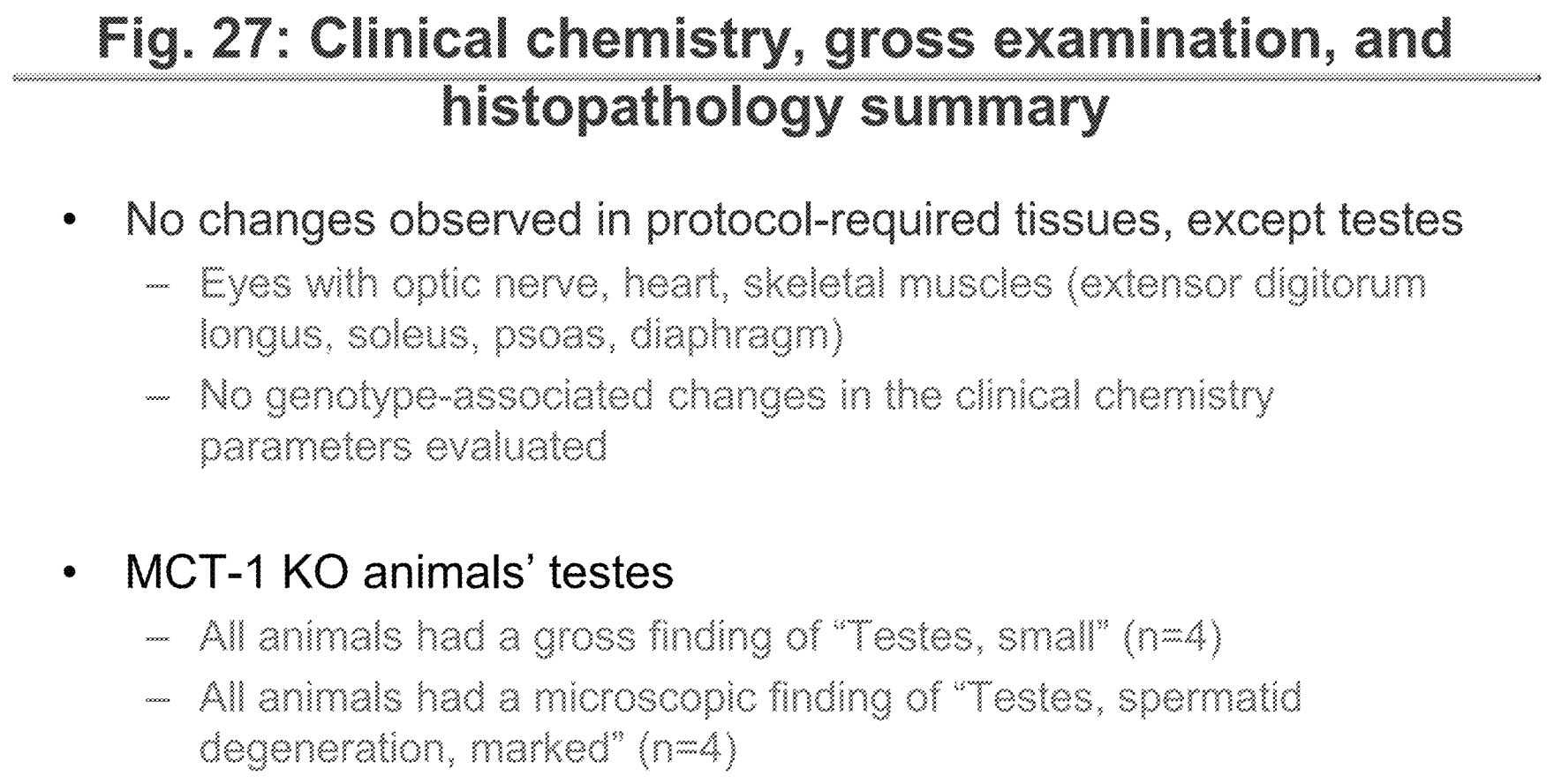

Fig. 27: Clinical chemistry, gross examination, and histopathology summary

- No changes observed in protocol-required tissues, except testes
  - Eyes with optic nerve, heart, skeletal muscles (extensor digitorum longus, soleus, psoas, diaphragm)
  - No genotype-associated changes in the clinical chemistry parameters evaluated

- MCT-1 KO animals' testes
  - All animals had a gross finding of "Testes, small" (n=4)
  - All animals had a microscopic finding of "Testes, spermatid degeneration, marked" (n=4)

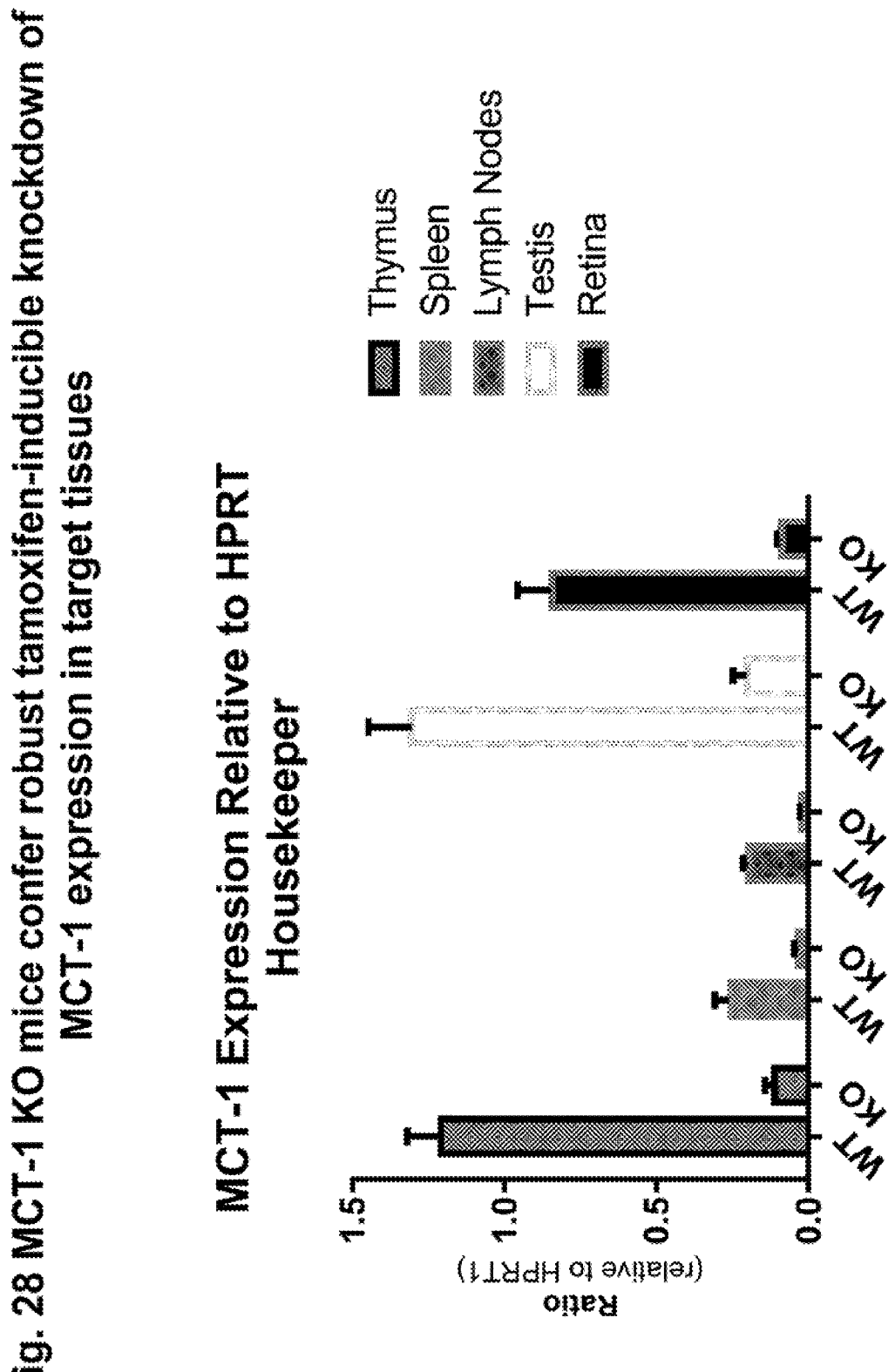
Fig. 28 MCT-1 KO mice confer robust tamoxifen-inducible knockdown of MCT-1 expression in target tissues

Fig. 29 Conditional KO-only observe changes in the testis

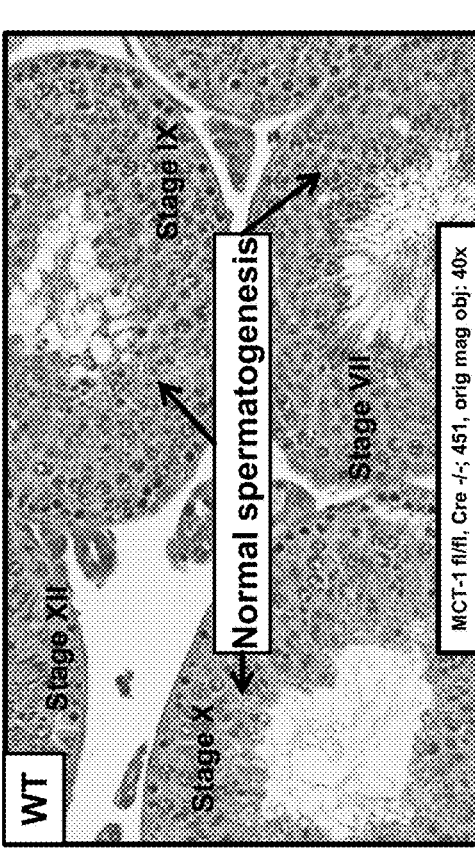
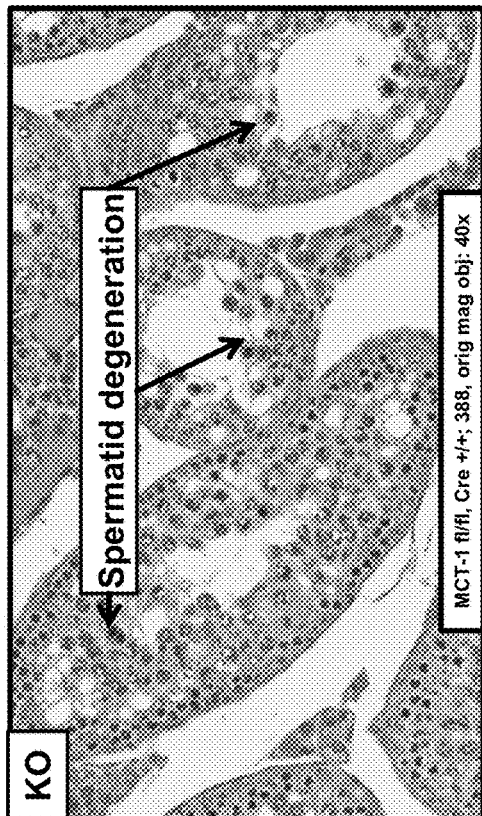

- Targeted phenotyping of tissues from MCT-1 WT and MCT-1 heterozygous KO mice

- Marked spermatid degeneration observed in testis of all MCT-1 knockout mice (Lack of late-stage spermatids and spermatocytes, decreased tubular cellularity, vacuolation, and cell debris)

– Correlated to gross necropsy observation of small testis

– Efficient knockdown of MCT-1 in testes by PCR

– No other genotype-associated changes in protocol tissues or clinical chemistry parameters

- Conclusion: Gross and histologic testis changes in tox studies are MCT-1-related (on-target)

Fig. 30 WT to MCT-1 KO comparison of testis
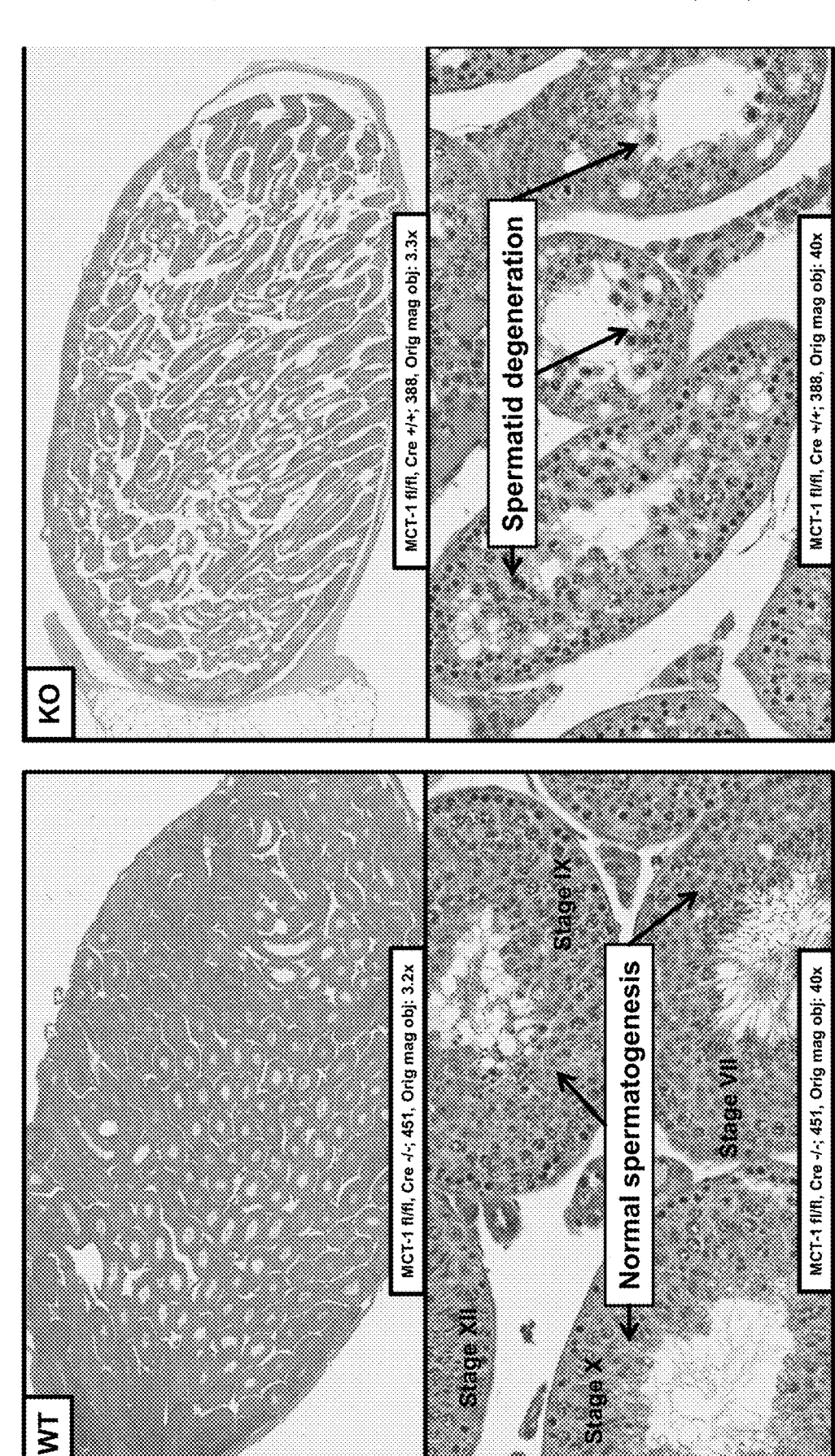

FIGURE 32: Antagonistic Activity of Different Anti-MCT1 Antibodies
Bromopyruvate Functional Assay:  INX300 and INX400 series antibodies
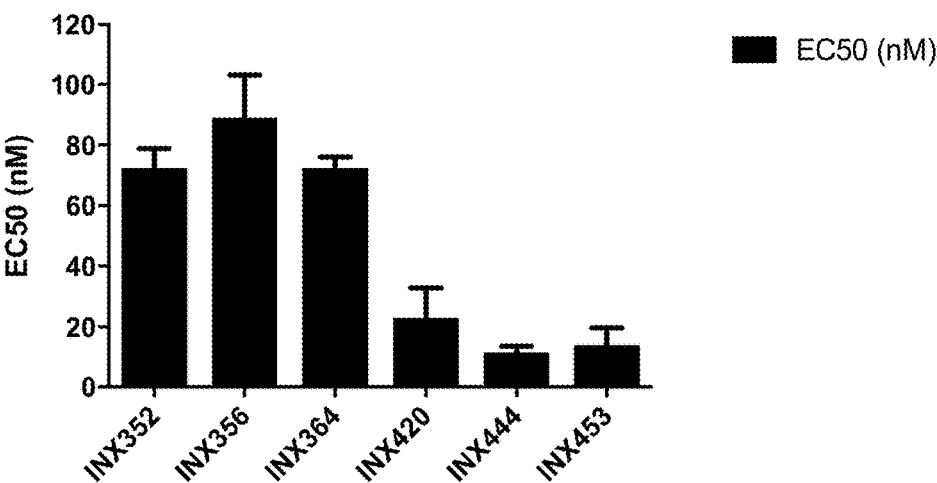
INX420, INX444 and INX453 were selected from 48
antibodies based on function and sequence diversity

Figure 33: Anti-MCT1 VH alignment

Notes:
- CDRs bolded, changes (to CDR3) from parental shown in red
- Framework differences are highlighted by boxes

```
INX420_VH   QVQLKESGPGLVKPSQTLSLTCTVSGFSLTNYHLQWVRQPPGKGLEWIGFIRSSGNTEYN   60
INX444_VH   QVQLKESGPGLVKPSQTLSLTCTVSGFSLTNYHLQWVRQPPGKGLEWIGFIRSSGNTEYN   60
INX453_VH   QVQLQESGPGLVKPSETLSLTCTVSGFSLTNYHLQWIRQPPGKGLEWIGFIRSSGNTEYN   60
INX356_VH   QVQLQESGPGLVKPSETLSLTCTVSGFSLTNYHLQWIRQPPGKGLEWIGFIRSSGNTEYN   60
INX352_VH   QVQLKESGPGLVKPSQTLSLTCTVSGFSLTNYHLQWVRQPPGKGLEWIGFIRSSGNTEYN   60
INX364_VH   QVQLQESGPGLVKPSQTLSLTCTVSGFSLTNYHLQWIRQPPGKGLEWIGFIRSSGNTEYN   60
            ****:********.*:***************:**********************

INX420_VH   PSLKSRVTISRDTSKNQVSLKLSSVTAADTAVYYCARNRFVHGTWYSPGYYLMDAWGQGT   120
INX444_VH   PSLKSRVTISRDTSKNQVSLKLSSVTAADTAVYYCARKRWVHGTWYSPGYYVMDAWGQGT   120
INX453_VH   PSLKSRVTISRDTSKNQVSLKLSSVTAADTAVYYCARNRWVQGWWYSPGYYLMDAWGQGT   120
INX356_VH   PSLKSRVTISRDTSKNQVSLKLSSVTAADTAVYYCARNSWYHGTYYSPGYYVMDAWGQGT   120
INX352_VH   PSLKSRVTISRDTSKNQVSLKLSSVTAADTAVYYCARNSWYHGTYYSPGYYVMDAWGQGT   120
INX364_VH   PSLKSRVTISRDTSKNQVSLKLSSVTAADTAVYYCARNSWYHGTYYSPGYYVMDAWGQGT   120
            ***********************************. :  : :*.:.*******:******

INX420_VH   LVTVSS   126
INX444_VH   LVTVSS   126
INX453_VH   MVTVSS   126
INX356_VH   MVTVSS   126
INX352_VH   LVTVSS   126
INX364_VH   LVTVSS   126
            :*****
```

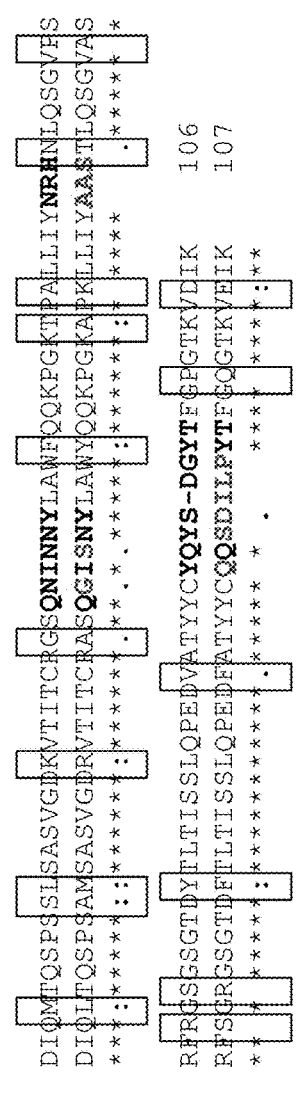

Figure 34: Anti-MCT1 VL alignment

Notes:
- CDRs bolded, changes from parental shown in red
- Framework differences are highlighted by boxes

```
INX352|INX356|INX364|INX420_VL    DIQMTQSPSSLSASVGDKVTITCRGSQNINNYLAWFQQKPGKTPALLIYNRHNLQSGVES    60
INX444|INX453_VL                  DIQLTQSPSAMSASVGDRVTITCRASQGISNYLAWYQQKPGKAPKLLIYAASTLQSGVAS    60
                                  ***:****:*****:******:**  *:*****  ******* *****  *.*****:*

INX352|INX356|INX364|INX420_VL    RFRGSGSGTDYTLTISSLQPEDVATYYCYQYS-DGYTFGPGTKVDIK    106
INX444|INX453_VL                  RFSGRGSGTDFTFTITISSLQPEDFATYYCQQSDILPYTFGQGTKVEIK    107
                                  **.* *****:*:****:*****.***** :* *  :* **.****:**
```

Other Functional MCT1 Binding Abs

Binding of MCT1⁺ 293 cells

Function in bromopyruvate toxin transport assay

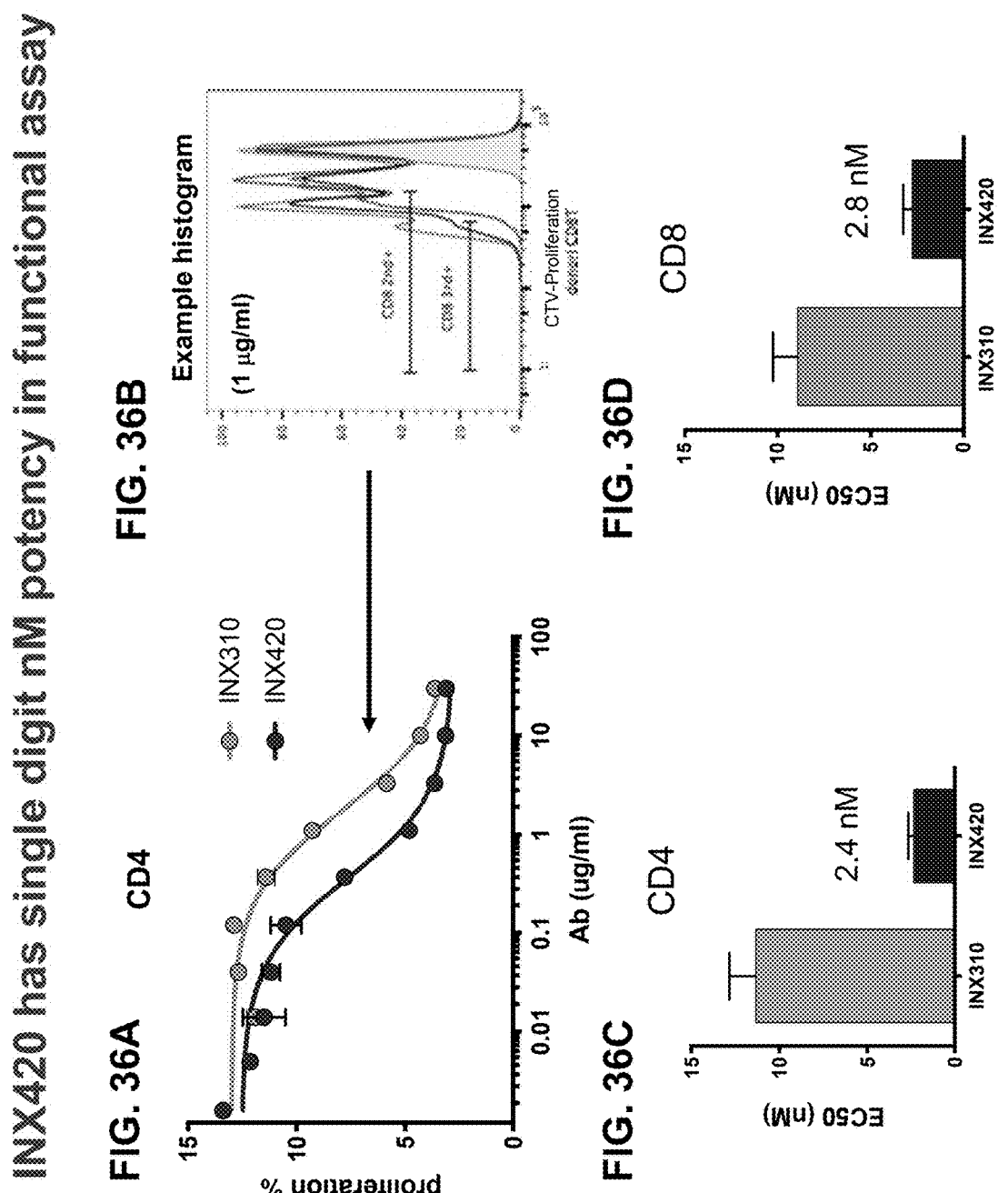
INX420 has single digit nM potency in functional assay

INX420 increases frequency of PD1+ TIGIT+ cells *in vitro*

CD3/CD28 no Ab

CD3/CD28 +SMi

CD3/CD28 + INX420

Cell # TIGIT+ PD1+

SMi = AZ3965 200 nM
INX420= 10 µg/ml

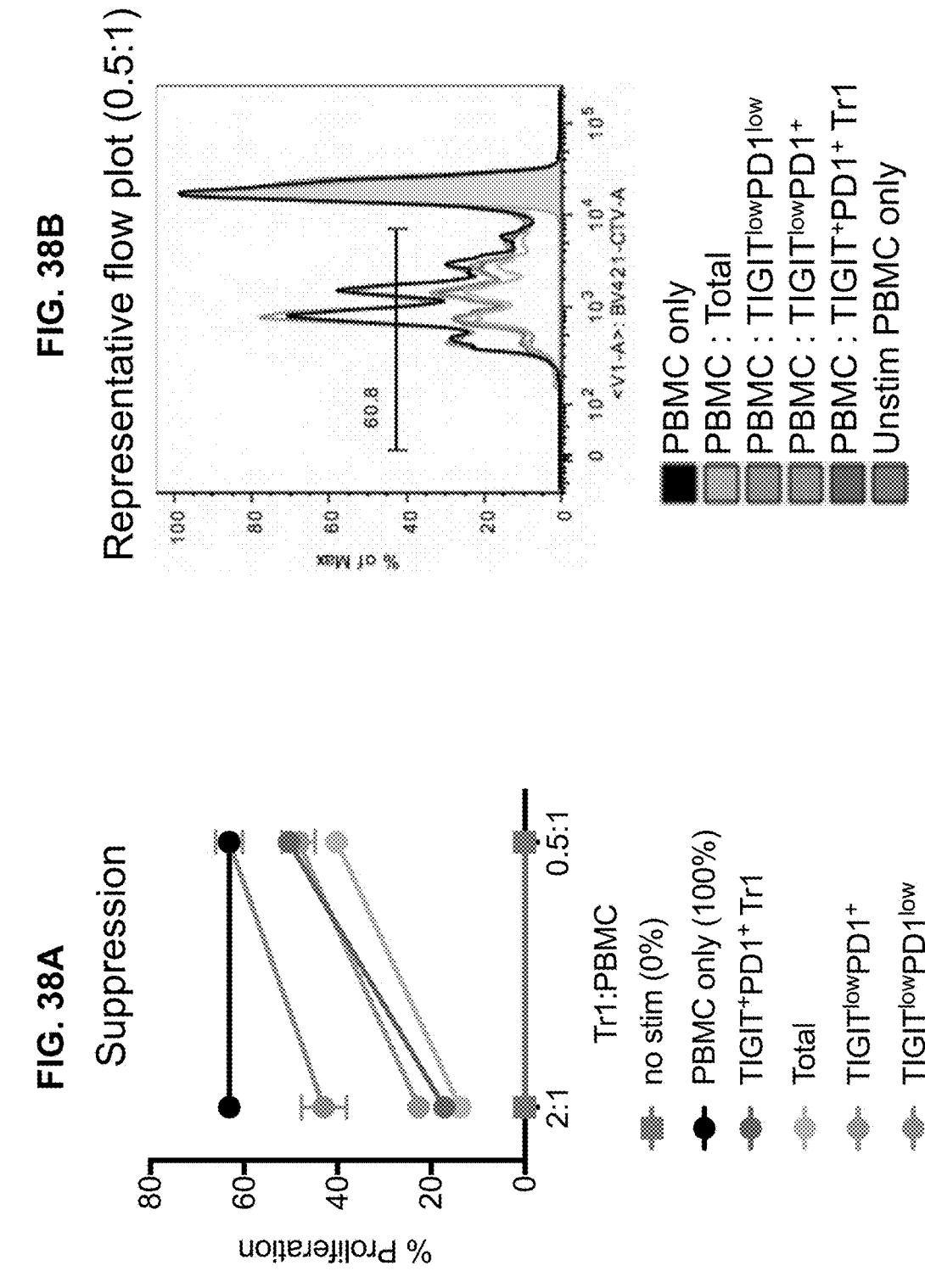

Blocking IL10 signaling does not
interfere with Tr1-mediated Suppression

Donor 319 INX420

Anti-MCT1 Ab Treatment decreases number of effector T cells and increases Tr1 cell frequency in xeno-GvHD

• Effector T cells (day 11 ALC)

• Tr1 cells (day 36*)

*different experiment

Anti-MCT1 Abs elicit tolerance in xeno-GvHD Model

Long-term protection

Tolerance induction

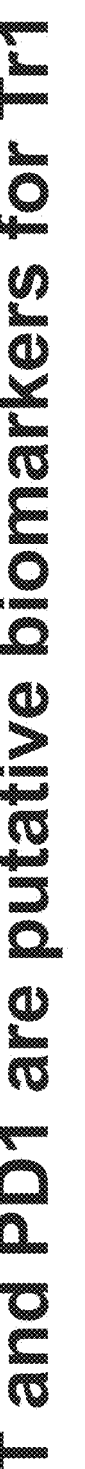
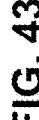
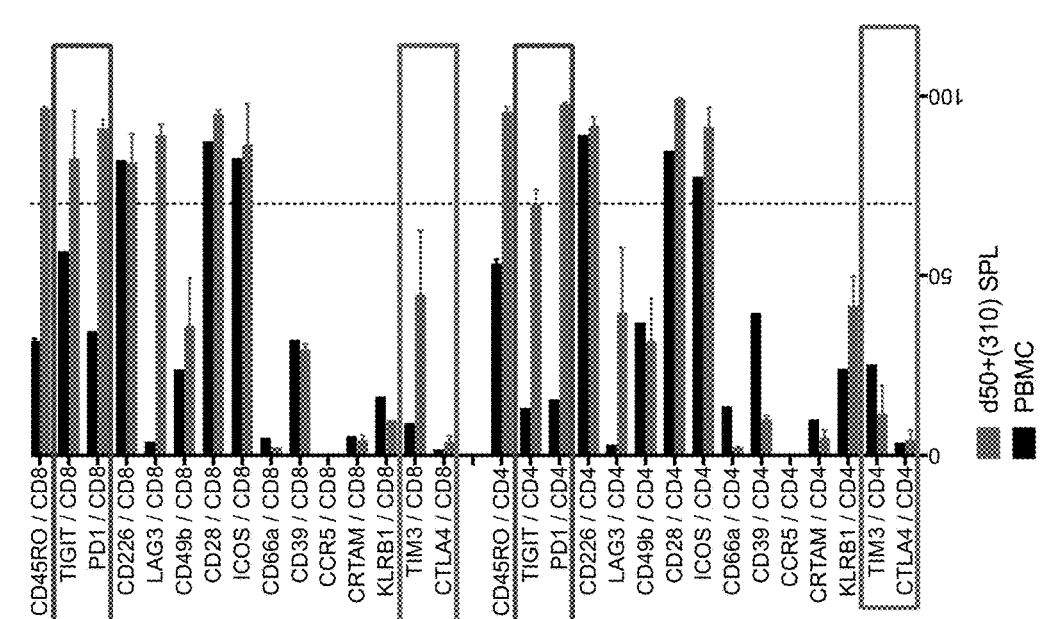
TIGIT and PD1 are putative biomarkers for Tr1
- TIGIT and PD1 are expressed on over 75% of human T cells in xeno-GvHD model
- No other immune regulator follow that pattern
FIG. 43

TIGIT and PD1 are putative markers for Tr1

Tr1 express high levels of Granzyme B, but not FOXP3 or Blimp1

Tr1 suppress proliferation of hCD3+ cells

D109 ~60% suppression

*Ex vivo* Tr1 survival factors

- Killing of target cells is not a mechanism of suppression for Tr1

- Tr1 survive upon co-culture with target cells, but die if individually cultured

- Anti-TIGIT Ab or PVR ligands do not improve ex vivo Tr1 survival

- IL2+IL7+IL15 increases ex vivo Tr1 survival in a dose dependent manner, reaching ~75%

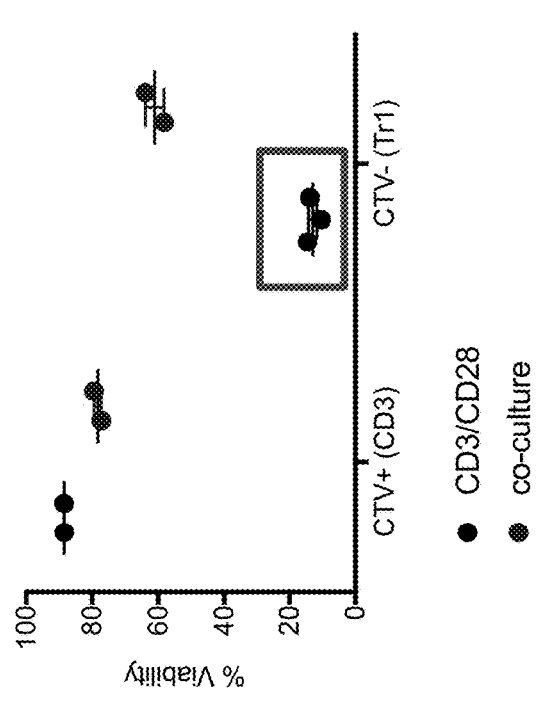
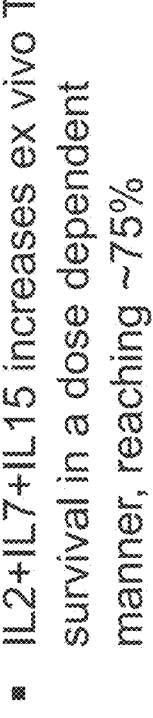

FIG. 49B

CD3:Tr1 viability

- CD3/CD28
- co-culture

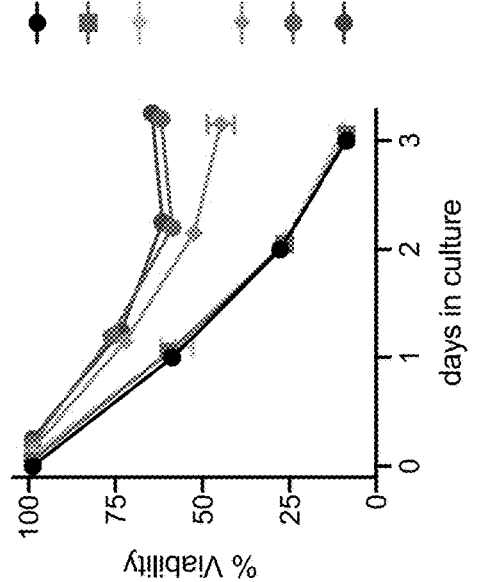
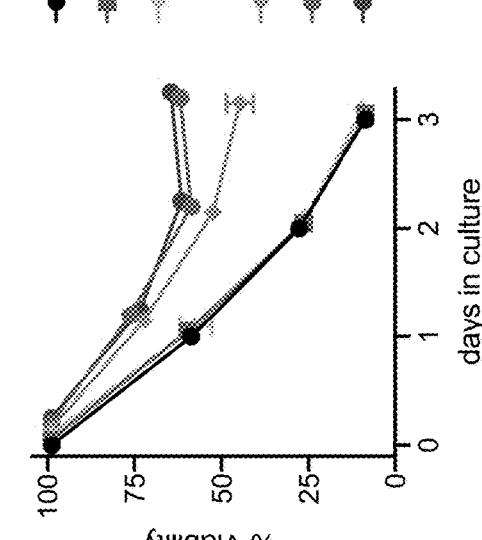

FIG. 49A

Tr1 survival (ex vivo)

- untreated Tr1
- a-TIGIT
- CD155/CD112
- IL2/IL7/IL15 0.1 ng/ml
- IL2/IL7/IL15 1 ng/ml
- IL2/IL7/IL15 10 ng/ml SMi-driven ketosis is evident after 8h of starvation Blood Ketones Blood Glucose

- 8-24h, but not 5h starvation triggers ketosis, potentiated by MCT1 Small molecule inhibitor(Smi)
- SMi-driven ketosis proceeds hypoglycemia upon starvation (see 8h)
- SMi treatment potentiates starvation-driven ketosis and hypoglycemia

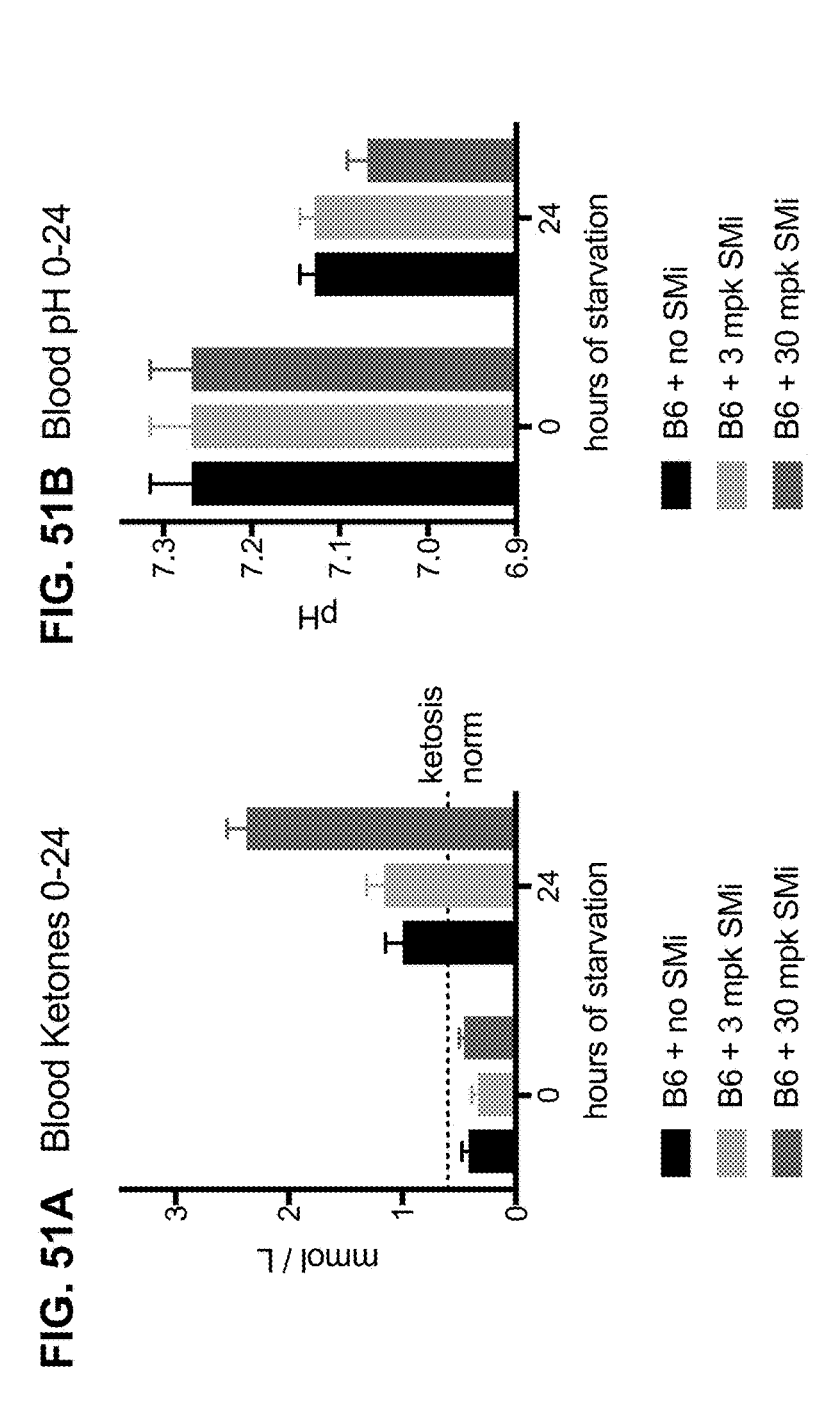
Starvation (24h) +/- SMi does not trigger ketoacidosis
SMi triggers/potentiates ketosis
FIG. 51A  Blood Ketones 0-24
FIG. 51B  Blood pH 0-24
- We observed starvation-dependent pH reduction (7.3 to 7.1, modest <0.2 pH)
- We observed slight (~0.05 pH) additional SMi (high dose)-dependent pH reduction

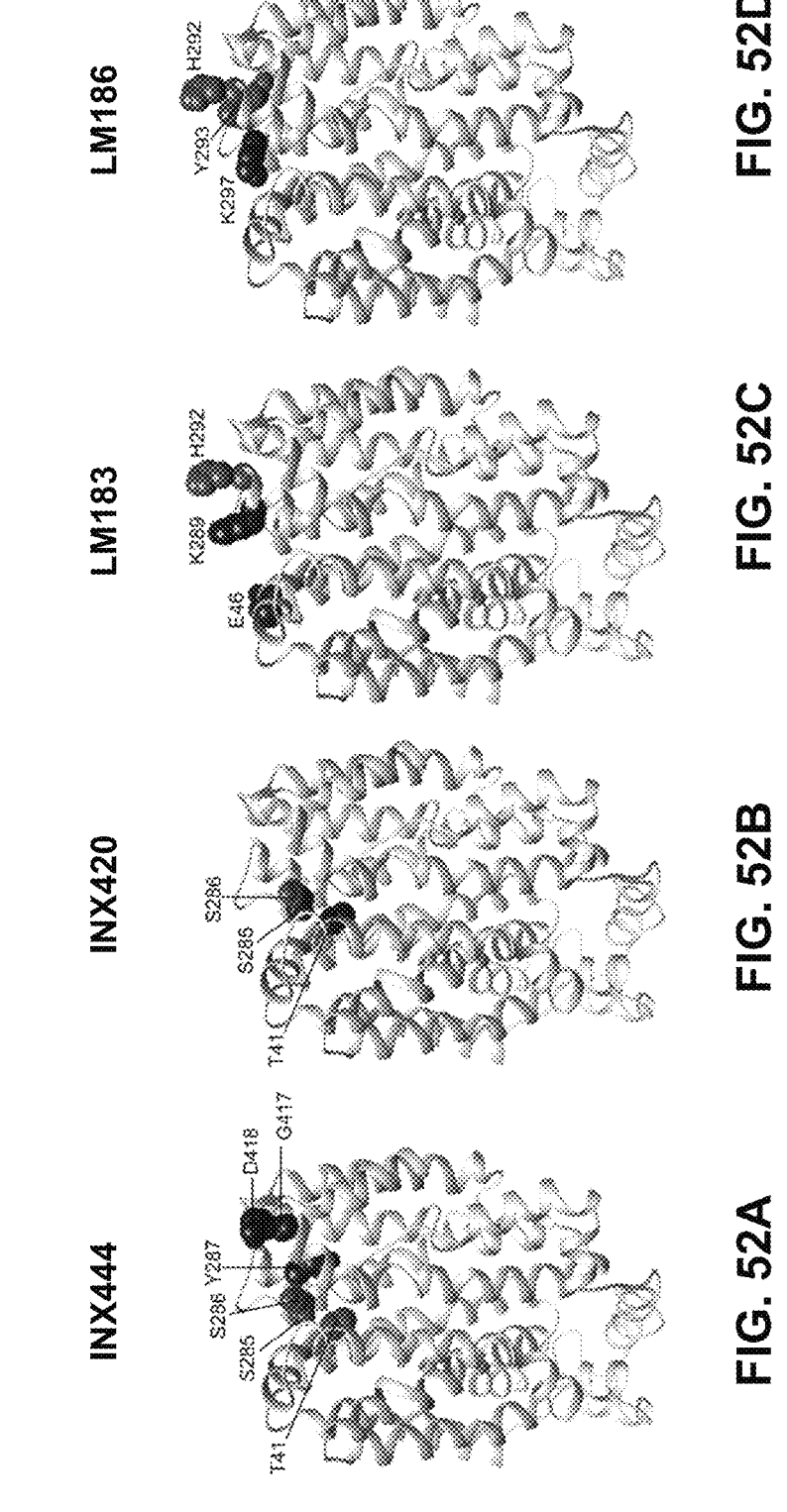
Anti-MCT1 Epitope: Structures
INX444 — FIG. 52A
INX420 — FIG. 52B
LM183 — FIG. 52C
LM186 — FIG. 52D Anti-MCT1 Epitope mapping

FIG. 54

■ Rat anti-human

■ Chicken anti-human

*420 350mM NaCl

Transmembrane
Cytoplasmic
Extracellular

T41    (20/44)    E46 (83)    I47 (20*)

```
MOT1_HUMAN      MPPAVGGPVG YTPPD                      PKSI TYTTKEIEGI FSAATSEVS- NKYGSR          TVQ Q          120
MOT1_MOUSE      MPPAIGGPVG YTPPD                      PKSI TYTTKEIKVI FSAATSKVS- NKYGSR          TVQ E          120
MOT1_RAT        MPPAIGGPVG YTPPD                      PKSI TYTTKEIKII FSATTSKVS- NKYGSR          TVQ E          120
I7GN62_MACFA    MPPAVGGPVG YTPPD                      PKSI TYTTKEIEGI FRAATSEVS- NKYGSR          TVQ Q          120
                *::** *****   *                       *: *.:**  *:*  ****: ***    *****           .: *  :*
```

```
MOT1_HUMAN              KTMIGKYFY KRR                          RQ     CCV AGALMRPIGP KPTKAGKDKS KASLEKAGKS GVKRDLHDAN TDLIGRHPKQ  240
MOT1_MOUSE              KTMIGKYFX KKR                          NQ     CCV AGSLMRPIGP BQVKLEKLKS KBSLQEAGKS             --DAN TDLIGGSPKG  233
MOT1_RAT               KTMIGKYFX KKR                          NQ     CCV AGSLMRPIGP QQGKVEKLKS KBSLQEAGKS             --DAN TDLIGGSPKG  233
I7GN62_MACFA           KTMIGKYFY KRR                          RQ     CCV AGALMRPIGP KPTKAGKDKS KASLQKAGKS GVKKGRHDAN TDLIGRHPKR  240
                ****   :*****:    ***                          .*     ***  **.********   :   : **  * :: :****        **:   ****   **
```

S285    H292 (83/86)    Y293 (86)

(20/44)
(20/44/44)

```
MOT1_HUMAN      EKRSVFQTIN QFLDLILFTH RG                          A NTKPIRPR    TTT          360
MOT1_MOUSE      EKLSVFQTIN KFLDLSLFTH RG                          A NTKWIRPR    TTY          353
MOT1_RAT        EKLSVPQTVN MRSVFQTIN RG                          A MTRWIRPR    TTY          353
I7GN62_MACFA    EKRSVFQTIN QFLDLILFTH RG                          A NTKPIRPR    TTY          360
                **:**: *:   :*** : **                              *   * *:** *    *:
```

K289 (83)  K297 (86)

```
MOT1_HUMAN              FETLMD LVGPQRFSSA                           NYRLLAK EQKANEQ-KK ESKEETSID VAGKPMEVTK  479
MOT1_MOUSE              FETLMD LIGPQRFSSA                           NYRLLAK EGKABEKQKR EGKEDEASTD VDEKPKETMK  473
MOT1_RAT               FETLMD LVGPQRFSSA                           NVPLVAK EQKAEEK-KR DGKKDETSTD VDEKPKTMK   472
I7GN62_MACFA           FETLMD LVGPQRFSSA                           NYRLLAK EQKANEQ-KK ESKEETSID VAGKPKEVTK  479
                       ******  *:*******                           .*:*;*; *:   ; .: .: *: .; *  **;;   *
```

G417 (20*/44)
D418 (20*/44)

```
MOT1_HUMAN      AAESPDQ-KD TDGGPKEEES PV 500
MOT1_MOUSE      AAQSP--QQH SSGDPTEEES PV 493
MOT1_RAT        ETQSPAPLQN SSGDPABEES PV 494
I7GN62_MACFA    AAESPDQ-KD TEEGPNEEDS PV 500
                ::***  :.  ...* **:* **
```

Other sites
P37, I40, K45, E48, T55 (loop 1)
Q111 (loop 2)
Q166 (loop 3)
L284, E296, S298 (loop 4)
Y353 (loop 5)
Y419, T422 (loop 6)

SEQUENCE LISTING

<160> NUMBER OF SEQ ID NOS: 533

<210> SEQ ID NO 1
<211> LENGTH: 500
<212> TYPE: PRT
<213> ORGANISM: Artificial Sequence
<220> FEATURE:
<223> OTHER INFORMATION: Human MCT1 amino acid sequence

<400> SEQUENCE: 1

Met Pro Pro Ala Val Gly Gly Pro Val Gly Tyr Thr Pro Pro Asp Gly
1               5                   10                  15

Gly Trp Gly Trp Ala Val Val Ile Gly Ala Phe Ile Ser Ile Gly Phe
            20                  25                  30

Ser Tyr Ala Phe Pro Lys Ser Ile Thr Val Phe Phe Lys Glu Ile Glu
        35                  40                  45

Gly Ile Phe His Ala Thr Thr Ser Glu Val Ser Trp Ile Ser Ser Ile
    50                  55                  60

Met Leu Ala Val Met Tyr Gly Gly Gly Pro Ile Ser Ser Ile Leu Val
65                  70                  75                  80

Asn Lys Tyr Gly Ser Arg Ile Val Met Ile Val Gly Gly Cys Leu Ser
                85                  90                  95

Gly Cys Gly Leu Ile Ala Ala Ser Phe Cys Asn Thr Val Gln Gln Leu
            100                 105                 110

Tyr Val Cys Ile Gly Val Ile Gly Gly Leu Gly Leu Ala Phe Asn Leu
        115                 120                 125

Asn Pro Ala Leu Thr Met Ile Gly Lys Tyr Phe Tyr Lys Arg Arg Pro
    130                 135                 140

Leu Ala Asn Gly Leu Ala Met Ala Gly Ser Pro Val Phe Leu Cys Thr
145                 150                 155                 160

Leu Ala Pro Leu Asn Gln Val Phe Phe Gly Ile Phe Gly Trp Arg Gly

-continued

```
                165                 170                 175

Ser Phe Leu Ile Leu Gly Gly Leu Leu Leu Asn Cys Cys Val Ala Gly
            180                 185                 190

Ala Leu Met Arg Pro Ile Gly Pro Lys Pro Thr Lys Ala Gly Lys Asp
            195                 200                 205

Lys Ser Lys Ala Ser Leu Glu Lys Ala Gly Lys Ser Gly Val Lys Lys
        210                 215                 220

Asp Leu His Asp Ala Asn Thr Asp Leu Ile Gly Arg His Pro Lys Gln
225                 230                 235                 240

Glu Lys Arg Ser Val Phe Gln Thr Ile Asn Gln Phe Leu Asp Leu Thr
                245                 250                 255

Leu Phe Thr His Arg Gly Phe Leu Leu Tyr Leu Ser Gly Asn Val Ile
            260                 265                 270

Met Phe Phe Gly Leu Phe Ala Pro Leu Val Phe Leu Ser Ser Tyr Gly
            275                 280                 285

Lys Ser Gln His Tyr Ser Ser Glu Lys Ser Ala Phe Leu Leu Ser Ile
        290                 295                 300

Leu Ala Phe Val Asp Met Val Ala Arg Pro Ser Met Gly Leu Val Ala
305                 310                 315                 320

Asn Thr Lys Pro Ile Arg Pro Arg Ile Gln Tyr Phe Phe Ala Ala Ser
                325                 330                 335

Val Val Ala Asn Gly Val Cys His Met Leu Ala Pro Leu Ser Thr Thr
            340                 345                 350

Tyr Val Gly Phe Cys Val Tyr Ala Gly Phe Phe Gly Phe Ala Phe Gly
            355                 360                 365

Trp Leu Ser Ser Val Leu Phe Glu Thr Leu Met Asp Leu Val Gly Pro
        370                 375                 380

Gln Arg Phe Ser Ser Ala Val Gly Leu Val Thr Ile Val Glu Cys Cys
385                 390                 395                 400

Pro Val Leu Leu Gly Pro Pro Leu Leu Gly Arg Leu Asn Asp Met Tyr
                405                 410                 415

Gly Asp Tyr Lys Tyr Thr Tyr Trp Ala Cys Gly Val Val Leu Ile Ile
            420                 425                 430

Ser Gly Ile Tyr Leu Phe Ile Gly Met Gly Ile Asn Tyr Arg Leu Leu
            435                 440                 445

Ala Lys Glu Gln Lys Ala Asn Glu Gln Lys Lys Glu Ser Lys Glu Glu
        450                 455                 460

Glu Thr Ser Ile Asp Val Ala Gly Lys Pro Asn Glu Val Thr Lys Ala
465                 470                 475                 480

Ala Glu Ser Pro Asp Gln Lys Asp Thr Asp Gly Gly Pro Lys Glu Glu
                485                 490                 495

Glu Ser Pro Val
            500

<210> SEQ ID NO 2
<211> LENGTH: 126
<212> TYPE: PRT
<213> ORGANISM: Artificial Sequence
<220> FEATURE:
<223> OTHER INFORMATION: MCT1 Ab1 (INX310) VH

<400> SEQUENCE: 2

Gln Val Gln Leu Lys Ala Thr Gly Pro Gly Leu Val Gln Pro Thr Gln
1               5                   10                  15

Thr Leu Ser Ile Thr Cys Thr Val Ser Gly Phe Ser Leu Thr Asn Tyr
```

-continued

```
              20              25              30

His Leu Gln Trp Val Arg Gln Thr Pro Gly Lys Gly Leu Glu Trp Met
          35              40              45

Gly Phe Ile Arg Ser Ser Gly Asn Thr Glu Tyr Asn Ser Glu Phe Lys
      50              55              60

Ser Arg Leu Ser Ile Ser Arg Asp Thr Ser Lys Asn Gln Val Phe Leu
65              70              75              80

Lys Met Asn Ser Leu Lys Thr Asp Asp Thr Gly Val Tyr Tyr Cys Ala
              85              90              95

Arg Asn Ser Trp Tyr His Gly Thr Tyr Tyr Ser Pro Gly Tyr Tyr Val
              100             105             110

Met Asp Ala Trp Gly Gln Gly Ala Ser Val Thr Val Ser Ser
          115             120             125
```

<210> SEQ ID NO 3
<211> LENGTH: 106
<212> TYPE: PRT
<213> ORGANISM: Artificial Sequence
<220> FEATURE:
<223> OTHER INFORMATION: MCT1 Ab1 (INX310) VL

<400> SEQUENCE: 3

```
Asn Ile His Leu Thr Gln Ser Pro Ser Leu Leu Ser Ala Ser Val Gly
1               5               10              15

Asp Arg Val Thr Leu Ser Cys Lys Gly Ser Gln Asn Ile Asn Asn Tyr
              20              25              30

Leu Ala Trp Phe Gln Gln Lys Phe Gly Glu Thr Pro Lys Leu Leu Ile
          35              40              45

Tyr Asn Arg His Asn Leu Gln Thr Gly Ile Pro Ser Arg Phe Ser Gly
          50              55              60

Ser Gly Ser Gly Thr Asp Tyr Thr Leu Thr Ile Asn Ser Leu Gln Pro
65              70              75              80

Glu Asp Val Ala Thr Tyr Phe Cys Tyr Gln Tyr Ser Asp Gly Tyr Thr
              85              90              95

Phe Gly Ala Gly Thr Lys Leu Glu Leu Lys
              100             105
```

<210> SEQ ID NO 4
<211> LENGTH: 8
<212> TYPE: PRT
<213> ORGANISM: Artificial Sequence
<220> FEATURE:
<223> OTHER INFORMATION: MCT1 Ab1 (INX310) VH CDR1

<400> SEQUENCE: 4

```
Gly Phe Ser Leu Thr Asn Tyr His
1               5
```

<210> SEQ ID NO 5
<211> LENGTH: 7
<212> TYPE: PRT
<213> ORGANISM: Artificial Sequence
<220> FEATURE:
<223> OTHER INFORMATION: MCT1 Ab1 (INX310) VH CDR2

<400> SEQUENCE: 5

```
Ile Arg Ser Ser Gly Asn Thr
1               5
```

<210> SEQ ID NO 6

-continued

```
<211> LENGTH: 22
<212> TYPE: PRT
<213> ORGANISM: Artificial Sequence
<220> FEATURE:
<223> OTHER INFORMATION: MCT1 Ab1 (INX310) VH CDR3

<400> SEQUENCE: 6

Ala Arg Asn Ser Trp Tyr His Gly Thr Tyr Tyr Ser Pro Gly Tyr Tyr
1               5                   10                  15

Val Met Asp Ala Trp Gly
            20

<210> SEQ ID NO 7
<211> LENGTH: 6
<212> TYPE: PRT
<213> ORGANISM: Artificial Sequence
<220> FEATURE:
<223> OTHER INFORMATION: MCT1 Ab1 (INX310) VL CDR1

<400> SEQUENCE: 7

Gln Asn Ile Asn Asn Tyr
1               5

<210> SEQ ID NO 8
<211> LENGTH: 3
<212> TYPE: PRT
<213> ORGANISM: Artificial Sequence
<220> FEATURE:
<223> OTHER INFORMATION: MCT1 Ab1 (INX310) VL CDR2

<400> SEQUENCE: 8

Asn Arg His
1

<210> SEQ ID NO 9
<211> LENGTH: 8
<212> TYPE: PRT
<213> ORGANISM: Artificial Sequence
<220> FEATURE:
<223> OTHER INFORMATION: MCT1 Ab1 (INX310) VL CDR3

<400> SEQUENCE: 9

Tyr Gln Tyr Ser Asp Gly Tyr Thr
1               5

<210> SEQ ID NO 10
<211> LENGTH: 126
<212> TYPE: PRT
<213> ORGANISM: Artificial Sequence
<220> FEATURE:
<223> OTHER INFORMATION: >INX310_VH

<400> SEQUENCE: 10

Gln Val Gln Leu Lys Ala Thr Gly Pro Gly Leu Val Gln Pro Thr Gln
1               5                   10                  15

Thr Leu Ser Ile Thr Cys Thr Val Ser Gly Phe Ser Leu Thr Asn Tyr
            20                  25                  30

His Leu Gln Trp Val Arg Gln Thr Pro Gly Lys Gly Leu Glu Trp Met
        35                  40                  45

Gly Phe Ile Arg Ser Ser Gly Asn Thr Glu Tyr Asn Ser Glu Phe Lys
    50                  55                  60

Ser Arg Leu Ser Ile Ser Arg Asp Thr Ser Lys Asn Gln Val Phe Leu
65                  70                  75                  80

Lys Met Asn Ser Leu Lys Thr Asp Asp Thr Gly Val Tyr Tyr Cys Ala
```

-continued

```
                85              90              95

Arg Asn Ser Trp Tyr His Gly Thr Tyr Tyr Ser Pro Gly Tyr Tyr Val
            100             105             110

Met Asp Ala Trp Gly Gln Gly Ala Ser Val Thr Val Ser Ser
        115             120             125

<210> SEQ ID NO 11
<211> LENGTH: 106
<212> TYPE: PRT
<213> ORGANISM: Artificial Sequence
<220> FEATURE:
<223> OTHER INFORMATION: >INX310_VL

<400> SEQUENCE: 11

Asn Ile His Leu Thr Gln Ser Pro Ser Leu Leu Ser Ala Ser Val Gly
1               5               10              15

Asp Arg Val Thr Leu Ser Cys Lys Gly Ser Gln Asn Ile Asn Asn Tyr
            20              25              30

Leu Ala Trp Phe Gln Gln Lys Phe Gly Glu Thr Pro Lys Leu Leu Ile
        35              40              45

Tyr Asn Arg His Asn Leu Gln Thr Gly Ile Pro Ser Arg Phe Ser Gly
    50              55              60

Ser Gly Ser Gly Thr Asp Tyr Thr Leu Thr Ile Asn Ser Leu Gln Pro
65              70              75              80

Glu Asp Val Ala Thr Tyr Phe Cys Tyr Gln Tyr Ser Asp Gly Tyr Thr
                85              90              95

Phe Gly Ala Gly Thr Lys Leu Glu Leu Lys
            100             105

<210> SEQ ID NO 12
<211> LENGTH: 126
<212> TYPE: PRT
<213> ORGANISM: Artificial Sequence
<220> FEATURE:
<223> OTHER INFORMATION: Ab2 (INX352)

<400> SEQUENCE: 12

Gln Val Gln Leu Lys Glu Ser Gly Pro Gly Leu Val Lys Pro Ser Gln
1               5               10              15

Thr Leu Ser Leu Thr Cys Thr Val Ser Gly Phe Ser Leu Thr Asn Tyr
            20              25              30

His Leu Gln Trp Val Arg Gln Pro Pro Gly Lys Gly Leu Glu Trp Ile
        35              40              45

Gly Phe Ile Arg Ser Ser Gly Asn Thr Glu Tyr Asn Pro Ser Leu Lys
    50              55              60

Ser Arg Val Thr Ile Ser Arg Asp Thr Ser Lys Asn Gln Val Ser Leu
65              70              75              80

Lys Leu Ser Ser Val Thr Ala Ala Asp Thr Ala Val Tyr Tyr Cys Ala
                85              90              95

Arg Asn Ser Trp Tyr His Gly Thr Tyr Tyr Ser Pro Gly Tyr Tyr Val
            100             105             110

Met Asp Ala Trp Gly Gln Gly Thr Leu Val Thr Val Ser Ser
        115             120             125

<210> SEQ ID NO 13
<211> LENGTH: 106
<212> TYPE: PRT
<213> ORGANISM: Artificial Sequence
<220> FEATURE:
```

<223> OTHER INFORMATION: >INX352X356X364_VL

<400> SEQUENCE: 13

```
Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105
```

<210> SEQ ID NO 14
<211> LENGTH: 126
<212> TYPE: PRT
<213> ORGANISM: Artificial Sequence
<220> FEATURE:
<223> OTHER INFORMATION: Ab3 (INX356)

<400> SEQUENCE: 14

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Met Val Thr Val Ser Ser
        115                 120                 125
```

<210> SEQ ID NO 15
<211> LENGTH: 106
<212> TYPE: PRT
<213> ORGANISM: Artificial Sequence
<220> FEATURE:
<223> OTHER INFORMATION: >INX352X356X364_VL

<400> SEQUENCE: 15

```
Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
```

-continued

```
        50              55              60

Ser Gly Ser Gly Thr Asp Tyr Thr Leu Thr Ile Ser Ser Leu Gln Pro
65              70              75              80

Glu Asp Val Ala Thr Tyr Tyr Cys Tyr Gln Tyr Ser Asp Gly Tyr Thr
                85              90              95

Phe Gly Pro Gly Thr Lys Val Asp Ile Lys
            100             105
```

```
<210> SEQ ID NO 16
<211> LENGTH: 126
<212> TYPE: PRT
<213> ORGANISM: Artificial Sequence
<220> FEATURE:
<223> OTHER INFORMATION: Ab4 (INX364)

<400> SEQUENCE: 16

Gln Val Gln Leu Gln Glu Ser Gly Pro Gly Leu Val Lys Pro Ser Gln
1               5               10              15

Thr Leu Ser Leu Thr Cys Thr Val Ser Gly Phe Ser Leu Thr Asn Tyr
            20              25              30

His Leu Gln Trp Ile Arg Gln Pro Pro Gly Lys Gly Leu Glu Trp Ile
        35              40              45

Gly Phe Ile Arg Ser Ser Gly Asn Thr Glu Tyr Asn Pro Ser Leu Lys
    50              55              60

Ser Arg Val Thr Ile Ser Arg Asp Thr Ser Lys Asn Gln Val Ser Leu
65              70              75              80

Lys Leu Ser Ser Val Thr Ala Ala Asp Thr Ala Val Tyr Tyr Cys Ala
                85              90              95

Arg Asn Ser Trp Tyr His Gly Thr Tyr Tyr Ser Pro Gly Tyr Tyr Val
            100             105             110

Met Asp Ala Trp Gly Gln Gly Thr Leu Val Thr Val Ser Ser
        115             120             125
```

```
<210> SEQ ID NO 17
<211> LENGTH: 106
<212> TYPE: PRT
<213> ORGANISM: Artificial Sequence
<220> FEATURE:
<223> OTHER INFORMATION: >INX352X356X364_VL

<400> SEQUENCE: 17

Asp Ile Gln Met Thr Gln Ser Pro Ser Ser Leu Ser Ala Ser Val Gly
1               5               10              15

Asp Lys Val Thr Ile Thr Cys Arg Gly Ser Gln Asn Ile Asn Asn Tyr
            20              25              30

Leu Ala Trp Phe Gln Gln Lys Pro Gly Lys Thr Pro Ala Leu Leu Ile
        35              40              45

Tyr Asn Arg His Asn Leu Gln Ser Gly Val Pro Ser Arg Phe Arg Gly
    50              55              60

Ser Gly Ser Gly Thr Asp Tyr Thr Leu Thr Ile Ser Ser Leu Gln Pro
65              70              75              80

Glu Asp Val Ala Thr Tyr Tyr Cys Tyr Gln Tyr Ser Asp Gly Tyr Thr
                85              90              95

Phe Gly Pro Gly Thr Lys Val Asp Ile Lys
            100             105
```

```
<210> SEQ ID NO 18
<211> LENGTH: 330
```

```
<212> TYPE: PRT
<213> ORGANISM: Artificial Sequence
<220> FEATURE:
<223> OTHER INFORMATION: silent IgG1 (constant)

<400> SEQUENCE: 18

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Arg Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 19
<211> LENGTH: 120
<212> TYPE: PRT
<213> ORGANISM: Artificial Sequence
<220> FEATURE:
<223> OTHER INFORMATION: HUMANIZED Ab1 (INX310) VARIABLE HEAVY CHAIN
      POLYPEPTIDE
```

```
<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr
        115                 120

<210> SEQ ID NO 20
<211> LENGTH: 456
<212> TYPE: PRT
<213> ORGANISM: Artificial Sequence
<220> FEATURE:
<223> OTHER INFORMATION: HUMANIZED Ab1 (INX310) HEAVY CHAIN POLYPEPTIDE

<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
```

-continued

```
225                   230                   235                   240

Pro Glu Leu Leu Gly Gly Pro Ser Val Phe Leu Phe Pro Pro Lys Pro
                  245                   250                   255

Lys Asp Thr Leu Met Ile Ser Arg Thr Pro Glu Val Thr Cys Val Val
                  260                   265                   270

Val Asp Val Ser His Arg Asp Pro Glu Val Lys Phe Asn Trp Tyr Val
                  275                   280                   285

Asp Gly Val Glu Val His Asn Ala Lys Thr Lys Pro Arg Glu Glu Gln
    290                   295                   300

Tyr Asn Ser Thr Tyr Arg Val Val Ser Val Leu Thr Val Leu His Gln
305                   310                   315                   320

Asp Trp Leu Asn Gly Lys Glu Tyr Lys Cys Ala Val Ser Asn Lys Ala
                  325                   330                   335

Leu Pro Ala Pro Ile Glu Lys Thr Ile Ser Lys Ala Lys Gly Gln Pro
                  340                   345                   350

Arg Glu Pro Gln Val Tyr Thr Leu Pro Pro Ser Arg Asp Glu Leu Thr
                  355                   360                   365

Lys Asn Gln Val Ser Leu Thr Cys Leu Val Lys Gly Phe Tyr Pro Ser
    370                   375                   380

Asp Ile Ala Val Glu Trp Glu Ser Asn Gly Gln Pro Glu Asn Asn Tyr
385                   390                   395                   400

Lys Thr Thr Pro Pro Val Leu Asp Ser Asp Gly Ser Phe Phe Leu Tyr
                  405                   410                   415

Ser Lys Leu Thr Val Asp Lys Ser Arg Trp Gln Gln Gly Asn Val Phe
                  420                   425                   430

Ser Cys Ser Val Met His Glu Ala Leu His Asn His Tyr Thr Gln Lys
                  435                   440                   445

Ser Leu Ser Leu Ser Pro Gly Lys
    450                   455

<210> SEQ ID NO 21
<211> LENGTH: 126
<212> TYPE: PRT
<213> ORGANISM: Artificial Sequence
<220> FEATURE:
<223> OTHER INFORMATION: HUMANIZED Ab1 (INX310) VARIABLE HEAVY CHAIN
      POLYPEPTIDE

<400> SEQUENCE: 21

Gln Val Gln Leu Lys Glu Ser Gly Pro Gly Leu Val Lys Pro Ser Glu
1                 5                   10                  15

Thr Leu Ser Leu Thr Cys Thr Val Ser Gly Phe Ser Leu Thr Asn Tyr
                  20                  25                  30

His Leu Gln Trp Val Arg Gln Pro Pro Gly Lys Gly Leu Glu Trp Ile
          35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                  85                  90                  95

Arg Asn Ser Trp Tyr His Gly Thr Tyr Tyr Ser Pro Gly Tyr Tyr Val
                  100                 105                 110

Met Asp Ala Trp Gly Gln Gly Thr Met Val Thr Val Ser Ser
                  115                 120                 125
```

<210> SEQ ID NO 22
<211> LENGTH: 456
<212> TYPE: PRT
<213> ORGANISM: Artificial Sequence
<220> FEATURE:
<223> OTHER INFORMATION: HUMANIZED Ab1 (INX310) HEAVY CHAIN POLYPEPTIDE

<400> SEQUENCE: 22

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Arg Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Ala Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

-continued

```
Lys Asn Gln Val Ser Leu Thr Cys Leu Val Lys Gly Phe Tyr Pro Ser
    370             375             380

Asp Ile Ala Val Glu Trp Glu Ser Asn Gly Gln Pro Glu Asn Asn Tyr
385             390             395             400

Lys Thr Thr Pro Pro Val Leu Asp Ser Asp Gly Ser Phe Phe Leu Tyr
            405             410             415

Ser Lys Leu Thr Val Asp Lys Ser Arg Trp Gln Gln Gly Asn Val Phe
            420             425             430

Ser Cys Ser Val Met His Glu Ala Leu His Asn His Tyr Thr Gln Lys
            435             440             445

Ser Leu Ser Leu Ser Pro Gly Lys
    450             455
```

```
<210> SEQ ID NO 23
<211> LENGTH: 126
<212> TYPE: PRT
<213> ORGANISM: Artificial Sequence
<220> FEATURE:
<223> OTHER INFORMATION: HUMANIZED Ab1 (INX310) VARIABLE HEAVY CHAIN
      POLYPEPTIDE

<400> SEQUENCE: 23

Gln Val Gln Leu Gln Glu Ser Gly Pro Gly Leu Val Lys Pro Ser Gln
1               5               10              15

Thr Leu Ser Leu Thr Cys Thr Val Ser Gly Phe Ser Leu Thr Asn Tyr
            20              25              30

His Leu Gln Trp Ile Arg Gln Pro Pro Gly Lys Gly Leu Glu Trp Ile
        35              40              45

Gly Phe Ile Arg Ser Ser Gly Asn Thr Glu Tyr Asn Pro Ser Leu Lys
    50              55              60

Ser Arg Val Thr Ile Ser Arg Asp Thr Ser Lys Asn Gln Val Ser Leu
65              70              75              80

Lys Leu Ser Ser Val Thr Ala Ala Asp Thr Ala Val Tyr Tyr Cys Ala
            85              90              95

Arg Asn Ser Trp Tyr His Gly Thr Tyr Tyr Ser Pro Gly Tyr Tyr Val
            100             105             110

Met Asp Ala Trp Gly Gln Gly Thr Leu Val Thr Val Ser Ser
        115             120             125
```

```
<210> SEQ ID NO 24
<211> LENGTH: 456
<212> TYPE: PRT
<213> ORGANISM: Artificial Sequence
<220> FEATURE:
<223> OTHER INFORMATION: HUMANIZED Ab1 (INX310) HEAVY CHAIN POLYPEPTIDE

<400> SEQUENCE: 24

Gln Val Gln Leu Gln Glu Ser Gly Pro Gly Leu Val Lys Pro Ser Gln
1               5               10              15

Thr Leu Ser Leu Thr Cys Thr Val Ser Gly Phe Ser Leu Thr Asn Tyr
            20              25              30

His Leu Gln Trp Ile Arg Gln Pro Pro Gly Lys Gly Leu Glu Trp Ile
        35              40              45

Gly Phe Ile Arg Ser Ser Gly Asn Thr Glu Tyr Asn Pro Ser Leu Lys
    50              55              60

Ser Arg Val Thr Ile Ser Arg Asp Thr Ser Lys Asn Gln Val Ser Leu
65              70              75              80

Lys Leu Ser Ser Val Thr Ala Ala Asp Thr Ala Val Tyr Tyr Cys Ala
```

-continued

```
                  85                  90                  95
Arg Asn Ser Trp Tyr His Gly Thr Tyr Tyr Ser Pro Gly Tyr Val
              100                 105                 110

Met Asp Ala Trp Gly Gln Gly Thr Leu Val Thr Val Ser Ser Ala Ser
          115                 120                 125

Thr Lys Gly Pro Ser Val Phe Pro Leu Ala Pro Ser Ser Lys Ser Thr
      130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
              165                 170                 175

His Thr Phe Pro Ala Val Leu Gln Ser Ser Gly Leu Tyr Ser Leu Ser
          180                 185                 190

Ser Val Val Thr Val Pro Ser Ser Ser Leu Gly Thr Gln Thr Tyr Ile
          195                 200                 205

Cys Asn Val Asn His Lys Pro Ser Asn Thr Lys Val Asp Lys Lys Val
      210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
              245                 250                 255

Lys Asp Thr Leu Met Ile Ser Arg Thr Pro Glu Val Thr Cys Val Val
              260                 265                 270

Val Asp Val Ser His Arg Asp Pro Glu Val Lys Phe Asn Trp Tyr Val
          275                 280                 285

Asp Gly Val Glu Val His Asn Ala Lys Thr Lys Pro Arg Glu Glu Gln
      290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Ala Val Ser Asn Lys Ala
              325                 330                 335

Leu Pro Ala Pro Ile Glu Lys Thr Ile Ser Lys Ala Lys Gly Gln Pro
              340                 345                 350

Arg Glu Pro Gln Val Tyr Thr Leu Pro Pro Ser Arg Asp Glu Leu Thr
          355                 360                 365

Lys Asn Gln Val Ser Leu Thr Cys Leu Val Lys Gly Phe Tyr Pro Ser
      370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
              405                 410                 415

Ser Lys Leu Thr Val Asp Lys Ser Arg Trp Gln Gln Gly Asn Val Phe
          420                 425                 430

Ser Cys Ser Val Met His Glu Ala Leu His Asn His Tyr Thr Gln Lys
          435                 440                 445

Ser Leu Ser Leu Ser Pro Gly Lys
      450                 455
```

```
<210> SEQ ID NO 25
<211> LENGTH: 126
<212> TYPE: PRT
<213> ORGANISM: Artificial Sequence
<220> FEATURE:
<223> OTHER INFORMATION: HUMANIZED Ab1 (INX310) VARIABLE HEAVY CHAIN
      POLYPEPTIDE
```

```
<400> SEQUENCE: 25

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Leu Val Thr Val Ser Ser
            115                 120                 125

<210> SEQ ID NO 26
<211> LENGTH: 456
<212> TYPE: PRT
<213> ORGANISM: Artificial Sequence
<220> FEATURE:
<223> OTHER INFORMATION: HUMANIZED Ab1 (INX310) HEAVY CHAIN POLYPEPTIDE

<400> SEQUENCE: 26

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220
```

```
Glu Pro Lys Ser Cys Asp Lys Thr His Thr Cys Pro Pro Cys Pro Ala
225             230             235             240

Pro Glu Leu Leu Gly Gly Pro Ser Val Phe Leu Phe Pro Pro Lys Pro
            245             250             255

Lys Asp Thr Leu Met Ile Ser Arg Thr Pro Glu Val Thr Cys Val Val
            260             265             270

Val Asp Val Ser His Arg Asp Pro Glu Val Lys Phe Asn Trp Tyr Val
            275             280             285

Asp Gly Val Glu Val His Asn Ala Lys Thr Lys Pro Arg Glu Glu Gln
            290             295             300

Tyr Asn Ser Thr Tyr Arg Val Val Ser Val Leu Thr Val Leu His Gln
305             310             315             320

Asp Trp Leu Asn Gly Lys Glu Tyr Lys Cys Ala Val Ser Asn Lys Ala
            325             330             335

Leu Pro Ala Pro Ile Glu Lys Thr Ile Ser Lys Ala Lys Gly Gln Pro
            340             345             350

Arg Glu Pro Gln Val Tyr Thr Leu Pro Pro Ser Arg Asp Glu Leu Thr
            355             360             365

Lys Asn Gln Val Ser Leu Thr Cys Leu Val Lys Gly Phe Tyr Pro Ser
            370             375             380

Asp Ile Ala Val Glu Trp Glu Ser Asn Gly Gln Pro Glu Asn Asn Tyr
385             390             395             400

Lys Thr Thr Pro Pro Val Leu Asp Ser Asp Gly Ser Phe Phe Leu Tyr
            405             410             415

Ser Lys Leu Thr Val Asp Lys Ser Arg Trp Gln Gln Gly Asn Val Phe
            420             425             430

Ser Cys Ser Val Met His Glu Ala Leu His Asn His Tyr Thr Gln Lys
            435             440             445

Ser Leu Ser Leu Ser Pro Gly Lys
    450             455
```

```
<210> SEQ ID NO 27
<211> LENGTH: 126
<212> TYPE: PRT
<213> ORGANISM: Artificial Sequence
<220> FEATURE:
<223> OTHER INFORMATION: HUMANIZED Ab1 (INX310) VARIABLE HEAVY CHAIN
      POLYPEPTIDE

<400> SEQUENCE: 27

Gln Val Gln Leu Gln Glu Ser Gly Pro Gly Leu Val Gln Pro Thr Gln
1               5               10              15

Thr Leu Ser Ile Thr Cys Thr Val Ser Gly Phe Ser Leu Thr Asn Tyr
            20              25              30

His Leu Gln Trp Val Arg Gln Thr Pro Gly Lys Gly Leu Glu Trp Met
        35              40              45

Gly Phe Ile Arg Ser Ser Gly Asn Thr Glu Tyr Asn Ser Glu Phe Lys
    50              55              60

Ser Arg Leu Ser Ile Ser Arg Asp Thr Ser Lys Asn Gln Val Phe Leu
65              70              75              80

Lys Met Asn Ser Leu Lys Thr Glu Asp Thr Gly Val Tyr Tyr Cys Ala
            85              90              95

Arg Asn Ser Trp Tyr His Gly Thr Tyr Tyr Ser Pro Gly Tyr Tyr Val
            100             105             110

Met Asp Ala Trp Gly Gln Gly Thr Thr Val Thr Val Ser Ser
            115             120             125
```

```
<210> SEQ ID NO 28
<211> LENGTH: 456
<212> TYPE: PRT
<213> ORGANISM: Artificial Sequence
<220> FEATURE:
<223> OTHER INFORMATION: HUMANIZED Ab1 (INX310) HEAVY CHAIN POLYPEPTIDE

<400> SEQUENCE: 28

Gln Val Gln Leu Gln Glu Ser Gly Pro Gly Leu Val Gln Pro Thr Gln
1               5                   10                  15

Thr Leu Ser Ile Thr Cys Thr Val Ser Gly Phe Ser Leu Thr Asn Tyr
            20                  25                  30

His Leu Gln Trp Val Arg Gln Thr Pro Gly Lys Gly Leu Glu Trp Met
        35                  40                  45

Gly Phe Ile Arg Ser Ser Gly Asn Thr Glu Tyr Asn Ser Glu Phe Lys
    50                  55                  60

Ser Arg Leu Ser Ile Ser Arg Asp Thr Ser Lys Asn Gln Val Phe Leu
65                  70                  75                  80

Lys Met Asn Ser Leu Lys Thr Glu Asp Thr Gly Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Arg Asp Pro Glu Val Lys Phe Asn Trp Tyr Val
            275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Ala Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365
```

-continued

```
Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

```
<210> SEQ ID NO 29
<211> LENGTH: 126
<212> TYPE: PRT
<213> ORGANISM: Artificial Sequence
<220> FEATURE:
<223> OTHER INFORMATION: HUMANIZED Ab1 (INX310) VARIABLE HEAVY CHAIN
      POLYPEPTIDE

<400> SEQUENCE: 29

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Met
        35                  40                  45

Gly Phe Ile Arg Ser Ser Gly Asn Thr Glu Tyr Asn Ser Glu Phe Lys
    50                  55                  60

Ser Arg Leu Ser Ile Ser Arg Asp Thr Ser Lys Asn Gln Val Tyr Leu
65                  70                  75                  80

Gln Met Asn Ser Leu Lys Thr Glu Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Thr Val Thr Val Ser Ser
        115                 120                 125
```

```
<210> SEQ ID NO 30
<211> LENGTH: 456
<212> TYPE: PRT
<213> ORGANISM: Artificial Sequence
<220> FEATURE:
<223> OTHER INFORMATION: HUMANIZED Ab1 (INX310) HEAVY CHAIN POLYPEPTIDE

<400> SEQUENCE: 30

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Met
        35                  40                  45

Gly Phe Ile Arg Ser Ser Gly Asn Thr Glu Tyr Asn Ser Glu Phe Lys
    50                  55                  60

Ser Arg Leu Ser Ile Ser Arg Asp Thr Ser Lys Asn Gln Val Tyr Leu
65                  70                  75                  80
```

-continued

```
Gln Met Asn Ser Leu Lys Thr Glu Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Arg Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Ala Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
    450                 455
```

```
<210> SEQ ID NO 31
<211> LENGTH: 126
<212> TYPE: PRT
<213> ORGANISM: Artificial Sequence
<220> FEATURE:
<223> OTHER INFORMATION: HUMANIZED Ab1 (INX310) VARIABLE HEAVY CHAIN
```

-continued

POLYPEPTIDE

<400> SEQUENCE: 31

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Met
        35                  40                  45

Gly Phe Ile Arg Ser Ser Gly Asn Thr Glu Tyr Asn Ser Glu Phe Lys
    50                  55                  60

Ser Arg Leu Thr Ile Ser Lys Asp Thr Ser Lys Asn Gln Val Tyr Leu
65                  70                  75                  80

Gln Met Asn Ser Leu Lys Thr Glu Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Thr Val Thr Val Ser Ser
            115                 120                 125
```

<210> SEQ ID NO 32
<211> LENGTH: 456
<212> TYPE: PRT
<213> ORGANISM: Artificial Sequence
<220> FEATURE:
<223> OTHER INFORMATION: HUMANIZED Ab1 (INX310) HEAVY CHAIN POLYPEPTIDE

<400> SEQUENCE: 32

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Met
        35                  40                  45

Gly Phe Ile Arg Ser Ser Gly Asn Thr Glu Tyr Asn Ser Glu Phe Lys
    50                  55                  60

Ser Arg Leu Thr Ile Ser Lys Asp Thr Ser Lys Asn Gln Val Tyr Leu
65                  70                  75                  80

Gln Met Asn Ser Leu Lys Thr Glu Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
        210                 215                 220
```

```
Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Arg Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Ala Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys
    450                 455
```

```
<210> SEQ ID NO 33
<211> LENGTH: 106
<212> TYPE: PRT
<213> ORGANISM: Artificial Sequence
<220> FEATURE:
<223> OTHER INFORMATION: HUMANIZED Ab1 (INX310) VARIABLE LIGHT CHAIN
      POLYPEPTIDE

<400> SEQUENCE: 33
```

```
Asp Ile Gln Met Thr Gln Ser Pro Ser Ser Leu Ser Ala Ser Val Gly
1               5                   10                  15

Asp Arg Val Thr Ile Thr Cys Arg Gly Ser Gln Asn Ile Asn Asn Tyr
            20                  25                  30

Leu Ala Trp Phe Gln Gln Lys Pro Gly Lys Thr Pro Lys Leu Leu Ile
        35                  40                  45

Tyr Asn Arg His Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Val Ala Thr Tyr Tyr Cys Tyr Gln Tyr Ser Asp Gly Tyr Thr
                85                  90                  95

Phe Gly Gln Gly Thr Lys Leu Glu Ile Lys
            100                 105
```

-continued

```
<210> SEQ ID NO 34
<211> LENGTH: 213
<212> TYPE: PRT
<213> ORGANISM: Artificial Sequence
<220> FEATURE:
<223> OTHER INFORMATION: HUMANIZED Ab1 (INX310) LIGHT CHAIN POLYPEPTIDE

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Gly Ser Gln Asn Ile Asn Asn Tyr
            20                  25                  30

Leu Ala Trp Phe Gln Gln Lys Pro Gly Lys Thr Pro Lys Leu Leu Ile
        35                  40                  45

Tyr Asn Arg His Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 35
<211> LENGTH: 106
<212> TYPE: PRT
<213> ORGANISM: Artificial Sequence
<220> FEATURE:
<223> OTHER INFORMATION: HUMANIZED Ab1 (INX310) VARIABLE LIGHT CHAIN
      POLYPEPTIDE

<400> SEQUENCE: 35

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95
```

```
Phe Gly Pro Gly Thr Lys Val Asp Ile Lys
            100                 105

<210> SEQ ID NO 36
<211> LENGTH: 213
<212> TYPE: PRT
<213> ORGANISM: Artificial Sequence
<220> FEATURE:
<223> OTHER INFORMATION: HUMANIZED Ab1 (INX310) LIGHT CHAIN POLYPEPTIDE

<400> SEQUENCE: 36

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
            35                  40                  45

Tyr Asn Arg His Asn Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 37
<211> LENGTH: 106
<212> TYPE: PRT
<213> ORGANISM: Artificial Sequence
<220> FEATURE:
<223> OTHER INFORMATION: HUMANIZED Ab1 (INX310) VARIABLE LIGHT CHAIN
      POLYPEPTIDE

<400> SEQUENCE: 37

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
            35                  40                  45

Tyr Asn Arg His Asn Leu Gln Ser Gly Val Pro Ser Arg Phe Arg Gly
    50                  55                  60
```

-continued

```
Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
                100                 105
```

<210> SEQ ID NO 38
<211> LENGTH: 213
<212> TYPE: PRT
<213> ORGANISM: Artificial Sequence
<220> FEATURE:
<223> OTHER INFORMATION: HUMANIZED Ab1 (INX310) LIGHT CHAIN POLYPEPTIDE

<400> SEQUENCE: 38

```
Asp Ile Gln Met Thr Gln Ser Pro Ser Ser Leu Ser Ala Ser Val Gly
1                   5                   10                  15

Asp Lys Val Thr Ile Thr Cys Arg Gly Ser Gln Asn Ile Asn Asn Tyr
                20                  25                  30

Leu Ala Trp Phe Gln Gln Lys Pro Gly Lys Thr Pro Ala Leu Leu Ile
            35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```

<210> SEQ ID NO 39
<211> LENGTH: 106
<212> TYPE: PRT
<213> ORGANISM: Artificial Sequence
<220> FEATURE:
<223> OTHER INFORMATION: HUMANIZED Ab1 (INX310) VARIABLE LIGHT CHAIN
      POLYPEPTIDE

<400> SEQUENCE: 39

```
Asn Ile Gln Met Thr Gln Ser Pro Ser Leu Leu Ser Ala Ser Val Gly
1                   5                   10                  15

Asp Arg Val Thr Leu Ser Cys Lys Gly Ser Gln Asn Ile Asn Asn Tyr
                20                  25                  30

Leu Ala Trp Phe Gln Gln Lys Phe Gly Glu Thr Pro Lys Leu Leu Ile
```

-continued

```
                35                  40                  45

Tyr Asn Arg His Asn Leu Gln Thr Gly Ile Pro Ser Arg Phe Ser Gly
    50                  55                  60

Ser Gly Ser Gly Thr Asp Tyr Thr Leu Thr Ile Asn Ser Leu Gln Pro
65                  70                  75                  80

Glu Asp Val Ala Thr Tyr Phe Cys Tyr Gln Tyr Ser Asp Gly Tyr Thr
                85                  90                  95

Phe Gly Gly Gly Thr Lys Val Glu Ile Lys
            100                 105

<210> SEQ ID NO 40
<211> LENGTH: 213
<212> TYPE: PRT
<213> ORGANISM: Artificial Sequence
<220> FEATURE:
<223> OTHER INFORMATION: HUMANIZED Ab1 (INX310) LIGHT CHAIN POLYPEPTIDE

<400> SEQUENCE: 40

Asn Ile Gln Met Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
                20                  25                  30

Leu Ala Trp Phe Gln Gln Lys Phe Gly Glu Thr Pro Lys Leu Leu Ile
            35                  40                  45

Tyr Asn Arg His Asn Leu Gln Thr Gly Ile Pro Ser Arg Phe Ser Gly
    50                  55                  60

Ser Gly Ser Gly Thr Asp Tyr Thr Leu Thr Ile Asn Ser Leu Gln Pro
65                  70                  75                  80

Glu Asp Val Ala Thr Tyr Phe Cys Tyr Gln Tyr Ser Asp Gly Tyr Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 41
<211> LENGTH: 106
<212> TYPE: PRT
<213> ORGANISM: Artificial Sequence
<220> FEATURE:
<223> OTHER INFORMATION: HUMANIZED Ab1 (INX310) VARIABLE LIGHT CHAIN
      POLYPEPTIDE

<400> SEQUENCE: 41

Asn Ile Gln Met Thr Gln Ser Pro Ser Leu Leu Ser Ala Ser Val Gly
1               5                   10                  15
```

```
Asp Arg Val Thr Ile Ser Cys Lys Gly Ser Gln Asn Ile Asn Asn Tyr
        20                  25                  30

Leu Ala Trp Phe Gln Gln Lys Phe Gly Glu Thr Pro Lys Leu Leu Ile
        35                  40                  45

Tyr Asn Arg His Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Tyr Gln Tyr Ser Asp Gly Tyr Thr
                85                  90                  95

Phe Gly Gly Gly Thr Lys Val Glu Ile Lys
            100                 105
```

<210> SEQ ID NO 42
<211> LENGTH: 213
<212> TYPE: PRT
<213> ORGANISM: Artificial Sequence
<220> FEATURE:
<223> OTHER INFORMATION: HUMANIZED Ab1 (INX310) LIGHT CHAIN POLYPEPTIDE

<400> SEQUENCE: 42

```
Asn Ile Gln Met Thr Gln Ser Pro Ser Leu Leu Ser Ala Ser Val Gly
1               5                   10                  15

Asp Arg Val Thr Ile Ser Cys Lys Gly Ser Gln Asn Ile Asn Asn Tyr
        20                  25                  30

Leu Ala Trp Phe Gln Gln Lys Phe Gly Glu Thr Pro Lys Leu Leu Ile
        35                  40                  45

Tyr Asn Arg His Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Tyr Gln Tyr Ser Asp Gly Tyr Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210
```

<210> SEQ ID NO 43
<211> LENGTH: 106
<212> TYPE: PRT
<213> ORGANISM: Artificial Sequence
<220> FEATURE:
<223> OTHER INFORMATION: HUMANIZED Ab1 (INX310) VARIABLE LIGHT CHAIN
      POLYPEPTIDE

```
<400> SEQUENCE: 43

Asn Ile Gln Met Thr Gln Ser Pro Ser Leu Leu Ser Ala Ser Val Gly
1               5                   10                  15

Asp Arg Val Thr Ile Ser Cys Lys Gly Ser Gln Asn Ile Asn Asn Tyr
            20                  25                  30

Leu Ala Trp Phe Gln Gln Lys Phe Gly Gln Pro Pro Lys Leu Leu Ile
        35                  40                  45

Tyr Asn Arg His Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Gly Gly Thr Lys Val Glu Ile Lys
                100                 105

<210> SEQ ID NO 44
<211> LENGTH: 213
<212> TYPE: PRT
<213> ORGANISM: Artificial Sequence
<220> FEATURE:
<223> OTHER INFORMATION: HUMANIZED Ab1 (INX310) LIGHT CHAIN POLYPEPTIDE

<400> SEQUENCE: 44

Asn Ile Gln Met Thr Gln Ser Pro Ser Leu Leu Ser Ala Ser Val Gly
1               5                   10                  15

Asp Arg Val Thr Ile Ser Cys Lys Gly Ser Gln Asn Ile Asn Asn Tyr
            20                  25                  30

Leu Ala Trp Phe Gln Gln Lys Phe Gly Gln Pro Pro Lys Leu Leu Ile
        35                  40                  45

Tyr Asn Arg His Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 45
<211> LENGTH: 126
```

<212> TYPE: PRT
<213> ORGANISM: Artificial Sequence
<220> FEATURE:
<223> OTHER INFORMATION: Ab5 (INX402)

<400> SEQUENCE: 45

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Met Val Thr Val Ser Ser
        115                 120                 125
```

<210> SEQ ID NO 46
<211> LENGTH: 106
<212> TYPE: PRT
<213> ORGANISM: Artificial Sequence
<220> FEATURE:
<223> OTHER INFORMATION: >LC

<400> SEQUENCE: 46

```
Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105
```

<210> SEQ ID NO 47
<211> LENGTH: 126
<212> TYPE: PRT
<213> ORGANISM: Artificial Sequence
<220> FEATURE:
<223> OTHER INFORMATION: Ab6 (INX403)

<400> SEQUENCE: 47

```
Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
```

-continued

```
                 35                  40                  45
Gly Phe Ile Arg Ser Ser Gly Asn Thr Glu Tyr Asn Pro Ser Leu Lys
    50                  55                  60
Ser Arg Val Thr Ile Ser Arg Asp Thr Ser Lys Asn Gln Val Ser Leu
65                  70                  75                  80
Lys Leu Ser Ser Val Thr Ala Ala Asp Thr Ala Val Tyr Tyr Cys Ala
                85                  90                  95
Arg Asn Ser Trp Tyr His Gly Thr Tyr Tyr Ser Pro Gly Tyr Tyr Val
                100                 105                 110
Met Asp Ala Trp Gly Gln Gly Thr Leu Val Thr Val Ser Ser
            115                 120                 125
```

```
<210> SEQ ID NO 48
<211> LENGTH: 106
<212> TYPE: PRT
<213> ORGANISM: Artificial Sequence
<220> FEATURE:
<223> OTHER INFORMATION: >VL

<400> SEQUENCE: 48
```

```
Asp Ile Gln Met Thr Gln Ser Pro Ser Ser Leu Ser Ala Ser Val Gly
1               5                   10                  15
Asp Lys Val Thr Ile Thr Cys Arg Gly Ser Gln Asn Ile Asn Asn Tyr
                20                  25                  30
Leu Ala Trp Phe Gln Gln Lys Pro Gly Lys Thr Pro Ala Leu Leu Ile
            35                  40                  45
Tyr Asn Arg His Asn Leu Gln Ser Gly Val Pro Ser Arg Phe Arg Gly
    50                  55                  60
Ser Gly Ser Gly Thr Asp Tyr Thr Leu Thr Ile Ser Ser Leu Gln Pro
65                  70                  75                  80
Glu Asp Val Ala Thr Tyr Tyr Cys Tyr Gln Tyr Ser Asp Gly Tyr Thr
                85                  90                  95
Phe Gly Pro Gly Thr Lys Val Asp Ile Lys
            100                 105
```

```
<210> SEQ ID NO 49
<211> LENGTH: 126
<212> TYPE: PRT
<213> ORGANISM: Artificial Sequence
<220> FEATURE:
<223> OTHER INFORMATION: Ab7 (INX404)

<400> SEQUENCE: 49
```

```
Gln Val Gln Leu Lys Glu Ser Gly Pro Gly Leu Val Lys Pro Ser Gln
1               5                   10                  15
Thr Leu Ser Leu Thr Cys Thr Val Ser Gly Phe Ser Leu Thr Asn Tyr
                20                  25                  30
His Leu Gln Trp Val Arg Gln Pro Pro Gly Lys Gly Leu Glu Trp Ile
            35                  40                  45
Gly Phe Ile Arg Ser Ser Gly Asn Thr Glu Tyr Asn Pro Ser Leu Lys
    50                  55                  60
Ser Arg Val Thr Ile Ser Arg Asp Thr Ser Lys Asn Gln Val Ser Leu
65                  70                  75                  80
Lys Leu Ser Ser Val Thr Ala Ala Asp Thr Ala Val Tyr Tyr Cys Ala
                85                  90                  95
Arg Asn Ser Trp Arg His Gly Thr Trp Tyr Ser Pro Gly Tyr Tyr Val
                100                 105                 110
```

-continued

```
Met Asp Ala Trp Gly Gln Gly Thr Leu Val Thr Val Ser Ser
        115                 120                 125

<210> SEQ ID NO 50
<211> LENGTH: 106
<212> TYPE: PRT
<213> ORGANISM: Artificial Sequence
<220> FEATURE:
<223> OTHER INFORMATION: >VL

<400> SEQUENCE: 50

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
                20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
                100                 105

<210> SEQ ID NO 51
<211> LENGTH: 126
<212> TYPE: PRT
<213> ORGANISM: Artificial Sequence
<220> FEATURE:
<223> OTHER INFORMATION: Ab8 (INX405)

<400> SEQUENCE: 51

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
                20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Phe Val His Gly Thr Trp Tyr Ser Pro Gly Tyr Tyr Val
                100                 105                 110

Met Asp Ala Trp Gly Gln Gly Thr Leu Val Thr Val Ser Ser
        115                 120                 125

<210> SEQ ID NO 52
<211> LENGTH: 106
<212> TYPE: PRT
<213> ORGANISM: Artificial Sequence
<220> FEATURE:
<223> OTHER INFORMATION: >VL

<400> SEQUENCE: 52

Asp Ile Gln Met Thr Gln Ser Pro Ser Ser Leu Ser Ala Ser Val Gly
```

-continued

```
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105
```

<210> SEQ ID NO 53
<211> LENGTH: 126
<212> TYPE: PRT
<213> ORGANISM: Artificial Sequence
<220> FEATURE:
<223> OTHER INFORMATION: Ab9 (INX406)

<400> SEQUENCE: 53

```
Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Lys Trp Ile His Gly Thr Trp Tyr Ser Pro Gly Tyr Tyr Val
            100                 105                 110

Met Asp Ala Trp Gly Gln Gly Thr Leu Val Thr Val Ser Ser
        115                 120                 125
```

<210> SEQ ID NO 54
<211> LENGTH: 106
<212> TYPE: PRT
<213> ORGANISM: Artificial Sequence
<220> FEATURE:
<223> OTHER INFORMATION: >VL

<400> SEQUENCE: 54

```
Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80
```

```
Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105

<210> SEQ ID NO 55
<211> LENGTH: 126
<212> TYPE: PRT
<213> ORGANISM: Artificial Sequence
<220> FEATURE:
<223> OTHER INFORMATION: Ab10 (INX407)

<400> SEQUENCE: 55

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Ser Trp Tyr His Gly Thr Tyr Tyr Ser Pro Gly Tyr Tyr Met
            100                 105                 110

Met Asp Ala Trp Gly Gln Gly Thr Leu Val Thr Val Ser Ser
        115                 120                 125

<210> SEQ ID NO 56
<211> LENGTH: 106
<212> TYPE: PRT
<213> ORGANISM: Artificial Sequence
<220> FEATURE:
<223> OTHER INFORMATION: >VL

<400> SEQUENCE: 56

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
            85                  90                  95

Phe Gly Pro Gly Thr Lys Val Asp Ile Lys
            100                 105

<210> SEQ ID NO 57
<211> LENGTH: 126
<212> TYPE: PRT
<213> ORGANISM: Artificial Sequence
<220> FEATURE:
<223> OTHER INFORMATION: Ab11 (INX408)
```

-continued

```
<400> SEQUENCE: 57

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Ser Trp Tyr His Gly Thr Tyr Tyr Ser Pro Gly Tyr Tyr Leu
            100                 105                 110

Met Asp Ala Trp Gly Gln Gly Thr Leu Val Thr Val Ser Ser
        115                 120                 125

<210> SEQ ID NO 58
<211> LENGTH: 106
<212> TYPE: PRT
<213> ORGANISM: Artificial Sequence
<220> FEATURE:
<223> OTHER INFORMATION: >VL

<400> SEQUENCE: 58

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
            85                  90                  95

Phe Gly Pro Gly Thr Lys Val Asp Ile Lys
            100                 105

<210> SEQ ID NO 59
<211> LENGTH: 126
<212> TYPE: PRT
<213> ORGANISM: Artificial Sequence
<220> FEATURE:
<223> OTHER INFORMATION: Ab12 (INX409)

<400> SEQUENCE: 59

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60
```

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Ile His Gly Thr Trp Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 60
<211> LENGTH: 106
<212> TYPE: PRT
<213> ORGANISM: Artificial Sequence
<220> FEATURE:
<223> OTHER INFORMATION: >VL

<400> SEQUENCE: 60

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
                20                  25                  30

Leu Ala Trp Phe Gln Gln Lys Pro Gly Lys Thr Pro Ala Leu Leu Ile
            35                  40                  45

Tyr Asn Arg His Asn Leu Gln Ser Gly Val Pro Ser Arg Phe Arg Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105

<210> SEQ ID NO 61
<211> LENGTH: 126
<212> TYPE: PRT
<213> ORGANISM: Artificial Sequence
<220> FEATURE:
<223> OTHER INFORMATION: Ab13 (INX410)

<400> SEQUENCE: 61

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
                20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Trp Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 62

<211> LENGTH: 106
<212> TYPE: PRT
<213> ORGANISM: Artificial Sequence
<220> FEATURE:
<223> OTHER INFORMATION: >VL

<400> SEQUENCE: 62

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105

<210> SEQ ID NO 63
<211> LENGTH: 126
<212> TYPE: PRT
<213> ORGANISM: Artificial Sequence
<220> FEATURE:
<223> OTHER INFORMATION: Ab14 (INX411)

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val His Gly Thr Trp Tyr Ser Pro Gly Tyr Tyr Val
            100                 105                 110

Met Asp Ala Trp Gly Gln Gly Thr Met Val Thr Val Ser Ser
        115                 120                 125

<210> SEQ ID NO 64
<211> LENGTH: 106
<212> TYPE: PRT
<213> ORGANISM: Artificial Sequence
<220> FEATURE:
<223> OTHER INFORMATION: VL

<400> SEQUENCE: 64

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

-continued

```
Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105

<210> SEQ ID NO 65
<211> LENGTH: 126
<212> TYPE: PRT
<213> ORGANISM: Artificial Sequence
<220> FEATURE:
<223> OTHER INFORMATION: Ab15 (INX412)

<400> SEQUENCE: 65

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
        20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val Gln Gly Trp Trp Tyr Ser Pro Gly Tyr Tyr Val
            100                 105                 110

Met Asp Ala Trp Gly Gln Gly Thr Met Val Thr Val Ser Ser
        115                 120                 125

<210> SEQ ID NO 66
<211> LENGTH: 106
<212> TYPE: PRT
<213> ORGANISM: Artificial Sequence
<220> FEATURE:
<223> OTHER INFORMATION: >VL

<400> SEQUENCE: 66

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
        20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105
```

```
<210> SEQ ID NO 67
<211> LENGTH: 126
<212> TYPE: PRT
<213> ORGANISM: Artificial Sequence
<220> FEATURE:
<223> OTHER INFORMATION: Ab16 (INX413)

<400> SEQUENCE: 67

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Phe Ser Pro Gly Tyr Tyr Leu
            100                 105                 110

Met Asp Ala Trp Gly Gln Gly Thr Leu Val Thr Val Ser Ser
        115                 120                 125

<210> SEQ ID NO 68
<211> LENGTH: 106
<212> TYPE: PRT
<213> ORGANISM: Artificial Sequence
<220> FEATURE:
<223> OTHER INFORMATION: >VL

<400> SEQUENCE: 68

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105

<210> SEQ ID NO 69
<211> LENGTH: 126
<212> TYPE: PRT
<213> ORGANISM: Artificial Sequence
<220> FEATURE:
<223> OTHER INFORMATION: Ab17 (INX414)

<400> SEQUENCE: 69

Gln Val Gln Leu Lys Glu Ser Gly Pro Gly Leu Val Lys Pro Ser Gln
1               5                   10                  15
```

-continued

```
Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Lys Arg Trp Val His Gly Thr Trp Tyr Ser Pro Gly Tyr Tyr Val
            100                 105                 110

Met Asp Ala Trp Gly Gln Gly Thr Leu Val Thr Val Ser Ser
            115                 120                 125
```

<210> SEQ ID NO 70
<211> LENGTH: 106
<212> TYPE: PRT
<213> ORGANISM: Artificial Sequence
<220> FEATURE:
<223> OTHER INFORMATION: >VL

<400> SEQUENCE: 70

```
Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105
```

<210> SEQ ID NO 71
<211> LENGTH: 126
<212> TYPE: PRT
<213> ORGANISM: Artificial Sequence
<220> FEATURE:
<223> OTHER INFORMATION: Ab18 (INX415)

<400> SEQUENCE: 71

```
Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95
```

-continued

Arg Asn Arg Trp Met His Gly Thr Trp Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 72
<211> LENGTH: 106
<212> TYPE: PRT
<213> ORGANISM: Artificial Sequence
<220> FEATURE:
<223> OTHER INFORMATION: >VL SEQ ID NO:72

<400> SEQUENCE: 72

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105

<210> SEQ ID NO 73
<211> LENGTH: 126
<212> TYPE: PRT
<213> ORGANISM: Artificial Sequence
<220> FEATURE:
<223> OTHER INFORMATION: Ab19 (INX416)

<400> SEQUENCE: 73

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Trp Val His Gly Thr Tyr Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 74
<211> LENGTH: 106
<212> TYPE: PRT
<213> ORGANISM: Artificial Sequence
<220> FEATURE:
<223> OTHER INFORMATION: >VL -continued

<400> SEQUENCE: 74

```
Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
                100                 105
```

<210> SEQ ID NO 75
<211> LENGTH: 126
<212> TYPE: PRT
<213> ORGANISM: Artificial Sequence
<220> FEATURE:
<223> OTHER INFORMATION: Ab20 (INX417)

<400> SEQUENCE: 75

```
Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val Gln Gly Thr Tyr Tyr Ser Pro Gly Tyr Tyr Val
                100                 105                 110

Met Asp Ala Trp Gly Gln Gly Thr Leu Val Thr Val Ser Ser
            115                 120                 125
```

<210> SEQ ID NO 76
<211> LENGTH: 106
<212> TYPE: PRT
<213> ORGANISM: Artificial Sequence
<220> FEATURE:
<223> OTHER INFORMATION: >VL

<400> SEQUENCE: 76

```
Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60
```

-continued

```
Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105

<210> SEQ ID NO 77
<211> LENGTH: 126
<212> TYPE: PRT
<213> ORGANISM: Artificial Sequence
<220> FEATURE:
<223> OTHER INFORMATION: Ab21 (INX418)

<400> SEQUENCE: 77

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val His Gly Thr Trp Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 78
<211> LENGTH: 106
<212> TYPE: PRT
<213> ORGANISM: Artificial Sequence
<220> FEATURE:
<223> OTHER INFORMATION: >VL

<400> SEQUENCE: 78

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105

<210> SEQ ID NO 79
<211> LENGTH: 126
<212> TYPE: PRT
```

```
<213> ORGANISM: Artificial Sequence
<220> FEATURE:
<223> OTHER INFORMATION: Ab22 (INX419)

<400> SEQUENCE: 79

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Arg Trp Val Gln Gly Ser Tyr Tyr Ser Pro Gly Tyr Tyr Val
            100                 105                 110

Met Asp Ala Trp Gly Gln Gly Thr Met Val Thr Val Ser Ser
        115                 120                 125

<210> SEQ ID NO 80
<211> LENGTH: 106
<212> TYPE: PRT
<213> ORGANISM: Artificial Sequence
<220> FEATURE:
<223> OTHER INFORMATION: >VL

<400> SEQUENCE: 80

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
            85                  90                  95

Phe Gly Pro Gly Thr Lys Val Asp Ile Lys
            100                 105

<210> SEQ ID NO 81
<211> LENGTH: 126
<212> TYPE: PRT
<213> ORGANISM: Artificial Sequence
<220> FEATURE:
<223> OTHER INFORMATION: Ab23 (NX420)

<400> SEQUENCE: 81

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45
```

-continued

```
Gly Phe Ile Arg Ser Ser Gly Asn Thr Glu Tyr Asn Pro Ser Leu Lys
    50              55              60

Ser Arg Val Thr Ile Ser Arg Asp Thr Ser Lys Asn Gln Val Ser Leu
65              70              75              80

Lys Leu Ser Ser Val Thr Ala Ala Asp Thr Ala Val Tyr Tyr Cys Ala
                85              90              95

Arg Asn Arg Phe Val His Gly Thr Trp Tyr Ser Pro Gly Tyr Tyr Leu
            100             105             110

Met Asp Ala Trp Gly Gln Gly Thr Leu Val Thr Val Ser Ser
        115             120             125
```

```
<210> SEQ ID NO 82
<211> LENGTH: 106
<212> TYPE: PRT
<213> ORGANISM: Artificial Sequence
<220> FEATURE:
<223> OTHER INFORMATION: >VL

<400> SEQUENCE: 82

Asp Ile Gln Met Thr Gln Ser Pro Ser Ser Leu Ser Ala Ser Val Gly
1               5               10              15

Asp Lys Val Thr Ile Thr Cys Arg Gly Ser Gln Asn Ile Asn Asn Tyr
            20              25              30

Leu Ala Trp Phe Gln Gln Lys Pro Gly Lys Thr Pro Ala Leu Leu Ile
        35              40              45

Tyr Asn Arg His Asn Leu Gln Ser Gly Val Pro Ser Arg Phe Arg Gly
    50              55              60

Ser Gly Ser Gly Thr Asp Tyr Thr Leu Thr Ile Ser Ser Leu Gln Pro
65              70              75              80

Glu Asp Val Ala Thr Tyr Tyr Cys Tyr Gln Tyr Ser Asp Gly Tyr Thr
                85              90              95

Phe Gly Pro Gly Thr Lys Val Asp Ile Lys
            100             105
```

```
<210> SEQ ID NO 83
<211> LENGTH: 126
<212> TYPE: PRT
<213> ORGANISM: Artificial Sequence
<220> FEATURE:
<223> OTHER INFORMATION: Ab24 (INX421)

<400> SEQUENCE: 83

Gln Val Gln Leu Lys Glu Ser Gly Pro Gly Leu Val Lys Pro Ser Gln
1               5               10              15

Thr Leu Ser Leu Thr Cys Thr Val Ser Gly Phe Ser Leu Thr Asn Tyr
            20              25              30

His Leu Gln Trp Val Arg Gln Pro Pro Gly Lys Gly Leu Glu Trp Ile
        35              40              45

Gly Phe Ile Arg Ser Ser Gly Asn Thr Glu Tyr Asn Pro Ser Leu Lys
    50              55              60

Ser Arg Val Thr Ile Ser Arg Asp Thr Ser Lys Asn Gln Val Ser Leu
65              70              75              80

Lys Leu Ser Ser Val Thr Ala Ala Asp Thr Ala Val Tyr Tyr Cys Ala
                85              90              95

Arg Asn Arg Trp Ile His Gly Thr Trp Tyr Ser Pro Gly Tyr Tyr Leu
            100             105             110

Met Asp Ala Trp Gly Gln Gly Thr Leu Val Thr Val Ser Ser
```

```
          115                 120                 125

<210> SEQ ID NO 84
<211> LENGTH: 106
<212> TYPE: PRT
<213> ORGANISM: Artificial Sequence
<220> FEATURE:
<223> OTHER INFORMATION: >VL

<400> SEQUENCE: 84

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105

<210> SEQ ID NO 85
<211> LENGTH: 126
<212> TYPE: PRT
<213> ORGANISM: Artificial Sequence
<220> FEATURE:
<223> OTHER INFORMATION: Ab25 (INX422)

<400> SEQUENCE: 85

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val His Gly Thr Trp Tyr Ser Pro Gly Tyr Tyr Leu
            100                 105                 110

Met Asp Ala Trp Gly Gln Gly Thr Met Val Thr Val Ser Ser
        115                 120                 125

<210> SEQ ID NO 86
<211> LENGTH: 106
<212> TYPE: PRT
<213> ORGANISM: Artificial Sequence
<220> FEATURE:
<223> OTHER INFORMATION: >VL

<400> SEQUENCE: 86

Asp Ile Gln Met Thr Gln Ser Pro Ser Ser Leu Ser Ala Ser Val Gly
1               5                   10                  15
```

-continued

```
Asp Lys Val Thr Ile Thr Cys Arg Gly Ser Gln Asn Ile Asn Asn Tyr
        20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105
```

<210> SEQ ID NO 87
<211> LENGTH: 126
<212> TYPE: PRT
<213> ORGANISM: Artificial Sequence
<220> FEATURE:
<223> OTHER INFORMATION: Ab26 (INX423)

<400> SEQUENCE: 87

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
        20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val Gln Gly Trp Trp Tyr Ser Pro Gly Tyr Tyr Leu
            100                 105                 110

Met Asp Ala Trp Gly Gln Gly Thr Met Val Thr Val Ser Ser
            115                 120                 125
```

<210> SEQ ID NO 88
<211> LENGTH: 106
<212> TYPE: PRT
<213> ORGANISM: Artificial Sequence
<220> FEATURE:
<223> OTHER INFORMATION: >VL

<400> SEQUENCE: 88

```
Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
        20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
```

```
                    85              90              95

Phe Gly Pro Gly Thr Lys Val Asp Ile Lys
            100             105

<210> SEQ ID NO 89
<211> LENGTH: 126
<212> TYPE: PRT
<213> ORGANISM: Artificial Sequence
<220> FEATURE:
<223> OTHER INFORMATION: Ab27 (INX424)

<400> SEQUENCE: 89

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Arg Trp Met His Gly Thr Trp Tyr Ser Pro Gly Tyr Tyr Leu
            100             105             110

Met Asp Ala Trp Gly Gln Gly Thr Leu Val Thr Val Ser Ser
        115             120             125

<210> SEQ ID NO 90
<211> LENGTH: 106
<212> TYPE: PRT
<213> ORGANISM: Artificial Sequence
<220> FEATURE:
<223> OTHER INFORMATION: >VL

<400> SEQUENCE: 90

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
            85                  90                  95

Phe Gly Pro Gly Thr Lys Val Asp Ile Lys
            100             105

<210> SEQ ID NO 91
<211> LENGTH: 126
<212> TYPE: PRT
<213> ORGANISM: Artificial Sequence
<220> FEATURE:
<223> OTHER INFORMATION: Ab28 (INX425)

<400> SEQUENCE: 91
```

```
Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
            35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Trp Val His Gly Thr Tyr Phe Ser Pro Gly Tyr Tyr Leu
            100                 105                 110

Met Asp Ala Trp Gly Gln Gly Thr Leu Val Thr Val Ser Ser
            115                 120                 125
```

```
<210> SEQ ID NO 92
<211> LENGTH: 106
<212> TYPE: PRT
<213> ORGANISM: Artificial Sequence
<220> FEATURE:
<223> OTHER INFORMATION: >VL

<400> SEQUENCE: 92
```

```
Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
            35                  40                  45

Tyr Asn Arg His Asn Leu Gln Ser Gly Val Pro Ser Arg Phe Arg Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105
```

```
<210> SEQ ID NO 93
<211> LENGTH: 126
<212> TYPE: PRT
<213> ORGANISM: Artificial Sequence
<220> FEATURE:
<223> OTHER INFORMATION: Ab29 (INX426)

<400> SEQUENCE: 93
```

```
Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
            35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
```

-continued

```
65              70              75              80

Lys Leu Ser Ser Val Thr Ala Ala Asp Thr Ala Val Tyr Tyr Cys Ala
                85              90              95

Arg Asn Arg Trp Val His Gly Thr Trp Tyr Ser Pro Gly Tyr Tyr Leu
            100             105             110

Met Asp Ala Trp Gly Gln Gly Thr Leu Val Thr Val Ser Ser
        115             120             125

<210> SEQ ID NO 94
<211> LENGTH: 106
<212> TYPE: PRT
<213> ORGANISM: Artificial Sequence
<220> FEATURE:
<223> OTHER INFORMATION: >VL

<400> SEQUENCE: 94

Asp Ile Gln Met Thr Gln Ser Pro Ser Ser Leu Ser Ala Ser Val Gly
1               5               10              15

Asp Lys Val Thr Ile Thr Cys Arg Gly Ser Gln Asn Ile Asn Asn Tyr
            20              25              30

Leu Ala Trp Phe Gln Gln Lys Pro Gly Lys Thr Pro Ala Leu Leu Ile
        35              40              45

Tyr Asn Arg His Asn Leu Gln Ser Gly Val Pro Ser Arg Phe Arg Gly
    50              55              60

Ser Gly Ser Gly Thr Asp Tyr Thr Leu Thr Ile Ser Ser Leu Gln Pro
65              70              75              80

Glu Asp Val Ala Thr Tyr Tyr Cys Tyr Gln Tyr Ser Asp Gly Tyr Thr
                85              90              95

Phe Gly Pro Gly Thr Lys Val Asp Ile Lys
            100             105

<210> SEQ ID NO 95
<211> LENGTH: 126
<212> TYPE: PRT
<213> ORGANISM: Artificial Sequence
<220> FEATURE:
<223> OTHER INFORMATION: Ab30 (INX427)

<400> SEQUENCE: 95

Gln Val Gln Leu Gln Glu Ser Gly Pro Gly Leu Val Lys Pro Ser Glu
1               5               10              15

Thr Leu Ser Leu Thr Cys Thr Val Ser Gly Phe Ser Leu Thr Asn Tyr
            20              25              30

His Leu Gln Trp Ile Arg Gln Pro Pro Gly Lys Gly Leu Glu Trp Ile
        35              40              45

Gly Phe Ile Arg Ser Ser Gly Asn Thr Glu Tyr Asn Pro Ser Leu Lys
    50              55              60

Ser Arg Val Thr Ile Ser Arg Asp Thr Ser Lys Asn Gln Val Ser Leu
65              70              75              80

Lys Leu Ser Ser Val Thr Ala Ala Asp Thr Ala Val Tyr Tyr Cys Ala
                85              90              95

Arg Asn Arg Trp Val Gln Gly Ser Tyr Tyr Ser Pro Gly Tyr Tyr Leu
            100             105             110

Met Asp Ala Trp Gly Gln Gly Thr Met Val Thr Val Ser Ser
        115             120             125

<210> SEQ ID NO 96
<211> LENGTH: 106
```

```
<212> TYPE: PRT
<213> ORGANISM: Artificial Sequence
<220> FEATURE:
<223> OTHER INFORMATION: >VL

<400> SEQUENCE: 96

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105

<210> SEQ ID NO 97
<211> LENGTH: 126
<212> TYPE: PRT
<213> ORGANISM: Artificial Sequence
<220> FEATURE:
<223> OTHER INFORMATION: Ab31 (INX428)

<400> SEQUENCE: 97

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 98
<211> LENGTH: 114
<212> TYPE: PRT
<213> ORGANISM: Artificial Sequence
<220> FEATURE:
<223> OTHER INFORMATION: >VL

<400> SEQUENCE: 98

Glu Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Phe Tyr Asn
            20                  25                  30

Ser Tyr Asn Arg Asn Tyr Leu Ala Trp Tyr Gln Gln Lys Pro Gly Gln
```

-continued

```
             35                40                45
Pro Pro Lys Leu Leu Ile Tyr Trp Ala Ser Thr Arg Glu Ser Gly Val
    50                55                60
Pro Asp Arg Phe Ser Gly Ser Gly Ser Gly Thr Asp Phe Thr Leu Thr
65                70                75                80
Ile Ser Ser Leu Gln Ala Glu Asp Val Ala Val Tyr Tyr Cys Gln Gln
                85                90                95
Tyr Tyr Ser Thr Pro Ser Phe Thr Phe Gly Pro Gly Thr Lys Val Asp
            100               105               110
Ile Lys

<210> SEQ ID NO 99
<211> LENGTH: 126
<212> TYPE: PRT
<213> ORGANISM: Artificial Sequence
<220> FEATURE:
<223> OTHER INFORMATION: Ab32 (INX429)

<400> SEQUENCE: 99

Gln Val Gln Leu Lys Glu Ser Gly Pro Gly Leu Val Lys Pro Ser Gln
1               5                10                15
Thr Leu Ser Leu Thr Cys Thr Val Ser Gly Phe Ser Leu Thr Asn Tyr
                20                25                30
His Leu Gln Trp Val Arg Gln Pro Pro Gly Lys Gly Leu Glu Trp Ile
        35                40                45
Gly Phe Ile Arg Ser Ser Gly Asn Thr Glu Tyr Asn Pro Ser Leu Lys
    50                55                60
Ser Arg Val Thr Ile Ser Arg Asp Thr Ser Lys Asn Gln Val Ser Leu
65                70                75                80
Lys Leu Ser Ser Val Thr Ala Ala Asp Thr Ala Val Tyr Tyr Cys Ala
                85                90                95
Arg Asn Ser Trp Tyr His Gly Thr Tyr Tyr Ser Pro Gly Tyr Tyr Val
            100               105               110
Met Asp Ala Trp Gly Gln Gly Thr Leu Val Thr Val Ser Ser
        115               120               125

<210> SEQ ID NO 100
<211> LENGTH: 107
<212> TYPE: PRT
<213> ORGANISM: Artificial Sequence
<220> FEATURE:
<223> OTHER INFORMATION: >VL

<400> SEQUENCE: 100

Ala Ile Gln Met Thr Gln Ser Pro Ser Ser Leu Ser Ala Ser Val Gly
1               5                10                15
Asp Arg Val Thr Ile Thr Cys Arg Ala Ser Gln Gly Ile Ser Asn Tyr
                20                25                30
Leu Ala Trp Phe Gln Gln Lys Pro Gly Lys Ala Pro Lys Ser Leu Ile
        35                40                45
Tyr Ala Ala Ser Ser Leu Gln Ser Gly Val Pro Ser Arg Phe Ser Gly
    50                55                60
Ser Gly Ser Gly Thr Asp Phe Thr Leu Thr Ile Ser Ser Leu Gln Pro
65                70                75                80
Glu Asp Phe Ala Thr Tyr Tyr Cys Gln Gln Ser Asp Ser Pro Pro Tyr
                85                90                95
Thr Phe Gly Leu Gly Thr Lys Leu Glu Ile Lys
```

-continued

```
                100              105

<210> SEQ ID NO 101
<211> LENGTH: 126
<212> TYPE: PRT
<213> ORGANISM: Artificial Sequence
<220> FEATURE:
<223> OTHER INFORMATION: Ab33 (INX430)

<400> SEQUENCE: 101

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 102
<211> LENGTH: 107
<212> TYPE: PRT
<213> ORGANISM: Artificial Sequence
<220> FEATURE:
<223> OTHER INFORMATION: >VL

<400> SEQUENCE: 102

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
            85                  90                  95

Thr Phe Gly Gln Gly Thr Lys Val Glu Ile Lys
            100                 105

<210> SEQ ID NO 103
<211> LENGTH: 126
<212> TYPE: PRT
<213> ORGANISM: Artificial Sequence
<220> FEATURE:
<223> OTHER INFORMATION: Ab34 (INX431)

<400> SEQUENCE: 103

Gln Val Gln Leu Lys Glu Ser Gly Pro Gly Leu Val Lys Pro Ser Gln
1               5                   10                  15
```

-continued

```
Thr Leu Ser Leu Thr Cys Thr Val Ser Gly Phe Ser Leu Thr Asn Tyr
        20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Leu Val Thr Val Ser Ser
        115                 120                 125
```

```
<210> SEQ ID NO 104
<211> LENGTH: 107
<212> TYPE: PRT
<213> ORGANISM: Artificial Sequence
<220> FEATURE:
<223> OTHER INFORMATION: >VL

<400> SEQUENCE: 104
```

```
Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
        20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Asn Gly Leu Gln Pro
65                  70                  75                  80

Glu Asp Phe Ala Thr Tyr Tyr Cys Gln Gln Thr Asp Ser Leu Pro Tyr
                85                  90                  95

Thr Phe Gly Gln Gly Thr Lys Leu Glu Ile Lys
            100                 105
```

```
<210> SEQ ID NO 105
<211> LENGTH: 126
<212> TYPE: PRT
<213> ORGANISM: Artificial Sequence
<220> FEATURE:
<223> OTHER INFORMATION: Ab35 (INX432)

<400> SEQUENCE: 105
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
        20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
```

-continued

```
                    85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Met Val Thr Val Ser Ser
        115                 120                 125

<210> SEQ ID NO 106
<211> LENGTH: 106
<212> TYPE: PRT
<213> ORGANISM: Artificial Sequence
<220> FEATURE:
<223> OTHER INFORMATION: >VL

<400> SEQUENCE: 106

Asn Ile His Leu Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Phe Gln Gln Lys Phe Gly Glu Thr Pro Lys Leu Leu Ile
        35                  40                  45

Tyr Asn Arg His Asn Leu Gln Thr Gly Ile Pro Ser Arg Phe Ser Gly
    50                  55                  60

Ser Gly Ser Gly Thr Asp Tyr Thr Leu Thr Ile Asn Ser Leu Gln Pro
65                  70                  75                  80

Glu Asp Val Ala Thr Tyr Phe Cys Tyr Gln Tyr Ser Asp Gly Tyr Thr
                85                  90                  95

Phe Gly Ala Gly Thr Lys Leu Glu Leu Lys
            100                 105

<210> SEQ ID NO 107
<211> LENGTH: 126
<212> TYPE: PRT
<213> ORGANISM: Artificial Sequence
<220> FEATURE:
<223> OTHER INFORMATION: Ab36 (INX433)

<400> SEQUENCE: 107

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 108
<211> LENGTH: 106
<212> TYPE: PRT
<213> ORGANISM: Artificial Sequence
<220> FEATURE:
```

-continued

<223> OTHER INFORMATION: >VL

<400> SEQUENCE: 108

Asn Ile His Leu Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Phe Gln Gln Lys Phe Gly Glu Thr Pro Lys Leu Leu Ile
        35                  40                  45

Tyr Asn Arg His Asn Leu Gln Thr Gly Ile Pro Ser Arg Phe Ser Gly
    50                  55                  60

Ser Gly Ser Gly Thr Asp Tyr Thr Leu Thr Ile Asn Ser Leu Gln Pro
65                  70                  75                  80

Glu Asp Val Ala Thr Tyr Phe Cys Tyr Gln Tyr Ser Asp Gly Tyr Thr
                85                  90                  95

Phe Gly Ala Gly Thr Lys Leu Glu Leu Lys
            100                 105

<210> SEQ ID NO 109
<211> LENGTH: 126
<212> TYPE: PRT
<213> ORGANISM: Artificial Sequence
<220> FEATURE:
<223> OTHER INFORMATION: Ab37 (INX434)

<400> SEQUENCE: 109

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Arg His Gly Thr Trp Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 110
<211> LENGTH: 107
<212> TYPE: PRT
<213> ORGANISM: Artificial Sequence
<220> FEATURE:
<223> OTHER INFORMATION: >VL

<400> SEQUENCE: 110

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly

-continued

```
        50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105
```

```
<210> SEQ ID NO 111
<211> LENGTH: 126
<212> TYPE: PRT
<213> ORGANISM: Artificial Sequence
<220> FEATURE:
<223> OTHER INFORMATION: Ab38 (INX435)

<400> SEQUENCE: 111

Gln Val Gln Leu Lys Glu Ser Gly Pro Gly Leu Val Lys Pro Ser Gln
1                   5                   10                  15

Thr Leu Ser Leu Thr Cys Thr Val Ser Gly Phe Ser Leu Thr Asn Tyr
                20                  25                  30

His Leu Gln Trp Val Arg Gln Pro Pro Gly Lys Gly Leu Glu Trp Ile
            35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Phe Val His Gly Thr Trp Tyr Ser Pro Gly Tyr Tyr Val
            100                 105                 110

Met Asp Ala Trp Gly Gln Gly Thr Leu Val Thr Val Ser Ser
            115                 120                 125
```

```
<210> SEQ ID NO 112
<211> LENGTH: 107
<212> TYPE: PRT
<213> ORGANISM: Artificial Sequence
<220> FEATURE:
<223> OTHER INFORMATION: >VL

<400> SEQUENCE: 112

Asp Ile Gln Leu Thr Gln Ser Pro Ser Ala Met Ser Ala Ser Val Gly
1                   5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Ala Ser Arg Phe Ser Gly
        50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105
```

```
<210> SEQ ID NO 113
<211> LENGTH: 126
```

```
<212> TYPE: PRT
<213> ORGANISM: Artificial Sequence
<220> FEATURE:
<223> OTHER INFORMATION: Ab39 (INX436)

<400> SEQUENCE: 113

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Lys Trp Ile His Gly Thr Trp Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 114
<211> LENGTH: 107
<212> TYPE: PRT
<213> ORGANISM: Artificial Sequence
<220> FEATURE:
<223> OTHER INFORMATION: >VL

<400> SEQUENCE: 114

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 115
<211> LENGTH: 126
<212> TYPE: PRT
<213> ORGANISM: Artificial Sequence
<220> FEATURE:
<223> OTHER INFORMATION: Ab40 (INX437)

<400> SEQUENCE: 115

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
```

-continued

```
                35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Met
                100                 105                 110

Met Asp Ala Trp Gly Gln Gly Thr Leu Val Thr Val Ser Ser
            115                 120                 125

<210> SEQ ID NO 116
<211> LENGTH: 107
<212> TYPE: PRT
<213> ORGANISM: Artificial Sequence
<220> FEATURE:
<223> OTHER INFORMATION: >VL

<400> SEQUENCE: 116

Asp Ile Gln Leu Thr Gln Ser Pro Ser Ala Met Ser Ala Ser Val Gly
1                   5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 117
<211> LENGTH: 126
<212> TYPE: PRT
<213> ORGANISM: Artificial Sequence
<220> FEATURE:
<223> OTHER INFORMATION: Ab41 (INX438)

<400> SEQUENCE: 117

Gln Val Gln Leu Lys Glu Ser Gly Pro Gly Leu Val Lys Pro Ser Gln
1                   5                   10                  15

Thr Leu Ser Leu Thr Cys Thr Val Ser Gly Phe Ser Leu Thr Asn Tyr
                20                  25                  30

His Leu Gln Trp Val Arg Gln Pro Pro Gly Lys Gly Leu Glu Trp Ile
            35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Leu
                100                 105                 110
```

-continued

Met Asp Ala Trp Gly Gln Gly Thr Leu Val Thr Val Ser Ser
        115                 120                 125

<210> SEQ ID NO 118
<211> LENGTH: 107
<212> TYPE: PRT
<213> ORGANISM: Artificial Sequence
<220> FEATURE:
<223> OTHER INFORMATION: >VL

<400> SEQUENCE: 118

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 119
<211> LENGTH: 126
<212> TYPE: PRT
<213> ORGANISM: Artificial Sequence
<220> FEATURE:
<223> OTHER INFORMATION: Ab42 (INX439)

<400> SEQUENCE: 119

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Ile His Gly Thr Trp Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 120
<211> LENGTH: 107
<212> TYPE: PRT
<213> ORGANISM: Artificial Sequence
<220> FEATURE:
<223> OTHER INFORMATION: >VL

<400> SEQUENCE: 120

Asp Ile Gln Leu Thr Gln Ser Pro Ser Ala Met Ser Ala Ser Val Gly

-continued

```
1               5               10              15

Asp Arg Val Thr Ile Thr Cys Arg Ala Ser Gln Gly Ile Ser Asn Tyr
            20              25              30

Leu Ala Trp Tyr Gln Gln Lys Pro Gly Lys Ala Pro Lys Leu Leu Ile
        35              40              45

Tyr Ala Ala Ser Thr Leu Gln Ser Gly Val Ala Ser Arg Phe Ser Gly
    50              55              60

Arg Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Asp Ile Leu Pro Tyr
            85              90              95

Thr Phe Gly Gln Gly Thr Lys Val Glu Ile Lys
        100             105
```

<210> SEQ ID NO 121
<211> LENGTH: 126
<212> TYPE: PRT
<213> ORGANISM: Artificial Sequence
<220> FEATURE:
<223> OTHER INFORMATION: Ab43 (INX440)

<400> SEQUENCE: 121

```
Gln Val Gln Leu Lys Glu Ser Gly Pro Gly Leu Val Lys Pro Ser Gln
1               5               10              15

Thr Leu Ser Leu Thr Cys Thr Val Ser Gly Phe Ser Leu Thr Asn Tyr
            20              25              30

His Leu Gln Trp Val Arg Gln Pro Pro Gly Lys Gly Leu Glu Trp Ile
        35              40              45

Gly Phe Ile Arg Ser Ser Gly Asn Thr Glu Tyr Asn Pro Ser Leu Lys
    50              55              60

Ser Arg Val Thr Ile Ser Arg Asp Thr Ser Lys Asn Gln Val Ser Leu
65              70              75              80

Lys Leu Ser Ser Val Thr Ala Ala Asp Thr Ala Val Tyr Tyr Cys Ala
            85              90              95

Arg Asn Ser Trp Tyr His Gly Thr Tyr Trp Ser Pro Gly Tyr Tyr Val
            100             105             110

Met Asp Ala Trp Gly Gln Gly Thr Leu Val Thr Val Ser Ser
        115             120             125
```

<210> SEQ ID NO 122
<211> LENGTH: 107
<212> TYPE: PRT
<213> ORGANISM: Artificial Sequence
<220> FEATURE:
<223> OTHER INFORMATION: >VL

<400> SEQUENCE: 122

```
Asp Ile Gln Leu Thr Gln Ser Pro Ser Ala Met Ser Ala Ser Val Gly
1               5               10              15

Asp Arg Val Thr Ile Thr Cys Arg Ala Ser Gln Gly Ile Ser Asn Tyr
            20              25              30

Leu Ala Trp Tyr Gln Gln Lys Pro Gly Lys Ala Pro Lys Leu Leu Ile
        35              40              45

Tyr Ala Ala Ser Thr Leu Gln Ser Gly Val Ala Ser Arg Phe Ser Gly
    50              55              60

Arg Gly Ser Gly Thr Asp Phe Thr Leu Thr Ile Ser Ser Leu Gln Pro
65              70              75              80
```

-continued

```
Glu Asp Phe Ala Thr Tyr Tyr Cys Gln Gln Ser Asp Ile Leu Pro Tyr
                85              90                  95

Thr Phe Gly Gln Gly Thr Lys Val Glu Ile Lys
            100             105

<210> SEQ ID NO 123
<211> LENGTH: 126
<212> TYPE: PRT
<213> ORGANISM: Artificial Sequence
<220> FEATURE:
<223> OTHER INFORMATION: Ab44 (INX441)

<400> SEQUENCE: 123

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val His Gly Thr Trp Tyr Ser Pro Gly Tyr Tyr Val
            100                 105                 110

Met Asp Ala Trp Gly Gln Gly Thr Met Val Thr Val Ser Ser
            115                 120                 125

<210> SEQ ID NO 124
<211> LENGTH: 107
<212> TYPE: PRT
<213> ORGANISM: Artificial Sequence
<220> FEATURE:
<223> OTHER INFORMATION: >VL

<400> SEQUENCE: 124

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 125
<211> LENGTH: 126
<212> TYPE: PRT
<213> ORGANISM: Artificial Sequence
<220> FEATURE:
<223> OTHER INFORMATION: Ab45 (INX442)
```

```
<400> SEQUENCE: 125

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val Gln Gly Trp Trp Tyr Ser Pro Gly Tyr Tyr Val
            100                 105                 110

Met Asp Ala Trp Gly Gln Gly Thr Met Val Thr Val Ser Ser
        115                 120                 125

<210> SEQ ID NO 126
<211> LENGTH: 107
<212> TYPE: PRT
<213> ORGANISM: Artificial Sequence
<220> FEATURE:
<223> OTHER INFORMATION: >VL

<400> SEQUENCE: 126

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 127
<211> LENGTH: 126
<212> TYPE: PRT
<213> ORGANISM: Artificial Sequence
<220> FEATURE:
<223> OTHER INFORMATION: Ab46 (INX443)

<400> SEQUENCE: 127

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60
```

```
Ser Arg Val Thr Ile Ser Arg Asp Thr Ser Lys Asn Gln Val Ser Leu
65              70              75              80

Lys Leu Ser Ser Val Thr Ala Ala Asp Thr Ala Val Tyr Tyr Cys Ala
            85              90              95

Arg Asn Ser Trp Tyr His Gly Thr Tyr Phe Ser Pro Gly Tyr Tyr Leu
            100             105             110

Met Asp Ala Trp Gly Gln Gly Thr Leu Val Thr Val Ser Ser
        115             120             125
```

<210> SEQ ID NO 128
<211> LENGTH: 107
<212> TYPE: PRT
<213> ORGANISM: Artificial Sequence
<220> FEATURE:
<223> OTHER INFORMATION: >VL

<400> SEQUENCE: 128

```
Asp Ile Gln Leu Thr Gln Ser Pro Ser Ala Met Ser Ala Ser Val Gly
1               5               10              15

Asp Arg Val Thr Ile Thr Cys Arg Ala Ser Gln Gly Ile Ser Asn Tyr
            20              25              30

Leu Ala Trp Tyr Gln Gln Lys Pro Gly Lys Ala Pro Lys Leu Leu Ile
        35              40              45

Tyr Ala Ala Ser Thr Leu Gln Ser Gly Val Ala Ser Arg Phe Ser Gly
    50              55              60

Arg Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Asp Ile Leu Pro Tyr
            85              90              95

Thr Phe Gly Gln Gly Thr Lys Val Glu Ile Lys
            100             105
```

<210> SEQ ID NO 129
<211> LENGTH: 126
<212> TYPE: PRT
<213> ORGANISM: Artificial Sequence
<220> FEATURE:
<223> OTHER INFORMATION: Ab47 (INX444)

<400> SEQUENCE: 129

```
Gln Val Gln Leu Lys Glu Ser Gly Pro Gly Leu Val Lys Pro Ser Gln
1               5               10              15

Thr Leu Ser Leu Thr Cys Thr Val Ser Gly Phe Ser Leu Thr Asn Tyr
            20              25              30

His Leu Gln Trp Val Arg Gln Pro Pro Gly Lys Gly Leu Glu Trp Ile
        35              40              45

Gly Phe Ile Arg Ser Ser Gly Asn Thr Glu Tyr Asn Pro Ser Leu Lys
    50              55              60

Ser Arg Val Thr Ile Ser Arg Asp Thr Ser Lys Asn Gln Val Ser Leu
65              70              75              80

Lys Leu Ser Ser Val Thr Ala Ala Asp Thr Ala Val Tyr Tyr Cys Ala
            85              90              95

Arg Lys Arg Trp Val His Gly Thr Trp Tyr Ser Pro Gly Tyr Tyr Val
            100             105             110

Met Asp Ala Trp Gly Gln Gly Thr Leu Val Thr Val Ser Ser
        115             120             125
```

<210> SEQ ID NO 130

-continued

<211> LENGTH: 107
<212> TYPE: PRT
<213> ORGANISM: Artificial Sequence
<220> FEATURE:
<223> OTHER INFORMATION: >VL

<400> SEQUENCE: 130

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Ala Ser Arg Phe Ser Gly
        50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 131
<211> LENGTH: 126
<212> TYPE: PRT
<213> ORGANISM: Artificial Sequence
<220> FEATURE:
<223> OTHER INFORMATION: Ab48 (INX445)

<400> SEQUENCE: 131

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
                20                  25                  30

His Leu Gln Trp Val Arg Gln Pro Pro Gly Lys Gly Leu Glu Trp Ile
            35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Met His Gly Thr Trp Tyr Ser Pro Gly Tyr Tyr Val
                100                 105                 110

Met Asp Ala Trp Gly Gln Gly Thr Leu Val Thr Val Ser Ser
            115                 120                 125

<210> SEQ ID NO 132
<211> LENGTH: 107
<212> TYPE: PRT
<213> ORGANISM: Artificial Sequence
<220> FEATURE:
<223> OTHER INFORMATION: >VL

<400> SEQUENCE: 132

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
                20                  25                  30

-continued

```
Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
        50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105
```

<210> SEQ ID NO 133
<211> LENGTH: 126
<212> TYPE: PRT
<213> ORGANISM: Artificial Sequence
<220> FEATURE:
<223> OTHER INFORMATION: Ab49 (INX446)

<400> SEQUENCE: 133

```
Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
        20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Trp Val His Gly Thr Tyr Tyr Ser Pro Gly Tyr Tyr Val
            100                 105                 110

Met Asp Ala Trp Gly Gln Gly Thr Leu Val Thr Val Ser Ser
        115                 120                 125
```

<210> SEQ ID NO 134
<211> LENGTH: 107
<212> TYPE: PRT
<213> ORGANISM: Artificial Sequence
<220> FEATURE:
<223> OTHER INFORMATION: >VL

<400> SEQUENCE: 134

```
Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
        20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
        50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105
```

-continued

```
<210> SEQ ID NO 135
<211> LENGTH: 126
<212> TYPE: PRT
<213> ORGANISM: Artificial Sequence
<220> FEATURE:
<223> OTHER INFORMATION: Ab50 (INX447)

<400> SEQUENCE: 135

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val Gln Gly Thr Tyr Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 136
<211> LENGTH: 107
<212> TYPE: PRT
<213> ORGANISM: Artificial Sequence
<220> FEATURE:
<223> OTHER INFORMATION: >VL

<400> SEQUENCE: 136

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 137
<211> LENGTH: 126
<212> TYPE: PRT
<213> ORGANISM: Artificial Sequence
<220> FEATURE:
<223> OTHER INFORMATION: Ab51 (INX448)

<400> SEQUENCE: 137

Gln Val Gln Leu Lys Glu Ser Gly Pro Gly Leu Val Lys Pro Ser Gln
1               5                   10                  15
```

-continued

```
Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val His Gly Thr Trp Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 138
<211> LENGTH: 107
<212> TYPE: PRT
<213> ORGANISM: Artificial Sequence
<220> FEATURE:
<223> OTHER INFORMATION: >VL

<400> SEQUENCE: 138

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 139
<211> LENGTH: 126
<212> TYPE: PRT
<213> ORGANISM: Artificial Sequence
<220> FEATURE:
<223> OTHER INFORMATION: Ab52 (INX449)

<400> SEQUENCE: 139

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95
```

-continued

Arg Asn Arg Trp Val Gln Gly Ser Tyr Tyr Ser Pro Gly Tyr Tyr Val
            100                 105                 110

Met Asp Ala Trp Gly Gln Gly Thr Met Val Thr Val Ser Ser
        115                 120                 125

<210> SEQ ID NO 140
<211> LENGTH: 107
<212> TYPE: PRT
<213> ORGANISM: Artificial Sequence
<220> FEATURE:
<223> OTHER INFORMATION: >VL

<400> SEQUENCE: 140

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 141
<211> LENGTH: 126
<212> TYPE: PRT
<213> ORGANISM: Artificial Sequence
<220> FEATURE:
<223> OTHER INFORMATION: Ab53 (INX450)

<400> SEQUENCE: 141

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Phe Val His Gly Thr Trp Tyr Ser Pro Gly Tyr Tyr Leu
            100                 105                 110

Met Asp Ala Trp Gly Gln Gly Thr Leu Val Thr Val Ser Ser
        115                 120                 125

<210> SEQ ID NO 142
<211> LENGTH: 107
<212> TYPE: PRT
<213> ORGANISM: Artificial Sequence
<220> FEATURE:
<223> OTHER INFORMATION: >VL

<400> SEQUENCE: 142

```
Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105
```

<210> SEQ ID NO 143
<211> LENGTH: 126
<212> TYPE: PRT
<213> ORGANISM: Artificial Sequence
<220> FEATURE:
<223> OTHER INFORMATION: Ab54 (INX451)

<400> SEQUENCE: 143

```
Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Ile His Gly Thr Trp Tyr Ser Pro Gly Tyr Tyr Leu
            100                 105                 110

Met Asp Ala Trp Gly Gln Gly Thr Leu Val Thr Val Ser Ser
        115                 120                 125
```

<210> SEQ ID NO 144
<211> LENGTH: 107
<212> TYPE: PRT
<213> ORGANISM: Artificial Sequence
<220> FEATURE:
<223> OTHER INFORMATION: >VL

<400> SEQUENCE: 144

```
Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60
```

-continued

```
Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 145
<211> LENGTH: 126
<212> TYPE: PRT
<213> ORGANISM: Artificial Sequence
<220> FEATURE:
<223> OTHER INFORMATION: Ab55 (INX452)

<400> SEQUENCE: 145

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
                20                  25                  30

His Leu Gln Trp Ile Arg Gln Pro Pro Gly Lys Gly Leu Glu Trp Ile
            35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val His Gly Thr Trp Tyr Ser Pro Gly Tyr Tyr Leu
            100                 105                 110

Met Asp Ala Trp Gly Gln Gly Thr Met Val Thr Val Ser Ser
            115                 120                 125

<210> SEQ ID NO 146
<211> LENGTH: 107
<212> TYPE: PRT
<213> ORGANISM: Artificial Sequence
<220> FEATURE:
<223> OTHER INFORMATION: >VL

<400> SEQUENCE: 146

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Ala Ser Arg Phe Ser Gly
        50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 147
<211> LENGTH: 126
<212> TYPE: PRT
```

```
<213> ORGANISM: Artificial Sequence
<220> FEATURE:
<223> OTHER INFORMATION: Ab56 (INX453)

<400> SEQUENCE: 147

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Arg Trp Val Gln Gly Trp Trp Tyr Ser Pro Gly Tyr Tyr Leu
            100                 105                 110

Met Asp Ala Trp Gly Gln Gly Thr Met Val Thr Val Ser Ser
        115                 120                 125

<210> SEQ ID NO 148
<211> LENGTH: 107
<212> TYPE: PRT
<213> ORGANISM: Artificial Sequence
<220> FEATURE:
<223> OTHER INFORMATION: >VL

<400> SEQUENCE: 148

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
            85                  90                  95

Thr Phe Gly Gln Gly Thr Lys Val Glu Ile Lys
        100                 105

<210> SEQ ID NO 149
<211> LENGTH: 126
<212> TYPE: PRT
<213> ORGANISM: Artificial Sequence
<220> FEATURE:
<223> OTHER INFORMATION: Ab57 (INX454)

<400> SEQUENCE: 149

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45
```

```
Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Met His Gly Thr Trp Tyr Ser Pro Gly Tyr Tyr Leu
                100                 105                 110

Met Asp Ala Trp Gly Gln Gly Thr Leu Val Thr Val Ser Ser
            115                 120                 125
```

```
<210> SEQ ID NO 150
<211> LENGTH: 107
<212> TYPE: PRT
<213> ORGANISM: Artificial Sequence
<220> FEATURE:
<223> OTHER INFORMATION: >VL

<400> SEQUENCE: 150
```

```
Asp Ile Gln Leu Thr Gln Ser Pro Ser Ala Met Ser Ala Ser Val Gly
1                   5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105
```

```
<210> SEQ ID NO 151
<211> LENGTH: 126
<212> TYPE: PRT
<213> ORGANISM: Artificial Sequence
<220> FEATURE:
<223> OTHER INFORMATION: Ab58 (INX455)

<400> SEQUENCE: 151
```

```
Gln Val Gln Leu Lys Glu Ser Gly Pro Gly Leu Val Lys Pro Ser Gln
1                   5                   10                  15

Thr Leu Ser Leu Thr Cys Thr Val Ser Gly Phe Ser Leu Thr Asn Tyr
                20                  25                  30

His Leu Gln Trp Val Arg Gln Pro Pro Gly Lys Gly Leu Glu Trp Ile
            35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg Trp Val His Gly Thr Tyr Phe Ser Pro Gly Tyr Tyr Leu
                100                 105                 110

Met Asp Ala Trp Gly Gln Gly Thr Leu Val Thr Val Ser Ser
```

-continued

```
              115                  120                  125
```

```
<210> SEQ ID NO 152
<211> LENGTH: 107
<212> TYPE: PRT
<213> ORGANISM: Artificial Sequence
<220> FEATURE:
<223> OTHER INFORMATION: >VL

<400> SEQUENCE: 152

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105

<210> SEQ ID NO 153
<211> LENGTH: 126
<212> TYPE: PRT
<213> ORGANISM: Artificial Sequence
<220> FEATURE:
<223> OTHER INFORMATION: Ab59 (INX456)

<400> SEQUENCE: 153

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val His Gly Thr Trp Tyr Ser Pro Gly Tyr Tyr Leu
            100                 105                 110

Met Asp Ala Trp Gly Gln Gly Thr Leu Val Thr Val Ser Ser
        115                 120                 125

<210> SEQ ID NO 154
<211> LENGTH: 107
<212> TYPE: PRT
<213> ORGANISM: Artificial Sequence
<220> FEATURE:
<223> OTHER INFORMATION: >VL

<400> SEQUENCE: 154

Asp Ile Gln Leu Thr Gln Ser Pro Ser Ala Met Ser Ala Ser Val Gly
1               5                   10                  15
```

-continued

```
Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
                85                  90                  95

Thr Phe Gly Gln Gly Thr Lys Val Glu Ile Lys
            100                 105
```

```
<210> SEQ ID NO 155
<211> LENGTH: 126
<212> TYPE: PRT
<213> ORGANISM: Artificial Sequence
<220> FEATURE:
<223> OTHER INFORMATION: Ab60 (INX457)

<400> SEQUENCE: 155

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Arg Trp Val Gln Gly Ser Tyr Tyr Ser Pro Gly Tyr Tyr Leu
            100                 105                 110

Met Asp Ala Trp Gly Gln Gly Thr Met Val Thr Val Ser Ser
        115                 120                 125
```

```
<210> SEQ ID NO 156
<211> LENGTH: 107
<212> TYPE: PRT
<213> ORGANISM: Artificial Sequence
<220> FEATURE:
<223> OTHER INFORMATION: >VL

<400> SEQUENCE: 156

Asp Ile Gln Leu Thr Gln Ser Pro Ser Ala Met Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Ala Ser Arg Phe Ser Gly
    50                  55                  60

Arg Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ile Leu Pro Tyr
```

```
                  85              90              95
Thr Phe Gly Gln Gly Thr Lys Val Glu Ile Lys
            100             105

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161
<211> LENGTH: 7
<212> TYPE: PRT
<213> ORGANISM: Artificial Sequence
<220> FEATURE:
<223> OTHER INFORMATION: Ab61 (MCT1 3303 A07 or LM-183) - CDR1-HC

<400> SEQUENCE: 161

Gly Phe Asp Phe Ser Asn Tyr
1               5

<210> SEQ ID NO 162
<211> LENGTH: 6
<212> TYPE: PRT
<213> ORGANISM: Artificial Sequence
<220> FEATURE:
<223> OTHER INFORMATION: CDR2-HC

<400> SEQUENCE: 162

Gly Asp Ser Ala Ser Tyr
1               5

<210> SEQ ID NO 163
<211> LENGTH: 16
<212> TYPE: PRT
<213> ORGANISM: Artificial Sequence
<220> FEATURE:
<223> OTHER INFORMATION: CDR3-HC

<400> SEQUENCE: 163

Ala Ser Glu Gly Ser Tyr Trp Tyr Tyr Glu Ala Gly Gly Ile Asp Thr
1               5               10              15

<210> SEQ ID NO 164
<211> LENGTH: 125
<212> TYPE: PRT
<213> ORGANISM: Artificial Sequence
<220> FEATURE:
<223> OTHER INFORMATION: HC Protein
```

<400> SEQUENCE: 164

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Asn Tyr
            20                  25                  30

Glu Met Leu Trp Val Arg Gln Ala Pro Gly Lys Gly Leu Glu Tyr Val
        35                  40                  45

Ala Gly Ile Gly Asp Ser Ala Ser Tyr Ser Ala Tyr Gly Val Ala Val
        50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125

<210> SEQ ID NO 165
<211> LENGTH: 384
<212> TYPE: DNA
<213> ORGANISM: Artificial Sequence
<220> FEATURE:
<223> OTHER INFORMATION: HC DNA

<400> SEQUENCE: 165
acgaattcgg ccgtgacgtt ggacgagtcc gggggcggcc tccagacgcc cggaggaacg      60
ctcagcctcg tctgcaaggc ctccgggttc gacttcagca actacgaaat gctctgggtg     120
cgacaggcgc ccggcaaggg gctggaatac gtcgctggta ttggcgacag tgctagttac     180
tcagcatacg gggtggcggt gaagggccgt gccaccatct cgaggacaa cgggcagagc      240 acactgaggc tgcagctgaa cggcctcagg gctgaggaca ccggcaccta ctactgcacc     300
aaagcttccg agggttccta ctggtattat gaagctggtg gtatcgacac atggggccac     360
gggaccgaag tcatcgtctc ctcg                                            384

<210> SEQ ID NO 166
<211> LENGTH: 8
<212> TYPE: PRT
<213> ORGANISM: Artificial Sequence
<220> FEATURE:
<223> OTHER INFORMATION: CDR1-LC

<400> SEQUENCE: 166

Ser Gly Gly Gly Gly Ser Tyr Gly
1               5

<210> SEQ ID NO 167
<211> LENGTH: 7
<212> TYPE: PRT
<213> ORGANISM: Artificial Sequence
<220> FEATURE:
<223> OTHER INFORMATION: CDR2-LC

<400> SEQUENCE: 167

Asp Asn Asp Lys Arg Pro Ser
1               5

<210> SEQ ID NO 168

```
<211> LENGTH: 8
<212> TYPE: PRT
<213> ORGANISM: Artificial Sequence
<220> FEATURE:
<223> OTHER INFORMATION: CDR3-LC

<400> SEQUENCE: 168

Gly Ser Ala Gly Asn Ser Gly Ala
1               5

<210> SEQ ID NO 169
<211> LENGTH: 101
<212> TYPE: PRT
<213> ORGANISM: Artificial Sequence
<220> FEATURE:
<223> OTHER INFORMATION: LC Protein

<400> SEQUENCE: 169

Ala Leu Thr Gln Pro Ser Ser Val Ser Ala Asn Leu Gly Gly Thr Val
1               5                   10                  15

Lys Ile Thr Cys Ser Gly Gly Gly Gly Ser Tyr Gly Trp Tyr Gln Gln
            20                  25                  30

Lys Ser Pro Gly Ser Ala Pro Val Thr Val Ile Tyr Asp Asn Asp Lys
        35                  40                  45

Arg Pro Ser Asp Ile Pro Ser Arg Phe Ser Gly Ser Lys Ser Gly Ser
    50                  55                  60

Thr Ala Thr Leu Thr Ile Thr Gly Val Arg Ala Glu Asp Glu Ala Val
65                  70                  75                  80

Tyr Tyr Cys Gly Ser Ala Gly Asn Ser Gly Ala Phe Gly Ala Gly Thr
                85                  90                  95

Thr Leu Thr Val Leu
            100

<210> SEQ ID NO 170
<211> LENGTH: 303
<212> TYPE: DNA
<213> ORGANISM: Artificial Sequence
<220> FEATURE:
<223> OTHER INFORMATION: LC DNA

<400> SEQUENCE: 170
gccctgactc agccgtcctc ggtgtcagca aacctgggag gaaccgtcaa gatcacctgc      60
tccgggggtg gtggcagcta tggctggtat cagcagaagt cacctggcag tgcccctgtc     120
actgtgatct atgacaacga caagagaccc tcggacatcc cttcacgatt ctccggttcc     180
aagtccggct ccacagccac attaaccatc actggggttc gagccgagga cgaggctgtc     240
tattactgtg gcagtgcagg caatagtggt gcatttgggg ccgggacaac cctgaccgtc     300
ctt                                                                   303

<210> SEQ ID NO 171
<211> LENGTH: 7
<212> TYPE: PRT
<213> ORGANISM: Artificial Sequence
<220> FEATURE:
<223> OTHER INFORMATION: Ab62 (LM-185 or MCT1 3303 B04-1) - CDR1-HC

<400> SEQUENCE: 171

Gly Phe Asp Phe Ser Asn Tyr
1               5

<210> SEQ ID NO 172
```

-continued

```
<211> LENGTH: 6
<212> TYPE: PRT
<213> ORGANISM: Artificial Sequence
<220> FEATURE:
<223> OTHER INFORMATION: CDR2-HC

<400> SEQUENCE: 172

Gly Asp Ser Ala Ser Tyr
1               5

<210> SEQ ID NO 173
<211> LENGTH: 16
<212> TYPE: PRT
<213> ORGANISM: Artificial Sequence
<220> FEATURE:
<223> OTHER INFORMATION: CDR3-HC

<400> SEQUENCE: 173

Ala Ser Glu Gly Ser Tyr Trp Tyr Tyr Glu Ala Gly Gly Ile Asp Thr
1               5                  10                  15

<210> SEQ ID NO 174
<211> LENGTH: 125
<212> TYPE: PRT
<213> ORGANISM: Artificial Sequence
<220> FEATURE:
<223> OTHER INFORMATION: HC Protein

<400> SEQUENCE: 174

Ala Val Thr Leu Asp Glu Ser Gly Gly Gly Leu Gln Thr Pro Gly Gly
1               5                  10                  15

Thr Leu Ser Leu Val Cys Lys Ala Ser Gly Phe Asp Phe Ser Asn Tyr
            20                  25                  30

Glu Met Leu Trp Val Arg Gln Ala Pro Gly Lys Gly Leu Glu Tyr Val
        35                  40                  45

Ala Gly Ile Gly Asp Ser Ala Ser Tyr Ser Ala Tyr Gly Val Ala Val
    50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125

<210> SEQ ID NO 175
<211> LENGTH: 384
<212> TYPE: DNA
<213> ORGANISM: Artificial Sequence
<220> FEATURE:
<223> OTHER INFORMATION: HC DNA

<400> SEQUENCE: 175
acgaattcgg ccgtgacgtt ggacgagtcc gggggcggcc tccagacgcc cggaggaacg      60
ctcagcctcg tctgcaaggc ctccgggttc gacttcagca actacgaaat gctctgggtg     120
cgacaggcgc ccggcaaggg gctggaatac gtcgctggta ttggcgacag tgctagttac     180
tcagcatacg gggtggcggt gaagggccgt gccaccatct cgaggacaa cgggcagagc      240 acactgaggc tgcagctgaa cggcctcagg gctgaggaca ccggcaccta ctactgcacc     300
aaagcttccg agggttccta ctggtattat gaagctggtg gtatcgacac atggggccac     360
```

-continued gggaccgaag tcatcgtctc ctcg                                            384

<210> SEQ ID NO 176
<211> LENGTH: 7
<212> TYPE: PRT
<213> ORGANISM: Artificial Sequence
<220> FEATURE:
<223> OTHER INFORMATION: CDR1-LC

<400> SEQUENCE: 176

Ser Gly Gly Ser Ser Tyr Gly
1               5

<210> SEQ ID NO 177
<211> LENGTH: 7
<212> TYPE: PRT
<213> ORGANISM: Artificial Sequence
<220> FEATURE:
<223> OTHER INFORMATION: CDR2-LC

<400> SEQUENCE: 177

Tyr Asn Asp Lys Arg Pro Ser
1               5

<210> SEQ ID NO 178
<211> LENGTH: 10
<212> TYPE: PRT
<213> ORGANISM: Artificial Sequence
<220> FEATURE:
<223> OTHER INFORMATION: CDR3-LC

<400> SEQUENCE: 178

Gly Ser Arg Asp Ser Ser Gly Ala Asp Leu
1               5               10

<210> SEQ ID NO 179
<211> LENGTH: 102
<212> TYPE: PRT
<213> ORGANISM: Artificial Sequence
<220> FEATURE:
<223> OTHER INFORMATION: LC Protein

<400> SEQUENCE: 179

Ala Leu Thr Gln Pro Ser Ser Val Ser Ala Asn Leu Gly Gly Thr Val
1               5                   10                  15

Lys Ile Thr Cys Ser Gly Gly Ser Ser Tyr Gly Trp Phe Gln Gln Lys
            20                  25                  30

Ser Pro Gly Ser Ala Leu Val Thr Leu Ile Tyr Tyr Asn Asp Lys Arg
        35                  40                  45

Pro Ser Asn Ile Pro Ser Arg Phe Ser Gly Ser Lys Ser Gly Ser Thr
    50                  55                  60

Gly Ile Leu Thr Ile Ser Gly Val Gln Ala Glu Asp Glu Ala Val Tyr
65                  70                  75                  80

Tyr Cys Gly Ser Arg Asp Ser Ser Gly Ala Asp Leu Phe Gly Ala Gly
                85                  90                  95

Thr Thr Leu Thr Val Leu
            100

<210> SEQ ID NO 180
<211> LENGTH: 306
<212> TYPE: DNA
<213> ORGANISM: Artificial Sequence
<220> FEATURE:

<223> OTHER INFORMATION: LC DNA

<400> SEQUENCE: 180

```
gccctgactc agccgtcctc ggtgtcagca aacctgggag gaaccgtcaa gatcacctgc        60 tccggggggca gcagttatgg ctggttccag cagaagtctc ctggcagtgc ccttgtcact       120
ctgatctatt acaacgacaa gagaccctcg aacatccctt cacgattctc cggttccaaa       180
tccggctcca cgggcatttt gaccatctct ggggtccaag ccgaggacga ggctgtctat       240
tactgtggga gcaggacag cagtggtgct gatctatttg gggccgggac aaccctgacc       300
gtcctt                                                                   306
```

<210> SEQ ID NO 181
<211> LENGTH: 7
<212> TYPE: PRT
<213> ORGANISM: Artificial Sequence
<220> FEATURE:
<223> OTHER INFORMATION: Ab63 (LM-186 or MCT1 3308 B04-2) - CDR1-HC

<400> SEQUENCE: 181

```
Gly Phe Ser Phe Ser Ser Arg
1               5
```

<210> SEQ ID NO 182
<211> LENGTH: 7
<212> TYPE: PRT
<213> ORGANISM: Artificial Sequence
<220> FEATURE:
<223> OTHER INFORMATION: CDR2-HC

<400> SEQUENCE: 182

```
Asp Asn Asp Gly Gly Tyr Pro
1               5
```

<210> SEQ ID NO 183
<211> LENGTH: 15
<212> TYPE: PRT
<213> ORGANISM: Artificial Sequence
<220> FEATURE:
<223> OTHER INFORMATION: CDR3-HC

<400> SEQUENCE: 183

```
Gly Ala Tyr Gly Gly Gly Trp Tyr Ala Ala Ser Ser Ile Asp Ala
1               5                   10                  15
```

<210> SEQ ID NO 184
<211> LENGTH: 124
<212> TYPE: PRT
<213> ORGANISM: Artificial Sequence
<220> FEATURE:
<223> OTHER INFORMATION: HC Protein

<400> SEQUENCE: 184

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Ser Phe Ser Ser Arg
            20                  25                  30

Gly Met Phe Trp Val Arg Gln Ala Pro Gly Lys Gly Leu Glu Tyr Val
        35                  40                  45

Ala Gly Ile Asp Asn Asp Gly Gly Tyr Pro Asn Tyr Gly Ser Ala Val
    50                  55                  60

Lys Gly Arg Ala Thr Ile Ser Arg Asp Asn Arg Gln Ser Thr Val Arg
65                  70                  75                  80
```

```
Leu Gln Leu Asn Asn Leu Arg Ala Asp Asp Thr Gly Thr Tyr Tyr Cys
            85                  90                  95

Ala Lys Gly Ala Tyr Gly Gly Gly Trp Tyr Ala Ala Ser Ser Ile Asp
            100                 105                 110

Ala Trp Gly His Gly Thr Glu Val Ile Val Ser Ser
        115                 120
```

```
<210> SEQ ID NO 185
<211> LENGTH: 384
<212> TYPE: DNA
<213> ORGANISM: Artificial Sequence
<220> FEATURE:
<223> OTHER INFORMATION: HC DNA

<400> SEQUENCE: 185
gtcacgaatt cggccgtgac gttggacgag tccgggggcg gcctccagac gcccggagga        60
gggctcagcc tcgtctgcaa ggcctccggg ttctccttca gcagccgggg catgttctgg       120
gtgcgacagg cacctggcaa ggggctggaa tacgttgcgg gtattgataa tgatggtggt       180
tacccaaact acgggtcggc ggtgaagggc cgtgccacca tctcgaggga caacaggcag       240
agcacagtga ggctgcagct gaacaacctc agggctgacg acaccggcac ctactactgc       300
gccaagggtg cttatggtgg tggttggtat gccgctagta gcatcgacgc atggggccac       360
gggaccgaag tcatcgtctc ctcg                                              384
```

```
<210> SEQ ID NO 186
<211> LENGTH: 9
<212> TYPE: PRT
<213> ORGANISM: Artificial Sequence
<220> FEATURE:
<223> OTHER INFORMATION: CDR1-LC

<400> SEQUENCE: 186

Ser Gly Gly Val Gly Gln Trp Tyr Gly
1               5
```

```
<210> SEQ ID NO 187
<211> LENGTH: 7
<212> TYPE: PRT
<213> ORGANISM: Artificial Sequence
<220> FEATURE:
<223> OTHER INFORMATION: CDR2-LC

<400> SEQUENCE: 187

Asp Asn Thr Asn Arg Pro Ser
1               5
```

```
<210> SEQ ID NO 188
<211> LENGTH: 11
<212> TYPE: PRT
<213> ORGANISM: Artificial Sequence
<220> FEATURE:
<223> OTHER INFORMATION: CDR3-LC

<400> SEQUENCE: 188

Ala Asn Thr Tyr Ser Asp Gly Asn Asp Ala Pro
1               5                   10
```

```
<210> SEQ ID NO 189
<211> LENGTH: 105
<212> TYPE: PRT
<213> ORGANISM: Artificial Sequence
<220> FEATURE:
```

```
<223> OTHER INFORMATION: LC Protein

<400> SEQUENCE: 189

Ala Leu Thr Gln Pro Ser Ser Val Ser Ala Asn Pro Gly Glu Ala Val
1               5                   10                  15

Lys Ile Thr Cys Ser Gly Gly Val Gly Gln Trp Tyr Gly Trp Phe Gln
                20                  25                  30

Gln Lys Ala Pro Gly Ser Ala Pro Val Thr Val Ile His Asp Asn Thr
        35                  40                  45

Asn Arg Pro Ser Asp Ile Pro Ser Arg Phe Ser Gly Ser Lys Ser Gly
    50                  55                  60

Ser Thr Gly Thr Leu Thr Ile Thr Gly Val Gln Ala Glu Asp Glu Ala
65                  70                  75                  80

Val Tyr Phe Cys Ala Asn Thr Tyr Ser Asp Gly Asn Asp Ala Pro Phe
                85                  90                  95

Gly Ala Gly Thr Thr Leu Thr Val Leu
            100                 105

<210> SEQ ID NO 190
<211> LENGTH: 315
<212> TYPE: DNA
<213> ORGANISM: Artificial Sequence
<220> FEATURE:
<223> OTHER INFORMATION: LC DNA

<400> SEQUENCE: 190
gccctgactc agccgtcctc ggtgtcagca aacccgggag aagccgtcaa gatcacctgc      60
agtggaggtg tcggccagtg gtatggctgg ttccagcaga aggcacctgg cagtgcccct     120
gtcactgtga tccatgacaa caccaacaga ccctcggaca tcccttcacg attctccggt     180
tccaaatccg gctccacggg cacattaacc atcactgggg tccaagccga ggacgaggct     240
gtctatttct gtgcgaatac atacagcgac ggtaatgatg ctccatttgg ggccgggaca     300
accctgaccg tcctt                                                      315

<210> SEQ ID NO 191
<211> LENGTH: 7
<212> TYPE: PRT
<213> ORGANISM: Artificial Sequence
<220> FEATURE:
<223> OTHER INFORMATION: Ab64  (LM-188 or MCT1 3308 E08) - CDR1-HC

<400> SEQUENCE: 191

Gly Phe Thr Phe Ser Ser Arg
1               5

<210> SEQ ID NO 192
<211> LENGTH: 7
<212> TYPE: PRT
<213> ORGANISM: Artificial Sequence
<220> FEATURE:
<223> OTHER INFORMATION: CDR2-HC

<400> SEQUENCE: 192

Asp Asn Asp Gly Gly Tyr Pro
1               5

<210> SEQ ID NO 193
<211> LENGTH: 15
<212> TYPE: PRT
<213> ORGANISM: Artificial Sequence
<220> FEATURE:
```

-continued

<223> OTHER INFORMATION: CDR3-HC

<400> SEQUENCE: 193

```
Gly Ala Tyr Gly Gly Gly Trp Tyr Ala Ala Ser Ser Ile Asp Ala
1               5                   10                  15
```

<210> SEQ ID NO 194
<211> LENGTH: 124
<212> TYPE: PRT
<213> ORGANISM: Artificial Sequence
<220> FEATURE:
<223> OTHER INFORMATION: HC Protein

<400> SEQUENCE: 194

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Thr Phe Ser Ser Arg
            20                  25                  30

Gly Met Phe Trp Val Arg Arg Ala Pro Gly Lys Gly Leu Glu Tyr Val
        35                  40                  45

Ala Gly Ile Asp Asn Asp Gly Gly Tyr Pro Asn Tyr Gly Ser Ala Val
    50                  55                  60

Lys Gly Arg Ala Thr Ile Ser Arg Asp Asn Arg Gln Ser Thr Val Arg
65                  70                  75                  80

Leu Gln Leu Asn Asn Leu Arg Ala Asp Asp Thr Gly Thr Tyr Tyr Cys
                85                  90                  95

Ala Lys Gly Ala Tyr Gly Gly Gly Trp Tyr Ala Ala Ser Ser Ile Asp
            100                 105                 110

Ala Trp Gly His Gly Thr Glu Val Ile Val Ser Ser
        115                 120
```

<210> SEQ ID NO 195
<211> LENGTH: 384
<212> TYPE: DNA
<213> ORGANISM: Artificial Sequence
<220> FEATURE:
<223> OTHER INFORMATION: HC DNA

<400> SEQUENCE: 195

```
gtcacgaatt cggccgtgac gttggacgag tccggggggcg gcctccagac gcccggagga      60
gggctcagcc tcgtctgcaa ggcctccggg ttcaccttca gcagccgggg catgttctgg     120
gtgcgacggg cacctggcaa ggggctggaa tacgttgcgg gtattgataa tgatggtggt     180
tacccaaact acgggtcggc ggtgaagggc cgtgccacca tctcgaggga caacaggcag     240
agcacagtga ggctgcagct gaacaacctc agggctgacg acaccggcac ctactactgc     300
gccaagggtg cttatggtgg tggttggtat gccgctagta gcatcgacgc atggggccac     360
gggaccgaag tcatcgtctc ctcg                                            384
```

<210> SEQ ID NO 196
<211> LENGTH: 9
<212> TYPE: PRT
<213> ORGANISM: Artificial Sequence
<220> FEATURE:
<223> OTHER INFORMATION: CDR1-LC

<400> SEQUENCE: 196

```
Ser Gly Gly Val Gly Gln Trp Tyr Gly
1               5
```

-continued

```
<210> SEQ ID NO 197
<211> LENGTH: 7
<212> TYPE: PRT
<213> ORGANISM: Artificial Sequence
<220> FEATURE:
<223> OTHER INFORMATION: CDR2-LC

<400> SEQUENCE: 197

Asp Asn Thr Asn Arg Pro Ser
1               5

<210> SEQ ID NO 198
<211> LENGTH: 11
<212> TYPE: PRT
<213> ORGANISM: Artificial Sequence
<220> FEATURE:
<223> OTHER INFORMATION: CDR3-LC

<400> SEQUENCE: 198

Ala Asn Thr Tyr Ser Asp Gly Asn Asp Ala Pro
1               5                   10

<210> SEQ ID NO 199
<211> LENGTH: 105
<212> TYPE: PRT
<213> ORGANISM: Artificial Sequence
<220> FEATURE:
<223> OTHER INFORMATION: LC Protein

<400> SEQUENCE: 199

Ala Leu Thr Gln Pro Ser Ser Val Ser Ala Asn Pro Gly Glu Ala Val
1               5                   10                  15

Lys Ile Thr Cys Ser Gly Gly Val Gly Gln Trp Tyr Gly Trp Phe Gln
            20                  25                  30

Gln Lys Ala Pro Gly Ser Ala Pro Val Thr Val Ile Tyr Asp Asn Thr
        35                  40                  45

Asn Arg Pro Ser Asp Ile Pro Ser Arg Phe Ser Gly Ser Lys Ser Gly
    50                  55                  60

Ser Thr Gly Thr Leu Thr Ile Thr Gly Val Gln Ala Glu Asp Glu Ala
65                  70                  75                  80

Val Tyr Phe Cys Ala Asn Thr Tyr Ser Asp Gly Asn Asp Ala Pro Phe
                85                  90                  95

Gly Ala Gly Thr Thr Leu Thr Val Leu
            100                 105

<210> SEQ ID NO 200
<211> LENGTH: 315
<212> TYPE: DNA
<213> ORGANISM: Artificial Sequence
<220> FEATURE:
<223> OTHER INFORMATION: LC DNA

<400> SEQUENCE: 200
gccctgactc agccgtcctc ggtgtcagca aacccgggag aagccgtcaa gatcacctgc      60
agtggaggtg tcggccagtg gtatggctgg ttccagcaga aggcacctgg cagtgcccct     120
gtcactgtga tctatgacaa caccaacaga ccctcggaca tcccttcacg attctccggt     180
tccaaatccg gctccacggg cacattaacc atcactgggg tccaagccga ggacgaggct     240
gtctatttct gtgcgaatac atacagcgac ggtaatgatg ctccatttgg ggccgggaca     300
accctgaccg tcctt                                                     315
```

-continued

```
<210> SEQ ID NO 201
<211> LENGTH: 7
<212> TYPE: PRT
<213> ORGANISM: Artificial Sequence
<220> FEATURE:
<223> OTHER INFORMATION: Ab65 (LM-189 or MCT1 3308 G12) - CDR1-HC

<400> SEQUENCE: 201

Gly Phe Ser Phe Ser Ser Arg
1               5

<210> SEQ ID NO 202
<211> LENGTH: 7
<212> TYPE: PRT
<213> ORGANISM: Artificial Sequence
<220> FEATURE:
<223> OTHER INFORMATION: CDR2-HC

<400> SEQUENCE: 202

Asp Asn Asp Gly Gly Tyr Pro
1               5

<210> SEQ ID NO 203
<211> LENGTH: 15
<212> TYPE: PRT
<213> ORGANISM: Artificial Sequence
<220> FEATURE:
<223> OTHER INFORMATION: CDR3-HC

<400> SEQUENCE: 203

Gly Ala Tyr Gly Gly Gly Trp Tyr Ala Ala Ser Ser Ile Asp Ala
1               5                   10                  15

<210> SEQ ID NO 204
<211> LENGTH: 124
<212> TYPE: PRT
<213> ORGANISM: Artificial Sequence
<220> FEATURE:
<223> OTHER INFORMATION: HC Protein

<400> SEQUENCE: 204

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Ser Phe Ser Ser Arg
                20                  25                  30

Gly Met Phe Trp Val Arg Gln Ala Pro Gly Lys Gly Leu Glu Tyr Val
            35                  40                  45

Ala Gly Ile Asp Asn Asp Gly Gly Tyr Pro Asn Tyr Gly Ser Ala Val
        50                  55                  60

Lys Gly Arg Ala Thr Ile Ser Arg Asp Asn Arg Gln Ser Thr Val Arg
65                  70                  75                  80

Leu Gln Leu Asn Asn Leu Arg Ala Asp Asp Thr Gly Thr Tyr Tyr Cys
                85                  90                  95

Ala Lys Gly Ala Tyr Gly Gly Gly Trp Tyr Ala Ala Ser Ser Ile Asp
            100                 105                 110

Ala Trp Gly His Gly Thr Glu Val Ile Val Ser Ser
        115                 120

<210> SEQ ID NO 205
<211> LENGTH: 384
<212> TYPE: DNA
<213> ORGANISM: Artificial Sequence
<220> FEATURE:
<223> OTHER INFORMATION: HC DNA
```

-continued

<400> SEQUENCE: 205
gtcacgaatt cggccgtgac gttggacgag tccgggggcg gcctccagac gcccggagga        60
gggctcagcc tcgtctgcaa ggcctccggg ttctccttca gcagccgggg catgttctgg       120
gtgcgacagg cacctggcaa ggggctggaa tacgttgcgg gtattgataa tgatggtggt       180
tacccaaact acgggtcggc ggtgaagggc cgtgccacca tctcgaggga caacaggcag       240
agcacagtga ggctgcagct gaacaacctc agggctgacg acaccggcac ctactactgc       300
gccaagggtg cttatggtgg tggttggtat gccgctagta gcatcgacgc atggggccac       360
gggaccgaag tcatcgtctc ctcg                                              384

<210> SEQ ID NO 206
<211> LENGTH: 9
<212> TYPE: PRT
<213> ORGANISM: Artificial Sequence
<220> FEATURE:
<223> OTHER INFORMATION: CDR1-LC

<400> SEQUENCE: 206

Ser Gly Gly Gly Gly Gly Trp Tyr Gly
1               5

<210> SEQ ID NO 207
<211> LENGTH: 7
<212> TYPE: PRT
<213> ORGANISM: Artificial Sequence
<220> FEATURE:
<223> OTHER INFORMATION: CDR2-LC

<400> SEQUENCE: 207

Asp Asn Thr Asn Arg Pro Ser
1               5

<210> SEQ ID NO 208
<211> LENGTH: 11
<212> TYPE: PRT
<213> ORGANISM: Artificial Sequence
<220> FEATURE:
<223> OTHER INFORMATION: CDR3-LC

<400> SEQUENCE: 208

Ala Asn Thr Asp Ser Asp Gly Asn Asp Ala Pro
1               5                   10

<210> SEQ ID NO 209
<211> LENGTH: 105
<212> TYPE: PRT
<213> ORGANISM: Artificial Sequence
<220> FEATURE:
<223> OTHER INFORMATION: LC Protein

<400> SEQUENCE: 209

Ala Leu Thr Gln Pro Ser Ser Val Ser Ala Asn Pro Gly Glu Thr Val
1               5                   10                  15

Lys Ile Thr Cys Ser Gly Gly Gly Gly Trp Tyr Gly Trp Tyr Gln
            20                  25                  30

Gln Lys Ser Pro Gly Ser Ala Pro Val Thr Val Ile Tyr Asp Asn Thr
            35                  40                  45

Asn Arg Pro Ser Asp Ile Pro Ser Arg Phe Ser Gly Ser Lys Ser Gly
        50                  55                  60

Ser Thr Gly Thr Leu Thr Ile Thr Gly Val Gln Ala Glu Asp Glu Ala

-continued

```
65              70              75              80

Val Tyr Phe Cys Ala Asn Thr Asp Ser Asp Gly Asn Asp Ala Pro Phe
                85              90              95

Gly Ala Gly Thr Thr Leu Thr Val Leu
            100             105

<210> SEQ ID NO 210
<211> LENGTH: 315
<212> TYPE: DNA
<213> ORGANISM: Artificial Sequence
<220> FEATURE:
<223> OTHER INFORMATION: LC DNA

<400> SEQUENCE: 210
gccctgactc agccgtcctc ggtgtcagcg aacccgggag aaaccgtcaa gatcacctgc       60
tccgggggtg gtggcggctg gtatggctgg tatcagcaga agtctcctgg cagtgcccct      120
gtcactgtga tctatgacaa caccaacaga ccctcggaca tcccttcacg attctccggt      180
tccaaatccg gctccacggg cacattaacc atcactgggg tccaagccga ggacgaggct      240
gtctatttct gtgcgaatac agacagcgac ggtaatgatg ctccatttgg ggccgggaca      300
accctgaccg tcctt                                                       315

<210> SEQ ID NO 211
<211> LENGTH: 7
<212> TYPE: PRT
<213> ORGANISM: Artificial Sequence
<220> FEATURE:
<223> OTHER INFORMATION: Ab66 (LM-190 or MCT1 3308 H02) - CDR1-HC

<400> SEQUENCE: 211

Gly Phe Ser Phe Ser Ser Arg
1               5

<210> SEQ ID NO 212
<211> LENGTH: 7
<212> TYPE: PRT
<213> ORGANISM: Artificial Sequence
<220> FEATURE:
<223> OTHER INFORMATION: CDR2-HC

<400> SEQUENCE: 212

Asp Asn Asp Gly Gly Tyr Pro
1               5

<210> SEQ ID NO 213
<211> LENGTH: 15
<212> TYPE: PRT
<213> ORGANISM: Artificial Sequence
<220> FEATURE:
<223> OTHER INFORMATION: CDR3-HC

<400> SEQUENCE: 213

Gly Ala Tyr Gly Gly Gly Trp Tyr Ala Ala Ser Ser Ile Asp Ala
1               5              10              15

<210> SEQ ID NO 214
<211> LENGTH: 124
<212> TYPE: PRT
<213> ORGANISM: Artificial Sequence
<220> FEATURE:
<223> OTHER INFORMATION: HC Protein

<400> SEQUENCE: 214
```

-continued

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Ser Phe Ser Ser Arg
            20                  25                  30

Gly Met Phe Trp Val Arg Gln Ala Pro Gly Lys Gly Leu Glu Tyr Val
            35                  40                  45

Ala Gly Ile Asp Asn Asp Gly Gly Tyr Pro Asn Tyr Gly Ser Ala Val
        50                  55                  60

Lys Gly Arg Ala Thr Ile Ser Arg Asp Asn Arg Gln Ser Thr Val Arg
65                  70                  75                  80

Leu Gln Leu Asn Asn Leu Arg Ala Asp Asp Thr Gly Thr Tyr Tyr Cys
                85                  90                  95

Ala Lys Gly Ala Tyr Gly Gly Gly Trp Tyr Ala Ala Ser Ser Ile Asp
            100                 105                 110

Ala Trp Gly His Gly Thr Glu Val Ile Val Ser Ser
            115                 120
```

```
<210> SEQ ID NO 215
<211> LENGTH: 375
<212> TYPE: DNA
<213> ORGANISM: Artificial Sequence
<220> FEATURE:
<223> OTHER INFORMATION: HC DNA

<400> SEQUENCE: 215
tccgccgtga cgttggacga gtccgggggc ggcctccaga cgcccggagg agggctcagc        60
ctcgtctgca aggcctccgg gttctccttc agcagccggg gcatgttctg ggtgcgacag       120
gcacctggca aggggctgga atacgttgcg ggtattgata atgatggtgg ttacccaaac       180
tacgggtcgg cggtgaaggg ccgtgccacc atctcgaggg acaacaggca gagcacagtg       240
aggctgcagc tgaacaacct cagggctgac gacaccggca cctactactg cgccaagggt       300
gcttatggtg gtggttggta tgccgctagt agcatcgacg catggggcca cgggaccgaa       360
gtcatcgtct cctcg                                                         375
```

```
<210> SEQ ID NO 216
<211> LENGTH: 9
<212> TYPE: PRT
<213> ORGANISM: Artificial Sequence
<220> FEATURE:
<223> OTHER INFORMATION: CDR1-LC

<400> SEQUENCE: 216

Ser Gly Gly Val Gly Gln Trp Tyr Gly
1               5
```

```
<210> SEQ ID NO 217
<211> LENGTH: 7
<212> TYPE: PRT
<213> ORGANISM: Artificial Sequence
<220> FEATURE:
<223> OTHER INFORMATION: CDR2-LC

<400> SEQUENCE: 217

Asp Asn Thr Lys Arg Pro Ser
1               5
```

```
<210> SEQ ID NO 218
<211> LENGTH: 11
<212> TYPE: PRT
<213> ORGANISM: Artificial Sequence
```

-continued

```
<220> FEATURE:
<223> OTHER INFORMATION: CDR3-LC

<400> SEQUENCE: 218

Ala Asn Thr Tyr Ser Asp Gly Asn Asp Ala Pro
1               5                   10

<210> SEQ ID NO 219
<211> LENGTH: 105
<212> TYPE: PRT
<213> ORGANISM: Artificial Sequence
<220> FEATURE:
<223> OTHER INFORMATION: LC Protein

<400> SEQUENCE: 219

Ala Leu Thr Gln Pro Ser Ser Val Ser Ala Asn Leu Gly Glu Ala Val
1               5                   10                  15

Lys Ile Thr Cys Ser Gly Gly Val Gly Gln Trp Tyr Gly Trp Tyr Gln
            20                  25                  30

Gln Lys Ala Pro Gly Ser Ala Pro Val Thr Val Ile Tyr Asp Asn Thr
        35                  40                  45

Lys Arg Pro Ser Asn Ile Pro Ser Arg Phe Ser Gly Ser Ala Ser Gly
    50                  55                  60

Ser Thr Ala Thr Leu Thr Ile Thr Gly Val Arg Ala Glu Asp Glu Ala
65                  70                  75                  80

Val Tyr Phe Cys Ala Asn Thr Tyr Ser Asp Gly Asn Asp Ala Pro Phe
                85                  90                  95

Gly Ala Gly Thr Thr Leu Thr Val Leu
            100                 105

<210> SEQ ID NO 220
<211> LENGTH: 315
<212> TYPE: DNA
<213> ORGANISM: Artificial Sequence
<220> FEATURE:
<223> OTHER INFORMATION: LC DNA

<400> SEQUENCE: 220
gccctgactc agccgtcctc ggtgtcagca aacctgggag aagccgtcaa gatcacctgc      60
agtggaggtg tcggccagtg gtatggctgg taccagcaga aggcacctgg cagtgcccct     120
gtcactgtga tctatgacaa caccaagaga ccctcaaaca tcccttcacg attctccggt     180
tccgcatccg gctccacagc cacactaacc atcactggag tccgagccga ggacgaggct     240
gtctatttct gtgcgaatac atacagcgac ggtaatgatg ctccatttgg ggccgggaca     300
accctgaccg tcctt                                                     315

<210> SEQ ID NO 221
<211> LENGTH: 7
<212> TYPE: PRT
<213> ORGANISM: Artificial Sequence
<220> FEATURE:
<223> OTHER INFORMATION: Ab67 (LM-193 or MCT1 3310 A07) - CDR1-HC

<400> SEQUENCE: 221

Gly Phe Asp Phe Ser Asn Tyr
1               5

<210> SEQ ID NO 222
<211> LENGTH: 6
<212> TYPE: PRT
<213> ORGANISM: Artificial Sequence
```

<220> FEATURE:
<223> OTHER INFORMATION: CDR2-HC

<400> SEQUENCE: 222

Gly Asp Ser Ala Ser Tyr
1               5

<210> SEQ ID NO 223
<211> LENGTH: 16
<212> TYPE: PRT
<213> ORGANISM: Artificial Sequence
<220> FEATURE:
<223> OTHER INFORMATION: CDR3-HC

<400> SEQUENCE: 223

Ala Ser Glu Gly Ser Tyr Trp Tyr Tyr Glu Ala Gly Gly Ile Asp Thr
1               5                   10                  15

<210> SEQ ID NO 224
<211> LENGTH: 125
<212> TYPE: PRT
<213> ORGANISM: Artificial Sequence
<220> FEATURE:
<223> OTHER INFORMATION: HC Protein

<400> SEQUENCE: 224

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Asn Tyr
                20                  25                  30

Glu Met Leu Trp Val Arg Gln Ala Pro Gly Lys Gly Leu Glu Tyr Val
            35                  40                  45

Ala Gly Ile Gly Asp Ser Ala Ser Tyr Ser Ala Tyr Gly Val Ala Val
        50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125

<210> SEQ ID NO 225
<211> LENGTH: 384
<212> TYPE: DNA
<213> ORGANISM: Artificial Sequence
<220> FEATURE:
<223> OTHER INFORMATION: HC DNA

<400> SEQUENCE: 225
acgaattcgg ccgtgacgtt ggacgagtcc gggggcggcc tccagacgcc cggaggaacg      60
ctcagcctcg tctgcaaggc ctccgggttc gacttcagca actacgaaat gctctgggtg     120
cgacaggcgc ccggcaaggg gctggaatac gtcgctggta ttggcgacag tgctagttac     180
tcagcatacg gggtggcggt gaagggccgt gccaccatct cgaggacaa cgggcagagc      240 acactgaggc tgcagctgaa cggcctcagg gctgaggaca ccggcaccta ctactgcacc     300
aaagcttccg agggttccta ctggtattat gaagctggtg gtatcgacac atggggccac     360
gggaccgaag tcatcgtctc ctcg                                           384

```
<210> SEQ ID NO 226
<211> LENGTH: 8
<212> TYPE: PRT
<213> ORGANISM: Artificial Sequence
<220> FEATURE:
<223> OTHER INFORMATION: CDR1-LC

<400> SEQUENCE: 226

Ser Gly Gly Ser Gly Ser Tyr Gly
1               5

<210> SEQ ID NO 227
<211> LENGTH: 7
<212> TYPE: PRT
<213> ORGANISM: Artificial Sequence
<220> FEATURE:
<223> OTHER INFORMATION: CDR2-LC

<400> SEQUENCE: 227

Tyr Asn Asp Lys Arg Pro Ser
1               5

<210> SEQ ID NO 228
<211> LENGTH: 8
<212> TYPE: PRT
<213> ORGANISM: Artificial Sequence
<220> FEATURE:
<223> OTHER INFORMATION: CDR3-LC

<400> SEQUENCE: 228

Gly Ser Ala Gly Asn Ser Gly Ala
1               5

<210> SEQ ID NO 229
<211> LENGTH: 101
<212> TYPE: PRT
<213> ORGANISM: Artificial Sequence
<220> FEATURE:
<223> OTHER INFORMATION: LC Protein

<400> SEQUENCE: 229

Ala Leu Thr Gln Pro Ser Ser Val Ser Ala Asn Leu Gly Gly Thr Val
1               5                   10                  15

Lys Ile Thr Cys Ser Gly Gly Ser Gly Ser Tyr Gly Trp Phe Arg Gln
            20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Ala Thr Leu Thr Ile Thr Gly Val Arg Ala Glu Asp Glu Ala Val
65                  70                  75                  80

Tyr Phe Cys Gly Ser Ala Gly Asn Ser Gly Ala Phe Gly Ala Gly Thr
                85                  90                  95

Thr Leu Thr Val Leu
            100

<210> SEQ ID NO 230
<211> LENGTH: 303
<212> TYPE: DNA
<213> ORGANISM: Artificial Sequence
<220> FEATURE:
<223> OTHER INFORMATION: LC DNA

<400> SEQUENCE: 230
```

-continued

```
gccctgactc agccgtcctc ggtgtcagca aacctgggag gaacagtcaa gatcacctgc      60 tccggggggta gtggcagcta tggctggttc cggcagaagt ctcctggcag tgccctgtc      120 actgtgatct attacaacga caagagaccc tcggacatcc cttcacgatt ctccggttcc      180
aaatccggct ccacagccac attaaccatc actggggtcc gagccgagga cgaggctgtc      240
tatttctgtg ggagtgcagg caacagtggt gcatttgggg ccgggacaac cctgaccgtc      300
ctt                                                                   303
```

<210> SEQ ID NO 231
<211> LENGTH: 7
<212> TYPE: PRT
<213> ORGANISM: Artificial Sequence
<220> FEATURE:
<223> OTHER INFORMATION: Ab68 (LM-194 or MCT1 3310 B07-1) - CDR1-HC

<400> SEQUENCE: 231

Gly Phe Asp Phe Ser Ser Tyr
1               5

<210> SEQ ID NO 232
<211> LENGTH: 6
<212> TYPE: PRT
<213> ORGANISM: Artificial Sequence
<220> FEATURE:
<223> OTHER INFORMATION: CDR2-HC

<400> SEQUENCE: 232

Gly Asp Gly Ala Ser Tyr
1               5

<210> SEQ ID NO 233
<211> LENGTH: 16
<212> TYPE: PRT
<213> ORGANISM: Artificial Sequence
<220> FEATURE:
<223> OTHER INFORMATION: CDR3-HC

<400> SEQUENCE: 233

Ala Ser Glu Gly Ser Tyr Trp Tyr Tyr Glu Thr Gly Gly Ile Asp Thr
1               5                   10                  15

<210> SEQ ID NO 234
<211> LENGTH: 125
<212> TYPE: PRT
<213> ORGANISM: Artificial Sequence
<220> FEATURE:
<223> OTHER INFORMATION: HC Protein

<400> SEQUENCE: 234

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Ser Tyr
            20                  25                  30

Glu Met Leu Trp Val Arg Gln Ala Pro Gly Lys Gly Leu Ala Tyr Val
        35                  40                  45

Ala Gly Ile Gly Asp Gly Ala Ser Tyr Ser Ala Tyr Gly Val Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

-continued

```
Ala Lys Ala Ser Glu Gly Ser Tyr Trp Tyr Tyr Glu Thr Gly Gly Ile
            100                 105                 110

Asp Thr Trp Gly His Gly Thr Glu Val Ile Val Ser Ser
        115                 120                 125

<210> SEQ ID NO 235
<211> LENGTH: 384
<212> TYPE: DNA
<213> ORGANISM: Artificial Sequence
<220> FEATURE:
<223> OTHER INFORMATION: HC DNA

<400> SEQUENCE: 235
acgaattcgg ccgtgacgtt ggacgagtcc gggggcggcc tccagacgcc cggaggaacg        60
ctcagcctcg tctgcaaggc ctccgggttc gacttcagca gctacgaaat gctctgggtg       120
cgacaggcgc ccggcaaggg gctggcatac gtcgctggta tcggcgacgg tgctagttac       180
tcagcatacg gggtggcggt gaagggccga gccaccatct cgaggacaa cgggcagagc        240 acagtgaggc tgcagctgaa caacctcagg gctgaggaca ccggcaccta ctactgcgcc       300
aaagcttccg aggggttccta ctggtattat gaaactggtg gtatcgacac atggggccac       360
gggaccgaag tcatcgtctc ctcg                                             384

<210> SEQ ID NO 236
<211> LENGTH: 8
<212> TYPE: PRT
<213> ORGANISM: Artificial Sequence
<220> FEATURE:
<223> OTHER INFORMATION: CDR1-LC

<400> SEQUENCE: 236

Ser Gly Gly Gly Gly Ser Tyr Gly
1               5

<210> SEQ ID NO 237
<211> LENGTH: 7
<212> TYPE: PRT
<213> ORGANISM: Artificial Sequence
<220> FEATURE:
<223> OTHER INFORMATION: CDR2-LC

<400> SEQUENCE: 237

Tyr Asn Asp Lys Arg Pro Ser
1               5

<210> SEQ ID NO 238
<211> LENGTH: 8
<212> TYPE: PRT
<213> ORGANISM: Artificial Sequence
<220> FEATURE:
<223> OTHER INFORMATION: CDR3-LC

<400> SEQUENCE: 238

Gly Ser Ala Gly Asn Ser Gly Ala
1               5

<210> SEQ ID NO 239
<211> LENGTH: 101
<212> TYPE: PRT
<213> ORGANISM: Artificial Sequence
<220> FEATURE:
<223> OTHER INFORMATION: LC Protein

<400> SEQUENCE: 239
```

-continued

```
Ala Leu Thr Gln Pro Ser Ser Val Ser Ala Asn Leu Gly Gly Thr Val
1               5                   10                  15

Lys Ile Thr Cys Ser Gly Gly Gly Ser Tyr Gly Trp Phe Gln Gln
            20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Ala Thr Leu Thr Ile Thr Gly Val Arg Ala Glu Asp Glu Ala Val
65                  70                  75                  80

Tyr Phe Cys Gly Ser Ala Gly Asn Ser Gly Ala Phe Gly Ala Gly Thr
            85                  90                  95

Thr Leu Thr Val Leu
            100
```

```
<210> SEQ ID NO 240
<211> LENGTH: 303
<212> TYPE: DNA
<213> ORGANISM: Artificial Sequence
<220> FEATURE:
<223> OTHER INFORMATION: LC DNA

<400> SEQUENCE: 240
gccctgactc agccgtcctc ggtgtcagca aacctgggag gaaccgtcaa gatcacctgc        60
tccgggggtg gtggcagcta tggctggttc cagcagaagt ctcctggcag tgcccctgtc       120
actgtgatct attacaacga caagagaccc tcggacatcc cttcacgatt ctccggttcc       180
aaatccggct ccacagccac attaaccatc actggggtcc gagccgagga cgaggctgtc       240
tatttctgtg ggagtgcagg caacagtggt gcatttgggg ccgggacaac cctgaccgtc       300
ctt                                                                     303
```

```
<210> SEQ ID NO 241
<211> LENGTH: 7
<212> TYPE: PRT
<213> ORGANISM: Artificial Sequence
<220> FEATURE:
<223> OTHER INFORMATION: Ab69 (LM-195 or MCT1 3310 B07-2) - CDR1-HC

<400> SEQUENCE: 241

Gly Phe Asp Phe Ser Ser Tyr
1               5
```

```
<210> SEQ ID NO 242
<211> LENGTH: 6
<212> TYPE: PRT
<213> ORGANISM: Artificial Sequence
<220> FEATURE:
<223> OTHER INFORMATION: CDR2-HC

<400> SEQUENCE: 242

Gly Asp Gly Ala Ser Tyr
1               5
```

```
<210> SEQ ID NO 243
<211> LENGTH: 16
<212> TYPE: PRT
<213> ORGANISM: Artificial Sequence
<220> FEATURE:
<223> OTHER INFORMATION: CDR3-HC

<400> SEQUENCE: 243
```

-continued

```
Ala Ser Glu Gly Ser Tyr Trp Tyr Tyr Glu Thr Gly Gly Ile Asp Thr
1               5                   10                  15
```

<210> SEQ ID NO 244
<211> LENGTH: 125
<212> TYPE: PRT
<213> ORGANISM: Artificial Sequence
<220> FEATURE:
<223> OTHER INFORMATION: HC Protein

<400> SEQUENCE: 244

```
Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Ser Tyr
            20                  25                  30

Glu Met Leu Trp Val Arg Gln Ala Pro Gly Lys Gly Leu Ala Tyr Val
        35                  40                  45

Ala Gly Ile Gly Asp Gly Ala Ser Tyr Ser Ala Tyr Gly Val Ala Val
    50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Ala Lys Ala Ser Glu Gly Ser Tyr Trp Tyr Tyr Glu Thr Gly Gly Ile
            100                 105                 110

Asp Thr Trp Gly His Gly Thr Glu Val Ile Val Ser Ser
        115                 120                 125
```

<210> SEQ ID NO 245
<211> LENGTH: 384
<212> TYPE: DNA
<213> ORGANISM: Artificial Sequence
<220> FEATURE:
<223> OTHER INFORMATION: HC DNA

<400> SEQUENCE: 245

```
acgaattcgg ccgtgacgtt ggacgagtcc gggggcggcc tccagacgcc cggaggaacg        60
ctcagcctcg tctgcaaggc ctccgggttc gacttcagca gctacgaaat gctctgggtg       120
cgacaggcgc ccggcaaggg gctggcatac gtcgctggta tcggcgacgg tgctagttac       180
tcagcatacg gggtggcggt gaagggccgt gccaccatct cgagggacaa cgggcagagc       240
acactgaggc tgcagctgaa cggcctcagg gctgaggaca ccggcaccta ctactgcgcc       300
aaagcttccg agggttccta ctggtattat gaaactggtg gtatcgacac atggggccac       360
gggaccgaag tcatcgtctc ctcg                                              384
```

<210> SEQ ID NO 246
<211> LENGTH: 8
<212> TYPE: PRT
<213> ORGANISM: Artificial Sequence
<220> FEATURE:
<223> OTHER INFORMATION: CDR1-LC

<400> SEQUENCE: 246

```
Ser Gly Gly Gly Gly Ser Tyr Gly
1               5
```

<210> SEQ ID NO 247
<211> LENGTH: 7
<212> TYPE: PRT

-continued

```
<213> ORGANISM: Artificial Sequence
<220> FEATURE:
<223> OTHER INFORMATION: CDR2-LC

<400> SEQUENCE: 247

Tyr Asn Asp Lys Arg Pro Ser
1               5

<210> SEQ ID NO 248
<211> LENGTH: 8
<212> TYPE: PRT
<213> ORGANISM: Artificial Sequence
<220> FEATURE:
<223> OTHER INFORMATION: CDR3-LC

<400> SEQUENCE: 248

Gly Ser Ala Gly Asn Ser Gly Ala
1               5

<210> SEQ ID NO 249
<211> LENGTH: 101
<212> TYPE: PRT
<213> ORGANISM: Artificial Sequence
<220> FEATURE:
<223> OTHER INFORMATION: LC Protein

<400> SEQUENCE: 249

Ala Leu Thr Gln Pro Ser Ser Val Ser Ala Asn Leu Gly Gly Thr Val
1               5                   10                  15

Lys Ile Thr Cys Ser Gly Gly Gly Gly Ser Tyr Gly Trp Phe Gln Gln
                20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
        50                  55                  60

Thr Ala Thr Leu Thr Ile Thr Gly Val Arg Ala Glu Asp Glu Ala Val
65                  70                  75                  80

Tyr Phe Cys Gly Ser Ala Gly Asn Ser Gly Ala Phe Gly Ala Gly Thr
                85                  90                  95

Thr Leu Thr Val Leu
                100

<210> SEQ ID NO 250
<211> LENGTH: 303
<212> TYPE: DNA
<213> ORGANISM: Artificial Sequence
<220> FEATURE:
<223> OTHER INFORMATION: LC DNA

<400> SEQUENCE: 250
gccctgactc agccgtcctc ggtgtcagca aacctgggag gaaccgtcaa gatcacctgc      60 tccggggggtg gtggcagcta tggctggttc cagcagaagt ctcctggcag tgcccctgtc     120
actgtgatct attacaacga caagagaccc tcggacatcc cttcacgatt ctccggttcc     180
aaatccggct ccacagccac attaaccatc actggggtcc gagccgagga cgaggctgtc     240
tatttctgtg ggagtgcagg caacagtggt gcatttgggg ccgggacaac cctgaccgtc     300
ctt                                                                    303

<210> SEQ ID NO 251
<211> LENGTH: 7
<212> TYPE: PRT
```

<213> ORGANISM: Artificial Sequence
<220> FEATURE:
<223> OTHER INFORMATION: Ab70 (LM-197 or MCT1 3310 E01) - CDR1-HC

<400> SEQUENCE: 251

Gly Phe Asp Phe Ser Ser Tyr
1               5

<210> SEQ ID NO 252
<211> LENGTH: 6
<212> TYPE: PRT
<213> ORGANISM: Artificial Sequence
<220> FEATURE:
<223> OTHER INFORMATION: CDR2-HC

<400> SEQUENCE: 252

Gly Asn Ser Ala Ser Tyr
1               5

<210> SEQ ID NO 253
<211> LENGTH: 16
<212> TYPE: PRT
<213> ORGANISM: Artificial Sequence
<220> FEATURE:
<223> OTHER INFORMATION: CDR3-HC

<400> SEQUENCE: 253

Pro Ser Asp Gly Ser Tyr Trp Tyr Tyr Glu Ala Gly Gly Ile Asp Thr
1               5                   10                  15

<210> SEQ ID NO 254
<211> LENGTH: 125
<212> TYPE: PRT
<213> ORGANISM: Artificial Sequence
<220> FEATURE:
<223> OTHER INFORMATION: HC Protein

<400> SEQUENCE: 254

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Ser Tyr
            20                  25                  30

Glu Met Leu Trp Val Arg Gln Ala Pro Gly Lys Gly Leu Glu Phe Val
        35                  40                  45

Ala Gly Ile Gly Asn Ser Ala Ser Tyr Ser Ala Tyr Gly Val Ala Val
    50                  55                  60

Lys Gly Arg Ala Thr Ile Ser Arg Asp Asn Gly Gln Ser Thr Val Arg
65                  70                  75                  80

Leu Lys Leu Asn Asn Leu Arg Ala Glu Asp Thr Gly Thr Tyr Tyr Cys
                85                  90                  95

Ala Lys Pro Ser Asp Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125

<210> SEQ ID NO 255
<211> LENGTH: 384
<212> TYPE: DNA
<213> ORGANISM: Artificial Sequence
<220> FEATURE:
<223> OTHER INFORMATION: HC DNA

<400> SEQUENCE: 255

-continued

```
acgaattcgg ccgtgacgtt ggacgagtcc gggggcggcc tccagacgcc cggaggaacg      60
ctcagcctcg tctgcaaggc ctccgggttc gacttcagca gctacgaaat gctctgggtg     120
cgacaggcgc ccggcaaggg gctggaattc gtcgctggta ttggcaacag tgctagttac     180
tcagcatacg gggtggcggt gaagggccgt gccaccatct cgaggacaa cgggcagagc       240 acagtgaggc tgaagctgaa caacctcagg gctgaggaca ccggcaccta ctactgcgcc      300
aaaccttccg atggttccta ctggtattat gaagctggtg gtatcgacac atggggccac      360
gggaccgaag tcatcgtctc ctcg                                            384
```

```
<210> SEQ ID NO 256
<211> LENGTH: 8
<212> TYPE: PRT
<213> ORGANISM: Artificial Sequence
<220> FEATURE:
<223> OTHER INFORMATION: CDR1-LC

<400> SEQUENCE: 256

Ser Gly Gly Gly Gly Ser Tyr Gly
1               5

<210> SEQ ID NO 257
<211> LENGTH: 7
<212> TYPE: PRT
<213> ORGANISM: Artificial Sequence
<220> FEATURE:
<223> OTHER INFORMATION: CDR2-LC

<400> SEQUENCE: 257

Asp Asn Asp Lys Arg Pro Ser
1               5

<210> SEQ ID NO 258
<211> LENGTH: 8
<212> TYPE: PRT
<213> ORGANISM: Artificial Sequence
<220> FEATURE:
<223> OTHER INFORMATION: CDR3-LC

<400> SEQUENCE: 258

Gly Ser Ala Gly Asn Ser Gly Ala
1               5

<210> SEQ ID NO 259
<211> LENGTH: 101
<212> TYPE: PRT
<213> ORGANISM: Artificial Sequence
<220> FEATURE:
<223> OTHER INFORMATION: LC Protein

<400> SEQUENCE: 259

Ala Leu Thr Gln Pro Ser Ser Val Ser Ala Asn Pro Gly Gly Thr Val
1               5                   10                  15

Lys Ile Thr Cys Ser Gly Gly Gly Ser Tyr Gly Trp Tyr Gln Gln
            20                  25                  30

Lys Ser Pro Gly Ser Ala Pro Val Thr Val Ile Tyr Asp Asn Asp Lys
        35                  40                  45

Arg Pro Ser Asp Ile Pro Ser Arg Phe Ser Gly Ser Lys Ser Gly Ser
    50                  55                  60

Thr Ala Thr Leu Thr Ile Thr Gly Val Arg Ala Glu Asp Glu Ala Val
65                  70                  75                  80

Tyr Tyr Cys Gly Ser Ala Gly Asn Ser Gly Ala Phe Gly Ala Gly Thr
```

-continued

```
                 85                 90                 95

Thr Leu Thr Val Leu
         100

<210> SEQ ID NO 260
<211> LENGTH: 303
<212> TYPE: DNA
<213> ORGANISM: Artificial Sequence
<220> FEATURE:
<223> OTHER INFORMATION: LC DNA

<400> SEQUENCE: 260
gccctgactc agccgtcctc ggtgtcagca aacccgggag gaaccgtcaa gatcacctgc      60 tccggggggtg gtggcagcta tggctggtat cagcagaagt cacctggcag tgccctgtc    120 actgtgatct atgacaacga caagagaccc tcggacatcc cttcacgatt ctccggttcc    180
aagtccggct ccacagccac attaaccatc actggggttc gagccgagga cgaggctgtc    240
tattactgtg cagtgcagg caatagtggt gcatttgggg ccgggacaac cctgaccgtc     300
ctt                                                                  303

<210> SEQ ID NO 261
<211> LENGTH: 7
<212> TYPE: PRT
<213> ORGANISM: Artificial Sequence
<220> FEATURE:
<223> OTHER INFORMATION: Ab71 (LM-198 or MCT1 3310 E03) - CDR1-HC

<400> SEQUENCE: 261

Gly Phe Asp Phe Ser Asn Tyr
1               5

<210> SEQ ID NO 262
<211> LENGTH: 6
<212> TYPE: PRT
<213> ORGANISM: Artificial Sequence
<220> FEATURE:
<223> OTHER INFORMATION: CDR2-HC

<400> SEQUENCE: 262

Gly Asp Ser Ala Ser Tyr
1               5

<210> SEQ ID NO 263
<211> LENGTH: 16
<212> TYPE: PRT
<213> ORGANISM: Artificial Sequence
<220> FEATURE:
<223> OTHER INFORMATION: CDR3-HC

<400> SEQUENCE: 263

Ala Ser Glu Gly Ser Tyr Trp Tyr Tyr Glu Ala Gly Gly Ile Asp Thr
1               5                   10                  15

<210> SEQ ID NO 264
<211> LENGTH: 125
<212> TYPE: PRT
<213> ORGANISM: Artificial Sequence
<220> FEATURE:
<223> OTHER INFORMATION: HC Protein

<400> SEQUENCE: 264

Ala Val Thr Leu Asp Glu Ser Gly Gly Gly Leu Gln Thr Pro Gly Gly
1               5                   10                  15
```

-continued

```
Thr Leu Ser Leu Val Cys Lys Ala Ser Gly Phe Asp Phe Ser Asn Tyr
        20                  25                  30

Glu Met Leu Trp Val Arg Gln Ala Pro Gly Lys Gly Leu Glu Tyr Val
        35                  40                  45

Ala Gly Ile Gly Asp Ser Ala Ser Tyr Ser Ala Tyr Gly Val Ala Val
        50                  55                  60

Lys Gly Arg Ala Thr Ile Ser Arg Asp Asn Gly Gln Ser Ala Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125
```

```
<210> SEQ ID NO 265
<211> LENGTH: 384
<212> TYPE: DNA
<213> ORGANISM: Artificial Sequence
<220> FEATURE:
<223> OTHER INFORMATION: HC DNA

<400> SEQUENCE: 265
acgaattcgg ccgtgacgtt ggacgagtcc gggggcggcc tccagacgcc cggaggaacg      60
ctcagcctcg tctgcaaggc ctccgggttc gacttcagca actacgaaat gctctgggtg     120
cgacaggcgc ccggcaaggg gctggaatac gtcgctggta ttggcgacag tgctagttac     180
tcagcatacg gggtggcggt gaagggccgt gccaccatct cgagggacaa cgggcagagc     240
gcactgaggc tgcagctgaa cggcctcagg gctgaggaca ccggcaccta ctactgcacc     300
aaagcttccg agggttccta ctggtattat gaagctggtg gtatcgacac atggggccac     360
gggaccgaag tcatcgtctc ctcg                                            384
```

```
<210> SEQ ID NO 266
<211> LENGTH: 8
<212> TYPE: PRT
<213> ORGANISM: Artificial Sequence
<220> FEATURE:
<223> OTHER INFORMATION: CDR1-LC

<400> SEQUENCE: 266

Ser Gly Gly Gly Gly Ser Tyr Gly
1               5
```

```
<210> SEQ ID NO 267
<211> LENGTH: 7
<212> TYPE: PRT
<213> ORGANISM: Artificial Sequence
<220> FEATURE:
<223> OTHER INFORMATION: CDR2-LC

<400> SEQUENCE: 267

Tyr Asn Asp Lys Arg Pro Ser
1               5
```

```
<210> SEQ ID NO 268
<211> LENGTH: 9
<212> TYPE: PRT
<213> ORGANISM: Artificial Sequence
<220> FEATURE:
<223> OTHER INFORMATION: CDR3-LC
```

```
<400> SEQUENCE: 268

Gly Ser Gly Asp Ser Ser Gly Gly Ile
1               5

<210> SEQ ID NO 269
<211> LENGTH: 102
<212> TYPE: PRT
<213> ORGANISM: Artificial Sequence
<220> FEATURE:
<223> OTHER INFORMATION: LC Protein

<400> SEQUENCE: 269

Ala Leu Thr Gln Pro Ser Ser Val Ser Ala Asn Leu Gly Gly Thr Val
1               5                   10                  15

Lys Ile Thr Cys Ser Gly Gly Gly Gly Ser Tyr Gly Trp Phe Gln Gln
                20                  25                  30

Lys Ser Pro Gly Ser Ala Pro Val Thr Val Ile Tyr Tyr Asn Asp Lys
            35                  40                  45

Arg Pro Ser Asp Ile Pro Ser Arg Phe Ser Gly Ser Lys Ser Gly Ser
        50                  55                  60

Thr Ala Thr Leu Thr Ile Thr Gly Val Gln Val Asp Asp Glu Ala Val
65                  70                  75                  80

Tyr Phe Cys Gly Ser Gly Asp Ser Ser Gly Gly Ile Phe Gly Ala Gly
                85                  90                  95

Thr Thr Leu Thr Val Leu
            100

<210> SEQ ID NO 270
<211> LENGTH: 306
<212> TYPE: DNA
<213> ORGANISM: Artificial Sequence
<220> FEATURE:
<223> OTHER INFORMATION: LC DNA

<400> SEQUENCE: 270
gccctgactc agccgtcctc ggtgtcagca aacctgggag gaaccgtcaa gatcacctgc        60
tccgggggtg gtggcagcta tggctggttc cagcagaagt ctcctggcag tgcccctgtc       120
actgtgatct attacaacga caagagaccc tcggacatcc cttcacgatt ctccggctcc       180
aaatccggct ccacggccac attaaccatc actggggtcc aagtcgacga cgaggctgtc       240
tatttctgtg ggagtggaga cagcagtggt ggtatatttg gggccgggac aaccctgacc       300
gtcctt                                                                  306

<210> SEQ ID NO 271
<211> LENGTH: 7
<212> TYPE: PRT
<213> ORGANISM: Artificial Sequence
<220> FEATURE:
<223> OTHER INFORMATION: Ab72 (LM-199 or MCT1 3310 E04) - CDR1-HC

<400> SEQUENCE: 271

Gly Phe Asp Phe Ser Asn Tyr
1               5

<210> SEQ ID NO 272
<211> LENGTH: 6
<212> TYPE: PRT
<213> ORGANISM: Artificial Sequence
<220> FEATURE:
<223> OTHER INFORMATION: CDR2-HC
```

<400> SEQUENCE: 272

Gly Asp Ser Ala Ser Tyr
1               5

<210> SEQ ID NO 273
<211> LENGTH: 16
<212> TYPE: PRT
<213> ORGANISM: Artificial Sequence
<220> FEATURE:
<223> OTHER INFORMATION: CDR3-HC

<400> SEQUENCE: 273

Ala Ser Glu Gly Ser Tyr Trp Tyr Tyr Glu Ala Gly Gly Ile Asp Thr
1               5                   10                  15

<210> SEQ ID NO 274
<211> LENGTH: 125
<212> TYPE: PRT
<213> ORGANISM: Artificial Sequence
<220> FEATURE:
<223> OTHER INFORMATION: HC Protein

<400> SEQUENCE: 274

Ala Val Thr Leu Asp Glu Ser Gly Gly Gly Leu Arg Thr Pro Gly Gly
1               5                   10                  15

Thr Leu Ser Leu Val Cys Lys Ala Ser Gly Phe Asp Phe Ser Asn Tyr
            20                  25                  30

Glu Met Leu Trp Val Arg Gln Ala Pro Gly Lys Gly Leu Glu Tyr Val
            35                  40                  45

Ala Gly Ile Gly Asp Ser Ala Ser Tyr Ser Ala Tyr Gly Val Ala Val
        50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125

<210> SEQ ID NO 275
<211> LENGTH: 384
<212> TYPE: DNA
<213> ORGANISM: Artificial Sequence
<220> FEATURE:
<223> OTHER INFORMATION: HC DNA

<400> SEQUENCE: 275
acgaattcgg ccgtgacgtt ggacgagtcc gggggcggcc tccggacgcc cggaggaacg      60
ctcagcctcg tctgcaaggc ctccgggttc gacttcagca actacgaaat gctctgggtg     120
cgacaggcgc ccggcaaggg gctggaatac gtcgctggta ttggcgacag tgctagttac     180
tcagcatacg gggtggcggt gaagggccgt gccaccatct cgagggacaa cgggcagagc     240
acactgaggc tgcagctgaa cggcctcagg gctgaggaca ccggcaccta ctactgcacc     300
aaagcttccg agggttccta ctggtattat gaagctggtg gtatcgacac atggggccac     360
gggaccgaag tcatcgtctc ctcg                                           384

<210> SEQ ID NO 276
<211> LENGTH: 8

```
<212> TYPE: PRT
<213> ORGANISM: Artificial Sequence
<220> FEATURE:
<223> OTHER INFORMATION: CDR1-LC

<400> SEQUENCE: 276

Ser Gly Gly Gly Gly Ser Tyr Gly
1               5

<210> SEQ ID NO 277
<211> LENGTH: 7
<212> TYPE: PRT
<213> ORGANISM: Artificial Sequence
<220> FEATURE:
<223> OTHER INFORMATION: CDR2-LC

<400> SEQUENCE: 277

Tyr Asn Asp Lys Arg Pro Ser
1               5

<210> SEQ ID NO 278
<211> LENGTH: 8
<212> TYPE: PRT
<213> ORGANISM: Artificial Sequence
<220> FEATURE:
<223> OTHER INFORMATION: CDR3-LC

<400> SEQUENCE: 278

Gly Ser Ala Gly Asn Ser Gly Ala
1               5

<210> SEQ ID NO 279
<211> LENGTH: 101
<212> TYPE: PRT
<213> ORGANISM: Artificial Sequence
<220> FEATURE:
<223> OTHER INFORMATION: LC Protein

<400> SEQUENCE: 279

Ala Leu Thr Gln Pro Ser Ser Val Ser Ala Asn Leu Gly Gly Thr Val
1               5                   10                  15

Lys Ile Thr Cys Ser Gly Gly Gly Ser Tyr Gly Trp Phe Gln Gln
            20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Arg Ala Glu Asp Glu Ala Val
65                  70                  75                  80

Tyr Phe Cys Gly Ser Ala Gly Asn Ser Gly Ala Phe Gly Ala Gly Thr
                85                  90                  95

Thr Leu Thr Val Leu
            100

<210> SEQ ID NO 280
<211> LENGTH: 303
<212> TYPE: DNA
<213> ORGANISM: Artificial Sequence
<220> FEATURE:
<223> OTHER INFORMATION: LC DNA

<400> SEQUENCE: 280
gccctgactc agccgtcctc ggtgtcagca aacctgggag gaaccgtcaa gatcacctgc      60
```

-continued

```
tccggggggtg gtggcagcta tggctggttc cagcagaagt ctcctggcag tgcccctgtc      120
actgtgatct attacaacga caagagaccc tcagacatcc cttcacgatt ctccggttcc      180
aaatccggct ccacgggcac attaaccatc actggggtcc gagccgagga cgaggctgtc      240
tatttctgtg ggagtgcagg caacagtggt gcatttgggg ccgggacaac cctgaccgtc      300
ctt                                                                   303
```

<210> SEQ ID NO 281
<211> LENGTH: 7
<212> TYPE: PRT
<213> ORGANISM: Artificial Sequence
<220> FEATURE:
<223> OTHER INFORMATION: Ab73 (LM-201 or MCT1 3310 H09) - CDR1-HC

<400> SEQUENCE: 281

Gly Phe Asp Phe Ser Ser Tyr
1               5

<210> SEQ ID NO 282
<211> LENGTH: 6
<212> TYPE: PRT
<213> ORGANISM: Artificial Sequence
<220> FEATURE:
<223> OTHER INFORMATION: CDR2-HC

<400> SEQUENCE: 282

Gly Asp Gly Ala Ser Tyr
1               5

<210> SEQ ID NO 283
<211> LENGTH: 16
<212> TYPE: PRT
<213> ORGANISM: Artificial Sequence
<220> FEATURE:
<223> OTHER INFORMATION: CDR3-HC

<400> SEQUENCE: 283

Ala Ser Glu Gly Ser Tyr Trp Tyr Tyr Glu Thr Gly Gly Ile Asp Thr
1               5                   10                  15

<210> SEQ ID NO 284
<211> LENGTH: 125
<212> TYPE: PRT
<213> ORGANISM: Artificial Sequence
<220> FEATURE:
<223> OTHER INFORMATION: HC Protein

<400> SEQUENCE: 284

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Ser Tyr
            20                  25                  30

Glu Met Leu Trp Val Arg Gln Ala Pro Gly Lys Gly Leu Ala Tyr Val
        35                  40                  45

Ala Gly Ile Gly Asp Gly Ala Ser Tyr Ser Ala Tyr Gly Val Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ala Ser Glu Gly Ser Tyr Trp Tyr Tyr Glu Thr Gly Gly Ile
            100                 105                 110
```

-continued

Asp Thr Trp Gly His Gly Thr Glu Val Ile Val Ser Ser
        115                 120                 125

<210> SEQ ID NO 285
<211> LENGTH: 384
<212> TYPE: DNA
<213> ORGANISM: Artificial Sequence
<220> FEATURE:
<223> OTHER INFORMATION: HC DNA

<400> SEQUENCE: 285
acgaattcgg ccgtgacgtt ggacgagtcc gggggcggcc tccagacgcc cggaggaacg      60
ctcagcctcg tctgcaaggc ctccgggttc gacttcagca gctacgaaat gctctgggtg     120
cgacaggcgc ccggcaaggg gctggcatac gtcgctggta tcggcgacgg tgctagttac     180
tcagcatacg gggtggcggt gaagggccga gccaccatct cgaggacaa  cgggcagagc     240 acagtgaggc tgcagctgaa caacctcagg gctgaggaca ccggcaccta ctactgcgcc     300
aaagcttccg agggttccta ctggtattat gaaactggtg gtatcgacac atggggccac     360
gggaccgaag tcatcgtctc ctcg                                          384

<210> SEQ ID NO 286
<211> LENGTH: 8
<212> TYPE: PRT
<213> ORGANISM: Artificial Sequence
<220> FEATURE:
<223> OTHER INFORMATION: CDR1-LC

<400> SEQUENCE: 286

Ser Gly Gly Gly Gly Ser Tyr Gly
1               5

<210> SEQ ID NO 287
<211> LENGTH: 7
<212> TYPE: PRT
<213> ORGANISM: Artificial Sequence
<220> FEATURE:
<223> OTHER INFORMATION: CDR2-LC

<400> SEQUENCE: 287

Tyr Asn Asp Lys Arg Pro Ser
1               5

<210> SEQ ID NO 288
<211> LENGTH: 8
<212> TYPE: PRT
<213> ORGANISM: Artificial Sequence
<220> FEATURE:
<223> OTHER INFORMATION: CDR3-LC

<400> SEQUENCE: 288

Gly Ser Ala Gly Asn Ser Gly Ala
1               5

<210> SEQ ID NO 289
<211> LENGTH: 101
<212> TYPE: PRT
<213> ORGANISM: Artificial Sequence
<220> FEATURE:
<223> OTHER INFORMATION: LC Protein

<400> SEQUENCE: 289

Ala Leu Thr Gln Pro Ser Ser Val Ser Ala Asn Leu Gly Glu Thr Val
1               5                   10                  15

-continued

```
Lys Ile Thr Cys Ser Gly Gly Gly Ser Tyr Gly Trp Phe Gln Gln
        20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Ala Thr Leu Thr Ile Thr Gly Val Arg Ala Glu Asp Glu Ala Val
65                  70                  75                  80

Tyr Phe Cys Gly Ser Ala Gly Asn Ser Gly Ala Phe Gly Ala Gly Thr
                85                  90                  95

Thr Leu Thr Val Leu
            100
```

```
<210> SEQ ID NO 290
<211> LENGTH: 303
<212> TYPE: DNA
<213> ORGANISM: Artificial Sequence
<220> FEATURE:
<223> OTHER INFORMATION: LC DNA

<400> SEQUENCE: 290
gccctgactc agccgtcctc ggtgtcagca aacctaggag aaaccgtcaa gatcacctgc        60
tccgggggtg gtggcagcta tggctggttc cagcagaagt ctcctggcag tgcccctgtc       120
actgtgatct attacaacga caagagaccc tcggacatcc cttcacgatt ctccggttcc       180
aaatccggct ccacagccac attaaccatc actggggtcc gagccgagga cgaggctgtc       240
tatttctgtg ggagtgcagg caacagtggt gcatttgggg ccgggacaac cctgaccgtc       300
ctt                                                                      303
```

```
<210> SEQ ID NO 291
<211> LENGTH: 7
<212> TYPE: PRT
<213> ORGANISM: Artificial Sequence
<220> FEATURE:
<223> OTHER INFORMATION: Ab74 (LM-202 or MCT1 3310 H12) - CDR1-HC

<400> SEQUENCE: 291

Gly Phe Asp Phe Ser Ser Tyr
1               5
```

```
<210> SEQ ID NO 292
<211> LENGTH: 6
<212> TYPE: PRT
<213> ORGANISM: Artificial Sequence
<220> FEATURE:
<223> OTHER INFORMATION: CDR2-HC

<400> SEQUENCE: 292

Gly Asp Gly Ala Ser Tyr
1               5
```

```
<210> SEQ ID NO 293
<211> LENGTH: 16
<212> TYPE: PRT
<213> ORGANISM: Artificial Sequence
<220> FEATURE:
<223> OTHER INFORMATION: CDR3-HC

<400> SEQUENCE: 293

Ala Ser Glu Gly Ser Tyr Trp Tyr Tyr Glu Thr Gly Gly Ile Asp Thr
1               5                   10                  15
```

<210> SEQ ID NO 294
<211> LENGTH: 125
<212> TYPE: PRT
<213> ORGANISM: Artificial Sequence
<220> FEATURE:
<223> OTHER INFORMATION: HC Protein

<400> SEQUENCE: 294

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Ser Tyr
            20                  25                  30

Glu Met Leu Trp Val Arg Gln Ala Pro Gly Lys Gly Leu Ala Tyr Val
        35                  40                  45

Ala Gly Ile Gly Asp Gly Ala Ser Tyr Ser Ala Tyr Gly Val Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ala Ser Glu Gly Ser Tyr Trp Tyr Tyr Glu Thr Gly Gly Ile
            100                 105                 110

Asp Thr Trp Gly His Gly Thr Glu Val Ile Val Ser Ser
        115                 120                 125

<210> SEQ ID NO 295
<211> LENGTH: 384
<212> TYPE: DNA
<213> ORGANISM: Artificial Sequence
<220> FEATURE:
<223> OTHER INFORMATION: HC DNA

<400> SEQUENCE: 295
acgaattcgg ccgtgacgtt ggacgagtcc gggggcggcc tccagacgcc cggaggaacg      60
ctcagcctcg tctgcaaggc ctccgggttc gacttcagca gctacgaaat gctctgggtg     120
cgacaggcgc ccggcaaggg gctggcatac gtcgctggta tcggcgacgg tgctagttac     180
tcagcatacg gggtggcggt gaagggccga gccaccatct cgagggacaa cgggcagagc     240
acagtgaggc tgcagctgaa caacctcagg gctgaggaca ccggcaccta ctactgcgcc     300
aaagcttccg agggttccta ctggtattat gaaactggtg gtatcgacac atggggccac     360
gggaccgaag tcatcgtctc ctcg                                            384

<210> SEQ ID NO 296
<211> LENGTH: 8
<212> TYPE: PRT
<213> ORGANISM: Artificial Sequence
<220> FEATURE:
<223> OTHER INFORMATION: CDR1-LC

<400> SEQUENCE: 296

Ser Gly Gly Gly Gly Ser Tyr Gly
1               5

<210> SEQ ID NO 297
<211> LENGTH: 7
<212> TYPE: PRT
<213> ORGANISM: Artificial Sequence
<220> FEATURE:
<223> OTHER INFORMATION: CDR3-LC

<400> SEQUENCE: 297

Tyr Asn Asp Lys Arg Pro Ser
1               5

<210> SEQ ID NO 298
<211> LENGTH: 8
<212> TYPE: PRT
<213> ORGANISM: Artificial Sequence
<220> FEATURE:
<223> OTHER INFORMATION: CDR3-LC

<400> SEQUENCE: 298

Gly Ser Ala Gly Asn Ser Gly Ala
1               5

<210> SEQ ID NO 299
<211> LENGTH: 101
<212> TYPE: PRT
<213> ORGANISM: Artificial Sequence
<220> FEATURE:
<223> OTHER INFORMATION: LC Protein

<400> SEQUENCE: 299

Ala Leu Thr Gln Pro Ser Ser Val Ser Ala Asn Leu Gly Gly Thr Val
1               5                   10                  15

Lys Ile Thr Cys Ser Gly Gly Gly Gly Ser Tyr Gly Trp Phe Gln Gln
                20                  25                  30

Lys Ser Pro Gly Ser Ala Pro Val Thr Val Ile Tyr Tyr Asn Asp Lys
            35                  40                  45

Arg Pro Ser Asp Ile Pro Ser Arg Phe Ser Gly Ser Lys Ser Gly Ser
        50                  55                  60

Thr Ala Thr Leu Thr Ile Thr Gly Val Arg Ala Glu Asp Glu Ala Val
65                  70                  75                  80

Tyr Phe Cys Gly Ser Ala Gly Asn Ser Gly Ala Phe Gly Ala Gly Thr
                85                  90                  95

Thr Leu Thr Val Leu
            100

<210> SEQ ID NO 300
<211> LENGTH: 303
<212> TYPE: DNA
<213> ORGANISM: Artificial Sequence
<220> FEATURE:
<223> OTHER INFORMATION: LC DNA

<400> SEQUENCE: 300
gccctgactc agccgtcctc ggtgtcagca aacctgggag gaaccgtcaa gatcacctgc          60
tccgggggtg gtggcagcta tggctggttc cagcagaagt ctcctggcag tgccctgtc         120 actgtgatct attacaacga caagagaccc tcggacatcc cttcacgatt ctccggttcc        180
aaatccggct ccacagccac attaaccatc actggggtcc gagccgagga cgaggctgtc        240
tatttctgtg ggagtgcagg caacagtggt gcatttgggg ccgggacaac cctgaccgtc        300
ctt                                                                      303

<210> SEQ ID NO 301
<211> LENGTH: 7
<212> TYPE: PRT
<213> ORGANISM: Artificial Sequence
<220> FEATURE:
<223> OTHER INFORMATION: Ab75 (LM-203 or MCT1 3311 A07) - CDR1-HC -continued

<400> SEQUENCE: 301

Gly Phe Asp Phe Ser Asn Tyr
1               5

<210> SEQ ID NO 302
<211> LENGTH: 6
<212> TYPE: PRT
<213> ORGANISM: Artificial Sequence
<220> FEATURE:
<223> OTHER INFORMATION: CDR2-HC

<400> SEQUENCE: 302

Gly Asp Ser Ala Ser Tyr
1               5

<210> SEQ ID NO 303
<211> LENGTH: 16
<212> TYPE: PRT
<213> ORGANISM: Artificial Sequence
<220> FEATURE:
<223> OTHER INFORMATION: CDR3-HC

<400> SEQUENCE: 303

Ala Ser Glu Gly Ser Tyr Trp Tyr Tyr Glu Ala Gly Gly Ile Asp Thr
1               5                   10                  15

<210> SEQ ID NO 304
<211> LENGTH: 125
<212> TYPE: PRT
<213> ORGANISM: Artificial Sequence
<220> FEATURE:
<223> OTHER INFORMATION: HC Protein

<400> SEQUENCE: 304

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Asn Tyr
            20                  25                  30

Glu Met Leu Trp Val Arg Gln Ala Pro Gly Lys Gly Leu Glu Tyr Val
        35                  40                  45

Ala Gly Ile Gly Asp Ser Ala Ser Tyr Ser Ala Tyr Gly Val Ala Val
    50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125

<210> SEQ ID NO 305
<211> LENGTH: 384
<212> TYPE: DNA
<213> ORGANISM: Artificial Sequence
<220> FEATURE:
<223> OTHER INFORMATION: HC DNA

<400> SEQUENCE: 305
acgaattcgg ccgtgacgtt ggacgagtcc gggggcggcc tccagacgcc cggaggaacg      60
ctcagcctcg tctgcaaggc ctccgggttc gacttcagca actacgaaat gctctgggtg     120

-continued

```
cgacaggcgc ccggcaaggg gctggaatac gtcgctggta ttggcgacag tgctagttac      180
tcagcatacg gggtggcggt gaagggccgt gccaccatct cgagggacaa cgggcagagc      240
acactgaggc tgcagctgaa cggcctcagg gctgaggaca ccggcaccta ctactgcacc      300
aaagcttccg agggttccta ctggtattat gaagctggtg gtatcgacac atggggccac      360
gggaccgaag tcatcgtctc ctcg                                             384
```

```
<210> SEQ ID NO 306
<211> LENGTH: 8
<212> TYPE: PRT
<213> ORGANISM: Artificial Sequence
<220> FEATURE:
<223> OTHER INFORMATION: CDR1-LC

<400> SEQUENCE: 306

Ser Gly Gly Ser Gly Ser Tyr Gly
1               5

<210> SEQ ID NO 307
<211> LENGTH: 7
<212> TYPE: PRT
<213> ORGANISM: Artificial Sequence
<220> FEATURE:
<223> OTHER INFORMATION: CDR2-LC

<400> SEQUENCE: 307

Ala Asn Thr Asn Arg Pro Ser
1               5

<210> SEQ ID NO 308
<211> LENGTH: 10
<212> TYPE: PRT
<213> ORGANISM: Artificial Sequence
<220> FEATURE:
<223> OTHER INFORMATION: CDR3-LC

<400> SEQUENCE: 308

Gly Ser Ala Asp Ser Thr Gly Ala Gly Met
1               5                   10

<210> SEQ ID NO 309
<211> LENGTH: 103
<212> TYPE: PRT
<213> ORGANISM: Artificial Sequence
<220> FEATURE:
<223> OTHER INFORMATION: LC Protein

<400> SEQUENCE: 309

Ala Leu Thr Gln Pro Ser Ser Val Ser Leu Asn Leu Gly Gly Thr Val
1               5                   10                  15

Lys Ile Thr Cys Ser Gly Gly Ser Gly Ser Tyr Gly Trp Phe Gln Gln
            20                  25                  30

Lys Ser Pro Gly Ser Ala Pro Val Thr Leu Ile Tyr Ala Asn Thr Asn
        35                  40                  45

Arg Pro Ser Asp Ile Pro Ser Arg Phe Ser Gly Ser Lys Ser Gly Ser
    50                  55                  60

Thr Asn Thr Leu Thr Ile Thr Gly Val Gln Ala Glu Asp Glu Ala Ile
65                  70                  75                  80

Tyr Tyr Cys Gly Ser Ala Asp Ser Thr Gly Ala Gly Met Phe Gly Ala
                85                  90                  95

Gly Thr Thr Leu Thr Val Leu
```

-continued

```
            100
```

```
<210> SEQ ID NO 310
<211> LENGTH: 309
<212> TYPE: DNA
<213> ORGANISM: Artificial Sequence
<220> FEATURE:
<223> OTHER INFORMATION: LC DNA

<400> SEQUENCE: 310
gccctgactc agccgtcctc ggtgtcacta aacctgggag gaaccgtcaa gatcacctgc      60
tccgggggta gtggcagcta cggctggttc cagcagaagt cacctggcag tgccctgtc      120 actctgatct atgctaatac caacagaccc tcagacatcc cttcacgatt ctccggttcc      180
aaatctggct ccacaaacac attaaccatc actggggtcc aagccgagga cgaggctatc      240
tattactgtg ggagtgcaga cagcactggt gctggtatgt ttggggccgg dacaaccctg      300
accgtcctt                                                              309
```

```
<210> SEQ ID NO 311
<211> LENGTH: 7
<212> TYPE: PRT
<213> ORGANISM: Artificial Sequence
<220> FEATURE:
<223> OTHER INFORMATION: Ab76 (LM-204 or MCT1 3311 B11) - CDR1-HC

<400> SEQUENCE: 311

Gly Phe Asp Phe Ser Asn Tyr
1               5
```

```
<210> SEQ ID NO 312
<211> LENGTH: 6
<212> TYPE: PRT
<213> ORGANISM: Artificial Sequence
<220> FEATURE:
<223> OTHER INFORMATION: CDR2-HC

<400> SEQUENCE: 312

Gly Asp Ser Ala Ser Tyr
1               5
```

```
<210> SEQ ID NO 313
<211> LENGTH: 16
<212> TYPE: PRT
<213> ORGANISM: Artificial Sequence
<220> FEATURE:
<223> OTHER INFORMATION: CDR3-HC

<400> SEQUENCE: 313

Ala Ser Glu Gly Ser Tyr Trp Tyr Tyr Glu Ala Gly Gly Ile Asp Thr
1               5                   10                  15
```

```
<210> SEQ ID NO 314
<211> LENGTH: 125
<212> TYPE: PRT
<213> ORGANISM: Artificial Sequence
<220> FEATURE:
<223> OTHER INFORMATION: HC Protein

<400> SEQUENCE: 314

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Asn Tyr
            20                  25                  30
```

-continued

```
Glu Met Leu Trp Val Arg Gln Ala Pro Gly Lys Gly Leu Glu Tyr Val
    35                  40                  45

Ala Gly Ile Gly Asp Ser Ala Ser Tyr Ser Ala Tyr Gly Val Ala Val
    50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125
```

<210> SEQ ID NO 315
<211> LENGTH: 384
<212> TYPE: DNA
<213> ORGANISM: Artificial Sequence
<220> FEATURE:
<223> OTHER INFORMATION: HC DNA

<400> SEQUENCE: 315

```
acgaattcgg ccgtgacgtt ggacgagtcc gggggcggcc tccagacgcc cggaggaacg      60
ctcagcctcg tctgcaaggc ctccgggttc gacttcagca actacgaaat gctctgggtg     120
cgacaggcgc ccggcaaggg gctggaatac gtcgctggta ttggcgacag tgctagttac     180
tcagcatacg gggtggcggt gaagggccgt gccaccatct cgagggacaa cgggcagagc     240
acactgaggc tgcagctgaa cggcctcagg gctgaggaca ccggcaccta ctactgcacc     300
aaagcttccg agggttccta ctggtattat gaagctggtg gtatcgacac atggggccac     360
gggaccgaag tcatcgtctc ctcg                                            384
```

<210> SEQ ID NO 316
<211> LENGTH: 8
<212> TYPE: PRT
<213> ORGANISM: Artificial Sequence
<220> FEATURE:
<223> OTHER INFORMATION: CDR1-LC

<400> SEQUENCE: 316

```
Ser Gly Gly Gly Gly Ser Tyr Gly
1               5
```

<210> SEQ ID NO 317
<211> LENGTH: 7
<212> TYPE: PRT
<213> ORGANISM: Artificial Sequence
<220> FEATURE:
<223> OTHER INFORMATION: CDR2-LC

<400> SEQUENCE: 317

```
Tyr Asn Asp Lys Arg Pro Ser
1               5
```

<210> SEQ ID NO 318
<211> LENGTH: 8
<212> TYPE: PRT
<213> ORGANISM: Artificial Sequence
<220> FEATURE:
<223> OTHER INFORMATION: CDR3-LC

<400> SEQUENCE: 318

```
Gly Ser Ala Gly Asn Ser Gly Ala
```

1                5

<210> SEQ ID NO 319
<211> LENGTH: 101
<212> TYPE: PRT
<213> ORGANISM: Artificial Sequence
<220> FEATURE:
<223> OTHER INFORMATION: LC Protein

<400> SEQUENCE: 319

Ala Leu Thr Gln Pro Ser Ser Val Ser Ala Asn Leu Gly Gly Thr Val
1                5                    10                  15

Lys Ile Thr Cys Ser Gly Gly Gly Gly Ser Tyr Gly Trp Phe Gln Gln
            20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Arg Ala Glu Asp Glu Ala Val
65                  70                  75                  80

Tyr Phe Cys Gly Ser Ala Gly Asn Ser Gly Ala Phe Gly Ala Gly Thr
                85                  90                  95

Thr Leu Thr Val Leu
            100

<210> SEQ ID NO 320
<211> LENGTH: 303
<212> TYPE: DNA
<213> ORGANISM: Artificial Sequence
<220> FEATURE:
<223> OTHER INFORMATION: LC DNA

<400> SEQUENCE: 320
gccctgactc agccgtcctc ggtgtcagca aacctgggag gaaccgtcaa gatcacctgc      60
tccgggggtg gtggcagcta tggctggttc cagcagaagt ctcctggcag tgcccctgtc     120
actgtgatct attacaacga caagagaccc tcggacatcc cttcacgatt ctccggttcc     180
aaatccggct ccacgggcac attaaccatc actggggtcc gagccgagga cgaggctgtc     240
tatttctgtg ggagtgcagg caacagtggt gcatttgggg ccgggacaac cctgaccgtc     300
ctt                                                                 303

<210> SEQ ID NO 321
<211> LENGTH: 7
<212> TYPE: PRT
<213> ORGANISM: Artificial Sequence
<220> FEATURE:
<223> OTHER INFORMATION: Ab77 (LM-205 or MCT1 3311 C05) - CDR1-HC

<400> SEQUENCE: 321

Gly Phe Asp Phe Ser Asn Tyr
1                5

<210> SEQ ID NO 322
<211> LENGTH: 6
<212> TYPE: PRT
<213> ORGANISM: Artificial Sequence
<220> FEATURE:
<223> OTHER INFORMATION: CDR2-HC

<400> SEQUENCE: 322

Gly Asp Ser Ala Ser Tyr 1               5

<210> SEQ ID NO 323
<211> LENGTH: 16
<212> TYPE: PRT
<213> ORGANISM: Artificial Sequence
<220> FEATURE:
<223> OTHER INFORMATION: CDR3-HC

<400> SEQUENCE: 323

Ala Ser Glu Gly Ser Tyr Trp Tyr Tyr Glu Ala Gly Gly Ile Asp Thr
1               5                   10                  15

<210> SEQ ID NO 324
<211> LENGTH: 384
<212> TYPE: PRT
<213> ORGANISM: Artificial Sequence
<220> FEATURE:
<223> OTHER INFORMATION: HC Protein

<400> SEQUENCE: 324

Ala Cys Gly Ala Ala Thr Thr Cys Gly Gly Cys Cys Gly Thr Gly Ala
1               5                   10                  15

Cys Gly Thr Thr Gly Gly Ala Cys Gly Ala Gly Thr Cys Cys Gly Gly
                20                  25                  30

Gly Gly Gly Cys Gly Gly Cys Cys Thr Cys Cys Gly Gly Ala Cys Gly
            35                  40                  45

Cys Cys Cys Gly Gly Ala Gly Gly Ala Ala Cys Gly Cys Thr Cys Ala
        50                  55                  60

Gly Cys Cys Thr Cys Gly Thr Cys Thr Gly Cys Ala Ala Gly Gly Cys
65                  70                  75                  80

Cys Thr Cys Cys Gly Gly Gly Thr Thr Cys Gly Ala Cys Thr Thr Cys
                85                  90                  95

Ala Gly Cys Ala Ala Cys Thr Ala Cys Gly Ala Ala Thr Gly Cys
            100                 105                 110

Thr Cys Thr Gly Gly Gly Thr Gly Cys Gly Ala Cys Ala Gly Gly Cys
        115                 120                 125

Gly Cys Cys Cys Gly Gly Cys Ala Ala Gly Gly Gly Cys Thr Gly
    130                 135                 140

Gly Ala Ala Thr Ala Cys Gly Thr Cys Gly Cys Thr Gly Gly Thr Ala
145                 150                 155                 160

Thr Thr Gly Gly Cys Gly Ala Cys Ala Gly Thr Gly Cys Thr Ala Gly
                165                 170                 175

Thr Thr Ala Cys Thr Cys Ala Gly Cys Ala Thr Ala Cys Gly Gly Gly
            180                 185                 190

Gly Thr Gly Gly Cys Gly Gly Thr Gly Ala Ala Gly Gly Gly Cys Cys
            195                 200                 205

Gly Thr Gly Cys Cys Ala Cys Cys Ala Thr Cys Thr Cys Gly Ala Gly
    210                 215                 220

Gly Gly Ala Cys Ala Ala Cys Gly Gly Gly Cys Ala Gly Ala Gly Cys
225                 230                 235                 240

Ala Cys Ala Cys Thr Gly Ala Gly Gly Cys Thr Gly Cys Ala Gly Cys
            245                 250                 255

Thr Gly Ala Ala Cys Gly Gly Cys Cys Thr Cys Ala Gly Gly Gly Cys
            260                 265                 270

Thr Gly Ala Gly Gly Ala Cys Ala Cys Cys Gly Gly Cys Ala Cys Cys
        275                 280                 285

-continued

```
Thr Ala Cys Thr Ala Cys Thr Gly Cys Ala Cys Cys Ala Ala Ala Gly
    290                 295                 300

Cys Thr Thr Cys Cys Gly Ala Gly Gly Gly Thr Thr Cys Cys Thr Ala
305                 310                 315                 320

Cys Thr Gly Gly Thr Ala Thr Thr Ala Thr Gly Ala Ala Gly Cys Thr
                325                 330                 335

Gly Gly Thr Gly Gly Thr Ala Thr Cys Gly Ala Cys Ala Cys Ala Thr
                340                 345                 350

Gly Gly Gly Gly Cys Cys Ala Cys Gly Gly Ala Cys Cys Gly Ala
        355                 360                 365

Ala Gly Thr Cys Ala Thr Cys Gly Thr Cys Thr Cys Cys Thr Cys Gly
    370                 375                 380
```

<210> SEQ ID NO 325
<211> LENGTH: 384
<212> TYPE: DNA
<213> ORGANISM: Artificial Sequence
<220> FEATURE:
<223> OTHER INFORMATION: HC DNA

<400> SEQUENCE: 325

```
acgaattcgg ccgtgacgtt ggacgagtcc gggggcggcc tccggacgcc cggaggaacg      60
ctcagcctcg tctgcaaggc ctccgggttc gacttcagca actacgaaat gctctgggtg     120
cgacaggcgc ccggcaaggg gctggaatac gtcgctggta ttggcgacag tgctagttac     180
tcagcatacg gggtggcggt gaagggccgt gccaccatct cgagggacaa cgggcagagc     240
acactgaggc tgcagctgaa cggcctcagg gctgaggaca ccggcaccta ctactgcacc     300
aaagcttccg agggttccta ctggtattat gaagctggtg gtatcgacac atggggccac     360
gggaccgaag tcatcgtctc ctcg                                           384
```

<210> SEQ ID NO 326
<211> LENGTH: 8
<212> TYPE: PRT
<213> ORGANISM: Artificial Sequence
<220> FEATURE:
<223> OTHER INFORMATION: CDR1-LC

<400> SEQUENCE: 326

```
Ser Gly Gly Gly Gly Ser Tyr Gly
1               5
```

<210> SEQ ID NO 327
<211> LENGTH: 7
<212> TYPE: PRT
<213> ORGANISM: Artificial Sequence
<220> FEATURE:
<223> OTHER INFORMATION: CDR2-LC

<400> SEQUENCE: 327

```
Tyr Asn Asp Lys Arg Pro Ser
1               5
```

<210> SEQ ID NO 328
<211> LENGTH: 8
<212> TYPE: PRT
<213> ORGANISM: Artificial Sequence
<220> FEATURE:
<223> OTHER INFORMATION: CDR3-LC

<400> SEQUENCE: 328

```
Gly Ser Ala Gly Asn Ser Gly Ala
```

-continued

```
1               5

<210> SEQ ID NO 329
<211> LENGTH: 101
<212> TYPE: PRT
<213> ORGANISM: Artificial Sequence
<220> FEATURE:
<223> OTHER INFORMATION: LC Protein

<400> SEQUENCE: 329

Ala Leu Thr Gln Pro Ser Ser Val Ser Ala Asn Leu Gly Gly Thr Val
1               5                   10                  15

Lys Ile Thr Cys Ser Gly Gly Gly Gly Ser Tyr Gly Trp Phe Gln Gln
                20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Arg Ala Glu Asp Glu Ala Val
65                  70                  75                  80

Tyr Phe Cys Gly Ser Ala Gly Asn Ser Gly Ala Phe Gly Ala Gly Thr
                85                  90                  95

Thr Leu Thr Val Leu
            100

<210> SEQ ID NO 330
<211> LENGTH: 303
<212> TYPE: DNA
<213> ORGANISM: Artificial Sequence
<220> FEATURE:
<223> OTHER INFORMATION: LC DNA

<400> SEQUENCE: 330
gccctgactc agccgtcctc ggtgtcagca aacctgggag gaaccgtcaa gatcacctgc      60
tccgggggtg gtggcagcta tggctggttc cagcagaagt ctcctggcag tgccctgtc      120 actgtgatct attacaacga caagagaccc tcagacatcc cttcacgatt ctccggttcc      180
aaatccggct ccacgggcac attaaccatc actggggtcc gagccgagga cgaggctgtc      240
tatttctgtg ggagtgcagg caacagtggt gcatttgggg ccgggacaac cctgaccgtc      300
ctt                                                                    303

<210> SEQ ID NO 331
<211> LENGTH: 7
<212> TYPE: PRT
<213> ORGANISM: Artificial Sequence
<220> FEATURE:
<223> OTHER INFORMATION: Ab78 (LM-206 or MCT1 3311 F10) - CDR1-HC

<400> SEQUENCE: 331

Gly Phe Asp Phe Ser Asn Tyr
1               5

<210> SEQ ID NO 332
<211> LENGTH: 6
<212> TYPE: PRT
<213> ORGANISM: Artificial Sequence
<220> FEATURE:
<223> OTHER INFORMATION: CDR2-HC

<400> SEQUENCE: 332

Gly Asp Ser Ala Ser Tyr
```

```
1               5
```

<210> SEQ ID NO 333
<211> LENGTH: 16
<212> TYPE: PRT
<213> ORGANISM: Artificial Sequence
<220> FEATURE:
<223> OTHER INFORMATION: CDR3-HC

<400> SEQUENCE: 333

```
Ala Ser Glu Gly Ser Tyr Trp Tyr Tyr Glu Ala Gly Gly Ile Asp Thr
1               5                   10                  15
```

<210> SEQ ID NO 334
<211> LENGTH: 125
<212> TYPE: PRT
<213> ORGANISM: Artificial Sequence
<220> FEATURE:
<223> OTHER INFORMATION: HC Protein

<400> SEQUENCE: 334

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Asp Phe Ser Asn Tyr
                20                  25                  30

Glu Met Leu Trp Val Arg Gln Ala Pro Gly Lys Gly Leu Glu Tyr Val
            35                  40                  45

Ala Gly Ile Gly Asp Ser Ala Ser Tyr Ser Ala Tyr Gly Val Ala Val
        50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125
```

<210> SEQ ID NO 335
<211> LENGTH: 384
<212> TYPE: DNA
<213> ORGANISM: Artificial Sequence
<220> FEATURE:
<223> OTHER INFORMATION: HC DNA

<400> SEQUENCE: 335

```
acgaattcgg ccgtgacgtt ggacgagtcc gggggcggcc tccagacgcc cggaggagcg     60
ctcagcctcg tctgcaaggc ctccgggttc gacttcagca actacgaaat gctctgggtg    120
cgacaggcgc ccggcaaggg gctggaatac gtcgctggta ttggcgacag tgctagttac    180
tcagcatacg gggtggcggt gaagggccgt gccaccatct cgaggacaa cgggcagagc     240 acactgaggc tgcagctgaa cggcctcagg gctgaggaca ccggcaccta ctactgcacc    300
aaagcttccg agggttccta ctggtattat gaagctggtg gtatcgacac atggggccac    360
gggaccgaag tcatcgtctc ctcg                                           384
```

<210> SEQ ID NO 336
<211> LENGTH: 8
<212> TYPE: PRT
<213> ORGANISM: Artificial Sequence
<220> FEATURE:

<223> OTHER INFORMATION: CDR1-LC

<400> SEQUENCE: 336

Ser Gly Gly Gly Gly Ser Tyr Gly
1               5

<210> SEQ ID NO 337
<211> LENGTH: 7
<212> TYPE: PRT
<213> ORGANISM: Artificial Sequence
<220> FEATURE:
<223> OTHER INFORMATION: CDR2-LC

<400> SEQUENCE: 337

Tyr Asn Asp Lys Arg Pro Ser
1               5

<210> SEQ ID NO 338
<211> LENGTH: 8
<212> TYPE: PRT
<213> ORGANISM: Artificial Sequence
<220> FEATURE:
<223> OTHER INFORMATION: CDR3-LC

<400> SEQUENCE: 338

Gly Ser Ala Gly Asn Ser Gly Ala
1               5

<210> SEQ ID NO 339
<211> LENGTH: 101
<212> TYPE: PRT
<213> ORGANISM: Artificial Sequence
<220> FEATURE:
<223> OTHER INFORMATION: LC Protein

<400> SEQUENCE: 339

Ala Leu Thr Gln Pro Ser Ser Val Ser Ala Asn Leu Gly Gly Thr Val
1               5                   10                  15

Lys Ile Thr Cys Ser Gly Gly Gly Ser Tyr Gly Trp Phe Gln Gln
            20                  25                  30

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Arg Ala Glu Asp Glu Ala Val
65                  70                  75                  80

Tyr Phe Cys Gly Ser Ala Gly Asn Ser Gly Ala Phe Gly Ala Gly Thr
                85                  90                  95

Thr Leu Thr Val Leu
            100

<210> SEQ ID NO 340
<211> LENGTH: 303
<212> TYPE: DNA
<213> ORGANISM: Artificial Sequence
<220> FEATURE:
<223> OTHER INFORMATION: LC DNA

<400> SEQUENCE: 340
gccctgactc agccgtcctc ggtgtcagca aacctgggag gaaccgtcaa gatcacctgc      60
tccgggggtg gtggcagcta tggctggttc cagcagaagt ctcctggcag tgccctgtc      120 actgtgatct attacaacga caagagaccc tcggacatcc cttcacgatt ctccggttcc      180

```
aaatccggct ccacgggcac attaaccatc actggggtcc gagccgagga cgaggctgtc    240
tatttctgtg ggagtgcagg caacagtggt gcatttgggg ccgggacaac cctgaccgtc    300
ctt                                                                  303
```

<210> SEQ ID NO 341
<211> LENGTH: 7
<212> TYPE: PRT
<213> ORGANISM: Artificial Sequence
<220> FEATURE:
<223> OTHER INFORMATION: Ab79 (LM-207 or MCT1 3311 G09) - CDR1-HC

<400> SEQUENCE: 341

Gly Phe Asp Phe Ser Asn Tyr
1               5

<210> SEQ ID NO 342
<211> LENGTH: 6
<212> TYPE: PRT
<213> ORGANISM: Artificial Sequence
<220> FEATURE:
<223> OTHER INFORMATION: CDR2-HC

<400> SEQUENCE: 342

Gly Asp Ser Ala Ser Tyr
1               5

<210> SEQ ID NO 343
<211> LENGTH: 16
<212> TYPE: PRT
<213> ORGANISM: Artificial Sequence
<220> FEATURE:
<223> OTHER INFORMATION: CDR3-HC

<400> SEQUENCE: 343

Ala Ser Glu Gly Ser Tyr Trp Tyr Tyr Glu Ala Gly Gly Ile Asp Thr
1               5                   10                  15

<210> SEQ ID NO 344
<211> LENGTH: 125
<212> TYPE: PRT
<213> ORGANISM: Artificial Sequence
<220> FEATURE:
<223> OTHER INFORMATION: HC Protein

<400> SEQUENCE: 344

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Asn Tyr
            20                  25                  30

Glu Met Leu Trp Val Arg Gln Ala Pro Gly Lys Gly Leu Glu Tyr Val
            35                  40                  45

Ala Gly Ile Gly Asp Ser Ala Ser Tyr Ser Ala Tyr Gly Val Ala Val
        50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
            115                 120                 125

-continued

```
<210> SEQ ID NO 345
<211> LENGTH: 384
<212> TYPE: DNA
<213> ORGANISM: Artificial Sequence
<220> FEATURE:
<223> OTHER INFORMATION: HC DNA

<400> SEQUENCE: 345
acgaattcgg ccgtgacgtt ggacgagtcc gggggcggcc tccagacgcc cggaggaacg      60
ctcagcctcg tctgcaaggc ctccgggttc gacttcagca actacgaaat gctctgggtg     120
cgacaggcgc ccggcaaggg gctggaatac gtcgctggta ttggcgacag tgctagttac     180
tcagcatacg gggtggcggt gaagggccgt gccaccatct cgagggacaa cgggcagagc     240
acactgaggc tgcagctgaa cggcctcagg gctgaggaca ccggcaccta ctactgcacc     300
aaagcttccg agggttccta ctggtattat gaagctggtg gtatcgacac atggggccac     360
gggaccgaag tcatcgtctc ctcg                                           384

<210> SEQ ID NO 346
<211> LENGTH: 8
<212> TYPE: PRT
<213> ORGANISM: Artificial Sequence
<220> FEATURE:
<223> OTHER INFORMATION: CDR1-LC

<400> SEQUENCE: 346

Ser Gly Gly Gly Gly Ser Tyr Gly
1               5

<210> SEQ ID NO 347
<211> LENGTH: 7
<212> TYPE: PRT
<213> ORGANISM: Artificial Sequence
<220> FEATURE:
<223> OTHER INFORMATION: CDR2-LC

<400> SEQUENCE: 347

Tyr Asn Asp Lys Arg Pro Ser
1               5

<210> SEQ ID NO 348
<211> LENGTH: 8
<212> TYPE: PRT
<213> ORGANISM: Artificial Sequence
<220> FEATURE:
<223> OTHER INFORMATION: CDR3-LC

<400> SEQUENCE: 348

Gly Ser Ala Gly Asn Ser Gly Ala
1               5

<210> SEQ ID NO 349
<211> LENGTH: 101
<212> TYPE: PRT
<213> ORGANISM: Artificial Sequence
<220> FEATURE:
<223> OTHER INFORMATION: LC Protein

<400> SEQUENCE: 349

Ala Leu Thr Gln Pro Ser Ser Val Ser Ala Asn Leu Gly Gly Thr Val
1               5                   10                  15

Lys Ile Thr Cys Ser Gly Gly Gly Gly Ser Tyr Gly Trp Phe Gln Gln
            20                  25                  30
```

-continued

Lys Ser Pro Gly Ser Ala Pro Val Thr Val Ile Tyr Tyr Asn Asp Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Arg Ala Glu Asp Glu Ala Val
65                  70                  75                  80

Tyr Phe Cys Gly Ser Ala Gly Asn Ser Gly Ala Phe Gly Ala Gly Thr
                85                  90                  95

Thr Leu Thr Val Leu
            100

<210> SEQ ID NO 350
<211> LENGTH: 303
<212> TYPE: DNA
<213> ORGANISM: Artificial Sequence
<220> FEATURE:
<223> OTHER INFORMATION: LC DNA

<400> SEQUENCE: 350
gccctgactc agccgtcctc ggtgtcagca aacctgggag gaaccgtcaa gatcacctgc      60
tccgggggtg gtggcagcta tggctggttc cagcagaagt ctcctggcag tgcccctgtc     120
actgtgatct attacaacga caagagaccc tcggacatcc cttcacgatt ctccggttcc     180
aaatccggct ccacgggcac attaaccatc actggggtcc gagccgagga cgaggctgtc     240
tatttctgtg ggagtgcagg caacagtggt gcatttgggg ccgggacaac cctgaccgtc     300
ctt                                                                    303

<210> SEQ ID NO 351
<211> LENGTH: 7
<212> TYPE: PRT
<213> ORGANISM: Artificial Sequence
<220> FEATURE:
<223> OTHER INFORMATION: Ab80 (LM-208 or MCT1 3312 H10) - CDR1-HC

<400> SEQUENCE: 351

Gly Phe Ser Phe Ser Ser Arg
1               5

<210> SEQ ID NO 352
<211> LENGTH: 6
<212> TYPE: PRT
<213> ORGANISM: Artificial Sequence
<220> FEATURE:
<223> OTHER INFORMATION: CDR2-HC

<400> SEQUENCE: 352

Asp Asn Asp Gly Gly Tyr
1               5

<210> SEQ ID NO 353
<211> LENGTH: 15
<212> TYPE: PRT
<213> ORGANISM: Artificial Sequence
<220> FEATURE:
<223> OTHER INFORMATION: CDR3-HC

<400> SEQUENCE: 353

Gly Ala Tyr Gly Gly Gly Trp Tyr Ala Ala Ser Ser Ile Asp Ala
1               5                   10                  15

<210> SEQ ID NO 354

<211> LENGTH: 124
<212> TYPE: PRT
<213> ORGANISM: Artificial Sequence
<220> FEATURE:
<223> OTHER INFORMATION: HC Protein

<400> SEQUENCE: 354

```
Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Ser Phe Ser Ser Arg
            20                  25                  30

Gly Met Phe Trp Val Arg Gln Ala Pro Gly Lys Gly Leu Glu Tyr Val
        35                  40                  45

Ala Gly Ile Asp Asn Asp Gly Gly Tyr Pro Asn Tyr Gly Ser Ala Val
    50                  55                  60

Lys Gly Arg Ala Thr Ile Ser Arg Asp Asn Arg Gln Ser Thr Val Arg
65                  70                  75                  80

Leu Gln Leu Asn Asn Leu Arg Ala Asp Asp Thr Gly Thr Tyr Tyr Cys
                85                  90                  95

Ala Lys Gly Ala Tyr Gly Gly Gly Trp Tyr Ala Ala Ser Ser Ile Asp
            100                 105                 110

Ala Trp Gly His Gly Thr Glu Val Ile Val Ser Ser
            115                 120
```

<210> SEQ ID NO 355
<211> LENGTH: 384
<212> TYPE: DNA
<213> ORGANISM: Artificial Sequence
<220> FEATURE:
<223> OTHER INFORMATION: HC DNA

<400> SEQUENCE: 355

```
gtcacgaatt cggccgtgac gttggacgag tccggggggcg gcctccagac gcccggagga      60
gggctcagcc tcgtctgcaa ggcctccggg ttctccttca gcagccgggg catgttctgg     120
gtgcgacagg cacctggcaa ggggctggaa tacgttgcgg gtattgataa tgatggtggt     180
tacccaaact acgggtcggc ggtgaagggc cgtgccacca tctcgaggga caacaggcag     240
agcacagtga ggctgcagct gaacaacctc agggctgacg acaccggcac ctactactgc     300
gccaagggtg cttatggtgg tggttggtat gccgctagta gcatcgacgc atggggccac     360
gggaccgaag tcatcgtctc ctcg                                          384
```

<210> SEQ ID NO 356
<211> LENGTH: 10
<212> TYPE: PRT
<213> ORGANISM: Artificial Sequence
<220> FEATURE:
<223> OTHER INFORMATION: CDR1-LC

<400> SEQUENCE: 356

```
Ser Gly Gly Gly Ser Ser Ser Tyr Tyr Gly
1               5                   10
```

<210> SEQ ID NO 357
<211> LENGTH: 7
<212> TYPE: PRT
<213> ORGANISM: Artificial Sequence
<220> FEATURE:
<223> OTHER INFORMATION: CDR2-LC

<400> SEQUENCE: 357

-continued

```
Asp Asn Asn Lys Arg Pro Ser
1               5

<210> SEQ ID NO 358
<211> LENGTH: 11
<212> TYPE: PRT
<213> ORGANISM: Artificial Sequence
<220> FEATURE:
<223> OTHER INFORMATION: CDR3-LC

<400> SEQUENCE: 358

Ala Asn Thr Tyr Ser Asp Gly Asn Asp Ala Pro
1               5                   10

<210> SEQ ID NO 359
<211> LENGTH: 106
<212> TYPE: PRT
<213> ORGANISM: Artificial Sequence
<220> FEATURE:
<223> OTHER INFORMATION: LC Protein

<400> SEQUENCE: 359

Ala Leu Thr Gln Pro Ser Ser Val Ser Ala Lys Ser Gly Glu Thr Val
1               5                   10                  15

Lys Ile Thr Cys Ser Gly Gly Gly Ser Ser Ser Tyr Tyr Gly Trp Tyr
            20                  25                  30

Gln Gln Lys Ser Pro Gly Ser Ala Pro Val Thr Val Ile Tyr Asp Asn
        35                  40                  45

Asn Lys Arg Pro Ser Asn Ile Pro Ser Gln Phe Ser Gly Ser Lys Ser
    50                  55                  60

Gly Ser Thr Ser Thr Leu Thr Ile Thr Gly Val Gln Ala Asp Asp Glu
65                  70                  75                  80

Ala Val Tyr Phe Cys Ala Asn Thr Tyr Ser Asp Gly Asn Asp Ala Pro
                85                  90                  95

Phe Gly Ala Gly Thr Thr Leu Thr Val Leu
            100                 105

<210> SEQ ID NO 360
<211> LENGTH: 318
<212> TYPE: DNA
<213> ORGANISM: Artificial Sequence
<220> FEATURE:
<223> OTHER INFORMATION: LC DNA

<400> SEQUENCE: 360
gccctgactc agccgtcctc ggtgtcagca aagtcaggag aaaccgtcaa gatcacctgc      60
tccgggggtg gtagcagcag ctactatggc tggtatcagc agaagtcacc tggcagtgcc     120
cctgtcactg tgatctatga caacaacaag agaccctcga acatcccttc acaattctcc     180
ggttccaaat ctggctccac aagcacatta accatcactg gggtccaagc cgacgacgag     240
gctgtctatt tctgtgcgaa tacatacagc gacggtaatg atgctccatt tggggccggg     300
acaaccctga ccgtcctt                                                     318

<210> SEQ ID NO 361
<211> LENGTH: 7
<212> TYPE: PRT
<213> ORGANISM: Artificial Sequence
<220> FEATURE:
<223> OTHER INFORMATION: Ab81 (LM-209 or MCT1 3313 A11) - CDR1-HC

<400> SEQUENCE: 361
```

Gly Phe Ser Phe Ser Ser Arg
1               5

<210> SEQ ID NO 362
<211> LENGTH: 6
<212> TYPE: PRT
<213> ORGANISM: Artificial Sequence
<220> FEATURE:
<223> OTHER INFORMATION: CDR2-HC

<400> SEQUENCE: 362

Asp Asn Asp Gly Gly Tyr
1               5

<210> SEQ ID NO 363
<211> LENGTH: 15
<212> TYPE: PRT
<213> ORGANISM: Artificial Sequence
<220> FEATURE:
<223> OTHER INFORMATION: CDR3-HC

<400> SEQUENCE: 363

Gly Ala Tyr Gly Gly Gly Trp Tyr Ala Ala Ser Ser Ile Asp Ala
1               5                   10                  15

<210> SEQ ID NO 364
<211> LENGTH: 124
<212> TYPE: PRT
<213> ORGANISM: Artificial Sequence
<220> FEATURE:
<223> OTHER INFORMATION: HC Protein

<400> SEQUENCE: 364

Ala Val Thr Leu Asp Glu Ser Gly Gly Gly Leu Gln Thr Pro Gly Gly
1               5                   10                  15

Ala Leu Ser Leu Ile Cys Lys Ala Ser Gly Phe Ser Phe Ser Ser Arg
            20                  25                  30

Gly Met Phe Trp Val Arg Gln Ala Pro Gly Lys Gly Leu Glu Tyr Val
            35                  40                  45

Ala Gly Ile Asp Asn Asp Gly Gly Tyr Pro Asn Tyr Gly Ser Ala Val
        50                  55                  60

Lys Gly Arg Ala Thr Ile Ser Arg Asp Asn Arg Gln Ser Thr Val Arg
65                  70                  75                  80

Leu Gln Leu Asn Asn Leu Arg Ala Asp Asp Thr Gly Thr Tyr Tyr Cys
                85                  90                  95

Ala Lys Gly Ala Tyr Gly Gly Gly Trp Tyr Ala Ala Ser Ser Ile Asp
            100                 105                 110

Ala Trp Gly His Gly Thr Glu Val Ile Val Ser Ser
        115                 120

<210> SEQ ID NO 365
<211> LENGTH: 384
<212> TYPE: DNA
<213> ORGANISM: Artificial Sequence
<220> FEATURE:
<223> OTHER INFORMATION: HC DNA

<400> SEQUENCE: 365
gtcacgaatt cggccgtgac gttggacgag tccgggggcg gcctccagac gcccggagga      60
gctctcagcc tcatctgcaa ggcctccggg ttctccttca gcagccgggg catgttctgg     120
gtgcgacagg cacctggcaa ggggctggaa tacgttgcgg gtattgataa tgatggtggt     180

-continued

```
tacccaaact acgggtcggc ggtgaagggc cgtgccacca tctcgaggga caacaggcag      240
agcacagtga ggctgcagct gaacaacctc agggctgacg acaccggcac ctactactgc      300
gccaagggtg cttatggtgg tggttggtat gccgctagta gcatcgacgc atggggccac      360
gggaccgaag tcatcgtctc ctcg                                             384
```

```
<210> SEQ ID NO 366
<211> LENGTH: 9
<212> TYPE: PRT
<213> ORGANISM: Artificial Sequence
<220> FEATURE:
<223> OTHER INFORMATION: CDR1-LC

<400> SEQUENCE: 366

Ser Gly Gly Val Gly Gln Trp Tyr Gly
1               5

<210> SEQ ID NO 367
<211> LENGTH: 7
<212> TYPE: PRT
<213> ORGANISM: Artificial Sequence
<220> FEATURE:
<223> OTHER INFORMATION: CDR2-LC

<400> SEQUENCE: 367

Asp Asn Thr Asn Arg Pro Ser
1               5

<210> SEQ ID NO 368
<211> LENGTH: 11
<212> TYPE: PRT
<213> ORGANISM: Artificial Sequence
<220> FEATURE:
<223> OTHER INFORMATION: CDR3-LC

<400> SEQUENCE: 368

Ala Asn Thr Tyr Ser Asp Gly Asn Asp Ala Pro
1               5                   10

<210> SEQ ID NO 369
<211> LENGTH: 105
<212> TYPE: PRT
<213> ORGANISM: Artificial Sequence
<220> FEATURE:
<223> OTHER INFORMATION: LC Protein

<400> SEQUENCE: 369

Ala Leu Thr Gln Pro Ser Ser Val Ser Ala Asn Pro Gly Glu Ala Val
1               5                   10                  15

Lys Ile Thr Cys Ser Gly Gly Val Gly Gln Trp Tyr Gly Trp Tyr Gln
            20                  25                  30

Gln Lys Ala Pro Gly Ser Ala Pro Val Thr Val Ile Tyr Asp Asn Thr
        35                  40                  45

Asn Arg Pro Ser Asp Ile Pro Ser Arg Phe Ser Gly Ser Lys Ser Gly
    50                  55                  60

Ser Thr Asn Thr Leu Thr Ile Thr Gly Val Gln Ala Glu Asp Glu Ala
65                  70                  75                  80

Val Tyr Phe Cys Ala Asn Thr Tyr Ser Asp Gly Asn Asp Ala Pro Phe
                85                  90                  95

Gly Ala Gly Thr Thr Leu Thr Val Leu
            100                 105
```

```
<210> SEQ ID NO 370
<211> LENGTH: 315
<212> TYPE: DNA
<213> ORGANISM: Artificial Sequence
<220> FEATURE:
<223> OTHER INFORMATION: LC DNA

<400> SEQUENCE: 370
gccctgactc agccgtcctc ggtgtcagca aacccgggag aagccgtcaa gatcacctgc      60
agtggaggtg tcggccagtg gtatggctgg taccagcaga aggcacctgg cagtgcccct     120
gtcactgtga tctatgacaa caccaacaga ccctcggaca tcccttcacg attctccggt     180
tccaaatccg gctccacaaa cacattaacc atcactgggg tccaagccga ggacgaggct     240
gtctatttct gtgcgaatac atacagcgac ggtaatgatg ctccatttgg ggccgggaca     300
accctgaccg tcctt                                                       315
```

```
<210> SEQ ID NO 371
<211> LENGTH: 7
<212> TYPE: PRT
<213> ORGANISM: Artificial Sequence
<220> FEATURE:
<223> OTHER INFORMATION: Ab82 (LM-210 or MCT1 3313 B10) - CDR1-HC

<400> SEQUENCE: 371

Gly Phe Ser Phe Ser Ser Arg
1               5
```

```
<210> SEQ ID NO 372
<211> LENGTH: 6
<212> TYPE: PRT
<213> ORGANISM: Artificial Sequence
<220> FEATURE:
<223> OTHER INFORMATION: CDR2-HC

<400> SEQUENCE: 372

Asp Asn Asp Gly Gly Tyr
1               5
```

```
<210> SEQ ID NO 373
<211> LENGTH: 15
<212> TYPE: PRT
<213> ORGANISM: Artificial Sequence
<220> FEATURE:
<223> OTHER INFORMATION: CDR3-HC

<400> SEQUENCE: 373

Gly Ala Tyr Gly Gly Gly Trp Tyr Ala Ala Ser Ser Ile Asp Ala
1               5                   10                  15
```

```
<210> SEQ ID NO 374
<211> LENGTH: 124
<212> TYPE: PRT
<213> ORGANISM: Artificial Sequence
<220> FEATURE:
<223> OTHER INFORMATION: HC Protein

<400> SEQUENCE: 374

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Ser Phe Ser Ser Arg
            20                  25                  30

Gly Met Phe Trp Val Arg Gln Ala Pro Gly Lys Gly Leu Glu Tyr Val
        35                  40                  45
```

-continued

```
Ala Gly Ile Asp Asn Asp Gly Gly Tyr Pro Asn Tyr Gly Ser Ala Val
    50              55                  60

Lys Gly Arg Ala Thr Ile Ser Arg Asp Asn Arg Gln Ser Thr Val Arg
65              70                  75                  80

Leu Gln Leu Asn Asn Leu Arg Ala Asp Asp Thr Gly Thr Tyr Tyr Cys
                85                  90                  95

Ala Lys Gly Ala Tyr Gly Gly Gly Trp Tyr Ala Ala Ser Ser Ile Asp
            100                 105                 110

Ala Trp Gly His Gly Thr Glu Val Ile Val Ser Ser
        115                 120
```

<210> SEQ ID NO 375
<211> LENGTH: 384
<212> TYPE: DNA
<213> ORGANISM: Artificial Sequence
<220> FEATURE:
<223> OTHER INFORMATION: HC DNA

<400> SEQUENCE: 375

```
gtcacgaatt cggccgtgac gttggacgag tccgggggcg gcctccagac gcccggagga      60
gggctcagcc tcgtctgcaa ggcctccggg ttctccttca gcagccgggg catgttctgg     120
gtgcgacagg cacctggcaa ggggctggaa tacgttgcgg gtattgataa tgatggtggt     180
tacccaaact acgggtcggc ggtgaagggc cgtgccacca tctcgaggga caacaggcag     240
agcacagtga ggctgcagct gaataacctc agggctgacg acaccggcac ctactactgc     300
gccaagggtg cttatggtgg tggttggtat gccgctagta gcatcgacgc atggggccac     360
gggaccgaag tcatcgtctc ctcg                                            384
```

<210> SEQ ID NO 376
<211> LENGTH: 9
<212> TYPE: PRT
<213> ORGANISM: Artificial Sequence
<220> FEATURE:
<223> OTHER INFORMATION: CDR1-LC

<400> SEQUENCE: 376

```
Ser Gly Gly Val Gly Gln Trp Tyr Gly
1               5
```

<210> SEQ ID NO 377
<211> LENGTH: 7
<212> TYPE: PRT
<213> ORGANISM: Artificial Sequence
<220> FEATURE:
<223> OTHER INFORMATION: CDR2-LC

<400> SEQUENCE: 377

```
Asp Asn Ala Asn Arg Pro Ser
1               5
```

<210> SEQ ID NO 378
<211> LENGTH: 11
<212> TYPE: PRT
<213> ORGANISM: Artificial Sequence
<220> FEATURE:
<223> OTHER INFORMATION: CDR3-LC

<400> SEQUENCE: 378

```
Ala Asn Thr Tyr Ser Asp Gly Asn Asp Ala Pro
1               5                   10
```

-continued

```
<210> SEQ ID NO 379
<211> LENGTH: 105
<212> TYPE: PRT
<213> ORGANISM: Artificial Sequence
<220> FEATURE:
<223> OTHER INFORMATION: LC Protein

<400> SEQUENCE: 379

Ala Leu Thr Gln Pro Ser Ser Val Ser Ala Asn Pro Gly Glu Ala Val
1               5                   10                  15

Lys Ile Thr Cys Ser Gly Gly Val Gly Gln Trp Tyr Gly Trp Tyr Gln
            20                  25                  30

Gln Lys Ala Pro Gly Ser Ala Pro Val Thr Val Ile Tyr Asp Asn Ala
        35                  40                  45

Asn Arg Pro Ser Asp Ile Pro Ser Arg Phe Ser Gly Ser Lys Ser Gly
        50                  55                  60

Ser Thr Gly Thr Leu Thr Ile Thr Gly Val Gln Ala Glu Asp Glu Ala
65                  70                  75                  80

Val Tyr Phe Cys Ala Asn Thr Tyr Ser Asp Gly Asn Asp Ala Pro Phe
                85                  90                  95

Gly Ala Gly Thr Thr Leu Thr Val Leu
            100                 105

<210> SEQ ID NO 380
<211> LENGTH: 315
<212> TYPE: DNA
<213> ORGANISM: Artificial Sequence
<220> FEATURE:
<223> OTHER INFORMATION: LC DNA

<400> SEQUENCE: 380
gccctgactc agccgtcctc ggtgtcagca aacccgggag aagccgtcaa gatcacctgc      60
agtggaggtg tcggccagtg gtatggctgg taccagcaga aggcacctgg cagtgcccct     120
gtcactgtga tctatgacaa cgccaacaga ccctcggaca tccttcacg attctccggt      180 tccaaatccg gctccacggg cacattaacc atcactgggg tccaagccga ggacgaggct     240
gtctatttct gtgcgaatac atacagcgac ggtaatgatg ctccatttgg ggccgggaca     300
accctgaccg tcctt                                                      315

<210> SEQ ID NO 381
<211> LENGTH: 7
<212> TYPE: PRT
<213> ORGANISM: Artificial Sequence
<220> FEATURE:
<223> OTHER INFORMATION: Ab83 (LM-211 or MCT1 3309 B01) - CDR1-HC

<400> SEQUENCE: 381

Gly Phe Ser Phe Ser Ser Arg
1               5

<210> SEQ ID NO 382
<211> LENGTH: 6
<212> TYPE: PRT
<213> ORGANISM: Artificial Sequence
<220> FEATURE:
<223> OTHER INFORMATION: CDR2-HC

<400> SEQUENCE: 382

Asp Asn Asp Gly Gly Tyr
1               5
```

-continued

```
<210> SEQ ID NO 383
<211> LENGTH: 15
<212> TYPE: PRT
<213> ORGANISM: Artificial Sequence
<220> FEATURE:
<223> OTHER INFORMATION: CDR3-HC

<400> SEQUENCE: 383

Gly Ala Tyr Gly Gly Gly Trp Tyr Ala Ala Ser Ser Ile Asp Ala
1               5                   10                  15

<210> SEQ ID NO 384
<211> LENGTH: 124
<212> TYPE: PRT
<213> ORGANISM: Artificial Sequence
<220> FEATURE:
<223> OTHER INFORMATION: HC Protein

<400> SEQUENCE: 384

Ala Val Thr Leu Asp Glu Ser Gly Gly Gly Leu Gln Thr Pro Gly Gly
1               5                   10                  15

Ala Leu Ser Leu Ile Cys Lys Ala Ser Gly Phe Ser Phe Ser Ser Arg
            20                  25                  30

Gly Met Phe Trp Val Arg Gln Ala Pro Gly Lys Gly Leu Glu Tyr Val
            35                  40                  45

Ala Gly Ile Asp Asn Asp Gly Gly Tyr Pro Asn Tyr Gly Ser Ala Val
            50                  55                  60

Lys Gly Arg Ala Thr Ile Ser Arg Asp Asn Arg Gln Ser Thr Val Arg
65                  70                  75                  80

Leu Gln Leu Asn Asn Leu Arg Ala Asp Asp Thr Gly Thr Tyr Tyr Cys
                    85                  90                  95

Ala Lys Gly Ala Tyr Gly Gly Gly Trp Tyr Ala Ala Ser Ser Ile Asp
                100                 105                 110

Ala Trp Gly His Gly Thr Glu Val Ile Val Ser Ser
            115                 120

<210> SEQ ID NO 385
<211> LENGTH: 384
<212> TYPE: DNA
<213> ORGANISM: Artificial Sequence
<220> FEATURE:
<223> OTHER INFORMATION: HC DNA

<400> SEQUENCE: 385
gtcacgaatt cggccgtgac gttggacgag tccgggggcg gcctccagac gcccggagga      60
gctctcagcc tcatctgcaa ggcctccggg ttctccttca gcagccgggg catgttctgg     120
gtgcgacagg cacctggcaa ggggctggaa tacgttgcgg gtattgataa tgatggtggt     180
tacccaaact acgggtcggc ggtgaagggc cgtgccacca tctcgaggga caacaggcag     240
agcacagtga ggctgcagct gaacaacctc agggctgacg acaccggcac ctactactgc     300
gccaagggtg cttatggtgg tggttggtat gccgctagta gcatcgacgc atggggccac     360
gggaccgaag tcatcgtctc ctcg                                          384

<210> SEQ ID NO 386
<211> LENGTH: 9
<212> TYPE: PRT
<213> ORGANISM: Artificial Sequence
<220> FEATURE:
<223> OTHER INFORMATION: CDR1-LC

<400> SEQUENCE: 386
```

-continued

Ser Gly Gly Val Gly Gln Trp Tyr Gly
1               5

<210> SEQ ID NO 387
<211> LENGTH: 7
<212> TYPE: PRT
<213> ORGANISM: Artificial Sequence
<220> FEATURE:
<223> OTHER INFORMATION: CDR2-LC

<400> SEQUENCE: 387

Asp Asn Thr Asn Arg Pro Ser
1               5

<210> SEQ ID NO 388
<211> LENGTH: 11
<212> TYPE: PRT
<213> ORGANISM: Artificial Sequence
<220> FEATURE:
<223> OTHER INFORMATION: CDR3-LC

<400> SEQUENCE: 388

Ala Asn Thr Tyr Ser Asp Gly Asn Asp Ala Pro
1               5                   10

<210> SEQ ID NO 389
<211> LENGTH: 105
<212> TYPE: PRT
<213> ORGANISM: Artificial Sequence
<220> FEATURE:
<223> OTHER INFORMATION: LC Protein

<400> SEQUENCE: 389

Ala Leu Thr Gln Pro Ser Ser Val Ser Ala Asn Pro Gly Glu Ala Val
1               5                   10                  15

Lys Ile Thr Cys Ser Gly Gly Val Gly Gln Trp Tyr Gly Trp Tyr Gln
            20                  25                  30

Gln Lys Ala Pro Gly Ser Ala Pro Val Thr Val Ile Tyr Asp Asn Thr
        35                  40                  45

Asn Arg Pro Ser Asp Ile Pro Ser Arg Phe Ser Gly Ser Lys Ser Gly
    50                  55                  60

Ser Thr Asn Thr Leu Thr Ile Thr Gly Val Gln Ala Glu Asp Glu Ala
65                  70                  75                  80

Val Tyr Phe Cys Ala Asn Thr Tyr Ser Asp Gly Asn Asp Ala Pro Phe
                85                  90                  95

Gly Ala Gly Thr Thr Leu Thr Val Leu
            100                 105

<210> SEQ ID NO 390
<211> LENGTH: 315
<212> TYPE: DNA
<213> ORGANISM: Artificial Sequence
<220> FEATURE:
<223> OTHER INFORMATION: LC DNA

<400> SEQUENCE: 390
gccctgactc agccgtcctc ggtgtcagca aacccgggag aagccgtcaa gatcacctgc      60
agtggaggtg tcggccagtg gtatggctgg taccagcaga aggcacctgg cagtgcccct     120
gtcactgtga tctatgacaa caccaacaga ccctcggaca tccccttcacg attctccggt     180 tccaaatccg gctccacaaa cacattaacc atcactgggg tccaagccga ggacgaggct     240

-continued gtctatttct gtgcgaatac atacagcgac ggtaatgatg ctccatttgg ggccgggaca    300
accctgaccg tcctt                                                     315

<210> SEQ ID NO 391
<211> LENGTH: 7
<212> TYPE: PRT
<213> ORGANISM: Artificial Sequence
<220> FEATURE:
<223> OTHER INFORMATION: Ab84 (LM-184 or MCT1  3303 C03) - CDR1-HC

<400> SEQUENCE: 391

Gly Phe Asp Phe Ser Asn Tyr
1               5

<210> SEQ ID NO 392
<211> LENGTH: 6
<212> TYPE: PRT
<213> ORGANISM: Artificial Sequence
<220> FEATURE:
<223> OTHER INFORMATION: CDR2-HC

<400> SEQUENCE: 392

Gly Asp Ser Ala Ser Tyr
1               5

<210> SEQ ID NO 393
<211> LENGTH: 16
<212> TYPE: PRT
<213> ORGANISM: Artificial Sequence
<220> FEATURE:
<223> OTHER INFORMATION: CDR3-HC

<400> SEQUENCE: 393

Ala Ser Glu Gly Ser Tyr Trp Tyr Tyr Glu Ala Gly Gly Ile Asp Thr
1               5                   10                  15

<210> SEQ ID NO 394
<211> LENGTH: 125
<212> TYPE: PRT
<213> ORGANISM: Artificial Sequence
<220> FEATURE:
<223> OTHER INFORMATION: HC Protein

<400> SEQUENCE: 394

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Asn Tyr
            20                  25                  30

Glu Met Leu Trp Val Arg Gln Ala Pro Gly Lys Gly Leu Glu Tyr Val
        35                  40                  45

Ala Gly Ile Gly Asp Ser Ala Ser Tyr Ser Ala Tyr Gly Val Ala Val
    50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125

<210> SEQ ID NO 395

-continued

```
<211> LENGTH: 384
<212> TYPE: DNA
<213> ORGANISM: Artificial Sequence
<220> FEATURE:
<223> OTHER INFORMATION: HC DNA

<400> SEQUENCE: 395
acgaattcgg ccgtgacgtt ggacgagtcc gggggcggcc tccagacgcc cggaggaacg      60
ctcagcctcg tctgcaaggc ctccgggttc gacttcagca actacgaaat gctctgggtg     120
cgacaggcgc ccggcaaggg gctggaatac gtcgctggta ttggcgacag tgctagttac     180
tcagcatacg gggtggcggt gaagggccgt gccaccatct cgagggacaa cgggcagagc     240
acactgaggc tgcagctgaa cggcctcagg gctgaggaca ccggcaccta ctactgcacc     300
aaagcttccg agggttccta ctggtattat gaagctggtg gtatcgacac atggggccac     360
gggaccgaag tcatcgtctc ctcg                                           384

<210> SEQ ID NO 396
<211> LENGTH: 8
<212> TYPE: PRT
<213> ORGANISM: Artificial Sequence
<220> FEATURE:
<223> OTHER INFORMATION: CDR1-LC

<400> SEQUENCE: 396

Ser Gly Gly Thr Tyr Ser Tyr Gly
1               5

<210> SEQ ID NO 397
<211> LENGTH: 7
<212> TYPE: PRT
<213> ORGANISM: Artificial Sequence
<220> FEATURE:
<223> OTHER INFORMATION: CDR2-LC

<400> SEQUENCE: 397

Gln Asn Asp Lys Arg Pro Ser
1               5

<210> SEQ ID NO 398
<211> LENGTH: 9
<212> TYPE: PRT
<213> ORGANISM: Artificial Sequence
<220> FEATURE:
<223> OTHER INFORMATION: CDR3-LC

<400> SEQUENCE: 398

Gly Ser Gly Asp Thr Thr Gly Gly Ile
1               5

<210> SEQ ID NO 399
<211> LENGTH: 102
<212> TYPE: PRT
<213> ORGANISM: Artificial Sequence
<220> FEATURE:
<223> OTHER INFORMATION: LC Protein

<400> SEQUENCE: 399

Ala Leu Thr Gln Pro Ser Ser Val Ser Ala Asn Pro Gly Glu Thr Val
1               5                   10                  15

Lys Ile Thr Cys Ser Gly Gly Thr Tyr Ser Tyr Gly Trp Phe Gln Gln
            20                  25                  30

Lys Ser Pro Gly Ser Ala Pro Val Thr Val Ile Tyr Gln Asn Asp Lys
        35                  40                  45
```

Arg Pro Ser Asp Ile Pro Ser Arg Phe Ser Gly Ser Lys Ser Gly Ser
    50                  55                  60

Thr Gly Thr Leu Thr Ile Thr Gly Val Gln Ala Glu Asp Glu Ala Val
65                  70                  75                  80

Tyr Phe Cys Gly Ser Gly Asp Thr Thr Gly Gly Ile Phe Gly Ala Gly
                85                  90                  95

Thr Thr Leu Thr Val Leu
          100

<210> SEQ ID NO 400
<211> LENGTH: 306
<212> TYPE: DNA
<213> ORGANISM: Artificial Sequence
<220> FEATURE:
<223> OTHER INFORMATION: LC DNA

<400> SEQUENCE: 400
gccctgactc agccgtcctc ggtgtcagca aacccaggag aaaccgtcaa gatcacctgc      60
tctgggggca cctatagtta tggctggttc cagcagaagt ctcctggcag tgcccctgtc     120
actgtgatct atcaaaacga caagagaccc tcggacatcc cttcacgatt ctccggttcc     180
aaatccggct ccacgggcac attaaccatc actggggtcc aagccgagga cgaggctgtc     240
tatttctgtg ggagtggaga caccaccggt ggtatatttg gggccgggac aaccctgacc     300
gtcctt                                                                306

<210> SEQ ID NO 401
<211> LENGTH: 7
<212> TYPE: PRT
<213> ORGANISM: Artificial Sequence
<220> FEATURE:
<223> OTHER INFORMATION: Ab85 (LM-187 or MCT1 3308 B07) - CDR1-HC

<400> SEQUENCE: 401

Gly Phe Gly Phe Thr Asn Tyr
1               5

<210> SEQ ID NO 402
<211> LENGTH: 6
<212> TYPE: PRT
<213> ORGANISM: Artificial Sequence
<220> FEATURE:
<223> OTHER INFORMATION: CDR2-HC

<400> SEQUENCE: 402

Ser Ser Gly Gly Ala Tyr
1               5

<210> SEQ ID NO 403
<211> LENGTH: 19
<212> TYPE: PRT
<213> ORGANISM: Artificial Sequence
<220> FEATURE:
<223> OTHER INFORMATION: CDR3-HC

<400> SEQUENCE: 403

Ala Pro Cys Gly Ser Trp Cys Gly Trp Gly Tyr Thr Gly Val Asp Asn
1               5                   10                  15

Ile Asp Ala

<210> SEQ ID NO 404
<211> LENGTH: 128

<212> TYPE: PRT
<213> ORGANISM: Artificial Sequence
<220> FEATURE:
<223> OTHER INFORMATION: HC Protein

<400> SEQUENCE: 404

Ala Val Thr Leu Asp Glu Ser Gly Gly Gly Leu Gln Thr Pro Gly Gly
1                5                  10                  15

Leu Val Ser Leu Val Cys Lys Ala Ser Gly Phe Gly Phe Thr Asn Tyr
            20                  25                  30

Glu Ile His Trp Val Arg Gln Ala Pro Gly Lys Gly Leu Glu Trp Val
        35                  40                  45

Gly Phe Val Ser Ser Gly Gly Ala Tyr Ala Asp Tyr Ala Pro Ala Val
    50                  55                  60

Lys Gly Arg Ala Thr Ile Thr Arg Asp Asn Gly Gln Ser Thr Val Arg
65                  70                  75                  80

Leu Gln Leu Val Asn Leu Arg Ala Glu Asp Thr Gly Thr Tyr Tyr Cys
                85                  90                  95

Thr Arg Ala Pro Cys Gly Ser Trp Cys Gly Trp Gly Tyr Thr Gly Val
            100                 105                 110

Asp Asn Ile Asp Ala Trp Gly His Gly Thr Glu Val Ile Val Ser Ser
        115                 120                 125

<210> SEQ ID NO 405
<211> LENGTH: 384
<212> TYPE: DNA
<213> ORGANISM: Artificial Sequence
<220> FEATURE:
<223> OTHER INFORMATION: HC DNA

<400> SEQUENCE: 405
gccgtgacgt tggacgagtc cgggggcggc ctccagacgc ccggaggact ggtcagtctc        60
gtctgcaagg cctccgggtt cggcttcacc aattatgaga tccactgggt gcgacaggcg       120
cccggcaagg ggctggagtg ggtcggtttt gttagtagtg gtggtgctta cgcagattac       180
gcgccggcgg tgaagggccg tgccaccatc acgagggaca cgggcagag cacagtgagg        240 ctgcagctgg tcaacctcag ggcggaggac accggcacct actactgcac cagagctcct       300
tgtggtagtt ggtgtggttg gggttatact ggtgtcgata acatcgacgc gtggggccac       360
gggaccgaag tcatcgtctc ctcg                                             384

<210> SEQ ID NO 406
<211> LENGTH: 10
<212> TYPE: PRT
<213> ORGANISM: Artificial Sequence
<220> FEATURE:
<223> OTHER INFORMATION: CDR1-LC

<400> SEQUENCE: 406

Ser Gly Gly Gly Arg Gly Ser His Tyr Gly
1                5                  10

<210> SEQ ID NO 407
<211> LENGTH: 7
<212> TYPE: PRT
<213> ORGANISM: Artificial Sequence
<220> FEATURE:
<223> OTHER INFORMATION: CDR2-LC

<400> SEQUENCE: 407

Ala Asn Asn Gln Arg Pro Ser

-continued

```
1               5
```

<210> SEQ ID NO 408
<211> LENGTH: 8
<212> TYPE: PRT
<213> ORGANISM: Artificial Sequence
<220> FEATURE:
<223> OTHER INFORMATION: CDR3-LC

<400> SEQUENCE: 408

```
Gly Gly Tyr Asp Ser Gly Ala Thr
1               5
```

<210> SEQ ID NO 409
<211> LENGTH: 103
<212> TYPE: PRT
<213> ORGANISM: Artificial Sequence
<220> FEATURE:
<223> OTHER INFORMATION: LC Protein

<400> SEQUENCE: 409

```
Ala Leu Thr Gln Pro Ser Ser Val Ser Ala Asn Pro Gly Gly Ile Val
1               5                   10                  15

Lys Ile Thr Cys Ser Gly Gly Gly Arg Gly Ser His Tyr Gly Trp Tyr
            20                  25                  30

Gln Gln Lys Ser Pro Gly Ser Ala Pro Val Thr Leu Ile Tyr Ala Asn
        35                  40                  45

Asn Gln Arg Pro Ser Asp Ile Pro Ser Arg Phe Ser Gly Ser Glu Ser
    50                  55                  60

Gly Ser Thr Ala Thr Leu Thr Ile Thr Gly Val Gln Ala Glu Asp Glu
65                  70                  75                  80

Ala Val Tyr Phe Cys Gly Gly Tyr Asp Ser Gly Ala Thr Phe Gly Ala
                85                  90                  95

Gly Thr Thr Leu Thr Val Leu
            100
```

<210> SEQ ID NO 410
<211> LENGTH: 309
<212> TYPE: DNA
<213> ORGANISM: Artificial Sequence
<220> FEATURE:
<223> OTHER INFORMATION: LC DNA

<400> SEQUENCE: 410

```
gccctgactc agccgtcctc ggtgtcagcg aacccaggag gaatcgtcaa gatcacctgc      60 tccggggggtg gtcgcggcag ccactatggc tggtatcagc agaagtctcc tggcagtgcc     120
cctgtcactc tgatctatgc taacaaccag agacccctcgg acatcccttc gcgattctcc     180
ggttccgaat ccggctccac ggccacatta accatcactg gggtccaagc cgaggacgag     240
gctgtctatt tctgtggtgg ctacgacagc ggtgctacat ttggggccgg gacaaccctg     300
accgtcctt                                                             309
```

<210> SEQ ID NO 411
<211> LENGTH: 7
<212> TYPE: PRT
<213> ORGANISM: Artificial Sequence
<220> FEATURE:
<223> OTHER INFORMATION: Ab86 (LM-191 or MCT1 3310 A01) - CDR1-HC

<400> SEQUENCE: 411

```
Gly Phe Asp Phe Ser Asn Tyr
```

```
1                 5
```

```
<210> SEQ ID NO 412
<211> LENGTH: 6
<212> TYPE: PRT
<213> ORGANISM: Artificial Sequence
<220> FEATURE:
<223> OTHER INFORMATION: CDR2-HC

<400> SEQUENCE: 412

Gly Asp Ser Ala Ser Tyr
1                 5
```

```
<210> SEQ ID NO 413
<211> LENGTH: 16
<212> TYPE: PRT
<213> ORGANISM: Artificial Sequence
<220> FEATURE:
<223> OTHER INFORMATION: CDR3-HC

<400> SEQUENCE: 413

Ala Ser Glu Gly Ser Tyr Trp Tyr Tyr Glu Ala Gly Gly Ile Asp Thr
1                 5                 10                15
```

```
<210> SEQ ID NO 414
<211> LENGTH: 125
<212> TYPE: PRT
<213> ORGANISM: Artificial Sequence
<220> FEATURE:
<223> OTHER INFORMATION: HC Protein

<400> SEQUENCE: 414

Ala Val Thr Leu Asp Glu Ser Gly Gly Gly Leu Gln Thr Pro Gly Gly
1                 5                 10                15

Thr Leu Ser Leu Val Cys Lys Ala Ser Gly Phe Asp Phe Ser Asn Tyr
            20                25                30

Glu Met Leu Trp Val Arg Gln Ala Pro Gly Lys Gly Leu Glu Tyr Val
        35                40                45

Ala Gly Ile Gly Asp Ser Ala Ser Tyr Ser Ala Tyr Gly Val Ala Val
    50                55                60

Lys Gly Arg Ala Thr Ile Ser Arg Asp Asn Gly Gln Ser Thr Leu Arg
65                70                75                80

Leu Gln Leu Asn Gly Leu Arg Ala Glu Asp Thr Gly Thr Tyr Tyr Cys
                85                90                95

Thr Lys Ala Ser Glu Gly Ser Tyr Trp Tyr Tyr Glu Ala Gly Gly Ile
            100               105               110

Asp Thr Trp Gly His Gly Thr Glu Val Ile Val Ser Ser
            115               120               125
```

```
<210> SEQ ID NO 415
<211> LENGTH: 384
<212> TYPE: DNA
<213> ORGANISM: Artificial Sequence
<220> FEATURE:
<223> OTHER INFORMATION: HC DNA

<400> SEQUENCE: 415
acgaattcgg ccgtgacgtt ggacgagtcc gggggcggcc tccagacgcc cggaggaacg     60
ctcagcctcg tctgcaaggc ctccgggttc gacttcagca actacgaaat gctctgggtg    120
cgacaggcgc ccggcaaggg gctggaatac gtcgctggta ttggcgacag tgctagttac    180
tcagcatacg gggtggcggt gaagggccgt gccaccatct cgagggacaa cgggcagagc    240
```

-continued

```
acactgaggc tgcagctgaa cggcctcagg gctgaggaca ccggcaccta ctactgcacc      300
aaagcttccg agggttccta ctggtattat gaagctggtg gtatcgacac atggggccac      360
gggaccgaag tcatcgtctc ctcg                                            384
```

<210> SEQ ID NO 416
<211> LENGTH: 8
<212> TYPE: PRT
<213> ORGANISM: Artificial Sequence
<220> FEATURE:
<223> OTHER INFORMATION: CDR1-LC

<400> SEQUENCE: 416

Ser Gly Ser Ser Gly Ser Tyr Gly
1               5

<210> SEQ ID NO 417
<211> LENGTH: 7
<212> TYPE: PRT
<213> ORGANISM: Artificial Sequence
<220> FEATURE:
<223> OTHER INFORMATION: CDR2-LC

<400> SEQUENCE: 417

Tyr Asn Asp Lys Arg Pro Ser
1               5

<210> SEQ ID NO 418
<211> LENGTH: 10
<212> TYPE: PRT
<213> ORGANISM: Artificial Sequence
<220> FEATURE:
<223> OTHER INFORMATION: CDR3-LC

<400> SEQUENCE: 418

Gly Ser Tyr Gly Ser Thr Asp Ala Ala Ile
1               5                   10

<210> SEQ ID NO 419
<211> LENGTH: 103
<212> TYPE: PRT
<213> ORGANISM: Artificial Sequence
<220> FEATURE:
<223> OTHER INFORMATION: LC Protein

<400> SEQUENCE: 419

Ala Leu Thr Gln Pro Ser Ser Val Ser Ala Ser Pro Gly Gly Thr Val
1               5                   10                  15

Lys Ile Thr Cys Ser Gly Ser Ser Gly Ser Tyr Gly Trp Tyr Gln Gln
                20                  25                  30

Lys Ser Pro Gly Ser Ala Pro Val Thr Val Ile Tyr Tyr Asn Asp Lys
            35                  40                  45

Arg Pro Ser Asp Ile Pro Ser Arg Phe Ser Gly Ser Lys Ser Gly Ser
        50                  55                  60

Thr Gly Thr Leu Thr Ile Thr Gly Val Gln Ala Glu Asp Glu Ala Val
65                  70                  75                  80

Tyr Phe Cys Gly Ser Tyr Gly Ser Thr Asp Ala Ala Ile Phe Gly Ala
                85                  90                  95

Gly Thr Thr Leu Thr Val Leu
            100

<210> SEQ ID NO 420

```
<211> LENGTH: 309
<212> TYPE: DNA
<213> ORGANISM: Artificial Sequence
<220> FEATURE:
<223> OTHER INFORMATION: LC DNA

<400> SEQUENCE: 420
gccctgactc agccgtcctc ggtgtccgcg agcccaggag gaaccgtcaa gatcacctgc     60
tccgggagta gtggcagcta tggctggtat cagcagaagt cacctggcag tgcccctgtc    120
actgtgatct attacaacga caagagaccc tcggacatcc cttcacgatt ctccggttcc    180
aaatccggct ccacgggcac attaaccatc actggggtcc aagccgagga cgaggctgtc    240
tatttctgtg ggagctacgg cagcactgat gctgctatat ttggggccgg gacaaccctg    300
accgtcctt                                                            309

<210> SEQ ID NO 421
<211> LENGTH: 7
<212> TYPE: PRT
<213> ORGANISM: Artificial Sequence
<220> FEATURE:
<223> OTHER INFORMATION: Ab87 (LM-192 or MCT1 3310 A02-1) - CDR1-HC

<400> SEQUENCE: 421

Gly Phe Asp Phe Ser Asn Tyr
1               5

<210> SEQ ID NO 422
<211> LENGTH: 6
<212> TYPE: PRT
<213> ORGANISM: Artificial Sequence
<220> FEATURE:
<223> OTHER INFORMATION: CDR2-HC

<400> SEQUENCE: 422

Gly Asp Ser Ala Ser Tyr
1               5

<210> SEQ ID NO 423
<211> LENGTH: 16
<212> TYPE: PRT
<213> ORGANISM: Artificial Sequence
<220> FEATURE:
<223> OTHER INFORMATION: CDR3-HC

<400> SEQUENCE: 423

Ala Ser Glu Gly Ser Tyr Trp Tyr Tyr Glu Ala Gly Gly Ile Asp Thr
1               5                   10                  15

<210> SEQ ID NO 424
<211> LENGTH: 125
<212> TYPE: PRT
<213> ORGANISM: Artificial Sequence
<220> FEATURE:
<223> OTHER INFORMATION: HC Protein

<400> SEQUENCE: 424

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Asn Tyr
            20                  25                  30

Glu Met Leu Trp Val Arg Gln Ala Pro Gly Lys Gly Leu Glu Tyr Val
        35                  40                  45

Ala Gly Ile Gly Asp Ser Ala Ser Tyr Ser Ala Tyr Gly Val Ala Val
```

-continued

```
              50               55               60
Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
                100                 105                 110

Asp Thr Trp Gly His Gly Thr Glu Val Ile Val Ser Ser
        115                 120                 125
```

```
<210> SEQ ID NO 425
<211> LENGTH: 384
<212> TYPE: DNA
<213> ORGANISM: Artificial Sequence
<220> FEATURE:
<223> OTHER INFORMATION: HC DNA

<400> SEQUENCE: 425
acgaattcgg ccgtgacgtt ggacgagtcc gggggcggcc tccagacgcc cggaggaacg       60
ctcagcctcg tctgcaaggc ctccgggttc gacttcagca actacgaaat gctctgggtg      120
cgacaggcgc ccggcaaggg gctggaatac gtcgctggta ttggcgacag tgctagttac      180
tcagcatacg gggtggcggt gaagggccgt gccaccatct cgagggacaa cgggcagagc      240
acactgaggc tgcagctgaa cggcctcagg gctgaggaca ccggcaccta ctactgcacc      300
aaagcttccg agggttccta ctggtattat gaagctggtg gtatcgacac atggggccac      360
gggaccgaag tcatcgtctc ctcg                                            384
```

```
<210> SEQ ID NO 426
<211> LENGTH: 8
<212> TYPE: PRT
<213> ORGANISM: Artificial Sequence
<220> FEATURE:
<223> OTHER INFORMATION: CDR1-LC

<400> SEQUENCE: 426

Ser Gly Gly Tyr Ser Ser Tyr Gly
1               5
```

```
<210> SEQ ID NO 427
<211> LENGTH: 7
<212> TYPE: PRT
<213> ORGANISM: Artificial Sequence
<220> FEATURE:
<223> OTHER INFORMATION: CDR2-LC

<400> SEQUENCE: 427

Tyr Asn Ala Lys Arg Pro Ser
1               5
```

```
<210> SEQ ID NO 428
<211> LENGTH: 10
<212> TYPE: PRT
<213> ORGANISM: Artificial Sequence
<220> FEATURE:
<223> OTHER INFORMATION: CDR3-LC

<400> SEQUENCE: 428

Gly Thr Ala Asp Arg Ser Ser Thr Ala Leu
1               5                   10
```

```
<210> SEQ ID NO 429
```

```
<211> LENGTH: 103
<212> TYPE: PRT
<213> ORGANISM: Artificial Sequence
<220> FEATURE:
<223> OTHER INFORMATION: LC Protein

<400> SEQUENCE: 429

Ala Leu Thr Gln Pro Ser Ser Val Ser Ala Asn Leu Gly Gly Thr Val
1               5                   10                  15

Lys Ile Thr Cys Ser Gly Gly Tyr Ser Ser Tyr Gly Trp Tyr Gln Gln
            20                  25                  30

Lys Ser Pro Gly Ser Ala Pro Val Thr Leu Ile Tyr Tyr Asn Ala Lys
        35                  40                  45

Arg Pro Ser Asn Ile Pro Ser Arg Phe Ser Gly Ser Lys Ser Gly Ser
    50                  55                  60

Thr Ala Thr Leu Thr Ile Thr Gly Val Gln Ala Glu Asp Glu Ala Val
65                  70                  75                  80

Tyr Phe Cys Gly Thr Ala Asp Arg Ser Ser Thr Ala Leu Phe Gly Ala
                85                  90                  95

Gly Thr Thr Leu Thr Val Leu
            100

<210> SEQ ID NO 430
<211> LENGTH: 309
<212> TYPE: DNA
<213> ORGANISM: Artificial Sequence
<220> FEATURE:
<223> OTHER INFORMATION: LC DNA

<400> SEQUENCE: 430
gccctgactc agccgtcctc ggtgtcagca aacctgggag gaaccgtcaa gatcacctgc      60
tccgggggtt acagcagcta tggctggtat cagcagaagt ctcctggcag tgctcctgtc     120
actctgatct attacaacgc caagagaccc tcgaacatcc cttcacgatt ctccggttcc     180
aaatccggct ccacagccac attaaccatc actggggtcc aagccgagga cgaggctgtc     240
tatttctgtg ggactgcaga caggagcagt actgctttat ttggggccgg acaaccctg      300 accgtcctt                                                              309

<210> SEQ ID NO 431
<211> LENGTH: 7
<212> TYPE: PRT
<213> ORGANISM: Artificial Sequence
<220> FEATURE:
<223> OTHER INFORMATION: Ab88 (LM-196 or MCT1 3310 C01) - CDR1-HC

<400> SEQUENCE: 431

Gly Phe Asp Phe Ser Ser Tyr
1               5

<210> SEQ ID NO 432
<211> LENGTH: 6
<212> TYPE: PRT
<213> ORGANISM: Artificial Sequence
<220> FEATURE:
<223> OTHER INFORMATION: CDR2-HC

<400> SEQUENCE: 432

Gly Asp Gly Ala Ser Tyr
1               5

<210> SEQ ID NO 433
```

<211> LENGTH: 16
<212> TYPE: PRT
<213> ORGANISM: Artificial Sequence
<220> FEATURE:
<223> OTHER INFORMATION: CDR3-HC

<400> SEQUENCE: 433

Ala Ser Glu Gly Ser Tyr Trp Tyr Tyr Glu Thr Gly Gly Ile Asp Thr
1               5                   10                  15

<210> SEQ ID NO 434
<211> LENGTH: 125
<212> TYPE: PRT
<213> ORGANISM: Artificial Sequence
<220> FEATURE:
<223> OTHER INFORMATION: HC Protein

<400> SEQUENCE: 434

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Ser Tyr
            20                  25                  30

Glu Met Leu Trp Val Arg Gln Ala Pro Gly Lys Gly Leu Ala Tyr Val
        35                  40                  45

Ala Gly Ile Gly Asp Gly Ala Ser Tyr Ser Ala Tyr Gly Val Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Ala Ser Glu Gly Ser Tyr Trp Tyr Tyr Glu Thr Gly Gly Ile
            100                 105                 110

Asp Thr Trp Gly His Gly Thr Glu Val Ile Val Ser Ser
        115                 120                 125

<210> SEQ ID NO 435
<211> LENGTH: 384
<212> TYPE: DNA
<213> ORGANISM: Artificial Sequence
<220> FEATURE:
<223> OTHER INFORMATION: HC DNA

<400> SEQUENCE: 435
acgaattcgg ccgtgacgtt ggacgagtcc gggggcggcc tccagacgcc cggaggaacg        60
ctcagcctcg tctgcaaggc ctccgggttc gacttcagca gctacgaaat gctctgggtg       120
cgacaggcgc ccggcaaggg gctggcatac gtcgctggta tcggcgacgg tgctagttac       180
tcagcatacg gggtggcggt gaagggccga gccaccatct cgaggacaa cgggcagagc        240 acagtgaggc tgcagctgaa caacctcagg gctgaggaca ccggcaccta ctactgcgcc       300
aaagcttccg agggttccta ctggtattat gaaactggtg gtatcgacac atggggccac       360
gggaccgaag tcatcgtctc ctcg                                             384

<210> SEQ ID NO 436
<211> LENGTH: 8
<212> TYPE: PRT
<213> ORGANISM: Artificial Sequence
<220> FEATURE:
<223> OTHER INFORMATION: CDR1-LC

<400> SEQUENCE: 436

Ser Gly Gly Ser Gly Ser Tyr Gly
1               5

<210> SEQ ID NO 437
<211> LENGTH: 7
<212> TYPE: PRT
<213> ORGANISM: Artificial Sequence
<220> FEATURE:
<223> OTHER INFORMATION: CDR2-LC

<400> SEQUENCE: 437

Tyr Asn Asp Lys Arg Pro Ser
1               5

<210> SEQ ID NO 438
<211> LENGTH: 10
<212> TYPE: PRT
<213> ORGANISM: Artificial Sequence
<220> FEATURE:
<223> OTHER INFORMATION: CDR3-LC

<400> SEQUENCE: 438

Gly Ser Gly Asp Arg Ser Tyr Asp Gly Met
1               5                   10

<210> SEQ ID NO 439
<211> LENGTH: 103
<212> TYPE: PRT
<213> ORGANISM: Artificial Sequence
<220> FEATURE:
<223> OTHER INFORMATION: LC Protein

<400> SEQUENCE: 439

Ala Leu Thr Gln Pro Ser Ser Val Ser Ala Asn Pro Gly Glu Thr Val
1               5                   10                  15

Glu Ile Thr Cys Ser Gly Gly Ser Gly Ser Tyr Gly Trp Tyr Gln Gln
                20                  25                  30

Lys Ser Pro Gly Ser Ala Pro Val Thr Val Ile His Tyr Asn Asp Lys
            35                  40                  45

Arg Pro Ser Asp Ile Pro Ser Arg Phe Ser Gly Ser Ala Ser Gly Ser
        50                  55                  60

Thr Ala Thr Leu Thr Ile Thr Gly Val Gln Val Glu Asp Glu Ala Val
65                  70                  75                  80

Tyr Phe Cys Gly Ser Gly Asp Arg Ser Tyr Asp Gly Met Phe Gly Ala
                85                  90                  95

Gly Thr Thr Leu Thr Val Leu
            100

<210> SEQ ID NO 440
<211> LENGTH: 309
<212> TYPE: DNA
<213> ORGANISM: Artificial Sequence
<220> FEATURE:
<223> OTHER INFORMATION: LC DNA

<400> SEQUENCE: 440
gccctgactc agccgtcctc ggtgtcagca aacccgggag aaaccgtcga gatcacctgc      60
tccgggggta gtggcagcta cggctggtac cagcagaagt ctcctggcag tgcccctgtc     120
actgtgatcc attacaacga caagagaccc tcggacatcc cttcacgatt ctccggttcc     180
gcatccggct ccacagccac attaaccatc actgggtcc aagtcgagga cgaggctgtc     240
tatttctgtg ggagtggaga caggagttat gatggtatgt tcgggccgg gacaaccctg     300

-continued accgtcctt                                                            309

<210> SEQ ID NO 441
<211> LENGTH: 7
<212> TYPE: PRT
<213> ORGANISM: Artificial Sequence
<220> FEATURE:
<223> OTHER INFORMATION: Ab89 (LM-200 or MCT1 3310 F12) - CDR1-HC

<400> SEQUENCE: 441

Gly Phe Asp Phe Ser Asn Tyr
1               5

<210> SEQ ID NO 442
<211> LENGTH: 6
<212> TYPE: PRT
<213> ORGANISM: Artificial Sequence
<220> FEATURE:
<223> OTHER INFORMATION: CDR2-HC

<400> SEQUENCE: 442

Gly Asp Ser Ala Ser Tyr
1               5

<210> SEQ ID NO 443
<211> LENGTH: 16
<212> TYPE: PRT
<213> ORGANISM: Artificial Sequence
<220> FEATURE:
<223> OTHER INFORMATION: CDR3-HC

<400> SEQUENCE: 443

Ala Ser Glu Gly Ser Tyr Trp Tyr Tyr Glu Ala Gly Gly Ile Asp Thr
1               5                   10                  15

<210> SEQ ID NO 444
<211> LENGTH: 125
<212> TYPE: PRT
<213> ORGANISM: Artificial Sequence
<220> FEATURE:
<223> OTHER INFORMATION: HC Protein

<400> SEQUENCE: 444

Ala Val Thr Leu Asp Glu Ser Gly Gly Gly Leu Gln Thr Pro Gly Gly
1               5                   10                  15

Thr Leu Ser Leu Val Cys Lys Ala Ser Gly Phe Asp Phe Ser Asn Tyr
            20                  25                  30

Glu Met Leu Trp Val Arg Gln Ala Pro Gly Lys Gly Leu Glu Tyr Val
        35                  40                  45

Ala Gly Ile Gly Asp Ser Ala Ser Tyr Ser Ala Tyr Gly Val Ala Val
    50                  55                  60

Lys Gly Arg Ala Thr Ile Ser Arg Asp Asn Gly Gln Ser Thr Leu Arg
65                  70                  75                  80

Leu Gln Leu Asn Gly Leu Arg Ala Glu Asp Thr Gly Thr Tyr Tyr Cys
                85                  90                  95

Thr Lys Ala Ser Glu Gly Ser Tyr Trp Tyr Tyr Glu Ala Gly Gly Ile
            100                 105                 110

Asp Thr Trp Gly His Gly Thr Glu Val Ile Val Ser Ser
        115                 120                 125

<210> SEQ ID NO 445
<211> LENGTH: 384

-continued

```
<212> TYPE: DNA
<213> ORGANISM: Artificial Sequence
<220> FEATURE:
<223> OTHER INFORMATION: HC DNA

<400> SEQUENCE: 445
acgaattcgg ccgtgacgtt ggacgagtcc gggggcggcc tccagacgcc cggaggaacg      60
ctcagcctcg tctgcaaggc ctccgggttc gacttcagca actacgaaat gctctgggtg     120
cgacaggcgc ccggcaaggg gctggaatac gtcgctggta ttggcgacag tgctagttac     180
tcagcatacg gggtggcggt gaagggccgt gccaccatct cgagggacaa cgggcagagc     240
acactgaggc tgcagctgaa cggcctcagg gctgaggaca ccgcacccta ctactgcacc     300
aaagcttccg agggttccta ctggtattat gaagctggtg gtatcgacac atggggccac     360
gggaccgaag tcatcgtctc ctcg                                           384

<210> SEQ ID NO 446
<211> LENGTH: 8
<212> TYPE: PRT
<213> ORGANISM: Artificial Sequence
<220> FEATURE:
<223> OTHER INFORMATION: CDR1-LC

<400> SEQUENCE: 446

Ser Gly Gly Ser Ser Thr Tyr Gly
1               5

<210> SEQ ID NO 447
<211> LENGTH: 7
<212> TYPE: PRT
<213> ORGANISM: Artificial Sequence
<220> FEATURE:
<223> OTHER INFORMATION: CDR2-LC

<400> SEQUENCE: 447

Arg Asn Asp Asn Arg Pro Ser
1               5

<210> SEQ ID NO 448
<211> LENGTH: 9
<212> TYPE: PRT
<213> ORGANISM: Artificial Sequence
<220> FEATURE:
<223> OTHER INFORMATION: CDR3-LC

<400> SEQUENCE: 448

Gly Ser Ala Asp Ser Ser Gly Ala Ile
1               5

<210> SEQ ID NO 449
<211> LENGTH: 102
<212> TYPE: PRT
<213> ORGANISM: Artificial Sequence
<220> FEATURE:
<223> OTHER INFORMATION: LC Protein

<400> SEQUENCE: 449

Ala Leu Thr Gln Pro Ser Ser Val Ser Ala Asn Leu Gly Gly Thr Val
1               5                   10                  15

Glu Ile Thr Cys Ser Gly Gly Ser Ser Thr Tyr Gly Trp Tyr Gln Gln
                20                  25                  30

Lys Ser Pro Gly Ser Ala Pro Val Thr Val Ile Tyr Arg Asn Asp Asn
            35                  40                  45
```

-continued

```
Arg Pro Ser Asn Ile Pro Ser Arg Phe Ser Gly Ser Lys Tyr Gly Ser
    50                  55                  60

Thr Gly Thr Leu Thr Ile Thr Gly Val Gln Ala Glu Asp Glu Ala Val
65                  70                  75                  80

Tyr Leu Cys Gly Ser Ala Asp Ser Ser Gly Ala Ile Phe Gly Ala Gly
                85                  90                  95

Thr Thr Leu Thr Val Leu
            100
```

```
<210> SEQ ID NO 450
<211> LENGTH: 306
<212> TYPE: DNA
<213> ORGANISM: Artificial Sequence
<220> FEATURE:
<223> OTHER INFORMATION: LC DNA

<400> SEQUENCE: 450
gccctgactc agccgtcctc ggtgtcagca aacctgggag gaaccgtcga gatcacctgc      60
tccgggggta gcagcaccta tggctggtac cagcagaagt ctcctggcag tgcccctgtc     120
actgtgatct ataggaacga caacagaccc tcaaacatcc cttcacgatt ctccggttcc     180
aaatacggct ccacgggcac attaaccatc actggggtcc aagccgagga cgaggctgtc     240
tatttatgtg ggagtgcaga cagcagtggt gctatatttg gggccgggac aaccctgacc     300
gtcctt                                                               306
```

```
<210> SEQ ID NO 451
<211> LENGTH: 7
<212> TYPE: PRT
<213> ORGANISM: Artificial Sequence
<220> FEATURE:
<223> OTHER INFORMATION: Ab90 (MCT1 3308 A05) - CDR1-HC

<400> SEQUENCE: 451

Gly Phe Ser Phe Ser Gly Phe
1               5
```

```
<210> SEQ ID NO 452
<211> LENGTH: 6
<212> TYPE: PRT
<213> ORGANISM: Artificial Sequence
<220> FEATURE:
<223> OTHER INFORMATION: CDR2-HC

<400> SEQUENCE: 452

Asp Asp Gly Gly Ser Ser
1               5
```

```
<210> SEQ ID NO 453
<211> LENGTH: 18
<212> TYPE: PRT
<213> ORGANISM: Artificial Sequence
<220> FEATURE:
<223> OTHER INFORMATION: CDR3-HC

<400> SEQUENCE: 453

Asp Thr Ala Ala Cys Thr Tyr Pro Cys Gly Ser Tyr Val His Thr Ile
1               5                   10                  15

Asp Thr
```

```
<210> SEQ ID NO 454
<211> LENGTH: 127
<212> TYPE: PRT
```

-continued

<213> ORGANISM: Artificial Sequence
<220> FEATURE:
<223> OTHER INFORMATION: HC Protein

<400> SEQUENCE: 454

```
Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Ser Phe Ser Gly Phe
            20                  25                  30

Ser Met Gly Trp Val Arg Gln Thr Pro Gly Lys Gly Leu Glu Trp Val
        35                  40                  45

Ala Gly Ile Asp Asp Gly Gly Ser Ser Thr Tyr Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Ser Asn Leu Arg Ala Glu Asp Thr Gly Ile Tyr Tyr Cys
                85                  90                  95

Ala Arg Asp Thr Ala Ala Cys Thr Tyr Pro Cys Gly Ser Tyr Val His
            100                 105                 110

Thr Ile Asp Thr Trp Gly His Gly Thr Glu Val Ile Val Ser Ser
        115                 120                 125
```

<210> SEQ ID NO 455
<211> LENGTH: 384
<212> TYPE: DNA
<213> ORGANISM: Artificial Sequence
<220> FEATURE:
<223> OTHER INFORMATION: HC DNA

<400> SEQUENCE: 455

```
tcggccgtga cgttggacga gtccgggggc ggcctccaga cgcccggagg agcgctcagt      60
ctcgtctgca aggcctccgg gttctccttc agtggtttca gcatgggttg ggtgcgccag     120
acgcccggca aagggctgga atgggtcgct ggtattgatg atggtggcag tagcacctac     180 tacgggcgg cggtgaaggg ccgtgccacc atctcgaggg acaacgggca gagcacagtg     240
aggctgcagc tgagcaacct cagggctgag gacaccggca tctactactg cgccagagat     300
actgctgctt gtacttatcc ttgtggttct tatgtgcata cgatagacac atggggccac     360
gggaccgaag tcatcgtctc ctcg                                            384
```

<210> SEQ ID NO 456
<211> LENGTH: 8
<212> TYPE: PRT
<213> ORGANISM: Artificial Sequence
<220> FEATURE:
<223> OTHER INFORMATION: CDR1-LC

<400> SEQUENCE: 456

```
Ser Gly Gly Gly Gly Asp Tyr Gly
1               5
```

<210> SEQ ID NO 457
<211> LENGTH: 7
<212> TYPE: PRT
<213> ORGANISM: Artificial Sequence
<220> FEATURE:
<223> OTHER INFORMATION: CDR2-LC

<400> SEQUENCE: 457

```
Tyr Ser Asp Lys Arg Pro Pro
1               5
```

<210> SEQ ID NO 458
<211> LENGTH: 10
<212> TYPE: PRT
<213> ORGANISM: Artificial Sequence
<220> FEATURE:
<223> OTHER INFORMATION: CDR3-LC

<400> SEQUENCE: 458

```
Gly Gly Trp Asp Asp Thr Asn Gly Gly Ile
1               5                   10
```

<210> SEQ ID NO 459
<211> LENGTH: 103
<212> TYPE: PRT
<213> ORGANISM: Artificial Sequence
<220> FEATURE:
<223> OTHER INFORMATION: LC Protein

<400> SEQUENCE: 459

```
Ala Leu Thr Gln Pro Ser Ser Val Ser Ala Asn Leu Gly Gly Thr Val
1               5                   10                  15

Lys Ile Thr Cys Ser Gly Gly Gly Gly Asp Tyr Gly Trp Phe Gln Gln
            20                  25                  30

Lys Ser Pro Gly Ser Ala Pro Val Thr Val Ile Tyr Tyr Ser Asp Lys
        35                  40                  45

Arg Pro Pro Asn Ile Pro Ser Arg Phe Ser Gly Ser Leu Ser Gly Ser
    50                  55                  60

Thr Ala Thr Leu Thr Ile Thr Gly Val Gln Ala Glu Asp Glu Ala Val
65                  70                  75                  80

Tyr Tyr Cys Gly Gly Trp Asp Asp Thr Asn Gly Gly Ile Phe Gly Ala
                85                  90                  95

Gly Thr Thr Leu Thr Val Leu
            100
```

<210> SEQ ID NO 460
<211> LENGTH: 309
<212> TYPE: DNA
<213> ORGANISM: Artificial Sequence
<220> FEATURE:
<223> OTHER INFORMATION: LC DNA

<400> SEQUENCE: 460

```
gccctgactc agccgtcctc ggtgtcagca aacctgggag gaaccgtcaa gatcacctgc      60
tccgggggtg gtggcgacta tggctggttc cagcagaagt ctcctggcag tgcccctgtc     120
actgtgatct attacagcga caagagaccc ccgaacatcc cttcacgatt ctccggttcc     180
ctatccggct ccacagccac attaaccatc actggggtcc aagccgagga cgaggctgtc     240
tattactgtg gtggctggga cgatactaat ggtggtatat ttggggccgg gacaaccctg     300
accgtcctt                                                             309
```

<210> SEQ ID NO 461
<211> LENGTH: 7
<212> TYPE: PRT
<213> ORGANISM: Artificial Sequence
<220> FEATURE:
<223> OTHER INFORMATION: Ab91 (MCT1 3309 D07) - CDR1-HC

<400> SEQUENCE: 461

```
Gly Phe Ser Phe Ser Ser Tyr
1               5
```

-continued

<210> SEQ ID NO 462
<211> LENGTH: 6
<212> TYPE: PRT
<213> ORGANISM: Artificial Sequence
<220> FEATURE:
<223> OTHER INFORMATION: CDR2-HC

<400> SEQUENCE: 462

Arg Ser Ser Gly Ser Ser
1               5

<210> SEQ ID NO 463
<211> LENGTH: 16
<212> TYPE: PRT
<213> ORGANISM: Artificial Sequence
<220> FEATURE:
<223> OTHER INFORMATION: CDR3-HC

<400> SEQUENCE: 463

Ala Gly Cys Ser Asp Cys Trp Arg Ser Thr Pro Gly Arg Ile Asp Ala
1               5                   10                  15

<210> SEQ ID NO 464
<211> LENGTH: 125
<212> TYPE: PRT
<213> ORGANISM: Artificial Sequence
<220> FEATURE:
<223> OTHER INFORMATION: HC Protein

<400> SEQUENCE: 464

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Ser Phe Ser Ser Tyr
            20                  25                  30

Gly Met Gly Trp Val Arg Gln Ala Pro Gly Lys Gly Leu Glu Phe Ile
        35                  40                  45

Ala Gly Ile Arg Ser Ser Gly Ser Ser Thr Tyr Tyr Gly Ala Ala Val
    50                  55                  60

Lys Gly Arg Ala Thr Ile Thr Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Ala Lys Ala Gly Cys Ser Asp Cys Trp Arg Ser Thr Pro Gly Arg Ile
            100                 105                 110

Asp Ala Trp Gly His Gly Thr Glu Val Ile Val Ser Ser
        115                 120                 125

<210> SEQ ID NO 465
<211> LENGTH: 384
<212> TYPE: DNA
<213> ORGANISM: Artificial Sequence
<220> FEATURE:
<223> OTHER INFORMATION: HC DNA

<400> SEQUENCE: 465
acgaattcgg ccgtgacgtt ggacgagtct gggggcggcc tccagacgcc cggaggaggg        60
ctcagcctcg tctgcaaggc ctccgggttc tccttcagca gttatggcat gggctgggtg       120
cgacaggcgc ccggcaaggg gctggaattc atcgcgggta ttagaagcag tggtagtagc       180
acatactacg gggcggcggt gaagggccgt gccaccatca cgaggacaa cgggcagagc        240

-continued acagtgaggc tgcagctgaa caacctcagg gctgaggaca ccgccaccta ctactgcgcc      300
aaagctggtt gtagtgattg ttggcgtagt actcctggta ggatcgacgc atggggccac      360
gggaccgaag tcatcgtctc ctcg      384

<210> SEQ ID NO 466
<211> LENGTH: 10
<212> TYPE: PRT
<213> ORGANISM: Artificial Sequence
<220> FEATURE:
<223> OTHER INFORMATION: CDR1-LC

<400> SEQUENCE: 466

Ser Gly Ser Ser Ser Gly Tyr Gly Tyr Gly
1               5               10

<210> SEQ ID NO 467
<211> LENGTH: 7
<212> TYPE: PRT
<213> ORGANISM: Artificial Sequence
<220> FEATURE:
<223> OTHER INFORMATION: CDR2-LC

<400> SEQUENCE: 467

Thr Asn Thr Asn Arg Pro Ser
1               5

<210> SEQ ID NO 468
<211> LENGTH: 11
<212> TYPE: PRT
<213> ORGANISM: Artificial Sequence
<220> FEATURE:
<223> OTHER INFORMATION: CDR3-LC

<400> SEQUENCE: 468

Gly Ser Tyr Asp Ser Asn Thr Tyr Leu Gly Leu
1               5               10

<210> SEQ ID NO 469
<211> LENGTH: 106
<212> TYPE: PRT
<213> ORGANISM: Artificial Sequence
<220> FEATURE:
<223> OTHER INFORMATION: LC Protein

<400> SEQUENCE: 469

Ala Leu Thr Gln Pro Ser Ser Val Ser Ala Asn Leu Gly Gly Thr Val
1               5                   10                  15

Glu Ile Thr Cys Ser Gly Ser Ser Ser Gly Tyr Gly Tyr Gly Trp Tyr
                20                  25                  30

Gln Gln Lys Ser Pro Gly Ser Ala Pro Val Thr Leu Ile Tyr Thr Asn
            35                  40                  45

Thr Asn Arg Pro Ser Asp Ile Pro Ser Arg Phe Ser Gly Ser Thr Ser
        50                  55                  60

Gly Ser Thr Asn Thr Leu Thr Ile Ala Gly Val Gln Ala Glu Asp Glu
65                  70                  75                  80

Ala Val Tyr Tyr Cys Gly Ser Tyr Asp Ser Asn Thr Tyr Leu Gly Leu
                85                  90                  95

Phe Gly Ala Gly Thr Thr Leu Thr Val Leu
            100                 105

<210> SEQ ID NO 470
<211> LENGTH: 318

-continued

<212> TYPE: DNA
<213> ORGANISM: Artificial Sequence
<220> FEATURE:
<223> OTHER INFORMATION: LC DNA

<400> SEQUENCE: 470
gccctgactc agccgtcctc ggtgtcagca aacctgggag gaaccgtcga gatcacctgc        60
tccgggagta gcagtggcta tggttatggc tggtatcagc agaagtcacc tggcagtgcc       120
cctgtcactc tgatctatac taacaccaac agaccctcgg acatcccttc gcgattctcc       180
ggttccacat ccggctccac aaacacatta cgatcgctg gggtccaagc cgaggacgag        240
gctgtctatt attgtgggag ctacgacagc aacacttatc ttggtctatt tggggccggg       300
acaaccctga ccgtcctt                                                       318

<210> SEQ ID NO 471
<211> LENGTH: 7
<212> TYPE: PRT
<213> ORGANISM: Artificial Sequence
<220> FEATURE:
<223> OTHER INFORMATION: Ab92 (MCT1 3310 A05) - CDR1-HC

<400> SEQUENCE: 471

Gly Phe Thr Phe Ser Ser Tyr
1               5

<210> SEQ ID NO 472
<211> LENGTH: 7
<212> TYPE: PRT
<213> ORGANISM: Artificial Sequence
<220> FEATURE:
<223> OTHER INFORMATION: CDR2-HC

<400> SEQUENCE: 472

Ser Lys Asp Gly Gly Ser Asp
1               5

<210> SEQ ID NO 473
<211> LENGTH: 9
<212> TYPE: PRT
<213> ORGANISM: Artificial Sequence
<220> FEATURE:
<223> OTHER INFORMATION: CDR3-HC

<400> SEQUENCE: 473

Gly Ile Gly Val Gly Asn Ile Asp Ala
1               5

<210> SEQ ID NO 474
<211> LENGTH: 119
<212> TYPE: PRT
<213> ORGANISM: Artificial Sequence
<220> FEATURE:
<223> OTHER INFORMATION: HC Protein

<400> SEQUENCE: 474

Ala Val Thr Leu Asp Glu Ser Glu Gly Gly Leu His Thr Pro Gly Gly
1               5                   10                  15

Gly Leu Ser Leu Val Cys Lys Ala Ser Gly Phe Thr Phe Ser Ser Tyr
            20                  25                  30

Ala Met Tyr Trp Ile Arg Gln Ala Pro Gly Lys Gly Leu Glu Trp Val
        35                  40                  45

Ala Tyr Ile Ser Lys Asp Gly Gly Ser Asp Thr Ala Tyr Glu Thr Ala
    50                  55                  60

```
Val Lys Gly Arg Ala Thr Ile Ser Arg Asp Asp Gly Gln Ser Thr Val
65                  70                  75                  80

Arg Leu Gln Leu Asn Asn Leu Arg Ala Glu Asp Thr Ala Thr Tyr Tyr
                85                  90                  95

Cys Ala Arg Gly Ile Gly Val Gly Asn Ile Asp Ala Trp Gly His Gly
            100                 105                 110

Thr Glu Val Ile Val Ser Ser
        115

<210> SEQ ID NO 475
<211> LENGTH: 357
<212> TYPE: DNA
<213> ORGANISM: Artificial Sequence
<220> FEATURE:
<223> OTHER INFORMATION: HC DNA

<400> SEQUENCE: 475
gccgtgacgt tggacgagtc cgagggcggc ctccatacac ccggaggagg gctcagcctc     60
gtctgcaagg cctccgggtt caccttcagc agttatgcca tgtactggat ccgacaggcg    120
cccggcaagg ggctggagtg ggtcgcctat attagcaagg atggtggtag tgacacagca    180
tacgagacag cggtgaaggg ccgtgccacc atctcgaggg acgacgggca gagcacagtg    240
aggctgcagc tgaacaacct cagggctgag gacaccgcca cctactactg cgccagaggt    300
attggtgttg gtaacatcga cgcatggggc cacgggaccg aagtcatcgt ctcctcc       357

<210> SEQ ID NO 476
<211> LENGTH: 10
<212> TYPE: PRT
<213> ORGANISM: Artificial Sequence
<220> FEATURE:
<223> OTHER INFORMATION: CDR1-LC

<400> SEQUENCE: 476

Ser Gly Ser Ser Ser Gly Tyr Gly Tyr Gly
1               5                   10

<210> SEQ ID NO 477
<211> LENGTH: 7
<212> TYPE: PRT
<213> ORGANISM: Artificial Sequence
<220> FEATURE:
<223> OTHER INFORMATION: CDR2-LC

<400> SEQUENCE: 477

Thr Asn Thr Asn Arg Pro Ser
1               5

<210> SEQ ID NO 478
<211> LENGTH: 11
<212> TYPE: PRT
<213> ORGANISM: Artificial Sequence
<220> FEATURE:
<223> OTHER INFORMATION: CDR3-LC

<400> SEQUENCE: 478

Gly Ser Tyr Asp Ser Asn Thr Tyr Leu Gly Leu
1               5                   10

<210> SEQ ID NO 479
<211> LENGTH: 106
<212> TYPE: PRT
<213> ORGANISM: Artificial Sequence
```

```
<220> FEATURE:
<223> OTHER INFORMATION: LC Protein

<400> SEQUENCE: 479

Ala Leu Thr Gln Pro Ser Ser Val Ser Ala Asn Leu Gly Glu Thr Val
1               5                   10                  15

Lys Ile Thr Cys Ser Gly Thr Ser Asp Asn Asn Tyr Phe Gly Trp Tyr
            20                  25                  30

Gln Gln Lys Ser Pro Gly Ser Ala Pro Val Thr Val Ile Tyr Gly Asn
        35                  40                  45

Asp Lys Arg Pro Ser Asp Ile Pro Ser Arg Phe Ser Gly Ser Lys Ser
    50                  55                  60

Gly Ser Thr Ala Thr Leu Thr Ile Thr Gly Val Gln Ala Asp Asp Glu
65                  70                  75                  80

Ala Val Tyr Phe Cys Gly Ser Tyr Asp Thr Tyr Val Asn Asp Asp Ile
                85                  90                  95

Phe Gly Ala Gly Thr Thr Leu Thr Val Leu
            100                 105

<210> SEQ ID NO 480
<211> LENGTH: 318
<212> TYPE: DNA
<213> ORGANISM: Artificial Sequence
<220> FEATURE:
<223> OTHER INFORMATION: LC DNA

<400> SEQUENCE: 480
gccctgactc agccgtcctc ggtgtcagca aacctgggag aaaccgtcaa gatcacctgc      60
tccgggacta gtgacaataa ctactttggt tggtatcagc agaagtctcc tggcagtgcc     120
cctgtcacgg tgatctatgg caacgacaag agaccctcgg acatcccttc acgattctcc     180
ggttccaaat ccggctccac ggccacatta accatcactg gggtccaagc cgacgacgag     240
gctgtctatt tctgtgggag ctatgacacc tatgttaatg atgatatatt tggggccggg     300
acaaccctga ccgtccta                                                    318

<210> SEQ ID NO 481
<211> LENGTH: 7
<212> TYPE: PRT
<213> ORGANISM: Artificial Sequence
<220> FEATURE:
<223> OTHER INFORMATION: Ab93 (MCT1 3310 A12) - CDR1-HC

<400> SEQUENCE: 481

Gly Phe Asp Phe Ser Ser Tyr
1               5

<210> SEQ ID NO 482
<211> LENGTH: 7
<212> TYPE: PRT
<213> ORGANISM: Artificial Sequence
<220> FEATURE:
<223> OTHER INFORMATION: CDR2-HC

<400> SEQUENCE: 482

Tyr Lys Asp Gly Gly Ser Asp
1               5

<210> SEQ ID NO 483
<211> LENGTH: 9
<212> TYPE: PRT
<213> ORGANISM: Artificial Sequence
```

```
<220> FEATURE:
<223> OTHER INFORMATION: CDR3-HC

<400> SEQUENCE: 483

Gly Ile Gly Ile Gly Asn Ile Asp Ala
1               5

<210> SEQ ID NO 484
<211> LENGTH: 119
<212> TYPE: PRT
<213> ORGANISM: Artificial Sequence
<220> FEATURE:
<223> OTHER INFORMATION: HC Protein

<400> SEQUENCE: 484

Ala Val Thr Leu Asp Glu Ser Gly Gly Gly Leu Gln Thr Pro Gly Gly
1               5                   10                  15

Gly Leu Ser Leu Val Cys Lys Ala Ser Gly Phe Asp Phe Ser Ser Tyr
            20                  25                  30

Ala Met Tyr Trp Ile Arg Gln Ala Pro Gly Lys Gly Leu Glu Trp Val
        35                  40                  45

Ala Tyr Ile Tyr Lys Asp Gly Gly Ser Asp Thr Ala Tyr Glu Thr Ala
    50                  55                  60

Val Lys Gly Arg Ala Thr Ile Ser Arg Asp Asp Gly Gln Ser Thr Met
65                  70                  75                  80

Arg Leu Gln Leu Asn Asn Leu Arg Ala Glu Asp Thr Ala Thr Tyr Tyr
                85                  90                  95

Cys Ala Arg Gly Ile Gly Ile Gly Asn Ile Asp Ala Trp Gly His Gly
            100                 105                 110

Thr Glu Val Ile Val Ser Ser
        115

<210> SEQ ID NO 485
<211> LENGTH: 357
<212> TYPE: PRT
<213> ORGANISM: Artificial Sequence
<220> FEATURE:
<223> OTHER INFORMATION: HC DNA

<400> SEQUENCE: 485

Gly Cys Cys Gly Thr Gly Ala Cys Gly Thr Thr Gly Gly Ala Cys Gly
1               5                   10                  15

Ala Gly Thr Cys Cys Gly Gly Gly Gly Cys Gly Gly Cys Cys Thr
            20                  25                  30

Cys Cys Ala Gly Ala Cys Gly Cys Cys Gly Gly Ala Gly Gly Ala
        35                  40                  45

Gly Gly Gly Cys Thr Cys Ala Gly Cys Thr Cys Gly Thr Cys Thr
    50                  55                  60

Gly Cys Ala Ala Gly Gly Cys Cys Thr Cys Gly Gly Gly Thr Thr
65                  70                  75                  80

Thr Gly Ala Cys Thr Thr Cys Ala Gly Cys Ala Gly Thr Thr Ala Cys
                85                  90                  95

Gly Cys Cys Ala Thr Gly Thr Ala Cys Thr Gly Gly Ala Thr Cys Cys
            100                 105                 110

Gly Ala Cys Ala Gly Gly Cys Gly Cys Cys Gly Gly Cys Ala Ala
        115                 120                 125

Gly Gly Gly Gly Cys Thr Gly Gly Ala Gly Thr Gly Gly Gly Thr Cys
    130                 135                 140
```

-continued

```
Gly Cys Cys Thr Ala Thr Ala Thr Thr Ala Cys Ala Ala Gly Gly
145             150             155             160

Ala Thr Gly Gly Thr Gly Gly Thr Ala Gly Thr Gly Ala Cys Ala Cys
            165             170             175

Ala Gly Cys Ala Thr Ala Cys Gly Ala Gly Ala Cys Ala Gly Cys Gly
        180             185             190

Gly Thr Gly Ala Ala Gly Gly Gly Cys Cys Gly Thr Gly Cys Cys Ala
    195             200             205

Cys Cys Ala Thr Cys Thr Cys Gly Ala Gly Gly Gly Ala Cys Gly Ala
    210             215             220

Cys Gly Gly Gly Cys Ala Gly Ala Gly Thr Ala Cys Gly Ala Thr Gly
225             230             235             240

Ala Gly Gly Cys Thr Gly Cys Ala Gly Cys Thr Gly Ala Ala Cys Ala
        245             250             255

Ala Cys Cys Thr Cys Ala Gly Gly Gly Cys Thr Gly Ala Gly Gly Ala
        260             265             270

Cys Ala Cys Cys Gly Cys Cys Ala Cys Cys Thr Ala Cys Thr Ala Cys
        275             280             285

Thr Gly Thr Gly Cys Cys Ala Gly Ala Gly Gly Thr Ala Thr Thr Gly
    290             295             300

Gly Thr Ala Thr Thr Gly Gly Thr Ala Ala Cys Ala Thr Cys Gly Ala
305             310             315             320

Cys Gly Cys Ala Thr Gly Gly Gly Gly Cys Cys Ala Cys Gly Gly Gly
        325             330             335

Ala Cys Cys Gly Ala Ala Gly Thr Cys Ala Thr Cys Gly Thr Cys Thr
        340             345             350

Cys Cys Thr Cys Cys
        355
```

```
<210> SEQ ID NO 486
<211> LENGTH: 10
<212> TYPE: PRT
<213> ORGANISM: Artificial Sequence
<220> FEATURE:
<223> OTHER INFORMATION: CDR1-LC

<400> SEQUENCE: 486

Ser Gly Asn Ser Asp Asn Asn Tyr Phe Gly
1               5                   10
```

```
<210> SEQ ID NO 487
<211> LENGTH: 7
<212> TYPE: PRT
<213> ORGANISM: Artificial Sequence
<220> FEATURE:
<223> OTHER INFORMATION: CDR2-LC

<400> SEQUENCE: 487

Gly Asn Asp Lys Arg Pro Ser
1               5
```

```
<210> SEQ ID NO 488
<211> LENGTH: 11
<212> TYPE: PRT
<213> ORGANISM: Artificial Sequence
<220> FEATURE:
<223> OTHER INFORMATION: CDR3-LC

<400> SEQUENCE: 488

Gly Ser Tyr Asp Thr Tyr Val Asn Asp Asp Met
```

-continued

```
1               5                   10
```

<210> SEQ ID NO 489
<211> LENGTH: 106
<212> TYPE: PRT
<213> ORGANISM: Artificial Sequence
<220> FEATURE:
<223> OTHER INFORMATION: LC Protein

<400> SEQUENCE: 489

```
Ala Leu Thr Gln Pro Ser Ser Val Ser Ala Asn Pro Gly Gly Thr Val
1               5                   10                  15

Glu Ile Thr Cys Ser Gly Asn Ser Asp Asn Asn Tyr Phe Gly Trp Phe
                20                  25                  30

Gln Gln Lys Ser Pro Gly Ser Ala Pro Val Thr Val Ile Tyr Gly Asn
        35                  40                  45

Asp Lys Arg Pro Ser Asp Ile Pro Ser Arg Phe Ser Gly Ser Lys Ser
    50                  55                  60

Gly Ser Thr Ala Thr Leu Thr Ile Thr Gly Val Gln Ala Asp Asp Glu
65                  70                  75                  80

Ala Val Tyr Phe Cys Gly Ser Tyr Asp Thr Tyr Val Asn Asp Asp Met
                85                  90                  95

Phe Gly Ala Gly Thr Thr Leu Thr Val Leu
            100                 105
```

<210> SEQ ID NO 490
<211> LENGTH: 318
<212> TYPE: DNA
<213> ORGANISM: Artificial Sequence
<220> FEATURE:
<223> OTHER INFORMATION: LC DNA

<400> SEQUENCE: 490

```
gccctgactc agccgtcctc ggtgtcagca aacccgggag gaaccgtcga gatcacctgc      60
tccgggaata gtgacaataa ctactttggc tggttccagc agaagtctcc tggcagtgcc     120
ccagtcactg tgatctatgg caacgacaag agaccctcgg acatcccttc acgattctcc     180
ggttccaaat ccggctccac ggccacatta accatcactg gggtccaagc cgacgacgag     240
gctgtctatt tctgtgggag ctacgacacc tatgtcaatg atgacatgtt tgggccgggg     300
acaaccctga ccgtcctt                                                    318
```

<210> SEQ ID NO 491
<211> LENGTH: 7
<212> TYPE: PRT
<213> ORGANISM: Artificial Sequence
<220> FEATURE:
<223> OTHER INFORMATION: Ab94 (MCT1 3311 B04) - CDR1-HC

<400> SEQUENCE: 491

```
Gly Phe Thr Phe Ser Ser Phe
1               5
```

<210> SEQ ID NO 492
<211> LENGTH: 6
<212> TYPE: PRT
<213> ORGANISM: Artificial Sequence
<220> FEATURE:
<223> OTHER INFORMATION: CDR2-HC

<400> SEQUENCE: 492

```
Ser Asn Asp Gly Gly Gly
```

```
1               5
```

```
<210> SEQ ID NO 493
<211> LENGTH: 9
<212> TYPE: PRT
<213> ORGANISM: Artificial Sequence
<220> FEATURE:
<223> OTHER INFORMATION: CDR3-HC

<400> SEQUENCE: 493

Gly Gly Gly Ala Ser Ser Ile Asp Ala
1               5

<210> SEQ ID NO 494
<211> LENGTH: 118
<212> TYPE: PRT
<213> ORGANISM: Artificial Sequence
<220> FEATURE:
<223> OTHER INFORMATION: HC Protein

<400> SEQUENCE: 494

Ala Val Thr Leu Asp Glu Ser Glu Gly Gly Leu Gln Thr Pro Gly Gly
1               5                   10                  15

Thr Leu Ser Leu Val Cys Lys Gly Ser Gly Phe Thr Phe Ser Ser Phe
            20                  25                  30

Asn Met Phe Trp Val Arg Gln Ala Pro Gly Lys Gly Leu Glu Phe Val
        35                  40                  45

Ala Ala Val Ser Asn Asp Gly Gly Thr Trp Tyr Ala Thr Ala Val
    50                  55                  60

Lys Gly Arg Ala Thr Ile Ser Lys Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Arg Gly Gly Gly Ala Ser Ser Ile Asp Ala Trp Gly His Gly Thr
            100                 105                 110

Glu Val Ile Val Ser Ser
        115

<210> SEQ ID NO 495
<211> LENGTH: 354
<212> TYPE: DNA
<213> ORGANISM: Artificial Sequence
<220> FEATURE:
<223> OTHER INFORMATION: HC DNA

<400> SEQUENCE: 495
gccgtgacgt tggacgagtc cgagggcggc ctccagacgc ccggaggaac gctcagcctc     60
gtctgcaagg gctccgggtt caccttcagc agcttcaaca tgttctgggt gcgacaggcg    120
cccggcaagg ggctggaatt cgtcgctgct gttagcaatg atggtggtgg cacatggtac    180
gcgacggcgg tgaagggccg tgccaccatc tcgaaggaca cgggcagag cacagtgagg    240 ctgcagctga caacctcag ggctgaggac accggcacct actactgcgc cagaggtggt    300
ggtgccagta gtatcgacgc atggggccac gggaccgaag tcatcgtctc ctcc           354

<210> SEQ ID NO 496
<211> LENGTH: 8
<212> TYPE: PRT
<213> ORGANISM: Artificial Sequence
<220> FEATURE:
<223> OTHER INFORMATION: CDR1-LC
```

<400> SEQUENCE: 496

Ser Gly Gly Ser Gly Arg Tyr Gly
1               5

<210> SEQ ID NO 497
<211> LENGTH: 7
<212> TYPE: PRT
<213> ORGANISM: Artificial Sequence
<220> FEATURE:
<223> OTHER INFORMATION: CDR2-LC

<400> SEQUENCE: 497

Ala Asn Thr Lys Arg Pro Ser
1               5

<210> SEQ ID NO 498
<211> LENGTH: 10
<212> TYPE: PRT
<213> ORGANISM: Artificial Sequence
<220> FEATURE:
<223> OTHER INFORMATION: CDR3-LC

<400> SEQUENCE: 498

Gly Ser Ile Asp Asn Asn Tyr Val Gly Ile
1               5                   10

<210> SEQ ID NO 499
<211> LENGTH: 103
<212> TYPE: PRT
<213> ORGANISM: Artificial Sequence
<220> FEATURE:
<223> OTHER INFORMATION: LC Protein

<400> SEQUENCE: 499

Ala Leu Thr Gln Pro Ser Ser Val Ser Ala Asn Pro Gly Glu Thr Val
1               5                   10                  15

Lys Ile Thr Cys Ser Gly Gly Ser Gly Arg Tyr Gly Trp Tyr Gln Gln
            20                  25                  30

Lys Ser Pro Gly Ser Ala Pro Val Thr Val Ile Arg Ala Asn Thr Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Gln Val Glu Asp Glu Ala Val
65                  70                  75                  80

Tyr Phe Cys Gly Ser Ile Asp Asn Asn Tyr Val Gly Ile Phe Gly Ala
                85                  90                  95

Gly Thr Thr Leu Thr Val Leu
            100

<210> SEQ ID NO 500
<211> LENGTH: 309
<212> TYPE: DNA
<213> ORGANISM: Artificial Sequence
<220> FEATURE:
<223> OTHER INFORMATION: LC DNA

<400> SEQUENCE: 500
gccctgactc agccgtcctc ggtgtcagca aacccaggag aaaccgtcaa gatcacctgc        60
tccgggggta gtggcaggta cggctggtat cagcagaagt cacctggcag tgcccctgtc       120
actgtgatca gggctaacac caagagaccc tcggacatcc cttcacgatt ctccggttcc       180
aaatccggct ccacgggcac attaaccatc actgggggtcc aagtcgagga cgaggctgtc       240

-continued

```
tatttctgtg ggagcataga caacaactat gttggtatat ttggggccgg gacaaccctg        300
accgtccta                                                                309
```

```
<210> SEQ ID NO 501
<211> LENGTH: 7
<212> TYPE: PRT
<213> ORGANISM: Artificial Sequence
<220> FEATURE:
<223> OTHER INFORMATION: CDR1-HC

<400> SEQUENCE: 501

Gly Phe Thr Ile Ser Ser Tyr
1               5

<210> SEQ ID NO 502
<211> LENGTH: 6
<212> TYPE: PRT
<213> ORGANISM: Artificial Sequence
<220> FEATURE:
<223> OTHER INFORMATION: CDR2-HC

<400> SEQUENCE: 502

Ser Gly Ser Gly Arg Tyr
1               5

<210> SEQ ID NO 503
<211> LENGTH: 15
<212> TYPE: PRT
<213> ORGANISM: Artificial Sequence
<220> FEATURE:
<223> OTHER INFORMATION: CDR3-HC

<400> SEQUENCE: 503

Asp Gly Gly Gly Asn Tyr Trp Asn Ala Ala Gly Gly Ile Asp Ala
1               5                   10                  15

<210> SEQ ID NO 504
<211> LENGTH: 124
<212> TYPE: PRT
<213> ORGANISM: Artificial Sequence
<220> FEATURE:
<223> OTHER INFORMATION: HC Protein

<400> SEQUENCE: 504

Ala Val Thr Leu Asp Glu Ser Gly Gly Gly Leu Gln Thr Pro Gly Gly
1               5                   10                  15

Thr Leu Ser Leu Val Cys Lys Gly Ser Gly Phe Thr Ile Ser Ser Tyr
            20                  25                  30

Thr Met Gln Trp Val Arg Gln Ala Pro Asp Lys Gly Leu Glu Tyr Val
        35                  40                  45

Ala Ser Ile Ser Gly Ser Gly Arg Tyr Thr Gly Tyr Gly Ala Ala Val
    50                  55                  60

Lys Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Gly Thr Tyr Tyr Cys
                85                  90                  95

Ala Lys Asp Gly Gly Gly Asn Tyr Trp Asn Ala Ala Gly Gly Ile Asp
            100                 105                 110

Ala Trp Gly His Gly Thr Glu Val Ile Val Ser Ser
        115                 120
```

<210> SEQ ID NO 505
<211> LENGTH: 372
<212> TYPE: DNA
<213> ORGANISM: Artificial Sequence
<220> FEATURE:
<223> OTHER INFORMATION: HC DNA

<400> SEQUENCE: 505

```
gccgtgacgt tggacgagtc cgggggcggc ctccagacgc ccggaggaac gctcagcctc        60
gtctgcaagg gctccgggtt caccatcagc agttacacca tgcagtgggt gcgacaggcg       120
cccgacaagg ggttggaata tgtcgccagt attagcggca gtggtagata cacaggctac       180
ggggcggcgg tgaagggccg tgccaccatc tcgagggaca cgggcagag cacagtgagg        240 ctgcagctga caacctcag ggctgaggac accggcacct actactgcgc caaagatggt        300
ggtggtaatt actggaatgc tgctggtggt atcgacgcat ggggccacgg gaccgaagtc       360
atcgtctcct cc                                                          372
```

<210> SEQ ID NO 506
<211> LENGTH: 8
<212> TYPE: PRT
<213> ORGANISM: Artificial Sequence
<220> FEATURE:
<223> OTHER INFORMATION: CDR1-LC

<400> SEQUENCE: 506

```
Ser Gly Gly Ser Ser Thr Tyr Gly
1               5
```

<210> SEQ ID NO 507
<211> LENGTH: 7
<212> TYPE: PRT
<213> ORGANISM: Artificial Sequence
<220> FEATURE:
<223> OTHER INFORMATION: CDR2-LC

<400> SEQUENCE: 507

```
Asn Asp Asp Glu Arg Pro Ser
1               5
```

<210> SEQ ID NO 508
<211> LENGTH: 12
<212> TYPE: PRT
<213> ORGANISM: Artificial Sequence
<220> FEATURE:
<223> OTHER INFORMATION: CDR3-LC

<400> SEQUENCE: 508

```
Gly Asn Glu Asp Ser Ser Ala Gly Lys Gly Gly Ile
1               5                   10
```

<210> SEQ ID NO 509
<211> LENGTH: 105
<212> TYPE: PRT
<213> ORGANISM: Artificial Sequence
<220> FEATURE:
<223> OTHER INFORMATION: LC Protein

<400> SEQUENCE: 509

```
Ala Leu Thr Gln Pro Ser Ser Val Ser Ala Asn Leu Gly Gly Thr Val
1               5                   10                  15

Glu Ile Thr Cys Ser Gly Gly Ser Ser Thr Tyr Gly Trp Tyr Gln Gln
            20                  25                  30

Lys Ser Pro Gly Ser Ala Pro Val Thr Leu Ile Tyr Asn Asp Asp Glu
```

-continued

```
             35                40                45
Arg Pro Ser Asn Ile Pro Ser Arg Phe Ser Gly Ser Thr Ser Asp Phe
    50                55                60
Thr Gly Thr Leu Thr Ile Thr Gly Val Gln Ala Asp Asp Glu Ala Val
65                  70                75                80
Tyr Phe Cys Gly Asn Glu Asp Ser Ser Ala Gly Lys Gly Gly Ile Phe
                85                90                95
Gly Ala Gly Thr Thr Leu Thr Val Leu
            100               105
```

```
<210> SEQ ID NO 510
<211> LENGTH: 315
<212> TYPE: DNA
<213> ORGANISM: Artificial Sequence
<220> FEATURE:
<223> OTHER INFORMATION: LC DNA

<400> SEQUENCE: 510
gccctgactc agccgtcctc ggtgtcagcg aacctgggag gaaccgtcga gatcacctgc      60
tccgggggta gcagcaccta tggctggtac cagcagaagt ctcctggcag tgcccctgtc     120
actctgattt ataatgatga tgagagaccc tcgaacatcc cttcacgatt ctccggttcc     180
acatccgact tcacgggcac attaaccatc actggggtcc aagccgacga cgaggctgtc     240
tatttctgtg ggaatgaaga cagcagtgct ggtaaaggtg gcatatttgg ggccgggaca     300
accctgaccg tccta                                                      315
```

```
<210> SEQ ID NO 511
<211> LENGTH: 456
<212> TYPE: PRT
<213> ORGANISM: Artificial Sequence
<220> FEATURE:
<223> OTHER INFORMATION: Humanized Heavy Chain

<400> SEQUENCE: 511

Gln Val Gln Leu Gln Glu Ser Gly Pro Gly Leu Val Lys Pro Ser Glu
1               5                 10                15
Thr Leu Ser Leu Thr Cys Thr Val Ser Gly Phe Ser Leu Thr Asn Tyr
            20                25                30
His Leu Gln Trp Ile Arg Gln Pro Pro Gly Lys Gly Leu Glu Trp Ile
        35                40                45
Gly Phe Ile Arg Ser Ser Gly Asn Thr Glu Tyr Asn Pro Ser Leu Lys
    50                55                60
Ser Arg Val Thr Ile Ser Arg Asp Thr Ser Lys Asn Gln Val Ser Leu
65                  70                75                80
Lys Leu Ser Ser Val Thr Ala Ala Asp Thr Ala Val Tyr Tyr Cys Ala
                85                90                95
Arg Asn Ser Trp Tyr His Gly Thr Tyr Tyr Ser Pro Gly Tyr Tyr Val
            100               105               110
Met Asp Ala Trp Gly Gln Gly Thr Met Val Thr Val Ser Ser Ala Ser
            115               120               125
Thr Lys Gly Pro Ser Val Phe Pro Leu Ala Pro Ser Ser Lys Ser Thr
        130               135               140
Ser Gly Gly Thr Ala Ala Leu Gly Cys Leu Val Lys Asp Tyr Phe Pro
145               150               155               160
Glu Pro Val Thr Val Ser Trp Asn Ser Gly Ala Leu Thr Ser Gly Val
            165               170               175
```

```
His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Arg Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Ala Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455
```

```
<210> SEQ ID NO 512
<211> LENGTH: 456
<212> TYPE: PRT
<213> ORGANISM: Artificial Sequence
<220> FEATURE:
<223> OTHER INFORMATION: Humanized Heavy Chain

<400> SEQUENCE: 512

Gln Val Gln Leu Lys Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
        50                  55                  60

Ser Arg Val Thr Ile Ser Arg Asp Thr Ser Lys Asn Gln Val Ser Leu
65                  70                  75                  80
```

-continued

```
Lys Leu Ser Ser Val Thr Ala Ala Asp Thr Ala Val Tyr Tyr Cys Ala
                85              90              95

Arg Asn Ser Trp Tyr His Gly Thr Tyr Tyr Ser Pro Gly Tyr Tyr Val
            100             105             110

Met Asp Ala Trp Gly Gln Gly Thr Met Val Thr Val Ser Ser Ala Ser
        115             120             125

Thr Lys Gly Pro Ser Val Phe Pro Leu Ala Pro Ser Ser Lys Ser Thr
    130             135             140

Ser Gly Gly Thr Ala Ala Leu Gly Cys Leu Val Lys Asp Tyr Phe Pro
145             150             155             160

Glu Pro Val Thr Val Ser Trp Asn Ser Gly Ala Leu Thr Ser Gly Val
            165             170             175

His Thr Phe Pro Ala Val Leu Gln Ser Ser Gly Leu Tyr Ser Leu Ser
        180             185             190

Ser Val Val Thr Val Pro Ser Ser Ser Leu Gly Thr Gln Thr Tyr Ile
    195             200             205

Cys Asn Val Asn His Lys Pro Ser Asn Thr Lys Val Asp Lys Lys Val
    210             215             220

Glu Pro Lys Ser Cys Asp Lys Thr His Thr Cys Pro Pro Cys Pro Ala
225             230             235             240

Pro Glu Leu Leu Gly Gly Pro Ser Val Phe Leu Phe Pro Pro Lys Pro
            245             250             255

Lys Asp Thr Leu Met Ile Ser Arg Thr Pro Glu Val Thr Cys Val Val
        260             265             270

Val Asp Val Ser His Arg Asp Pro Glu Val Lys Phe Asn Trp Tyr Val
    275             280             285

Asp Gly Val Glu Val His Asn Ala Lys Thr Lys Pro Arg Glu Glu Gln
    290             295             300

Tyr Asn Ser Thr Tyr Arg Val Val Ser Val Leu Thr Val Leu His Gln
305             310             315             320

Asp Trp Leu Asn Gly Lys Glu Tyr Lys Cys Ala Val Ser Asn Lys Ala
            325             330             335

Leu Pro Ala Pro Ile Glu Lys Thr Ile Ser Lys Ala Lys Gly Gln Pro
        340             345             350

Arg Glu Pro Gln Val Tyr Thr Leu Pro Pro Ser Arg Asp Glu Leu Thr
        355             360             365

Lys Asn Gln Val Ser Leu Thr Cys Leu Val Lys Gly Phe Tyr Pro Ser
    370             375             380

Asp Ile Ala Val Glu Trp Glu Ser Asn Gly Gln Pro Glu Asn Asn Tyr
385             390             395             400

Lys Thr Thr Pro Pro Val Leu Asp Ser Asp Gly Ser Phe Phe Leu Tyr
            405             410             415

Ser Lys Leu Thr Val Asp Lys Ser Arg Trp Gln Gln Gly Asn Val Phe
        420             425             430

Ser Cys Ser Val Met His Glu Ala Leu His Asn His Tyr Thr Gln Lys
        435             440             445

Ser Leu Ser Leu Ser Pro Gly Lys
    450             455
```

```
<210> SEQ ID NO 513
<211> LENGTH: 456
<212> TYPE: PRT
<213> ORGANISM: Artificial Sequence
<220> FEATURE:
<223> OTHER INFORMATION: Humanized Heavy Chain
```

```
<400> SEQUENCE: 513

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Arg Asp Pro Glu Val Lys Phe Asn Trp Tyr Val
            275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Ala Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
```

-continued

```
              405                 410                 415
Ser Lys Leu Thr Val Asp Lys Ser Arg Trp Gln Gln Gly Asn Val Phe
          420                 425                 430

Ser Cys Ser Val Met His Glu Ala Leu His Asn His Tyr Thr Gln Lys
      435                 440                 445

Ser Leu Ser Leu Ser Pro Gly Lys
    450                 455

<210> SEQ ID NO 514
<211> LENGTH: 456
<212> TYPE: PRT
<213> ORGANISM: Artificial Sequence
<220> FEATURE:
<223> OTHER INFORMATION: Humanized Heavy Chain

<400> SEQUENCE: 514

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
          20                  25                  30

His Leu Gln Trp Val Arg Gln Pro Pro Gly Lys Gly Leu Glu Trp Ile
      35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
              85                  90                  95

Arg Asn Ser Trp Tyr His Gly Thr Tyr Tyr Ser Pro Gly Tyr Tyr Val
          100                 105                 110

Met Asp Ala Trp Gly Gln Gly Thr Leu Val Thr Val Ser Ser Ala Ser
          115                 120                 125

Thr Lys Gly Pro Ser Val Phe Pro Leu Ala Pro Ser Ser Lys Ser Thr
      130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
              165                 170                 175

His Thr Phe Pro Ala Val Leu Gln Ser Ser Gly Leu Tyr Ser Leu Ser
          180                 185                 190

Ser Val Val Thr Val Pro Ser Ser Ser Leu Gly Thr Gln Thr Tyr Ile
          195                 200                 205

Cys Asn Val Asn His Lys Pro Ser Asn Thr Lys Val Asp Lys Lys Val
      210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
              245                 250                 255

Lys Asp Thr Leu Met Ile Ser Arg Thr Pro Glu Val Thr Cys Val Val
          260                 265                 270

Val Asp Val Ser His Arg Asp Pro Glu Val Lys Phe Asn Trp Tyr Val
          275                 280                 285

Asp Gly Val Glu Val His Asn Ala Lys Thr Lys Pro Arg Glu Glu Gln
      290                 295                 300

Tyr Asn Ser Thr Tyr Arg Val Val Ser Val Leu Thr Val Leu His Gln
```

-continued

```
      305                 310                 315                 320

Asp Trp Leu Asn Gly Lys Glu Tyr Lys Cys Ala Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys
    450                 455

<210> SEQ ID NO 515
<211> LENGTH: 456
<212> TYPE: PRT
<213> ORGANISM: Artificial Sequence
<220> FEATURE:
<223> OTHER INFORMATION: Humanized Heavy Chain

<400> SEQUENCE: 515

Gln Val Gln Leu Gln Glu Ser Gly Pro Gly Leu Val Gln Pro Thr Gln
1               5                   10                  15

Thr Leu Ser Ile Thr Cys Thr Val Ser Gly Phe Ser Leu Thr Asn Tyr
                20                  25                  30

His Leu Gln Trp Val Arg Gln Thr Pro Gly Lys Gly Leu Glu Trp Met
            35                  40                  45

Gly Phe Ile Arg Ser Ser Gly Asn Thr Glu Tyr Asn Ser Glu Phe Lys
    50                  55                  60

Ser Arg Leu Ser Ile Ser Arg Asp Thr Ser Lys Asn Gln Val Phe Leu
65                  70                  75                  80

Lys Met Asn Ser Leu Lys Thr Glu Asp Thr Gly Val Tyr Tyr Cys Ala
                85                  90                  95

Arg Asn Ser Trp Tyr His Gly Thr Tyr Tyr Ser Pro Gly Tyr Tyr Val
                100                 105                 110

Met Asp Ala Trp Gly Gln Gly Thr Thr Val Thr Val Ser Ser Ala Ser
            115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
```

-continued

```
             210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Arg Asp Pro Glu Val Lys Phe Asn Trp Tyr Val
            275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Ala Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
                355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro Gly Lys
    450                 455
```

```
<210> SEQ ID NO 516
<211> LENGTH: 456
<212> TYPE: PRT
<213> ORGANISM: Artificial Sequence
<220> FEATURE:
<223> OTHER INFORMATION: Humanized Heavy Chain

<400> SEQUENCE: 516

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
                20                  25                  30

His Leu Gln Trp Val Arg Gln Pro Pro Gly Lys Gly Leu Glu Trp Met
            35                  40                  45

Gly Phe Ile Arg Ser Ser Gly Asn Thr Glu Tyr Asn Ser Glu Phe Lys
    50                  55                  60

Ser Arg Leu Ser Ile Ser Arg Asp Thr Ser Lys Asn Gln Val Tyr Leu
65                  70                  75                  80

Gln Met Asn Ser Leu Lys Thr Glu Asp Thr Ala Val Tyr Tyr Cys Ala
                85                  90                  95

Arg Asn Ser Trp Tyr His Gly Thr Tyr Tyr Ser Pro Gly Tyr Tyr Val
                100                 105                 110

Met Asp Ala Trp Gly Gln Gly Thr Thr Val Thr Val Ser Ser Ala Ser
```

-continued

```
                115                  120                  125
Thr Lys Gly Pro Ser Val Phe Pro Leu Ala Pro Ser Ser Lys Ser Thr
    130                  135                  140

Ser Gly Gly Thr Ala Ala Leu Gly Cys Leu Val Lys Asp Tyr Phe Pro
145                  150                  155                  160

Glu Pro Val Thr Val Ser Trp Asn Ser Gly Ala Leu Thr Ser Gly Val
                165                  170                  175

His Thr Phe Pro Ala Val Leu Gln Ser Ser Gly Leu Tyr Ser Leu Ser
                180                  185                  190

Ser Val Val Thr Val Pro Ser Ser Ser Leu Gly Thr Gln Thr Tyr Ile
                195                  200                  205

Cys Asn Val Asn His Lys Pro Ser Asn Thr Lys Val Asp Lys Lys Val
    210                  215                  220

Glu Pro Lys Ser Cys Asp Lys Thr His Thr Cys Pro Pro Cys Pro Ala
225                  230                  235                  240

Pro Glu Leu Leu Gly Gly Pro Ser Val Phe Leu Phe Pro Pro Lys Pro
                245                  250                  255

Lys Asp Thr Leu Met Ile Ser Arg Thr Pro Glu Val Thr Cys Val Val
                260                  265                  270

Val Asp Val Ser His Arg Asp Pro Glu Val Lys Phe Asn Trp Tyr Val
                275                  280                  285

Asp Gly Val Glu Val His Asn Ala Lys Thr Lys Pro Arg Glu Glu Gln
    290                  295                  300

Tyr Asn Ser Thr Tyr Arg Val Val Ser Val Leu Thr Val Leu His Gln
305                  310                  315                  320

Asp Trp Leu Asn Gly Lys Glu Tyr Lys Cys Ala Val Ser Asn Lys Ala
                325                  330                  335

Leu Pro Ala Pro Ile Glu Lys Thr Ile Ser Lys Ala Lys Gly Gln Pro
                340                  345                  350

Arg Glu Pro Gln Val Tyr Thr Leu Pro Pro Ser Arg Asp Glu Leu Thr
                355                  360                  365

Lys Asn Gln Val Ser Leu Thr Cys Leu Val Lys Gly Phe Tyr Pro Ser
    370                  375                  380

Asp Ile Ala Val Glu Trp Glu Ser Asn Gly Gln Pro Glu Asn Asn Tyr
385                  390                  395                  400

Lys Thr Thr Pro Pro Val Leu Asp Ser Asp Gly Ser Phe Phe Leu Tyr
                405                  410                  415

Ser Lys Leu Thr Val Asp Lys Ser Arg Trp Gln Gln Gly Asn Val Phe
                420                  425                  430

Ser Cys Ser Val Met His Glu Ala Leu His Asn His Tyr Thr Gln Lys
                435                  440                  445

Ser Leu Ser Leu Ser Pro Gly Lys
    450                  455

<210> SEQ ID NO 517
<211> LENGTH: 456
<212> TYPE: PRT
<213> ORGANISM: Artificial Sequence
<220> FEATURE:
<223> OTHER INFORMATION: Humanized Heavy Chain

<400> SEQUENCE: 517

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
```

```
                 20              25              30
His Leu Gln Trp Val Arg Gln Pro Pro Gly Lys Gly Leu Glu Trp Met
            35              40              45

Gly Phe Ile Arg Ser Ser Gly Asn Thr Glu Tyr Asn Ser Glu Phe Lys
        50              55              60

Ser Arg Leu Thr Ile Ser Lys Asp Thr Ser Lys Asn Gln Val Tyr Leu
65              70              75              80

Gln Met Asn Ser Leu Lys Thr Glu Asp Thr Ala Val Tyr Tyr Cys Ala
            85              90              95

Arg Asn Ser Trp Tyr His Gly Thr Tyr Tyr Ser Pro Gly Tyr Tyr Val
            100             105             110

Met Asp Ala Trp Gly Gln Gly Thr Thr Val Thr Val Ser Ser Ala Ser
        115             120             125

Thr Lys Gly Pro Ser Val Phe Pro Leu Ala Pro Ser Ser Lys Ser Thr
    130             135             140

Ser Gly Gly Thr Ala Ala Leu Gly Cys Leu Val Lys Asp Tyr Phe Pro
145             150             155             160

Glu Pro Val Thr Val Ser Trp Asn Ser Gly Ala Leu Thr Ser Gly Val
            165             170             175

His Thr Phe Pro Ala Val Leu Gln Ser Ser Gly Leu Tyr Ser Leu Ser
        180             185             190

Ser Val Val Thr Val Pro Ser Ser Ser Leu Gly Thr Gln Thr Tyr Ile
        195             200             205

Cys Asn Val Asn His Lys Pro Ser Asn Thr Lys Val Asp Lys Lys Val
    210             215             220

Glu Pro Lys Ser Cys Asp Lys Thr His Thr Cys Pro Pro Cys Pro Ala
225             230             235             240

Pro Glu Leu Leu Gly Gly Pro Ser Val Phe Leu Phe Pro Pro Lys Pro
            245             250             255

Lys Asp Thr Leu Met Ile Ser Arg Thr Pro Glu Val Thr Cys Val Val
            260             265             270

Val Asp Val Ser His Arg Asp Pro Glu Val Lys Phe Asn Trp Tyr Val
        275             280             285

Asp Gly Val Glu Val His Asn Ala Lys Thr Lys Pro Arg Glu Glu Gln
    290             295             300

Tyr Asn Ser Thr Tyr Arg Val Val Ser Val Leu Thr Val Leu His Gln
305             310             315             320

Asp Trp Leu Asn Gly Lys Glu Tyr Lys Cys Ala Val Ser Asn Lys Ala
            325             330             335

Leu Pro Ala Pro Ile Glu Lys Thr Ile Ser Lys Ala Lys Gly Gln Pro
            340             345             350

Arg Glu Pro Gln Val Tyr Thr Leu Pro Pro Ser Arg Asp Glu Leu Thr
            355             360             365

Lys Asn Gln Val Ser Leu Thr Cys Leu Val Lys Gly Phe Tyr Pro Ser
    370             375             380

Asp Ile Ala Val Glu Trp Glu Ser Asn Gly Gln Pro Glu Asn Asn Tyr
385             390             395             400

Lys Thr Thr Pro Pro Val Leu Asp Ser Asp Gly Ser Phe Phe Leu Tyr
            405             410             415

Ser Lys Leu Thr Val Asp Lys Ser Arg Trp Gln Gln Gly Asn Val Phe
        420             425             430

Ser Cys Ser Val Met His Glu Ala Leu His Asn His Tyr Thr Gln Lys
        435             440             445
```

```
Ser Leu Ser Leu Ser Pro Gly Lys
    450                 455

<210> SEQ ID NO 518
<211> LENGTH: 213
<212> TYPE: PRT
<213> ORGANISM: Artificial Sequence
<220> FEATURE:
<223> OTHER INFORMATION: Humanized Light Chain

<400> SEQUENCE: 518

Asp Ile Gln Met Thr Gln Ser Pro Ser Ser Leu Ser Ala Ser Val Gly
1               5                   10                  15

Asp Arg Val Thr Ile Thr Cys Arg Gly Ser Gln Asn Ile Asn Asn Tyr
                20                  25                  30

Leu Ala Trp Phe Gln Gln Lys Pro Gly Lys Thr Pro Lys Leu Leu Ile
        35                  40                  45

Tyr Asn Arg His Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 519
<211> LENGTH: 213
<212> TYPE: PRT
<213> ORGANISM: Artificial Sequence
<220> FEATURE:
<223> OTHER INFORMATION: Humanized Light Chain

<400> SEQUENCE: 519

Asp Ile Gln Met Thr Gln Ser Pro Ser Ser Leu Ser Ala Ser Val Gly
1               5                   10                  15

Asp Arg Val Thr Ile Thr Cys Arg Gly Ser Gln Asn Ile Asn Asn Tyr
                20                  25                  30

Leu Ala Trp Phe Gln Gln Lys Pro Gly Lys Thr Pro Lys Leu Leu Ile
        35                  40                  45

Tyr Asn Arg His Asn Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
```

-continued

```
65                  70                  75                  80

Glu Asp Val Ala Thr Tyr Tyr Cys Tyr Gln Tyr Ser Asp Gly Tyr Thr
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
        210

<210> SEQ ID NO 520
<211> LENGTH: 213
<212> TYPE: PRT
<213> ORGANISM: Artificial Sequence
<220> FEATURE:
<223> OTHER INFORMATION: Humanized Light Chain

<400> SEQUENCE: 520

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
                20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
```

-continued

210

<210> SEQ ID NO 521
<211> LENGTH: 213
<212> TYPE: PRT
<213> ORGANISM: Artificial Sequence
<220> FEATURE:
<223> OTHER INFORMATION: Humanized Light Chain

<400> SEQUENCE: 521

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
                20                  25                  30

Leu Ala Trp Phe Gln Gln Lys Pro Gly Lys Thr Pro Ala Leu Leu Ile
            35                  40                  45

Tyr Asn Arg His Asn Leu Gln Ser Gly Val Pro Ser Arg Phe Arg Gly
        50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 522
<211> LENGTH: 213
<212> TYPE: PRT
<213> ORGANISM: Artificial Sequence
<220> FEATURE:
<223> OTHER INFORMATION: Humanized Light Chain

<400> SEQUENCE: 522

Asn Ile Gln Met Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
                20                  25                  30

Leu Ala Trp Phe Gln Gln Lys Phe Gly Glu Thr Pro Lys Leu Leu Ile
            35                  40                  45

Tyr Asn Arg His Asn Leu Gln Thr Gly Ile Pro Ser Arg Phe Ser Gly
        50                  55                  60

Ser Gly Ser Gly Thr Asp Tyr Thr Leu Thr Ile Asn Ser Leu Gln Pro
65                  70                  75                  80

```
Glu Asp Val Ala Thr Tyr Phe Cys Tyr Gln Tyr Ser Asp Gly Tyr Thr
            85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 523
<211> LENGTH: 153
<212> TYPE: PRT
<213> ORGANISM: Artificial Sequence
<220> FEATURE:
<223> OTHER INFORMATION: Humanized Light Chain

<400> SEQUENCE: 523

Arg Phe Ser Gly Ser Gly Ser Gly Thr Asp Tyr Thr Leu Thr Ile Ser
1               5                   10                  15

Ser Leu Gln Pro Glu Asp Val Ala Thr Tyr Phe Cys Tyr Gln Tyr Ser
            20                  25                  30

Asp Gly Tyr Thr Phe Gly Gly Gly Thr Lys Val Glu Ile Lys Arg Thr
            35                  40                  45

Val Ala Ala Pro Ser Val Phe Ile Phe Pro Pro Ser Asp Glu Gln Leu
    50                  55                  60

Lys Ser Gly Thr Ala Ser Val Val Cys Leu Leu Asn Asn Phe Tyr Pro
65                  70                  75                  80

Arg Glu Ala Lys Val Gln Trp Lys Val Asp Asn Ala Leu Gln Ser Gly
            85                  90                  95

Asn Ser Gln Glu Ser Val Thr Glu Gln Asp Ser Lys Asp Ser Thr Tyr
            100                 105                 110

Ser Leu Ser Ser Thr Leu Thr Leu Ser Lys Ala Asp Tyr Glu Lys His
            115                 120                 125

Lys Val Tyr Ala Cys Glu Val Thr His Gln Gly Leu Ser Ser Pro Val
    130                 135                 140

Thr Lys Ser Phe Asn Arg Gly Glu Cys
145                 150

<210> SEQ ID NO 524
<211> LENGTH: 213
<212> TYPE: PRT
<213> ORGANISM: Artificial Sequence
<220> FEATURE:
<223> OTHER INFORMATION: Humanized Light Chain

<400> SEQUENCE: 524

Asn Ile Gln Met Thr Gln Ser Pro Ser Leu Leu Ser Ala Ser Val Gly
1               5                   10                  15
```

```
Asp Arg Val Thr Ile Ser Cys Lys Gly Ser Gln Asn Ile Asn Asn Tyr
            20              25              30

Leu Ala Trp Phe Gln Gln Lys Phe Gly Gln Pro Pro Lys Leu Leu Ile
            35              40              45

Tyr Asn Arg His Asn Leu Gln Thr Gly Ile Pro Ser Arg Phe Ser Gly
    50              55              60

Ser Gly Ser Gly Thr Asp Tyr Thr Leu Thr Ile Ser Ser Leu Gln Pro
65              70              75              80

Glu Asp Val Ala Thr Tyr Tyr Cys Tyr Gln Tyr Ser Asp Gly Tyr Thr
            85              90              95

Phe Gly Gly Gly Thr Lys Val Glu Ile Lys Arg Thr Val Ala Ala Pro
            100             105             110

Ser Val Phe Ile Phe Pro Pro Ser Asp Glu Gln Leu Lys Ser Gly Thr
            115             120             125

Ala Ser Val Val Cys Leu Leu Asn Asn Phe Tyr Pro Arg Glu Ala Lys
    130             135             140

Val Gln Trp Lys Val Asp Asn Ala Leu Gln Ser Gly Asn Ser Gln Glu
145             150             155             160

Ser Val Thr Glu Gln Asp Ser Lys Asp Ser Thr Tyr Ser Leu Ser Ser
            165             170             175

Thr Leu Thr Leu Ser Lys Ala Asp Tyr Glu Lys His Lys Val Tyr Ala
            180             185             190

Cys Glu Val Thr His Gln Gly Leu Ser Ser Pro Val Thr Lys Ser Phe
            195             200             205

Asn Arg Gly Glu Cys
    210

<210> SEQ ID NO 525
<211> LENGTH: 126
<212> TYPE: PRT
<213> ORGANISM: Artificial Sequence
<220> FEATURE:
<223> OTHER INFORMATION: Rat Anti-MCT1 antibody (Ab1 or INX310)

<400> SEQUENCE: 525

Gln Val Gln Leu Lys Ala Thr Gly Pro Gly Leu Val Gln Pro Thr Gln
1               5               10              15

Thr Leu Ser Ile Thr Cys Thr Val Ser Gly Phe Ser Leu Thr Asn Tyr
            20              25              30

His Leu Gln Trp Val Arg Gln Thr Pro Gly Lys Gly Leu Glu Trp Met
            35              40              45

Gly Phe Ile Arg Ser Ser Gly Asn Thr Glu Tyr Asn Ser Glu Phe Lys
    50              55              60

Ser Arg Leu Ser Ile Ser Arg Asp Thr Ser Lys Asn Gln Val Phe Leu
65              70              75              80

Lys Met Asn Ser Leu Lys Thr Asp Asp Thr Gly Val Tyr Tyr Cys Ala
            85              90              95

Arg Asn Ser Trp Tyr His Gly Thr Tyr Tyr Ser Pro Gly Tyr Tyr Val
            100             105             110

Met Asp Ala Trp Gly Gln Gly Ala Ser Val Thr Val Ser Ser
            115             120             125

<210> SEQ ID NO 526
<211> LENGTH: 106
<212> TYPE: PRT
<213> ORGANISM: Artificial Sequence
```

```
<220> FEATURE:
<223> OTHER INFORMATION: Rat Anti-MCT1 Ab _VL

<400> SEQUENCE: 526

Asn Ile His Leu Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Phe Gln Gln Lys Phe Gly Glu Thr Pro Lys Leu Leu Ile
        35                  40                  45

Tyr Asn Arg His Asn Leu Gln Thr Gly Ile Pro Ser Arg Phe Ser Gly
    50                  55                  60

Ser Gly Ser Gly Thr Asp Tyr Thr Leu Thr Ile Asn Ser Leu Gln Pro
65                  70                  75                  80

Glu Asp Val Ala Thr Tyr Phe Cys Tyr Gln Tyr Ser Asp Gly Tyr Thr
                85                  90                  95

Phe Gly Ala Gly Thr Lys Leu Glu Leu Lys
            100                 105

<210> SEQ ID NO 527
<211> LENGTH: 126
<212> TYPE: PRT
<213> ORGANISM: Artificial Sequence
<220> FEATURE:
<223> OTHER INFORMATION: Humanized Anti-MCT1 antibody 1_VH

<400> SEQUENCE: 527

Gln Val Gln Leu Lys Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Val Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 528
<211> LENGTH: 106
<212> TYPE: PRT
<213> ORGANISM: Artificial Sequence
<220> FEATURE:
<223> OTHER INFORMATION: Humanized Anti-MCT1 antibody 1, 2 and 3 _VL

<400> SEQUENCE: 528

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45
```

-continued

```
Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105
```

```
<210> SEQ ID NO 529
<211> LENGTH: 126
<212> TYPE: PRT
<213> ORGANISM: Artificial Sequence
<220> FEATURE:
<223> OTHER INFORMATION: Humanized Anti-MCT1 antibody 2_VH

<400> SEQUENCE: 529
```

```
Gln Val Gln Leu Gln Glu Ser Gly Pro Gly Leu Val Lys Pro Ser Glu
1                   5                   10                  15

Thr Leu Ser Leu Thr Cys Thr Val Ser Gly Phe Ser Leu Thr Asn Tyr
                20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Met Val Thr Val Ser Ser
        115                 120                 125
```

```
<210> SEQ ID NO 530
<211> LENGTH: 106
<212> TYPE: PRT
<213> ORGANISM: Artificial Sequence
<220> FEATURE:
<223> OTHER INFORMATION: Humanized Anti-MCT1 antibody 1, 2 and 3 _VL

<400> SEQUENCE: 530
```

```
Asp Ile Gln Met Thr Gln Ser Pro Ser Ser Leu Ser Ala Ser Val Gly
1                   5                   10                  15

Asp Lys Val Thr Ile Thr Cys Arg Gly Ser Gln Asn Ile Asn Asn Tyr
                20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
                85                  90                  95

Phe Gly Pro Gly Thr Lys Val Asp Ile Lys
            100                 105
```

```
<210> SEQ ID NO 531
```

-continued

```
<211> LENGTH: 126
<212> TYPE: PRT
<213> ORGANISM: Artificial Sequence
<220> FEATURE:
<223> OTHER INFORMATION: Humanized Anti-MCT1 antibody 3 _VH

<400> SEQUENCE: 531

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Asn Tyr
            20                  25                  30

His Leu Gln Trp Ile Arg Gln Pro Pro Gly Lys Gly Leu Glu Trp Ile
        35                  40                  45

Gly Phe Ile Arg Ser Ser Gly Asn Thr Glu Tyr Asn Pro Ser Leu Lys
    50                  55                  60

Ser Arg Val Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
            85                  90                  95

Arg Asn Ser Trp Tyr His Gly Thr Tyr Tyr Ser Pro Gly Tyr Tyr Val
            100                 105                 110

Met Asp Ala Trp Gly Gln Gly Thr Leu Val Thr Val Ser Ser
        115                 120                 125

<210> SEQ ID NO 532
<211> LENGTH: 106
<212> TYPE: PRT
<213> ORGANISM: Artificial Sequence
<220> FEATURE:
<223> OTHER INFORMATION: Humanized Anti-MCT1 antibody 1, 2 and 3 _VL

<400> SEQUENCE: 532

Asp Ile Gln Met Thr Gln Ser Pro Ser Ser Leu Ser Ala Ser Val Gly
1               5                   10                  15

Asp Lys Val Thr Ile Thr Cys Arg Gly Ser Gln Asn Ile Asn Asn Tyr
            20                  25                  30

Leu Ala Trp Phe Gln Gln Lys Pro Gly Lys Thr Pro Ala Leu Leu Ile
        35                  40                  45

Tyr Asn Arg His Asn Leu Gln Ser Gly Val Pro Ser Arg Phe Arg Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Ser Asp Gly Tyr Thr
            85                  90                  95

Phe Gly Pro Gly Thr Lys Val Asp Ile Lys
            100                 105

<210> SEQ ID NO 533
<211> LENGTH: 330
<212> TYPE: PRT
<213> ORGANISM: Artificial Sequence
<220> FEATURE:
<223> OTHER INFORMATION: >IgG1_INX_Silent

<400> SEQUENCE: 533

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35              40              45

Gly Val His Thr Phe Pro Ala Val Leu Gln Ser Ser Gly Leu Tyr Ser
    50              55              60

Leu Ser Ser Val Val Thr Val Pro Ser Ser Ser Leu Gly Thr Gln Thr
65                  70              75              80

Tyr Ile Cys Asn Val Asn His Lys Pro Ser Asn Thr Lys Val Asp Lys
                85              90              95

Lys Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
        115             120             125

Lys Pro Lys Asp Thr Leu Met Ile Ser Arg Thr Pro Glu Val Thr Cys
    130             135             140

Val Val Val Asp Val Ser His Arg Asp Pro Glu Val Lys Phe Asn Trp
145             150             155             160

Tyr Val Asp Gly Val Glu Val His Asn Ala Lys Thr Lys Pro Arg Glu
            165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Ala Val Ser Asn
        195             200             205

Lys Ala Leu Pro Ala Pro Ile Glu Lys Thr Ile Ser Lys Ala Lys Gly
    210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
    290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330
```

ANTI-MCT1 ANTIBODIES AND USES THEREOF

RELATED APPLICATIONS

This application claims priority to U.S. Provisional No. 62/613,447 filed on Jan. 4, 2018, U.S. Provisional No. 62/684,870 filed on Jun. 14, 2018, and U.S. Provisional No. 62/736,025 filed on Sep. 25, 2018 and U.S. Provisional No. 62/773,630 filed on Nov. 30, 2018. The contents of each of these provisional applications are incorporated by reference in its entirety herein.

SEQUENCE LISTING

The sequence listing in the file named "43260.4209.txt" having a size of 412,471 bytes that was created Jan. 4, 2019, is hereby incorporated by reference in its entirety.

FIELD OF THE INVENTION

This invention generally pertains to anti-MCT1 antibodies and antigen-binding fragments thereof, e.g., humanized, chimeric, and human antibodies and antigen-binding fragments thereof, e.g., antagonistic anti-MCT1 antibodies and antigen-binding fragments thereof, and compositions containing such antibodies and antigen-binding fragments thereof. Such antibodies and antigen-binding fragments include those which specifically bind to MCT1, e.g., MCT1 expressed on the surface of endogenous MCT1 expressing human cells or recombinant cells engineered to express MCT1 and which antagonize one or more functions associated with MCT1, e.g., its ability to promote lactate transport. The invention also relates to fusion or multispecific proteins comprising one or more anti-MCT1 antibody binding sequences, e.g., multispecific and bispecific antibodies. The invention further relates to therapeutic and diagnostic uses for such antibodies, antigen-binding fragments, fusion and multispecific polypeptides, and compositions containing same. The invention specifically relates to the use of these antibodies and antigen-binding fragments thereof as prophylactics or therapeutics, e.g., for the treatment of autoimmunity, inflammation, allergy, transplant, GVHD, cancer and other conditions wherein suppression of MCT1 activity and/or increased TR1 cell numbers/activity and/or decreased numbers/activity of T effector cells are therapeutically desirable.

BACKGROUND OF THE INVENTION

The monocarboxylate nutrient transporter SLC16A1 (MCT1) is a multipass transmembrane protein responsible for the facilitated transport of critical metabolites, including products of glycolysis. MCT1 is a member of one of the largest family of surface membrane proteins, known as solute channel proteins (SLCs), whose functions involve the transport across membranes of critical cellular nutrients, metabolites, ions, hormones and lipids. MCT1 belongs to the SLC16 family of transporters, five of which have been shown to transport monocarboxylates, such as pyruvate, lactate and ketones (REF. 34-36) in a facilitated, pH dependent and bidirectional manner. SLC16A1 (MCT1), SLC16A7 (MCT2), SLC16A8 (MCT3) and SLC16A3 (MCT4) have all been shown to transport monocarboxylates with Km in the 1-40 mM range (REF. 37). MCT1, MCT3 and MCT4 are co-expressed with the Ig-domain containing surface protein CD147 (Basigin), which in many cells is critical for proper cell surface expression (REF. 38, 37). Besides these MCTs, other lactate transporters include the recently characterized SLC16A11 (REF. 39) and sodium-dependent SLC5A8 and SLC5A12 (REF. 40), AQP9 (REF. 41, 42) as well as SLC4A1 (Band 3) expressed on red blood cells. Thus, nine independent proteins can control and regulate the transport of lactate into, between, and out of cells throughout the body. MCT1 is especially relevant to the transport of lactate in T and B cells (REF. 43).

Immune cells undergo shifts in their metabolic demand throughout growth, and require specific metabolic states for employing their effector functions. The blocking of glycolysis in inflammatory disease models has shown efficacy (REF. 53). For example, the development of lupus in disease-prone mice is prevented when lymphocytes were blocked from using the glycolytic pathway following activation (REF. 53). Indeed, the lack of IFNγ production in these models is consistent with previous reports that have shown glycolysis is required for the production of IFNγ (REF. 54). Blocking the export of lactate reduces flux through the glycolytic pathway (REF. 55) and, by altering Myc, can shift T cells away from effector functions (REF. 56). Inhibition of MCT1 function blocks effector T cell activity in several animal models of disease, including collagen-induced arthritis, allograft rejection and GVHD (REF. 45, 47, 50, 57-59).

However, the ubiquity of these pathways in non-immune cells and the lack of immune-specific targets have prevented therapeutic intervention. Given the broad expression of MCTs across many tissues, small molecule approaches that hit multiple MCTs pose particular challenges including tissue toxicities. For example, AZ3965 is a small molecule that binds to MCT1 and MCT2 (REF. 45, 46). This MCT1/2 small molecule inhibitor had potential applications in the treatment of autoimmune disease/transplant (REF. 47), but promiscuous binding resulted in toxicities to the retina, heart and testis in preclinical models (REF. 48, 85).

Adult humans deficient in MCT1 are healthy (REF. 49, 68). Individuals with homozygous MCT1 loss-of-function (LOF) mutations were identified only under stress (infection, starvation) due to alterations in ketone utilization and metabolism. Infants presented with ketone utilization defects and, sometimes, exercise intolerance. These various symptoms disappeared as they aged, possibly due to growth of skeletal muscle mass during adolescence. Heterozygous family members of individuals with homozygous MCT1 mutations had no history of ketoacidosis, suggesting that LOF mutations cause ketoacidosis only in conjunction with additional genetic/environmental factors (REF. 68). Outside the immune system, MCT1 is expressed in multiple organs, including skeletal muscle, kidney, liver, testis, heart and brain along with other MCTs. The absence of broad toxicity in individuals with MCT1 mutations is likely due to the vast redundancy of MCTs. For example, MCT1, MCT2 & MCT4 are all expressed in the retina (REF. 69), and no retinal defects were observed in MCT1-deficient individuals suggesting functional redundancy. At this time, no overt immune deficiencies have been observed in MCT1-deficient individuals. Additionally, MCT1-deficient humans do not present with any RBC dysfunction.

There are metabolic differences between cancerous and normal cells: in particular, tumor cells rely upon a high rate of aerobic glycolysis rather than oxidative phosphorylation to produce energy for maintenance of cellular functions. Indeed, cancer cells have up to a 60-fold enhanced rate of glycolysis relative to normal cells, even with sufficient oxygen. This dependence upon glycolysis, and its consequences, is termed "the Warburg effect" (REF. 94, 95). Malignant cells are highly anabolic and require very high levels of nutrients, ATP, and building blocks to synthesize components needed for their growth and survival. Use of the glycolytic pathway provides ATP but also drives production of lactate, which is produced from pyruvate at the end of the glycolytic pathway. Massive lactate production by the tumor cell requires an efficient means for its consumption or elimination, to prevent intracellular acidification of the cancer cell.

One of the ways by which lactate homeostasis is maintained is via the monocarboxylate transporters. Expression profiling studies have established that most aggressive tumor types express markedly elevated levels of MCT1, MCT4 or both (REF. 96). The expression of MCT1 and MCT4 is regulated by two major oncogenic transcription factors, MYC and hypoxia inducible factor-Ia (HIF-1a), respectively (REF. 96, 97) that direct marked increases in the production of key proteins that support aerobic glycolysis, including amino acid transporters and enzymes involved in the catabolism of glutamine and glucose (REF. 98). Malignancies having MYC involvement and hypoxic tumors are generally resistant to current frontline therapies, with high rates of treatment failure, relapse and high patient mortality (REF. 99, 100). Importantly, inhibition of MCT1 can kill tumor cells ex vivo and provoke tumor regression in vivo, and their potency is augmented by agents such as metformin that force a glycolytic phenotype upon the cancer cell (REF. 96, 100).

MCT1 is normally expressed at very low levels in pancreatic islets and in beta-cells in particular (REF. 101, 102). This likely explains the very slow uptake of lactate by these cells. A hallmark of exercise-induced hyperinsulinism (EIHI) is inappropriate insulin secretion following vigorous physical activity, which leads to hypoglycemia (REF. 103). EIHI has been associated with elevated expression of MCT1 in beta-cells and transgenic mice engineered to overexpress MCT1 in part displayed many of the hallmarks of EIHI (REF. 104).

As described above, various small molecule MCT inhibitors have been developed, but many of these small molecule inhibitors lack specificity for MCT1, thereby leading to off-target toxicities. In spite of these drawbacks, small molecule MCT1 inhibitors have been shown to disable tumor cell metabolism, proliferation and survival, and impair tumorigenic potential in vivo in tumors highly expressing MCT1 (REF. 96). Antitumor effects of such small molecule MCT1 inhibitors are augmented by co-administration of the biguanide metformin, which is thought to further enhance the reliance of tumor cells upon aerobic glycolysis and thus increase the demand to MCT1-mediated efflux of lactate (REF. 96). However, heretofore no antibodies which bind to surface expressed MCT1 have been reported, e.g., those which bind to MCT1 expressed on the surface of endogenous or engineered MCT1 expressing human or non-human cells. Moreover to the best of Applicants' knowledge no functional antibodies have been reported in the literature, i.e., those which bind to MCT1 and thereby antagonize, inhibit or block the effects of MCT1.

SUMMARY OF THE INVENTION

For the first time this invention provides antibodies and antigen-binding fragments thereof that specifically bind to human MCT1 expressed on the surface of endogenous or recombinant MCT1 expressing cells, e.g., human cells which antibodies moreover are functional, i.e., such antibodies antagonize MCT1 related functions.

More specifically the invention provides novel antibodies and antigen-binding fragments thereof that specifically bind to human MCT1 which antagonize MCT1 related functions such as inhibiting MCT1-mediated lactate transport.

The invention further provides MCT1-binding fusion proteins and MCT1-binding multispecific polypeptides which comprise one or more MCT1 binding antibody variable domains and optionally other moieties, e.g., another polypeptide such as another antigen binding variable domain, cytokine, or a receptor.

The invention further provides an isolated antibody or antigen-binding fragment thereof that binds to one or more residues comprised in an extracellular domain or region of human or non-human MCT1.

The invention further provides an isolated antibody or antigen-binding fragment thereof that binds to human or non-human MCT1 which antagonizes, inhibits or blocks one or more MCT1-related functions, e.g., in vitro and/or in vivo.

The invention further provides an isolated antibody or antigen-binding fragment that binds to a non-human MCT1, e.g., rodent such as mouse or rat MCT1, which optionally antagonizes, inhibits or blocks one or more MCT1-related functions, e.g., in vitro and/or in vivo, e.g., which optionally further binds to human MCT1.

The invention further provides an isolated anti-MCT1 antibody or antigen-binding fragment thereof that competes for binding to human or non-human MCT1 as any one of anti-human MCT1 antibodies Ab1-Ab95.

The invention further provides isolated anti-MCT1 antibodies or antigen-binding fragments thereof that bind to the same or overlapping epitope on human MCT1 as any one of anti-human MCT1 antibodies Ab1-Ab95.

The invention further provides isolated anti-MCT1 antibodies or antigen-binding fragments thereof that bind to an epitope on human MCT1 selected from the following:

(i) one which comprises one or more of residues T41, E46, S285, S286, Y287, K289, H292, Y293, K297, G417, I47, and D418;

(ii) one which comprises least three residues wherein at least one, two, or all three of said residues comprise a residue selected from T41, E46, S285, S286, Y287, K289, H292, Y293, G417, I47 and D418;

(iii) one which comprises three residues wherein three residues wherein at least one, two, or all three of said residues comprise T41, E46, S285, S286, Y287, K289, H292, Y293, G417, I47 and D418;

(iv) one which comprises three to six residues wherein one, two, three, four, five or six of said residues comprise T41, E46, S285, S286, Y287, K289, H292, Y293, G417, I47 and D418;

(v) one which comprises at least one, two or all three of residues T41, S285 and S286;

(vi) one which comprises T41;

(vii) one which comprises S286;

(viii) one which comprises S285;

(ix) one which comprises H292;

(x) one which comprises residues T41, S285, S286, Y287, G417 and D418;

(xi) one which comprises residues T41, S285 and S286;

(xii) one which comprises residues T41, I47, S285, S286, G417 and D418, (xiii) one which comprises residues E46, K289, and H292;

(xiv) one which comprises residues K297, Y293 and H292;

(xv) one which comprises one or more of the corresponding residues of a non-human MCT1, e.g., selected from rodent (e.g., mouse, rat, guinea pig), rabbit, chicken, non-human primate (e.g., cynomolgus monkey, chimp, orangutan), bovine, ovine, canine, and feline; wherein optionally the residues present in said epitope are identified by use of alanine scanning.

The invention further provides isolated anti-MCT1 antibodies or antigen-binding fragments thereof that bind to an epitope on human MCT1 selected, wherein said antibody or antigen-binding fragment further interacts with one or more of the following residues:

(i) one or more of residues P37, I40, K45, E48, and T55 (loop 1);

(ii) residue Q111 (loop 2);

(iii) residue Q166 (loop 3);

(iv) one or more of residues L284, E296, S298 (loop 4);

(v) residue Y353 (loop 5);

(vi) one or both of residues Y419, T422 (loop 6); and/or (vii) any combination of the foregoing.

The invention further provides isolated anti-MCT1 antibodies or antigen-binding fragments thereof that bind to an epitope on non-human MCT1 which non-human MCT1 is optionally selected from rodent (e.g., mouse, rat, guinea pig), rabbit, avian (e.g., chicken, turkey, goose), non-human primate (e.g., cynomolgus monkey, chimp, orangutan), bovine, ovine, canine, feline wherein optionally said epitope on non-human MCT1 comprises one or more of the corresponding residues in the non-human MCT1 as one or more of T41, S285, S286, Y287, G417, I47 and D418 of human MCT1, e.g., which antagonize, inhibit or block one or more of the activity(ies) of said non-human MCT1, e.g., in vitro and/or in vivo.

The invention further provides isolated anti-MCT1 antibodies or antigen-binding fragments thereof that are human, humanized, non-human primate, primatized, chicken, rodent or chimeric.

The invention further provides isolated anti-MCT1 antibodies or antigen-binding fragments thereof that inhibit human MCT1-mediated lactate transport, e.g., in vitro and/or in vivo.

The invention further provides isolated anti-MCT1 antibodies or antigen-binding fragments thereof that bind to endogenous MCT1-expressing cells and/or binds to recombinant or engineered MCT1-expressing cells, e.g., human MCT1 expressing 293 cells.

The invention further provides isolated anti-MCT1 antibodies or antigen-binding fragments thereof wherein the antibody or antigen-binding fragment thereof is selected from the group consisting of: a human or humanized monoclonal antibody; monospecific antibody; polyspecific antibody; a multispecific antibody-like polypeptide, a humanized antibody; a human or humanized tetrameric antibody; a human or humanized tetravalent antibody; a human or humanized multispecific antibody; a single chain antibody; a domain-specific antibody; a single domain antibody; a domain-deleted antibody; an scFc fusion protein; a chimeric antibody; a synthetic antibody; a recombinant antibody; a hybrid antibody; multispecific antibody, bispecific antibody, ByTE, a mutated antibody; CDR-grafted antibodies; an antibody fragment; an Fab; an F(ab')2; an Fab' fragment; an Fv fragment; a single-chain Fv (scFv) fragment; an Fd fragment; a dAb fragment; diabodies; a nanobody; a bivalent nanobody; a VHH antibody; and a minibody.

The invention further provides isolated anti-MCT1 antibodies or antigen-binding fragments thereof which comprise humanized antibodies or antigen-binding fragments thereof.

The invention further provides isolated anti-MCT1 antibodies or antigen-binding fragments thereof which comprises at least 1, 2, 3, 4, 5 or all 6 CDRs of any of anti-MCT1 antibodies Ab1-Ab95, wherein optionally said CDRs are defined according to Kabat or according to Chothia and Lesk, or an isolated antibody or antigen-binding fragment thereof which competes for binding with MCT1 or which binds the same epitope with any of anti-MCT1 antibodies Ab1-Ab95 or an affinity-matured variant of any of the foregoing.

The invention further provides isolated anti-MCT1 antibodies or antigen-binding fragments thereof that are humanized which comprise the same CDRs of any of anti-MCT1 antibodies Ab1-Ab95, wherein optionally said CDRs are defined according to Kabat or according to Chothia and Lesk.

The invention further provides isolated anti-MCT1 antibodies or antigen-binding fragments thereof that comprise the same $V_H$ polypeptide as is comprised in an anti-MCT1 antibody selected from Ab1-Ab95 or a humanized variant thereof.

The invention further provides isolated anti-MCT1 antibodies or antigen-binding fragments thereof that comprise the same VL polypeptide as is comprised in an anti-MCT1 antibody selected from Ab1-Ab95 or a humanized variant thereof.

The invention further provides isolated anti-MCT1 antibodies or antigen-binding fragments thereof that comprise a $V_H$ polypeptide and a VL polypeptide which are identical to those comprised in an anti-MCT1 antibody selected from Ab1-Ab95 or a humanized variant thereof.

The invention further provides isolated anti-MCT1 antibodies or antigen-binding fragments thereof which comprise a variable heavy polypeptide and/or a variable light chain polypeptide respectively possessing at least 80, 90, 95, 96, 97, 98, 99 or 100% sequence identity to a variable heavy polypeptide and/or a variable light chain polypeptide contained in any of anti-MCT1 antibodies Ab1-Ab95.

The invention further provides isolated anti-MCT1 antibodies or antigen-binding fragments thereof which comprise the $V_H$ CDR1, 2 and 3 polypeptides respectively having the amino acid sequences of SEQ ID NO: 4-6 and the VL CDR1, 2 and 3 polypeptides respectively having the amino acid sequences of SEQ ID NO: 7-9.

The invention further provides isolated anti-MCT1 antibodies or antigen-binding fragments thereof that which is a humanized anti-MCT1 antibody or antigen binding fragment derived from any of Ab1-Ab95, optionally containing the same CDRs as any of Ab1-Ab95, wherein optionally said CDRs are defined according to Kabat or according to Chothia and Lesk.

The invention further provides affinity-matured anti-MCT1 antibodies or antigen binding fragments derived from any of Ab1-Ab95, wherein at most 1, 2, 3, 4, 5, 6, 7, 8, 9, 10, 11, 12 or 13 CDR residues are mutated relative to the CDR residues which are comprised in the 6 CDR polypeptides of any one of Ab1-Ab95, wherein optionally said affinity-matured anti-MCT1 antibody binds to human MCT1 with at least the same or greater affinity as the anti-MCT1 antibody from which it is derived and/or the affinity-matured antibody or antigen binding fragment antagonizes human MCT1, e.g., in vitro and/or in vivo, wherein optionally said CDRs are defined according to Kabat or according to Chothia and Lesk optionally wherein at most 1, 2, 3, 4, 5, 6 or 7 CDR residues are mutated relative to the CDR poly-peptides of any one of Ab1-Ab95 or at most 1, 2, 3 or 4 CDR residues are mutated relative to the CDR polypeptides of any one of Ab1-Ab95 or at most 1 or 2 CDR residues are mutated relative to the CDR polypeptides of any one of Ab1-Ab95.

The invention further provides an anti-human MCT1 antibody or antigen binding fragment according to any of the foregoing, which further binds to a non-human MCT1, optionally rodent, rabbit, chicken or non-human primate MCT1.

The invention further provides anti-MCT1 antibodies comprising the VH and VL polypeptides of SEQ ID NO: 2 and 3; SEQ ID NO: 12 and 13; SEQ ID NO: 14 and 15; SEQ ID NO: 16 and 17; or one comprising the VL and/or VH polypeptides of any of one of antibodies Ab5-Ab95, or comprising humanized or affinity-matured variants of the VL and/or VH polypeptides of any of one of antibodies Ab5-Ab95.

The invention further provides anti-MCT1 antibodies or antigen binding fragments comprising a variable heavy chain polypeptide or heavy chain polypeptide having an amino acid sequence selected from SEQ ID NO: 2, 12, 14, 16, 19-32, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153 and 155; and a variable light chain polypeptide or light chain polypeptide having an amino acid sequence selected from SEQ ID NO: 3, 13, 15, 17, 33-44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154 and 156.

The invention further provides anti-MCT1 antibodies or antigen binding fragments comprising a variable heavy chain polypeptide and a variable light chain polypeptide having an amino acid sequence respectively selected from the following: SEQ ID NO: 2 and 3; SEQ ID NO: 12 and 13; SEQ ID NO: 14 and 15; SEQ ID NO: 16 and 17; SEQ ID NO: 45 and 46; SEQ ID NO: 47 and 48; SEQ ID NO: 49 and 50; SEQ ID NO: 51 and 52; SEQ ID NO: 53 and 54; SEQ ID NO: 55 and 56; SEQ ID NO: 57 and 58; SEQ ID NO: 59 and 60; SEQ ID NO: 61 and 62; SEQ ID NO: 63 and 64; SEQ ID NO: 65 and 66; SEQ ID NO: 67 and 68; SEQ ID NO: 69 and 70; SEQ ID NO: 71 and 72; SEQ ID NO: 73 and 74; SEQ ID NO: 75 and 76; SEQ ID NO: 77 and 78; SEQ ID NO: 79 and 80; SEQ ID NO: 81 and 82; SEQ ID NO: 83 and 84; SEQ ID NO: 85 and 86; SEQ ID NO: 87 and 88; SEQ ID NO: 89 and 90; SEQ ID NO: 91 and 92; SEQ ID NO: 93 and 94; SEQ ID NO: 95 and 96; SEQ ID NO: 97 and 98; SEQ ID NO: 99 and 100; SEQ ID NO: 101 and 102; SEQ ID NO: 103 and 104; SEQ ID NO: 105 and 106; SEQ ID NO: 107 and 108; SEQ ID NO: 109 and 110; SEQ ID NO: 111 and 112; SEQ ID NO: 113 and 114; SEQ ID NO: 115 and 116; SEQ ID NO: 117 and 118; SEQ ID NO: 119 and 120; SEQ ID NO: 121 and 122; SEQ ID NO: 123 and 124; SEQ ID NO: 125 and 126; SEQ ID NO: 127 and 128; SEQ ID NO: 129 and 130; SEQ ID NO: 131 and 132; SEQ ID NO: 133 and 134; SEQ ID NO: 135 and 136; SEQ ID NO: 137 and 138; SEQ ID NO: 139 and 140; SEQ ID NO: 141 and 142; SEQ ID NO: 143 and 144; SEQ ID NO: 145 and 146; SEQ ID NO: 147 and 148; SEQ ID NO: 149 and 150; SEQ ID NO: 151 and 152; SEQ ID NO: 153 and 154 and SEQ ID NO: 155 and 156.

The invention further provides humanized and/or affinity matured anti-MCT1 antibodies or antigen-binding frag-ments according to any of the foregoing embodiments which comprise a VL polypeptide having an amino acid sequence selected from those of SEQ ID NO: 3, 13, 15, 17 and 33-44 or that of any of antibodies Ab5-Ab60.

The invention further provides humanized anti-MCT1 antibodies or antigen-binding fragments according to any of the foregoing embodiments which comprise a $V_H$ polypep-tide having an amino acid sequence selected from those of SEQ ID NO: 2, 12, 14, 16 and 19-32 or that of any of antibodies Ab5-Ab60.

The invention further provides humanized anti-MCT1 antibodies or antigen-binding fragments according to any of the foregoing which comprise a VL polypeptide having an amino acid sequence selected from those of SEQ ID NO: 13, 15, 17 and 33-44 and a $V_H$ polypeptide having an amino acid sequence selected from those of SEQ ID NO: 12, 14, 16 and 19-32 or that of any of antibodies Ab5-Ab60.

The invention further provides humanized anti-MCT1 antibodies or antigen-binding fragments according to any of the foregoing which comprise a VL polypeptide having a sequence having at least 80, 85, 90, 95, 96, 97, 98 or 99% sequence identity to any of SEQ ID NO: 3, 13, 15, 17, 33-44 or to a VL polypeptide comprised in any of antibodies Ab5-Ab95.

The invention further provides humanized anti-MCT1 antibodies or antigen-binding fragments according to any of the foregoing which comprise a $V_H$ polypeptide having a sequence having at least 80, 85, 90, 95, 96, 97, 98, 99% or 100% sequence identity to any of SEQ ID NO: 2, 12, 14, 16, 19-32 or to a $V_H$ polypeptide comprised in any of antibodies Ab5-Ab95.

The invention further provides humanized anti-MCT1 antibodies or antigen-binding fragment according to any of the foregoing which comprise a VL polypeptide having a sequence possessing at least 80, 85, 90, 95, 96, 97, 98 or 99% sequence identity to any of SEQ ID NO: 3, 13, 15, 17, 33-44 or to a VL polypeptide comprised in any of antibodies Ab5-Ab95 and/or a VH polypeptide having a sequence having at least 90, 95, 96, 97, 98, 99% or 100% sequence identity to the $V_H$ polypeptide of SEQ ID NO: 2, 12, 14, 16, 19-32 or to a $V_H$ polypeptide comprised in any of antibodies Ab5-Ab95.

The invention further provides a humanized anti-MCT1 antibody or antigen-binding fragment according to any of the foregoing, wherein the heavy chain CDR3 sequence comprises 18, 19, 20, 21, 22, 23 or 24 amino acid residues.

The invention further provides a humanized anti-MCT1 antibody or antigen-binding fragment according to any of the foregoing, wherein the heavy chain CDR3 sequence comprises 21, 22, 23 or 24 amino acid residues.

The invention further provides an isolated anti-MCT1 human or antigen-binding fragment according to any of the foregoing, wherein the heavy chain CDR3 sequence is identical to SEQ ID NO:6 or differs therefrom by at most 5, 4, 3, 2 or 1 residues, optionally wherein said differences if present comprise conservative amino acid substitutions or comprise substituting amino acids which are prevalent at the same position in the heavy chain CDR3 of human or rodent antibodies comprising a CDR3 of the same length.

The invention further provides an isolated anti-MCT1 human or humanized antibody or antigen-binding fragment thereof according to of any of the foregoing which competes for binding to MCT1 with a reference antibody, wherein the reference antibody is selected from Ab1-Ab95.

The invention further provides anti-human MCT1 anti-bodies or antigen-binding fragments thereof comprising the same variable heavy and/or variable light CDR polypeptides as an anti-human MCT1 antibody selected from Ab1-Ab95.

The invention further provides anti-MCT1 antibodies comprising the variable heavy and/or light polypeptides of an antibody selected from Ab1-Ab95.

The invention further provides anti-MCT1 human or humanized antibodies or antigen-binding fragments thereof according to of any of the foregoing, which comprises heavy and/or light chain constant regions, optionally human IgG1, IgG2, IgG3 or IgG4 heavy and/or light chain constant regions which constant region(s) optionally are mutated to impair or enhance at least one effector function, e.g., wherein said effector functions include FcR binding, complement binding, ADCC function, FcRN binding, and glycosylation.

The invention further provides anti-MCT1 antibodies or antigen-binding fragment thereof according to of any of the foregoing, wherein the CDRs of the antibody or antigen-binding fragment thereof form a similar three-dimensional antibody structure similar or the same as those of Ab1, as indicated by the positions of the alpha carbons in corresponding CDRs differing by an average root-mean-squared deviation (RMSD) of less than 2.0 Å, less than 1.0 Å, or less than 0.5 Å, as determined via structural alignment.

The invention further provides humanized antibodies or antigen-binding fragments thereof comprising the variable heavy chain CDR sequences of Ab1 (SEQ ID NOS: 4, 5, 6) and the variable light chain CDR sequences of Ab1 (SEQ ID NOS: 7, 8, 9).

The invention further provides anti-MCT1 antibodies or antigen-binding fragment thereof comprising a $V_H$ domain having at least 80%, at least 85%, at least 90%, at least 95%, at least 98%, at least 99%, or 100% identity to the amino acid sequence of the $V_H$ domain of MCT1 Ab1 (SEQ ID NO: 2); and comprising a VL domain having at least 80%, at least 85%, at least 90%, at least 95%, at least 98%, at least 99%, or 100% identity to the amino acid sequence of the VL domain of MCT1 Ab1 (SEQ ID NO: 3).

The invention further provides anti-MCT1 antibodies or antigen-binding fragment thereof according to any of the foregoing embodiments which comprises human constant domains, optionally IgG1, IgG2, IgG3 or IgG4, further optionally modified to enhance at least one Fc effector function selected from glycosylation, FcR binding, FcRN binding, complement binding, and ADCC function.

The invention further provides anti-MCT1 antibodies or antigen-binding fragment thereof according to any of the foregoing embodiments which comprises human IgG1 constant regions, optionally modified to decrease FcR binding and/or complement binding, further optionally comprising E269R and/or K322A mutations and/or said human IgG1 constant regions comprise the amino acid sequence of SEQ ID NO:18.

The invention further provides fusion polypeptides, chimeric antigen receptors (CARs), multispecific antigen binding polypeptides or multispecific or bispecific antibody polypeptides comprising at least one anti-MCT1 antibody or antigen binding fragment according to any of the foregoing.

The invention further provides an anti-MCT1 antibody or fusion polypeptide, chimeric antigen receptor (CAR), multispecific antigen binding polypeptide or multispecific or bispecific antibody polypeptide of any of the foregoing embodiments which decreases T effector cell activity and/or numbers of T effector cells, e.g., CD3+, CD4+ or CD8+ T effector cells.

The invention further provides anti-MCT1 antibodies or fusion polypeptides, chimeric antigen receptors (CARs), multispecific antigen binding polypeptides or multispecific or bispecific antibody polypeptides of any of the foregoing embodiments which increases the activity and/or numbers of Tr1 cells.

The invention further provides anti-MCT1 antibodies or fusion polypeptides, chimeric antigen receptor (CARs), multispecific antigen binding polypeptide or multispecific or bispecific antibody polypeptide of any of the foregoing embodiments which decreases T effector cell activity and/or numbers of T effector cells, e.g., CD3+, CD4+ or CD8+ T effector cells and further which increases the activity and/or numbers of Tr1 cells.

The invention further provides cells which express at least one anti-MCT1 antibody or antigen binding fragment, fusion polypeptide, chimeric antigen receptor (CAR), multispecific antigen binding polypeptide or multispecific or bispecific antibody polypeptide according to any of the foregoing, e.g., human, non-human mammalian, yeast, bacterial, amphibian, plant, insect or reptile cells or a human cell, optionally a human immune cell, e.g., a T cell. NK cell, monocyte, T regulatory cell, or macrophage.

The invention further provides anti-idiotypic antibodies produced against an anti-MCT1 antibody or antigen-binding fragment thereof according to of any of the foregoing, optionally which is human, humanized and/or affinity matured.

The invention further provides anti-anti-idiotypic antibodies produced against an anti-idiotypic antibody as above-described which optionally binds MCT1 and further optionally blocks or antagonizes one or more MCT1 activities.

The invention further provides fusion proteins which comprise an anti-MCT1 antibody or antigen-binding fragment thereof according to of any of the foregoing or the $V_H$ CDR3 polypeptide of SEQ ID NO: 6 or a variant possessing at least 80% sequence identity therewith, which is directly or indirectly linked to another polypeptide, e.g., an antibody polypeptide or antibody domain, serum albumin, human or other primate serum albumin, adnectin, an affibody, a DAR-Pin, an anticalin, glycol (PEG), monomethoxy PEG (mPEG), an XTEN molecule, an rPEG molecule or fragment or variant of any of the foregoing, e.g., wherein the antibody polypeptide or domain comprises an Fc polypeptide or fragment thereof, e.g., a human IgG1, IgG2, IgG3 or IgG4 Fc region or fragment thereof.

The invention further provides anti-MCT1 antibodies or antigen-binding fragments thereof or fusion polypeptides, chimeric antigen receptors (CARs), multispecific antigen binding polypeptides or multispecific or bispecific antibody polypeptides according to any of the foregoing, or a cell which expresses any of the foregoing, which elicits one or more of the following properties upon binding to MCT1 on the surface of a cell, e.g., an activated T cell or B cell, further optionally a human cell:

(i) inhibits the transport of lactate;

(ii) inhibits the transport of bromopyruvate;

(iii) inhibits the transport of one or more of monocarboxylates, pyruvate, branched-chain oxo acids derived from leucine, valine and isoleucine, ketone bodies, acetoacetate, beta-hydroxybutyrate, acetate, lactic acid, cellular nutrients, metabolites, ions, hormones, lipids, and ketones;

(iv) inhibits the proliferation of CD3/CD28 stimulated T cells;

(v) inhibits the proliferation of the activated T cell or B cell;

(vi) inhibits the production of one or more inflammatory cytokines;

(vii) decreases the activity and/or numbers of T effector cells, e.g., CD3$^+$, CD4$^+$ and/or CD8$^+$ effector T cells;

(viii) increases the proportion or activity of regulatory T (Treg) cells;

(ix) inhibits allogeneic activation in a mixed lymphocyte reaction;

(x) or a combination of any of the foregoing.

The invention further provides anti-MCT1 antibodies or antigen-binding fragments thereof or fusion polypeptides, chimeric antigen receptors (CARs), multispecific antigen binding polypeptides or multispecific or bispecific antibody polypeptides according to any of the foregoing, or a cell which expresses any of the foregoing, e.g., according to any of the foregoing embodiments, which inhibits the production of one or more inflammatory cytokines upon binding to MCT1.

The invention further provides anti-MCT1 antibodies or antigen-binding fragments thereof or fusion polypeptides, chimeric antigen receptor (CARs), multispecific antigen binding polypeptides or multispecific or bispecific antibody polypeptides according to any of the foregoing embodiments, or a cell which expresses any of the foregoing, wherein at least one of the one or more inflammatory cytokines is selected from FGF2, FLT-3L, Fractalkine, G-CSF, GM-CSF, GRO, IFNα2, IFNγ, IL-3, IL-5, IL-9, IL-10, IL-12p40, IL-12p70, IL-13, IL-17a, IP-10, MCP-1, MDC, MIP-1a, MIP-1b, sCD40L, TNFα, and TNFβ.

The invention further provides anti-MCT1 antibodies or antigen-binding fragments thereof or fusion polypeptides, chimeric antigen receptors (CARs), multispecific antigen binding polypeptides or multispecific or bispecific antibody polypeptides according to any of the foregoing, or a cell which expresses any of the foregoing, wherein at least one of the one or more inflammatory cytokines is selected from IFNγ, GM-CSF, TNFα, IL-10, and IL-6.

The invention further provides anti-MCT1 antibodies or antigen-binding fragments thereof or fusion polypeptides, chimeric antigen receptors (CARs), multispecific antigen binding polypeptides or multispecific or bispecific antibody polypeptides according to any of the foregoing embodiments, or a cell which expresses any of the foregoing, which inhibits MCT1-mediated lactate transport in activated T cells with a Kd of less than 100 nM, less than 50 nM, or less than 10 nM as measured via a lactate FLIPR assay.

The invention further provides anti-MCT1 antibodies or antigen-binding fragments thereof or fusion polypeptides, chimeric antigen receptors (CARs), multispecific antigen binding polypeptides or multispecific or bispecific antibody polypeptides according to any of the foregoing, or a cell which expresses any of the foregoing, which does not:

(i) bind to MCT2, MCT3, MCT4, and/or CD147 as measured via flow cytometry;

(ii) inhibit MCT2, MCT3, and/or MCT4 transport;

(iii) inhibit the production of IL-2;

(iv) inhibit lactate transport in monocytes;

(v) inhibit the proliferation of naïve, resting, and/or regulatory T cells;

(vi) inhibit lactate transport in RBCs;

(vii) alter the expression of one or more T cell activation markers, optionally selected from CD25, CD54, CD69, CD95, CD98, CD147, CD154, CD278, CD279, and HLA-DR/DP/DQ.

The invention further provides anti-MCT1 antibodies or antigen-binding fragments thereof or fusion polypeptides, chimeric antigen receptors (CARs), multispecific antigen binding polypeptides or multispecific or bispecific antibody polypeptides according to any of the foregoing, or a cell which expresses any of the foregoing, which comprises a human IgG1, IgG2, IgG3, or IgG4 Fc region, optionally an Fc region that has been modified to alter at least one of effector function, half-life, proteolysis, or glycosylation, wherein optionally the Fc region contains one or more mutations that alters or eliminates N- and/or O-glycosylation.

The invention further provides anti-MCT1 antibodies or antigen-binding fragments thereof or fusion polypeptides, chimeric antigen receptors (CARs), multispecific antigen binding polypeptides or multispecific or bispecific antibody polypeptides according to any of the foregoing, or a cell which expresses any of the foregoing, which binds to human MCT1 with an affinity (KD) of less than 100 nM, less than 50 nM, or less than 10 nM.

The invention further provides anti-MCT1 antibodies or antigen-binding fragments thereof or fusion polypeptides, chimeric antigen receptors (CARs), multispecific antigen binding polypeptides or multispecific or bispecific antibody polypeptides according to any of the foregoing, or a cell which expresses any of the foregoing according to any of the foregoing embodiments, which additionally has one or more of the following modifications:

(i) is conjugated to a cytotoxic agent;

(ii) is comprised in a bispecific antibody;

(iii) is comprised in a multispecific antigen-binding protein;

(iv) is conjugated to a label; and (v) is conjugated to another therapeutic agent, optionally an immunosuppressive agent or a chemotherapeutic agent.

The invention further provides anti-MCT1 antibodies or antigen-binding fragments thereof or fusion polypeptides, chimeric antigen receptors (CARs), multispecific antigen binding polypeptides or multispecific or bispecific antibody polypeptides according to any of the foregoing, or a cell which expresses any of the foregoing, wherein the label is a chemiluminescent label, a paramagnetic label, an MRI contrast agent, a fluorescent label, a bioluminescent label, or a radioactive label or the cytotoxic agent is a moiety that inhibits DNA, RNA, or protein synthesis; a radionuclide; or a ribosomal inhibiting protein.

The invention further provides anti-MCT1 antibodies or antigen-binding fragments thereof or fusion polypeptides, chimeric antigen receptors (CARs), multispecific antigen binding polypeptides or multispecific or bispecific antibody polypeptides according to any of the foregoing, or a cell which expresses any of the foregoing according to any of the foregoing, which is suitable for treating a human subject having an autoimmune, inflammatory, or allergic condition; metabolic disorder (e.g., diabetes), polycystic kidney disease (ADPKD), cancer; transplant recipient or EIHI or any other condition wherein decreased T effector cell numbers and/or activity, e.g., CD3+ T cells, CD4+ T cells and/or CD8+ T cells and/or increased Tr1 or T suppressor cell activity and/or numbers is therapeutically desirable.

The invention further provides anti-idiotypic antibodies or antigen-binding fragments thereof produced against an anti-MCT1 antibody or antigen-binding fragment thereof according to any of the foregoing, which optionally neutralizes one or more biological effects of the anti-MCT1 antibody or antigen-binding fragment thereof to which it binds.

The invention further provides anti-anti-idiotypic antibodies or antigen-binding fragments thereof produced against an anti-idiotypic antibody or antigen-binding fragment thereof according to the foregoing, optionally wherein the anti-anti-idiotypic antibody or antigen-binding fragment thereof neutralizes the anti-idiotypic antibody or antigen-binding fragment thereof to which it binds.

The invention further provides methods of using the above-described anti-idiotypic antibody to monitor the in vivo levels of said anti-MCT1 antibody or antigen-binding fragment thereof in a subject or to neutralize the in vivo effects of said anti-MCT1 antibody or antigen-binding fragment thereof in a subject.

The invention further provides polynucleotides encoding the anti-MCT1 antibody or antigen-binding fragment thereof or fusion polypeptide, chimeric antigen receptor (CAR), multispecific antigen binding polypeptide or multispecific or bispecific antibody polypeptide or anti-anti-MCT1 antibody or antigen-binding fragment or anti-anti-MCT1 antibody or antigen-binding fragment according to any of the foregoing, expression vectors containing same and host cells comprising said polynucleotides or expression vectors optionally a human immune cell, e.g., a T cell, B cell, or an NK cell.

The invention further provides pharmaceutical or diagnostic compositions comprising an effective amount of the anti-MCT1 antibody or antigen-binding fragment thereof or fusion polypeptide, chimeric antigen receptor (CAR), multispecific antigen binding polypeptide or multispecific or bispecific antibody polypeptide or anti-anti-MCT1 antibody or antigen-binding fragment or anti-anti-MCT1 antibody or antigen-binding fragment according to any one of the foregoing or a cell which expresses any of the foregoing, e.g., which are suitable for use in human or non-human therapy or prophylaxis.

The invention further provides methods of producing an isolated anti-MCT1 antibody or antigen-binding fragment thereof comprising culturing a host cell as above-described under conditions that allow expression of the antibody or antigen-binding fragment thereof; and recovering the antibody or antigen-binding fragment thereof from the culture medium or host cell.

The invention further provides pharmaceutical compositions comprising a pharmaceutically effective amount of an isolated anti-MCT1 antibody or antigen-binding fragment thereof, anti-idiotypic antibody, fusion polypeptide, chimeric antigen receptor (CAR), multispecific antigen binding polypeptide or multispecific or bispecific antibody polypeptide or a cell which expresses any of the foregoing, e.g., those comprising a pharmaceutical diluent, carrier, or excipient and optionally which may comprise another therapeutic agent, e.g., a mitochondrial inhibitor and/or a biguanide and/or another Monocarboxylate transporter (MCT inhibitor), e.g., a SLC16A1, SLC16A2, SLC16A3, SLC16A4, SLC16A5, SLC16A6, SLC16A7, SLC16A8, SLC16A9, SLC16A10, SLC16A11, SLC16A12, SLC16A13, or SLC16A14 inhibitor or a MCT1, MCT2, MCT3, MCT4, MCT5, MCT6, MCT7, MCT8, MCT9 or MCT10 inhibitor wherein said inhibitor may inhibit one or more of the foregoing transporters and further said inhibitor optionally comprises a small molecule, RNAi, antibody, antibody fragment or a fusion protein or wherein said other active agent is selected from Metformin, Phenformin, Alexidine, Bisbiguanide, Buformin, Chlorohexidine, Chlorproguanil, Phenylbiguanide, Polyaminopropyl biguanide, Polyhexanide, Moroxydine, Glipizide, Glyburide, Repaglinide, Saxagliptin, Sitagliptin, Pyrvinium Pamoate, Proguanil, Doxycycline, Atovaquone, Canagliflozin, Glitazones (e.g. Troglitazone, Pioglitazone, Rosiglitazone), Tigecycline, Thiazolides (e.g., Nitazoxanide), Salicylanilides (e.g. Closantel, Oxyclozanide, Niclosamide), Perhexiline, Propranolol, Fenofibrate, Miconazole, Nefazodone, Pentamidine, Hydrocortisone, Metaiodobenzylguanidine, Lonidamine, alpha tocopheryl succinate (primary form of Vitamin E), Carbonic anhydrase, ME344 (MEI Pharma), HIF1a inhibitors (e.g. Chrysin, Chetomin, Dimethy-bisphenol A, BAY84-2243), SR13800, Dimethyloxaloylglycine (DMOG), carbonylcyanide p-triflouromethoxyphenylhydrazone (FCCP), carbonylcyanide m-chlorophenylhydrazone (CCCP), Antimycin A, Oligomycin, Salinomycin, Dinitrophenol, Rotenone, Phenformin, Tyrphostin 9, Atpenin A5, Berberine, Azide, Cyanide, Nitrous oxide, Arsenic trioxide, Pyrvinium, Canagliflozin, Rosiglitazone, Amobarbital, Honokiol, Arctigenin, Caffeic acid phenyl ester, Perphenazine, Trifluoroperazine, Methylglyoxal and combinations comprising any of the foregoing.

The invention further provides methods for inhibiting the activity and/or numbers of T effector cells, e.g., CD3+, CD4+ and/or CD8+ T effector cells in a subject in need thereof comprising administering to the subject a therapeutically or prophylactically effective amount of an anti-MCT1 antibody or antigen-binding fragment thereof or fusion polypeptide, chimeric antigen receptor (CAR), multispecific antigen binding polypeptide or multispecific or bispecific antibody polypeptide according to any of the foregoing or a cell which expresses at least one of the foregoing or a pharmaceutical composition containing a therapeutically or prophylactically effective amount of any of the foregoing.

The invention further provides methods for increasing the activity and/or numbers of T suppressor or Tr1 cells in a subject in need thereof comprising administering to the subject a therapeutically or prophylactically effective amount of an anti-MCT1 antibody or antigen-binding fragment thereof or fusion polypeptide, chimeric antigen receptor (CAR), multispecific antigen binding polypeptide or multispecific or bispecific antibody polypeptide according to any of the foregoing or a cell which expresses at least one of the foregoing or a pharmaceutical composition containing a therapeutically or prophylactically effective amount of any of the foregoing.

The invention further provides methods for inhibiting the activity and/or numbers of T effector cells, e.g., CD3+, CD4+ and/or CD8+ T effector cells and increasing the activity and/or numbers of T suppressor or Tr1 cells in a subject in need thereof comprising administering to the subject a therapeutically or prophylactically effective amount of an anti-MCT1 antibody or antigen-binding fragment thereof or fusion polypeptide, chimeric antigen receptor (CAR), multispecific antigen binding polypeptide or multispecific or bispecific antibody polypeptide according to any of the foregoing or a cell which expresses at least one of the foregoing or a pharmaceutical composition containing a therapeutically or prophylactically effective amount of any of the foregoing, e.g., wherein the subject has an autoimmune condition, allergic condition, inflammatory condition, metabolic disorder, cancer, transplant recipient, cell therapy recipient, EIHI condition, polycystic kidney disease (ADPKD) characterized by increased T effector cell activity, e.g., CD3+, CD4+ or CD8+ and/or decreased T suppressor or Tr1 activity and/or decreased T suppressor or Tr1 cell numbers.

The invention further provides methods for preventing or treating an autoimmune condition, allergic condition, inflammatory condition, metabolic disorder, cancer, transplant recipient, cell therapy recipient, EIHI condition, polycystic kidney disease (ADPKD), or symptoms associated with any of said conditions comprising administering to a subject in need thereof a therapeutically or prophylactically effective amount of an anti-MCT1 antibody or antigen-binding fragment thereof or fusion polypeptide, chimeric antigen receptor (CAR), multispecific antigen binding polypeptide or multispecific or bispecific antibody polypeptide according to any of the foregoing or a cell which expresses at least one of the foregoing or a pharmaceutical composition containing a therapeutically or prophylactically effective amount of any of the foregoing, e.g., wherein the autoimmune condition, allergic condition, inflammatory condition, metabolic disorder, cancer, transplant recipient, cell therapy recipient, EIHI condition, polycystic kidney disease (ADPKD) characterized by increased T effector cell activity, e.g., CD3+, CD4+ or CD8+ and/or decreased T suppressor or Tr1 activity and/or decreased T suppressor or Tr1 cell numbers or optionally wherein the metabolic disorder comprises Danon disease, diabetes mellitus, Duarte galactosemia, MDP syndrome, metabolic myopathy, methylenetetrahydrofolate reductase deficiency, Winchester syndrome, salicylate sensitivity, X-linked hypophosphatemia, alcoholic ketoacidosis, alcohol flush reaction, Alpha-aminoadipic and alpha-ketoadipic aciduria, High anion gap metabolic acidosis, gout, refeeding syndrome, Exercise-associated hyponatremia, pancreatitis, pancreatitis, and Metab-L or optionally wherein the condition is mediated at least in part by activated T cells or B cells and/or MCT1 expressing cells.

The invention further provides methods according to any of the foregoing, wherein administration of the antibody or antigen-binding fragment thereof or fusion protein has one or more of the following effects:

(i) inhibits lactate transport in activated T cells or B cells;

(ii) inhibits the transport of bromopyruvate toxin in activated T cells or B cells;

(iii) inhibits the proliferation of CD3/CD28 stimulated T cells;

(iv) inhibits the proliferation of activated T cells;

(v) inhibits the production and/or secretion of one or more inflammatory cytokines;

(vi) does not inhibit the production and/or secretion of IL-2;

(vii) increases the production of urine ketones;

(viii) increases survival time;

(ix) decreases graft rejection;

(x) increases the proportion or activity of regulatory T (Treg) cells;

(xi) increases the proportion of CD4$^+$ T cells that are Tregs;

(xii) decreases the proportion of IgG1$^+$ B cells;

(xiii) decreases the proportion of germinal center B cells;

(xiv) does not inhibit lactate transport in human RBCs;

(xv) decreases T cell activation; and (xvi) decreases cytotoxic T cell activity.

The invention further provides methods according to any of the foregoing, which are used to treat or prevent at least one of lupus, graft rejection, graft versus host disease (GVHD), type 1 or 2 diabetes, or obesity.

The invention further provides methods according to any of the foregoing, wherein treatment efficacy is monitored via the measurement of urine ketones, an increase in the number of TR1 cells, reduced or increased expression of a biomarker selected from an inflammatory cytokine, IFNγ, GM-CSF, TNFα, IL-10, IL-6, IL-2, TIGIT, PD1, granzyme B, by a decrease in the number of effector T cells and/or hCD3+ cells, suppression of PMBC proliferation or a combination of any of the foregoing.

The invention further provides methods of assessing the therapeutic efficacy of an anti-MCT1 antagonist antibody which comprises detecting its effect in vitro or in vivo on any of the foregoing: urine ketones, the number of TR1 cells, the expression of a biomarker selected from an inflammatory cytokine, IFNγ, GM-CSF, TNFα, IL-10, IL-6, IL-2, TIGIT, PD1, granzyme B, a decrease in the number of effector T cells and/or hCD3+ cells, suppression of PMBC proliferation or a combination of any of the foregoing.

The invention further provides methods according to any of the foregoing, for treating, or preventing a recurrence of, cancer comprising administering to a subject in need thereof a therapeutically or prophylactically effective amount of an anti-MCT1 antibody or antigen-binding fragment thereof or fusion polypeptide, chimeric antigen receptor (CAR), multispecific antigen binding polypeptide or multispecific or bispecific antibody polypeptide according to any of the foregoing or a cell which expresses at least one of the foregoing or a pharmaceutical composition containing a therapeutically or prophylactically effective amount of any of the foregoing, e.g., wherein the tumor cells express MCT1 or the subject is a mammal or the subject is a mammal selected from human, non-human primate or a rodent.

The invention further provides methods for inhibiting, or reducing the activity of, activated T cells or B cells, comprising contacting said activated cells with of an anti-MCT1 antibody or antigen-binding fragment thereof or fusion polypeptide, chimeric antigen receptor (CAR), multispecific antigen binding polypeptide or multispecific or bispecific antibody polypeptide or a cell which expresses at least one of the foregoing according to any of the foregoing.

The invention further provides methods according to any of the foregoing, wherein an anti-MCT1 antibody or antigen-binding fragment thereof or fusion polypeptide, chimeric antigen receptor (CAR), multispecific antigen binding polypeptide or multispecific or bispecific antibody polypeptide or a cell which expresses at least one of the foregoing according to any of the foregoing is administered as a monotherapy.

The invention further provides methods according to any of the foregoing, wherein an anti-MCT1 antibody or antigen-binding fragment thereof or fusion polypeptide, chimeric antigen receptor (CAR), multispecific antigen binding polypeptide or multispecific or bispecific antibody polypeptide or a cell which expresses at least one of the foregoing according to any of the foregoing is administered in combination with a second therapeutic agent e.g., wherein the therapeutic agent is selected from an immunosuppressive drug, a chemotherapeutic agent, biguanide, e.g., metformin or another anti-diabetic agent, or an anti-inflammatory agent or said other therapeutic agent is a mitochondrial inhibitor and/or a biguanide or said other therapeutic agent is selected from Metformin, Phenformin, Alexidine, Bisbiguanide, Buformin, Chlorohexidine, Chlorproguanil, Phenylbiguanide, Polyaminopropyl biguanide, Polyhexanide, Moroxydine, Glipizide, Glyburide, Repaglinide, Saxagliptin, Sitagliptin, Pyrvinium Pamoate, Proguanil, Doxycycline, Atovaquone, Canagliflozin, Glitazones (e.g. Troglitazone, Pioglitazone, Rosiglitazone), Tigecycline, Thiazolides (e.g., Nitazoxanide), Salicylanilides (e.g. Closantel, Oxyclozanide, Niclosamide), Perhexiline, Propranolol, Fenofibrate, Miconazole, Nefazodone, Pentamidine, Hydrocortisone, Metaiodobenzylguanidine, Lonidamine, alpha tocopheryl succinate (primary form of Vitamin E), Carbonic anhydrase, ME344 (MEI Pharma), HIF1a inhibitors (e.g. Chrysin, Chetomin, Dimethy-bisphenol A, BAY84-2243), SR13800, Dimethyloxaloylglycine (DMOG), carbonylcyanide p-triflouromethoxyphenylhydrazone (FCCP), carbonylcyanide m-chlorophenylhydrazone (CCCP), Antimycin A, Oligomycin, Salinomycin, Dinitrophenol, Rotenone, Phenformin, Tyrphostin 9, Atpenin A5, Berberine, Azide, Cyanide, Nitrous oxide, Arsenic trioxide, Pyrvinium, Canagliflozin, Rosiglitazone, Amobarbital, Honokiol, Arctigenin, Caffeic acid phenyl ester, Perphenazine, Trifluoroperazine, Methylglyoxal and combinations comprising any of the foregoing.

The invention further provides methods according to any of the foregoing, wherein the anti-MCT1 antibody, antigen-binding fragment thereof, fusion protein, or pharmaceutical composition is administered enterally, parenterally, or topically.

The invention further provides methods for monitoring the efficacy of treatment with an antibody or antigen-binding fragment thereof or fusion protein that binds to MCT1 and reduces MCT1-mediated lactate transport comprising measuring the level of urine ketones.

The invention further provides methods for diagnosing a condition selected from an autoimmune, inflammatory, or allergic condition; a cancer; EIHI; polycystic kidney disease (ADPKD); diabetes or other metabolic disorder, and/or a condition associated with upregulation of MCT1, said method comprising:

(i) isolating the cells responsible for mediating the condition;

(ii) contacting said cells with an anti-MCT1 antibody or antigen-binding fragment thereof or MCT1-binding fusion protein; and (iii) detecting the level of anti-MCT1 antibody or antigen-binding fragment or MCT1-binding fusion protein thereof bound to said cells.

The invention further provides treatment and detection methods as above-described wherein the condition is an autoimmune, inflammatory, transplant, GVHD, metabolic disorder (e.g., diabetes), EIHI; polycystic kidney disease (ADPKD); or allergic condition, e.g., wherein the condition is an autoimmune, inflammatory, transplant, GVHD, metabolic disorder (e.g., diabetes), polycystic kidney disease (ADPKD), or allergic condition, and the cells are activated T cells or B cells or the condition is cancer and the cells are tumor cells or the condition is EIHI and the cells are beta cells.

The invention further provides treatment and detection methods as above-described wherein the anti-MCT1 antibody or antigen-binding fragment thereof or MCT1-binding fusion protein comprises one or more of the following:

(i) competes with an anti-MCT1 antibody selected from any of Ab1-Ab95 or another anti-MCT1 antibody comprising the same CDRs as any of the foregoing an anti-MCT1 antibodies;

(ii) comprises the same CDRs as an anti-human MCT1 antibody selected from Ab1-Ab95;

(iii) comprises an affinity-matured or humanized variant of an anti-human MCT1 antibody selected from Ab1-Ab95;

(iv) competes with an antibody comprising a $V_H$ domain having at least 80%, at least 85%, at least 90%, at least 95%, at least 98%, at least 99%, or 100% identity to the amino acid sequence of the $V_H$ domain of MCT1 Ab1 (SEQ ID NO: 2) or with any of Ab1-Ab59; and comprising a $V_L$ domain having at least 80%, at least 85%, at least 90%, at least 95%, at least 98%, at least 99%, or 100% identity to the amino acid sequence of the $V_L$ domain of MCT1 Ab1 (SEQ ID NO: 3) or with any of Ab2-Ab95;

(v) comprises the heavy chain CDR sequences of MCT1 Ab1 (SEQ ID NOS: 4, 5, 6) and the light chain CDR sequences of MCT1 Ab1 (SEQ ID NOS: 7, 8, 9) or those of any of Ab2-Ab95;

(vi) competes with an antibody comprising or itself comprises a $V_H$ domain having at least 80%, at least 85%, at least 90%, at least 95%, at least 98%, at least 99%, or 100% identity to the amino acid sequence of the $V_H$ domain of MCT1 Ab1 (SEQ ID NO: 2) or with any of Ab2-Ab60; and comprises a $V_L$ domain having at least 80%, at least 85%, at least 90%, at least 95%, at least 98%, at least 99%, or 100% identity to the amino acid sequence of the $V_L$ domain of MCT1 Ab1 (SEQ ID NO: 3) or with any of Ab2-Ab60;

(vii) competes with an antibody comprising or itself comprises a $V_H$ domain having at least 80%, at least 85%, at least 90%, at least 95%, at least 98%, at least 99%, or 100% identity to the amino acid sequence of the $V_H$ domain selected from those of SEQ ID NO: 2, 12, 14, 16, 19-32 or with any of Ab5-Ab60; and/or (viii) competes with an antibody comprising or itself comprises a $V_L$ domain having at least 80%, at least 85%, at least 90%, at least 95%, at least 98%, at least 99%, or 100% identity to the amino acid sequence of the $V_H$ domain selected from those of SEQ ID NO: 13, 15, 17 or 33-44 or with any of Ab5-Ab60; and/or (ix) comprises at least one peptide comprising a sequence identical to SEQ ID NO: 6 or comprising a sequence which differs therefrom by at most 5, 4, 3, 2, or 1 residues, wherein said peptide is directly or indirectly linked to another polypeptide, e.g., an antibody polypeptide or antibody domain, serum albumin, human or other primate serum albumin, adnectin, an affibody, a DARPin, an anticalin, glycol (PEG), monomethoxy PEG (mPEG), an XTEN molecule, an rPEG molecule or fragment or variant of any of the foregoing.

The invention methods of detecting the expression of MCT1, optionally functional MCT1, by a cell comprising determining whether any of the anti-MCT1 antibodies according to any of the foregoing embodiments which bind to MCT1 expressed by said cell, e.g., wherein the cell is human or non-human, e.g., wherein the cell is obtained from a patient having or suspected of comprising an autoimmune condition, allergic condition, inflammatory condition, metabolic disorder, cancer, transplant recipient, cell therapy recipient, EIHI condition, polycystic kidney disease (ADPKD) or wherein the detection method is used to diagnose or monitor a disease or disease prognosis using a cell sample obtained from a patient having or suspected of comprising an autoimmune condition, allergic condition, inflammatory condition, metabolic disorder, cancer, transplant recipient, cell therapy recipient, EIHI condition, polycystic kidney disease (ADPKD) characterized by cells which comprise aberrant (increased) MCT1 expression or activity.

In some embodiments, the antibody or antigen-binding fragment thereof is selected from the group consisting of: a monoclonal antibody; a monospecific antibody; a polyspecific antibody; a humanized antibody; a tetrameric antibody; a tetravalent antibody; a multispecific antibody; a single chain antibody; a domain-specific antibody; a single domain antibody; a domain-deleted antibody; an scFc fusion protein; a chimeric antibody; a synthetic antibody; a recombinant antibody; a hybrid antibody; a mutated antibody; CDR-grafted antibodies; an antibody fragment; an Fab; an F(ab')2; an Fab' fragment; an Fv fragment; a single-chain Fv (scFv) fragment; an Fd fragment; a dAb fragment; multiple specific antibodies, diabodies; ByTEs, bivalent antibodies, a nanobody; a bivalent nanobody; a shark variable IgNAR domain; a VHH antibody; a camelid antibody; and a minibody.

In some embodiments, the antibody or antigen-binding fragment thereof is a human, humanized, or chimeric antibody or antigen-binding fragment thereof.

In some embodiments, the antibody or antigen-binding fragment thereof is an anti-MCT1 antibody which competes or which binds to the same or overlapping epitope as any of the antibodies which are identified as Ab1-Ab95 herein, wherein such antibody or antigen binding fragment optionally antagonizes one or more MCT1 associated functions, e.g., it inhibits MCT1-mediated lactate transport.

In some embodiments, the antibody or antigen-binding fragment thereof is an anti-MCT1 antibody which comprises at least 1, 2, 3, 4, 5 or all 6 CDRs as any of the anti-MCT1 antibodies which are identified as Ab1-Ab95 herein, wherein such antibody or antigen binding fragment optionally antagonizes one or more MCT1 associated functions, e.g., it inhibits MCT1-mediated lactate transport.

In some embodiments, the antibody or antigen-binding fragment thereof is an anti-MCT1 antibody or antigen-binding fragment which comprises a humanized, chimeric, scFv, or affinity-matured derivative of any of the anti-MCT1 antibodies which are identified as Ab1-Ab95 herein, wherein such antibody or antigen binding fragment optionally antagonizes one or more MCT1 associated functions, e.g., it inhibits MCT1-mediated lactate transport.

In some embodiments, the antibody or antigen-binding fragment thereof is a fusion polypeptide or multispecific polypeptide which comprises at least one anti-MCT1 antigen binding domain which comprises the same CDRs or heavy and/or light variable regions as any of the anti-MCT1 antibodies which are identified as Ab1-Ab95 herein, wherein such fusion polypeptide or multispecific polypeptide optionally antagonizes one or more MCT1 associated functions, e.g., it inhibits MCT1-mediated lactate transport.

In some embodiments the anti-MCT1 antibody or antigen binding fragment will comprise a heavy chain CDR3 sequence comprises 19, 20, 21, 22, 23 or 24 amino acid residues. In some embodiments, the heavy chain CDR3 sequence comprises 21, 22 or 23 amino acid residues. In some embodiments, the heavy chain CDR3 sequence is identical to SEQ ID NO:6 or differs therefrom by at most 5, 4, 3, 2 or 1 residues. In some embodiments, said substitutions if present comprise conservative amino acid substitutions or comprise substituting amino acids which are prevalent at the same position in the heavy chain CDR3 of human or rodent antibodies.

In some embodiments, the antibody or antigen-binding fragment thereof competes for binding to MCT1 with a reference antibody, wherein the reference antibody comprises:
  i. the heavy chain CDR sequences of MCT1 Ab1 (SEQ ID NOS: 4, 5, 6), and the light chain CDR sequences of MCT1 Ab1 (SEQ ID NOS: 7, 8, 9); or
  ii. a $V_H$ domain having at least 80%, at least 85%, at least 90%, at least 95%, at least 98%, at least 99%, or 100% identity to the amino acid sequence of the $V_H$ domain of MCT1 Ab1 (SEQ ID NO: 2); and comprising a $V_L$ domain having at least 80%, at least 85%, at least 90%, at least 95%, at least 98%, at least 99%, or 100% identity to the amino acid sequence of the $V_L$ domain of MCT1 Ab1 (SEQ ID NO: 3).

In some embodiments, the antibody or antigen-binding fragment thereof comprises the heavy chain CDR sequences of MCT1 Ab1 (SEQ ID NOS: 4, 5, 6) and the light chain CDR sequences of MCT1 Ab1 (SEQ ID NOS: 7, 8, 9).

In some embodiments, the antibody or antigen-binding fragment thereof comprises a VH domain having at least 80%, at least 85%, at least 90%, at least 95%, at least 98%, at least 99%, or 100% identity to the amino acid sequence of the $V_H$ domain of MCT1 Ab1 (SEQ ID NO: 2); and comprises a VL domain having at least 80%, at least 85%, at least 90%, at least 95%, at least 98%, at least 99%, or 100% identity to the amino acid sequence of the VL domain of MCT1 Ab1 (SEQ ID NO: 3).

In some embodiments, the antibody or antigen-binding fragment thereof comprises a VH domain comprising the same CDRs as comprised in the $V_H$ domain of any of anti-MCT1 antibodies identified herein as Ab1-Ab95 and/or comprises a VL domain comprising the same CDRs as the $V_H$ domain of any of anti-MCT1 antibodies identified herein as Ab1-Ab83.

In some embodiments, the antibody or antigen-binding fragment thereof comprises a VH domain having at least 80%, at least 85%, at least 90%, at least 95%, at least 98%, at least 99%, or 100% identity to the amino acid sequence of the $V_H$ domain of any of anti-MCT1 antibodies identified herein as Ab1-Ab95 and/or comprises a VL domain having at least 80%, at least 85%, at least 90%, at least 95%, at least 98%, at least 99%, or 100% identity to the to the amino acid sequence of the $V_H$ domain of any of anti-MCT1 antibodies identified herein as Ab1-Ab83.

In some embodiments the anti-MCT1 antibody or antigen binding fragment will bind to one or more of the following residues of the epitope bound by anti-MCT1 antibodies according to the invention, i.e., any of Ab1-Ab95, optionally wherein the residues which constitute the epitope are identified by alanine scanning.

In some embodiments, the CDRs of the anti-MCT1 antibody or antigen-binding fragment thereof will have a similar three-dimensional structure to those of MCT1 Ab1, as indicated by the positions of the alpha carbons in corresponding CDRs differing by an average root-mean-squared deviation (RMSD) of less than 2.0 Å, less than 1.0 Å, or less than 0.5 Å, as determined via structural alignment as shown in FIG. 21.

The invention additionally provides an isolated anti-MCT1 antibody or antigen-binding fragment thereof comprising a variable heavy chain polypeptide or heavy chain polypeptide having an amino acid sequence selected from SEQ ID NO: 2, 12, 14, 16, 19-32, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153 and 155, and a variable light chain polypeptide or light chain polypeptide having an amino acid sequence selected from SEQ ID NO: 3, 13, 15, 17, 33-44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 150, 152, 144, 146, 148, 150, 152, 154 and 156.

The invention specifically provides an isolated anti-MCT1 antibody or antigen-binding fragment thereof comprising a variable heavy chain polypeptide and variable light chain polypeptide having an amino acid sequence respectively selected from the following: SEQ ID NO: 2 and 3; SEQ ID NO: 12 and 13; SEQ ID NO: 14 and 15; SEQ ID NO: 16 and 17; SEQ ID NO: 45 and 46; SEQ ID NO: 47 and 48; SEQ ID NO: 49 and 50; SEQ ID NO: 51 and 52; SEQ ID NO: 53 and 54; SEQ ID NO: 55 and 56; SEQ ID NO: 57 and 58; SEQ ID NO: 59 and 60; SEQ ID NO: 61 and 62; SEQ ID NO: 63 and 64; SEQ ID NO: 65 and 66; SEQ ID NO: 67 and 68; SEQ ID NO: 69 and 70; SEQ ID NO: 71 and 72; SEQ ID NO: 73 and 74; SEQ ID NO: 75 and 76; SEQ ID NO: 77 and 78; SEQ ID NO: 79 and 80; SEQ ID NO: 81 and 82; SEQ ID NO: 83 and 84; SEQ ID NO: 85 and 86; SEQ ID NO: 87 and 88; SEQ ID NO: 89 and 90; SEQ ID NO: 91 and 92; SEQ ID NO: 93 and 94; SEQ ID NO: 95 and 96; SEQ ID NO: 97 and 98; SEQ ID NO: 99 and 100; SEQ ID NO: 101 and 102; SEQ ID NO: 103 and 104; SEQ ID NO: 105 and 106; SEQ ID NO: 107 and 108; SEQ ID NO: 109 and 110; SEQ ID NO: 111 and 112; SEQ ID NO: 113 and 114; SEQ ID NO: 115 and 116; SEQ ID NO: 117 and 118; SEQ ID NO: 119 and 120; SEQ ID NO: 121 and 122; SEQ ID NO: 123 and 124; SEQ ID NO: 125 and 126; SEQ ID NO: 127 and 128; SEQ ID NO: 129 and 130; SEQ ID NO: 131 and 132; SEQ ID NO: 133 and 134; SEQ ID NO: 135 and 136; SEQ ID NO: 137 and 138; SEQ ID NO: 139 and 140; SEQ ID NO: 141 and 142; SEQ ID NO: 143 and 144; SEQ ID NO: 145 and 146; SEQ ID NO: 147 and 148; SEQ ID NO: 149 and 150; SEQ ID NO: 151 and 152; SEQ ID NO: 153 and 154 and SEQ ID NO: 155 and 156.

The invention further provides an isolated antibody or antigen-binding fragment thereof comprising a $V_H$ domain having at least 80%, at least 85%, at least 90%, at least 95%, at least 98%, at least 99%, or 100% identity to the amino acid sequence of the $V_H$ domain of MCT1 Ab1 (SEQ ID NO: 2); and comprising a VL domain having at least 80%, at least 85%, at least 90%, at least 95%, at least 98%, at least 99%, or 100% identity to the amino acid sequence of the VL domain of MCT1 Ab1 (SEQ ID NO: 3).

The invention also provides a fusion protein which comprises at least one peptide comprising a sequence identical to SEQ ID NO:6 or comprising a sequence which differs therefrom by at most 5, 4, 3, 2, or 1 residues, wherein said peptide is directly or indirectly linked to another polypeptide, e.g., an antibody polypeptide or antibody domain, serum albumin, human or other primate serum albumin, adnectin, an affibody, a DARPin, an anticalin, glycol (PEG), monomethoxy PEG (mPEG), an XTEN molecule, an rPEG molecule or fragment or variant of any of the foregoing. In some embodiments, the antibody polypeptide or domain comprises an Fc polypeptide or fragment thereof, e.g., a human IgG1, IgG2, IgG3 or IgG4 Fc region or fragment thereof. In some embodiments, said substitutions if present comprise conservative amino acid substitutions or comprise substituting amino acids which are prevalent at the same position in the heavy chain CDR3 of human or rodent antibodies.

In some embodiments, the antibody or antigen-binding fragment thereof or fusion protein has one or more of the following properties upon binding to MCT1 on the surface of an activated T cell or B cell:
  i. inhibits the transport of lactate;
  ii. inhibits the transport of bromopyruvate;
  iii. inhibits the transport of one or more of monocarboxylates, pyruvate, branched-chain oxo acids derived from leucine, valine and isoleucine, ketone bodies, acetoacetate, beta-hydroxybutyrate, acetate, lactic acid, cellular nutrients, metabolites, ions, hormones, lipids, and ketones;
  iv. inhibits the proliferation of CD3/CD28 stimulated T cells;
  v. inhibits the proliferation of the activated T cell or B cell;
  vi. inhibits the production of one or more inflammatory cytokines;
  vii. increases the proportion or activity of regulatory T (Treg) cells; and viii. inhibits allogeneic activation in a mixed lymphocyte reaction.

In some embodiments, the antibody or antigen-binding fragment thereof or fusion protein inhibits the production of one or more inflammatory cytokines upon binding to MCT1. In some embodiments, at least one of the one or more cytokines, e.g., inflammatory cytokines wherein such cytokines may include any of the following: FGF2, FLT-3L, Fractalkine, G-CSF, GM-CSF, GRO, IFNα2, IFNγ, IL-3, IL-5, IL-9, IL-10, IL-12p40, IL-12p70, IL-13, IL-17a, IP-10, MCP-1, MDC, MIP-1a, MIP-1b, sCD40L, TNFα, and TNFβ. In some embodiments, at least one of the one or more inflammatory cytokines is selected from IFNγ, GM-CSF, TNFα, IL-10, and IL-6.

In some embodiments, the antibody or antigen-binding fragment thereof or fusion protein inhibits MCT1-mediated lactate transport in activated T cells with a Kd of less than 100 nM, less than 50 nM, or less than 10 nM as measured via a lactate FLIPR assay.

In some embodiments, the antibody or antigen-binding fragment thereof or fusion protein does not:
  i. bind to MCT2, MCT3, MCT4, and/or CD147 as measured via flow cytometry;
  ii. inhibit MCT2, MCT3, and/or MCT4 transport;
  iii. inhibit the production of IL-2;
  iv. inhibit lactate transport in monocytes;
  v. inhibit the proliferation of naïve, resting, and/or regulatory T cells;
  vi. inhibit lactate transport in RBCs;
  vii. alter the expression of one or more T cell activation markers, optionally selected from CD25, CD54, CD69, CD95, CD98, CD147, CD154, CD278, CD279, and HLA-DR/DP/DQ.

In some embodiments, the antibody or antigen-binding fragment thereof or fusion protein comprises a human IgG1, IgG2, IgG3, or IgG4 Fc region.

In some embodiments, the antibody or antigen-binding fragment thereof or fusion protein comprises an Fc region that has been modified to alter at least one of effector function, half-life, proteolysis, or glycosylation, wherein optionally the Fc region contains one or more mutations that alters or eliminates N- and/or O-glycosylation.

In some embodiments, the antibody or antigen-binding fragment thereof or fusion protein binds MCT1 with an affinity ($K_D$) of less than 100 nM, less than 50 nM, or less than 10 nM.

In some embodiments, the antibody or antigen-binding fragment thereof or fusion protein additionally has one or more of the following modifications:
  i. is conjugated to a cytotoxic agent;
  ii. is comprised in a bispecific antibody;
  iii. is comprised in a multispecific antigen-binding protein;
  iv. is conjugated to a label; and
  v. is conjugated to another therapeutic agent, optionally an immunosuppressive agent or a chemotherapeutic agent.

In some embodiments, the label is a chemiluminescent label, a paramagnetic label, an MRI contrast agent, a fluorescent label, a bioluminescent label, or a radioactive label.

In some embodiments, the cytotoxic agent is a moiety that inhibits DNA, RNA, or protein synthesis; a radionuclide; or a ribosomal inhibiting protein.

In some embodiments, the antibody or antigen-binding fragment thereof or fusion protein is suitable for treating a human subject having an autoimmune, inflammatory, or allergic condition; cancer; or EIHI.

The invention also provides an anti-idiotypic antibody or antigen-binding fragment thereof produced against an anti-MCT1 antibody or antigen-binding fragment thereof according to any of the preceding embodiments, which optionally neutralizes one or more biological effects of the anti-MCT1 antibody or antigen-binding fragment thereof to which it binds. The invention further provides an anti-anti-idiotypic antibody or antigen-binding fragment thereof produced against the anti-idiotypic antibody or antigen-binding fragment thereof, optionally wherein the anti-anti-idiotypic antibody or antigen-binding fragment thereof neutralizes the anti-idiotypic antibody or antigen-binding fragment thereof to which it binds.

Further, in some embodiments, the invention concerns a method of using the anti-idiotypic antibody to monitor the in vivo levels of said anti-MCT1 antibody or antigen-binding fragment thereof in a subject or to neutralize the in vivo effects of said anti-MCT1 antibody or antigen-binding fragment thereof in a subject.

The invention also provides an isolated polynucleotide encoding the anti-MCT1 antibody or antigen-binding fragment thereof or fusion protein according to any of the foregoing embodiments. Additionally provided are expression vectors comprising such polynucleotides. The invention also provides a host cell comprising the expression vector. The invention further relates to a method of producing an isolated anti-MCT1 antibody or antigen-binding fragment thereof comprising culturing the host cell under conditions that allow expression of the antibody or antigen-binding fragment thereof; and recovering the antibody or antigen-binding fragment thereof from the culture medium or host cell.

The invention further provides a pharmaceutical composition comprising a pharmaceutically effective amount of an isolated anti-MCT1 antibody or antigen-binding fragment thereof or fusion protein or an isolated cell which expresses same according to any of the foregoing embodiments which may further comprise a pharmaceutical diluent, carrier, or excipient.

Also provided herein is a method for treating or preventing an autoimmune, allergic, or inflammatory condition comprising administering to a subject in need thereof a therapeutically or prophylactically effective amount of an anti-MCT1 antibody, or antigen-binding fragment thereof, or fusion protein according to any of the foregoing embodiments or a pharmaceutical composition as described above.

In some embodiments, the condition is mediated at least in part by activated T cells or B cells.

In some embodiments, administration of the anti-MCT1 antibody or antigen-binding fragment thereof or fusion protein has one or more of the following effects:

i. inhibits lactate transport in activated T cells or B cells;
ii. inhibits the transport of bromopyruvate toxin in activated T cells or B cells;
iii. inhibits the proliferation of CD3/CD28 stimulated T cells;
iv. inhibits the proliferation of activated T cells;
v. inhibits the production and/or secretion of one or more inflammatory cytokines;
vi. does not inhibit the production and/or secretion of IL-2;
vii. increases the production of urine ketones;
viii. increases survival time;
ix. decreases graft rejection;
x. increases the proportion or activity of regulatory T (Treg) cells;
xi. increases the proportion of CD4⁺ T cells that are Tregs;

xii. decreases the proportion of IgG1⁺ B cells;
xiii. decreases the proportion of germinal center B cells;
xiv. does not inhibit lactate transport in human RBCs;
xv. decreases T cell activation; and
xvi. decreases cytotoxic T cell activity.

In some embodiments, the method is used to treat or prevent lupus.

In some embodiments, the method is used to treat or prevent graft rejection.

In some embodiments, the method is used to treat or prevent graft versus host disease (GVHD).

In some embodiments, the method is used to treat or prevent diabetes.

In some embodiments, the method is used to treat or prevent obesity.

In some embodiments, treatment efficacy is monitored via the measurement of urine ketones.

The invention further provides a method for treating, or preventing a recurrence of, cancer comprising administering to a subject in need thereof a therapeutically or prophylactically effective amount of an anti-MCT1 antibody, or antigen-binding fragment thereof, or fusion protein according to any one of the foregoing embodiments or a pharmaceutical composition according to the foregoing embodiments.

In some embodiments, the tumor cells express MCT1.

In some embodiments, the subject is a mammal. In some embodiments, the mammal is a human. In some embodiments, the mammal is a non-human primate. In some embodiments, the mammal is a rodent.

The invention also provides a method for inhibiting, or reducing the activity of, activated T cells or B cells, comprising contacting said activated cells with an anti-MCT1 antibody, or antigen-binding fragment thereof, or fusion protein according to any one of the foregoing embodiments.

In some embodiments, the anti-MCT1 antibody or antigen-binding fragment thereof or fusion protein is administered as a monotherapy.

In some embodiments, the anti-MCT1 antibody or antigen-binding fragment thereof or fusion protein is administered in combination with a second therapeutic agent.

In some embodiments, the therapeutic agent is selected from an immunosuppressive drug or a chemotherapeutic agent.

In some embodiments, the anti-MCT1 antibody, antigen-binding fragment thereof, fusion protein, or pharmaceutical composition is administered enterally, parenterally, or topically.

The invention additionally provides a method for monitoring the efficacy of treatment with an antibody or antigen-binding fragment thereof or fusion protein that binds to MCT1 and reduces MCT1-mediated lactate transport comprising measuring the level of urine ketones.

In a further aspect, the invention provides a method for diagnosing a condition selected from an autoimmune, inflammatory, or allergic condition; a cancer; EIHI; and a condition associated with upregulation of MCT1, said method comprising:

i. isolating the cells responsible for mediating the condition;
ii. contacting said cells with an anti-MCT1 antibody or antigen-binding fragment thereof or MCT1 binding fusion protein; and
iii. detecting the level of anti-MCT1 antibody or antigen-binding fragment or MCT1 binding fusion protein thereof bound to said cells.

In some embodiments, the condition is an autoimmune, inflammatory, or allergic condition, and the cells are activated T cells or B cells.

In some embodiments, the condition is cancer, and the cells are tumor cells.

In some embodiments, the condition is EIHI, and the cells are beta cells.

In some embodiments, the anti-MCT1 antibody or antigen-binding fragment thereof or MCT1 binding fusion protein:

i. competes with an antibody comprising the heavy chain CDR sequences of MCT1 Ab1 (SEQ ID NOS: 4, 5, 6) and the light chain CDR sequences of MCT1 Ab1 (SEQ ID NOS: 7, 8, 9) or an anti-MCT1 antibody selected from any of Ab1-Ab95;

ii. competes with an antibody comprising a $V_H$ domain having at least 80%, at least 85%, at least 90%, at least 95%, at least 98%, at least 99%, or 100% identity to the amino acid sequence of the $V_H$ domain of MCT1 Ab1 (SEQ ID NO: 2) or to the $V_H$ domain of any of Ab1-Ab95; and further comprising a $V_L$ domain having at least 80%, at least 85%, at least 90%, at least 95%, at least 98%, at least 99%, or 100% identity to the amino acid sequence of the Vl domain of MCT1 Ab1 (SEQ ID NO: 3) or the $V_L$ domain of any of Ab1-Ab95;

iii. comprises the heavy chain CDR sequences of MCT1 Ab1 (SEQ ID NOS: 4, 5, 6) and the light chain CDR sequences of MCT1 Ab1 (SEQ ID NOS: 7, 8, 9);

iv. comprises a $V_H$ domain having at least 80%, at least 85%, at least 90%, at least 95%, at least 98%, at least 99%, or 100% identity to the amino acid sequence of the $V_H$ domain of MCT1 Ab1 (SEQ ID NO: 2); and comprises a $V_L$ domain having at least 80%, at least 85%, at least 90%, at least 95%, at least 98%, at least 99%, or 100% identity to the amino acid sequence of the $V_L$ domain of MCT1 Ab1 (SEQ ID NO: 3); or v. comprises at least one peptide comprising a sequence identical to SEQ ID NO:6 or comprising a sequence which differs therefrom by at most 5, 4, 3, 2, or 1 residues, wherein said peptide is directly or indirectly linked to another polypeptide, e.g., an antibody polypeptide or antibody domain, serum albumin, human or other primate serum albumin, adnectin, an affibody, a DARPin, an anticalin, glycol (PEG), monomethoxy PEG (mPEG), an XTEN molecule, an rPEG molecule or fragment or variant of any of the foregoing.

DETAILED DESCRIPTION OF THE SEVERAL VIEWS OF THE DRAWINGS

FIG. 1 illustrates that the metabolic states of leukocytes are associated with distinct immunological properties (REF. 33). Resting, memory and Treg cells are dependent on oxidative phosphorylation (Oxphos) (left), whereas effector T cell proliferation and effector function are largely dependent on glycolysis after antigen activation (right).

FIG. 2 shows that CD3/CD28 activation induces higher MCT1 and MCT4 expression and that the $IC_{50}$ values for inhibition of proliferation by AZ3965 do not change in the presence of high (Donor 1) or low (Donor 2) expression levels of MCT4 (S=stimulated for 3 days; NS=not stimulated; BSG=Basigin/CD147). From left to right for Donor 1, the bars correspond to unstimulated expression of MCT2, MCT4, and BSG, followed by stimulated expression of MCT1, MCT2, MCT4, and BSG. Note: Donor 1 had no expression of MCT1 in unstimulated cells. From left to right for Donor 2, the bars correspond to unstimulated expression of MCT1, MCT2, MCT4, and BSG, followed by stimulated expression of MCT1, MCT2, MCT4, and BSG.

FIG. 3 contains the results of a lactate FLIPR assay with AZ3965. AZ3965 inhibits lactate transport in human CD4+ T cells (CD4), CD8+ T cells (CD8), B-cell lymphoma cells (Daudi), and peripheral blood mononuclear cells (PBMC), but not in monocytes (Mono). From top to bottom at 100 nM AZ3965, the curves correspond to Daudi, CD4, CD8, PBMC, and Mono.

FIG. 4 contains the results of a human T cell proliferation assay with a small molecule MCT1 inhibitor. MCT1 inhibition leads to inhibition of T cell proliferation with an $IC_{50}$ of 0.54 nM.

FIG. 5 contains the results of a human mixed lymphocyte reaction (MLR) assay with a small molecule MCT1 inhibitor. T cell proliferation in this MLR assay was inhibited with an $IC_{50}$ of 1.34 nM.

FIG. 6 shows the inhibition of T cell cytokine secretion in vitro following AZ3965 administration. T cells were CD3/CD28 activated for 5 days prior to drug administration. Red areas of the figure (higher expression) have been outlined in a black dotted line. All other areas are blue (lower expression). Intensity of shading also indicates expression. AZ3965 inhibits secretion of IFNγ, GM-CSF, TNFα, IL-10, and IL-6, but not IL-2.

FIG. 7A-J show the expression of various T cell surface markers on activated T cells following 4 days of treatment with 100 nM small molecule MCT1 inhibitor or no treatment, as compared with an unstained control. In each panel, the antibody non-staining control is the left most peak. In each panel, there is no significant difference in staining between the treated and untreated conditions. The untreated condition is the slightly taller curve for all panels except FIG. 7H, where the treated condition curve is slightly taller. The results shown here are for the following cell surface makers: CD25 (FIG. 7A); CD54 (FIG. 7B); CD69 (FIG. 7C); CD95 (FIG. 7D); CD98 (FIG. 7E); CD147 (FIG. 7F); CD154 (FIG. 7G); CD278 (FIG. 7H); CD279 (FIG. 7I); and HLA-DR, DP, DQ (FIG. 7J).

Figures 11A, 11B:
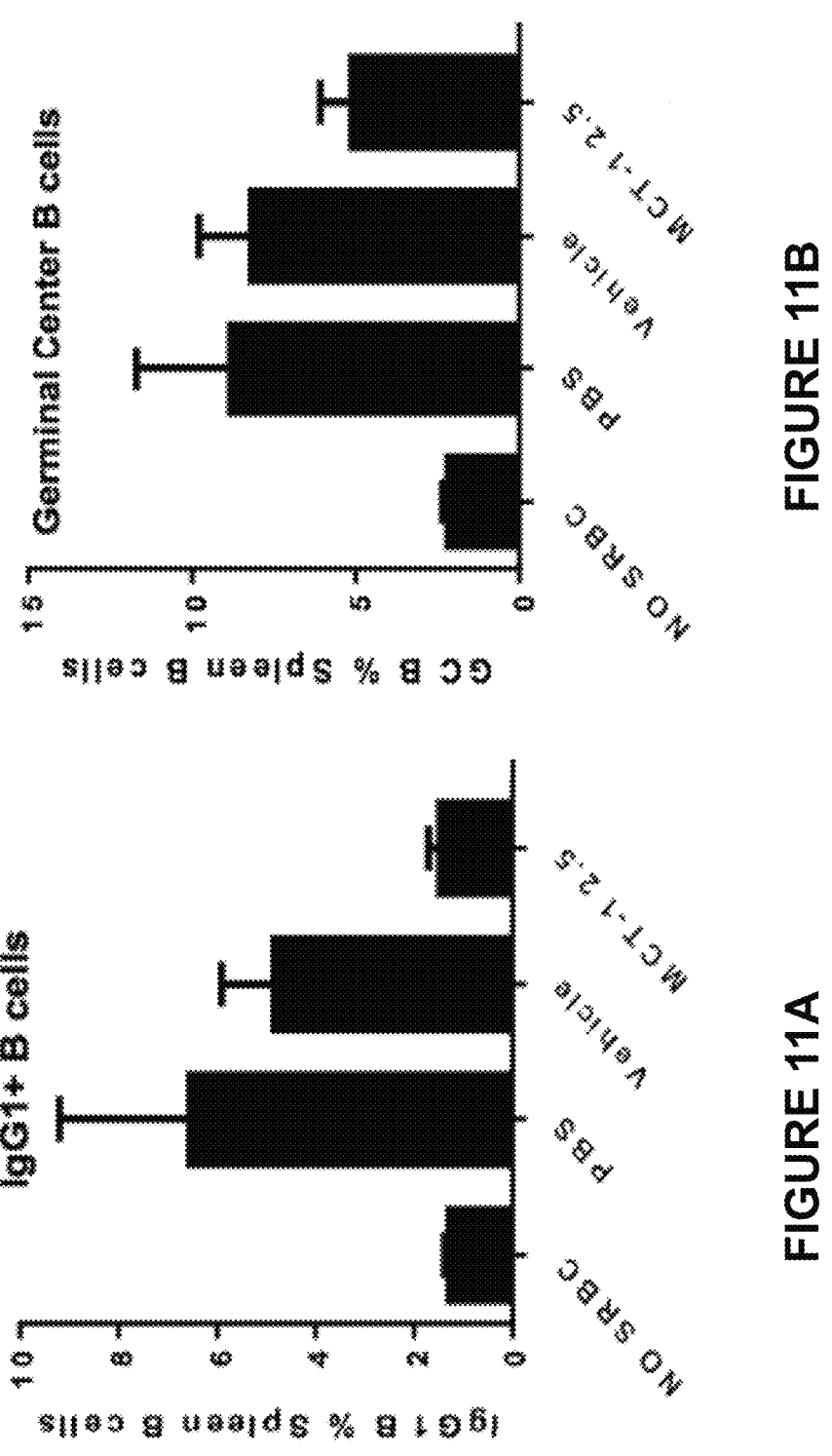

FIG. 11A-B show that AZ3965 administration reduces IgG1 B cell and germinal center B cell proportions in mice exposed to sheep RBC. FIG. 11A shows a decrease in IgG1 B cells with 2.5 mpk administration of AZ3965 and FIG. 11B shows a decrease in germinal center B cells with the same dosage.

Figure 12A:
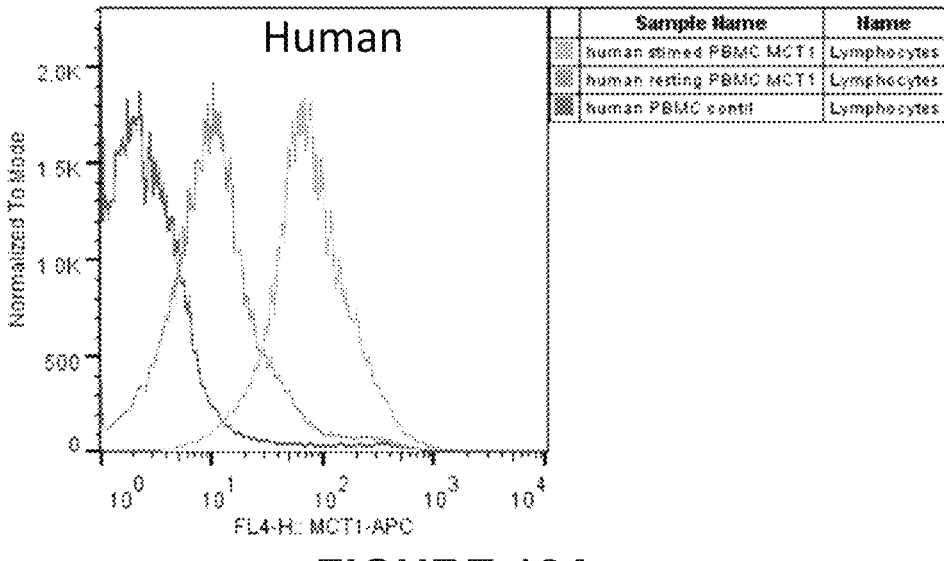
Figure 12B:
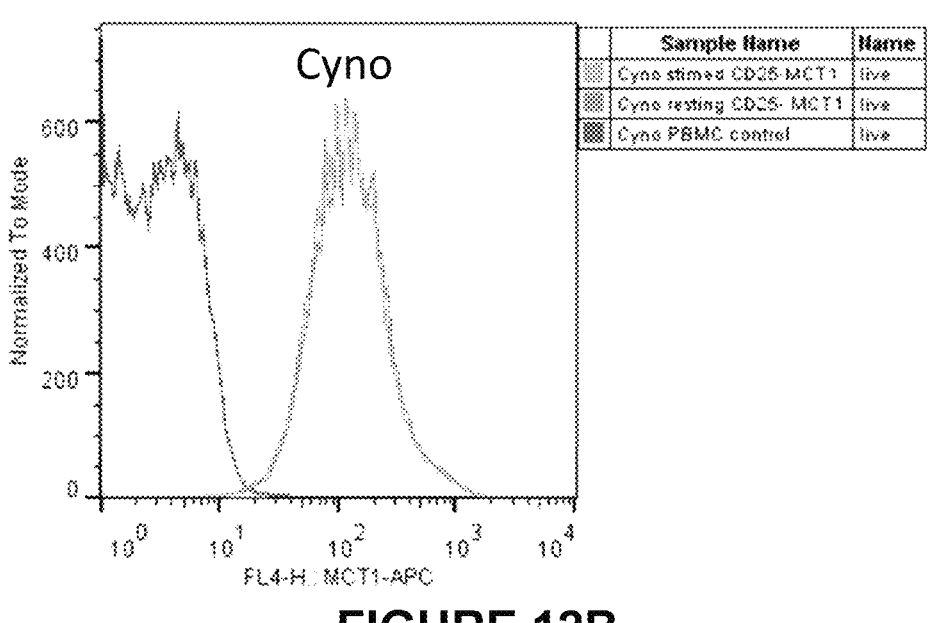
Figure 12C:
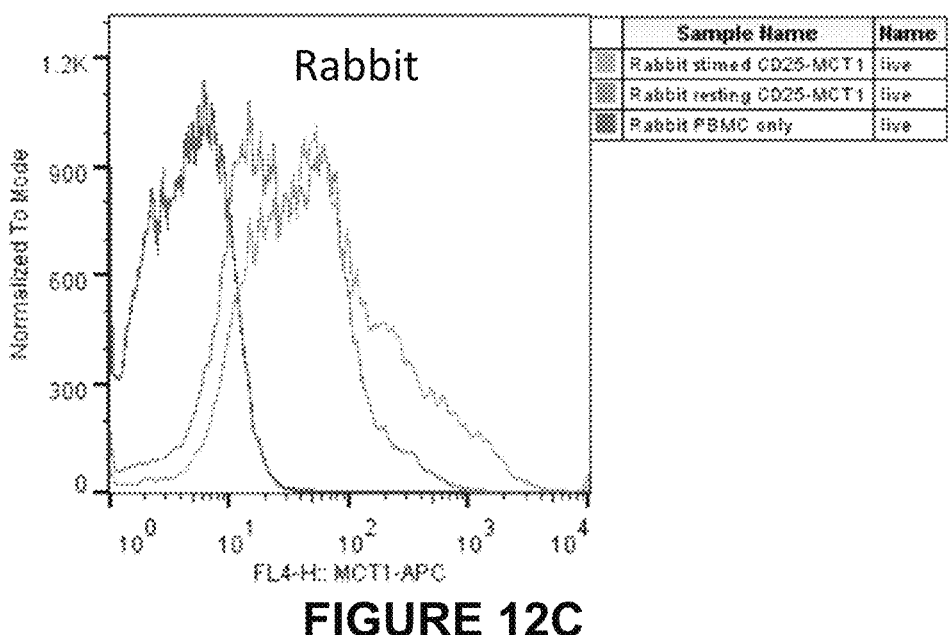
Figure 12D:
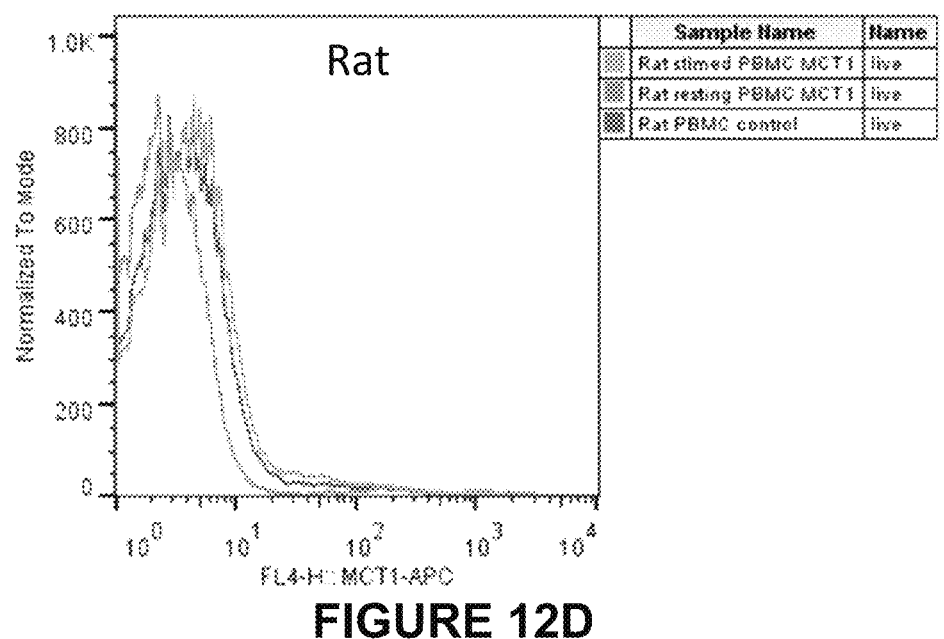

FIG. 12A-D show the cross-reactivity of MCT1 Ab1 as assessed via flow cytometry measurements of binding to MCT1 on the surface of different species' PBMCs. FIG. 12A shows that MCT1 Ab1 binds to MCT1 on the surface of human PBMCs, and that it binds to an even greater extent to stimulated cells. FIG. 12B shows that MCT1 Ab1 binds to cynomolgus MCT1. FIG. 12C shows that MCT1 Ab1 binds to rabbit MCT1. FIG. 12D shows that MCT1 Ab1 does not bind to rat MCT1.

Figure 13B:
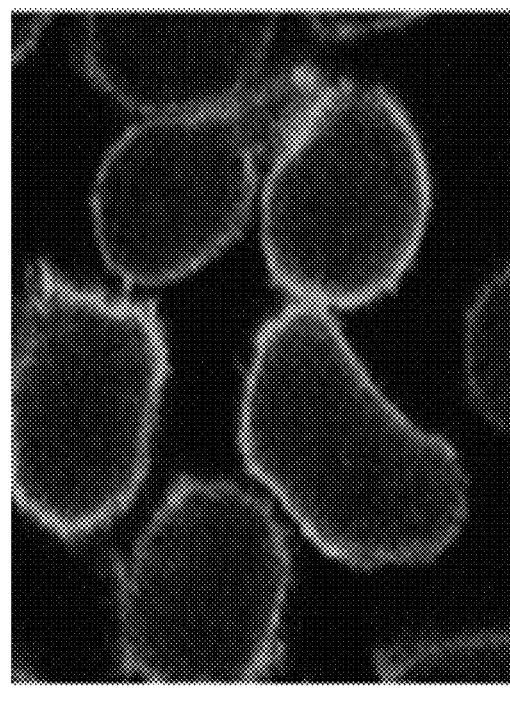
Figure 13A:
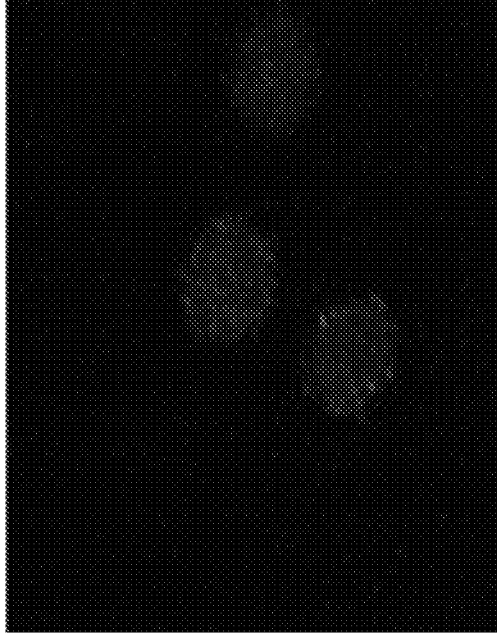

FIG. 13A-B show that MCT1 Ab1 binds to activated T cells. MCT1 Ab1 does not stain naïve cells (FIG. 13A), but stains the surface of CD3/CD28 activated cells on day 3

(FIG. 13B). The only staining in FIG. 13A corresponds to nucleus staining, confirming the presence of the naïve T cells.

Figure 14:
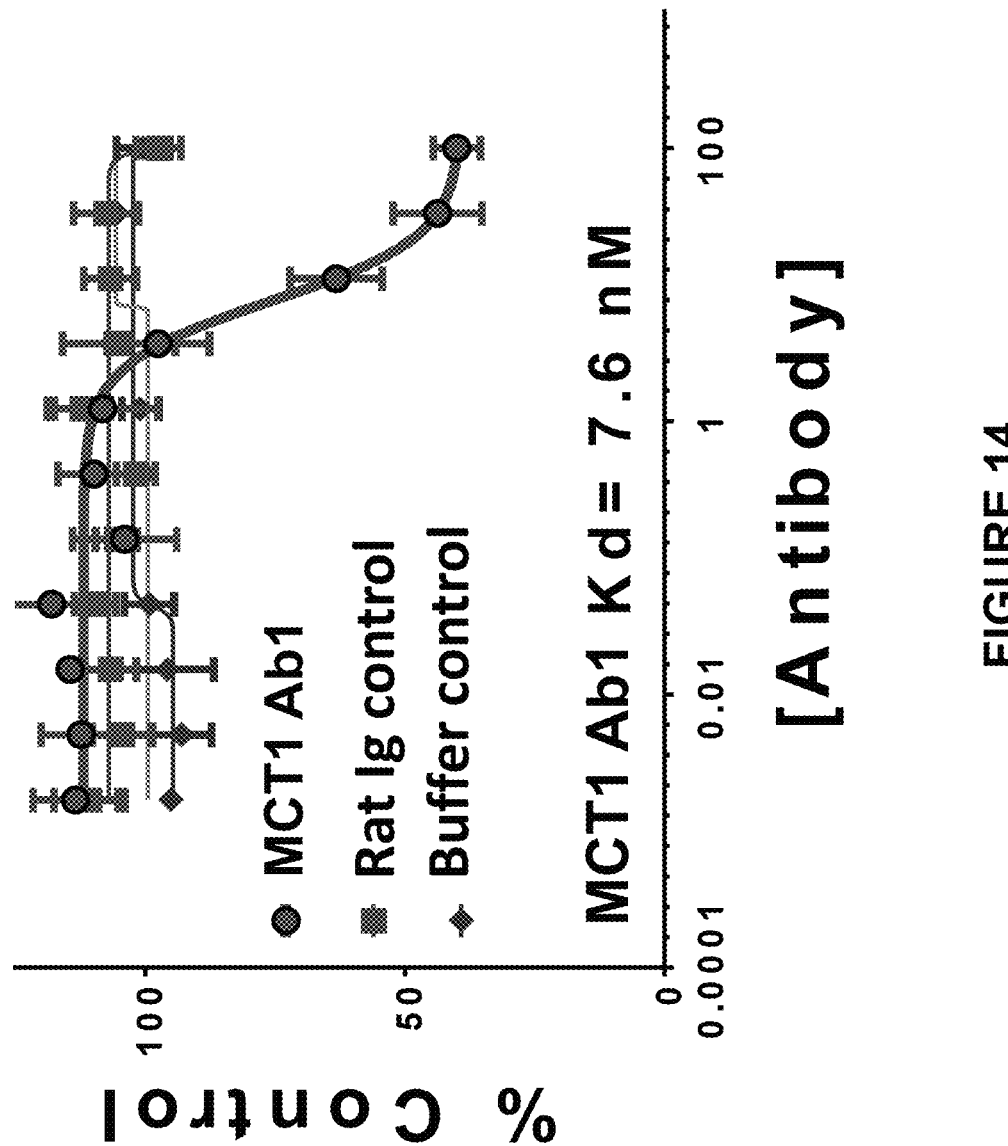

FIG. 14 shows that MCT1 Ab1 inhibits MCT1 transport of lactate in activated T cells in vitro. The rat Ig control and buffer control curves show no change compared to control, while MCT1 Ab1 resulted in decreased lactate transport compared to the control with a Kd of 7.6 nM (bottom curve on the right hand side).

Figure 15:
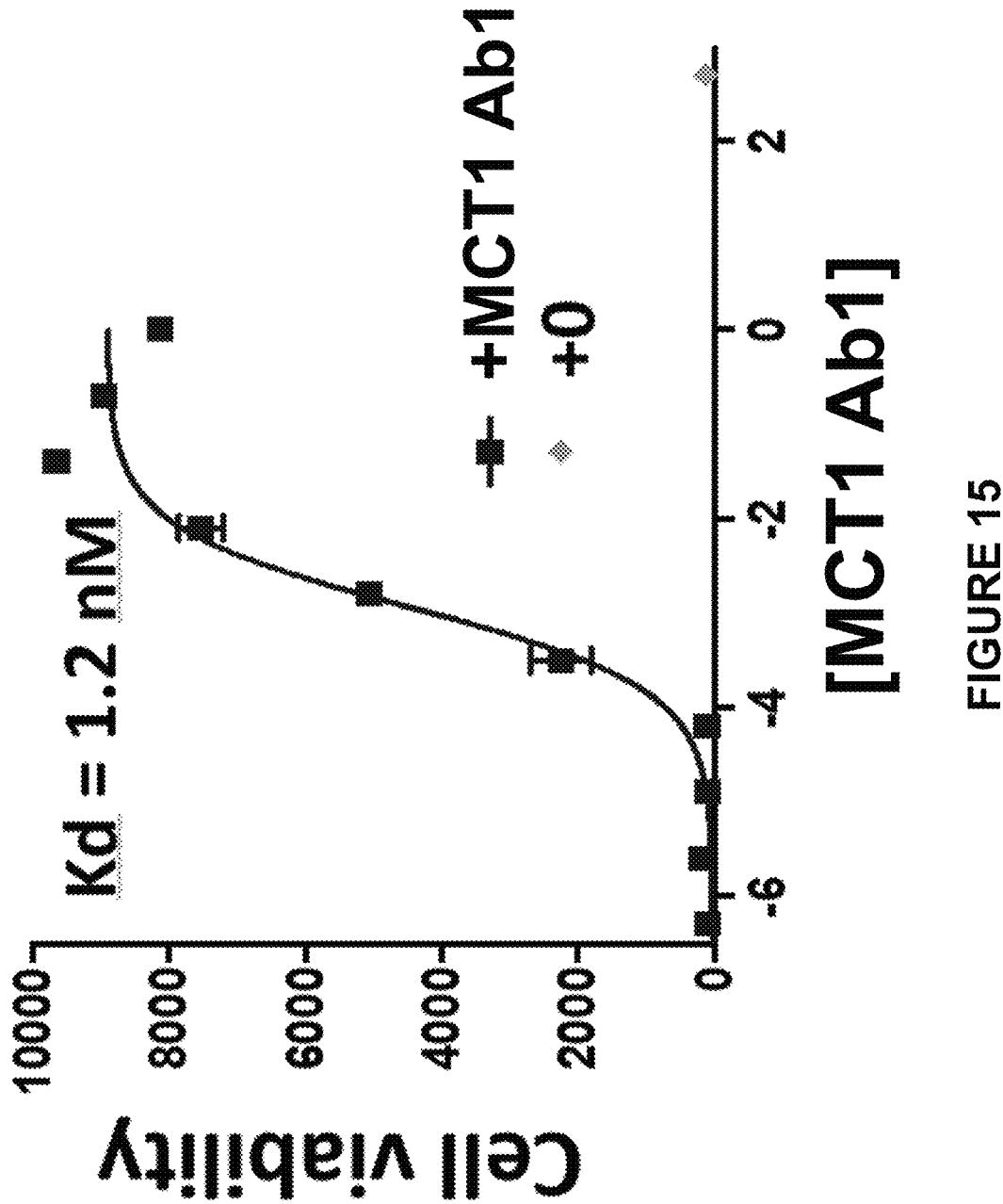

FIG. 15 shows that MCT1 Ab1 inhibits transport of bromopyruvate toxin as measured by MCT1 Ab1 protection from cell death using ATPlite (Kd=1.2 nM).

Figure 16:
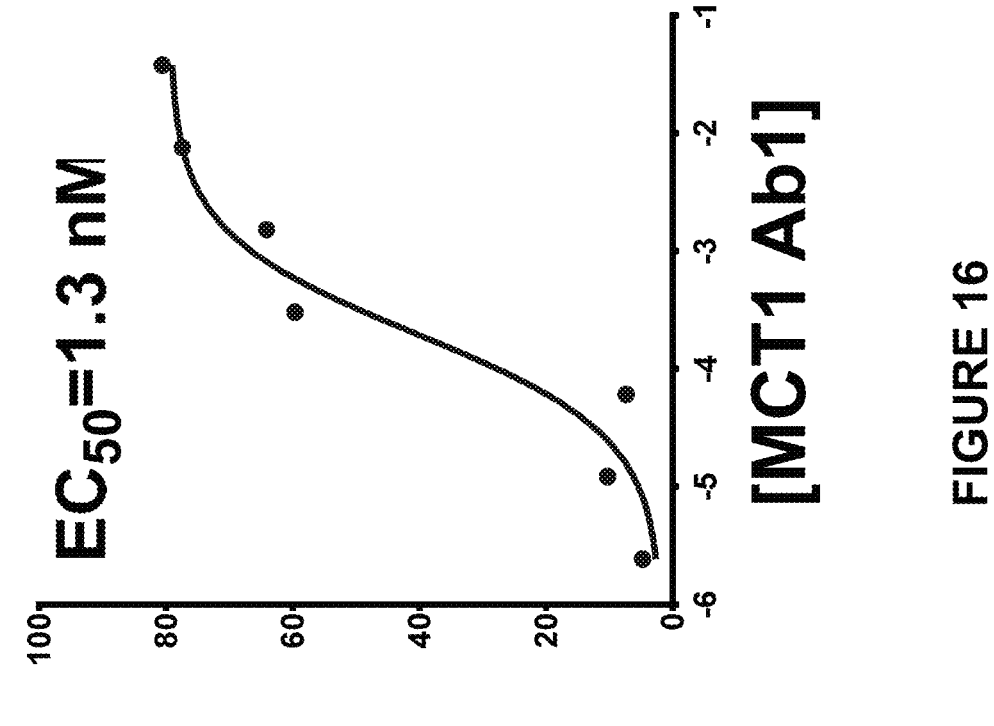

FIG. 16 contains the results of a T cell proliferation assay, in which MCT1 Ab1 inhibited T cell proliferation with an $EC_{50}$ of 1.3 nM.

Figure 17:
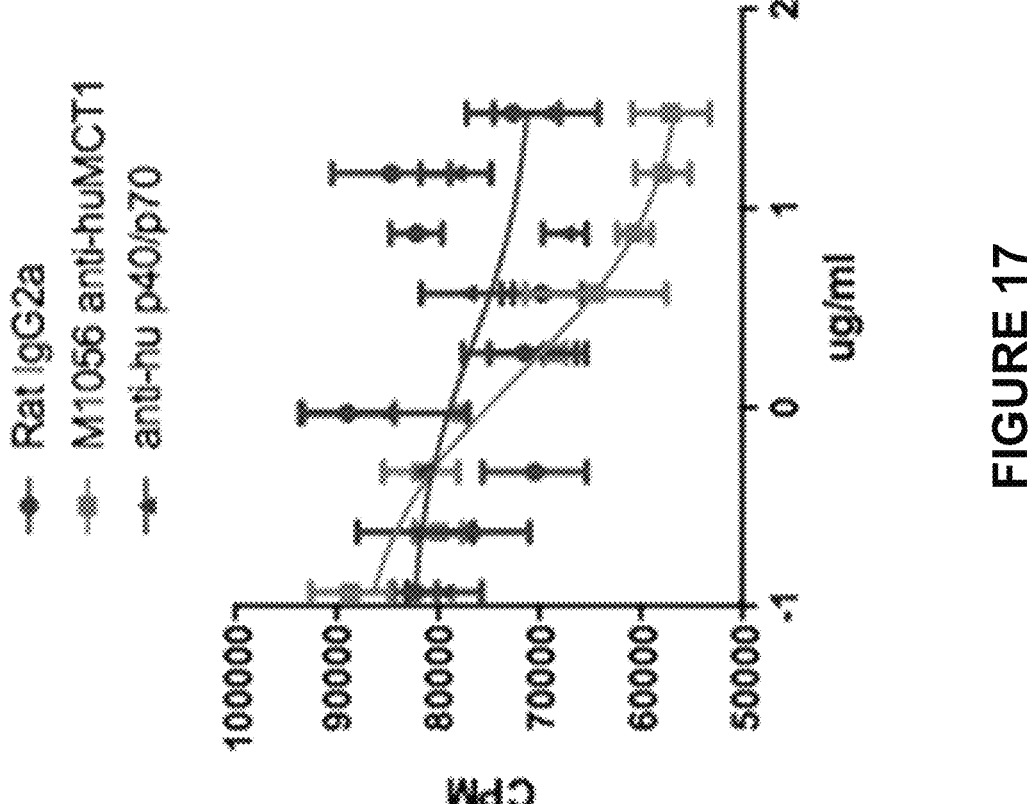

FIG. 17 shows that MCT1 Ab1 inhibited allogeneic activation in a dose dependent fashion in a human mixed lymphocyte reaction.

Figure 18A:
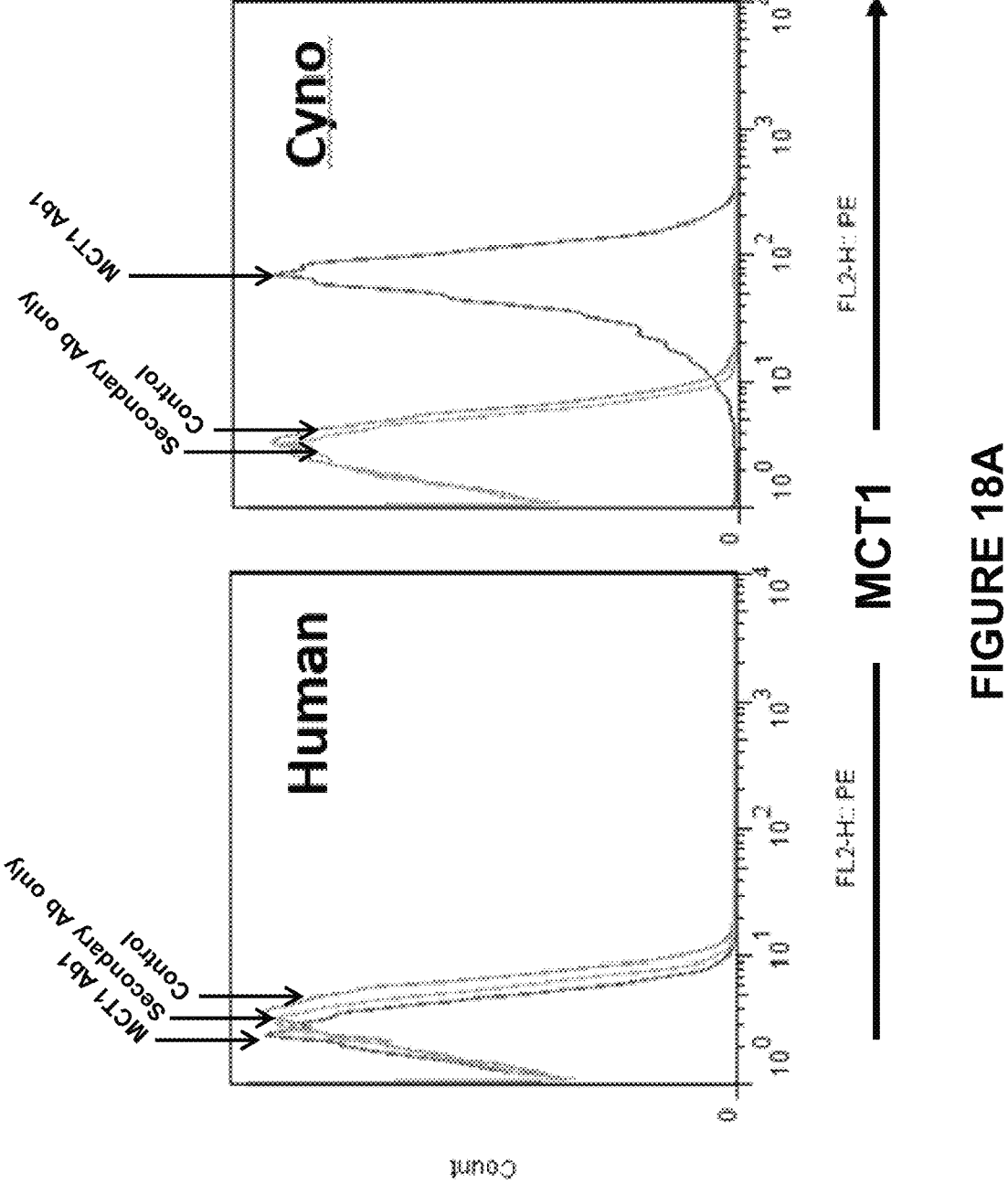
Figure 18B:
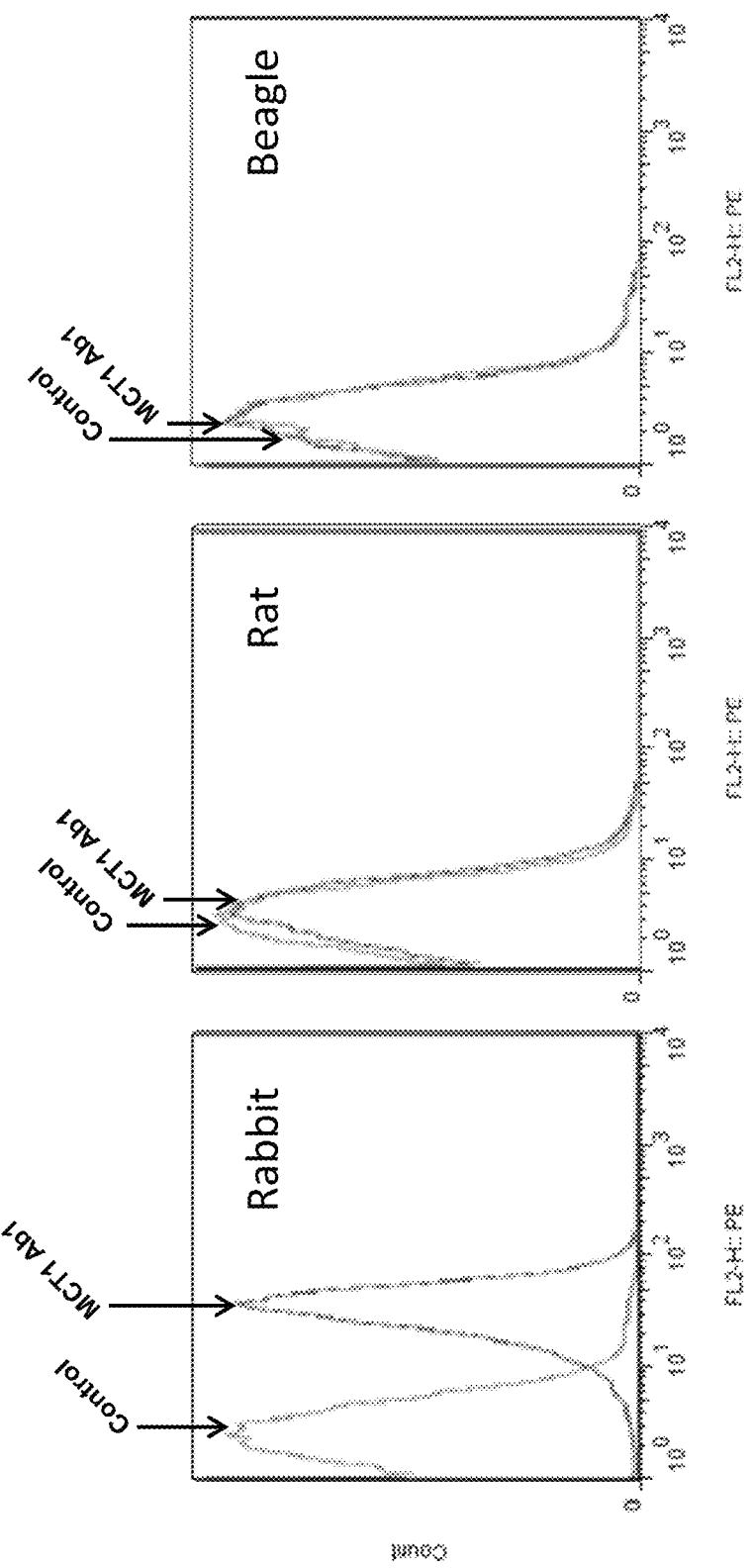

FIG. 18A-B show MCT1 expression on the surface of RBCs from five different species. In FIG. 18A, MCT1 Ab1 staining of purified cynomolgus RBCs (right) shows expression of MCT1 on the plasma membrane, in contrast to purified human RBCs (20 donors, left) which lack expression. In the left panel, the secondary Ab only condition, the control condition, and the MCT1 Ab1 stained condition all show no staining of MCT1. In FIG. 18B, staining shows MCT1 expression on the surface of rabbit RBCs (left), but none on the surface of rat (middle) or beagle (right) RBCs.

Figure 19:
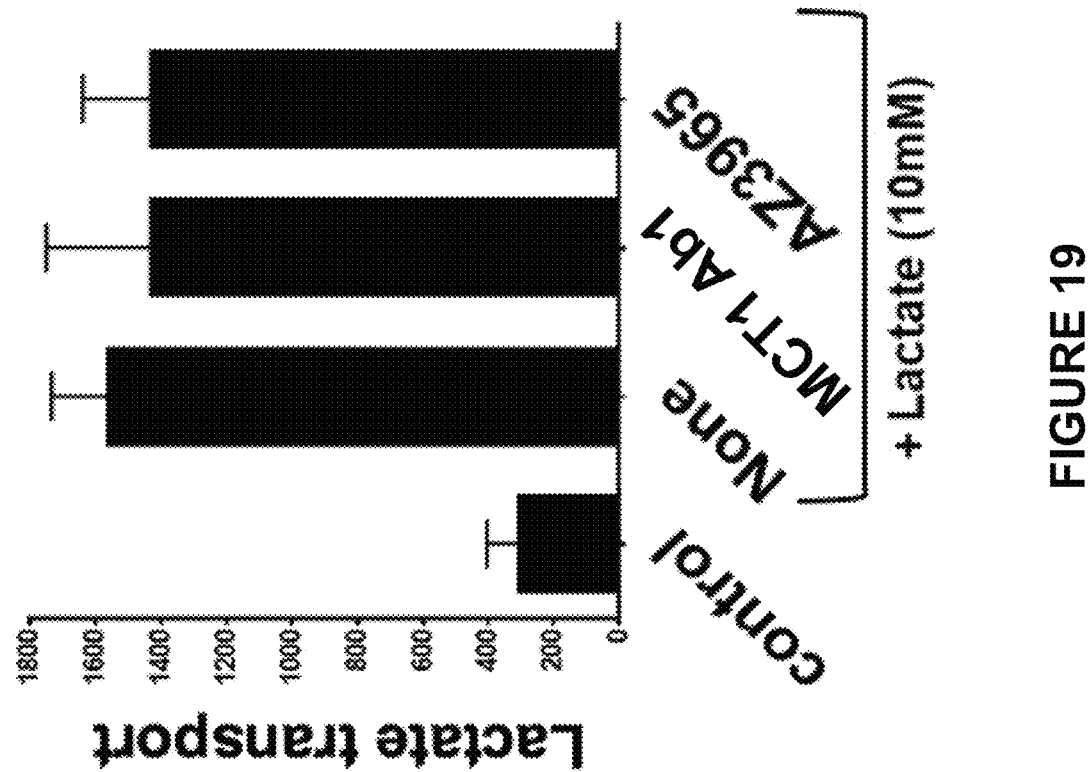

FIG. 19 shows that human RBCs do not require MCT1 for lactate transport. Neither MCT1 Ab1 nor AZ3965 inhibition of MCT1 blocked lactate transport in purified human RBCs using FLIPR based transport assays (REF. 1, 2). None=no inhibitor.

Figure 20:
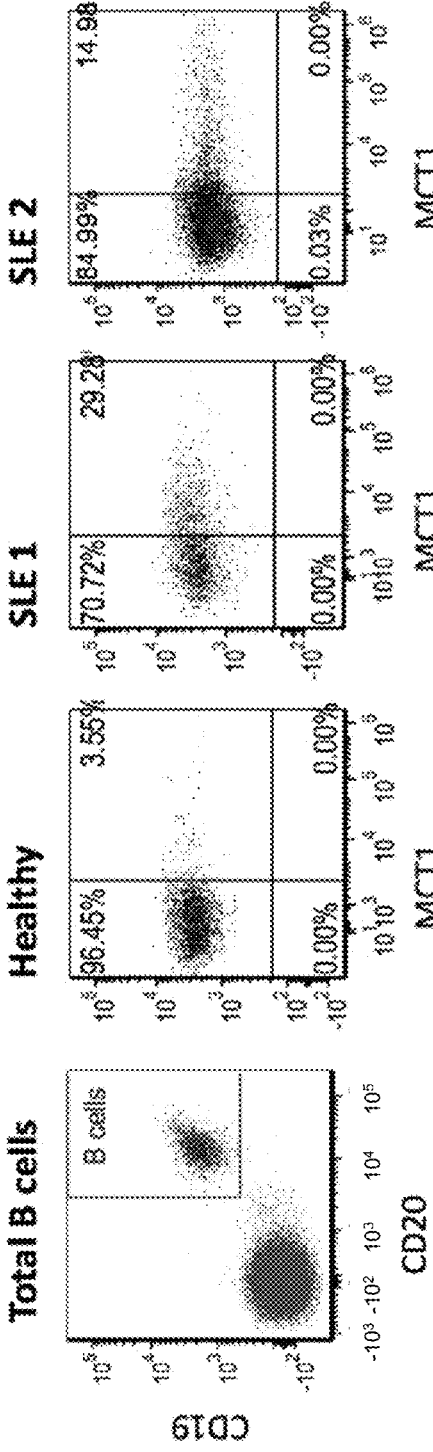

FIG. 20 contains the results of flow cytometry analysis of lupus B cells. Exemplary MCT1 staining of B cell populations from one healthy and two lupus patients indicates significantly increased MCT1 staining for the lupus patients.

Figure 21:
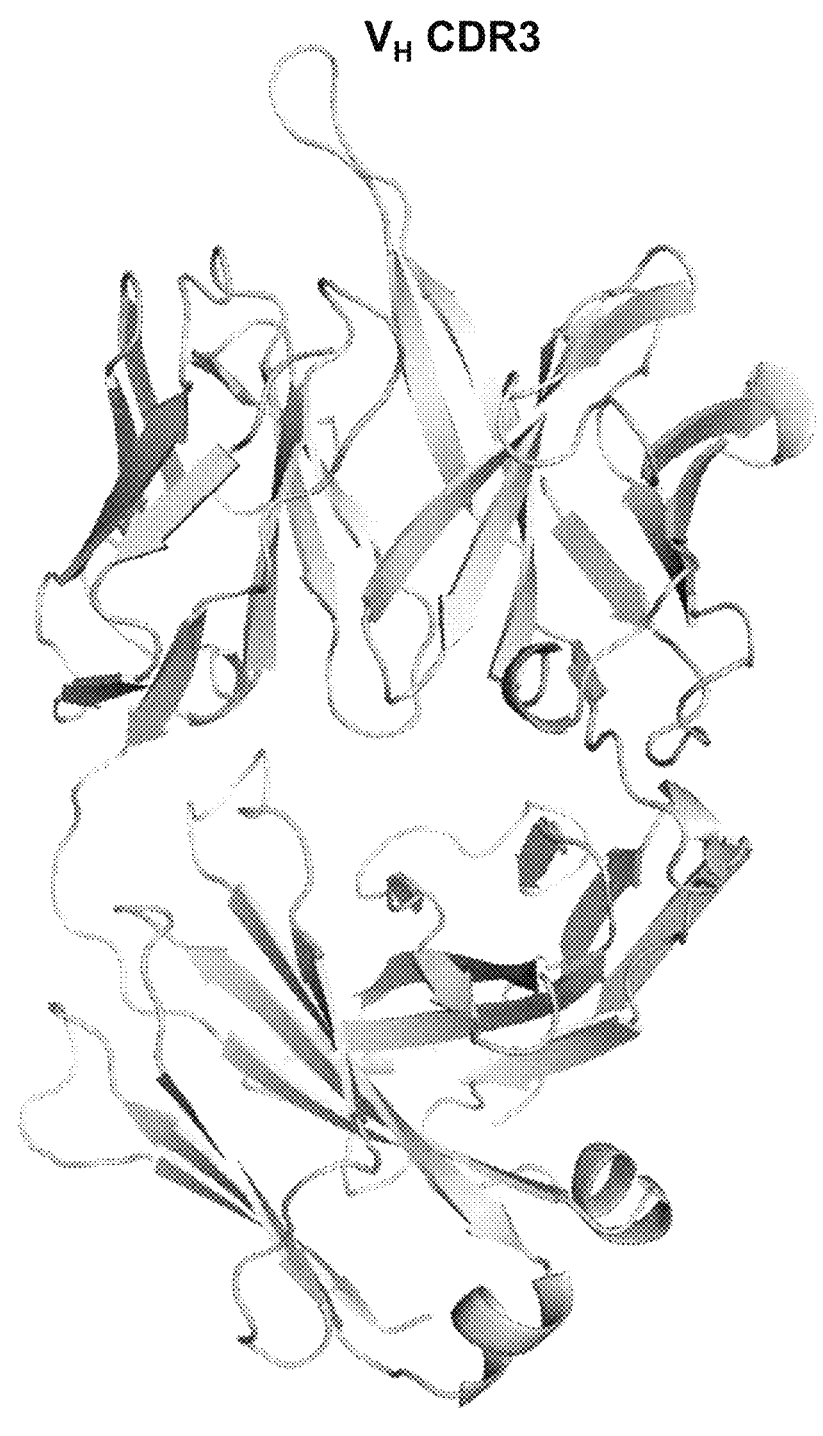

FIG. 21 contains a graphic rendering of the crystal structure of the MCT1 Ab1 Fab, deposited with this application as 43260_4200-MCT1_Ab1.pdb. In the image, the $V_H$ CDR3 can be seen to extend beyond the rest of the antigen binding surface.

FIG. 22 schematically shows that while MCT1 is involved in various functions there are redundant pathways which avoid toxicity outside the lymph system but that MCT1 has a sole transporter pathway in the lymphoid system (e.g., B, T cells).

FIG. 23 shows that cynomolgus red blood cells (RBCs) express high levels of MCT1.

FIG. 24 contains experiments indicating that cynos tolerate repeated dosing of an anti-MCT1 antibody (Ab1) at 50 mpk.

FIG. 25 contains PK data observed in cynos which suggest that there is good binding of the administered anti-MCT1 antibody (Ab1) and the results further indicate that at Ab1 dose rates ≥5 mpk that the RBC sink is saturated.

FIG. 26 contains experiments evaluating target tissues (muscle, testis and eye) in tamoxifen-inducible MCT1 knockout mouse.

FIG. 27 shows that the MCT1 knockout mice animals had smaller testes and a microscopic finding indicating some spermatid degeneration.

FIG. 28 shows that the MCT1 KO phenotype confers robust tamoxifen-inducible knockdown of MCT1 expression in various target tissues which were assayed, i.e., thymus, spleen, lymph nodes, tests and retina, relative to expression of a control housekeeper gene (HPRT).

FIG. 29 shows phenotypic changes in the testis observed in the knockout mice. As shown spermatid degeneration was observed in testis of all MCT1 knockout mice (Lack of late-stage spermatids and spermatocytes, decreased tubular cellularity, vacuolation, and cell debris).

FIG. 30 further compares the histology of testes in WT and MCT1 KO mice and shows increased spermatid degeneration in the knockout mice relative to the wild-type.

Figure 31:
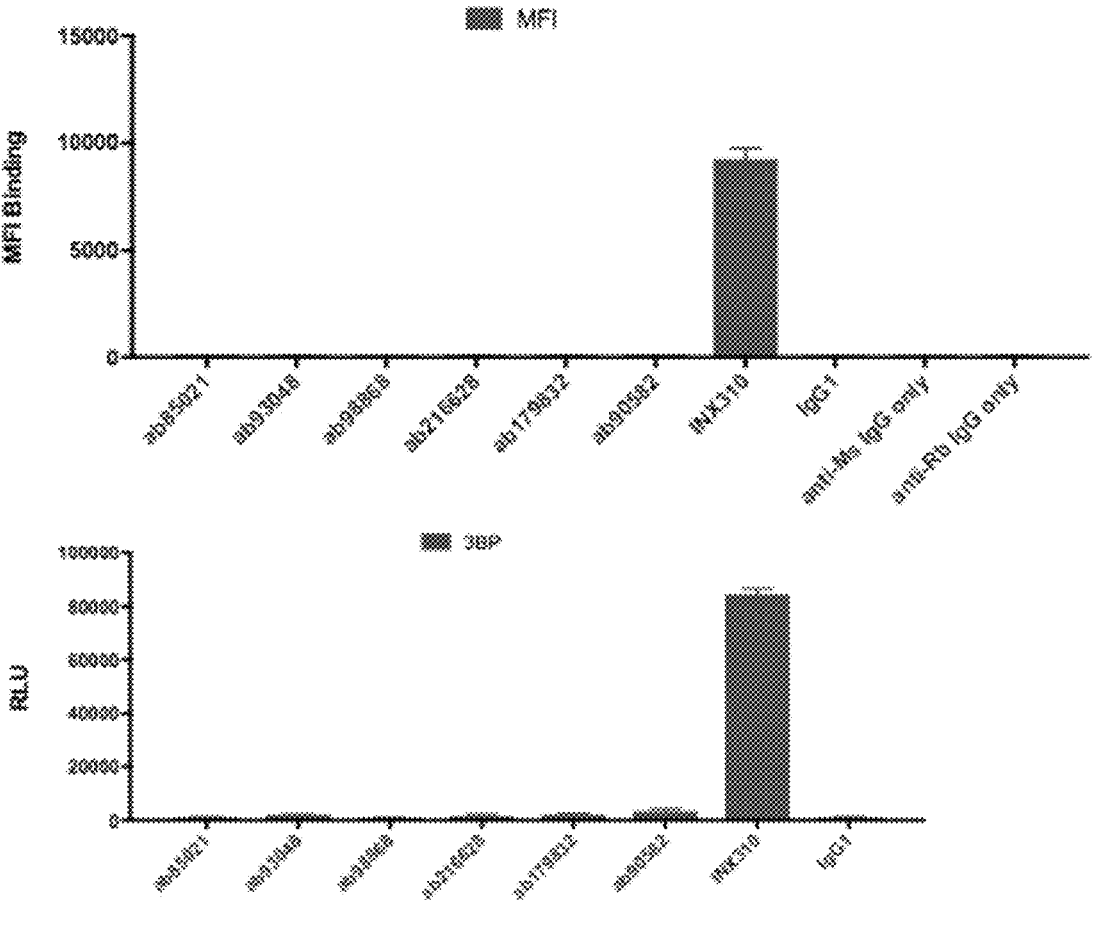

FIG. 31 summarizes binding and functional results comparing different commercially available anti-MCT1 antibodies. The Figure contains MFI (TOP, flow cytometry, cell binding of live cells) and Bromopyruvate functional assay results (Bottom, RLU) using all anti-MCT1 antibodies (Mabs and Polyclonal) sold by Abcam. (The catalogue numbers are listed in the figure).

FIG. 32 contains experiments results which detected the antagonist activity of different anti-MCT1 antibodies disclosed herein, i.e., INX420, INX444, INX356, INX352, and INX453 based on their relative ability to block MCT1 transporter activity in a bromopyruvate assay.

FIG. 33 contains an alignment of the variable heavy regions of different anti-MCT1 antibodies disclosed herein, i.e., INX420, INX444, INX356, INX352 and INX453.

FIG. 34 contains an alignment of the variable light regions of different anti-MCT1 antibodies disclosed herein, i.e., INX420, INX444, INX356, INX352 and INX453.

Figures 35A, 35B:
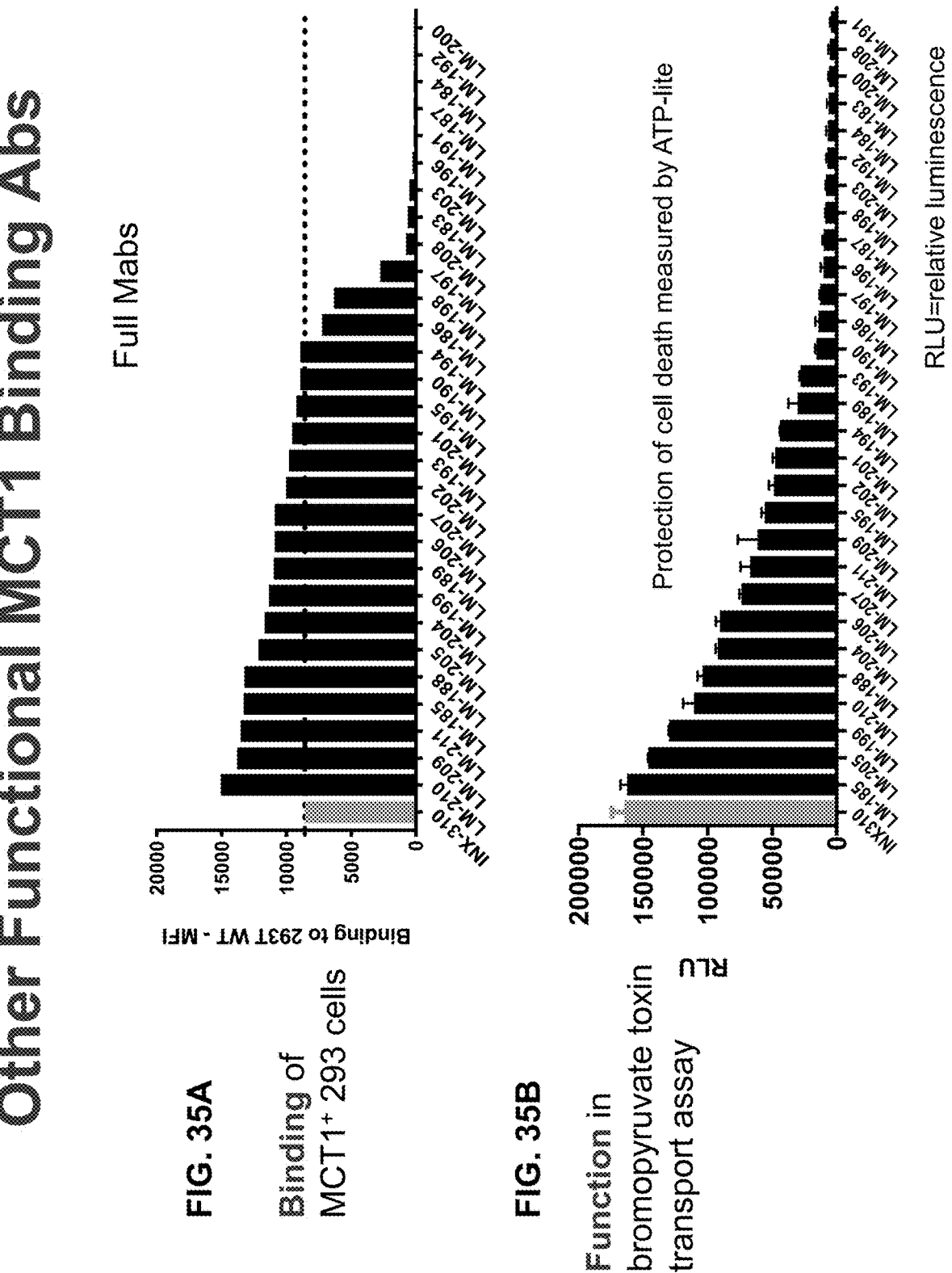
Figures 37A, 37B, 37C, 37D:
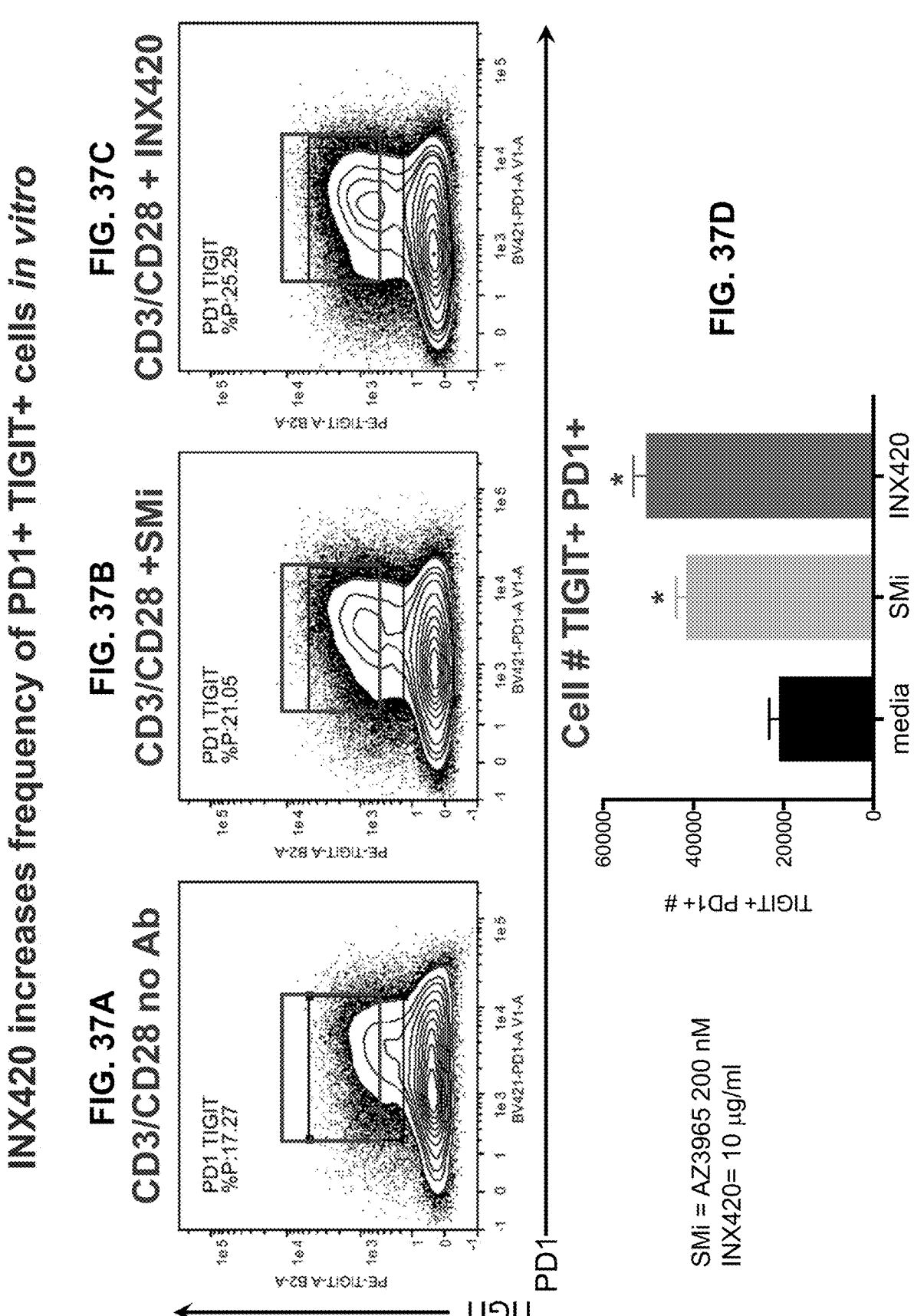

FIGS. 35A and B respectively show the binding of anti-MCT1 disclosed herein to MCT1+ 293 cells and their relative functionality in bromopyruvate toxin transport assays.

FIG. 36A-D contains experimental data which compare two anti-MCT1 antibodies disclosed herein, i.e. INX310 and INX420 with respect to their relative abilities to inhibit the proliferation of CD4+ and CD8+ T cells.

FIG. 37A-D contains experimental data which show that an anti-MCT1 antibody disclosed herein, i.e. INX420, increases the frequency of PD1+ TIGIT+ cells in vitro comparably to a small molecule MCT1 inhibitor compound.

FIG. 38A-B contains experimental data which show that of PD1+ TIGIT+Tr1 cells suppress the proliferation of PMBCs.

Figure 39:
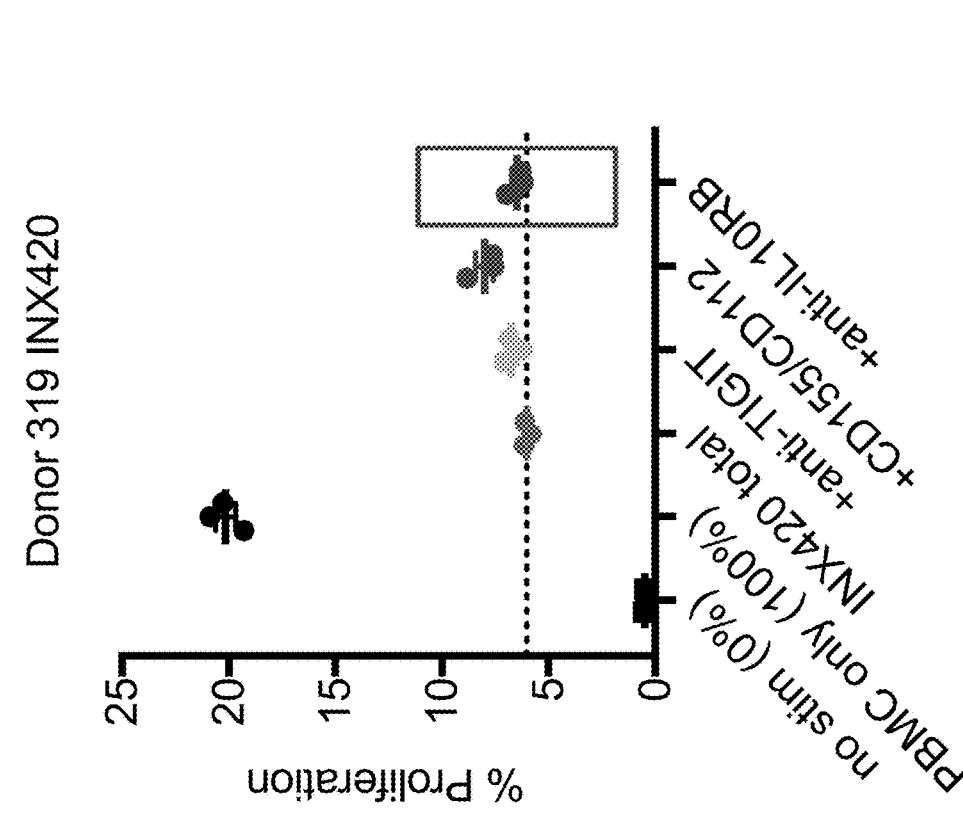

FIG. 39 contains experimental data which show that blocking IL-10 signaling with an IL-10 antagonist (anti-IL-10RB) does not impact the suppression of PMBC proliferation by an anti-MCT1 antibody disclosed herein, i.e. INX420.

Figures 40A, 40B, 40C, 40D:
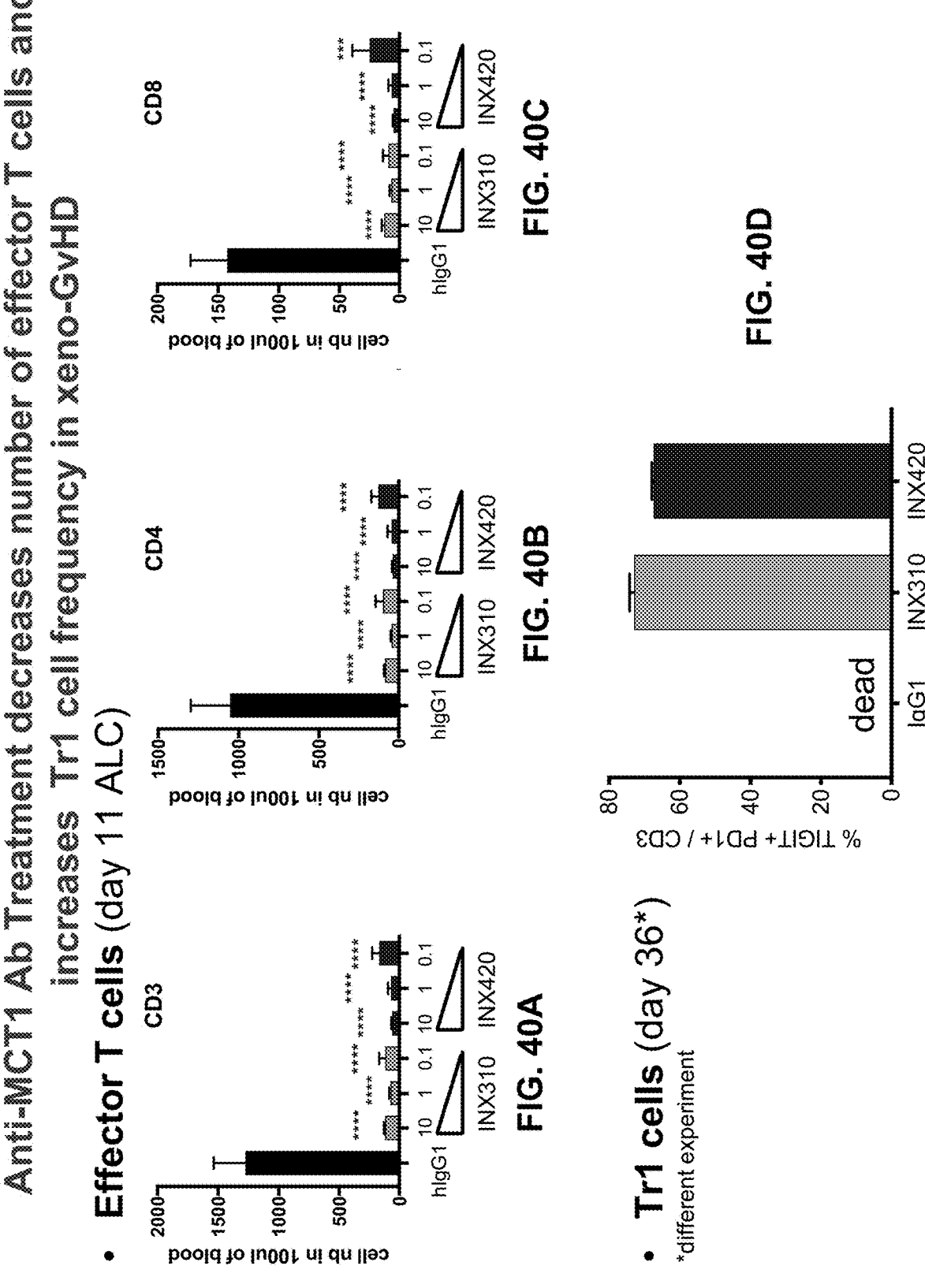

FIG. 40 contains experimental data which show treatment of xeno-GvHD animals with anti-MCT1 antibodies disclosed herein, i.e., INX420 and INX310, resulted in significant decreases in the number of CD3+, CD4+ and CD8+ effector T cells and increases in Tr1 cells compared to xeno-GvHD animals treated with a control antibody.

Figures 41A, 41B, 41C:
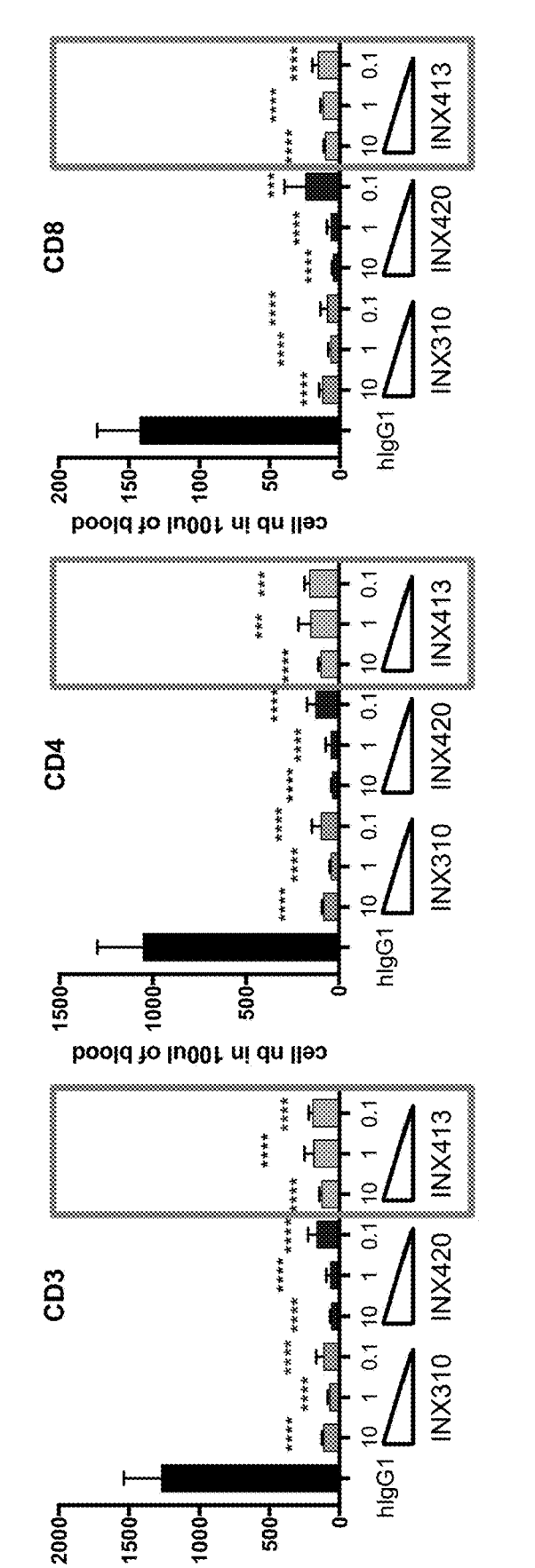

FIG. 41A-C contains experimental data which show treatment of xeno-GvHD animals with anti-MCT1 antibodies disclosed herein, i.e., INX420, INX413 and INX310, resulted in significant decreases in the number of CD3+, CD4+ and CD8+ effector T cells compared to xeno-GvHD animals treated with a control antibody.

FIG. 42: contains experiment results showing that the administration of anti-MCT1 antibodies, i.e., INX420 and INX310, in the xeno-GvHD animal model resulted in increased survival, long-term protection and tolerance induction compared to animals treated with control antibody.

FIG. 43 contains biomarker expression data showing that TIGIT and PD1 are expressed on a substantial (75%) of human T cells in the xeno-GvHD animal model and comprise putative biomarkers of Tr1 cells.

FIG. 44 contains biomarker expression data showing that TIGIT and PD1 comprise putative biomarkers of Tr1 cells and that putative Tr1 cells which express these markers suppress the proliferation of T effector cells.

Figures 45A, 45B, 45C:
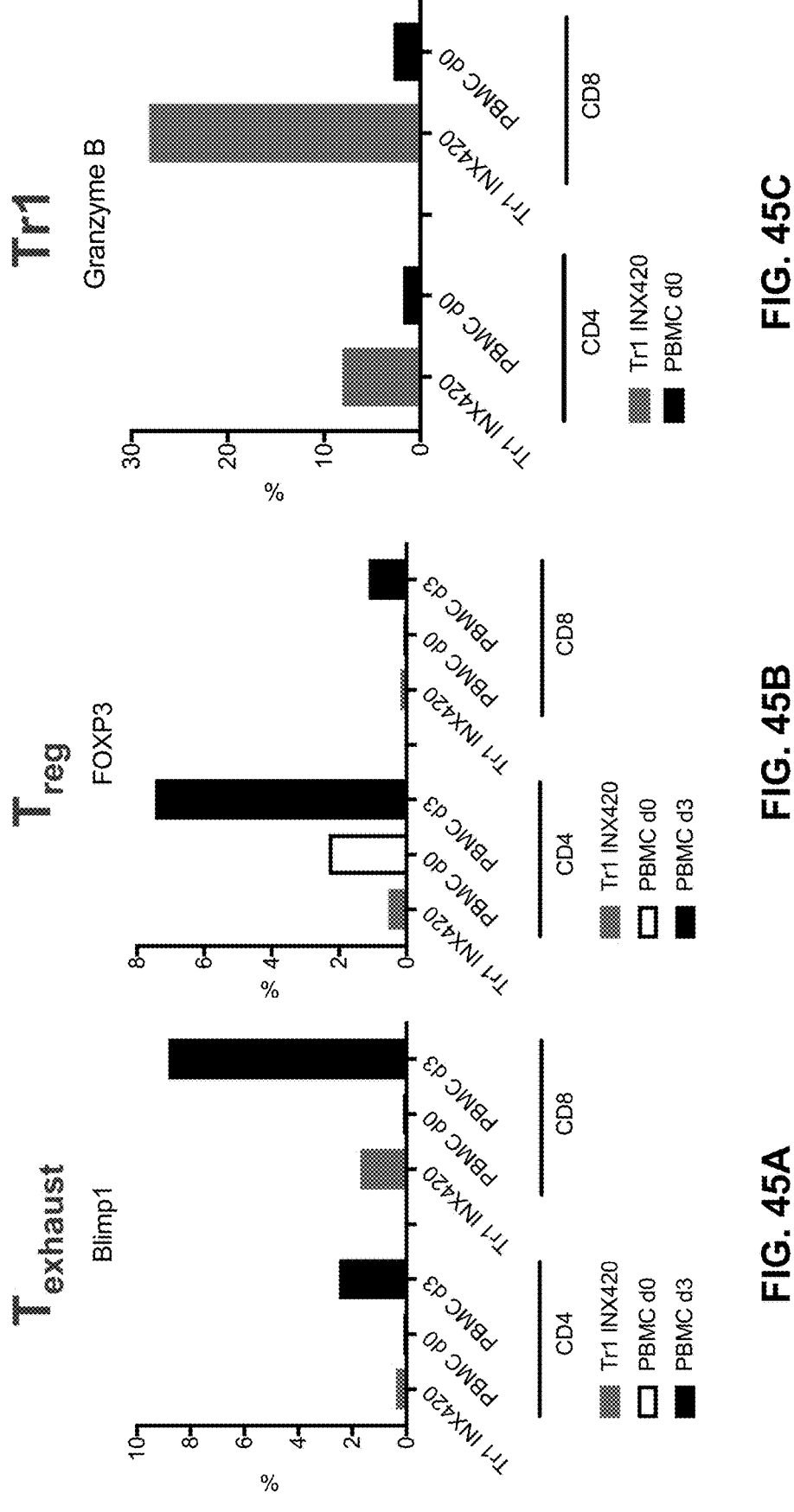

FIG. 45 contains biomarker expression data showing that Tr1 cells express high levels of Granzyme B and do not express FOXP3 or Blimp1.

Figures 46A, 46B, 46C:
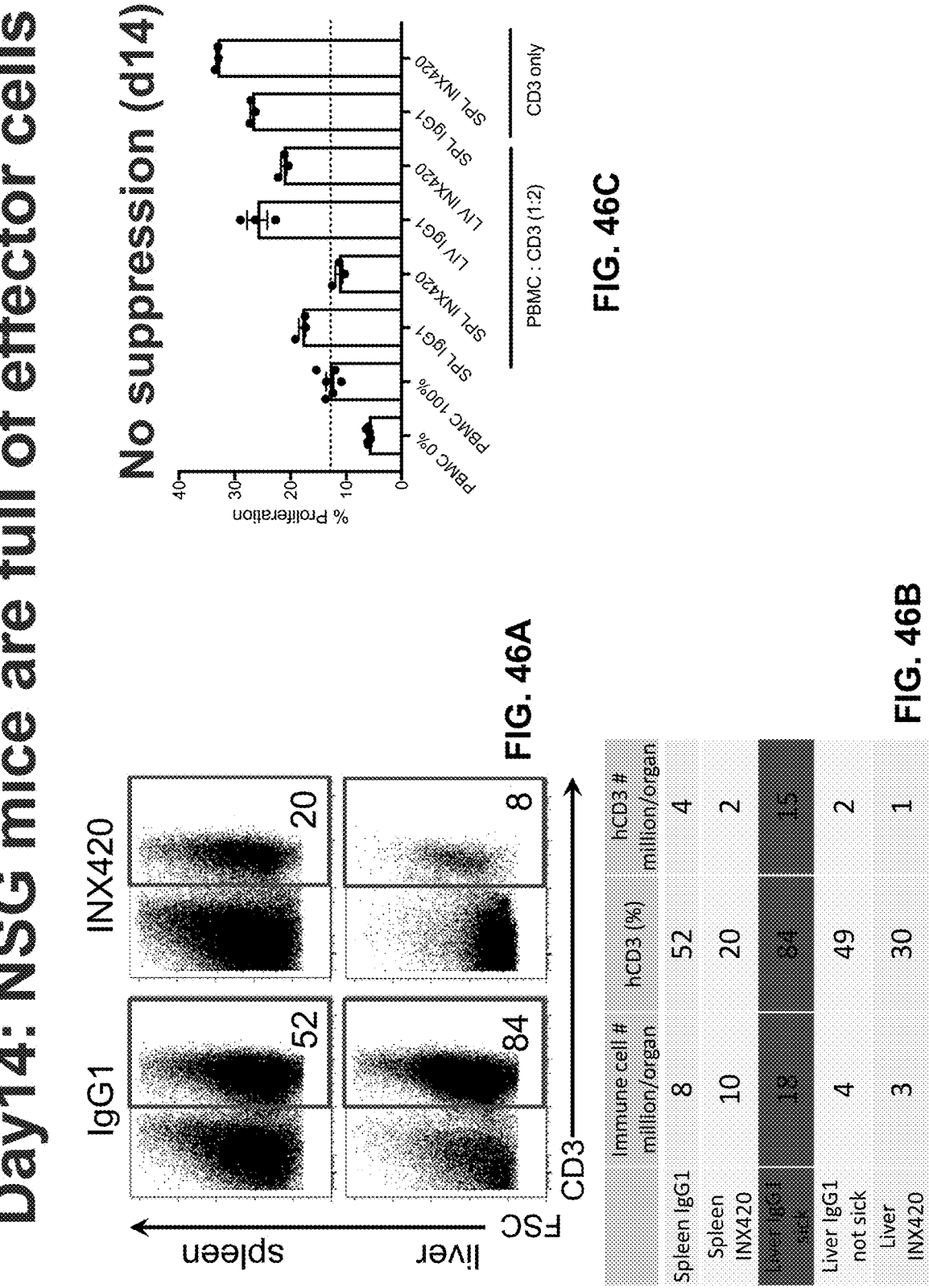

FIG. 46A-C contains experimental results showing that NSG mice treated with an anti-MCT1 antibody (INX420) comprise reduced numbers of hCD3+ T effector cells compared to animals treated with control antibody.

Figures 47A, 47B:
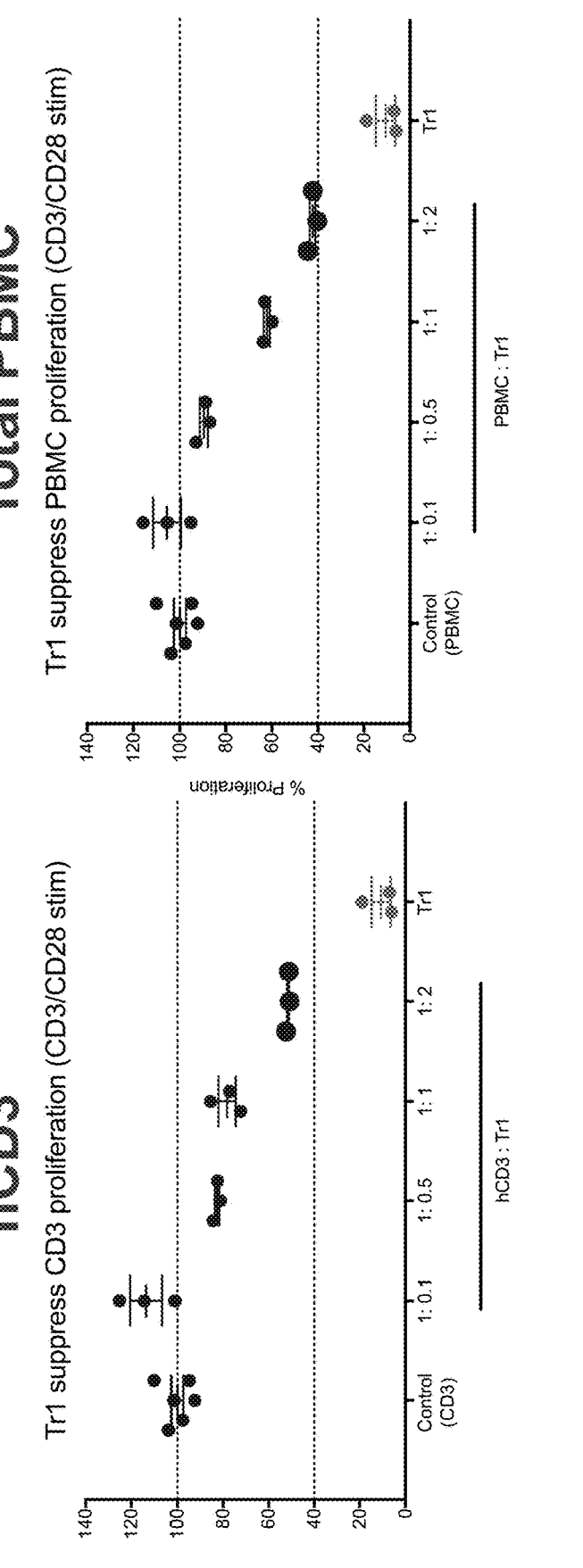

FIG. 47A-B contains experimental results showing that Tr1 cells suppress the proliferation of hCD3+ T effector cells and PMBCs after CD23/CD28 stimulation.

Figure 48:
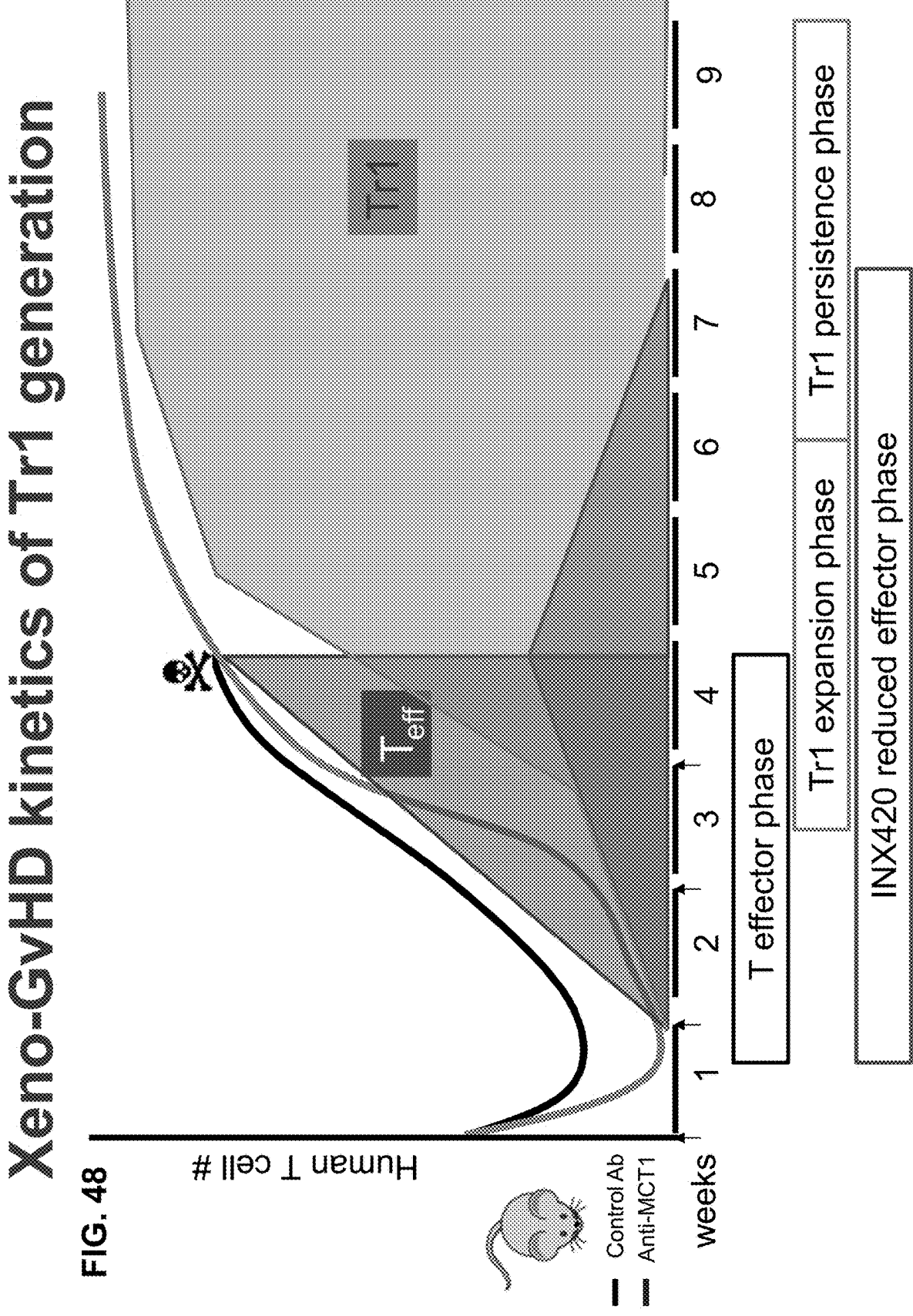

FIG. 48 schematically depicts the kinetics of Tr1 generation in the xeno-GvHD animal model and shows that treatment with an anti-MCT1 antibody suppresses proliferation in the effector phase.

FIG. 49A-B contains experimental data relating to ex vivo culture of Tr1 cells with various antibodies, cytokines and ligands. The observed results indicate that anti-TIGIT and PVR ligands did not enhance survival. By contrast treatment with IL-2, IL-17 and IL-15 increased ex vivo survival of Tr1 cells substantially (up to about 75% survival) in a dose dependent manner.

Figures 50A, 50B:
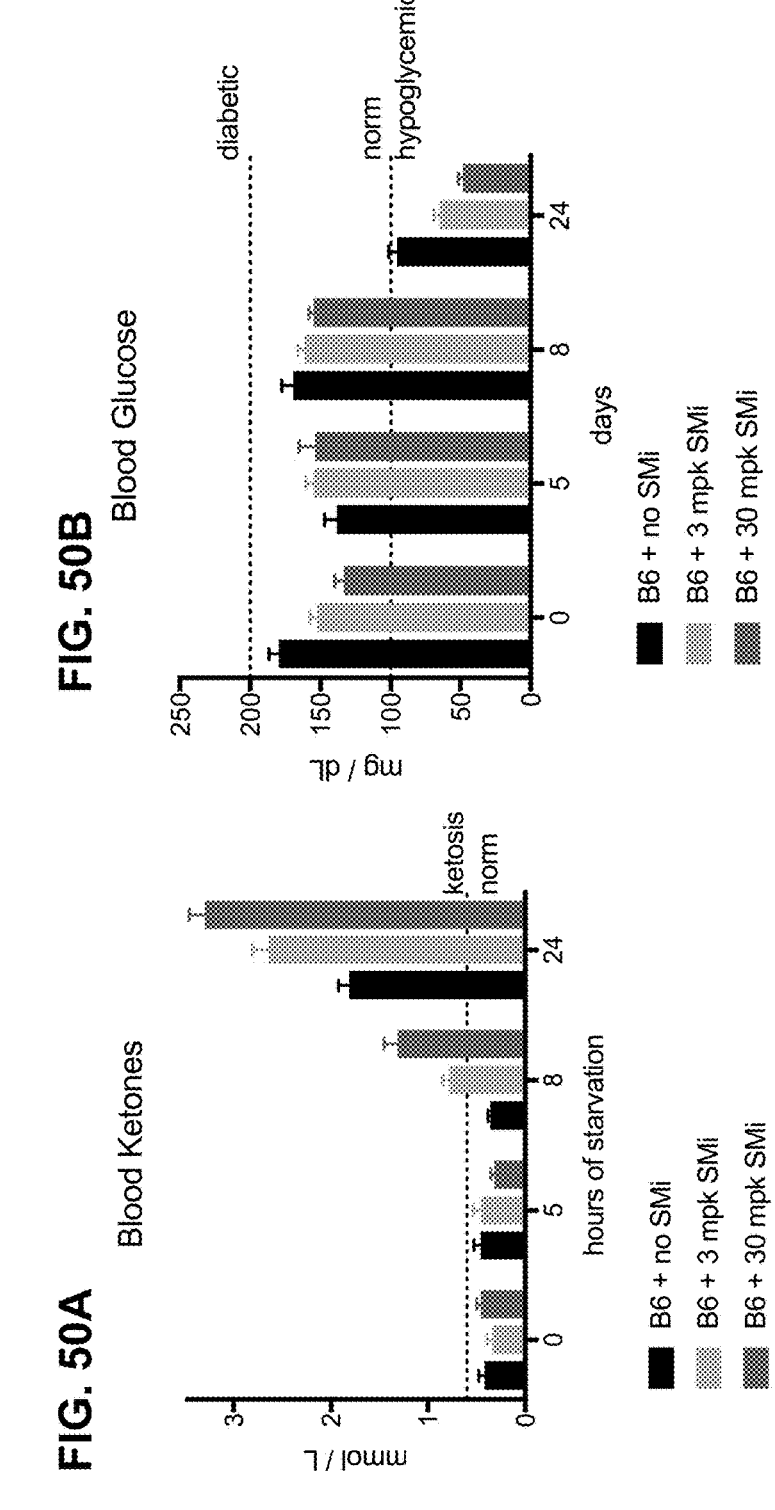

FIG. 50A-B contains experimental data showing the effects of the small molecule MCT1 inhibitor on ketosis after 8-24 hours of starvation conditions based on blood ketone and glucose levels.

FIG. 51A-B contains experimental data showing the small molecule MCT1 inhibitor does not trigger ketoacidosis after 24 hours of starvation and elicits only a minimal reduction in pH (about 0.05) compared to starvation in the absence of the small molecule MCT1 inhibitor.

FIG. 52 shows the residues of human MCT1 which constitute the predicted epitope bound by 4 exemplary anti-human MCT1 antibodies according to the invention as determined by alanine scanning. The results show that the epitope bound by all 4 antibodies comprises the same extracellular region of human MCT1 and substantially the same residues of human MCT1.

Figure 53:
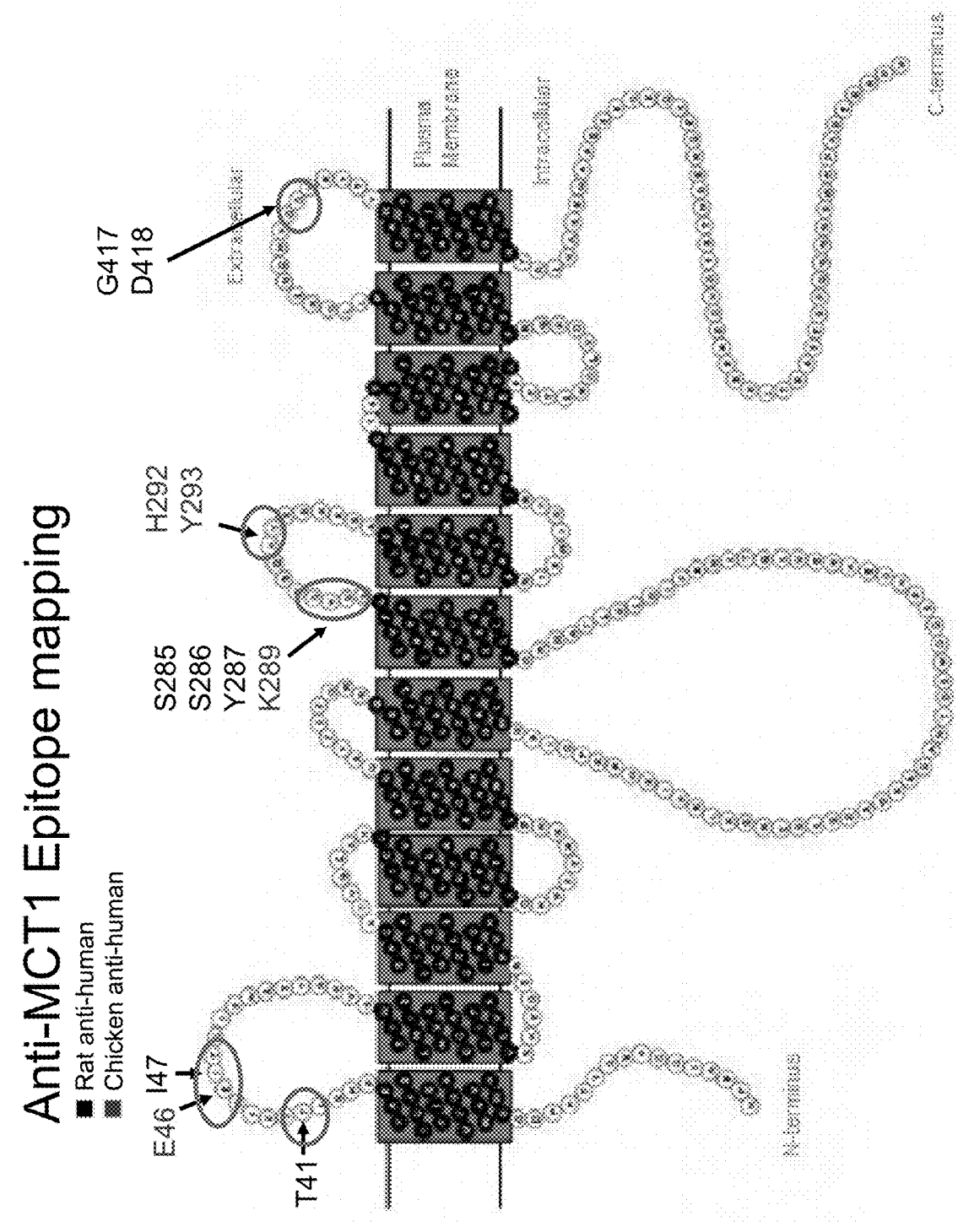

FIGS. 53 and 54 further map the specific residues of human MCT1 which constitute the predicted epitope bound by 4 anti-human MCT1 antibodies according to the invention as determined by alanine scanning. Again these results show that the epitope bound by all 4 antibodies comprises the same extracellular region of human MCT1 and substantially the same residues of human MCT1.

Figure 55:
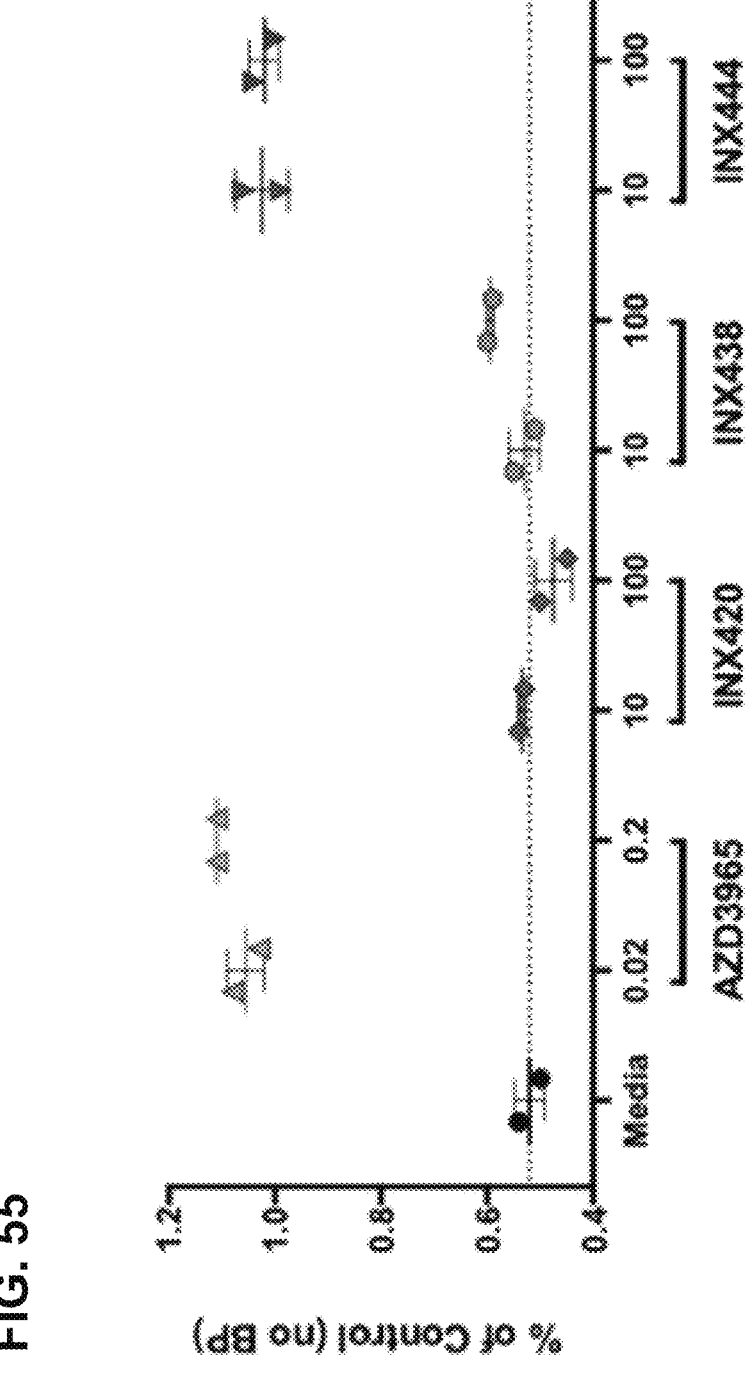

FIG. 55 contains experimental results which indicate an anti-human MCT1 antibody according to the invention which further binds mouse MCT1 protects mouse MCT1-expressing transfectants from the toxic effects of bromopyruvate.

DETAILED DESCRIPTION OF THE INVENTION

The present invention relates to antibodies and antigen-binding fragments thereof that bind to monocarboxylate transporter 1 ("MCT1"), nucleic acids encoding said anti-MCT1 antibodies and antigen-binding fragments thereof, compositions comprising said anti-MCT1 antibodies and antigen-binding fragments thereof, and methods of using said anti-MCT1 antibodies, antibody fragments, and compositions in diagnostics and therapy.

Antibody Target: MCT1

MCT1 is a multipass transmembrane protein responsible for the facilitated transport of critical metabolites, including products of glycolysis. The subject application provides novel anti-MCT1 antibodies, particularly anti-human MCT1 antibodies including those comprising the same CDRS as any of the antibodies identified in this application as Ab1-Ab83. Prior to the present invention, no anti-MCT1 antibodies or antibody fragments that block the function of MCT1 have been reported.

The binding of an anti-MCT1 antibody or antibody fragment to MCT1 according to the invention will reduce, suppress, diminish, or otherwise inhibit at least one of the functions of MCT1. As it pertains to immunity, this binding and inhibition of MCT1 may then have at least one suppressive effect on autoimmunity, e.g., activated T cells, B cells, and/or inflammatory cytokine expression. Importantly, MCT1 is the only immunologically relevant lactate transporter expressed on T and B cells. The anti-MCT1 antibodies of the invention particularly target activated T cells due to a shift to glycolysis during effector T cell activation, thus providing an innovative and powerful opportunity for controlling autoimmune, inflammatory, and allergic conditions. As demonstrated in the Examples, the anti-MCT1 antibodies of the invention provide selective inhibition of lymphocyte metabolism and an attractive safety profile, especially in light of the data on MCT1-deficiency in humans. The blocking of lymphocyte glycolysis in inflammatory disease models, e.g., models of lupus in disease-prone mice, prevents IFNγ production in these models and provides further proof that the inventive antibodies that block lymphocyte glycolysis in a safe and effective way have powerful potential as immunoregulatory drugs.

Anti-MCT1 antibodies that block or inhibit the functions of MCT1 may be used to reduce autoimmunity. In particular, these antibodies may be used to suppress undesired human immune responses such as autoimmune, allergic, lupus, GVHD, sepsis or undesirable inflammatory immune responses.

MCT1 expression has also been implicated in cancers, due to the particular energy requirements and dependence on glycolysis of tumor cells. The inventive antibodies and antigen-binding fragments thereof are therefore suitable for cancer treatment. Overexpression of MCT1 in beta cells is also an underlying cause of exercise-induced hyperinsulinism (EIHI), such that the antibodies of the invention may also be applied to the treatment of EIHI.

Notably, while small molecule inhibitors of MCT proteins have been associated with toxicities in the retina, heart and testes in preclinical models, humans deficient in MCT1 have no toxicities in any of these organs (REF. 49 and Examples), which supports the strong safety profile of MCT1-specific antibodies of the invention. In addition, MCT1-deficient individuals have been shown to be healthy, and these conclusions are supported by the data within the examples, showing that MCT1 is not involved in human RBC lactate transport.

Human MCT1 has the following amino acid sequence (SEQ ID NO:1), deposited in the UniProt database with identifier P53985-1:

SEQ ID NO: 1

```
MPPAVGGPVGYTPPDGGWGWAVVIGAFISIGFSYAFPKSITVFFKEIE

GIFHATTSEVSWISSIMLAVMYGGGPISSILVNKYGSRIVMIVGGCLS

GCGLIAASFCNTVQQLYVCIGVIGGLGLAFNLNPALTMIGKYFYKRRP

LANGLAMAGSPVFLCTLAPLNQVFFGIFGWRGSFLILGGLLLNCCVAG

ALMRPIGPKPTKAGKDKSKASLEKAGKSGVKKDLHDANTDLIGRHPKQ

EKRSVFQTINQFLDLTLFTHRGFLLYLSGNVIMFFGLFAPLVFLSSYG

KSQHYSSEKSAFLLSILAFVDMVARPSMGLVANTKPIRPRIQYFFAAS

VVANGVCHMLAPLSTTYVGFCVYAGFFGFAFGWLSSV$_L$FETLMDLVGP

QRFSSAVGLVTIVECCPV$_L$LGPPLLGRLNDMYGDYKYTYWACGVV$_L$II

SGIYLFIGMGINYRLLAKEQKANEQKKESKEEETSIDVAGKPNEVTKA

AESPDQKDTDGGPKEEESPV
```

Binding to MCT1 and Inhibition of MCT1 Function

An anti-MCT1 antibody of the invention can have any suitable affinity and/or avidity for MCT1. Affinity refers to the strength of binding of an anti-MCT1 antibody or other antigen-binding protein to an epitope or antigenic determinant. Typically, affinity is measured in terms of a dissociation constant $K_d$ defined as $[Ab] \times [Ag]/[Ab-Ag]$ where $[Ab-Ag]$ is the molar concentration of the antibody-antigen complex, $[Ab]$ is the molar concentration of the unbound antibody and $[Ag]$ is the molar concentration of the unbound antigen. The affinity constant $K_a$ is defined by $1/K_d$. Suitable methods for determining binding peptide specificity and affinity by competitive inhibition, equilibrium dialysis, and the like can be found in, e.g., Harlow, et al., Antibodies: A Laboratory Manual, Cold Spring Harbor Laboratory Press, Cold Spring Harbor, N.Y., 1988); Colligan et al., eds., *Current Protocols in Immunology*, Greene Publishing Assoc. and Wiley Interscience, N.Y., (1992, 1993), and Muller, *Meth. Enzymol.* 92:589-601 (1983).

Affinity can be determined by any of the methods described elsewhere herein or their known equivalents in the art. An example of one method that can be used to determine affinity is provided in Scatchard analysis of Munson & Pollard, *Anal. Biochem.* 107:220 (1980). Binding affinity also may be determined by KINEXA, equilibrium methods (e.g. enzyme-linked immunoabsorbent assay (ELISA) or radioimmunoassay (RIA)) or kinetics analysis (e.g. BIA-core™ analysis).

In yet another embodiment of the invention, anti-MCT1 antibodies and antigen binding fragments, e.g., human, humanized or chimerized anti-MCT1 antibodies or antibody fragments, may bind to MCT1 with a binding affinity ($K_D$) of less than or equal to $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$, $10^{-10}$, $5 \times 10^{-11}$, $10^{-11}$ M, $5 \times 10^{-12}$, $10^{-12}$ M, $5 \times 10^{-13}$ M, or $10^{-13}$ M, e.g., as determined by ELISA, bio-layer interferometry ("BLI"), KINEXA or surface plasmon resonance at 25° or 37° C. Typically, an anti-MCT1 antibody provided by the invention has an affinity for MCT1 in the range of about $10^{-4}$ to about $10^{-12}$ M (e.g., about $10^{-7}$ to about $10^{-10}$ M). The term immunoreact herein typically refers to binding of an anti-MCT1 antibody to MCT1 with an affinity lower than about $10^{-4}$ M. For example, in a particular aspect, the invention provides an anti-MCT1 antibody that has a binding affinity ($K_D$) of about $7 \times 10^{-9}$ M or less with respect to MCT1, as determined by, e.g., KINEXA.

Additionally, the anti-MCT1 antibodies and antigen binding fragments, e.g., human, humanized or chimerized anti-MCT1 antibodies or antibody fragments, of the invention may include anti-MCT1 antibodies or antibody fragments which bind to MCT1 with an off-rate ($k_{off}$) of less than or equal to $5 \times 10^{-4}$ s$^{-1}$, $10^{-4}$ s$^{-1}$, $5 \times 10^{-5}$ s$^{-1}$, or $10^{-5}$ s$^{-1}$.

Avidity refers to the overall strength of the total interactions between a binding protein and antigen (e.g., the total strength of interactions between an anti-MCT1 antibody and a MCT1). Affinity is the strength of the total noncovalent interactions between a single antigen-binding site on an antibody or other binding peptide and a single epitope or antigenic determinant. Avidity typically is governed by three major factors: the intrinsic affinity of the binding protein for the epitope(s) or antigenic determinant(s) to which it binds, the valence of the antibody or binding protein and antigen (e.g., an anti-MCT1 antibody with a valency of three, four, or more will typically exhibit higher levels of avidity for an antigen than a bivalent antibody and a bivalent antibody can will have a higher avidity for an antigen than a univalent antibody, especially where there are repeated epitopes in the antigen), and/or the geometric arrangement of the interacting components. Avidity typically is measured by the same type of techniques used to assess affinity.

Anti-MCT1 antibodies can be characterized on the basis of their ability to bind to MCT1 and thereby inhibit one or more functions of MCT1. Such anti-MCT1 antibodies may be used directly as therapeutic agents in a native form. Inhibitory anti-MCT1 antibodies may partially or fully inhibit the various functions of MCT1, such as the transport of monocarboxylates, ions, and various other molecules, e.g. toxins. In a particular embodiment, the antibodies of the invention inhibit the MCT1-mediated transport of lactate. Inhibition can be measured by any suitable method. In one aspect, inhibition is reflected in that the inhibiting anti-MCT1 antibody causes an least about 20%, e.g., at least about 30%, at least about 40%, at least about 50%, at least about 60%, at least about 75% or more (e.g., about 25-100%) decrease in MCT1-mediated lactate transport. The percentage decrease in this aspect can be determined when considering anti-MCT1 antibodies effect on lactate transport in comparison with controls, e.g., in comparison with the results of lactate transport assays from cells that do not express MCT1 or cells not blocked by the antibody.

Production of Anti-MCT1 Antibodies

Anti-MCT1 monoclonal antibodies (mAbs) and antigen-binding fragments according to the present invention potentially can be produced by different methods such as monoclonal antibody methodology e.g., the standard somatic cell hybridization technique of Kohler and Milstein (1975) *Nature* 256:495. Also other techniques for producing monoclonal antibody potentially can be employed e.g., viral or oncogenic transformation of B lymphocytes.

A preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known. Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter and U.S. Pat. Nos. 5,530,101; 5,585,089; 5,693, 762 and 6,180,370 to Queen et al.).

According to at least some embodiments of the invention, the antibodies are human monoclonal antibodies. Such human monoclonal antibodies directed against MCT1 can be generated using transgenic or transchromosomic mice carrying parts of the human immune system rather than the mouse system, e.g., HuMAb Mouse™, KM Mouse™ (see e.g., Lonberg, et al. (1994) *Nature* 368 (6474): 856-859). Accordingly, the mice exhibit reduced expression of mouse IgM or K and in response to immunization, the introduced human heavy and light chain transgenes undergo class switching and somatic mutation to generate high affinity human IgG K monoclonal (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13:65-93, and Harding, F. and Lonberg, N. (1995) *Ann. N. Y. Acad. Sci.* 764:536-546). In another embodiment, human antibodies according to at least some embodiments of the invention can be raised using a mouse that carries human immunoglobulin sequences on transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-MCT1 antibodies according to at least some embodiments of the invention. For example, an alternative transgenic system referred to as the Xenomouse (Abgenix, Inc.) can be used; such mice are described in, for example, U.S. Pat. Nos. 5,939,598; 6,075, 181; 6,114,598; 6,150,584 and 6,162,963 to Kucherlapati et al.

Moreover, alternative transchromosomic animal systems expressing human immunoglobulin genes are available in the art and can be used to raise anti-MCT1 antibodies according to at least some embodiments of the invention. For example, mice carrying both a human heavy chain transchromosome and a human light chain transchromosome, referred to as "TC mice" can be used; such mice are described in Tomizuka et al. (2000) *Proc. Natl. Acad Sci. USA* 97:722-727'. Furthermore, cows carrying human heavy and light chain transchromosome have been described in the art (Kuroiwa et al. (2002) *Nature Biotechnology* 20:889-894) and can be used to raise anti-MCT1 antibodies according to at least some embodiments of the invention.

Human monoclonal antibodies according to at least some embodiments of the invention can also be prepared using phage display methods for screening libraries of human immunoglobulin genes. Such phage display methods for isolating human antibodies are established in the art. See for example: U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885, 793; 6,521,404; 6,544,731; 6,555,313; 6,582,915 and 6,593, 081 to Griffiths et al.

Human monoclonal antibodies according to at least some embodiments of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In some embodiments human Ig mice are used to raise human anti-MCT1 antibodies according to the invention, e.g., by immunizing such mice with a purified or enriched preparation of MCT1 antigen and/or recombinant MCT1, or MCT1 fusion protein, as described by Lonberg, N. et al. (1994) *Nature* 368 (6474): 856-859; Fishwild, D. et al. (1996) *Nature Biotechnology* 14:845-851; and PCT Publication WO 98/24884 and WO 01/14424. Preferably, the mice will be 6-16 weeks of age upon the first infusion. For example, a purified or recombinant preparation (dose ranging from 0.5-500 μg) of MCT1 antigen can be used to immunize the human Ig mice intraperitoneally.

In general, transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA, and mice with sufficient titers of anti-MCT1 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen.

In certain embodiments, hybridomas producing a human monoclonal anti-MCT1 antibody according to the invention may be generated using splenocytes and/or lymph node cells from immunized mice which are isolated and fused to an appropriate immortalized cell line, such as a mouse myeloma cell line. The resulting hybridomas can be screened for the production of antigen-specific antibodies.

In certain embodiments, an anti-MCT1 antibody according to the invention can be produced in a host cell transfectoma using, for example, a combination of recombinant DNA techniques and gene transfection methods as is well known in the art (e.g., Morrison, S. (1985) *Science* 229: 1202). For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segments within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In some instances antagonistic anti-MCT1 antibodies may be obtained by immunizing animals, e.g., a non-human mammal, non-human primate, avian or amphibian; e.g., a cynomolgus monkey, rodent, rabbit, guinea pig, bovine, equine, canine, feline, chicken, frog, with virus-like particles (VLPS) which express on their surface an intact MCT1 protein, MCT1 fragment, MCT1 fusion protein or MCT1 multimer and optionally another adjuvant. The use of VLPs which express an antigen as immunogens in order to generate a cellular or humoral (antibody) immune response to an antigen expressed on the surface of the VLP is known in the art. (See e.g., U.S. Pat. Nos. 10,138,277; 10,130,696; 10,125,175; 10,086,056; 10,080,796; 10,072,058; 10,046, 026; 10,040,830; 9,969,986; 9,957,300; 9,833,504; 9,803, 189; 9,637,532; 9,566,327; 9,617,321; 9,585,954 9,518,096; 9,517,261; 9,381,239; 9,481,875; 9213027; 9,296,792; 9,216,229; 8,980,275; 8,889,144; 8,852,604; 8728985; 8,691,209; 8,680,244; 8,574,590; 8,529,906 8,324,149; 8,377,691; 8,158,130; 7,959,928; 7,875,450; 7,641,896; 7,494,656; 7,479,280; 7,320,793; 7,264,810; 7229624; 7,138,252; 6,991,795; 6,964,769; 6,534,064 and 5,667,782 among others, which patents are herein incorporated by reference in their entirety).

Expression of Anti-MCT1 Antibodies

A suitable host cell generally includes any cell wherein the subject anti-MCT1 antibodies and antigen-binding fragments thereof can be produced recombinantly using techniques and materials readily available. For example, the anti-MCT1 antibodies and antigen binding fragments thereof of the present invention can be produced in genetically engineered host cells according to conventional techniques. Suitable host cells are those cell types that can be transformed or transfected with exogenous DNA and grown in culture, and include bacteria, fungal cells (e.g., yeast), and cultured higher eukaryotic cells (including cultured cells of multicellular organisms), particularly cultured mammalian cells, e.g., human or non-human mammalian cells. In an exemplary embodiment these antibodies may be expressed in CHO cells or HEK-293 cells. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor, N.Y.: Cold Spring Harbor Laboratory Press (1989), and *Current Protocols in Molecular Biology,* Ausubel et al, editors, New York, NY: Green and Wiley and Sons (1993).

In some exemplary embodiments the antibodies may be expressed in mating competent yeast, e.g., any haploid, diploid, or tetraploid yeast that can be grown in culture. Yeast useful in fermentation expression methods may exist in a haploid, diploid, or other polyploid form. The cells of a given ploidy may, under appropriate conditions, proliferate for an indefinite number of generations in that form. Diploid cells can also sporulate to form haploid cells. Sequential mating can result in tetraploid strains through further mating or fusion of diploid strains. The present invention contemplates the use of haploid yeast, as well as diploid or other polyploid yeast cells produced, for example, by mating or spheroplast fusion. By way of example, such yeast may include members of the Saccharomycesceae family, which includes the genera *Arxiozyma; Ascobotryozyma; Citeromyces; Debaryomyces; Dekkera; Eremothecium; Issatchenkia; Kazachstania; Kluyveromyces; Kodamaea; Lodderomyces; Pachysolen; Pichia; Saccharomyces; Saturnispora; Tetrapisispora; Torulaspora; Williopsis*; and *Zygosaccharomyces.* Other types of yeast potentially useful in the invention include *Yarrowia; Rhodosporidium; Candida; Hansenula*; *Filobasium; Sporidiobolus; Bullera; Leucosporidium* and *Filobasidella.*

The polypeptide coding sequence of interest is operably linked to transcriptional and translational regulatory sequences that provide for expression of the polypeptide in the desired host cells, e.g., yeast or mammalian cells. These vector components may include, but are not limited to, one or more of the following: an enhancer element, a promoter, and a transcription termination sequence. Sequences for the secretion of the polypeptide may also be included, e.g. a signal sequence, and the like. An origin of replication, e.g., a yeast origin of replication, is optional, as expression vectors are often integrated into the host cell genome. In one embodiment of the invention, the polypeptide of interest is operably linked, or fused, to sequences providing for optimized secretion of the polypeptide from yeast diploid cells.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature. The promoter fragment may also serve as the site for homologous recombination and integration of the expression vector into the same site in the host cell, e.g., yeast or mammalian cell genome; alternatively, a selectable marker may be used as the site for homologous recombination.

The anti-MCT1 antibody polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected e.g., is one that is recognized and processed through one of the standard pathways available within the host cell, e.g., a mammalian cell, an insect cell, or a yeast cell. Additionally, these signal peptide sequences may be engineered to provide for enhanced secretion in expression systems. Secretion signals of interest also include mammalian and yeast signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. For example, see Hashimoto et. al, *Protein Eng.,* 11 (2):75 (1998); and Kobayashi et. al., *Therapeutic Apheresis,* 2(4):257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is e.g., located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion, and/or sequenced.

As an alternative to restriction and ligation of fragments, recombination methods based on specific attachment ("att") sites and recombination enzymes may be used to insert DNA sequences into a vector. Such methods are described, for example, by Landy, *Ann. Rev. Biochem.,* 58:913-949 (1989); and are known to those of skill in the art. Such methods utilize intermolecular DNA recombination that is mediated by a mixture of lambda and *E. coli*-encoded recombination proteins. Recombination occurs between att sites on the interacting DNA molecules. For a description of att sites see Weisberg and Landy, Site-Specific Recombination in Phage Lambda, in *Lambda II,* p. 211-250, Cold Spring Harbor, NY: Cold Spring Harbor Press (1983). The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. While non-covalent interactions are important in determining structure, usually the proteins of interest will have intra- and/or intermolecular covalent disulfide bonds formed by two cysteine residues. For naturally occurring proteins and polypeptides or derivatives and variants thereof, the proper folding is typically the arrangement that results in optimal biological activity, and can conveniently be monitored by assays for activity, e.g. ligand binding, enzymatic activity, etc.

In some instances, for example where the desired product is of synthetic origin, assays based on biological activity will be less meaningful. The proper folding of such molecules may be determined on the basis of physical properties, energetic considerations, modeling studies, and the like.

The expression host may be further modified by the introduction of sequences encoding one or more enzymes that enhance folding and disulfide bond formation, i.e. foldases, chaperonins, protein disulfide isomerases, etc. Such sequences may be constitutively or inducibly expressed in the yeast host cell, using vectors, markers, etc. as known in the art. Preferably the sequences, including transcriptional regulatory elements sufficient for the desired partem of expression, are stably integrated in the host cell genome through a targeted methodology.

For example, the eukaryotic protein disulfide isomerase ("PDI") is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of immunoglobulin heavy chain binding protein ("BIP"); cyclophilin; and the like. In one embodiment of the invention, each of the haploid parental strains expresses a distinct folding enzyme, e.g. one strain may express BIP, and the other strain may express PDI or combinations thereof.

Cultured mammalian cells are also preferred exemplary hosts for production of the disclosed anti-MCT1 antibodies and antigen binding fragments thereof. As mentioned, CHO cells are particularly suitable for expression of antibodies. Many procedures are known in the art for manufacturing monoclonal antibodies in mammalian cells. (See, Galfre, G. and Milstein, C, *Methods Enzym.,* 73:3-46, 1981; Basalp et al., *Turk. J. Biol,* 24:189-196, 2000; Wurm, F. M., *Nat. Biotechnol,* 22:1393-1398, 2004; and Li et al., mAbs, 2(5): 466-477, 2010). As mentioned in further detail infra, common host cell lines employed in mammalian monoclonal antibody manufacturing schemes include, but are not limited to, human embryonic retinoblast cell line PER.C6® (Crucell N. V., Leiden, The Netherlands), NSO murine myeloma cells (Medical Research Council, London, UK), CV1 monkey kidney cell line, 293 human embryonic kidney cell line, BHK baby hamster kidney cell line, VERO African green monkey kidney cell line, human cervical carcinoma cell line HELA, MDCK canine kidney cells, BRL buffalo rat liver cells, W138 human lung cells, HepG2 human liver cells, MMT mouse mammary tumor cells, TRI cells, MRC5 cells, Fs4 cells, myeloma or lymphoma cells, or Chinese Hamster (*Cricetulus griseus*) Ovary (CHO) cells, and the like. Many different subclones or sub-cell lines of CHO cells known in the art that are useful and optimized for production of recombinant monoclonal antibodies, such as the DP12 (CHO KI dhfr-) cell line. NSO cells are a non-Ig secreting, non-light chain-synthesizing subclone of NS-1 cells that are resistant to azaguanine. Other Chinese Hamster and CHO cells are commercially available (from ATCC, etc.), including CHO-DXB11 (CHO-DUKX), CHO-pro3, CHO-DG44, CHO 1-15, CHO DP-12, Lec2, M1WT3, Lec8, pgsA-745, and the like, all of which are genetically altered to optimize the cell line for various parameters. Monoclonal antibodies are commonly manufactured using a batch fed method whereby the monoclonal antibody chains are expressed in a mammalian cell line and secreted into the tissue culture medium in a bioreactor. Medium (or feed) is continuously supplied to the bioreactor to maximize recombinant protein expression. Recombinant monoclonal antibody is then purified from the collected media. In some circumstances, additional steps are needed to reassemble the antibodies through reduction of disulfide bonds, etc. Such production methods can be scaled to be as large as 10,000 L in a single batch or more. It is now routine to obtain as much as 20 pg/cell/day through the use of such cell lines and methodologies, providing titers as high as 10 g/L or more, amounting to 15 to 100 kg from bioreactors of 10 kL to 25 kL. (Li et al, 2010). Various details of this production methodology, including cloning of the polynucleotides encoding the antibodies into expression vectors, transfecting cells with these expression vectors, selecting for transfected cells, and expressing and purifying the recombinant monoclonal antibodies from these cells are provided below.

For recombinant production of an anti-MCT1 antibody or antigen binding fragment in mammalian cells, nucleic acids encoding the antibody or fragment thereof are generally inserted into a replicable vector for further cloning (amplification of the DNA) or for expression. DNA encoding the antibody is readily isolated or synthesized using conventional procedures (e.g., by using oligonucleotide probes that are capable of binding specifically to DNAs encoding the heavy and light chains of the antibody). The vector components generally include, but are not limited to, one or more of the following: a signal sequence, an origin of replication, one or more marker genes, an enhancer element, a promoter, and a transcription termination sequence. Selection of promoters, terminators, selectable markers, vectors, and other elements is a matter of routine design within the level of ordinary skill in the art. Many such elements are known in the art and are available through commercial suppliers.

The antibodies of this invention may be produced recombinantly not only directly, but also as a fusion polypeptide with a heterologous polypeptide, which is e.g., a signal sequence or other polypeptide having a specific cleavage site at the N-terminus of the mature protein or polypeptide. The homologous or heterologous signal sequence selected e.g., is one that is recognized and processed (i.e., cleaved by a signal peptidase) by the host cell. In mammalian cell expression, mammalian signal sequences as well as viral secretory leaders, for example, the herpes simplex gD signal, are available.

Such expression vectors and cloning vectors will generally contain a nucleic acid sequence that enables the vector to replicate in one or more selected host cells. Typically, in cloning vectors this sequence is one that enables the vector to replicate independently of the host chromosomal DNA, and includes origins of replication or autonomously replicating sequences. Such sequences are well known for a variety of bacteria, yeast, and viruses, e.g., the origin of replication from the plasmid pBR322 is suitable for most Gram-negative bacteria, the 2mu plasmid origin is suitable for yeast, and various viral origins (Simian Virus 40 ("SV40"), polyoma, adenovirus, vesicular stomatitis virus ("VSV"), or bovine papillomavirus ("BPV")) are useful for cloning vectors in mammalian cells. Generally, the origin of replication component is not needed for mammalian expression vectors (the SV40 origin may typically be used only because it contains the early promoter).

These vectors will also typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." Examples of such dominant selection use the drugs neomycin, mycophenolic acid, and hygromycin. An exemplary selectable marker is a gene encoding resistance to the antibiotic neomycin. Selection is carried out in the presence of a neomycin-type drug, such as G-418 or the like. Those cells that are successfully transformed with a heterologous gene produce a protein conferring drug resistance and thus survive the selection regimen.

Selection systems can also be used to increase the expression level of the gene of interest, a process referred to as "amplification." Amplification of transfectants typically occurs by culturing the cells in the presence of a low level of the selective agent and then increasing the amount of selective agent to select for cells that produce high levels of the products of the introduced genes. Exemplary suitable selectable markers for mammalian cells are those that enable the identification of cells competent to take up the antibody nucleic acid, such as dihydrofolate reductase ("DHFR"), thymidine kinase, metallothionein-I and -II, e.g., primate metallothionein genes, adenosine deaminase, ornithine decarboxylase, etc.

For example, an amplifiable selectable marker for mammalian cells is dihydrofolate reductase, which confers resistance to methotrexate. Other drug resistance genes (e.g. hygromycin resistance, multi-drug resistance, puromycin acetyltransferase) can also be used. Cells transformed with the DHFR selection gene are first identified by culturing all of the transformants in a culture medium that contains methotrexate ("MTX"), a competitive antagonist of DHFR. An appropriate host cell when wild-type DHFR is employed is the Chinese hamster ovary ("CHO") cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase ("APH") can be selected by cell growth in medium containing a selection agent for the selectable marker such as an aminoglycosidic antibiotic, e.g., kanamycin, neomycin, or G-418. See U.S. Pat. No. 4,965,199.

These vectors may comprise an enhancer sequence that facilitates transcription of a DNA encoding the antibody. Many enhancer sequences are known from mammalian genes (for example, globin, elastase, albumin, alpha-fetoprotein, and insulin). A frequently used enhancer is one derived from a eukaryotic cell virus. Examples thereof include the SV40 enhancer on the late side of the replication origin (bp 100-270), the cytomegalovirus early promoter enhancer, the polyoma enhancer on the late side of the replication origin, and adenovirus enhancers (See, also Yaniv, *Nature,* 297:17-18, 1982, on enhancing elements for activation of eukaryotic promoters). The enhancer may be spliced into the vector at a position 5' or 3' to the antibody-encoding sequence, but is e.g., located at a site 5' from the promoter.

Expression and cloning vectors will also generally comprise a promoter that is recognized by the host organism and is operably linked to the antibody nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At 3' end of most eukaryotic genes is an AATAAA sequence that may be the signal for addition of the poly A tail to the 3' end of the coding sequence. All of these sequences are suitably inserted into eukaryotic expression vectors.

Antibody transcription from vectors in mammalian host cells is controlled, for example, by promoters obtained from the genomes of viruses such as polyoma virus, fowlpox virus, adenovirus (such as Adenovirus 2), BPV, avian sarcoma virus, cytomegalovirus, a retrovirus, hepatitis-B virus, and most e.g., SV40, from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the BPV as a vector is disclosed in U.S. Pat. No. 4,419,446. A modification of this system is described in U.S. Pat. No. 4,601,978. See also Reyes et al., *Nature,* 297:598-601 (1982) on expression of human beta-interferon cDNA in mouse cells under the control of a thymidine kinase promoter from herpes simplex virus. Alternatively, the rous sarcoma virus long terminal repeat can be used as the promoter.

Strong transcription promoters can be used, such as promoters from SV40, cytomegalovirus, or myeloproliferative sarcoma virus. See, e.g., U.S. Pat. No. 4,956,288 and U.S. Patent Publication No. 20030103986. Other suitable promoters include those from metallothionein genes (U.S. Pat. Nos. 4,579,821 and 4,601,978) and the adenovirus major late promoter. Expression vectors for use in mammalian cells include pZP-1, pZP-9, and pZMP21, which have been deposited with the American Type Culture Collection, 10801 University Blvd., Manassas, VA. USA under accession numbers 98669, 98668, and PTA-5266, respectively, and derivatives of these vectors.

Expression vectors used in eukaryotic host cells (yeast, fungus, insect, plant, animal, human, or a nucleated cell from other multicellular organism) will also generally contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO 94/11026 and the expression vector disclosed therein.

Suitable host cells for cloning or expressing the subject antibodies include prokaryote, yeast, or higher eukaryote cells described above. However, interest has been greatest in vertebrate cells, and propagation of vertebrate cells in culture has become a routine procedure. Examples of useful mammalian host cell lines are monkey kidney CV1 line transformed by SV40 (COS-1 (ATCC No. CRL 1650); and COS-7, ATCC CRL 1651); human embryonic kidney line (293 or 293 cells subcloned for growth in suspension culture, (ATCC No. CRL 1573; Graham et al, *J. Gen. Virol,* 36:59-72 (1977)); baby hamster kidney cells (BHK, ATCC CCL 10, ATCC No. CRL 1632; BHK 570, ATCC No. CRL 10314); CHO cells (CHO-K1, ATCC No. CCL 61; CHO-DG44, Urlaub et al, *Proc. Natl. Acad. Sci. USA,* 77:4216-4220 (1980)); mouse Sertoli cells (TM4, Mather, *Biol. Reprod.,* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N. Y. Acad. Sci., 383:44-68 (1982)); MRC 5 cells; FS4 cells; and a human hepatoma line (Hep G2). Additional suitable cell lines are known in the art and available from public depositories such as the American Type Culture Collection, Manassas, VA.

Host cells are transformed with the above-described expression or cloning vectors for antibody production and cultured in conventional nutrient media modified as appropriate for inducing promoters, selecting transformants, or amplifying the genes encoding the desired sequences as discussed supra.

The mammalian host cells used to produce the antibody of this invention may be cultured in a variety of media. Commercially available media such as Ham's F10 (Sigma-Aldrich Corporation, St. Louis, MO), Minimal Essential Medium (("MEM" (Sigma-Aldrich Corporation, St. Louis, MO), Roswell Park Memorial Institute-1640 medium ("RPMI-1640", Sigma-Aldrich Corporation, St. Louis, MO), and Dulbecco's Modified Eagle's Medium (("DMEM" Sigma-Aldrich Corporation, St. Louis, MO) are suitable for culturing the host cells. In addition, any of the media described in Ham et al., *Meth. Era.,* 58:44 (1979); Barnes et al., *Anal. Biochem.,* 102:255 (1980); U.S. Pat. Nos. 4,767,704; 4,657,866; 4,927,762; 4,560,655; or 5,122, 469; WO 90/03430; WO 87/00195; or U.S. Patent Reexam No. 30,985, can be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. Methods of development and optimization of media and culture conditions are known in the art. (See, Gronemeyer et al, *Bioengineering,* 1(4): 188-212, 2014).

After culture conditions are optimized and a preferred cell line clone is selected, these cells are cultured (either adherent cells or suspension cultures) most typically in a batch-fed process in a bioreactor (many models are commercially available) that involves continuously feeding the cell culture with medium and feed, optimized for the particular cell line chosen and selected for this purpose. (See, Butler, M., *Appl. Microbiol. Biotechnol,* 68:283-291, 2005; and Kelley, B., *mAb,* I(5):443-452, 2009). Perfusion systems are also available in which media and feed are continuously supplied to the culture while the same volume of media is being withdrawn from the bioreactor. (Wurm, 2004). Synthetic media, also commercially available, are available for growing cells in a batch-fed culture, avoiding the possibility of contamination from outside sources, such as with the use of animal components, such as bovine serum albumin, etc. However, animal-component-free hydrolysates are commercially available to help boost cell density, culture viability and productivity. (Li et al., 2010). Many studies have been performed in an effort to optimize cell culture media, including careful attention to head space available in roller bottles, redox potentials during growth and expression phases, presence of reducing agents to maintain disulfide bonds during production, etc. (See, for instance, Hutterer et al., *mAbs,* 5(4):608-613, 2013; and Mullan et al, *BMC Proceed.,* 5(Suppl 8):P110, 2011). Various methodologies have been developed to address the possibility of harmful oxidation during recombinant monoclonal antibody production. (See, for example, U.S. Pat. No. 8,574,869). Cultured cells may be grown by feeding nutrients continuously or as separately administered amounts. Often various process parameters such as cell concentration, pH, temperature, $CO_2$, d02, osmolality, amount of metabolites such as glucose, lactate, glutamine and glutamate, and the like, are monitored by the use of probes during the cell growth either on-line by direct connection to calibrated analyzers or off-line by intervention of operators. The culturing step also typically involves ensuring that the cells growing in culture maintain the transfected recombinant genes by any means known in the art for cell selection.

Following fermentation, i.e., upon reaching maximum cell growth and recombinant protein expression, the culturing step is typically followed by a harvesting step, whereby the cells are separated from the medium and a harvested cell culture media is thereby obtained. (See, Liu et al, *mAbs,* 2(5):480-499, 2010). Typically various purification steps, involving column chromatography and the like, follow culturing to separate the recombinant monoclonal antibody from cell components and cell culture media components. The exact purification steps needed for this phase of the production of recombinant monoclonal antibodies depends on the site of expression of the proteins, i.e., in the cytosol of the cells themselves, or the more commonly preferred route of protein excreted into the cell culture medium. Various cell components may be separated using techniques known in the art such as differential centrifugation techniques, gravity-based cell settling, and/or size exclusion chromatograph/filtration techniques that can include tangential flow micro-filtration or depth filtration. (See, Pollock et al, *Biotechnol. Bioeng.,* 110:206-219, 2013, and Liu et al, 2010). Centrifugation of cell components may be achieved on a large scale by use of continuous disk stack centrifuges followed by clarification using depth and membrane filters. (See, Kelley, 2009). Most often, after clarification, the recombinant protein is further purified by Protein A chromatography due to the high affinity of Protein A for the Fc domain of antibodies, and typically occurs using a low pH/acidification elution step (typically the acidification step is combined with a precautionary virus inactivation step). Flocculation and/or precipitation steps using acidic or cationic polyelectrolytes may also be employed to separate animal cells in suspension cultures from soluble proteins. (Liu et al, *mAbs,* 2(5):480-499, 2010). Lastly, anion- and cation-exchange chromatography, hydrophobic interaction chromatograph ("HIC"), hydrophobic charge induction chromatograph (HCIC), hydroxyapatite chromatography using ceramic hydroxyapatite $(Ca_5(PO_4)_3OH)_2$, and combinations of these techniques are typically used to polish the solution of recombinant monoclonal antibody. Final formulation and concentration of the desired monoclonal antibody may be achieved by use of ultracentrifugation techniques. Purification yields are typically 70 to 80%. (Kelley, 2009).

Anti-Idiotypic Antibodies

Another aspect of the invention is directed to anti-idiotypic antibodies and anti-anti-idiotypic antibodies. An anti-idiotypic antibody is an antibody that recognizes determinants of another antibody (a target antibody). Generally, the anti-idiotypic antibody recognizes determinants of the antigen-binding site of the target antibody. Typically, the target antibody is a monoclonal antibody. An anti-idiotypic antibody is generally prepared by immunizing an animal (particularly, mice) of the same species and genetic type as the source of the target monoclonal antibody, with the target monoclonal antibody. The immunized animal mounts an immune response to the idiotypic determinants of the target monoclonal antibody and produces antibodies against the idiotypic determinants of the target monoclonal antibody. Antibody-producing cells, such as splenic cells, of the immunized animal may be used to generate anti-idiotypic monoclonal antibodies. Furthermore, an anti-idiotypic antibody may also be used to immunize animals to produce anti-anti-idiotypic antibodies. These immunized animals may be used to generate anti-anti-idiotypic monoclonal antibodies using standard techniques. The anti-anti-idiotypic antibodies may bind to the same epitope as the original, target monoclonal antibody used to prepare the anti-idiotypic antibody. The anti-anti-idiotypic antibodies represent other monoclonal antibodies with the same antigen specificity as the original target monoclonal antibody.

If the binding of the anti-idiotypic antibody with the target antibody is inhibited by the relevant antigen of the target antibody, and if the anti-idiotypic antibody induces an antibody response with the same specificity as the target antibody, it mimics the antigen of the target antibody. Such an anti-idiotypic antibody is an "internal image anti-idiotypic" and is capable of inducing an antibody response as if it were the original antigen. (Bona and Kohler, Anti-Idiotypic Antibodies And Internal Image, in *Monoclonal And Anti-Idiotypic Antibodies: Probes For Receptor Structure And Function,* Venter J. C., Frasser, C. M., Lindstrom, J. (Eds.), Alan R. Liss, N. Y., 1984. pp 141-149). Vaccines incorporating internal image anti-idiotype antibodies have been shown to induce protective responses against viruses, bacteria, and parasites (Kennedy et al., (1986) *Science,* 232:220-223; McNamara et al. (1985) *Science* 226:1325-1326). Internal image anti-idiotypic antibodies have also been shown to induce immunity to tumor related antigens (Raychauhuri el al. (1986) *J. Immunol.* 137:1743-1749; Raychauhuri et al. (1987) *J. Immunol.* 139:3902-3910; Bhatacharya-Chatterjee et al. (1987) *J. Immunol.* 139:1354-1360; Bhattacharya-Chatterjee et al. (1988) *J. Immunol.* 141:1398-1403; Herlyn, D. et al. (1989) *Intern. Rev. Immu-*

*nol.* 4:347-357; Chen, Z. J et al. (1990) *Cell Imm. Immunother. Cancer* 351-359; Herlyn, D. et al. (1991) *In Vivo* 5:615-624; Furuya et al. (1992) *Anticancer Res.* 12:27-32; Mittelman A. et al. (1992) *Proc. Natl. Acad. Sci., USA* 89:466-470; Durrant, L. G. et al. (1994) *Cancer Res.* 54:4837-4840; Mittelman, A. et al. (1994) *Cancer Res* 54:415-421; Schmitt, H. et al. (1994) Hybridoma 13:389-396; Chakrobarty, M. et al. (1995) *J. Immunother.* 18:95-103; Chakrobarty, M. et al. (1995) *Cancer Res.* 55:1525-1530; Foon, K. A. et al. (1995) Clin. *Cancer Res.* 1:1205-1294; Herlyn, D, et al. (1995) *Hybridoma* 14:159-166; Sclebusch, H. et al. (1995) *Hybridoma* 14:167-174; Herlyn, D. et al. (1996) *Cancer Immunol Immunother.* 43:65-76).

Anti-idiotypic antibodies for MCT1 may be prepared, for example, by immunizing an animal, such as a mouse, with an immunogenic amount of a composition comprising MCT1 or immunogenic portions thereof, containing at least one antigenic epitope of MCT1. The composition may also contain a suitable adjuvant, and any carrier necessary to provide immunogenicity. Monoclonal antibodies recognizing MCT1 may be prepared from the cells of the immunized animal as described above. A monoclonal antibody recognizing an epitope of MCT1 is then selected and used to prepare a composition comprising an immunogenic amount of the anti-MCT1 monoclonal antibody. Typically, a 25 to 200 μg dose of purified MCT1 monoclonal would be sufficient in a suitable adjuvant.

Animals may be immunized 2-6 times at 14 to 30 day intervals between doses. Typically, animals are immunized by any suitable route of administration, such as intraperitoneal, subcutaneous, intravenous, or a combination of these. Anti-idiotypic antibody production may be monitored during the immunization period using standard immunoassay methods. Animals with suitable titers of antibodies reactive with the target monoclonal antibodies may be re-immunized with the monoclonal antibody used as the immunogen three days before harvesting the antibody producing cells. Preferably, spleen cells are used, although other antibody producing cells may be selected. Antibody-producing cells are harvested and fused with myeloma cells to produce hybridomas, as described above, and suitable anti-idiotypic antibody-producing cells are selected.

Anti-anti-idiotypic antibodies are produced by another round of immunization and hybridoma production by using the anti-idiotypic monoclonal antibody as the immunogen.

Competition, Epitope Mapping, and Structural Similarity

The identification of one or more antibodies that bind(s) to substantially or essentially the same epitope as the monoclonal antibodies described herein can be readily determined using alanine scanning. Additionally, any one of a variety of immunological screening assays in which antibody competition can be assessed. A number of such assays are routinely practiced and well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same or overlapping epitope as the monoclonal antibody described herein.

For example, where the test antibodies to be examined are obtained from different source animals, or are even of a different Ig isotype, a simple competition assay may be employed in which the control antibody is mixed with the test antibody and then applied to a sample containing MCT1. Protocols based upon ELISAs, radioimmunoassays, Western blotting, and the use of BIACORE® (GE Healthcare Life Sciences, Marlborough, MA) analysis are suitable for use in such simple competition studies.

In certain embodiments, the control anti-MCT1 antibody is pre-mixed with varying amounts of the test antibody (e.g., in ratios of about 1:1, 1:2, 1:10, or about 1:100) for a period of time prior to applying to the MCT1 antigen sample. In other embodiments, the control and varying amounts of test antibody can simply be added separately and admixed during exposure to the MCT1 antigen sample. As long as bound antibodies can be distinguished from free antibodies (e.g., by using separation or washing techniques to eliminate unbound antibodies) and control antibody from the test antibody (e.g., by using species specific or isotype specific secondary antibodies or by specifically labeling the control antibody with a detectable label) it can be determined if the test antibody reduces the binding of the control antibody to the MCT1 antigen, indicating that the test antibody recognizes substantially the same epitope as the control anti-MCT1 antibody. The binding of the (labeled) control antibody in the presence of a completely irrelevant antibody (that does not bind MCT1) can serve as the control high value. The control low value can be obtained by incubating the labeled control antibody with the same but unlabeled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of the control antibody to MCT1 by at least about 50%, such as at least about 60%, or more e.g., at least about 70% (e.g., about 65-100%), at any ratio of test antibody between about 1:1 or 1:10 and about 1:100 is considered to be an antibody that binds to substantially the same or overlapping epitope or determinant as the control antibody.

Preferably, such test antibody will reduce the binding of the control antibody to MCT1 antigen e.g., at least about 50%, at least about 60%, at least about 80%, or at least about 90% (e.g., about 95%) of the binding of the control antibody observed in the absence of the test antibody.

A simple competition assay in which a test antibody is applied at saturating concentration to a surface onto which MCT1 (or a portion thereof) is immobilized also may be advantageously employed. The surface in the simple competition assay is e.g., a BIACORE® (GE Healthcare Life Sciences, Marlborough, MA) chip (or other media suitable for surface plasmon resonance ("SPR") analysis). The binding of a control antibody that binds MCT1 to the MCT1-coated surface is measured. This binding to the MCT1-containing surface of the control antibody alone is compared with the binding of the control antibody in the presence of a test antibody. A significant reduction in binding to the MCT1-containing surface by the control antibody in the presence of a test antibody indicates that the test antibody recognizes substantially the same epitope as the control antibody such that the test antibody "competes" with the control antibody. Any test antibody that reduces the binding of control antibody by at least about 20% or more, at least about 40%, at least about 50%, at least about 70%, or more, can be considered to be an antibody that binds to substantially the same epitope or determinant as the control antibody. Preferably, such test antibody will reduce the binding of the control antibody to MCT1 by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Alternatively, the antibody having greater affinity for MCT1 antigen is bound to the MCT1-containing surface first, as it will be expected that the decrease in binding seen for the second antibody (assuming the antibodies are competing) will be of greater magnitude. Further examples of such assays are provided in e.g., Saunal and Regenmortel, *J. Immunol. Methods,* 183:33-41 (1995), the disclosure of which is incorporated herein by reference.

In addition, whether an antibody binds the same or overlapping epitope(s) on MCT1 as another antibody or the epitope bound by a test antibody may in particular be determined using a Western-blot based assay. In this assay a library of peptides corresponding to the antigen bound by the antibody, the MCT1 protein, is made, that comprise overlapping portions of the protein, typically 10-25, 10-20, or 10-15 amino acids long. These different overlapping amino acid peptides encompassing the MCT1 sequence are synthesized and covalently bound to a PEPSPOTS™ nitrocellulose membrane (JPT Peptide Technologies, Berlin, Germany). Blots are then prepared and probed according to the manufacturer's recommendations.

Essentially, the immunoblot assay then detects by fluorometric means what peptides in the library bind to the test antibody and thereby can identify what residues on the antigen, i.e., MCT1, interact with the test antibody. (See U.S. Pat. No. 7,935,340, incorporated by reference herein).

Various epitope mapping techniques are known in the art. By way of example, X-ray co-crystallography of the antigen and antibody; NMR; SPR (e.g., at 25° or 37° C.); array-based oligo-peptide scanning (or "pepscan analysis"); site-directed mutagenesis (e.g., alanine scanning); mutagenesis mapping; hydrogen-deuterium exchange; phage display; and limited proteolysis are all epitope mapping techniques that are well known in the art (See, e.g., Epitope Mapping Protocols: Second Edition, Methods in Molecular Biology, editors Mike Schutkowski and Ulrich Reineke, 2nd Ed., New York, NY: Humana Press (2009), and Epitope Mapping Protocols, *Methods in Molecular Biology,* editor Glenn Morris, 1st Ed., New York, NY: Humana Press (1996), both of which are herein incorporated by referenced in their entirety).

The identification of one or more antibodies that bind(s) to substantially or essentially the same epitope as the monoclonal antibodies described herein, e.g., MCT1 Ab1 or a variant thereof, can be readily determined using any one of variety of immunological screening assays in which antibody competition can be assessed. A number of such assays are routinely practiced and well known in the art (see, e.g., U.S. Pat. No. 5,660,827, issued Aug. 26, 1997, which is incorporated herein by reference). It will be understood that determining the epitope to which an antibody described herein binds is not in any way required to identify an antibody that binds to the same or substantially the same epitope as the monoclonal antibody described herein.

For example, where the test antibodies to be examined are obtained from different source animals, or are even of a different Ig isotype, a simple competition assay may be employed in which the control antibody (e.g., MCT1 Ab1 or any of Ab1-Ab95 or a fragment or variant of any of the foregoing antibodies, for example) is mixed with the test antibody and then applied to a sample containing MCT1, which is known to be bound by MCT1 Ab1 and to any of Ab1-Ab95. Protocols based upon ELISAs, radioimmunoassays, Western blotting, and BIACORE® (GE Healthcare Life Sciences, Marlborough, MA) analysis (as described in the Examples section herein) are suitable for use in such simple competition studies.

In certain embodiments, the method comprises pre-mixing the control antibody with varying amounts of the test antibody (e.g., in ratios of about 1:1, 1:2, 1:10, or about 1:100) for a period of time prior to applying to the MCT1 antigen sample. In other embodiments, the control and varying amounts of test antibody can be added separately and admixed during exposure to the MCT1 antigen sample. As long as bound antibodies can be distinguished from free antibodies (e.g., by using separation or washing techniques to eliminate unbound antibodies) and control antibody from the test antibody (e.g., by using species specific or isotype specific secondary antibodies or by specifically labelling the control antibody with a detectable label), the method can be used to determine that the test antibody reduces the binding of the control antibody to the MCT1 antigen, indicating that the test antibody recognizes substantially the same epitope as the control antibody (e.g., MCT1 Ab1 or any of Ab1-Ab95). The binding of the (labeled) control antibody in the presence of a completely irrelevant antibody (that does not bind MCT1) can serve as the control high value. The control low value can be obtained by incubating the labeled control antibody with the same but unlabeled control antibody, where competition would occur and reduce binding of the labeled antibody. In a test assay, a significant reduction in labeled antibody reactivity in the presence of a test antibody is indicative of a test antibody that recognizes substantially the same epitope, i.e., one that competes with the labeled control antibody. For example, any test antibody that reduces the binding of MCT1 Ab1 to MCT1 by at least about 50%, such as at least about 60%, or more e.g., at least about 70% (e.g., about 65-100%), at any ratio of control MCT1 Ab1:test antibody between about 1:1 or 1:10 and about 1:100 is considered to be an antibody that binds to substantially the same epitope or determinant as MCT1 Ab1 or any of Ab1-Ab95. Preferably, such test antibody will reduce the binding of MCT1 Ab1 to MCT1 to at least about 50%, at least about 60%, at least about 80% or at least about 90% (e.g., about 95%) of the binding of MCT1 Ab1 observed in the absence of the test antibody. These methods can be adapted to identify and/or evaluate antibodies that compete with other control antibodies.

A simple competition assay in which a test antibody is applied at saturating concentration to a surface onto which MCT1 is immobilized also may be advantageously employed. The surface in the simple competition assay is e.g., of a media suitable for OCTET® and/or PROTEON®. The binding of a control antibody (e.g., MCT1 Ab1 or any of Ab2-Ab95) to the MCT1-coated surface is measured. This binding to the MCT1-containing surface of the control antibody alone is compared with the binding of the control antibody in the presence of a test antibody. A significant reduction in binding to the MCT1-containing surface by the control antibody in the presence of a test antibody indicates that the test antibody recognizes substantially the same epitope as the control antibody such that the test antibody "competes" with the control antibody. Any test antibody that reduces the binding of control antibody (such as MCT1 Ab1) to MCT1 by at least about 20% or more, at least about 40%, at least about 50%, at least about 70%, or more, can be considered to be an antibody that binds to substantially the same epitope or determinant as the control antibody (e.g., MCT1 Ab1). Preferably, such test antibody will reduce the binding of the control antibody (e.g., MCT1 Ab1) to the MCT1 antigen by at least about 50% (e.g., at least about 60%, at least about 70%, or more). It will be appreciated that the order of control and test antibodies can be reversed; i.e. the control antibody can be first bound to the surface and then the test antibody is brought into contact with the surface thereafter in a competition assay. Preferably, the antibody having higher affinity for MCT1 is bound to the MCT1-containing surface first, as it will be expected that the decrease in binding seen for the second antibody (assuming the antibodies are competing) will be of greater magnitude. Further examples of such assays are provided in, e.g., Saunal and Regenmortel, *J. Immunol. Methods*, 183:33-41 (1989), the disclosure of which is incorporated herein by reference.

Determination of whether an antibody, antigen binding fragment thereof, or antibody derivative binds within one of the epitope regions defined above can be carried out in ways known to the person skilled in the art. In another example of such mapping/characterization methods, an epitope region for an anti-MCT1 antibody may be determined by epitope "footprinting" using chemical modification of the exposed amines/carboxyls in the MCT1 protein. One specific example of such a foot-printing technique is the use of hydrogen-deuterium exchange detected by mass spectrometry ("HXMS"), wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry (See, e.g., Ehring H., *Analytical Biochemistry*, 267(2): 252-259 (1999) and Engen, J. R. & Smith, D. L., *Anal. Chem.*, 73:256A-265A (2001)). Another example of a suitable epitope identification technique is nuclear magnetic resonance epitope mapping ("NMR"), where typically the position of the signals in two-dimensional NMR spectres of the free antigen and the antigen complexed with the antigen binding peptide, such as an antibody, are compared. The antigen typically is selectively isotopically labeled with $^{15}$N so that only signals corresponding to the antigen and no signals from the antigen binding peptide are seen in the NMR-spectrum. Antigen signals originating from amino acids involved in the interaction with the antigen binding peptide typically will shift position in the spectres of the complex compared to the spectres of the free antigen, and the amino acids involved in the binding can be identified that way. See, e.g., Ernst Schering *Res. Found. Workshop*, (44): 149-67 (2004); Huang et al, *J. Mol. Biol*, 281(I):61-67 (1998); and Saito and Patterson, Methods, 9(3):516-24 (1996). Epitope mapping/characterization also can be performed using mass spectrometry ("MS") methods (See, e.g., Downard, *J. Mass Spectrom.*, 35(4):493-503 (2000) and Kiselar and Downard, *Anal. Chem.*, 71(9):1792-801 (1999)).

Protease digestion techniques also can be useful in the context of epitope mapping and identification. Antigenic determinant-relevant regions/sequences can be determined by protease digestion, e.g. by using trypsin in a ratio of about 1:50 to MCT1 overnight ("o/n") digestion at 37° C. and pH 7-8, followed by mass spectrometry ("MS") analysis for peptide identification. The peptides protected from trypsin cleavage by the anti-MCT1 antibody can subsequently be identified by comparison of samples subjected to trypsin digestion and samples incubated with antibody and then subjected to digestion by e.g. trypsin (thereby revealing a footprint for the antibody). Other enzymes like chymotrypsin or pepsin can be used in similar epitope characterization methods. Moreover, enzymatic digestion can provide a quick method for analyzing whether a potential antigenic determinant sequence is within a region of MCT1 in the context of a MCT1-binding polypeptide. If the polypeptide is not surface exposed, it is most likely not relevant in terms of immunogenicity/antigenicity (See, e.g., Manca, *Ann. 1st. Super. Sanita.*, 27(1): 15-9 (1991) for a discussion of similar techniques).

Site-directed mutagenesis is another technique useful for characterization of a binding epitope. For example, in "alanine-scanning" site-directed mutagenesis (also known as alanine scanning, alanine scanning mutagenesis, alanine scanning mutations, combinatorial alanine scanning, or creation of alanine point mutations, for example), each residue within a protein segment is replaced with an alanine residue (or another residue such as valine where alanine is present in the wild-type sequence) through such methodologies as direct peptide or protein synthesis, site-directed mutagenesis, the GENEART™ Mutagenesis Service (Thermo Fisher Scientific, Waltham, MA U.S.A.) or shotgun mutagenesis, for example. A series of single point mutants of the molecule is thereby generated using this technique; the number of mutants generated is equivalent to the number of residues in the molecule, each residue being replaced, one at a time, by a single alanine residue. Alanine is generally used to replace native (wild-type) residues because of its non-bulky, chemically inert, methyl functional group that can mimic the secondary structure preferences that many other amino acids may possess. Subsequently, the effects replacing a native residue with an alanine has on binding affinity of an alanine scanning mutant and its binding partner can be measured using such methods as, but not limited to, SPR binding experiments. If a mutation leads to a significant reduction in binding affinity, it is most likely that the mutated residue is involved in binding. Monoclonal antibodies specific for structural epitopes (i.e., antibodies that do not bind the unfolded protein) can be used as a positive control for binding affinity experiments to verify that the alanine-replacement does not influence the overall tertiary structure of the protein (as changes to the overall fold of the protein may indirectly affect binding and thereby produce a false positive result). See, e.g., Clackson and Wells, *Science*, 267:383-386 (1995); Weiss et al, *Proc. Natl. Acad. Sci. USA*, 97 (16): 8950-8954 (2000); and Wells, *Proc. Natl. Acad. Sci. USA*, 93:1-6 (1996).

Electron microscopy can also be used for epitope "footprinting". For example, Wang et al., Nature, 355:275-278 (1992) used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include SPR (sold commercially as the BIACORE® system, GE Healthcare Life Sciences, Marlborough, MA) and reflectometric interference spectroscopy ("RifS") (See, e.g., Fagerstam et al, *Journal of Molecular Recognition*, 3:208-14 (1990); Nice et al, *J. Chromatogr.*, 646:159-168 (1993); Leipert et al, *Angew. Chem. Int. Ed.*, 37:3308-3311 (1998); Kroger et al, *Biosensors and Bioelectronics*, 17:937-944 (2002)).

In some embodiments, an anti-MCT1 antibody of the invention may have the same or similar structure to another anti-MCT1 antibody. In a preferred embodiment, an anti-MCT1 antibody of the invention has a similar structure to MCT1 Ab1 or that of any of Ab1-Ab95. Structural similarity may be assessed via a structural alignment of three dimensional protein structures attained through x-ray crystallography, NMR, or other known methods. A similar structure may be determined through an analysis of the difference in positions between the C alpha carbons in the CDRs of the two proteins being compared. Generally, an average RMSD of less than 5 Å, less than 4 Å, less than 3 Å, less than 2 Å, less than 1 Å, or less than 0.5 Å in one or more of the CDRs is indicative of a similar protein structure. Thus, in one embodiment, an anti-MCT1 antibody of the invention has CDRs which adopt the same structure as those of MCT1 Ab1 with an average RMSD of less than 0.5 Å in a structural alignment.

In another embodiment, an anti-MCT1 antibody of the invention may be similar to MCT1 Ab1 in protein surface physicochemical properties. In a particular embodiment, the antibody has the same surface charge as MCT1 Ab1 or that of any of Ab1-Ab95 in the binding surface of the antibody. In another embodiment, it has the same electrostatic potential and/or hydrophobicity.

Exemplary Anti-MCT1 Antibodies, Antibody Fragments, and Fusion Proteins

In one embodiment, an antibody of the invention comprises the heavy chain and light chain CDRs of MCT1 Ab1. In one embodiment, an antibody of the invention comprises the heavy chain CDRs of SEQ ID NO:4, 5, 6 and the light chain CDRs of SEQ ID NO:7, 8, 9.

In one embodiment, an antibody or antibody fragment of the invention comprises the $V_H$ domain and the $V_L$ domain of MCT1 Ab1 or that of any of Ab2-Ab95. In one embodiment, an antibody or antibody fragment of the invention comprises a $V_H$ domain having at least 80%, at least 85%, at least 90%, at least 95%, at least 98%, at least 99%, or 100% identity to the amino acid sequence of SEQ ID NO:2 or to the $V_H$ domain any of Ab2-Ab95. In one embodiment, an antibody or antibody fragment of the invention comprises a $V_L$ domain having at least 80%, at least 85%, at least 90%, at least 95%, at least 98%, at least 99%, or 100% identity to the amino acid sequence of SEQ ID NO:3 or to the $V_L$ domain any of Ab1-Ab95. In one embodiment, an antibody or antibody fragment of the invention comprises a $V_H$ domain having at least 80%, at least 85%, at least 90%, at least 95%, at least 98%, at least 99%, or 100% identity to the amino acid sequence of SEQ ID NO:2 and a $V_L$ domain having at least 80%, at least 85%, at least 90%, at least 95%, at least 98%, at least 99%, or 100% identity to the amino acid sequence of SEQ ID NO: 3.

In one embodiment, an antibody or antibody fragment of the invention comprises a $V_H$ domain having at least 80%, at least 85%, at least 90%, at least 95%, at least 98%, at least 99%, or 100% identity to the amino acid sequence of the $V_H$ domain of any of Ab2-Ab95 and a $V_L$ domain an amino acid sequence having at least 80%, at least 85%, at least 90%, at least 95%, at least 98%, at least 99%, or 100% identity to the amino acid sequence of the $V_L$ domain Ab1-Ab95, preferably wherein these homologous $V_H$ and $V_L$ domains correspond to those of the same antibody, i.e., one of Ab2-Ab95.

In one embodiment, a fusion protein of the invention comprises the heavy chain CDR3 of MCT1 Ab1 (SEQ ID NO:6), or a variant thereof. In one embodiment, the fusion protein comprises a peptide having at least 80%, at least 85%, at least 90%, at least 95%, at least 98%, at least 99%, or 100% identity to the amino acid sequence of SEQ ID NO:6. In particular, as the heavy chain CDR3 of MCT1 Ab1 is longer than most CDRs and clearly extends beyond the plane of the antigen-binding surface on MCT1 Ab1, it is contemplated that a fusion protein comprising a peptide with this sequence (SEQ ID NO:6), or a variant thereof, could retain one or more functions or binding capabilities of MCT1 Ab1.

Further Modifications

Antibody Conjugates

In some embodiments, the present invention features antibody-drug conjugates (ADCs), consisting of an antibody (or antibody fragment such as a single-chain variable fragment (scFv) linked to a payload drug (often cytotoxic). The antibody causes the ADC to bind to the target cancer cells. Often the ADC is then internalized by the cell and the drug is released into the cell. Because of the targeting, the side effects are lower and give a wider therapeutic window. Hydrophilic linkers (e.g., PEG4Mal) help prevent the drug being pumped out of resistant cancer cells through MDR (multiple drug resistance) transporters.

In another aspect, the present invention features immunoconjugates comprising an anti-MCT1 antibody, or a fragment thereof, conjugated to a therapeutic agent, such as a cytotoxin, a drug (e.g., an immunosuppressant) or a radiotoxin. Such conjugates are referred to herein as "immunoconjugates". immunoconjugates that include one or more cytotoxins are referred to as "immunotoxins." A cytotoxin or cytotoxic agent includes any agent that is detrimental to (e.g., kills) cells. Examples include Taxol, cytochalasin B, gramicidin D, ethidium bromide, emetine, mitomycin, etoposide, teniposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody according to at least some embodiments of the invention include duocarmycins, calicheamicin, maytansines and auristatins, and derivatives thereof. An example of a calicheamicin antibody conjugate is commercially available (Mylotarg™ Wyeth).

Cytotoxins can be conjugated to antibodies according to at least some embodiments of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol.*

*Immunother.* 52:328-337; Payne, G. (2003) *Cancer Cell* 3:207-212; Allen, T. M. (2002) Nat. Rev. Cancer 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine 131, indium 111, yttrium 90 and lutetium 177. Methods for preparing radioimmunoconjugates are established in the art. Radioimmunoconjugates are commercially available, including Zevalin® (BiogenIDEC) and Bexxar®. (Corixa Pharmaceuticals), and similar methods can be used to prepare radioimmunoconjugates using the antibodies according to at least some embodiments of the invention.

The anti-human MCT1 antibodies and conjugates containing according to at least some embodiments of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303-16 (Academic Press 1985), and Thorpe et al., "The Preparation And Cytotoxic Properties Of Antibody-Toxin Conjugates", *Immunol. Rev.*, 62:119-58 (1982).

Modifications to the Constant Regions, Fc Domain, and Post-Translational Modifications In addition or as an alternative to modifications made within the framework or CDR regions, antibodies according to at least some embodiments of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody according to at least some embodiments of the invention may be chemically modified (e.g., one or more chemical moieties can be attached to the antibody) or be modified to alter its glycosylation, again to alter one or more functional properties of the antibody. Such embodiments are described further below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CHI is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, and T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In some embodiments, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues within amino acid positions 231 and 239 are altered to thereby alter the ability of the antibody to fix complement. This approach is described further in PCT Publication WO 94/29351 by Bodmer et al.

In yet another embodiment, the Fc region is modified to increase the affinity of the antibody for an Fγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 are shown to improve binding to FcγRIII. Additionally, the following combination mutants are shown to improve FcγRIII binding: T256A/S298A, S298A/E333A, S298A/ K224A and S298A/E333A/K334A. Furthermore, mutations such as M252Y/S254T/T256E or M428L/N434S improve binding to FcRn and increase antibody circulation half-life (see Chan C A and Carter P J (2010) *Nature Rev Immunol* 10:301-316).

In still another embodiment, the antibody can be modified to abrogate in vivo Fab arm exchange. Specifically, this process involves the exchange of IgG4 half-molecules (one heavy chain plus one light chain) between other IgG4 antibodies that effectively results in bi specific antibodies which are functionally monovalent. Mutations to the hinge region and constant domains of the heavy chain can abrogate this exchange (see Aalberse, R C, Schuurman J., 2002, *Immunology* 105:9-19).

In still another embodiment, the glycosylation of an antibody is modified. For example, an aglycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies according to at least some embodiments of the invention to thereby produce an antibody with altered glycosylation. For example, the cell lines Ms704, Ms705, and Ms709 lack the fucosyltransferase gene, FUT8 (a (1,6) fucosyltransferase), such that antibodies expressed in the Ms704, Ms705, and Ms709 cell lines lack fucose on their carbohydrates. The Ms704, Ms705, and Ms709 FUT8 cell lines are created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the a 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *Biol.*

*Chem.* 277:26733-26740). PCT Publication WO 99/54342 by Umana et al. describes cell lines engineered to express glycoprotein-modifying glycosyl transferases (e.g., P(I,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase-L-fucosidase removes fucosyl residues from antibodies (Tarentino, A. L. et al. (1975) *Biochem.* 14:5516-23).

Another modification of the antibodies herein that is contemplated by the invention is pegylation or the addition of other water soluble moieties, typically polymers, e.g., in order to enhance half-life. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (Ci-Cio) alkoxy-or aryloxy-polyethylene glycol or polyethylene glycol-maleimide. In certain embodiments, the antibody to be pegylated is an aglycosylated antibody. Methods for pegylating proteins are known in the art and can be applied to the antibodies according to at least some embodiments of the invention. See for example, EP 0 154 316 by Nishimura et al. and EP 0 401 384 by Ishikawa et al.

Nucleic Acid Molecules

The invention further provides nucleic acids which encode an anti-MCT1 antibody according to the invention, or a fragment or conjugate thereof. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See Ausubel, et al. (2011) *Current Protocols in Molecular Biology*, John Wiley & Sons, Inc. A nucleic acid according to at least some embodiments of the invention can be, for example, DNA or RNA and may or may not contain intronic sequences. In a preferred embodiment, the nucleic acid is a cDNA molecule.

Nucleic acids according to at least some embodiments of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA fragment encoding another protein, such as an antibody constant region or a flexible linker. As previously defined, "operatively linked" means that that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH I, CH2 and CH3). The sequences of human heavy chain constant region genes are known in the art (see e.g., Kabat, E. A., el al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most e.g., is an IgGI, IgG2 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL—The sequences of human light chain constant region genes are known in the art (see e.g., Kabat, E. A., et al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The light chain constant region can be a kappa (κ) or lambda (λ) constant region, but most e.g., is a κ constant region.

To create an scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al. (1988) *Science* 242:423-426; Huston et al. (1988) *Proc. Natl. Acad. Sci., USA* 85:5879-5883; McCafferty et al., (1990) *Nature* 348:552-554).

Vectors

The present invention also provides vectors in which a DNA of the present invention is inserted. Vectors derived from retroviruses are suitable tools to achieve long-term gene transfer since they allow for genetic stability and high expression, in addition to having a flexible genome. Furthermore, clinical experience with retroviral vectors provides guidance for optimizing efficacy and safety in their use.

In brief summary, the expression of natural or synthetic nucleic acids encoding antibodies or antigen-binding fragments thereof is typically achieved by operably linking a nucleic acid encoding the antibody or antigen-binding fragment thereof, or portions thereof, to a promoter, and incorporating the construct into an expression vector. The vectors can be suitable for replication and integration in eukaryotes.

Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, *Molecular Cloning: A Laboratory Manual*, Cold Spring Harbor Laboratory, New York), and in other virology and molecular biology manuals. Viruses, which are useful as vectors include, but are not limited to, retroviruses, gamma retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, retrovirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

Various promoter sequences may be used, including, but not limited to the immediate early cytomegalovirus (CMV) promoter, Elongation Growth Factor-1α (EF-1α), simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

In order to assess the expression of an antibody, antigen-binding fragment of an antibody, or a portion thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 *FEBS Letters* 479:79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Transduction

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, *Molecular Cloning: A Laboratory Manual*, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20 degrees Celsius. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 *Glycobiology* 5:505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Therapeutic Applications

Isolated anti-MCT1 antibodies or antigen-binding fragments thereof obtained through the above methods, or compositions containing the same, can be used as a medicament in the treatment of a disease, disorder, or condition in a subject. In some embodiments, such a medicament can be used for treating an autoimmune, inflammatory, or allergic condition. In some embodiments, the medicament can be used for the treatment of cancer. In some embodiments, the medicament can be used for the treatment of EIHI.

Subject

The subject referred to herein may be any living subject. In a preferred embodiment, the subject is a mammal. The mammal referred to herein can be any mammal. As used herein, the term "mammal" refers to any mammal, including, but not limited to, mammals of the order Rodentia, such as mice and hamsters, and mammals of the order Lagomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes)

In some embodiments, the subject, to whom the antibodies, antibody fragments, or compositions are administered is a primate, such as a human. In some embodiments, the primate is a monkey or an ape. The subject can be male or female and can be any suitable age, including infant, juvenile, adolescent, adult, and geriatric subjects. In some examples, the patient or subject is a validated animal model for disease, antibody therapy, and/or for assessing toxic outcomes.

In some embodiments, the subject has persistent or relapsed disease, e.g., following treatment with another immunotherapy and/or other therapy, including chemotherapy, radiation, and/or hematopoietic stem cell transplantation (HSCT), e.g., allogenic HSCT. In some embodiments, the administration effectively treats the subject despite the subject having become resistant to another therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the methods include administration of anti-MCT1 antibodies, antibody fragments, or compositions containing to a subject, tissue, or cell. The subject to be treated, or from whom the tissue or cell is derived, may be one having, at risk for, or suspected of having a disease, condition or disorder associated with the expression of MCT1. In some embodiments, the antibodies, antibody fragments, or compositions are administered to a subject having the particular disease or condition to be treated. In some embodiments, antibodies, antibody fragments, or compositions are administered to the subject, such as a subject having or at risk for the disease or condition. In some aspects, the methods thereby treat, e.g., ameliorate one or more symptom of the disease or condition, such as by lessening the proportion of activated T cells or B cells mediating an autoimmune disorder.

Functional Activity and/or Assessment

Inhibiting MCT1 may be used to downregulate autoimmune responses. Downregulation can be in the form of inhibiting or blocking an autoimmune response already in progress, or may involve preventing the induction of an autoimmune response. The functions of activated immune cells can be inhibited by inhibiting MCT1-mediated lactate transport. For example, MCT1 Ab1 may bind to MCT1 which is expressed and immunologically relevant on activated T cells and B cells, thereby downmodulating the autoimmune response mediated by these cells. As disclosed herein, other anti-MCT1 antibodies can be identified by, e.g., their ability to inhibit activated T cell activity or proliferation and/or based on their immunosuppressive effects in vitro or in inflammatory, allergic or autoimmune disease models.

A number of art-recognized readouts of cell activation can be employed to measure, e.g., cell proliferation or effector function (e.g., antibody production, cytokine production, phagocytosis) in the presence of the anti-MCT1 antibody or antigen-binding fragment thereof. The ability of a test antibody to inhibit MCT1 can be readily determined by measuring the ability of the antibody to effect a decrease in proliferation or effector function being measured. Accordingly, the ability of a test antibody to be immunosuppressive and to block autoimmune activation can be determined by measuring cytokine production and/or proliferation at different concentrations of antigen. In some embodiments, the production or secretion of inflammatory cytokines may be used to monitor the efficacy of the inventive treatment methods.

In some embodiments, the efficacy of treatment with the inventive antibodies may be measured by the detection of urine ketones. In particular, since MCT1 Ab1 does not cross-react with rodent MCT1, in vivo results in mouse studies may suggest that ketonuria could be induced directly from human leukocytes, since these are the only target cells in NSG mice. In addition, some of the observed immunomodulatory effects of MCT1 inhibition may result indirectly from the generation of ketones as studies have shown increased blood levels of ketones can suppress the inflammasome (REF. 67).

In some aspects the efficacy of treatment with the inventive antibodies is measured by assessing clinical outcome. For the treatment of autoimmune, inflammatory, or allergic conditions, treatment efficacy may be measured by the improvement of the condition. For example, decreased symptoms of lupus, improved survival in GVHD, reduced graft rejection, decreased autoantibody concentration, etc. In the case of the treatment of cancer, this could include reduction in tumor burden or load, stabilization of tumor, progression free survival, or overall survival. In the case of treatment of EIHI, such clinical outcome may include the reduction of hypoglycemia following physical activity.

Downregulation of Immune Responses

MCT1 inhibition may be used to downregulate immune responses. Downregulation can be in the form of inhibiting or blocking an immune response already in progress, or may involve preventing the induction of an immune response. The functions of activated immune cells can be inhibited by downregulating immune cell responses or by inducing specific anergy in immune cells, or both. For example, anti-MCT1 antibodies may bind to MCT1 on activated T cells and thereby downmodulate the immune response. This antibody may be monospecific or multispecific, e.g., it may comprise a bispecific antibody such as a BiTE. For example, such an antibody can comprise an MCT1 antigen binding moiety and another antigen binding moiety, e.g., which targets a cell surface receptor on an immune cell, e.g., an activated T cell or B cell. Such an antibody, in addition to comprising an MCT1 antigen binding site, may comprise a binding site which binds to a B cell antigen receptor, a T cell antigen receptor, or an Fc or other receptor, in order to target the molecule to a specific cell population. Selection of this second antigen for the bispecific antibody provides flexibility in selection of cell population to be targeted. As disclosed herein other human MCT1 binding antibodies can be identified by their ability to inhibit T cell or B cell activity or proliferation and/or based on their immunosuppressive effects in vitro or in inflammatory, allergic or autoimmune disease models.

Tolerance may be induced against specific antigens by co-administering an antigen with an anti-MCT1 antibody according to the invention. For example, tolerance may be induced to specific polypeptides. Immune responses to allergens or foreign polypeptides to which an immune response is undesirable can be inhibited. For example, patients that receive Factor VIII frequently generate antibodies against this clotting factor. Co-administration of an anti-MCT1 antibody according to the invention with recombinant factor VIII may suppress this undesired immune response.

An anti-MCT1 antibody according to the invention may be used in combination with another agent that blocks the activity of costimulatory receptors on an immune cell or which agonizes the activity of an immunosuppressive receptor or ligand expressed on immune cells in order to down-modulate immune responses. Exemplary molecules include: PD-1, PDL-1 agonists, soluble forms of CTLA-4, anti-B7-I antibodies, anti-B7-2 antibodies, antagonistic antibodies targeting one or more of LAG-3, TIM-3, BTLA, B7-H4, B7H3, et al. and/or agonistic antibodies targeting one or more of CD40, CD137, OX40, GITR, CD27, CD28, ICOS, or VISTA or combinations thereof. These moieties can be combined in a single composition or compound, e.g., a bispecific antibody containing an anti-MCT1 antibody according to the invention and further comprising an immune agonist antibody or it may comprise a fusion polypeptide containing an anti-MCT1 antibody according to the invention which is fused to another immunosuppressive polypeptide or other active agent. Alternatively these moieties may be administered as separate or discrete entities (simultaneously or sequentially) in the same or different compositions to downregulate immune cell mediated immune responses in a subject.

Examples of specific immunoinhibitory molecules that may be combined with anti-MCT1 antibodies according to the invention include antibodies that block a costimulatory signal (e.g., against CD28 or ICOS), antibodies that activate an inhibitory signal via CTLA4, and/or antibodies against other immune cell markers (e.g., against CD40, CD40 ligand, or cytokines), fusion proteins (e.g., CTLA4-Fc or PD-I-Fc), and immunosuppressive drugs (e.g., rapamycin, cyclosporine A, or FK506).

In a further embodiment, bispecific antibodies containing anti-MCT1 antibodies according to the invention are useful for targeting a specific cell population, e.g., using a marker found only on a certain type of cell, e.g., activated T cells or B lymphocytes. Downregulating immune responses by blocking MCT1 is useful in downmodulating the immune response, e.g., in situations of tissue, skin and organ transplantation, in graft-versus-host disease (GVHD), or allergies, or in autoimmune and inflammatory diseases such as systemic lupus erythematosus, IBD, RA, psoriasis and multiple sclerosis. For example, blockage of MCT1 function results in reduced tissue destruction in tissue transplantation. Typically, in tissue transplants, rejection of the transplant is initiated through its recognition as foreign by immune cells, followed by an immune reaction that destroys the transplant. The administration of a molecule which inhibits MCT1 on immune cells alone or in conjunction with another down-modulatory agent prior to or at the time of transplantation can inhibit the generation of a costimulatory signal. Moreover, blocking MCT1 may also be sufficient to anergize the immune cells, thereby inducing tolerance in a subject.

To achieve sufficient immunosuppression or tolerance in some diseases or in some subjects, it may be necessary to block the costimulatory function of other molecules. For example, it may be desirable to block the function of B7-1 and B7-2 by administering a soluble form of a combination of peptides having an activity of each of these antigens or blocking antibodies against these antigens (separately or together in a single composition) prior to or at the time of transplantation. Alternatively, it may be desirable to block MCT1 and to further inhibit a costimulatory activity of B7-1 and/or B7-2.

The subject anti-MCT1 antibodies are especially useful in treating autoimmune disease. Many autoimmune disorders are the result of inappropriate activation of immune cells that are reactive against self-tissue and which promote the production of cytokines and autoantibodies involved in the pathology of the diseases. Preventing the activation of autoreactive immune cells may reduce or eliminate disease symptoms. Administration of the subject anti-MCT1 antibodies may induce antigen-specific tolerance of autoreactive immune cells which could lead to long-term relief from the disease. Additionally, co-administration of agents which block costimulation of immune cells by disrupting receptor-ligand interactions of B7 molecules with costimulatory receptors may be useful in inhibiting immune cell activation to prevent production of autoantibodies or cytokines which may be involved in the disease process.

Downregulation of an immune response via the subject anti-MCT1 antibodies may also be useful in treating an autoimmune attack of autologous tissues. Thus, conditions that are caused or exacerbated by autoimmune attack (e.g., heart disease, myocardial infarction or atherosclerosis) may be ameliorated or improved by inhibiting MCT1. It is therefore within the scope of the invention to modulate conditions exacerbated by autoimmune attack, such as autoimmune disorders (as well as conditions such as heart disease, myocardial infarction, and atherosclerosis) by inhibiting MCT1 using the subject anti-human MCT1 antibodies.

As mentioned previously, the efficacy of anti-MCT1 antibodies according to the invention for preventing or alleviating autoimmune and inflammatory disorders can be determined using a number of well-characterized animal models of human autoimmune and inflammatory diseases. Examples include murine experimental autoimmune encephalitis, systemic lupus erythematosus in MRL/Ipr/Ipr mice or NZB hybrid mice, murine autoimmune collagen arthritis, diabetes mellitus in NOD mice and BB rats, and murine experimental myasthenia gravis. See Paul ed., *Fundamental Immunology*, Raven Press, New York, 1989, pages 840-856.

Inhibition of immune cell activation is further useful therapeutically in the treatment of allergies and allergic reactions, e.g., by inhibiting IgE production. The subject anti-MCT1 antibodies can be administered to an allergic subject to inhibit immune cell-mediated allergic responses in the subject. Inhibition of MCT1 can be accompanied by exposure to allergen in conjunction with appropriate MHC molecules. Allergic reactions can be systemic or local in nature, depending on the route of entry of the allergen and the pattern of deposition of IgE on mast cells or basophils. Thus, immune cell-mediated allergic responses can be inhibited locally or systemically by administration of the subject anti-human MCT1 antibodies.

Treatment of Autoimmune, Inflammatory, or Allergic Conditions

Antibodies, antibody fragments, and pharmaceutical compositions according to the invention may be used to inhibit activated T cells or B cells and to treat conditions where this is therapeutically desirable, such as autoimmunity, allergy, or inflammatory conditions. These compositions will comprise an amount of an antibody or antibody fragment according to the invention effective to suppress B cell activity or T cell activation or proliferation or cytokine expression in a subject in need thereof. Such autoimmune, inflammatory and allergic conditions include, for example, arthritic conditions such as rheumatoid arthritis (RA), psoriatic arthritis, psoriasis, scleroderma, multiple sclerosis, lupus, IBD, ITP, diabetes, GvHD, sarcoidosis, allergic asthma, and hepatitis-associated hepatotoxicity. These antibodies may also be used for inhibiting unwanted T cell immune responses against transplanted cells, tissues or organs, such as tissue grafts, CAR-T cell or gene therapy constructs or cells containing and the like.

Specific conditions wherein the inventive antibodies may be used alone or in association with other therapeutics, especially other immunosuppressant molecules include acquired immune deficiency syndrome (AIDS), acquired splenic atrophy, acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis, optionally, large vessel vasculitis, optionally, polymyalgia rheumatica and giant cell (Takayasu's) arthritis, allergic conditions, allergic contact dermatitis, allergic dermatitis, allergic granulomatous angiitis, allergic hypersensitivity disorders, allergic neuritis, allergic reaction, alopecia areata, alopecia totalis, Alport's syndrome, alveolitis, optionally allergic alveolitis or fibrosing alveolitis, Alzheimer's disease, amyloidosis, amylotrophic lateral sclerosis (ALS; Lou Gehrig's disease), an eosinophil-related disorder, optionally eosinophilia, anaphylaxis, ankylosing spondylitis, angiectasis, antibody-mediated nephritis, Anti-GBM/Anti-TBM nephritis, antigen-antibody complex-mediated diseases, antiglomerular basement membrane disease, anti-phospholipid antibody syndrome, antiphospholipid syndrome (APS), aphthae, aphthous stomatitis, aplastic anemia, arrhythmia, arteriosclerosis, arteriosclerotic disorders, arthritis, optionally rheumatoid arthritis such as acute arthritis, or chronic rheumatoid arthritis, arthritis chronica progrediente, arthritis deformans, ascariasis, aspergilloma, granulomas containing eosinophils, aspergillosis, aspermiogenese, asthma, optionally asthma bronchial, bronchial asthma, or auto-immune asthma, ataxia telangiectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, auto-immune disorders associated with collagen disease, autoimmune dysautonomia, autoimmune ear disease, optionally autoimmune inner ear disease (AGED), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenia purpura (ATP), autoimmune thyroid disease, autoimmune urticaria, autoimmune-mediated gastrointestinal diseases, Axonal & neuronal neuropathies, Balo disease, Behcet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonia aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebral degeneration, cerebral ischemia, and disease accompanying vascularization, Chagas disease, channelopathies, optionally epilepsy, channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy, optionally IgM polyneuropathies or IgM-mediated neuropathy, chronic obstructive airway disease, chronic pulmonary inflammatory disease, Chronic recurrent multifocal osteomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogan's syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis, optionally chronic cyclitis, heterochronic cyclitis, iridocyclitis, or Fuch's cyclitis, cystic fibrosis, cytokine-induced toxicity, deafness, degenerative arthritis, demyelinating diseases, optionally autoimmune demyelinating diseases, demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis, optionally allergic encephalomyelitis or encephalomyelitis allergica and experimental allergic encephalomyelitis (EAE), endarterial hyperplasia, endocarditis, endocrine ophthalmopathy, endometriosis, endomyocardial fibrosis, enophthalmia phacoanaphylactica, endophthalmitis, enteritis allergica, eosinophilia-myalgia syndrome, eosinophilic fascitis, epidemic keratoconjunctivitis, epidermolysis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, filariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, guttate psoriasis, hemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schönlein purpura, Herpes gestationis, human immunodeficiency virus (HIV) infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenia purpura (ITP), IgA nephropathy, IgE-mediated diseases, optionally anaphylaxis and allergic or atopic rhinitis, IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antibodies, inflammation of all or part of the uvea, inflammatory bowel disease (IBD) inflammatory hyperproliferative skin diseases, inflammatory myopathy, insulin-dependent diabetes (type 1), insulitis, Interstitial cystitis, interstitial lung disease, interstitial lung fibrosis, iritis, ischemic reperfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extra-renal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis nodosa), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes, optionally Lambert-Eaton myasthenic syndrome or Eaton-Lambert syndrome, parasitic diseases such as *Leishmania*, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including *Pemphigus vulgaris*), pemphigus erythematosus, *Pemphigus foliaceus*, pemphigus mucus-membrane pemphigoid, pemphigus, peptic ulcer, periodic paralysis, peripheral neuropathy, perivenous encephalomyelitis, pernicious anemia (*Anemia perniciosa*), pernicious anemia, phacoa ntigenic uveitis, pneumonocirrhosis, POEMS syndrome, polyarteritis nodosa, Type I, II, & III, polyarthritis chronica primaria, polychondritis (e.g., refractory or relapsed polychondritis), polyendocrine autoimmune disease, polyendocrine failure, polyglandular syndromes, optionally autoimmune polyglandular syndromes (or polyglandular endocrinopathy syndromes), polymyalgia rheumatica, polymyositis, polymyositis/dermatomyositis, polyneuropathies, polyradiculitis acuta, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis, optionally benign monoclonal gammopathy and monoclonal gammopathy of undetermined significance, MGUS, primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyroiditis, Raynaud's phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma, optionally systemic scleroderma, sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjögren's syndrome, sperm & testicular autoimmunity, sphenoid sinusitis, Stevens-Johnson syndrome, stiff-man (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes, cutaneous SLE, systemic necrotizing vasculitis, ANCA-associated vasculitis, optionally Churg-Strauss vasculitis or syndrome (CSS), tabes dorsalis, Takayasu's arteritis, telangiectasia, temporal arteritis/Giant cell arteritis, thromboangiitis ubiterans, thrombocytopenia, including thrombotic thrombocytopenia purpura (TTP) and autoimmune or immune-mediated thrombocytopenia such as idiopathic thrombocytopenia purpura (ITP) including chronic or acute ITP, thrombocytopenia purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria, optionally chronic allergic urticaria and chronic idiopathic urticaria, including chronic autoimmune urticaria, uveitis, anterior uveitis, uveoretinitis, valvulitis, vascular dysfunction, vasculitis, vertebral arthritis, vesiculobullous dermatosis, vitiligo, Wegener's granulomatosis (Granulomatosis with Polyangiitis (GPA)), Wiskott-Aldrich syndrome, or x-linked hyper IgM syndrome.

It should be understood that the disease conditions identified herein are intended to be exemplary and not exhaustive.

According to at least some embodiments, anti-MCT1 antibodies, fragments, conjugates thereof or a pharmaceutical composition comprising same, as described herein, which function to decrease MCT1-mediated transport of lactose, may be used for treating an immune system related disease.

Optionally, the immune system related condition comprises an immune related condition, autoimmune diseases as recited herein, lupus, transplant rejection and graft versus host disease and/or for blocking activated T cells and B cells, immune related diseases as recited herein and/or for immunotherapy (inhibiting immune stimulation).

Optionally the immune condition is selected from autoimmune disease, transplant rejection, inflammatory disease, allergic condition or graft versus host disease. In a particular embodiment, the anti-MCT1 antibodies of the invention may be used to treat lupus. In one embodiment, the anti-MCT1 antibodies of the invention may be used to treat graft versus host disease (GVHD). In another embodiment, the anti-MCT1 antibodies of the invention may be used to treat graft rejection. In yet another embodiment, the anti-MCT1 antibodies of the invention may be used to treat type I diabetes. In one embodiment, the anti-MCT1 antibodies of the invention may be used to treat type II diabetes. In another embodiment, the anti-MCT1 antibodies of the invention may be used to treat obesity.

In a particular embodiment, MCT1 Ab1 may be used to treat lupus. In one embodiment, MCT1 Ab1 may be used to treat graft versus host disease (GVHD). In another embodiment, MCT1 Ab1 may be used to treat graft rejection. In yet another embodiment, MCT1 Ab1 may be used to treat type I diabetes. In one embodiment, MCT1 Ab1 may be used to treat type II diabetes. In another embodiment, MCT1 Ab1 may be used to treat obesity. Equally, in each of these embodiments, a variant or fusion protein comprising one or more CDRs of MCT1 Ab1 may be used.

Optionally the treatment is combined with another moiety useful for treating an immune related condition, e.g., metformin.

Thus, treatment of systemic lupus erythematosus, using the subject antibodies may be combined with, for example, any known therapeutic agent or method for treating for systemic lupus erythematosus, optionally as described herein. Likewise, treatment of GVHD, using the subject antibodies may be combined with, for example, any known therapeutic agent or method for treating GVHD, optionally as described herein. Treatment of multiple sclerosis using the agents according to at least some embodiments of the present invention may be combined with, for example, any known therapeutic agent or method for treating multiple sclerosis, optionally as described herein. Similarly, treatment of rheumatoid arthritis or other arthritic condition, using the subject antibodies may be combined with, for example, any known therapeutic agent or method for treating rheumatoid arthritis, optionally as described herein. Additionally, treatment of type 1 diabetes using the subject antibodies may be combined with, for example, any known therapeutic agent or method for treating type 1 diabetes, optionally as described herein. Treatment of psoriasis using the subject antibodies may be combined with, for example, any known therapeutic agent or method for treating psoriasis, optionally as described herein.

In the above-described therapies, e.g., a subject with one of the aforementioned or other autoimmune or inflammatory conditions will be administered an anti-MCT1 antibody disclosed herein or antigen-binding fragment according to the invention, which antibody suppresses activated T cells and/or B cells and/or the production of proinflammatory cytokines which are involved in the disease pathology, thereby preventing or ameliorating the disease symptoms and potentially resulting in prolonged disease remission, e.g., because of the induction of Tregs which elicit T cell tolerance or prolonged immunosuppression.

The therapeutic agents and/or a pharmaceutical composition comprising same, as recited herein, according to at least some embodiments of the invention, may be administered as the sole active ingredient or together with other drugs in immunomodulating regimens or other anti-inflammatory agents e.g. for the treatment or prevention of alio- or xenograft acute or chronic rejection or inflammatory or autoimmune disorders, or to induce tolerance.

Treatment of Cancer

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the antibodies of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyngioma, ependymoma, pinealoma, hemangioblastoma, acoustic neuroma, oligodendroglioma, menangioma, neuroblastoma, retinoblastoma and brain metastases).

Preferably, the antibodies of the invention are used to treat a cancer wherein the tumorous cells are positive for expression of MCT1. In general, MCT1 positive tumor cells may be identified via known methods. For example, MCT1 expression on tumor cells may be identified via immunofluorescence or flow cytometry using the antibodies of the invention. Alternatively, MCT1 expression may be measured functionally through the observation of inhibition by the inventive antibodies against target cells.

A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer. With respect to detecting the presence of MCT1 expressing tumor cells in a host, the sample comprising cells of the host can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the host, e.g., the cells of any organ or tissue, including blood cells or endothelial cells.

Treatment of Other MCT1-Associated Conditions, e.g. EIHI

The antibodies and antibody fragments of the invention may also be used to treat, prevent, or diagnose any other conditions, disorders, or diseases involving the expression of MCT1 in healthy or diseased cells. For example, the invention also contemplates a method of treating or preventing EIHI in a subject, the method of which comprises administering antibodies or antibody fragments according to the invention.

Modes of Administration

The compositions of the present invention may be administered in a number of ways depending upon whether local or systemic treatment is desired.

In general, administration may be topical, parenteral, or enteral.

The compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, intrasynovial injection or infusions; and kidney dialytic infusion techniques. In a preferred embodiment, parenteral administration of the compositions of the present invention comprises subcutaneous or intraperitoneal administration.

Formulations of a pharmaceutical composition suitable for parenteral administration typically generally comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain excipients such as salts, carbohydrates and buffering agents (e.g., to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The terms "oral", "enteral", "enterally", "orally", "nonparenteral", "non-parenterally", and the like, refer to administration of a compound or composition to an individual by a route or mode along the alimentary canal. Examples of "oral" routes of administration of a composition include, without limitation, swallowing liquid or solid forms of a composition from the mouth, administration of a composition through a nasojejunal or gastrostomy tube, intraduodenal administration of a composition, and rectal administration, e.g., using suppositories for the lower intestinal tract of the alimentary canal.

Preferably, the formulated composition comprising isolated anti-MCT1 antibodies or antibody fragments is suitable for administration via injection.

Pharmaceutical compositions and formulations for topical administration may include transdermal patches, ointments, lotions, creams, gels, drops, suppositories, sprays, liquids, semi-solids, monophasic compositions, multiphasic compositions (e.g., oil-in-water, water-in-oil), foams, microsponges, liposomes, nanoemulsions, aerosol foams, polymers, fullerenes, and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal, or intraventricular administration may include sterile aqueous solutions that may also contain buffers, diluents and other suitable additives such as, but not limited to, penetration enhancers, carder compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, aerosols, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Formulations comprising anti-MCT1 antibodies or antigen-binding fragments thereof may include pharmaceutically acceptable excipient(s). Excipients included in the formulations will have different purposes depending, for example, on the antibody and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents. The formulations comprising anti-MCT1 antibodies will typically have been prepared and cultured in the absence of any non-human components, such as animal serum (e.g., bovine serum albumin).

The formulation or composition may also contain more than one active ingredient useful for the particular indication, disease, or condition being treated with the binding molecules or cells, e.g., those with activities complementary to the binding molecule or cell, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the pharmaceutically active agents or drugs may comprise immune checkpoint inhibitors, e.g., drugs that target PD-1, PD-L1, PD-L2, LAG3, CTLA4, KIR, CD244, B7-H3, B7-H4, BTLA, HVEM, GAL9, TIM3, and/or A2aR. Examples of these inhibitors include, but are not limited to, pidilizumab, nivolumab, pembrolizumab, atezolizumab, MDX-1105, BMS-936559, MEDI4736, MPDL3280A, MSB0010718C, tremelimumab, and ipilimumab, which may be administered alone or in combination with other agents, e.g., GM-CSF.

The antibodies may be combined with other therapeutics which may be administered in the same or different compositions, at the same or different time and in either order. For example, the inventive antibodies may be administered in a therapeutic regimen that includes the administration of a PD-1 or PD-L1 agonist, CTLA4-Ig, a cytokine, a cytokine agonist or antagonist, or another receptor agonist or antagonist.

The pharmaceutical composition in some aspects can employ time-released, delayed release, and sustained release delivery systems such that the delivery of the composition occurs prior to, and with sufficient time to cause, sensitization of the site to be treated. Many types of release delivery systems are available and known. Such systems can avoid repeated administrations of the composition, thereby increasing convenience to the subject and the physician.

Dosing

The pharmaceutical composition in some embodiments contains the anti-MCT1 antibodies or antibody fragments in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The antibodies or antibody fragments can be administrated in one or more doses. In some embodiments, said effective amount of antibodies can be administrated as a single dose. In some embodiments, said effective amount of antibodies can be administrated as more than one dose over a period time. Timing of administration is within the judgment of managing physician and depends on the clinical condition of the patient. While individual needs vary, determination of optimal ranges of effective amounts of a given antibody for a particular disease or conditions is within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired. In some embodiments, an effective amount of antibodies or composition comprising those antibodies are administrated parenterally. In some embodiments, administration can be an intravenous administration. In some embodiments, administration can be directly done by injection within a disease site.

For purposes of the invention, the amount or dose of the inventive antibodies administered should be sufficient to effect a therapeutic or prophylactic response in the subject or animal over a reasonable time frame. For example, the dose of the inventive antibody should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular antibody and the condition of the animal (e.g., human), as well as the body weight of the animal (e.g., human) to be treated.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, e.g., from about 0.1 percent to about 70 percent, most e.g., from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the anti-MCT1 antibody, or antigen-binding fragment thereof, disclosed herein, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an antibody disclosed herein according to at least some embodiments of the present invention include 1 mg/kg body weight or 3 mg/kg body weight via intravenous administration, with the antibody disclosed herein being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously in which case the dosage of each antibody disclosed herein administered falls within the ranges indicated. Antibody disclosed herein is usually administered on multiple occasions. Intervals between single dosages can be, for example, daily, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, a therapeutic agent can be administered as a sustained release formulation, in which case less frequent administration is required. Dosage and frequency vary depending on the half-life of the therapeutic agent in the patient. In general, human antibodies show the longest half-life, followed by humanized antibodies, chimeric antibodies, and nonhuman antibodies. The half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and e.g., until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

In some embodiments, the antibodies are administered as part of a combination treatment, such as simultaneously with or sequentially with, in any order, another therapeutic intervention, such as another antibody or engineered cell or receptor or agent, such as a cytotoxic or therapeutic agent. The antibodies in some embodiments are co-administered with one or more additional therapeutic agents or in connection with another therapeutic intervention, either simultaneously or sequentially in any order. In some contexts, the antibodies are co-administered with another therapy sufficiently close in time such that the antibodies enhance the effect of one or more additional therapeutic agents, or vice versa. In some embodiments, the antibodies are administered prior to the one or more additional therapeutic agents. In some embodiments, the antibodies are administered after to the one or more additional therapeutic agents.

Variations

Included in the scope of the invention are functional portions of the inventive antibodies described herein. The term "functional portion" when used in reference to an antibody refers to any part or fragment of the antibody of the invention, which part or fragment retains the biological activity of the antibody of which it is a part (the parent antibody). Functional portions encompass, for example, those parts of an antibody that retain the ability to recognize target cells, or detect, treat, or prevent a disease, to a similar extent, the same extent, or to a higher extent, as the parent antibody. In reference to the parent antibody, the functional portion can comprise, for instance, about 10%, 25%, 30%, 50%, 68%, 80%, 90%, 95%, or more, of the parent antibody.

The functional portion can comprise additional amino acids at the amino or carboxy terminus of the portion, or at both termini, which additional amino acids are not found in the amino acid sequence of the parent antibody. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent antibody.

Included in the scope of the invention are functional variants of the inventive antibodies described herein. The term "functional variant" as used herein refers to an antibody, polypeptide, or protein having substantial or significant sequence identity or similarity to a parent antibody, which functional variant retains the biological activity of the antibody of which it is a variant. Functional variants encompass, for example, those variants of the antibody described herein (the parent antibody) that retain the ability to recognize target cells to a similar extent, the same extent, or to a higher extent, as the parent antibody. In reference to the parent antibody, the functional variant can, for instance, be at least about 30%, 50%, 75%, 80%, 90%, 98% or more identical in amino acid sequence to the parent antibody.

A functional variant can, for example, comprise the amino acid sequence of the parent antibody with at least one conservative amino acid substitution. Alternatively or additionally, the functional variants can comprise the amino acid sequence of the parent antibody with at least one nonconservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent antibody.

Amino acid substitutions of the inventive antibodies are e.g., conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

Also, amino acids may be added or removed from the sequence based on vector design.

The antibody can consist essentially of the specified amino acid sequence or sequences described herein, such that other components, e.g., other amino acids, do not materially change the biological activity of the functional variant.

The antibodies of embodiments of the invention (including functional portions and functional variants) can be of any length, i.e., can comprise any number of amino acids, provided that the antibodies (or functional portions or functional variants thereof) retain their biological activity, e.g., the ability to specifically bind to antigen, detect diseased cells in a mammal, or treat or prevent disease in a mammal, etc. For example, the antibody can be about 50 to about 5000 amino acids long, such as 50, 70, 75, 100, 125, 150, 175, 200, 300, 400, 500, 600, 700, 800, 900, 1000 or more amino acids in length.

The antibodies of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3-and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocyclo-heptane carboxylic acid, α-(2-amino-2-norbornane)-carboxylic acid, α,γ-diaminobutyric acid, α,β-diaminopropionic acid, homophenylalanine, and α-tert-butylglycine.

The antibodies of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The antibodies of embodiments of the invention (including functional portions and functional variants thereof) can be obtained by methods known in the art. The antibodies may be made by any suitable method of making polypeptides or proteins. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994. Further, some of the antibodies of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the antibodies described herein (including functional portions and functional variants thereof) can be commercially synthesized by companies. In this respect, the inventive antibodies can be synthetic, recombinant, isolated, and/or purified.

Antibodies having $V_H$ and $V_L$ sequences disclosed herein may be used to create new variant antibodies by modifying the $V_H$ and/or $V_L$ sequences, or the constant region(s) attached thereto. Thus, the structural features of a variant antibody of the invention are used to create structurally related variant antibodies that retain at least one functional property of the antibodies of the invention, such as binding to MCT1. For example, one or more CDR regions of one anti-MCT1 variant antibody, e.g., one of Ab1-Ab95 or mutations thereof, may be combined recombinantly with known framework regions and/or other CDRs to create additional, recombinantly-engineered, anti-MCT1 antibodies (e.g., antibodies which bind to MCT1) of the invention, as discussed herein. The starting material for the engineering method may be one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein. Standard molecular biology techniques may be used to prepare and express altered antibody sequence.

The antibody encoded by the altered antibody sequence(s) may retain one, some or all of the functional properties of the anti-MCT1 antibodies produced by methods and with sequences provided herein, which functional properties include binding to variant MCT1 or variant MCT1 conjugate with a specific $K_D$ level or less and/or modulating immune cell activity, and/or selectively binding to desired target cells such as, for example, active T cells or B cells. The functional properties of the altered antibodies may be assessed using standard assays available in the art and/or described herein.

Mutations may be introduced randomly or selectively along all or part of an anti-MCT1 antibody coding sequence and the resulting modified anti-MCT1 antibodies may be screened for binding activity and/or other desired functional properties.

Definitions

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

As used herein, a "5' cap" (also termed an RNA cap, an RNA 7-methylguanosine cap or an RNA m⁷G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used in the description herein and throughout the claims that follow, the meaning of "a," "an," and "the" includes plural reference unless the context clearly dictates otherwise.

"Allergic disease," as used herein, refers broadly to a disease involving allergic reactions. More specifically, an "allergic disease" is defined as a disease for which an allergen is identified, where there is a strong correlation between exposure to that allergen and the onset of pathological change, and where that pathological change has been proven to have an immunological mechanism. Herein, an immunological mechanism means that leukocytes show an immune response to allergen stimulation.

The term "allogeneic" or "donor-derived" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

"Amino acid," as used herein refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified (e.g., hydroxyproline, γ-carboxyglutamate, and O-phosphoserine). Amino acid analogs refers to compounds that have the same basic chemical structure as a naturally occurring amino acid (i. e., a carbon that is bound to a hydrogen, a carboxyl group, an amino group), and an R group (e.g., homoserine, norleucine, methionine sulfoxide, methionine methyl sulfonium.) Analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "antibody," as used herein, refers to an immunoglobulin molecule which specifically binds with an antigen. In one aspect, the antigen is MCT1. Antibodies can be intact immunoglobulins derived from natural sources or from recombinant sources and can be immunoreactive portions of intact immunoglobulins. The term is used in the broadest sense and includes polyclonal and monoclonal antibodies, including intact antibodies and functional (antigen-binding) antibody fragments, including fragment antigen binding (Fab) fragments, F(ab')₂ fragments, Fab' fragments, Fv fragments, recombinant IgG (rIgG) fragments, single chain antibody fragments, including single chain variable fragments (scFv), ByTEs, multispecific antibody polypeptides, diabodies, and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific antibodies, diabodies, triabodies, and tetrabodies, tandem di-scFv, and tandem tri-scFv. Unless otherwise stated, the term "antibody" should further be understood to encompass functional antibody fragments thereof. The term also encompasses intact or full-length antibodies, including antibodies of any class or sub-class, including IgG and sub-classes thereof, IgM, IgE, IgA, and IgD.

The term "antigen-binding fragment" or "antibody fragment" refers to a portion of an intact antibody and refers to the antigenic determining variable regions of an intact antibody. Examples of antibody fragments include, but are not limited to, fragment antigen binding (Fab) fragments, F(ab')₂ fragments, Fab' fragments, Fv fragments, recombinant IgG (rIgG) fragments, single chain antibody fragments, including single chain variable fragments (scFv), single domain antibodies (e.g., sdAb, sdFv, nanobody) fragments, diabodies, and multispecific antibodies formed from antibody fragments. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird, et al. (1988) *Science* 242:423-426; Huston, et al. (1988) *Proc Natl. Acad. Sci. USA* 85:5879-5883; and Osbourn, et al. (1998) *Nat. Biotechnol.* 16:778. Single chain antibodies are also intended to be encompassed within the term "antigen-binding portion" of an antibody. Any $V_H$ and $V_L$ sequences of specific scFv can be linked to human immunoglobulin constant region cDNA or genomic sequences, in order to generate expression vectors encoding complete IgG molecules or other isotypes. $V_H$ and $V_L$ can also be used in the generation of Fab, Fv, or other fragments of immunoglobulins using either protein chemistry or recombinant DNA technology. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites. See e.g. Holliger, et al. (1993) *Proc Natl. Acad. Sci. USA* 90:6444-6448; Poljak, et al. (1994) *Structure* 2:1121-1123. Still further, an antibody or antigen-binding portion thereof (antigen-binding fragment, antibody fragment, antibody portion) may be part of a larger immunoadhesion molecules, formed by covalent or noncovalent association of the antibody or antibody portion with one or more other proteins or peptides. Examples of immunoadhesion molecules include use of the streptavidin core region to make a tetrameric scFv molecule (Kipriyanov, et al. (1995) *Hum. Antibodies Hybridomas* 6:93-101) and use of a cysteine residue, a marker peptide and a C-terminal polyhistidine tag to make bivalent and biotinylated scFv molecules. Kipriyanov, et al. (1994) *Mol. Immunol.* 31:1047-1058. Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Antibodies may be polyclonal, monoclonal, xenogeneic, allogeneic, syngeneic, or modified forms thereof, e.g., humanized, chimeric, bispecific or multispecific antibodies.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. Kappa and lambda light chains refer to the two major antibody light chain isotypes. By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" refers to a molecule that provokes an immune response, e.g., an autoantigen in the case of (humoral) autoimmunity or an alloantigen in the case of transplant or an allergen in the case of an allergic condition. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated, synthesized, or can be derived from a biological sample, or might be macromolecule besides a polypeptide. Such a biological sample can include, but is not limited to a tissue sample, a tumor sample, a cell or a fluid with other biological components. In one aspect, the antigen is MCT1.

"Autoimmunity" or "autoimmune disease or condition," as used herein, refers broadly to a disease or disorder arising from and directed against an individual's own tissues or a co-segregate or manifestation thereof or resulting condition therefrom, and includes. Herein autoimmune conditions include inflammatory or allergic conditions, e.g., chronic diseases characterized by a host immune reaction against self-antigens potentially associated with tissue destruction such as rheumatoid arthritis.

The term "autologous" refers to any material derived from the same individual to whom it is later to be re-introduced.

"AZ3965" is used herein to refer collectively to AZ3965 and its analogues with the same binding affinity, PK and MCT1/2 selectivity. (REF. 50)

The term "bind" refers to an attractive interaction between two molecules that results in a stable association in which the molecules are in close proximity to each other. The result of molecular binding is sometimes the formation of a molecular complex in which the attractive forces holding the components together are generally non-covalent, and thus are normally energetically weaker than covalent bonds.

"Cancer," as used herein, refers broadly to any neoplastic disease (whether invasive or metastatic) characterized by abnormal and uncontrolled cell division causing malignant growth or tumor (e.g., unregulated cell growth). The term "cancer" or "cancerous" as used herein should be understood to encompass any neoplastic disease (whether invasive, non-invasive or metastatic) which is characterized by abnormal and uncontrolled cell division causing malignant growth or tumor, non-limiting examples of which are described herein. This includes any physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblasts leukemia; multiple myeloma and post-transplant lymphoproliferative disorder (PTLD). Other cancers amenable for treatment by the present invention include, but are not limited to, carcinoma, lymphoma, blastoma, sarcoma, and leukemia or lymphoid malignancies. The cancerous conditions amenable for treatment of the invention include cancers that express MCT1.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) *Sequences of Proteins of Immunological Interest National Institutes of Health*, Bethesda, Md. These expressions include the hypervariable regions as defined by Kabat, et al. (1983) *Sequences of Proteins of Immunological Interest*, U. S. Dept. of Health and Human Services or the hypervariable loops in 3-dimensional structures of antibodies. Chothia and Lesk (1987) *J. Mol. Biol.* 196:901-917. The CDRs in each chain are held in close proximity by framework regions and, with the CDRs from the other chain, contribute to the formation of the antigen-binding site. Within the CDRs there are select amino acids that have been described as the selectivity determining regions (SDRs) which represent the critical contact residues used by the CDR in the antibody-antigen interaction. (Kashmiri *Methods* 36:25-34 (2005)).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein. In some embodiments, the antibody of the invention may compete or cross-compete with MCT1 Ab1 for binding to MCT1.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The term "cytokines" refers to a broad category of small proteins that are involved in cell signaling. Generally, their release has some effect on the behavior of cells around them. Cytokines may be involved in autocrine signalling, paracrine signalling and/or endocrine signalling as immunomodulating agents. Cytokines include chemokines, interferons, interleukins, lymphokines, and tumour necrosis factors. Cytokines are produced by a broad range of cells, including immune cells like macrophages, B lymphocytes, T lymphocytes and mast cells, as well as endothelial cells, fibroblasts, and various stromal cells. "Chemokines" are a family of cytokines generally involved in mediating chemotaxis.

The phrase "disease associated with expression of MCT1" includes, but is not limited to, a disease associated with expression of MCT1 or condition associated with cells which express MCT1 including, e.g., autoimmune diseases such as lupus; or a cancerous or noncancerous indication associated with cells which express MCT1.

The term "$EC_{50}$" as used herein refers to the dose of a test compound, e.g., anti-MCT1 antibody or antigen-binding fragment thereof, which produces 50% of its maximum response or effect in an assay.

An "effective amount" or "an amount effective to treat" refers to a dose that is adequate to prevent or treat a disease, condition, or disorder in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive antibodies in each or various rounds of administration.

An "epitope" or "binding site" is an area or region on an antigen to which an antigen-binding peptide (such as an antibody) specifically binds. A protein epitope may comprise amino acid residues directly involved in the binding (also called immunodominant component of the epitope) and other amino acid residues, which are not directly involved in the binding, such as amino acid residues that are effectively blocked by the specifically antigen binding peptide (in other words, the amino acid residue is within the "footprint" of the specifically antigen binding peptide). The term epitope herein includes both types of amino acid binding sites in any particular region of MCT1 that specifically binds to an anti-MCT1 antibody. MCT1 may comprise a number of different epitopes, which may include, without limitation, (1) linear peptide antigenic determinants, (2) conformational antigenic determinants that consist of one or more noncontiguous amino acids located near each other in a mature MCT1 conformation; and (3) post-translational antigenic determinants that consist, either in whole or part, of molecular structures covalently attached to a MCT1 protein such as carbohydrate groups. In particular, the term "epitope" includes the specific residues in a protein or peptide, e.g., MCT1, which are involved in the binding of an antibody to such protein or peptide as determined by known and accepted methods such as alanine scanning techniques. Such methods are exemplified herein.

An "expression vector" herein refers to DNA vectors containing elements that facilitate manipulation for the expression of a foreign protein within the target host cell, e.g., a bacterial, insect, yeast, plant, amphibian, reptile, avian, or mammalian cell, and most typically a yeast or mammalian cell, e.g., a CHO cell. Conveniently, manipulation of sequences and production of DNA for transformation is first performed in a bacterial host, e.g. E. coli, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Stearns, T., Methods in yeast genetics: a Cold Spring Harbor Laboratory course manual, Plainview, NY: Cold Spring Harbor Laboratory Press (2000). Expression vectors for use in the methods of the invention may include yeast or mammalian specific sequences, including a selectable auxotrophic or drug marker for identifying transformed host strains. A drug marker may further be used to amplify copy number of the vector in a yeast host cell.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody or antigen-binding fragment can be within the cytoplasm of the cell, and/or into the extracellular milieu such as the growth medium of a cell culture.

The terms "Fc receptor" and "FcR" describe a receptor that binds to the Fc region of an antibody. The preferred FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, *Ann. Rev. Immunol.*, 9:457-92 (1991); Capel et al., Immunomethods, 4:25-34 (1994); and de Haas et al, *J. Lab. Clin. Med.*, 126:330-41 (1995). "FcR" also includes the neonatal receptor, FcRn, which is responsible for the transfer of maternal IgGs to the fetus (Guyer et al, *J. Immunol.*, 117:587 (1976); and Kim et al., *J. Immunol.*, 24:249 (1994)), and which primarily functions to modulate and/or extend the half-life of antibodies in circulation. To the extent that the disclosed anti-MCT1 antibodies are aglycosylated, as a result of the expression system and/or sequence, the subject antibodies are expected to bind FcRn receptors, but not to bind (or to minimally bind) Fcγ receptors.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al, *Sequences of Proteins of Immunological Interest,* 5th edition, Bethesda, MD: U.S. Dept. of Health and Human Services, Public Health Service, National Institutes of Health (1991). The Fc region of an immunoglobulin generally comprises two constant domains, CH2 and CH3.

The expressions "framework region" or "FR" refer to one or more of the framework regions within the variable regions of the light and heavy chains of an antibody (See Kabat et al, *Sequences of Proteins of Immunological Interest, 4th* edition, Bethesda, MD: U.S. Dept. of Health and Human Services, Public Health Service, National Institutes of Health (1987)). These expressions include those amino acid sequence regions interposed between the CDRs within the variable regions of the light and heavy chains of an antibody.

A "functional Fc region" possesses at least one effector function of a native sequence Fc region. Exemplary "effector functions" include C1q binding; complement dependent cytotoxicity ("CDC"); Fc receptor binding; antibody-dependent cell-mediated cytotoxicity ("ADCC"); phagocytosis; down-regulation of cell surface receptors (e.g. B cell receptor ("BCR")), etc. Such effector functions generally require the Fc region to be combined with a binding domain (e.g. an antibody variable domain) and can be assessed using various assays known in the art for evaluating such antibody effector functions. A "native sequence Fc region" comprises an amino acid sequence identical to the amino acid sequence of an Fc region found in nature. A "variant Fc region" comprises an amino acid sequence that differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and e.g., from about one to about five amino acid substitutions in a native sequence Fc region or in the Fc region of the parent polypeptide. The variant Fc region herein will e.g., possess at least about 80% sequence identity with a native sequence Fc region and/or with an Fc region of a parent polypeptide, and most e.g., at least about 90% sequence identity therewith, more e.g., at least about 95%, at least about 96%, at least about 97%, at least about 98%, or at least about 99% sequence identity therewith.

"Graft versus Host Disease" (GVHD): as used herein refers to a common complication of allogeneic bone marrow transplantation or hematopoietic stem cells transplantation in which functional immune cells in the transplanted marrow recognize the recipient as "foreign" and produce an immune response to the host tissue. According to the 1959 Billingham Criteria, there are three criteria must be met in order for GVHD to occur: 1) Administration of an immunocompetent graft, with viable and functional immune cells; 2) the recipient is immunologically histocompatible; 3) The recipient is immunocompromised and therefore cannot destroy or inactivate the transplanted cells. Clinically, graft-versus-host-disease is divided into acute and chronic forms. The acute or fulminant form of the disease (aGVHD) is normally observed within the first 100 days post-transplant, and is a major challenge to the effectiveness of transplants owing to the associated morbidity and mortality. The chronic form of graft-versus-host-disease (cGVHD) normally occurs after 100 days. The appearance of moderate to severe cases of cGVHD adversely influences long-term survival. After bone marrow transplantation, T cells present in the graft, either as contaminants or intentionally introduced into the host, attack the tissues of the transplant recipient after perceiving host tissues as antigenically foreign. The T cells produce an excess of cytokines, including TNFα and interferon-gamma (IFNγ). A wide range of host antigens can initiate graft-versus-host-disease, among them the human leukocyte antigens (HLAs). However, graft-versus-host disease can occur even when HLA-identical siblings are the donors. Classically, acute graft-versus-host-disease is characterized by selective damage to the liver, skin and mucosa, and the gastrointestinal tract. Additional studies show that that graft-versus-host-disease targets organs including the immune system (such as the bone marrow and the thymus) itself, and the lungs in the form of idiopathic pneumonitis. Chronic graft-versus-host-disease also attacks the above organs, but over its long-term course can also cause damage to the connective tissue and exocrine glands.

"Host cell," as used herein, refers broadly to a cell into which a nucleic acid molecule of the invention, such as a recombinant expression vector of the invention, has been introduced. Host cells may be prokaryotic cells (e.g., *E. coli*), or eukaryotic cells such as yeast, insect (e.g., SF9), amphibian, or mammalian cells such as CHO, HeLa, HEK-293, e.g., cultured cells, explants, and cells in vivo. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, progeny may not, in fact, be identical to the parent cell, but are still included within the scope of the term as used herein.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., *Nature Biotechnology*, 14:309-314, 1996; Sheets et al., *Proc. Natl. Acad. Sci.* (USA) 95:6157-6162, 1998; Hoogenboom and Winter, *J. Mol. Biol.*, 227:381, 1991; Marks et al., *J. Mol. Biol.*, 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. *Monoclonal Antibodies and Cancer Therapy*, Alan R. Liss, p. 77, 1985; Boerner et al., *J. Immunol.*, 147 (1):86-95, 1991; and U.S. Pat. No. 5,750,373.

"Human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell. This includes fully human monoclonal antibodies and conjugates and variants thereof, e.g., which are bound to effector agents such as therapeutics or diagnostic agents.

"Humanized antibody," as used herein, broadly includes antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences. The term "humanized antibody", as used herein, also includes affinity-matured antibodies which are both humanized and affinity-matured, e.g., in order to enhance the binding of the antibody to MCT1 or another target antigen.

The term "IC$_{50}$" as used herein refers to the dose of a test compound, e.g., anti-MCT1 antibody or antigen-binding fragment thereof, which produces 50% inhibition in a biochemical assay.

"Inflammatory disorders", "inflammatory conditions" and/or "inflammation", used interchangeably herein, refers broadly to chronic or acute inflammatory diseases, and expressly includes inflammatory autoimmune diseases and inflammatory allergic conditions. These conditions include by way of example inflammatory abnormalities characterized by dysregulated immune response to harmful stimuli, such as pathogens, damaged cells, or irritants. Inflammatory disorders underlie a vast variety of human diseases. Non-immune diseases with etiological origins in inflammatory processes include cancer, atherosclerosis, and ischemic heart disease. Examples of disorders associated with inflammation include: chronic prostatitis, glomerulonephritis, hypersensitivities, pelvic inflammatory disease, reperfusion injury, sarcoidosis, vasculitis, interstitial cystitis, normocomplementemic urticarial vasculitis, pericarditis, myositis, antisynthetase syndrome, scleritis, macrophage activation syndrome, Behget's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, hyper IgD syndrome, Schnitzler's syndrome, TNF receptor-associated periodic syndrome (TRAPSP), gingivitis, periodontitis, hepatitis, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

The term "inhibitor" as used herein refers to a compound that binds to a target and renders it biologically inactive or less active. In a particular embodiment, the compound is an anti-MCT1 antibody or antigen-binding fragment thereof. In some embodiments, the inhibitory effect of the compound is measured via inhibition of MCT1-mediated lactate transport.

An "isolated" biological component (such as an isolated antibody or cell or vector or protein or nucleic acid) refers to a component that has been substantially separated or purified away from its environment or other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis. An isolated nucleic acid or protein can exist in substantially purified form, or can exist in a non-native environment such as, for example, a host cell.

"Isolated antibody", as used herein, is intended to refer to an antibody that is substantially free of other antibodies having different antigenic specificities (e.g., an isolated antibody that specifically binds MCT1 is substantially free of antibodies that specifically bind antigens other than MCT1). Moreover, an isolated antibody may be substantially free of other cellular material and/or chemicals.

"Label" or a "detectable moiety" as used herein, refers broadly to a composition detectable by spectroscopic, photochemical, biochemical, immunochemical, chemical, or other physical means.

"Lupus", as used herein, is intended to include all types of lupus. There are 4 types of lupus which are discussed below. "Lupus-like condition", as used herein, is intended to include inflammatory conditions with symptoms similar to lupus such as kidney inflammation, increased proteinuria, and splenomegaly. "Systemic Lupus Erythematosus" or ("SLE") the most common form of lupus which can be mild or severe and can affect major organ systems. This is the condition most people associate with "lupus". It is an autoimmune condition of unknown cause that may result in inflammation of the kidneys—called lupus nephritis—which can affect the body's ability to filter waste from the blood, and or if severe may result in kidney damage requiring dialysis or kidney transplant. Also SLE may result in an increase in blood pressure in the lungs—called pulmonary hypertension—can cause difficulty breathing. Further SLE may cause Inflammation of the nervous system and brain which can cause memory problems, confusion, headaches, and strokes. Further SLE may result in inflammation in the brain's blood vessels which can cause high fevers, seizures, and behavioral changes. Also SLE may result in hardening of the arteries or coronary artery disease—the buildup of deposits on coronary artery walls—can lead to a heart attack. "Skin Lupus" herein refers to lupus conditions that only affect the skin. There are three types of lupus that affect the skin chronic cutaneous lupus erythematosus (CCLE) (also known as Discoid Lupus Erythematosus [DLE]), subacute cutaneous lupus erythematosus (SCLE), and tumid lupus. Cutaneous Lupus Erythematosus or Discoid Lupus Erythematosus can cause many types of rashes and lesions (sores), the most common—called discoid rash—is raised, scaly and red, but not itchy. Areas of rash appear like disks, or circles. Another common example of cutaneous lupus is a rash over the cheeks and across the bridge of the nose, known as the butterfly rash. Other rashes or sores may appear on the face, neck, or scalp (areas of the skin that are exposed to sunlight or fluorescent light), or in the mouth, nose, or vagina. Hair loss and changes in the pigment, or color, of the skin are also symptoms of cutaneous lupus. Approximately 10 percent of people who have cutaneous lupus will develop systemic lupus. However, it is likely that these people already had systemic lupus, with the skin rash as their main symptom. "Drug-induced Lupus Erythematosus" is a condition caused by certain drugs which can cause lupus-like symptoms in people who do not have SLE. Generally, this form of lupus is temporary and usually subsides within months of the time that the medication is stopped. Medications known to induce lupus-like symptoms include the blood pressure medications hydralazine and methyldopa, a heart medication called procainamide, and a drug called D-penicillamine, which is used in cases of metal poisoning. Other causes of drug-induced lupus include minocycline (used to treat acne), Isoniazid—a treatment for tuberculosis and anti-TN F (used to treat rheumatoid arthritis). The symptoms of drug-induced lupus are similar to those of systemic lupus, however unlike SLE but it rarely affects major organs. Neonatal lupus is not a true form of lupus. It is a rare condition that affects infants of women who have lupus and is caused by antibodies from the mother acting upon the infant in the womb. At birth, the infant may have a skin rash, liver problems, or low blood cell counts but these symptoms generally disappear completely after several months with no lasting effects. Some infants with neonatal lupus can also have a serious heart defect.

"MCT1" is a proton-coupled monocarboxylate transporter. MCT1 is a multipass transmembrane protein responsible for the facilitated transport of critical metabolites, including products of glycolysis. It catalyzes the rapid transport across the plasma membrane of many monocarboxylates such as lactate, pyruvate, branched-chain oxo acids derived from leucine, valine and isoleucine, and the ketone bodies acetoacetate, beta-hydroxybutyrate and acetate. Depending on the tissue and on circumstances, MCT1 mediates the import or export of lactic acid and ketone bodies. MCT1 is a member of one of the largest family of surface membrane proteins, known as solute channel proteins (SLCs), whose functions involve the transport across membranes of critical cellular nutrients, metabolites, ions, hormones and lipids. MCT1 belongs to the SLC16 family of transporters, five of which have been shown to transport monocarboxylates, such as pyruvate, lactate and ketones in a facilitated, pH dependent and bidirectional manner. MCT1 may also be referred to by any of the following names: monocarboxylate transporter 1, SLC16A1, HHF7, MCT, MCT1, MCT1D, solute carrier family 16 member 1. In humans, it is encoded by the SLC16A1 gene.

"MCT2" is a proton-coupled monocarboxylate transporter. It catalyzes the rapid transport across the plasma membrane of many monocarboxylates such as lactate, pyruvate, branched-chain oxo acids derived from leucine, valine and isoleucine, and the ketone bodies acetoacetate, beta-hydroxybutyrate and acetate. It also functions as high-affinity pyruvate transporter. MCT2 may also be referred to by any of the following names: monocarboxylate transporter 2, SLC16A7, MCT2, solute carrier family 16 member 7. In humans, it is encoded by the SLC16A7 gene.

"MCT3" is a proton-coupled monocarboxylate transporter. It catalyzes the rapid transport across the plasma membrane of many monocarboxylates such as lactate, pyruvate, branched-chain oxo acids derived from leucine, valine and isoleucine, and the ketone bodies acetoacetate, beta-hydroxybutyrate and acetate. It also functions as high-affinity pyruvate transporter. Expression of MCT3 is confined to the retinal pigment epithelium and choroid plexus epithelia, where it is located on the basal membrane in contrast to MCT1 which is found on the apical membrane. MCT3 may also be referred to by any of the following names: monocarboxylate transporter 3, SLC16A8, MCT3, REMP, solute carrier family 16 member 8. In humans, it is encoded by the SLC16A8 gene.

"MCT4" is a proton-coupled monocarboxylate transporter. MCT4 may also be referred to by any of the following names: monocarboxylate transporter 4, SLC16A3, MCT 3, MCT 4, MCT-3, MCT-4, MCT3, MCT4, solute carrier family 16 member 3. In humans, it is encoded by the SLC16A3 gene.

"Multispecific antibody" or "multispecific antigen-binding protein" refers to a polypeptide or antibody with 2 or more antigen binding regions. This includes bispecific antibodies. These antigen binding regions may bind to different antigens or to different epitopes of the same antigen.

The term "nucleic acid" and "polynucleotide" refer to RNA or DNA that is linear or branched, single or double stranded, or a hybrid thereof. The term also encompasses RNA/DNA hybrids. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support. The polynucleotides can be obtained by chemical synthesis or derived from a microorganism. The term "gene" is used broadly to refer to any segment of polynucleotide associated with a biological function. Thus, genes include introns and exons as in genomic sequence, or just the coding sequences as in cDNAs and/or the regulatory sequences required for their expression. For example, gene also refers to a nucleic acid fragment that expresses mRNA or functional RNA, or encodes a specific protein, and which includes regulatory sequences.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (GATEWAY11 Technology; Invitrogen, Carlsbad California). If such sites do not exist, the synthetic oligonucleotide adapters or linkers are used in accordance with conventional practice.

A "pharmaceutically acceptable carrier" or "excipient" refers to compounds or materials conventionally used in pharmaceutical compositions during formulation and/or to permit storage.

"Polypeptide," "peptide" and "protein," are used interchangeably and refer broadly to a polymer of amino acid residues s of any length, regardless of modification (e.g., phosphorylation or glycosylation). The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" expressly include glycoproteins, as well as non-glycoproteins.

The term "promoter", as used herein, is defined as a DNA sequence recognized by the synthetic machinery of the cell, or introduced synthetic machinery, required to initiate the specific transcription of a polynucleotide sequence.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Recombinant" as used herein, refers broadly to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo A "selectable marker" herein refers to a gene or gene fragment that confers a growth phenotype (physical growth characteristic) to a cell receiving that gene as, for example through a transformation event. The selectable marker allows that cell to survive and grow in a selective growth medium under conditions in which cells that do not receive that selectable marker gene cannot grow. Selectable marker genes generally fall into several types, including positive selectable marker genes such as a gene that confers on a cell resistance to an antibiotic or other drug, temperature when two temperature sensitive ("ts") mutants are crossed or a ts mutant is transformed; negative selectable marker genes such as a biosynthetic gene that confers on a cell the ability to grow in a medium without a specific nutrient needed by all cells that do not have that biosynthetic gene, or a mutagenized biosynthetic gene that confers on a cell inability to grow by cells that do not have the wild type gene; and the like. Suitable markers include but are not limited to: ZEO; G418; LYS3; MET1; MET3a; ADE1; ADE3; URA3; and the like.

"Subject" or "patient" or "individual" in the context of therapy or diagnosis herein includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc., i.e., anyone suitable to be treated according to the present invention include, but are not limited to, avian and mammalian subjects, and are e.g., mammalian. Any mammalian subject in need of being treated according to the present invention is suitable. Human subjects of both genders and at any stage of development (i. e., neonate, infant, juvenile, adolescent, and adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "individuals" and "patients."

The phrase that an antibody (e.g., first antibody) binds "substantially" or "at least partially" the same epitope as another antibody (e.g., second antibody) means that the epitope binding site for the first antibody comprises at least 10%, 20%, 30%, 40%, 50%, 60%, 70%, 80%, 90%, or more of the amino acid residues on the antigen that constitutes the epitope binding site of the second antibody. Also, that a first antibody binds substantially or partially the same or overlapping epitope as a second antibody means that the first and second antibodies compete in binding to the antigen, as described above. Thus, the term "binds to substantially the same epitope or determinant as" a monoclonal antibody means that an antibody "competes" with the antibody. The phrase "binds to the same or overlapping epitope or determinant as" an antibody of interest means that an antibody "competes" with said antibody of interest for at least one, (e.g., at least 2, at least 3, at least 4, at least 5) or all residues on MCT1 to which said antibody of interest specifically binds. The identification of one or more antibodies that bind(s) to substantially or essentially the same epitope as the monoclonal antibodies described herein can be readily determined using alanine scanning. Additionally, any one of variety of immunological screening assays in which antibody competition can be assessed. A number of such assays are routinely practiced and well known in the art (see, e.g., U.S. Pat. No. 5,660,827, issued Aug. 26, 1997, which is specifically incorporated herein by reference). It will be understood that actually determining the epitope to which an antibody described herein binds is not in any way required to identify an antibody that binds to the same or substantially the same or overlapping epitope as the monoclonal antibody described herein.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., inflammation, pain). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., inflammation, pain). Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., inflammation, pain).

"Treg cell" (sometimes also referred to as suppressor T cells or inducible Treg cells or iTregs) as used herein refers to a subpopulation of T cells which modulate the immune system and maintain tolerance to self-antigens and can abrogate autoimmune diseases. Foxp3$^+$ CD4$^+$CD25$^+$ regulatory T cells (Tregs) are critical in maintaining peripheral tolerance under normal conditions.

The term "Tr1 cell" herein refers to a specific type or population of regulatory T cells, i.e., Type 1 regulatory T cells (Tr1) which comprise CD4$^+$ Foxp3$^-$ cells that express high levels of IL-10, which generally are characterized in the scientific literature based on their expression of CD49b and LAG-3. These cells are further characterized by their ability to secrete IL-10, TGF-β, and granzyme (Gz) B, in the absence of IL-4 and IL-17. The chief mechanisms by which Tr1 cells reportedly control immune responses comprise the secretion of IL-10 and TGF-β and killing of myeloid cells via GzB. Tr1 cells, were first observed in peripheral blood of patients who developed tolerance after HLA-mismatched fetal liver hematopoietic stem cell transplantation, have been reported to modulate inflammatory and effector T cell responses in several immune-mediated diseases. These cells may be generated and expanded in vitro in an Ag-specific manner which has led to their being evaluated for potential clinical use in cell therapy in treating patients with autoimmune conditions such as type 1 diabetes and multiple sclerosis.

"Variable region" or "VR," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

A "vector" is a replicon, such as a plasmid, phage, cosmid, or virus in which a nucleic acid segment may be operably inserted so as to bring about the replication or expression of the segment. The vector may contain one or more additional sequences such as, but not limited to, regulatory sequences (e.g., promoter, enhancer), a selection marker, and a polyadenylation signal. Vectors for transforming a wide variety of host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. The vectors described herein may be integrated into the host genome or maintained independently in the cell or nucleus.

The term "xenogeneic" refers to a graft derived from an animal of a different species.

Having described the invention the following examples are provided to further demonstrate the invention and its inherent advantages. The following examples are offered to illustrate, but not to limit, the claimed invention.

EXAMPLES

Example 1: Differential Expression of MCTs on T Cells

Materials and Methods

The SM compound AZ3965 (MedChem Express, NJ) and its related analogues, which are commercially available, were used to help reveal the unique biology of the MCT1 pathway in immune cells. For clarity, we will refer to AZ396 and its analogues with the same binding affinity, PK and MCT1/2 selectivity collectively as "AZ3965".

MCT1, MCT2, MCT4, and BSG (CD147) expression were measured in unstimulated and stimulated leukocytes from two different donors. For the "stimulated" condition, cells were CD3/CD28 activated for 3 days. Stimulated cells were tested for inhibition of proliferation by AZ3965.

Results

Figure 1:
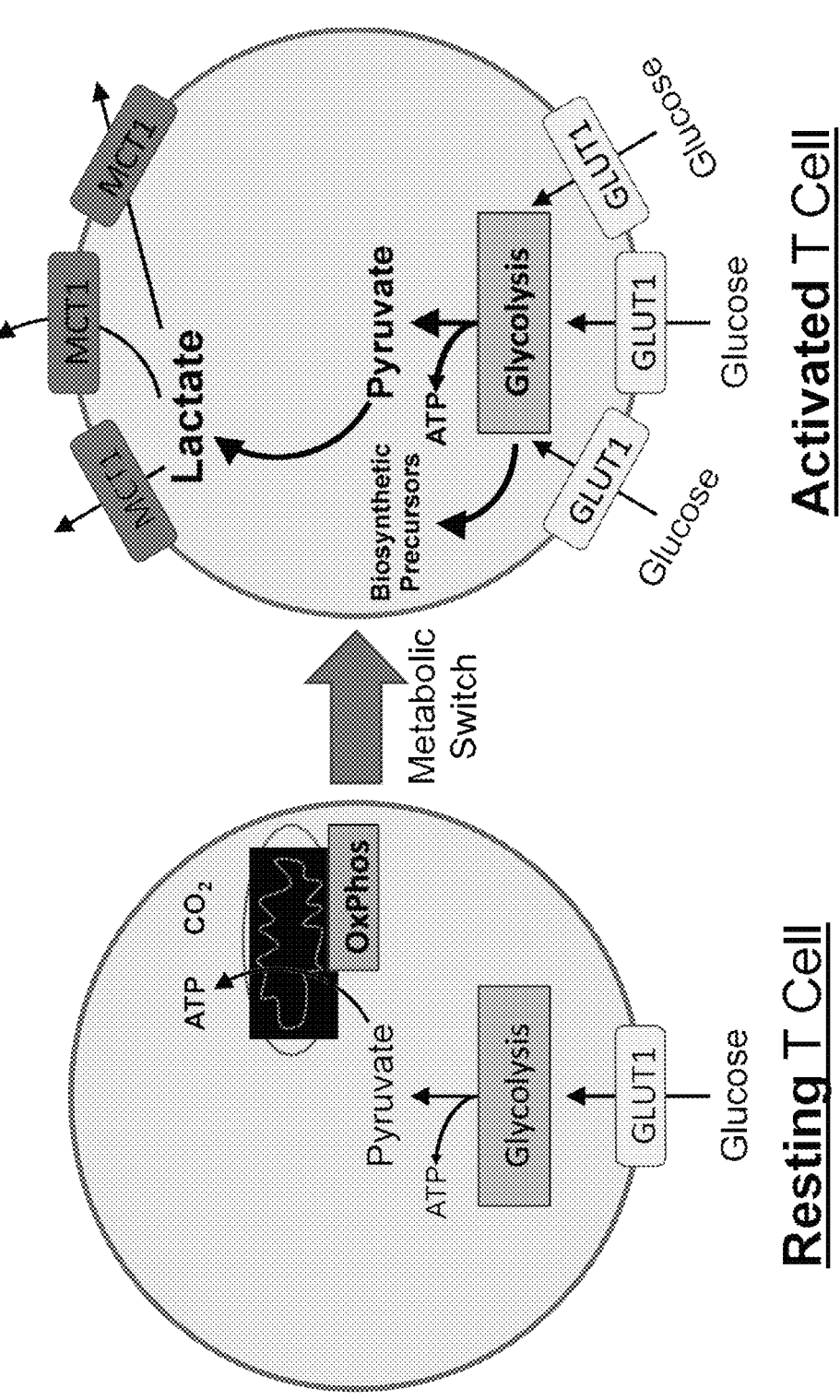
Figure 2:
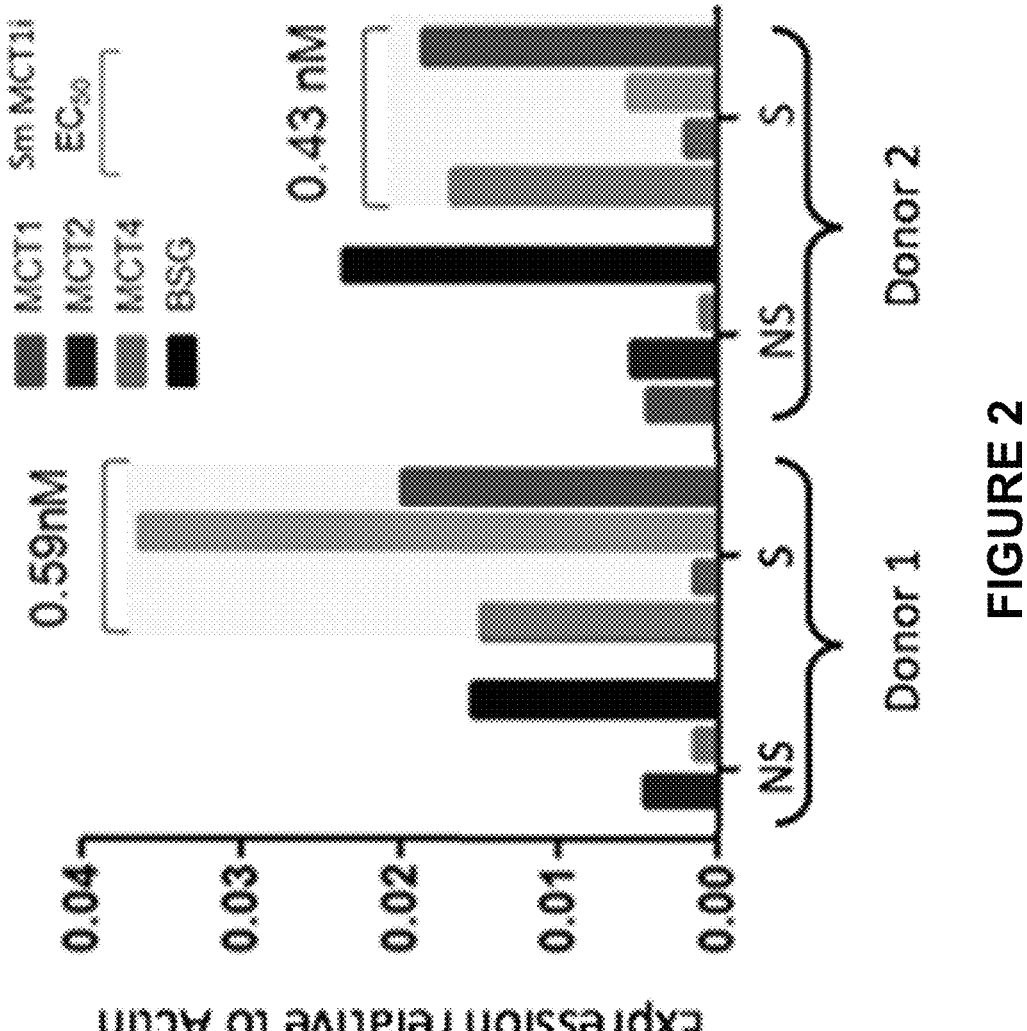

MCT1 facilitates the transfer of metabolites, including the products of glycolysis, which is more important in activated T/B cells (FIG. 1). The expression levels of MCT1, MCT2, MCT4, and BSG (CD147) for two donors are shown in FIG. 2, demonstrating that activated T cells upregulate MCT1 (also FIG. 13B) but not MCT2; neither resting nor activated T cells express MCT2 at high levels; and that across individuals, MCT4 expression in activated T cells is variable. The AZ3965 inhibition assay (results indicated on FIG. 2) shows that the $IC_{50}$ for suppression of T cell proliferation in individuals with high MCT4 expression (0.59 nM) vs. low MCT4 expression (0.43 nM) is indistinguishable. These results demonstrate that MCT4 does not significantly contribute to lactate transport in activated T cells and that MCT1-specific targeting will inhibit T cell functions even in the presence of MCT4.

Additional data shows that mouse MCT4-deficient T cells are identical to WT T cells following activation with CD3/CD28.

Figure 3:
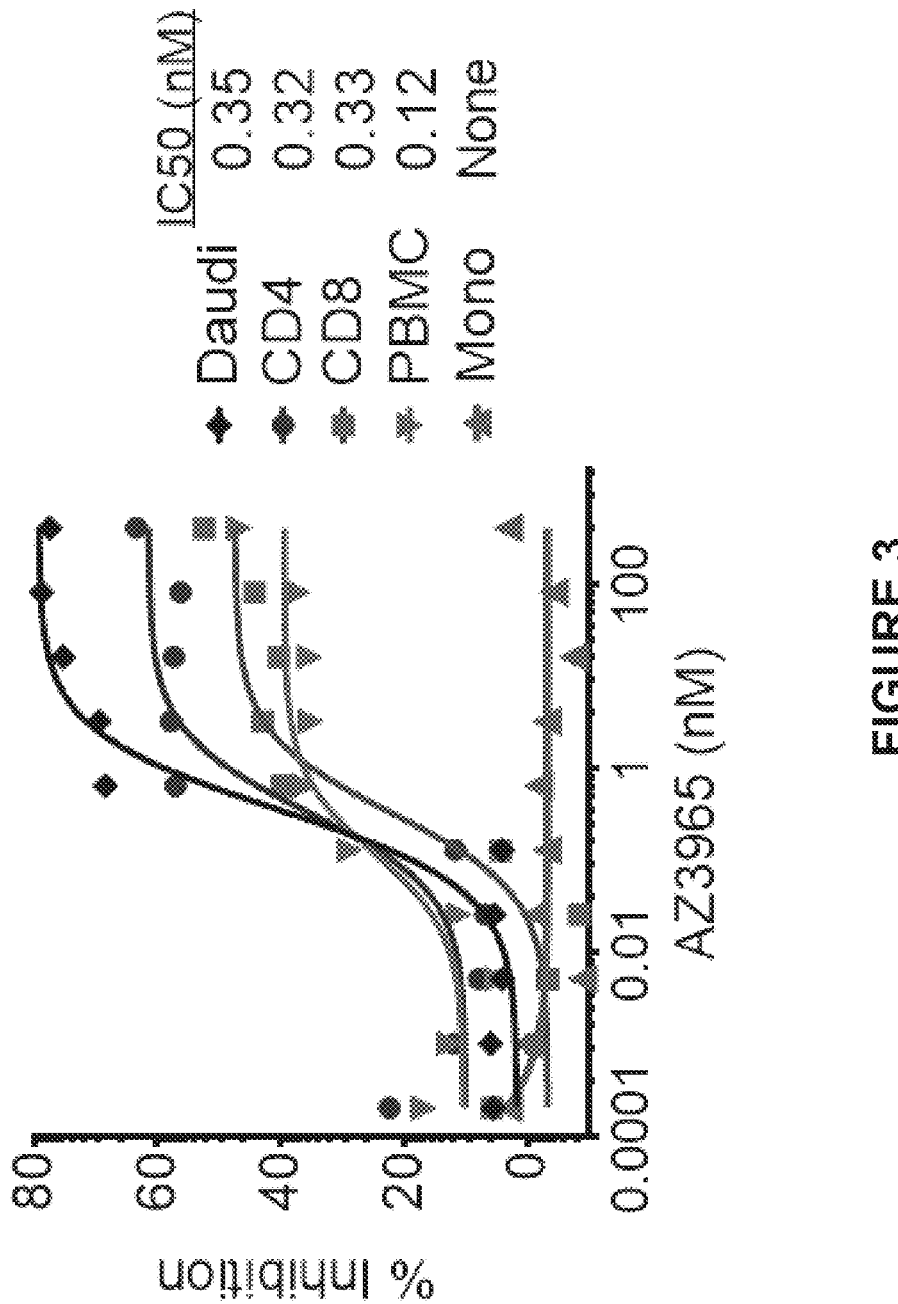

Example 2: Viability of Targeting MCT1 In Vitro and In Vivo for Inflammation/Autoimmune Disorders Verified Using AZ3965 Inhibitor In Vitro Effects on lactate transport. A lactate FLIPR assay was used to show that AZ3965 inhibits lactate transport in human T cells (both CD4[+] and CD8[+]), B cell lymphoma (Daudi), and PBMC, but not in monocytes (FIG. 3). AZ3965 inhibited lactate transport by up to 80% in affected cells, but did not affect transport in monocytes which is important for protecting innate immune responses in treated individuals.

Figure 4:
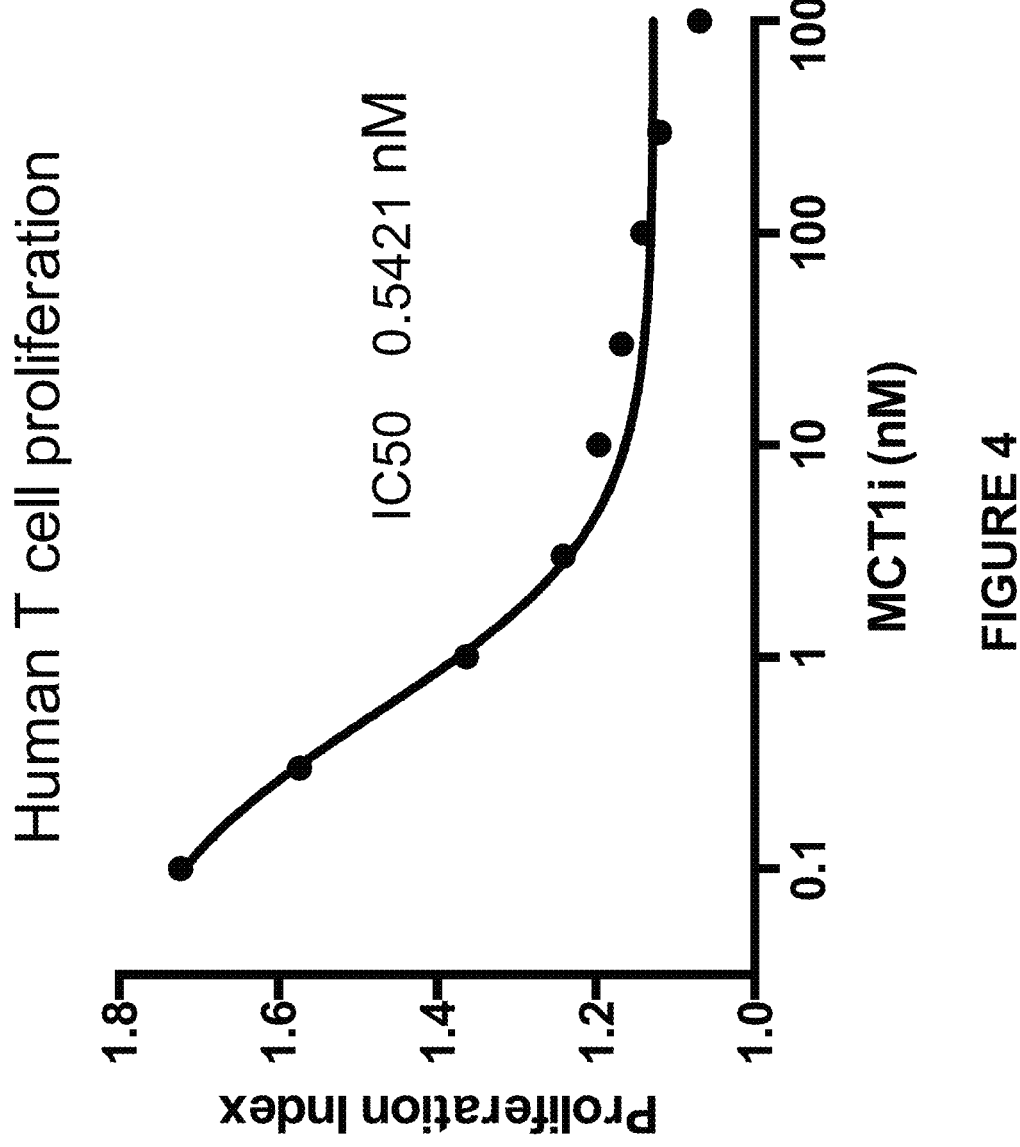

Human T cell proliferation. In a human T cell proliferation assay, MCT1 inhibitor administration reduced T cell proliferation with an $IC_{50}$ of 0.54 nM (FIG. 4).

Figure 5:
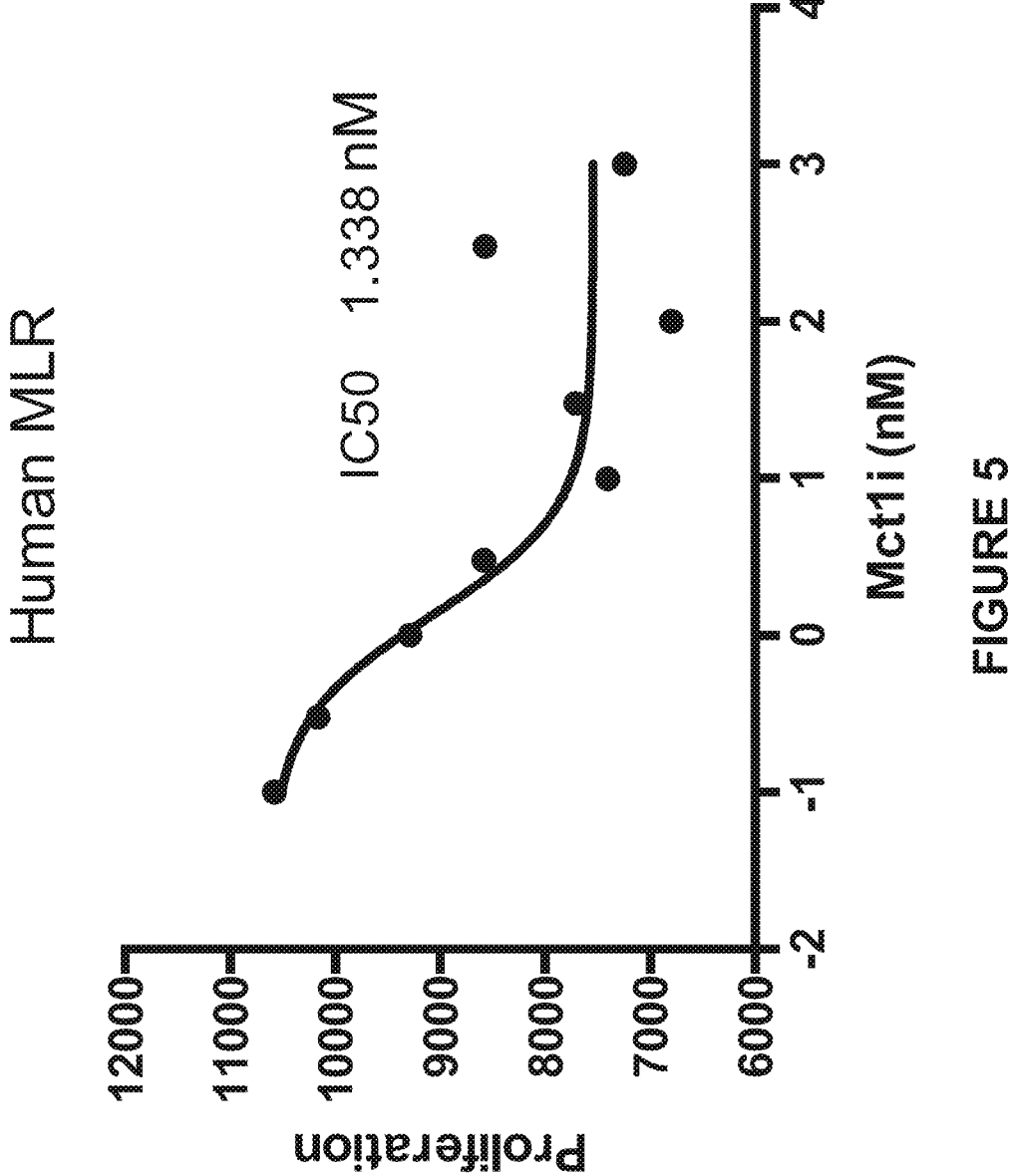

Human mixed lymphocyte reaction (MLR). In a human MLR assay, MCT1 inhibitor administration reduced T cell proliferation with an $IC_{50}$ of 1.34 nM (FIG. 5).

Figure 6:
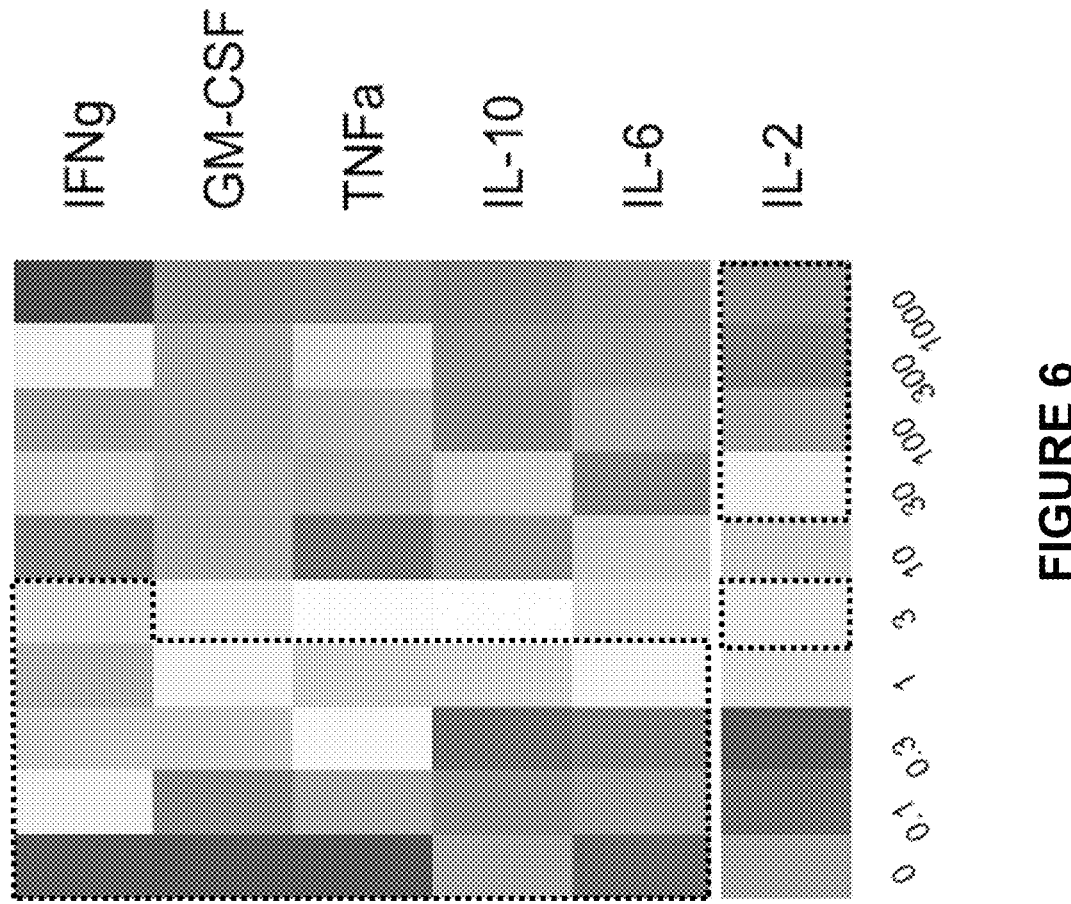
Figures 7A, 7B, 7C, 7D:
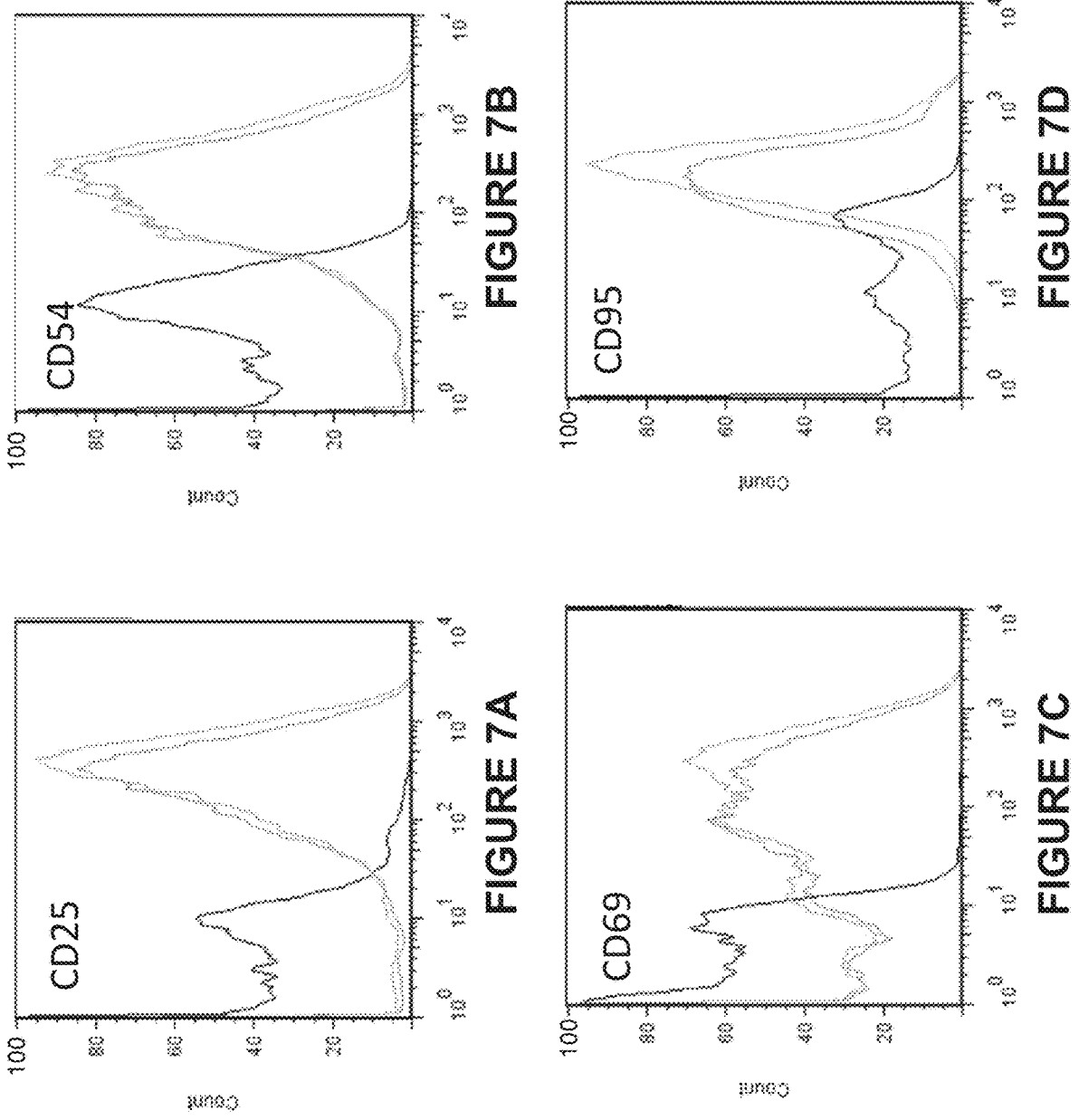
Figures 7E, 7F, 7G, 7H:
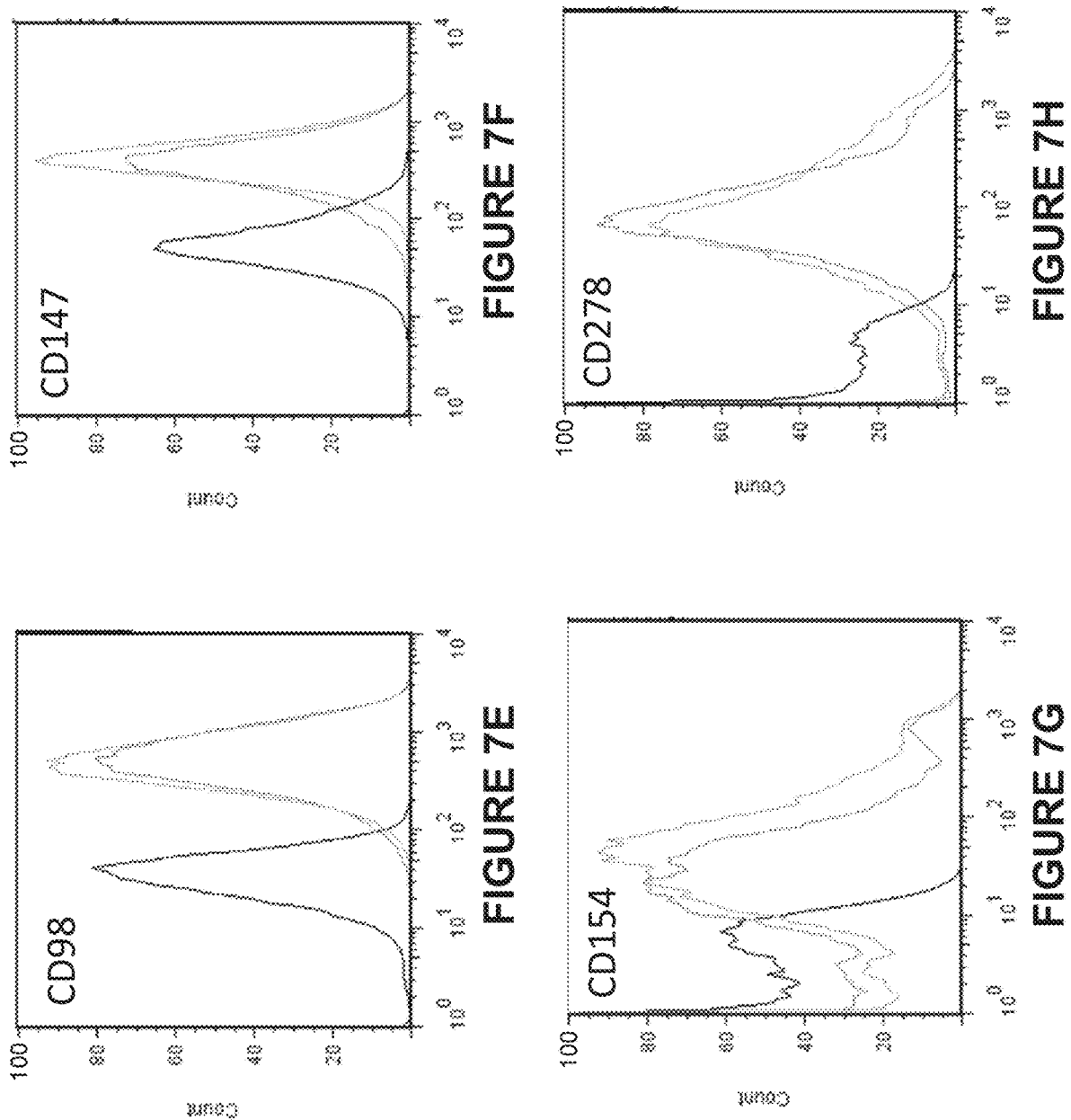
Figure 7J:
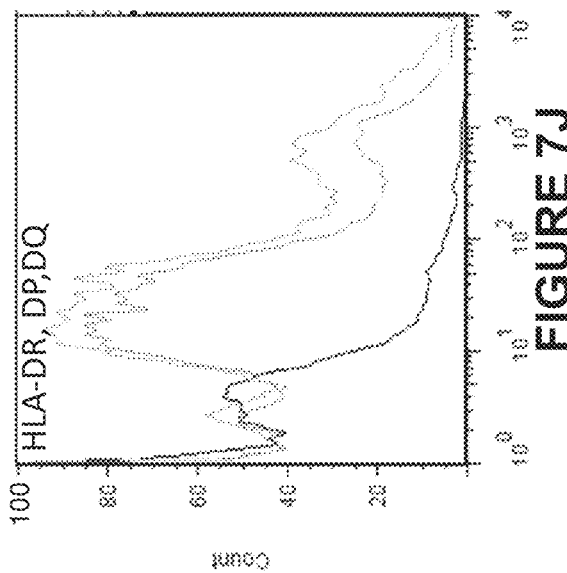
Figure 7I:
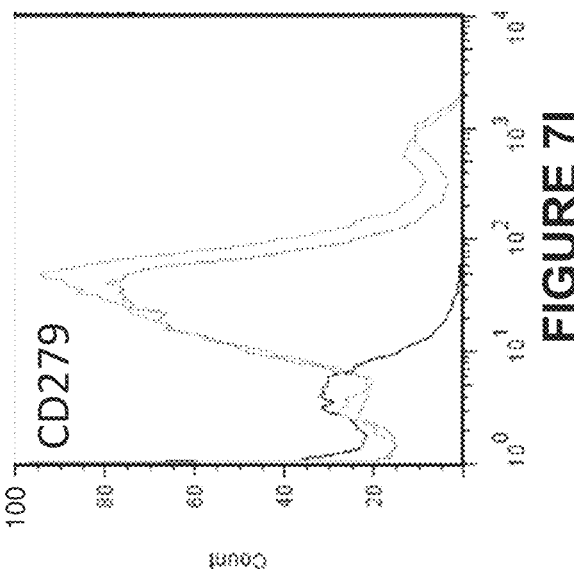

T cell cytokine secretion. T cells were CD3/CD28 activated for 5 days in vitro. Subsequent AZ3965 administration inhibited secretion of the following cytokines: IFNγ, GM-CSF, TNFα, IL-10 and IL-6 (FIG. 6).

Activation markers. CD3/CD28 activated T cells were treated for 4 days with 100 nM small molecule MCT1 inhibitor or were untreated for 4 days (untreated control). These conditions were compared to a negative (antibody non-staining) control. Over 200 CD markers were assessed via flow cytometric staining. MCT1 inhibition does not prevent T cell expression of cell surface markers (e.g., CD25, CD44, CD69, CD4, CD8, LFA, Class I/II, etc.; see FIG. 7A-J) as observed by flow cytometric staining following TCR stimulation, with the exception of slight increases in expression of surface PD1 and CTLA4. AZ3965 treatment of lymphocytes also has no impact on cell viability.

In Vivo

Figure 8:
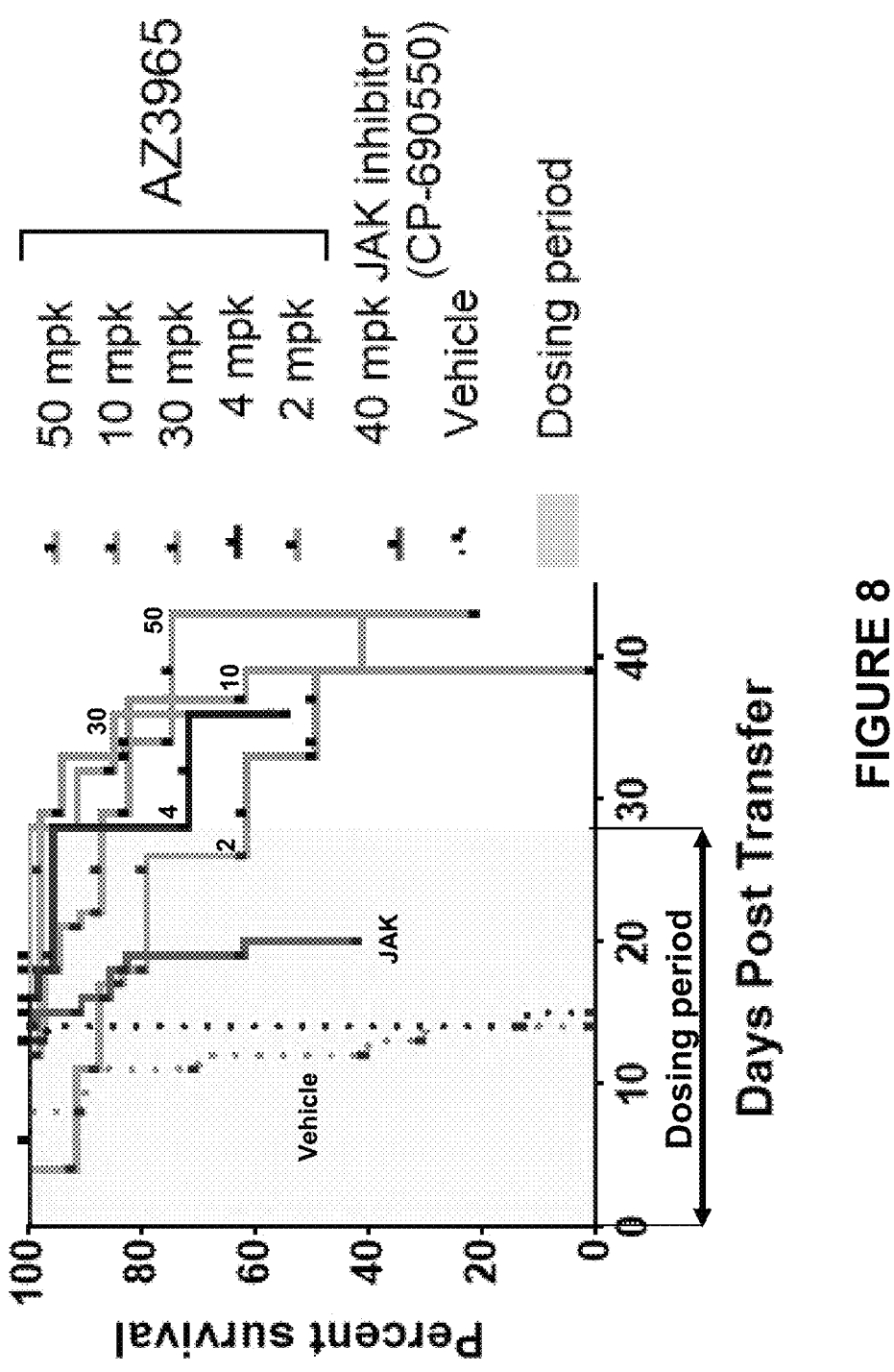
FIG. 8 shows the results of a xeno-GVHD assay with AZ3965. AZ3965 blocks GVHD morbidity until drug withdrawal and outperforms a JAK inhibitor.
Figure 9:
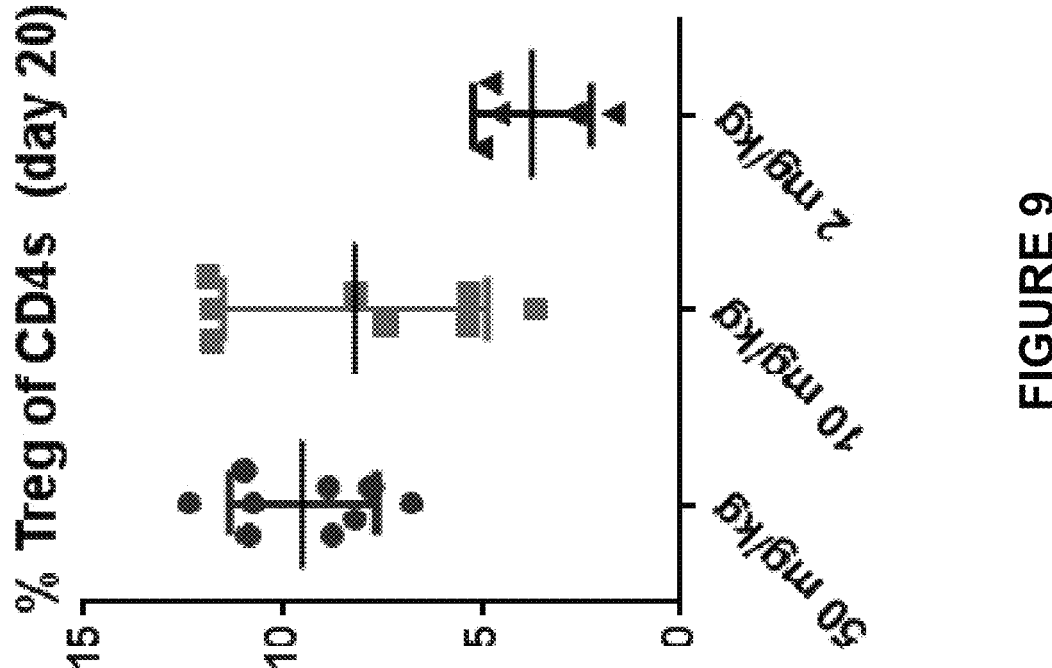
FIG. 9 shows a dose-dependent increase in the frequency of tissue Tregs for the xeno-GVHD experiment (FIG. 8) during the AZ3965 dosing period.

GVHD suppression and Treg frequency increase. Human PBMCs were transferred to immune-deficient NSG mice in a murine model of GVHD. AZ3965 administration prolonged mouse survival during xeno-GVHD in a manner superior to the JAK inhibitor CP-690550 and reduced GVHD morbidity until drug withdrawal (FIG. 8). On day 20 of this xeno-GVHD experiment, an AZ3965 dose-dependent increase in the percent of CD4[+] T cells that were regulatory T (Treg) cells was observed from 2 mg/kg (2.5% Tregs) to 50 mg/kg (10%) (FIG. 9). In this model, Tregs typically do not survive long after transfer into lymphopenic environments partly due to the inflammatory micro-environment (REF. 60-62). In another GVHD experiment, AZ3965 attenuated mouse GVHD (BALB/c→C57BL/6) as measured by CFSE-labeled T cell proliferation.

Figure 10:
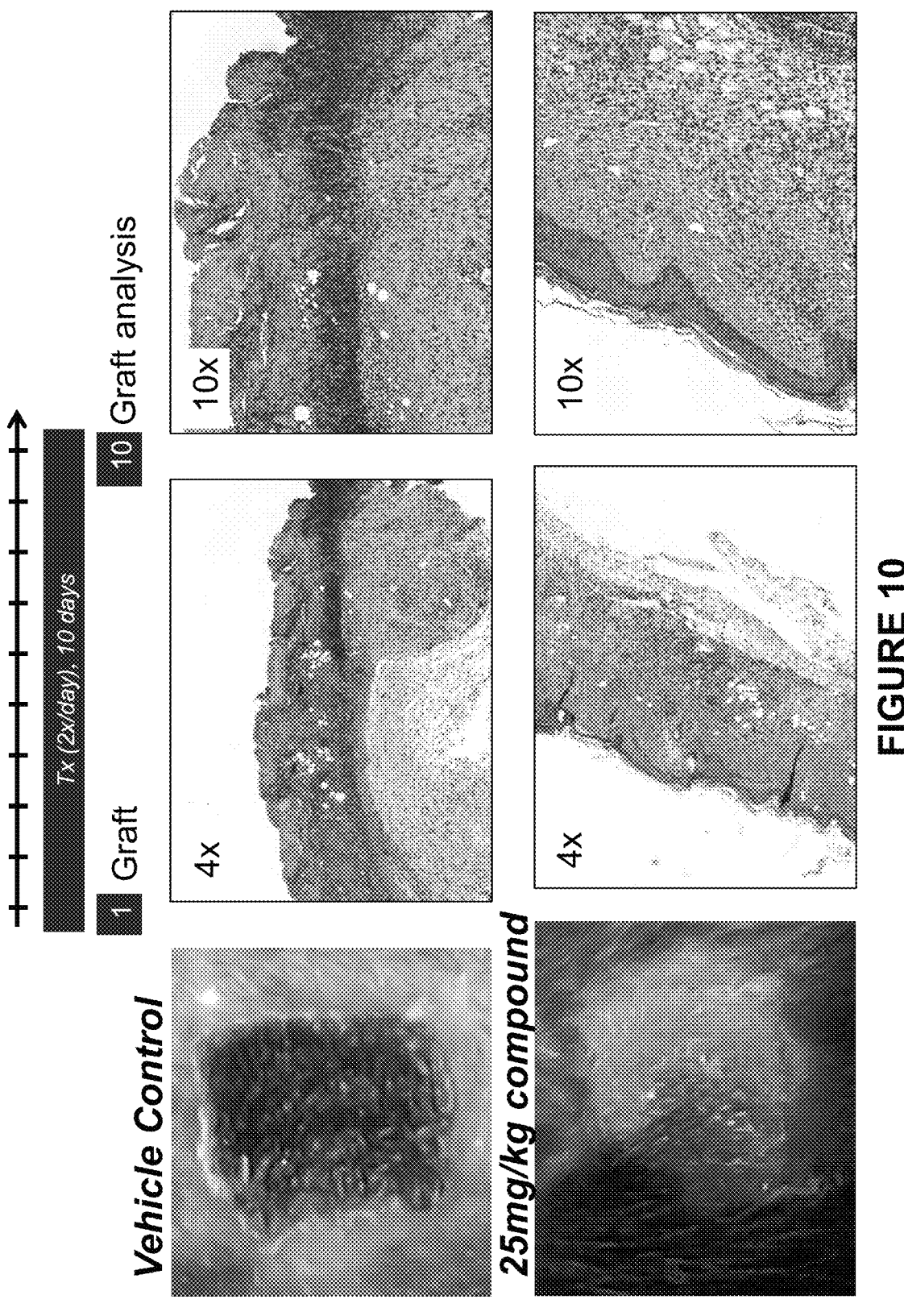
FIG. 10 shows the effects of an MCT1 small molecule inhibitor on graft rejection. Both visually and in a graft analysis on day 10, 25 mg/kg compound administration 2×/day reduced graft rejection.

Graft rejection. In a mouse allograft assay, 25 mg/kg compound administration reduced graft rejection (FIG. 10).

Inhibition of B cell IgG1 responses. AZ3965 administration (2.5 mpk/day) also inhibited B cell immunoglobulin production, as measured via IgG1 responses to sheep RBC (FIG. 11A). This administration also reduced the proportion of germinal center B cells by approximately 30% (FIG. 11B).

Increase in urine ketones. Consistent with loss of MCT1 in humans (REF. 49), mice dosed with AZ3965 showed measurable, but not adverse, increases in urine ketones without associated ketoacidosis.

Conclusions

These studies illustrate the efficacy of MCT1 inhibition in reducing both T and B cell responses, a feature important for therapeutic targeting in autoimmune diseases such as lupus. Thus, MCT1 is a viable drug target for controlling inflammation, with inhibition showing no effect on innate immunity, but profound effects on adaptive/humoral immunity.

Example 3: Development and Binding Characterization of Anti-Human MCT1 Antibody MCT1 Ab1 mAb selection. MCT1 Ab1 is a rat anti-human MCT1 monoclonal antibody that was selected following cell-based rodent immunizations and binding screens using MCT1 expressing and MCT1 knockout (KO) cell lines.

Binding affinity and MCT1 cross-reactivity. Kinetic Exclusion Assay (KinExA) analysis revealed that MCT1 Ab1 binds human MCT1 with a Kd of 6.3 nM. MCT1 Ab1 is also highly cross-reactive with cynomolgus (cyno) and rabbit MCT1, but not with rodent MCT1 (FIG. 12A-D).

Binding specificity. HEK-293 WT cells only express MCT1/CD147 and no other MCTs as measured by RT-PCR. To measure the binding specificity of an antibody of the invention, the HEK-293 MCT1/CD147 double KO cell line may be used as a negative control. Furthermore, this double KO cell line was engineered to express individual transporters (MCT1, MCT2, MCT3, MCT4, CD147). Using flow cytometry, these engineered cell lines may be measured for expression of each protein via detection of Flag-tagged proteins and for anti-MCT1 antibody binding via surface staining.

MCT1 Ab1 binding to activated T cells. MCT1 Ab1 bound specifically to MCT1 and confirmed increased cell surface expression on human CD3/CD28 activated T cells on day 3 (FIG. 13B), but showed low to no staining on resting naïve T cells (FIG. 13A). This binding confirms the expression data presented in FIG. 2 and confirms the prediction based on mRNA analysis.

Conclusions

MCT1 Ab1 is a highly specific rat anti-human MCT1 antibody.

Example 4: In Vitro Characterization of MCT1 Inhibition by Anti-MCT1 Antibody Inhibition of lactate transport. Cell-based lactate transport assays using FLIPR Tetra® and the pH sensitive dye, BCECF (References 63-65) proved that MCT1 Ab1 can block lactate transport (Kd=7.6 nM) in a dose-dependent fashion in activated T cells (FIG. 14).

Inhibition of bromopyruvate toxicity. Since MCT1 is the sole transporter necessary for the in vitro efficacy of the anti-cancer toxin bromopyruvate (Reference 66), a second cell-based functional assay was developed to measure the in vitro killing of cells using this toxin at a concentration of 150 μM. With this assay, a dose-dependent inhibition of bromopyruvate toxicity was observed, as measured by protection from cell death using ATPlite (Kd=1.2 nM) (FIG. 15).

Inhibition of T cell proliferation, inflammatory cytokine production, and allogeneic activation. MCT1 Ab1 inhibited T cell proliferation in CD3/CD28 stimulated cultures with an $EC_{50}$ of 1.3 nM (FIG. 16). An anti-MCT1 antibody or antibody fragment of the invention may also be tested for its ability to inhibit the production of inflammatory cytokines, relative to controls, in stimulated T cells on day 3 post-stimulation. MCT1 Ab1s with CD3/CD28 activation, MCT1 Ab1 inhibited allogeneic activation by 50-60% in a human mixed lymphocyte reaction (see, e.g., FIG. 17).

Example 5: In Vivo Immunoregulatory Effects of Anti-MCT1 Antibody Administration Protection from lethal GVHD. 3-week xeno-GVHD studies (using human PBMC→NSG mice) may be conducted with once/week drug or control administration and n=8 mice per group. Protection from lethal GVHD may be observed daily over the entire testing period MCT1 Ab1 for various doses of anti-MCT1 antibody. T cell populations indicated by absolute lymphocyte counts (ALC) and inflammatory cytokines may be measured on day 14, after two doses of MCT1 Ab1 anti-MCT1 antibody or control have been administered. Reductions in blood CD4+ T cell expansion and reductions in inflammatory cytokines are observed. If these data indicate a high potency at a low dosage, then in some embodiments, MCT1 Ab1 the anti-MCT1 antibody or antibody fragment may be administered subcutaneously as a therapeutic for autoimmune disease.

Increase in urine ketones. Ketonuria may be measured on day 4 of the xeno-GVHD studies for three experiments, and may be analyzed for dose dependency. MCT1 Ab1 Such a drug-induced increase in ketones may provide a pharmaco-dynamic (PD) biomarker that is proximal to on-target MCT1 inhibition for use in clinical studies.

Furthermore, preliminary metabolomics findings show an improved generation of ATP and NADH, along with increased oxidative metabolism and viability in MCT1 Ab1-treated human T cells.

Example 6: Safety of Targeting Human MCT1 with Anti-MCT1 Specific Antibodies

MCT1 is not expressed on human RBCs. MCT1 Ab1 was used to stain cyno RBCs and human RBCs (20 donors), with a control condition and a secondary antibody only condition. The results clearly show that MCT1 is not expressed on human RBCs, in stark contrast to cyno RBCs that do express MCT1 at high levels (FIG. 18A). MCT1 is also expressed on rabbit RBCs, but not rat or beagle RBCs (FIG. 18B).

MCT1 Ab1 and AZ3965 do not affect human RBC lactate transport. MCT1 Ab1 and AZ3965 were used to inhibit MCT1 lactate transport in purified human RBCs using FLIPR based transport assays (REF. 1, 2) in the presence of 10 mM lactate. The levels of lactate transport were compared to a no lactate control condition and a no inhibitor condition in the presence of lactate. The results indicate that lactate transport in human RBCs is unaffected by AZ3965 or MCT1 Ab1 treatment (FIG. 19), confirming that neither MCT1 nor MCT2 is necessary for lactate transport in RBCs.

Conditional MCT1 KO mouse strain confirms limited toxicity of MCT1 inhibition. To evaluate toxicological concerns, a conditional MCT1 KO mouse strain was developed. These mice were postnatally induced to delete both MCT1 alleles using tamoxifen in all tissues, and no serious adverse findings were found 4 months after deletion. Spermatid degeneration was observed prior to spermatozoa formation, but this loss was deemed reversible as this stage of spermiogenesis is glycolytic (REF. 82) and is in fact the target for a new class of reversible contraceptives (REF. 83, 84). Immunologically, the mice showed no changes in immune compartment cellularity supporting normal hematopoiesis. However, consistent with the impact observed on lymphocyte proliferation and activation by SM and mAb inhibitors, mice made conditionally deficient for MCT1 in all tissues showed significant reductions in antigen-specific immune responses as measured by OTII (OVA-specific transgenic TCR) T cell transfer studies with little impact on T cell memory. Therefore, the limited toxicity concerns raised in these studies and in MCT1-deficient individuals (REF. 49) provide proof that a specific anti-MCT1 mAb would have powerful immunoregulatory activities with no or limited toxicities.

Conclusions

Targeting MCT1 in humans with anti-MCT1 *mAbs* is safe. Existing data strongly indicate a good safety profile. Adult humans deficient in MCT1 are healthy (REF. 49, 68); no overt immune deficiencies have been observed in MCT1-deficient individuals; and adult MCT1-deficient humans are furthermore not neurologically impaired (REF. 49), suggesting a lack of effects in the human brain following loss of MCT1. The absence of broad toxicity in individuals with MCT1 mutations is likely due to the vast redundancy of MCTs.

In addition, our data confirm that MCT1 is not the major lactate transporter on human red blood cells (RBCs), and MCT1-deficient humans do not present with any RBC dysfunction.

Example 7: Treatment of Lupus Via B Cell Inhibition with Anti-MCT1 Antibodies Greatly increased expression of MCT1 on plasma cells in lupus patients. Plasma cells from lupus patients and healthy patients were stained with MCT1 Ab1 and measured via flow cytometry. FIG. 20 shows exemplary flow cytometry data for healthy B cell versus lupus B cell MCT1 expression, revealing much increased MCT1 expression for diseased cells.

Conclusions

With regard to B cells-key adaptive immune cells involved in the pathogenesis of lupus—the results show that MCT1 is much more highly expressed on plasma cells in lupus patients (FIG. 20). Thus, anti-MCT1 antibodies not only target effector cell metabolism, but have the potential to do so in all pathogenic lymphocytes of lupus patients.

Example 8: Humanization and Selection of Anti-MCT1 Antibodies

Humanization

The anti-MCT1 antibody MCT1 Ab1 is a rat/human chimera. Humanization of MCT1 Ab1 is performed in concert with immunogenicity testing (a.k.a. "deimmuniza-tion") (REF. 87). Humanization and deimmunization are combined, thereby retaining function, affinity, and specific-ity, while delivering low immunogenicity profiles. The removal of T cell epitopes minimizes the risk of immuno-genicity and therefore allows patients to receive an entire course of treatment. The approach combines careful analysis of the binding domains, selection of appropriate human sequence segments, and the application of in silico tools, to generate proposed humanized antibody sequences, produc-ing a panel of humanized antibodies. Three antibodies are selected based on affinity.

Evaluation of the three mAbs includes an immunogenicity assessment using EpiScreen™ technology which uses a time course dendritic cell: T cell co-culture assay with blood samples from >20 healthy volunteer donors. Immunogenic-ity, expressed as % of positive responders, is benchmarked against a database for various clinical grade biologics with known clinical immunogenicity. The target is <10% positive responders.

The three mAbs along with MCT1 Ab1 as control are converted to whole IgG format. A "silent" Fc domain is selected on an IgG1. Adding known antibody dependent cell mediated cytotoxicity (ADCC) silencing mutations, such as ala/ala, to the Fc domain reduces potential toxicity while retaining MCT1 anti-inflammatory efficacy. These mAbs are expressed and purified at a scale of 200 mg each, and this material is used to select a single lead candidate.

Affinity Measurements

A cell-based assay is used with CD147−/− HEK-293 cells engineered to express MCT1 (but no other MCTs), and affinity is measured using Sapidyne's immunosensor-based kinetic-exclusion analysis (KinExa). An MCT1 cDNA is also introduced in CD147−/− MCT1−/− cells with and without CD147 to estimate the effects of this partner protein on MCT1 Ab1 binding affinity since CD147 is known to influence MCT1 surface expression (REF. 88).

Functional Testing In Vitro

MAbs are ranked using a canonical T cell activation assay. CD4+ T cells are isolated by negative selection from human PBMC, and then incubated with each of the three humanized MCT1 mAbs or an isotype control for 30 minutes on ice. The T cells and antibody are placed on anti-CD3/CD28 coated 96-well flat-bottom plates and cultured for 72 hours, after which supernatant is collected for analysis of cytokine production by Luminex. Separately, tritiated thymidine (3H) is added to the culture for 8 hours to measure proliferation by 3H incorporation.

The mAbs are tested in three independent experiments using unique donors to confirm activity. Each antibody is tested at half-log dilutions (0.01→30 μg/ml), and $IC_{50}$ values are calculated to determine which is the most potent (highest efficacy at lowest concentration).

Nonhuman Primate (NHP) Cross-Reactivity

An identical assay to the human T cell activation assay is used to screen for the retention of functional activity in a relevant tox species, cynomolgus monkeys (cyno), through use of the anti-CD3 clone SP34, and CD28 which drives potent T cell proliferation in cyno. Whole blood from cyno is obtained from World Wide Primates (Florida), and T cells are isolated through negative selection. The T cells are incubated with antibody and cultured on CD3 coated plates for 72 hours. Cytokine production is analyzed with a non-human primate (NHP)-specific Luminex assay, and prolif-eration measured by 3H incorporation. $IC_{50}$ scores are compared to human.

Functional Testing In Vivo

Xeno-GVHD is a systemic disease mediated by the adop-tive transfer of xenogeneic human T cells into an irradiated mouse host. MCT1 Ab1 is tested at various doses to deter-mine a decrease in T cell expansion and reduce cytokine levels in the NSG model of xeno-GVHD. Each of the three mAbs is additionally tested, along with MCT1 Ab1 and a control IgG1 to confirm in vivo functionality. Eight mice per group are used in two replicate experiments, where 10, 3, 1 or 0.3 mpk of each antibody is administered at the time of human PBMC transfer, as well as at days 2 and 4 post transfer. At day 14, mice are bled, and absolute lymphocyte counts (ALC) and cytokine levels are determined by flow cytometry and Luminex analysis, respectively. The body weight of each mouse is tracked, and any mouse that loses more than 20% of its initial body weight is sacrificed. Kaplan-Meier curves are generated for each experiment with a statistical log-rank test comparing each anti-MCT1 anti-body to the control.

Further Modifications

Humanization as described often maintains binding, specificity, and potency without increasing immunogenicity. To further improve these features, back mutations around the CDRs may be introduced to increase binding and potency. Alternatively, antibodies may be humanized by maintaining sequences near the CDRs and eliminating by mutation any predicted immunogenic T cell epitopes in the variable domains. FcRn-binding mutations may be introduced to improve antibody half-life.

Characteristics of Humanized Antibodies

Some Humanized Antibodies of the Invention have:
    a. MCT1-specific binding as indicated by binding to HEK-293 cells that only express MCT1.
    b. Cross-reactivity with cynos at >90% of potency as with human T cells in the in vitro CD3/CD28 assay.
    c. Immunogenicity of <10% positive responders among the >20 healthy volunteer donors.
    d. Confirmation of in vivo potency in the xeno-GVHD model.

Conclusion

The humanized mAb anti-MCT1 Ab4 is selected by meeting the above criteria and by ranking $IC_{50}$ values using in vitro CD3/CD28 assays, with anti-MCT1 Ab4 having high potency and low variability (within and between experiments). The humanized variable heavy and variable light sequences of humanized anti-MCT1 antibody Ab4 as well as Ab3 and Ab2 (all derived from ab1) is contained in the Sequence Listing which precedes the claims.

Example 9: Affinity Maturation

The humanized antibody MCT1 Ab4 is affinity matured by using phage display technology.

The antibody is converted to a single chain Fv (scFv) format (either soluble or linked to M13 phage) and tested for binding to the MCT1+ HEK-293 cell line used during humanization to ensure the variable domains are compatible with the selected format, and establish a baseline. To achieve this scFv format, genes encoding the variable heavy ($V_H$)

and light ($V_L$) domains are linked via a 15-amino acid linker (REF. 89). Then, specific amino acids within the CDRs of the starting antibody are identified and targeted for randomized mutagenesis. In addition, specific framework residues may be deliberately or randomly mutated. The resulting mutants are used to generate an scFv phage display library (with approximately $1 \times 10^8$ members) presented on the surface of M13 phage. Three rounds of selection using the MCT1$^+$ cell line are performed by reducing antigen concentrations in each round to identify affinity-matured scFvs.

Affinity-matured scFvs are sequenced and <10 unique scFvs are selected and scaled up for soluble expression and IMAC purification. Three are selected based on affinity and converted to silent IgG format.

The three are ranked by (a) $IC_{50}$ potency in the in vitro T cell assay and (b) in vivo function in the xeno-GVHD model. The ranking incorporates both potency and variability, with an ideal candidate having high potency and low variability. The best ranked mAb is designated MCT1 Ab5.01, the others as MCT1 Ab5.02 and MCT1 Ab5.03.

Additional rounds of affinity maturation may be performed. Sequences of exemplary humanized, affinity matured variants of Ab1, i.e., Ab5-Ab60 may be found in the Sequence Listing which precedes the claims herein.

Conclusions

Affinity-matured humanized antibodies of the invention may have a potency of <2 mg/kg for optimized subcutaneous administration. Xeno-GVHD data for MCT1 Ab1 an antibody of interest may be used to determine efficacy at low doses.

Example 10: Physicochemical Assessment of Anti-MCT1 Antibodies

MCT1 Ab5.01 is assessed for suitable robustness, solubility and stability. It is particularly tested for (a) physicochemical stability at elevated temperature, (b) solubility, and (c) physical and low pH stresses seen in a typical manufacturing process setting.

Physicochemical stability assessment is performed in four formulations of different buffers, pH and excipients. Each of the formulations is stressed at an elevated temperature (40° C.) for up to 4 weeks, and then assessed for (a) the propensity to aggregate into dimers or high molecular weight species (by SEC-HPLC, cGE, and absorbance), and (b) any potential degradation by isomerization, deamidation and/or oxidation (as observed by changes in charge variants by iCE).

To evaluate suitability for subcutaneous administration, MCT1 Ab5.01 is prepared at 150 mg/ml in two separate formulations. These samples are analyzed with the same test panel used for the 4-week stability assessment followed by analytical assessments as above.

A stress study using physical and chemical means of forced degradation assesses MCT1 Ab5.01 susceptibility to degradation after multiple freeze thaws, agitation and low pH conditions. The low pH study mimics conditions typically used during antibody manufacturing for inactivation of potential viruses.

Further, 2.5 grams of purified antibody are manufactured using a CHO-DG44 DHFR mini-pool. The material is analyzed for purity by SDS-PAGE, SEC-HPLC, endotoxin by LAL and binding by flow cytometry.

In Some Embodiments, the Antibodies of the Invention May have:

a. Minimal (<10%) aggregation, loss of purity and change in charge variants during 4-week stability study b. Minimal (<5%) change of same characteristics in forced degradation stress studies c. Solubility of >100 mg/mL

Example 11: Cell Line Development

A high-expressing cell line is developed to enable cGMP commercial manufacture of MCT1 Ab5.01 using Chinese Hamster Ovary (CHO) cell lines.

Sequences are generated for codon optimization, gene synthesis and insertion into expression vectors. A total of six different codon optimized variants are prepared and confirmed by pilot protein production (<1 mg). The host cell line (CHO-M) is transfected using the six antibody variant sequences, and stable pools generated. One of the stable pools is selected and re-transfected to enhance cell line productivity. After two cloning steps, the 10-12 highest-titer clones are expanded and cryopreserved as a Research Cell Bank (RCB). Further assessment of the clones is performed in fed-batch cultures, and the top three clones are selected based on titer and productivity. To confirm clone stability, a phenotypic stability study is performed by continuous passaging of the cell lines for up to 60 generations, where antibody production and productivity are monitored. The highest titer clone is selected after confirming in vitro potency and in vivo function as described above. To confirm product quality, purified antibodies are assessed for aggregation and fragmentation (by SEC-HPLC), and for charge heterogeneity (by icIEF). Peptide mapping using RP-UPLC MS/MS is performed on the highest expressor to confirm expected amino acid sequence.

In some embodiments, a clone of the invention may produce at least 1 g/L. The top clones may be re-transfected to increase the copy number of the mAb gene.

Example 12: Biomarker Discovery & Disease Association

Pharmacodynamic (PD) Biomarker Discovery

Ketones may be used as a PD biomarker. These metabolites are (a) easily measured in urine or blood, (b) may be induced by anti-MCT1 antibody administration and (c) play a plausible role in the mechanism of action (MOA), showing significant immunomodulator functions on their own (REF. 67). MCT1 Ab5.01 is further used in in vitro T/B cell assays (both cell types involved in lupus) and in vivo assays to expand on PD biomarkers.

Metabolites. Metabolomics studies are used to assess the relative concentration profile of approximately 12,000 small-molecule entities, which include endogenous compounds, xenobiotics and their metabolites, as well as fully quantitative measurements of more than 1,100 lipid species. Plasma and human cells are isolated from the xeno-GVHD model (MCT1 Ab5.01 and control treated), along with cells from in vitro T and B cell assays. For xeno-GVHD, experiments are run with 10 different healthy donors, 1 dosage, and various time points for blood collection. For in vitro studies, human T and B cells from 10 healthy volunteers (stimulated with anti-CD3/CD28 or CD40L/IL4 respectively) or 10 lupus patients (without further stimulation) are treated with MCT1 Ab5.01 or control. Analyses are conducted with mass spectrometry-based metabolomics using global metabolomic and lipidomic technology to identify and measure the analytes present in each sample. Biochemical change analysis includes metabolic pathway analysis to indicate additional MOA in each assay, and novel metabolites are deconvoluted using follow-on MS analysis.

Cytokines. Data from Luminex studies may be used to compare the chimeric MCT1 Ab1 and control-treated leukocytes to yield several cytokines as putative biomarkers, including e.g., IFNγ and IL10. MCT1 Ab5.01 is also used to determine cytokine biomarkers. Differences are compared between treated and untreated cell populations from the xeno-GVHD model, and in vitro T and B cell assays. Xeno-GVHD experiments are run with 5 different donors, animals are treated with at least 2 MCT1 Ab5.01 dosages, and plasma is collected at 4 different time points. Correlation with clinical endpoints (graft acceptance or delay of rejection) is scored and additional cytokine biomarkers identified.

Transcripts. Transcriptomics by RNA-seq are used to identify differentially expressed genes and pathways that are linked to MCT1 Ab5.01 treatment on cells in the xeno-GVHD model (10 healthy donors) and in vitro T and B cell assays using healthy volunteers (stimulated with anti-CD3/CD28 or CD40L/IL-4 respectively) or lupus patients (without further stimulation). Cell pellets are subjected to RNA isolation, poly(A)-enriched library preparation, and paired-end sequencing on an Illumina instrument. Raw data are delivered in fastq format, and bioinformatics are performed using publicly available pipelines for differential expression (STAR aligner and DESeq2 from R/Bioconductor). Differentially expressed transcripts are validated across both in vivo and in vitro systems as described below.

Human T and T/B cell assays. In addition to the T cell and PBMC assays described above, effects on T and B cells are measured in a co-culture system. T cells are isolated by negative selection from human PBMC and co-cultured for 5 days with CD19-purified B cells on anti-CD3/CD28 coated 96-well flat-bottom plates. Supernatants are collected to measure Ig production (IgM and total IgG) as well as B cell activation markers (CD80, CD83, CD86, class II MHC and intracellular Ig). An MCT1 mAb or an isotype control is added at a range of concentrations (0.1 to 10 μg/mL) at the initiation of culture. To measure direct effects on B cell activation, CD19-purified B cells are cultured with an agonistic CD40L (100 ng/ml megaCD40L, Enzo Life Sciences), IL-2 (50 U/mL) and IL-4 (400 U/mL). B cell proliferation, activation and Ig production are assessed over a 5-day period. MCT1 Ab5.01 or control is added at the initiation of culture.

PD Biomarker Selection and Confirmation

Urine ketones may be a strong candidate biomarker. Other specimens are also examined (serum/plasma/cells), and analyzed to identity changing molecular components (e.g., acetone, acetoacidic acid, β-hydroxybutyric acid, and/or broader classes, such as cyclic, saturated or unsaturated ketones). This is accomplished in the metabolomics section with potentially corresponding (or new) gene/protein changes found by RNA-seq and/or flow or PhosFlow cytometry. PD biomarkers are chosen based on correlation to pathological endpoints. Data from xeno-GVHD may also be confirmed using additional models such as NSG-SGM3 mice (human stem cell reconstituted) and/or human-MCT1 knock in mouse.

SGM3 mice (stem cell reconstituted). NOD/scid/IL2 receptor gamma knockout mice (NSG) are the standard mouse strain for engraftment of human blood cells, particularly long-term engraftment using CD34[+] hematopoietic stem cells. This engraftment generates large numbers of human lymphocytes in the blood with much smaller numbers of myeloid cells. Recently a group of human cytokine genes has been incorporated into this model, (steel factor, GM-CSF and IL-3 a.k.a "SGM3"). The SGM3 model supports both high levels of lymphocytes and also high levels of human myeloid cells, providing more complete engraftment of human blood cells.

Human MCT1 knock in (KI) mice. A KI/KO mouse model is generated where human SLC16A1 (MCT1) cDNA is knocked in at exon 1, with a termination stop preventing expression of the mouse gene, thus creating a KO of the mouse SLC16A1 gene. This model provides a rodent strain that allows MCT1 Ab5.01 to bind the endogenous MCT1 target. This mouse strain is used to perform additional lupus-related studies such as the transfer of CD8 depleted splenocytes from MCT1 KI mice into (B6×DBA) F1 mice that approximate many of the phenotypes observed in human lupus (B cell activation, anti-ds DNA antibodies, glomerulonephritis, interferon-α gene signatures) (REF. 90, 91). In some embodiments, anti-MCT1 mAbs of the invention may suppress many of these lupus-like phenotypes.

Human Lupus Disease Association of MCT1 Healthy Control and Patient Samples

Data in mice and humans suggest that MCT1 expression is increased at sites of chronic inflammation. For example, cell surface expression of MCT1 by human plasma cells in the peripheral blood of lupus patients is dramatically increased compared to healthy donors (FIG. 20). MCT1 expression is studied in cells from lupus patients using MCT1 Ab5.01 and lineage analysis. Studies are performed on at least 3 healthy volunteers and 3 lupus patients.

Determine MCT1 expression in healthy and lupus cells. To determine the constitutive expression of MCT1 in blood leukocytes from healthy donors and from lupus patients, various immune populations, including T cells, B cells and NK cells, are characterized through flow staining for MCT1 (MCT1 Ab5.01), CD45, CD16, CD56, CD14, CD138, CD8, CD19, CD4 and CD3. Anti-Ki67 and Cell Trace Violet are used here and below for cell proliferation.

Measure MCT1 Ab5.01 inhibition of T/B cell proliferation. To determine whether MCT1 Ab5.01 inhibits T and B cell proliferation, purified T or B cells are stimulated with anti-CD3/CD28 beads+IL-2, or megaCD40L+IL-4+IL-2, respectively. Various cell sub-populations are identified using CD3, CD4, CD8, CCR7, CD45RA, CD127 and CD25 for T cells and CD19, CD20, CD38, CD27, IgD, and IgG for B cells. MCT1 is detected using commercial antibodies that bind intracellular epitopes on MCT1 (these antibodies do not compete with MCT1 Ab5.01).

MCT1 Ab5.01 inhibition of lymphocyte proliferation in lupus. MCT1 Ab5.01 inhibition of lymphocyte proliferation is performed using PBMCs from lupus patients. Various T and B cell populations are identified through staining for MCT1 (commercial), CD3, CD4, CD8, CCR7, CD45RA, CD127, CD25 and CD56 or separately CD19, CD20, CD38, CD27 and IgG.

Given the data presented in FIG. 20, MCT1 expression may be correlated to disease severity, type and/or stage of progression. Additional patients are evaluated and additional cell types are studied.

Example 13: Non-GLP Tox/PK/PD in Cynomolgus Monkeys

Manufacture of test material. 6 grams of MCT1 Ab5.01 are produced and material is analyzed for purity (SDS-PAGE, SEC-HPLC) and endotoxin levels (LAL).

Non-GLP Tox/PK/PD. A 4-phase study in cynos is performed, as summarized in Table 1, including a dose escalation target mediated drug disposition (TMDD) study followed by a repeat dose toxicity, a single dose PK and a PD/TDAR study. Bio-distribution and tissue analysis of the testis and retina may be performed.

TABLE 1

| | | | | # | | | |
|---|---|---|---|---|---|---|---|
| | | | # | Repeat | Animals | | |
| Study # | Study | Dose (mpk) | doses | dose | ♂ | ♀ | |
| 1 | Dose escalation (TMDD) | 1, 10, 100 | — | TBD | 2 | — | |
| 2 | Repeat dose (Toxicity) | 1 | 2 | weekly | 3 | — | |
| | | 20 | 4 | weekly | 2 | 2 | |
| 3 | Single dose (PK) | TBD | 1 | — | 3 | — | |
| 4 | PD (KLH TDAR) | TBD | 1 | — | 6 | 6 | |

NHP Study Design

Study 1—Dose escalating evaluation of target mediated drug disposition (TMDD). Although MCT1 is not present on human red blood cells (RBCs), it is present on the RBCs of cynos (FIG. 18A). Therefore, the first cyno study is performed on 2 animals to determine the dose needed to overcome the RBC sink, and estimate accurate PK and toxicity in the absence of RBC—a large TMDD target in cyno but not human blood. In NHP studies where antibodies bind RBC it is not uncommon to cause a transient anemia (REF. 92). During this anemic state, the animals are re-dosed and the serum levels of MCT1 Ab5.01 are compared to predicted PK for a typical antibody. Cynos receive increasing doses of MCT1 Ab5.01 and immunophenotyping/receptor occupancy analysis will suggest the best dose to remove all MCT1-binding RBCs in subsequent cyno studies. Time points for this analysis are chosen based on earlier studies (REF. 92). This allows for the evaluation of doses that approximate the binding of MCT1 Ab5.01 to leukocytes in humans.

TMDD assessment identifies a dose that allows for reasonable, achievable dosing in cynos for additional studies. Due to the unusual expression of MCT1 on cyno but not human RBC, an assessment of any TMDD in the RBC compartment of cynos is first performed prior to performing toxicity and PK studies. This is achieved by measuring serum levels of MCT1 Ab5.01 and comparing these values to predicted PK for a typical antibody while monitoring anemia.

Study 2-Toxicity. For toxicity testing, a pilot 2-week study is performed on 3 animals at a low dose, estimated to be 1 mpk which is higher than the minimum anticipated biological effect level (MABEL) for this drug. Following this, a >10-fold higher dose is examined on 4 animals to measure toxicity. Larger doses may be chosen, such as 50 mpk, if formulation allows. Bleeding schedule: Day 1 predose, 10 min, 1 and 24-hour post-dose, immediately prior to next dose and at release or necropsy. Clinical measurements and health observations are conducted daily and summarized weekly. Hematology, coagulation, serum chemistries, insulin, biomarkers and receptor occupancy are evaluated at standard time points. Animals treated at higher doses are necropsied, and tissues analyzed using histopathology.

A NOAEL (no observed adverse effect level) is determined for MCT1 Ab5.01 in cynos. The NOAEL is based on standard toxicological criteria or, if it is not observed in the toxicity study, the highest formulated dose level serves as the NOAEL. In some embodiments, an anti-MCT1 antibody according to the invention creates no significant toxicity and does not stimulate significant inflammatory cytokine release.

Study 3—PK. To determine the clearance of MCT1 Ab5.01, blood samples are collected from 3 cynos after 1 dose for PK analysis at Day 1 pre-dose, 10 min, 1, 24 and 168 hours, and 3 and 4-week post-dose. Serum PK is determined by ELISA, and the data examined for linearity, Cmax, AUC, CL and Vd and terminal t1/2 determination. Anti-drug antibody (ADA) response is also assessed. Anti-MCT1 Ab5.01 antibody tools necessary for sandwich ELISA ADA assays are produced following hyperimmunization of cynos (CRL) using MCT1 Ab5.01 as described (REF. 93). Serum from pre-dose and 4-week post-dose are compared using a qualified ADA assay.

An antibody of the invention may have a normal PK for a human IgG of approximately 20 days. If the PK is shorter, known FcRn binding mutations are explored to improve mAb half-life.

Study 4—PD/TDAR. To evaluate the immune modulating effects of MCT1 Ab5.01, a T cell dependent antibody response (TDAR) is performed at two dose levels. A total of 8 animals (2 males, 2 females at each dose) receive a single dose of MCT1 Ab5.01 intravenously. An additional 4 animals (2 males, 2 females) receive a negative control. Animals are immunized with KLH and MCT1 Ab5.01 on day 0. Blood samples are collected prior to study initiation and on Days 7, 10, 14, 21 and 28, and analyzed for anti-KLH titers by ELISA. In some embodiments, these titers are inhibited between 25-90% by an anti-MCT1 antibody of the invention.

An antibody of the invention may have potency that supports subcutaneous (SC) administration. The NSG model with human leukocytes shows effect at 1 mpk and the target for SC is ≤2 mpk. MCT1 Ab1 had a MABEL of ~1 mpk in xeno-GVHD. The TDAR is used to provide a more accurate MABEL for MCT1 Ab5.01 in humans.

Example 14: Pre-Clinical and Clinical Program Planning

Experiments described above provide an extensive data set on MOA, efficacy and safety.

The development of therapeutics using anti-MCT1 antibodies, including those for lupus, is based on compiled data on effects of MCT1 Ab5.01 in non-human primates and in human tissue. A Phase 1 single ascending dose trial in healthy volunteers and a multiple ascending dose trial in lupus patients will be performed. A second study plan will include a multiple-dose placebo-controlled randomized component to assess the clinical efficacy of treatment in lupus patients with active (non-renal) systemic disease.

Example 15: In Vitro MCT1 Function Assay: Bromopyruvate Sensitivity

HEK293T cells are pre-treated with anti-MCT1 antibody or small molecular MCT1 inhibitor at 37° C. for 1 hour. Cells are then incubated with a cytotoxic reagent 3-bromopyruvate (3-BrPy) at concentrations that rand from 25 to 500 μM for 2 to 6 hours. ATP from dying cells will be quantified using a commercial viability kit (ATPlite, PerkinElmer) in a 96-well plate and viability measured using luminescence. Reduction of ATP production indicates functionality of the antibody. A positive control antibody is the mouse or chimeric antibody before humanization. A negative control cell line is MCT1/CD147 double knockout 293T cells. Using this assay functional, i.e., antagonistic anti-MCT1 antibodies may be identified.

Example 16: In Vivo Studies in Non-Human Primates Corroborate Therapeutic Efficacy and Safety of Anti-MCT1 Antibodies Humans who do not express MCT1 (null mutants) reportedly exhibit no major toxicities. The only known abnormalities associated with no expression of MCT1 comprise Induced ketoacidosis which is observed only in pre-adolescent patients and not in older subjects. No overt immune phenotypes have been reported. Moreover, based on MCT1's effects on immunity it is theorized by the inventors that these subjects may even have some protection from developing autoimmune diseases or autoimmunity.

In order to further corroborate the safety and efficacy of anti-MCT1 antibodies for human therapy we administered dosages of 50 mpk of anti-human MCT1 antibodies to cynomolgus monkeys. As disclosed in this example and corroborated by the figure referenced herein no toxicity was observed after 30 days.

As shown in FIG. 22 while MCT1 is involved in various functions there are redundant pathways which avoid toxicity outside the lymph system. By contrast MCT1 has a sole transporter pathway in the lymphoid system (B, T cells) which permits the efficacy of the subject antagonistic anti-MCT1 antibodies for blocking this transporter pathway and its associated activities in the lymphoid system.

As shown in FIG. 23 cynomolgus red blood cells (RBCs) express high levels of MCT1. Based thereon we tested the effects of antagonistic anti-MCT1 antibodies in cyno monkeys and in particular looked at any effects on RBCs after anti-MCT1 antibody dosing. Also, we determined whether cynos could tolerate a therapeutic effective dosage of the antibody.

As evidenced by the results in FIG. 24 cynos tolerate repeated dosing of Ab1 at 50 mpk and while there is an initial reduction of RBC mass after dosing this resolves after a short time. These results indicate that antagonistic anti-MCT1 antibodies should be safe and effective in primates.

As further shown in FIG. 25, the PK data which was observed in cynos, albeit preliminary, further indicates that there was sufficient exposure of the anti-MCT1 antibodies and the results indicate that at Ab1 dose rates ≥5 mpk the RBC sink is saturated.

Moreover, it was further observed that 30 days after administration of anti-MCT1 antibodies no significant in-life toxicity was observed with good exposure, specifically after 4 weekly doses of antagonistic anti-MCT1 antibodies (Ab1) administered at 50 mpk. In particular no adverse histological findings were seen in all of the organs (Heart, muscle, testis and eye) we assessed using H & E.

Example 17: Mouse Conditional KO Toxicological Assessment

In order to further assess the potential safety and efficacy of antagonistic anti-MCT1 antibodies as therapeutics we studied the effects of conditional knock-out of MCT1 in mice.

As shown in FIG. 26 we evaluated target tissues (muscle, testis and eye) in tamoxifen-inducible MCT1 knockout mouse. All of the organs we studied (except the testis) were found to be normal with no genotype-associated changes. As shown in FIG. 27 the MCT1 knockout mice animals had smaller testes and a microscopic finding indicating some spermatid degeneration.

As further shown in FIG. 28 the MCT1 KO phenotype confers robust tamoxifen-inducible knockdown of MCT1 expression in various target tissues which were assayed, i.e., thymus, spleen, lymph nodes, tests and retina, relative to expression of a control housekeeper gene (HPRT). FIG. 29 further shows the phenotypic changes in the testis observed in the knockout mice. As shown spermatid degeneration was observed in testis of all MCT1 knockout mice (Lack of late-stage spermatids and spermatocytes, decreased tubular cellularity, vacuolation, and cell debris). FIG. 30 further compares the histology of testes in WT and MCT1 KO mice and shows increased spermatid degeneration in the knockout mice relative to the wild-type.

Example 18: Previously Reported Anti-MCT1 Antibodies Show No Antagonistic Activity There are a number of commercially available antibodies which purportedly bind to MCT1. Based on Applicant's screening of these antibodies none bind to cell surface-expressed MCT1 and moreover to the best of the inventors' knowledge none of these commercially available anti-MCT1 antibodies modulate or block the effects of MCT1.

FIG. 31 summarizes these results with different commercially available anti-MCT1 antibodies. The Figure contains MFI (TOP, flow cytometry, cell binding of live cells) and Bromopyruvate functional assay results (Bottom, RLU) using all commercially available Abcam anti-MCT1 antibodies (Mabs and Polyclonal). (The catalogue numbers are listed in the figure).

As can be seen from these results these commercially available anti-MCT1 antibodies do not bind to MCT1 expressing cells and as a result elicit no effect on MCT1-related activities. By contrast the inventive anti-MCT1 antibodies in these same assays bind to MCT1 cell-surface expressed MCT1 (on different cells) and potently block MCT1's transporter function (i.e., its ability to transport bromopyruvate). Similar results (not shown) have been observed for every other commercially available anti-MCT1 antibody which has been tested to date by the inventors.

Example 19: Humanization of Exemplary Anti-MCT1 Antibody (Ab1)

The variable heavy and light chain polypeptides of the rat anti-MCT1 antibody used in the foregoing example (Ab1 or INX310) were humanized using known methods in order to provide humanized anti-MCT1 antibodies for human therapy. Exemplary humanized heavy and light chains are shown below. In the depicted sequences the variable heavy or light chain polypeptides are underlined and the constant regions associated therewith (IgG1 constant regions) are in bold type. The exemplary sequences comprise a Fc-silent human IgG1/kappa backbone (human IgG1) (Uniprot P01857) modified to contain mutations which eliminate C1q and FcR binding (E269R/K322A mutations). The variable regions are underlined and the constant regions are in bold type. The signal sequences are not shown in the depicted exemplary humanized light and heavy chain sequences.

```
Humanized Heavy Chains
>aMCT1_Humanized_VH1_hIgG1_INXsilent_HC
QVQLQESGPGLVKPSETLSLTCTVSGFSLTNYHLQWIRQPPGKGLEWI

GFIRSSGNTEYNPSLKSRVTISRDTSKNQVSLKLSSVTAADTAVYYCA

RNSWYHGTYYSPGYYVMDAWGQGTMVTVSSASTKGPSVFPLAPSSKST

SGGTAALGCLVKDYFPEPVTVSWNSGALTSGVHTFPAVLQSSGLYSLS
```

SVVTVPSSSLGTQTYICNVNHKPSNTKVDKKVEPKSCDKTHTCPPCPA

PELLGGPSVFLFPPKPKDTLMISRTPEVTCVVVDVSHRDPEVKFNWYV

DGVEVHNAKTKPREEQYNSTYRVVSVLTVLHQDWLNGKEYKCAVSNKA

LPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVF

SCSVMHEALHNHYTQKSLSLSPGK

>aMCT1_Humanized_VH2_hIgG1_INXsilent_HC
QVQLKESGPGLVKPSETLSLTCTVSGFSLTNYHLQWVRQPPGKGLEWI

GFIRSSGNTEYNPSLKSRVTISRDTSKNQVSLKLSSVTAADTAVYYCA

RNSWYHGTYYSPGYYVMDAWGQGTMVTVSSASTKGPSVFPLAPSSKST

SGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPA

PELLGGPSVFLFPPKPKDTLMISRTPEVTCVVVDVSHRDPEVKFNWYV

DGVEVHNAKTKPREEQYNSTYRVVSVLTVLHQDWLNGKEYKCAVSNKA

LPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVF

SCSVMHEALHNHYTQKSLSLSPGK

>aMCT1_Humanized_VH3_hIgG1_INXsilent_HC
QVQLQESGPGLVKPSQTLSLTCTVSGFSLTNYHLQWIRQPPGKGLEWI

GFIRSSGNTEYNPSLKSRVTISRDTSKNQVSLKLSSVTAADTAVYYCA

RNSWYHGTYYSPGYYVMDAWGQGTLVTVSSASTKGPSVFPLAPSSKST

SGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPA

PELLGGPSVFLFPPKPKDTLMISRTPEVTCVVVDVSHRDPEVKFNWYV

DGVEVHNAKTKPREEQYNSTYRVVSVLTVLHQDWLNGKEYKCAVSNKA

LPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVF

SCSVMHEALHNHYTQKSLSLSPGK

>aMCT1_Humanized_VH4_hIgG1_INXsilent_HC
QVQLKESGPGLVKPSQTLSLTCTVSGFSLTNYHLQWVRQPPGKGLEWI

GFIRSSGNTEYNPSLKSRVTISRDTSKNQVSLKLSSVTAADTAVYYCA

RNSWYHGTYYSPGYYVMDAWGQGTLVTVSSASTKGPSVFPLAPSSKST

SGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPA

PELLGGPSVFLFPPKPKDTLMISRTPEVTCVVVDVSHRDPEVKFNWYV

DGVEVHNAKTKPREEQYNSTYRVVSVLTVLHQDWLNGKEYKCAVSNKA

LPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVF

SCSVMHEALHNHYTQKSLSLSPGK

>aMCT1_Humanized_VH_AmbCons_hIgG1_INXsilent_HC
QVQLQESGPGLVQPTQTLSITCTVSGFSLTNYHLQWVRQTPGKGLEWM

GFIRSSGNTEYNSEFKSRLSISRDTSKNQVFLKMNSLKTEDTGVYYCA

RNSWYHGTYYSPGYYVMDAWGQGTTVTVSSASTKGPSVFPLAPSSKST

SGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPA

PELLGGPSVFLFPPKPKDTLMISRTPEVTCVVVDVSHRDPEVKFNWYV

DGVEVHNAKTKPREEQYNSTYRVVSVLTVLHQDWLNGKEYKCAVSNKA

LPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVF

SCSVMHEALHNHYTQKSLSLSPGK

>aMCT1_Humanized_VH_AmbMod_hIgG1_INXsilent_HC
QVQLQESGPGLVKPSQTLSLTCTVSGFSLTNYHLQWVRQPPGKGLEWM

GFIRSSGNTEYNSEFKSRLSISRDTSKNQVYLQMNSLKTEDTAVYYCA

RNSWYHGTYYSPGYYVMDAWGQGTTVTVSSASTKGPSVFPLAPSSKST

SGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPA

PELLGGPSVFLFPPKPKDTLMISRTPEVTCVVVDVSHRDPEVKFNWYV

DGVEVHNAKTKPREEQYNSTYRVVSVLTVLHQDWLNGKEYKCAVSNKA

LPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVF

SCSVMHEALHNHYTQKSLSLSPGK

>aMCT1_Humanized_VH_AmbAgg_hIgG1_INXsilent_HC
QVQLQESGPGLVKPSQTLSLTCTVSGFSLTNYHLQWVRQPPGKGLEWM

GFIRSSGNTEYNSEFKSRLTISKDTSKNQVYLQMNSLKTEDTAVYYCA

RNSWYHGTYYSPGYYVMDAWGQGTTVTVSSASTKGPSVFPLAPSSKST

SGGTAALGCLVKDYFPEPVTVSWNSGALTSGVHTFPAVLQSSGLYSLS

SVVTVPSSSLGTQTYICNVNHKPSNTKVDKKVEPKSCDKTHTCPPCPA

PELLGGPSVFLFPPKPKDTLMISRTPEVTCVVVDVSHRDPEVKFNWYV

DGVEVHNAKTKPREEQYNSTYRVVSVLTVLHQDWLNGKEYKCAVSNKA

LPAPIEKTISKAKGQPREPQVYTLPPSRDELTKNQVSLTCLVKGFYPS

DIAVEWESNGQPENNYKTTPPVLDSDGSFFLYSKLTVDKSRWQQGNVF

SCSVMHEALHNHYTQKSLSLSPGK

Humanized Light Chains
>aMCT1_Humanized_VL1_hKappa_LC
DIQMTQSPSSLSASVGDRVTITCRGSQNINNYLAWFQQKPGKTPKLLI

YNRHNLQSGVPSRFSGSGSGTDFTLTISSLQPEDVATYYCYQYSDGYT

FGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC

>aMCT1_Humanized_VL2_hKappa_LC
DIQMTQSPSSLSASVGDRVTITCRGSQNINNYLAWFQQKPGKTPKLLI

YNRHNLQSGVPSRFSGSGSGTDYTLTISSLQPEDVATYYCYQYSDGYT

FGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC

-continued
>aMCT1_Humanized_VL3_hKappa_LC
DIQMTQSPSSLSASVGDKVTITCRGSQNINNYLAWFQQKPGKTPALLI

YNRHNLQSGVPSRFRGSGSGTDFTLTISSLQPEDVATYYCYQYSDGYT

FGPGTKVDIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC

>aMCT1_Humanized_VL4_hKappa_LC
DIQMTQSPSSLSASVGDKVTITCRGSQNINNYLAWFQQKPGKTPALLI

YNRHNLQSGVPSRFRGSGSGTDYTLTISSLQPEDVATYYCYQYSDGYT

FGPGTKVDIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC

>aMCT1_Humanized_VL_AmbCons_hKappa_LC
NIQMTQSPSLLSASVGDRVTLSCKGSQNINNYLAWFQQKFGETPKLLI

YNRHNLQTGIPSRFSGSGSGTDYTLTINSLQPEDVATYFCYQYSDGYT

FGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC

>aMCT1_Humanized_VL_AmbMod_hKappa_LC
NIQMTQSPSLLSASVGDRVTISCKGSQNINNYLAWFQQKFGETPKLLI

YNRHNLQTGIPSRFSGSGSGTDYTLTISSLQPEDVATYFCYQYSDGYT

FGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC

>aMCT1_Humanized_VL_AmbAgg_hKappa_LC
NIQMTQSPSLLSASVGDRVTISCKGSQNINNYLAWFQQKFGQPPKLLI

YNRHNLQTGIPSRFSGSGSGTDYTLTISSLQPEDVATYYCYQYSDGYT

FGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYA

CEVTHQGLSSPVTKSFNRGEC

Exemplary humanized anti-MCT1 antibodies according to the invention are further set forth below. The exemplary humanized antibodies comprise a common light chain. The bolded residues in the sequences are predicted CDRs (identified using IMGT DomainGapAlign).

Rat Anti-MCT1 antibody (Ab1 or INX310)
>Rat Anti-MCT1 Ab_VH
QVQLKATGPGLVQPTQTLSITCTVSGFSLTNYHLQWVRQTPGKGLEW

MGFIRSSGNTEYNSEFKSRLSISRDTSKNQVFLKMNSLKTDDTGVYY

CARNSWYHGTYYSPGYYVMDAWGQGASVTVSS

>Rat Anti-MCT1 Ab_VL
NIHLTQSPSLLSASVGDRVTLSCKGSQNINNYLAWFQQKFGETPKLL

IYNRHNLQTGIPSRFSGSGSGTDYTLTINSLQPEDVATYFCYQYSDG

YTFGAGTKLELK

Humanized Anti-MCT1 antibody 1 (Ab2 or INX352)
>Humanized Anti-MCT1 antibody 1_VH -continued
QVQLKESGPGLVKPSQTLSLTCTVSGFSLTNYHLQWVRQPPGKGLEW

IGFIRSSGNTEYNPSLKSRVTISRDTSKNQVSLKLSSVTAADTAVYY

CARNSWYHGTYYSPGYYVMDAWGQGTLVTVSS

>Humanized Anti-MCT1 antibody 1, 2 and 3_VL
DIQMTQSPSSLSASVGDKVTITCRGSQNINNYLAWFQQKPGKTPALL

IYNRHNLQSGVPSRFRGSGSGTDYTLTISSLQPEDVATYYCYQYSDG

YTFGPGTKVDIK

Humanized Anti-MCT1 antibody 2 (Ab3 or INX356)
>Humanized Anti-MCT1 antibody 2_VH
QVQLQESGPGLVKPSETLSLTCTVSGFSLTNYHLQWIRQPPGKGLEW

IGFIRSSGNTEYNPSLKSRVTISRDTSKNQVSLKLSSVTAADTAVYY

CARNSWYHGTYYSPGYYVMDAWGQGTMVTVSS

>Humanized Anti-MCT1 antibody 1, 2 and 3_VL
DIQMTQSPSSLSASVGDKVTITCRGSQNINNYLAWFQQKPGKTPALL

IYNRHNLQSGVPSRFRGSGSGTDYTLTISSLQPEDVATYYCYQYSDG

YTFGPGTKVDIK

Humanized Anti-MCT1 antibody 3 (Ab4 or INX364)
>Humanized Anti-MCT1 antibody 3_VH
QVQLQESGPGLVKPSQTLSLTCTVSGFSLTNYHLQWIRQPPGKGLEW

IGFIRSSGNTEYNPSLKSRVTISRDTSKNQVSLKLSSVTAADTAVYY

CARNSWYHGTYYSPGYYVMDAWGQGTLVTVSS

>Humanized Anti-MCT1 antibody 1, 2 and 3_VL
DIQMTQSPSSLSASVGDKVTITCRGSQNINNYLAWFQQKPGKTPALL

IYNRHNLQSGVPSRFRGSGSGTDYTLTISSLQPEDVATYYCYQYSDG

YTFGPGTKVDIK

Silent IgG1 (constant)
E269R/K322A
>IgG1_INX_Silent
ASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKV

DKKVEPKSCDKTHTCPPCPAPELLGGPSVFLFPPKPKDTLMISRTPE

VTCVVVDVSHRDPEVKFNWYVDGVEVHNAKTKPREEQYNSTYRVVSV

LTVLHQDWLNGKEYKCAVSNKALPAPIEKTISKAKGQPREPQVYTLP

PSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

K

Example 20: Affinity-Matured, Humanized Anti-MCT1 Antibodies

The variable heavy and light chain polypeptides of the rat anti-MCT1 antibody disclosed in the foregoing examples (Ab1 or INX310) were humanized and affinity-matured in order to provide humanized, affinity-matured anti-MCT1 antibodies suitable for human therapy. These antibodies bind to human MCT1 with high affinity and should be substantially non-immunogenic in human subjects. The $V_H$ and $V_L$ sequences of these humanized and affinity-matured anti-MCT1 antibodies (Ab5-Ab60) are contained in the Sequence Listing which immediately precedes the claims of this application. As with Ab1 (INX310) these antibodies may be used to antagonize the effects of MCT1 in vitro or in vivo and based on their increased affinity they should be more potent than Ab1 (INX310). FIG. 32 contains experimental results comparing the antagonistic activity of different anti-MCT1 antibodies according to the invention in bromopyruvate functional assays, i.e., INX420, INX356, INX364, INX444 and INX453.

FIG. 33 and FIG. 34 contain alignments comparing the sequences of the variable heavy and variable light regions of different anti-MCT1 antibodies disclosed herein. Particularly these figures respectively align the $V_H$ and $V_L$ sequences of Ab1 (INX310), 3 humanized antibodies derived therefrom, i.e., Ab2 (INX352), Ab3 (INX356) and Ab4 (INX364) to humanized, affinity matured anti-MCT1 antibodies which were derived from Ab1, i.e., Ab23 (INX420), Ab47 (INX444) and Ab56 (INX453). The boxed regions in these alignments show the sequences differences in the framework residues. The CDRs are in bold type and show the CDR changes in these affinity, matured antibodies compared to the CDRs of the parental antibody Ab1 and humanized variants thereof, i.e., Ab2 (INX352), Ab3 (INX356) and Ab4 (INX364).

Example 21: Isolation of Other High Affinity, Functional Anti-MCT1 Antibodies

Additional anti-human MCT1 antibodies were produced in chickens. Chickens were immunized with recombinant cells that express human MCT1 proteins on their surface in order to potentially elicit the production of functional anti-human MCT1 binding antibodies. Serum was obtained from these animals and screened anti-MCT1 binding antibodies. The nucleic acids encoding said antibodies were then cloned and expressed in host cells. Such methods have resulted in the isolation of over a 100 putative human MCT1-binding antibodies including the anti-human MCT1 antibodies Ab61 through Ab95 having the sequences contained in the Sequence Listing which precedes the claims.

These antibodies were further screened in order to identify those which specifically bound to MCT1-expressing 293 cells. FIG. 35A shows the binding of anti-MCT1 antibodies to MCT$^+$ 293 cells some of whose sequences are contained in the Sequence Listing which precedes the claims. These antibodies are identified as anti-MCT1 antibodies Ab61 through Ab95 in the Sequence Listing as well as being identified by alternative nomenclature ("LM-XXX" or "MCT" designation) by which some are identified in FIG. 35A and FIG. 35B. It can be seen from the binding results in FIG. 35A that many of these antibodies bind with comparable affinity to MCT1-expressing 293 cells as Ab1 (INX310).

The same anti-MCT1 antibodies which were demonstrated to specifically bind to human MCT1 expressed on the surface of 293 cells were further screened in functional assays which screen for those MCT1 binding antibodies which block or antagonize the effects of MCT1 in the bromopyruvate toxin transport assay previously described. As further shown in FIG. 35B these functional screening methods demonstrated that many of these anti-human MCT1 antibodies were functional in this assay, i.e., they provided protection from cell death as measured by ATP-lite. These additional anti-human MCT1 antibodies possess sequence diversity compared to the sequences of Ab1 and humanized and affinity matured variants thereof derived therefrom which are identified herein as Ab2-Ab60, i.e. none of these additional anti-MCT1 antibodies comprise the same CDRs as Ab1-Ab60.

The sequences for these 35 other anti-human MCT1 antibodies which are referred to as Ab61-Ab95 may be found in the Sequence Listing which precedes the claims of this application. The Sequence Listing contains the amino acid sequences for the heavy and light CDRs, variable heavy and light chain polypeptides, heavy and light chain polypeptides and further contains the sequences of nucleic acids which encode each of these 35 anti-human MCT1 antibodies. Based on their comparable binding affinity to human MCT1 as Ab1 and their functional activity in the bromopyruvate toxin assay it is expected that many of these antibodies may be used to develop other therapeutic anti-MCT1 antibodies, e.g., by humanization and/or affinity maturation.

The resultant antibodies will bind to human MCT1 with high affinity and further should be substantially non-immunogenic in human subjects. As with Ab1 (INX310) and humanized or affinity-matured variants derived therefrom (Ab2-Ab60), humanized and/or affinity matured anti-MCT1 antibodies derived from Ab61-Ab95 potentially may be used to antagonize the effects of MCT1 in vitro or in vivo and potentially may be used in the treatment of diseases such as inflammatory, autoimmune, and allergic conditions, cancer, transplant and GVHD and other conditions wherein increased TR1 cells and/or decreased T effector cells, or decreased MCT1 activity is therapeutically desirable.

Moreover it is contemplated different combinations of humanized or humanized affinity matured heavy and light polypeptides disclosed herein may be combined to produce other functional (antagonistic) anti-MCT1 antibodies. Also any of the exemplary humanized or humanized affinity matured heavy and light polypeptides disclosed herein may be further humanized or other humanized anti-MCT1 antibodies containing other humanized variable heavy and light chain polypeptides may be derived from Ab1 (INX310) or any of Ab2-Ab95 by known humanization methods in order to obtain other humanized anti-MCT1 antibodies suitable for human therapy. Also these humanized sequences may further be affinity matured in order to obtain anti-MCT1 antibodies having increased binding affinity. Further these humanized or affinity matured antibody polypeptides may be incorporated into multispecific binding polypeptides which can be of different formats such as bispecific antibodies, BsAbs, Dual Variable Domain-IgG (DVD-Ig) diabodies among other well-known multispecific antibody formats.

These humanized heavy and light polypeptides may further be associated with different human IgG constant domains, e.g., human IgG1, IgG2, IgG3 and IgG4 constant domains or domains or fragments thereof. These constant regions if desired may be modified to impair or enhance at least one effector function such as FcR binding, e.g., FcγR (IgG), FcεRI (IgE), FcαRI (IgA), FcµR (IgM) and FcδR (IgD) binding, complement binding, ADCC activity, CDC activity, FcRN binding, and the like. Exemplary "effector functions" include but are not limited to, C1q binding; complement dependent cytotoxicity (CDC); Fc receptor binding; antibody-dependent cell-mediated cytotoxicity (ADCC); phagocytosis; down-regulation of cell surface receptors (e.g., B cell receptor; BCR), and the like. Such effector functions generally require the Fc region to be combined with a binding domain (e.g., an antibody variable domain) and can be assessed using various assays known in the art for evaluating such antibody effector functions.

The exemplified humanized and humanized affinity matured sequences are intended to be exemplary as other humanization or affinity maturation methods may be used to derive alternative humanized heavy and light polypeptides derived from Ab1 or other anti-MCT1 antibodies disclosed herein which may be used to produce humanized anti-MCT1 antibodies for use in human or animal therapy. The invention in particular embraces any anti-MCT1 antibody comprising the same CDRs as any of Ab1-Ab95.

Example 22: Potency of Different Anti-MCT1 Antibodies According to the Invention The potency of two anti-MCT1 antibodies according to the invention, i.e., INX420 and INX310 were compared in assays which determined the effect of such antibodies on the proliferation of $CD4^+$ and $CD8^+$ T cells at different antibody concentrations. As shown in FIG. 36A-D both antibodies inhibited the proliferation of $CD4^+$ and $CD8^+$ T cells. Of these two antibodies the affinity matured antibody INX420 more potently inhibited the proliferation of $CD4^+$ and $CD8^+$ T cells and possesses single digit nM potency in these functional assays.

These results demonstrate that this anti-MCT1 antibody, which was derived by affinity maturation of Ab1, like the parental antibody Ab1, potently suppresses the proliferation of CD4+ and CD8+ T cells comparably to another anti-MCT1 antibody according to the invention (Ab1).

Example 23: In Vitro Effects of Anti-MCT1 Antibodies on Tr1 Cells

Anti-MCT1 antibodies according to the invention were further evaluated in in vitro assays to assess their effects on Tr1 cells. The methods used to generate Tr1 cells and assays using Tr1 cells are described below.
In Vitro Generation of Tr1 Cells and Tr1 Functional Assays
Tr1 cells are generated in vitro using CD3/CD28 stimulation (+INX420) of fresh total hPBMC's and these cells tested in vitro in functional assays with anti-MCT1 antibodies using methods and materials set forth below.
Reagents
1. 96 well tissue culture flat-bottom plates (Falcon, Catalog No. 353072)
2. 50 mL reagent reservoirs (Costar, Catalog No. 4870)
3. PBS (Corning, Catalog No. 21-040-CV)
4. Media-RPMI 1640 (HyClone, Catalog No. SH30096.01). 10% human serum, 1× Penicillin/Streptomycin/Glutamine, 10 mM HEPES
5. Media for Jurkat-RPMI 1640 (HyClone, Catalog No. SH30096.01). 10% FBS, 1× Penicillin/Streptomycin/Glutaine, 10 mM Hepes
6. Anti-CD3-Clone OKT3 (Bio X Cell. Catalog No. BE0001-2)
7. Anti-CD28-Clone 15E8 (Miltenyi Biotec, Catalog No. 130-093-375)
8. Apheresis cone blood
9. Histopaque 1077
10. INX420 lot 17069-8129269
11. Versene 1× (Gibco, Catalog No. 15040-066)

| Reagent | Stock concentration | Final concentration (1x) |
|---|---|---|
| a-CD3 (OKT3) | 5.46 mg/ml, lot 5480/1215 | 1 ug/ml |
| a-CD28 | 6.16 mg/ml | 2 ug/ml |
| INX420 | 10.03 mg/ml | 10 ug/ml |

Day −1/0: Coat Plates with Anti-CD3
1. Dilute stock OKT3 to 1 ug/ml in PBS
2. Add 100 ul of 1 µg/ml OKT3 to each well of 96 well flat-bottom plate 3. Incubate overnight at 4° C. or 1 h at 37° C.
Day 0: Stimulation of Fresh Human PBMCs
1. Prepare Fresh PBMC from Core Blood.
In sterile conditions transfer blood to a 50 ml falcon and dilute with PBS to 30 ml.
Slowly layer 13 ml of Histopaque 1077 under the diluted blood
Centrifuge at 850×g for 20 min at RT with mild acceleration (⅕ or ⅜) and brake off.
Collect the mononuclear cells from the plasma/ficoll interface and resuspend in 50 ml of PBS, centrifuge at 400×g for 5 min
Count cells (1:10 dilution) and prepare hPBMC at 200K/100 ul ($2*10^6$/ml)
2. Wash OKT3-Coated Plates 2× in RPMI
Remove PBS from plates.
Immediately add 200 ul of RPMI to wells.
Remove media and add 200 ul of RPMI to wells
3. Take OKT3 Coated Plate and Remove Remaining RPMI. Ensure that any Remaining Media is Removed by Blotting Plate on Sterile Gauze Covered Paper Towels
4. Prepare all Reagents and mAbs at 2× in RPMI, Add 100 ul Per Well
5. Add Cells at 200k in 100 Ul and Incubate at 37° C./5% $CO_2$ for Up to 7 Days. If Cells are Cultured Longer than 7 Days Replenish Culture with 20 ul of Media Containing 10× of mAb (CD28, INX420)
Tr1 Phenotyping
Tr1 cells derived from sera of animals treated with anti-MCT1 antibodies according to the invention are phenotyped as follows:
Materials and Methods:
−100 of total blood was used for analysis
blood was stained using a Stain-1 wash protocol to allow absolute cell count with Ab panel below followed by FACS lysis buffer 1× (BD Bioscience, #349202); whole blood was incubated with a 10× antibody (shown below) and after 30 min, the blood was lysed in a large volume of 1× lysis buffer (at least 6 times) following manufacturer instructions; or blood was first lysed with ACK (10 min), washed in PBS and stained with antibody mix, exactly as described in a table below.
Flow Panel Below (for Blood ALC)

| FACS | | | |
|---|---|---|---|
| Antibody | Dilution | Vendor, cat# | Volume (ul) |
| Fc-gamma block mouse + human | 1:200 each | Miltenyi Biotec, 130-092-575; Fisher Scientific (eBioscience), 50-112-9053 | 5 + 5 |
| hLAG3-BV421 | 1:200 | Biolegend, 369314 | 5 |
| hCD45-BV510 | 1:400 | Biolegend, 304036 | 2.5 |
| hCD3-FITC | 1:100 | Biolegend, 317306 | 10 |
| CD49b-PE | 1:50 | Biolegend, 359308 | 20 |
| mCD45-PercpCy5.5* | 1:400 | Biolegend, 103132 | 2.5 |
| hCD45-RO-PECy7 | 1:200 | Biolegend, 304230 | 5 |
| hCD8-APC | 1:100 | Biolegend, 344722 | 10 |
| hCD4-APCCy7 | 1:100 | Biolegend, 300518 | 10 |
| FACS | PBS/2% FBS/ 1 mM EDTA | NA | 1000 final |

| FACS (for human Tr1 phenotyping) | | | |
|---|---|---|---|
| Antibody | Dilution | Vendor, cat# | Volume (ul) |
| Fc-gamma block mouse + human | 1:200 each | Miltenyi Biotec, 130-092-575; Fisher Scientific (eBioscience), 50-112-9053 | 5 + 5 |
| hPD1-BV421 | 1:100 | Biolegend, 329919 | 10 |
| hCD45-BV510 | 1:400 | Biolegend, 304036 | 2.5 |
| hCD3-FITC | 1:100 | Biolegend, 317306 | 10 |
| hTIGIT-PE | 1:100 | Biolegend, 372703 | 10 |
| hCD62L-PercpCy5.5 | 1:200 | Biolegend, 304824 | 5 |
| hCD45-RO-PECy7 | 1:200 | Biolegend, 304230 | 5 |
| hCD8-APC | 1:100 | Biolegend, 344722 | 10 |
| hCD4-APCCy7 | 1:100 | Biolegend, 300518 | 10 |
| FACS | PBS/2% FBS/ 1 mM EDTA | NA | 1000 final |

The flow antibodies set forth below were additionally used for surface characterization of markers expressed on the surface of putative Tr1 cells.

| Bioledend 342304 | PE anti-human CD66a/c/e Antibody |
|---|---|
| Bioledend 339106 | PE anti-human CD355 (CRTAM) Antibody |
| Bioledend 359128 | Brilliant Violet 510 ™ anti-human CD195 (CCR5) Antibody |
| Bioledend 339938 | PE anti-human CD161 Antibody (aka KLRB1) |
| Biolegend 313524 | Brilliant Violet 421 ™ anti-human/mouse/rat CD278 (ICOS) Antibody |
| Biolegend 338332 | Brilliant Violet 421 ™ anti-human CD226 (DNAM-1) Antibody |
| Biolegend 302930 | Brilliant Violet 421 ™ anti-human CD28 Antibody |
| Biolegend 349906 | PE anti-human CD152 (CTLA-4) Antibody |
| Biolegend 328214 | Brilliant Violet 421 ™ anti-human CD39 Antibody |
| Biolegend 345005 | PE anti-human CD366 (Tim-3) Antibody |

The flow antibodies set forth below were additionally used for intracellular characterization of markers expressed intracellularly by putative Tr1 cells.

| BD Biosciences 560213 | Alexa Fluor ® 700 Mouse anti-Human Granzyme B Clone GB11 (APC) |
|---|---|
| BD Biosciences 565002 | Alexa Fluor ® 647 Rat Anti-HUMAN Blimp-1 |
| Biolegend 320124 | Brilliant Violet 421 ™ anti-human FOXP3 Antibody |

Day 7: Collect Cells for FACS and Suppression Assay
1. Collect cells from 200 ul of culture media (pool wells)
2. Dissociate leftover cells from plates by adding 150 ul of sterile Versene per well, incubate for 10 min at 37° C., combine with previously collected media
3. Stain cells in 50 ul of antibody mix (Panel for Tr1 purity check) for 30 min at RT with shaking (400 rpm) or proceed to suppression assay
In Vitro Assays Using Generated Tr1 Cells
The effects of anti-MCT1 antibodies according to the invention may be evaluated in in vitro assays using T1r1 cells generated as above-described in assays, e.g., assays set forth below.
1. % viability
2. number and % of TIGIT⁺PD1⁺ Cells
3. Suppression assay with human CD3+ (or TIGIT⁺PD1⁺) cells
4. Day 6/7: suppression of proliferation of fresh human PBMCs or T cells (including Jurkat)

Exemplary reagents and materials which may be used in said assays are described below.
Reagents and Materials
  CD3/CD28 Dynabeads (Life Technologies, cat #11131D)·
  Cell Trace Violet (Invitrogen #C34557)·
  Responder cells: PBMC, T cells, Jurkat cells

| Reagent | Stock concentration | Final concentration (1x) |
|---|---|---|
| Cell Trace Violet | 5 mM | 5 uM |
| Dynabeads | | 2.5 ul/well |

Results
As shown by the results in FIG. 37A-D in vitro treatment of PMBCs with an exemplary anti-MCT1 antibody, INX420, after CD3/CD28 stimulation resulted in a substantial increase in the number of PD1⁺ TIGIT⁺ cells. Also the observed results were comparable to those elicited by the small molecule MCT1 inhibitor in the same in vitro assay.

As additionally shown by the results in FIG. 38 these in vitro experiments further revealed that PD1⁺ TIGIT⁺Tr1 cells which were produced as a result of treatment with the same exemplary anti-MCT1 antibody, INX420, potently suppress the proliferation of PMBCs.

As further shown by the in vitro experimental results in FIG. 39 which experiments evaluated the proliferation of PMBCs in the presence of an anti-MCT1 antibody and IL-10 antagonists it was demonstrated that blocking IL-10 signaling with an IL-10 antagonist (e.g., anti-IL10RB) did not interfere with Tr1-mediated suppression of PMBC proliferation which resulted from treatment with the anti-MCT1 antibody.

The foregoing experimental results are clinically significant because defects in Tr1 cell frequency/function and the number thereof have been demonstrated in a number of autoimmune and inflammatory diseases (in preclinical and clinical models) to indicate that IL-10-producing Tr1 cells are relevant for disease protection and that drugs which result in Tr1 cell boosting in vivo have potential application in treating/preventing T cell-mediated diseases, e.g., autoimmune and inflammatory conditions, and allogeneic transplant.

Example 24: Effect of Anti-MCT1 Antibodies in Xeno-GvHD Assay

Exemplary anti-MCT1 antibodies according to the invention, i.e., INX420, INX413 and INX310 were further evaluated in an in vivo model of GVHD, i.e., the xeno-GvHD model.
Xeno-GvHD Model:
In this model of GvHD animals male NSG mice are treated with sub-lethal irradiation (250 rad), and afterward these mice receive 2.5×10⁶ of fresh human PBMC (day 0). First dose of anti-human MCT1 is combined with cells and injected i.v. The follow up treatment schedule is weekly (day 7, 14 and 21, IP). Both anti-MCT1 (INX420 or other) and human IgG1 control are dosed at 10 mg/Kg (or as specified).

For re-challenge experiments previously treated with anti-MCT1 (days 0, 7, 14, 21) NSG mice receive a second dose of 2.5×10⁶ of previously frozen human PBMC of the same donor (day 42). Survival and weight loss of these mice is monitored with no additional antibody treatments and compared to a new cohort of NSG mice receiving same donor PBMCs.
Absolute Lymphocyte Count (ALC).

100 ul of total blood is used for analysis: blood was stained using a Stain-1 wash protocol to allow absolute cell count with Ab panel below followed by FACS lysis buffer 1× (BD Bioscience, #349202); whole blood was incubated with a 10× antibody (shown below) and after 30 min, the blood was lysed in a large volume of 1× lysis buffer (at least 6 times) following manufacturer instructions; or blood was first lysed with ACK (10 min), washed in PBS and stained with antibody mix, exactly as described in the table below.

Ex Vivo Suppression Experiments

Humanized NSG mice (treated with anti-MCT1) were sacrificed on d67 or other day specified, single cells suspensions were prepared from spleen, followed by bead-based enrichment of hCD3+ cells. Isolated cells were plated with or without fresh human PBMC of different donor in classical anti-CD3/anti-CD28 stimulation (dynabeads, Life Technologies, #11131D) conditions for 72-96 hours, followed by pulsing with tritiated thymidine for 16 hours to assess proliferation.

TABLE

| ANTIBODY MIX | | |
| --- | --- | --- |
| Biolegend | 570304 | Recombinant Human IL-15 (carrier-free) |
| Biolegend | 581904 | Recombinant Human IL-7 (carrier-free) |
| Biolegend | 589104 | Recombinant Human IL2 (carrier-free) |
| Biolegend | 372720 | Ultra-LEAF ™ Purified anti-human TIGIT (VSTM3) Antibody |
| Biolegend | 337410 | PE anti-human CD112 (Nectin-2) Antibody |
| Biolegend | 337508 | PE anti-human CD155 (PVR) Antibody |

Alternatively, suppression of fresh PBMC proliferation was measured as diminished dilution of Cell Trace™ Violet dye. To this aim, cell labeling of responder PBMCs was done with Cell Trace™ Violet Cell Proliferation Kit, for flow cytometry (C34557, Thermo Fisher). Responder PBMC were then co-cultured with different amounts of Tr1 cells for 96 hours. Tr1 cells were defined as TIGIT+PD1+ cells, isolated using magnetic beads technology (Miltenyi Biotech).

Ex Vivo Tr1 Survival

Humanized NSG mice (treated with anti-MCT1) were sacrificed on d32 or other day specified, single cells suspensions were prepared from spleens, followed by bead-based enrichment of hCD3+ cells. Isolated cells were plated with the analytes (see above table) to access Tr1 survival:

Results

As shown by the results in FIGS. 40A-D and FIGS. 41A-C these experiments revealed that treatment with exemplary anti-MCT1 antibodies according to the invention, i.e., INX420, INX413 and INX310, in the xeno-GvHD model resulted in a significant decrease in the number of CD3+, CD4+ and CD8+ effector T cells compared to NSG mice treated with a control antibody. Further both of these anti-MCT1 antibodies elicited a significant increase in the number of Tr1 cells.

Figures 42A, 42B:
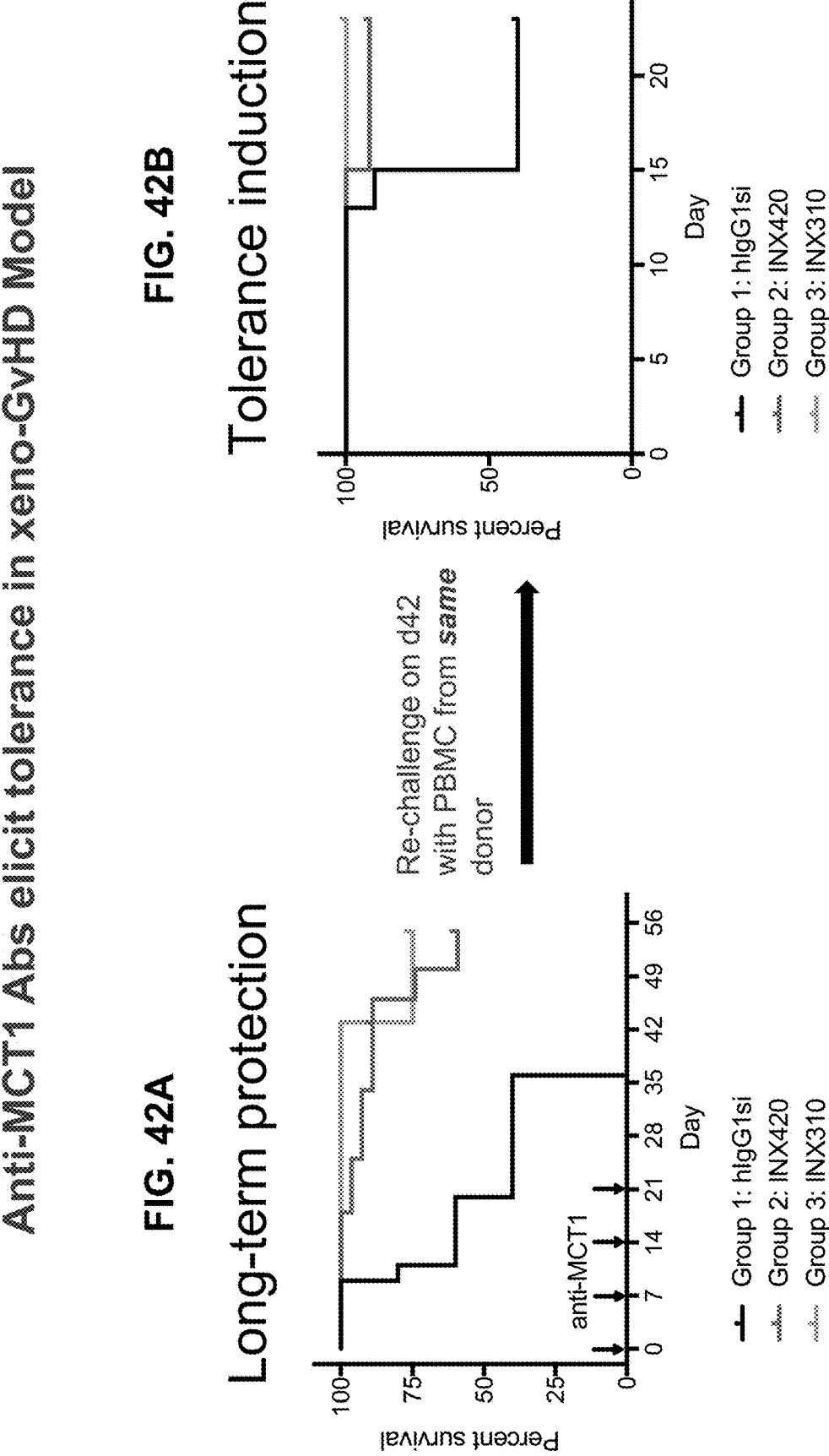

Further as shown by the experimental results in FIG. 42A-B these same exemplary tested anti-MCT1 antibodies further elicited long-term protection and tolerance in the xeno-GvHD model when these animals were re-challenged at day 42 with donor PMBC's from the same donor.

As further shown by the biomarker binding results contained in FIG. 43 and FIG. 44 TIGIT and PD1 are putative biomarkers of Tr1 cells as these biomarkers are expressed on over 75% of human T cells in the xeno-GvHD model. As further shown by the experimental results in FIG. 45 Tr1 cells express high levels of Granzyme B but do not express FOXP3 or Blimp1.

The experiments in FIG. 46A-C further demonstrated that at day 14 these NSG mice contain many effector cells and further shows that the proliferation of hCD3+ cells is suppressed by an exemplary anti-MCT1 antibody (INX420). The experimental results in FIG. 47A-B also show that Tr1 cells potently suppress the proliferation of hCD3+ cells and total PMBC's.

FIG. 48 shows schematically the kinetics of Tr1 cell generation in the xeno-GvHD model. Specifically the figure shows that anti-MCT1 antibodies reduce the T effector phase. FIG. 49A-B shows ex vivo Tr1 survival factors. FIG. 49B further shows that the killing of target cells is not the mechanism by which Tr1 cells elicit such suppression and that Tr1 cells survive upon co-culture with target cells but die if individually cultured. The experimental results shown in FIG. 49A reveal that anti-TIGIT and PVR ligands do not improve ex vivo Tr1 survival. By contrast as further shown in FIG. 49A IL-2, IL-7 and IL-15 increased ex vivo Tr1 survival in a dose-dependent manner with the rate of Tr1 cell survival increasing up to about 75%.

Example 25: Effect of Small Molecule MCT1 Antagonist on Ketosis

Experiments were further conducted to assess the effects of MCT1 inhibitors on safety based on their effects on ketosis. As shown by the experimental results in FIG. 50A-B the small molecule MCT1 inhibitor (SMi) potentiated ketosis triggered by starvation at 8-24 hours; that SMi-driven ketosis proceeds hypoglycemia upon starvation and that SMi treatment potentiates starvation-driven ketosis and hypoglycemia.

By contrast the experimental results in FIG. 51A-B showed that starvation at 24 hours in the presence and absence of the SMi did not trigger ketoacidosis. Rather the inventors only observed a slight starvation-dependent pH reduction (from 7.3 to 7.1) and a slight additional reduction (about 0.05) only at high doses of SMi.

Example 26: Epitope Characterization of Functional Anti-MCT1 Antibodies by Alanine Scanning Experiments Alanine scanning experiments were further conducted in order to identify the MCT1 residues that constitute the epitope or epitopes bound by functional anti-MCT1 antibodies of the present invention. Specifically the epitope bound by 4 exemplary functional anti-human MCT1 antibodies (INX444, INX420, LM183 and LM186) were visualized on a model structure of the target protein MCT1. These 4 antibodies were selected to be representative of those identified herein. In particular 2 of these antibodies are affinity matured variants of mouse anti-human MCT1 antibody INX310 (Ab1) and the other 2 are chicken anti-human MCT1 antibodies. All 4 of these antibodies are functional, i.e., all block human MCT1 function.

Binding of each test Fab to each mutant clone in a constructed alanine scanning library was determined, in duplicate, by high-throughput flow cytometry. For each point, background fluorescence was subtracted from the raw data, which were then normalized to Fab reactivity with WT target protein. For each mutant clone, the mean binding value was plotted as a function of expression (represented by control reactivity). To identify preliminary primary critical clones, a threshold of >70% WT binding to control MAb or Fab and <15% WT binding to test Fabs was applied. Secondary clones that did not meet the set thresholds but whose decreased binding activity and proximity to critical residues further suggested that the mutated residue may be part of the antibody.

The Table below contains the identified critical residues for binding of Fab(s) derived from all 4 tested anti-human MCT1 antibodies to the target (human MCT1 protein). Critical residues are those where mutation thereof gave the lowest reactivities with specific antibodies. Validated critical residues represent amino acids whose side chains make the highest energetic contributions to the antibody-epitope interaction (Bogan, A. A. and Thorn, K. S. (1998). "Anatomy of hot spots in protein interfaces". *J. Mol. Biol.* 280, 1-9; Lo Conte, L., Chothia, C., and Janin, J. (1999). The atomic structure of protein-protein recognition sites. *J. Mol. Biol.* 285, 2177-2198, 1999); therefore, these residues are likely the major energetic contributors to the binding epitope.

| Antibody Name | Residues |
| --- | --- |
| INX444 | T41, S285, S286, Y287, G417, D418 |
| INX420 | T41, S285, S286 |
| INX420 350 mM NaCl | T41, I47, S285, S286, G417, D418 |
| LM183 | E46, K289, H292 |
| LM186 | K297, Y293, H292 |

The Table below further contains the mean binding reactivities (and ranges) for the identified critical residues that constitute the MCT1 epitope for these same 4 antibodies. Critical residues for Fab binding were residues whose mutations were negative for binding to test Fabs, but positive for binding to control Fabs. Additional secondary residues were identified that did not meet the threshold guidelines, but whose decreased binding activity and proximity to critical residues suggested that they may be part of the antibody epitope.

| | Binding Reactivity (% WT) | | | | |
| --- | --- | --- | --- | --- | --- |
| Mu-tation | INX444 Fab | INX420 Fab HS | INX420 Fab HS 350 mM NaCl | LM183 MAb | LM186 MAb |
| T41A | 4.1 (0) | 40.7 (1) | 4.2 (8) | 135.6 (29) | 138.1 (6) |
| I47A | 101.3 (12) | 85.2 (10) | 14.8 (20) | 107.1 (19) | 104.3 (18) |
| S285A | 4.6 (1) | 33.4 (9) | 7.7 (31) | 104.3 (5) | 93.8 (20) |
| S286A | 0 (0) | 4.0 (0) | −4.7 (5) | 114.4 (4) | 131.9 (11) |
| Y287A | 22.7 (4) | 77.3 (12) | 35.6 (12) | 96.0 (40) | 86.2 (32) |
| G417A | 18.5 (6) | 51.6 (7) | 18.6 (26) | 96.2 (19) | 112.4 (23) |
| D418A | 15.4 (0) | 74.0 (4) | 13.8 (10) | 85.3 (26) | 95.2 (28) |

Critical residues and secondary residues involved in the binding of these 4 exemplary functional anti-human MCT1 antibodies (INX444, INX420, LM183 and LM186) were further visualized on a model structure of the target MCT1 protein. FIG. 52 shows the residues that comprise the predicted anti-MCT1 epitope for these 4 different antibodies as identified by alanine scanning. It can be seen that the residues which constitute the epitope for all 4 of these antibodies are comprised in the same extracellular region of human MCT1 which would suggest that many or all of the functional anti-human MCT1 antibodies disclosed herein likely bind to the same or overlapping epitope on human MCT1. FIG. 53 and FIG. 54 further map the specific human MCT1 residues bound by the 4 tested exemplary anti-MCT1 antibodies.

Based on the epitope analysis the invention at least embraces any isolated antibody or antigen-binding fragment thereof that binds to an epitope on human MCT1 selected from the following:

(x) one which comprises one or more of residues T41, E46, S285, S286, Y287, K289, H292, Y293, K297, G417, I47, and D418;

(xi) one which comprises least three residues wherein at least one, two, or all three of said residues comprise a residue selected from T41, E46, S285, S286, Y287, K289, H292, Y293, G417, I47 and D418;

(xii) one which comprises three residues wherein three residues wherein at least one, two, or all three of said residues comprise T41, E46, S285, S286, Y287, K289, H292, Y293, G417, I47 and D418;

(xiii) one which comprises three to six residues wherein one, two, three, four, five or six of said residues comprise T41, E46, S285, S286, Y287, K289, H292, Y293, G417, I47 and D418;

(xiv) one which comprises at least one, two or all three of residues T41, S285 and S286;

(xv) one which comprises T41;

(xvi) one which comprises S286;

(xvii) one which comprises S285;

(xviii) one which comprises H292;

(xix) one which comprises residues T41, S285, S286, Y287, G417 and D418;

(xx) one which comprises residues T41, S285 and S286;

(xxi) one which comprises residues T41, I47, S285, S286, G417 and D418, (xxii) one which comprises residues E46, K289, and H292;

(xxiii) one which comprises residues K297, Y293 and H292;

(xxiv) one which comprises one or more of the corresponding residues of a non-human MCT1 selected from rodent (e.g., mouse, rat, guinea pig), rabbit, chicken, non-human primate (e.g., cynomolgus monkey, chimp, orangutan), bovine, ovine, canine, feline; wherein optionally the residues present in said epitope are identified by use of alanine scanning.

Based on the same epitope analysis the invention at least further embraces any isolated antibody or antigen-binding fragment thereof that binds to an epitope on human MCT1 as above-described that may further comprise any of the following human MCT1 residues which are comprised in loop 1-6 of human MCT1 or the corresponding residues comprised in the loop 1-6 regions of a non-human MCT1, e.g., a rodent or non-human primate MCT1:

(i) one or more of residues P37,140, K45, E48, and T55 (loop 1);

(ii) residue Q111 (loop 2);

(iii) residue Q166 (loop 3);

(iv) one or more of residues L284, E296, S298 (loop 4);

(v) residue Y353 (loop 5);

(vi) one or both of residues Y419, T422 (loop 6); and/or (vii) any combination of the foregoing.

Example 27: Binding of Anti-Human MCT1 Antibody (INX444) to Mouse MCT1

At least functional one anti-human MCT1 antibody (INX444) disclosed herein also binds to mouse MCT1. This would further indicate that the region in human MCT1 or epitope or residues with which the subject anti-human MCT1 antibodies interact on the human MCT1 protein is likely conserved in MCT1 proteins of different species, e.g., human and murines and likely other species such as non-human primates.

Moreover this anti-human MCT1 antibody which binds to mouse MCT1 was further demonstrated to protect mouse MCT1-expressing transfectants from the toxic effects of bromopyruvate. Specifically as shown in FIG. 55 this same antibody when tested at 2 different Ab concentrations (low 10 µg/ml; high, 100 µg/ml) protected transfectants expressing mouse MCT1 from the toxic effects of bromopyruvate analogously to the positive control is AZ3965 (small molecule MCT1 inhibitor, green).

By contrast 2 other tested functional anti-human MCT1 antibodies, i.e., INX420 and INX438 in the same experiments did not block mouse MCT1 function (baseline). (Note that the media alone control does not reach zero because at 150 uM bromopyruvate because the transfectant cells are not completely killed at this bromopyruvate concentration).

This result further corroborates that the functional epitope or residues with which the subject anti-human MCT1 antibodies interact on the human MCT1 protein is likely conserved in MCT1 proteins of different species which would suggest that the subject anti-human MCT1 antibodies may be used in competitive binding assays to screen for other functional anti-MCT1 antibodies, i.e., those which antagonize, inhibit or block one or more activities of human MCT1 or those which antagonize, inhibit or block one or more activities of orthologs thereof, e.g., rodent or non-human primate MCT1 proteins.

REFERENCES

References in this list are incorporated by reference and are cited by reference number in the specification above.
1. Carpenter L, Halestrap A P. The kinetics, substrate and inhibitor specificity of the lactate transporter of Ehrlich-Lettre tumour cells studied with the intracellular pH indicator BCECF. *The Biochemical Journal.* 1994; 304 (Pt 3):751-60. Epub 1994 Dec. 15. PubMed PMID: 7818477; PMCID: PMC1137398.
2. Jackson V N, Halestrap A P. The kinetics, substrate, and inhibitor specificity of the monocarboxylate (lactate) transporter of rat liver cells determined using the fluorescent intracellular pH indicator, 2',7'-bis(carboxyethyl)-5 (6)-carboxyfluorescein. *The Journal of Biological Chemistry.* 1996; 271(2):861-8. Epub 1996 Jan. 12. PubMed PMID: 8557697.
3. Araki K, Myers D K. Aerobic Glycolysis of X-Irradiated Thymocytes. *Can J Biochem Physiol.* 1963; 41:2157-69. Epub 1963 Oct. 1. PubMed PMID: 14083980.
4. Ardawi M S, Newsholme E A. Glutamine metabolism in lymphocytes of the rat. *The Biochemical Journal.* 1983; 212 (3): 835-42. Epub 1983 Jun. 15. PubMed PMID: 6882397; PMCID: PMC1153161.
5. Frauwirth K A, Riley J L, Harris M H, Parry R V, Rathmell J C, Plas D R, Elstrom R L, June C H, Thompson C B. The CD28 signaling pathway regulates glucose metabolism. *Immunity.* 2002; 16(6):769-77. PubMed PMID: 12121659.
6. Pearce E J, Everts B. Dendritic cell metabolism. *Nature Reviews Immunology.* 2015; 15(1):18-29. doi: 10.1038/nri3771. PubMed PMID: 25534620; PMCID: PMC4495583.

126

7. Takeshima Y, Iwasaki Y, Okamura T, Fujio K, Yamamoto K. The metabolic regulation in immune cells and pathogenesis of systemic lupus erythematosus approximately toward new therapeutic applications approximately. *Nihon Rinsho Meneki Gakkai Kaishi.* 2017; 40 (1): 12-20. Epub 2017 May 26. doi: 10.2177/jsci.40.12. PubMed PMID: 28539549.
8. Pucino V, Bombardieri M, Pitzalis C, Mauro C. Lactate at the crossroads of metabolism, inflammation, and autoimmunity. *European Journal of Immunology.* 2017; 47(1): 14-21. Epub 2016 Nov. 25. doi: 10.1002/eji.201646477. PubMed PMID: 27883186.
9. Mak T W, Grusdat M, Duncan G S, Dostert C, Nonnenmacher Y, Cox M, Binsfeld C, Hao Z, Brustle A, Itsumi M, Jager C, Chen Y, Pinkenburg O, Camara B, Ollert M, Bindslev-Jensen C, Vasiliou V, Gorrini C, Lang P A, Lohoff M, Harris I S, Hiller K, Brenner D. Glutathione Primes T Cell Metabolism for Inflammation. *Immunity.* 2017; 46 (4): 675-89. Epub 2017 Apr. 20. doi: 10.1016/j.immuni.2017.03.019. PubMed PMID: 28423341.
10. Ma E H, Bantug G, Griss T, Condotta S, Johnson R M, Samborska B, Mainolfi N, Suri V, Guak H, Balmer M L, Verway M J, Raissi T C, Tsui H, Boukhaled G, Henriques da Costa S, Frezza C, Krawczyk C M, Friedman A, Manfredi M, Richer M J, Hess C, Jones R G. Serine Is an Essential Metabolite for Effector T Cell Expansion. *Cell Metab.* 2017; 25(2):345-57. Epub 2017 Jan. 24. doi: 10.1016/j.cmet.2016.12.011. PubMed PMID: 28111214.
11. Jellusova J, Cato M H, Apgar J R, Ramezani-Rad P, Leung C R, Chen C, Richardson A D, Conner E M, Benschop R J, Woodgett J R, Rickert R C. Gsk3 is a metabolic checkpoint regulator in B cells. *Nature Immunology.* 2017; 18(3):303-12. Epub 2017 Jan. 24. doi: 10.1038/ni.3664. PubMed PMID: 28114292; PMCID: PMC5310963.
12. Gnanaprakasam J N R, Sherman J W, Wang R. MYC and HIF in shaping immune response and immune metabolism. *Cytokine Growth Factor Rev.* 2017; 35:63-70. Epub 2017 Apr. 2. doi: 10.1016/j.cytogfr.2017.03.004. PubMed PMID: 28363691.
13. Mah A Y, Cooper M A. Metabolic Regulation of Natural Killer Cell IFN-gamma Production. Critical reviews in immunology. 2016; 36(2):131-47. Epub 2016 Dec. 3. doi: 10.1615/CritRevImmunol.2016017387. PubMed PMID: 27910764; PMCID: PMC5335907.
14. Loftus R M, Finlay D K. Immunometabolism: Cellular Metabolism Turns Immune Regulator. *The Journal of Biological Chemistry.* 2016; 291(1):1-10. Epub 2015 Nov. 5. doi: 10.1074/jbc.R115.693903. PubMed PMID: 26534957; PMCID: PMC4697146.
15. Keating S E, Zaiatz-Bittencourt V, Loftus R M, Keane C, Brennan K, Finlay D K, Gardiner C M. Metabolic Reprogramming Supports IFN-gamma Production by CD56 bright N K Cells. *Journal of Immunology.* 2016; 196(6): 2552-60. Epub 2016 Feb. 14. doi: 10.4049/jimmunol.1501783. PubMed PMID: 26873994.
16. Cretenet G, Clerc I, Matias M, Loisel S, Craveiro M, Oburoglu L, Kinet S, Mongellaz C, Dardalhon V, Taylor N. Cell surface Glut1 levels distinguish human CD4 and CD8 T lymphocyte subsets with distinct effector functions. *Sci Rep.* 2016; 6:24129. Epub 2016 Apr. 14. doi: 10.1038/srep24129. PubMed PMID: 27067254; PMCID: PMC4828702.
17. Adamia N, Jorjoliani L, Khachapuridze D, Katamadze N, Chkuaseli N. Allergic Diseases and Asthma in Adolescents. *Georgian Med News.* 2015 (243): 58-62. PubMed PMID: 26087732.

18. Yang Z, Matteson E L, Goronzy J J, Weyand C M. T-cell metabolism in autoimmune disease. *Arthritis Research & Therapy.* 2015; 17:29. Epub 2015 Apr. 19. doi: 10.1186/s13075-015-0542-4. PubMed PMID: 25890351; PMCID: PMC4324046.

19. Pollizzi K N, Patel C H, Sun I H, Oh M H, Waickman A T, Wen J, Delgoffe G M, Powell J D. mTORC1 and mTORC2 selectively regulate CD8(+) T cell differentiation. *The Journal of Clinical Investigation.* 2015; 125(5): 2090-108. Epub 2015 Apr. 22. doi: 10.1172/JCI77746. PubMed PMID: 25893604; PMCID: PMC4463194.

20. Medzhitov R. Bringing Warburg to lymphocytes. *Nature Reviews Immunology.* 2015; 15(10):598. Epub 2015 Sep. 26. doi: 10.1038/nri3918. PubMed PMID: 26403193.

21. Chen H, Yang T, Zhu L, Zhao Y. Cellular metabolism on T-cell development and function. *International Reviews of Immunology.* 2015; 34 (1): 19-33. Epub 2014 Apr. 9. doi: 10.3109/08830185.2014.902452. PubMed PMID: 24708060.

22. Matarese G, Colamatteo A, De Rosa V. Metabolic fueling of proper T cell functions. *Immunology Letters.* 2014; 161(2):174-8. Epub 2013 Dec. 25. doi: 10.1016/j.imlet.2013.12.012. PubMed PMID: 24365064.

23. Kugelberg E. Dendritic cells: TLR agonists trigger rapid metabolic changes. *Nature Reviews Immunology.* 2014; 14 (4): 209. Epub 2014 Mar. 26. doi: 10.1038/nri3652. PubMed PMID: 24662378.

24. Green D R, Rathmell J. Sweet nothings: sensing of sugar metabolites controls T cell function. *Cell Metab.* 2013; 18(1):7-8. Epub 2013 Jul. 5. doi: 10.1016/j.c-met.2013.06.009. PubMed PMID: 23823473; PMCID: PMC3749232.

25. Wang R, Green D R. Metabolic checkpoints in activated T cells. *Nature Immunology.* 2012; 13(10):907-15. Epub 2012 Sep. 20. doi: 10.1038/ni.2386. PubMed PMID: 22990888.

26. Marko A J, Miller R A, Kelman A, Frauwirth K A. Induction of glucose metabolism in stimulated T lymphocytes is regulated by mitogen-activated protein kinase signaling. *PloS One.* 2010; 5(11):e15425. Epub 2010 Nov. 19. doi: 10.1371/journal.pone.0015425. PubMed PMID: 21085672; PMCID: PMC2978105.

27. Jacobs S R, Michalek R D, Rathmell J C. IL-7 is essential for homeostatic control of T cell metabolism in vivo. *Journal of Immunology.* 2010; 184(7):3461-9. Epub 2010 Mar. 3. doi: 10.4049/jimmunol.0902593. PubMed PMID: 20194717; PMCID: PMC2980949.

28 Maciver N J, Jacobs S R, Wieman H L, Wofford J A, Coloff J L, Rathmell J C. Glucose metabolism in lymphocytes is a regulated process with significant effects on immune cell function and survival. *Journal of Leukocyte Biology.* 2008; 84(4):949-57. Epub 2008 Jun. 26. doi: 10.1189/jlb.0108024. PubMed PMID: 18577716; PMCID: PMC2638731.

29. Fox C J, Hammerman P S, Thompson C B. Fuel feeds function: energy metabolism and the T-cell response. *Nature Reviews Immunology.* 2005; 5(11):844-52. Epub 2005 Oct. 22. doi: 10.1038/nri1710. PubMed PMID: 16239903.

30. Cham C M, Gajewski T F. Glucose availability regulates IFN-gamma production and p70S6 kinase activation in CD8+ effector T cells. *Journal of Immunology.* 2005; 174 (8): 4670-7. Epub 2005 Apr. 9. PubMed PMID: 15814691.

31. Rathmell J C, Elstrom R L, Cinalli R M, Thompson C B. Activated Akt promotes increased resting T cell size, CD28-independent T cell growth, and development of autoimmunity and lymphoma. *European Journal of Immunology.* 2003; 33(8):2223-32. Epub 2003 Jul. 29. doi: 10.1002/eji.200324048. PubMed PMID: 12884297.

32. Brand K, Netzker R, Aulwurm U, Hermfisse U, Fabian D, Weigert C, Schaefer D, Hamm-Kuenzelmann B. Control of thymocyte proliferation via redox-regulated expression of glycolytic genes. Redox Rep. 2000; 5(1): 52-4. Epub 2000 Jul. 25. doi: 10.1179/rer.2000.5.1.52. PubMed PMID: 10905547.

33. Finlay D K. Regulation of glucose metabolism in T cells: new insight into the role of Phosphoinositide 3-kinases. *Frontiers in Immunology.* 2012; 3:247. Epub 2012 Aug. 15. doi: 10.3389/fimmu.2012.00247. PubMed PMID: 22891069; PMCID: PMC3413010.

34. Halestrap A P, Meredith D. The SLC16 gene family—from monocarboxylate transporters (MCTs) to aromatic amino acid transporters and beyond. *Pflugers Arch.* 2004; 447(5):619-28. doi: 10.1007/s00424-003-1067-2. PubMed PMID: 12739169.

35. Halestrap A P. Monocarboxylic acid transport. *Compr Physiol.* 2013; 3(4):1611-43. doi: 10.1002/cphy.c130008. PubMed PMID: 24265240.

36. Halestrap A P. The SLC16 gene family-structure, role and regulation in health and disease. *Mol Aspects Med.* 2013; 34(2-3):337-49. doi: 10.1016/j.mam.2012.05.003. PubMed PMID: 23506875.

37. Halestrap A P. The monocarboxylate transporter family—Structure and functional characterization. *IUBMB Life.* 2012; 64(1):1-9. doi: 10.1002/iub.573. PubMed PMID: 22131303.

38. Halestrap A P, Wilson M C. The monocarboxylate transporter family—role and regulation. *IUBMB Life.* 2012; 64(2):109-19. doi: 10.1002/iub.572. PubMed PMID: 22162139.

39. Rusu V, Hoch E, Mercader J M, Tenen D E, Gymrek M, Hartigan C R, DeRan M, von Grotthuss M, Fontanillas P, Spooner A, Guzman G, Deik A A, Pierce K A, Dennis C, Clish C B, Carr S A, Wagner B K, Schenone M, Ng M C Y, Chen B H, Consortium M, Consortium S T D, Centeno-Cruz F, Zerrweck C, Orozco L, Altshuler D M, Schreiber S L, Florez J C, Jacobs S B R, Lander E S. Type 2 Diabetes Variants Disrupt Function of SLC16A11 through Two Distinct Mechanisms. *Cell.* 2017; 170(1):199-212 e20. Epub 2017 Jul. 1. doi: 10.1016/j.cell.2017.06.011. PubMed PMID: 28666119.

40. Frank H, Groger N, Diener M, Becker C, Braun T, Boettger T. Lactaturia and loss of sodium-dependent lactate uptake in the colon of SLC5A8-deficient mice. *The Journal of Biological Chemistry.* 2008; 283 (36): 24729-37. doi: 10.1074/jbc.M802681200. PubMed PMID: 18562324; PMCID: PMC3259809.

41. Lewis I A, Campanella M E, Markley J L, Low P S. Role of band 3 in regulating metabolic flux of red blood cells. Proceedings of the National Academy of Sciences of the United States of America. 2009; 106 (44): 18515-20. Epub 2009 Oct. 23. doi: 10.1073/pnas.0905999106. PubMed PMID: 19846781; PMCID: PMC2773988.

42. Akashi A, Miki A, Kanamori A, Nakamura M. Aquaporin 9 expression is required for I-lactate to maintain retinal neuronal survival. Neuroscience Letters. 2015; 589:185-90. Epub 2015 Feb. 1. doi: 10.1016/j.neulet.2015.01.063. PubMed PMID: 25637697.

43. Fischer K, Hoffmann P, Voelkl S, Meidenbauer N, Ammer J, Edinger M, Gottfried E, Schwarz S, Rothe G, Hoves S, Renner K, Timischl B, Mackensen A, Kunz-Schughart L, Andreesen R, Krause S W, Kreutz M. Inhibitory effect of tumor cell-derived lactic acid on human T cells. *Blood.* 2007; 109(9):3812-9. Epub 2007 Jan. 27. doi: 10.1182/blood-2006-07-035972. PubMed PMID: 17255361.

44. Michne W F, Schroeder J D, Guiles J W, Treasurywala A M, Weigelt C A, Stansberry M F, McAvoy E, Shah C R, Baine Y, Sawutz D G, et al. Novel inhibitors of the nuclear factor of activated T cells (NFAT)-mediated transcription of beta-galactosidase: potential immunosuppressive and antiinflammatory agents. *J Med Chem.* 1995; 38(14):2557-69. Epub 1995 Jul. 7. PubMed PMID: 7629796.

45. Pahlman C, Qi Z, Murray C M, Ferguson D, Bundick R V, Donald D K, Ekberg H. Immunosuppressive properties of a series of novel inhibitors of the monocarboxylate transporter MCT-1. Transpl Int. 2013; 26(1):22-9. doi: 10.1111/j.1432-2277.2012.01579.x. PubMed PMID: 23137339.

46. Ovens M J, Davies A J, Wilson M C, Murray C M, Halestrap A P. A R-C155858 is a potent inhibitor of monocarboxylate transporters MCT1 and MCT2 that binds to an intracellular site involving transmembrane helices 7-10. *The Biochemical Journal.* 2010; 425(3):523-30. doi: 10.1042/BJ20091515. PubMed PMID: 19929853; PMCID: PMC2811425.

47. Bueno V, Binet I, Steger U, Bundick R, Ferguson D, Murray C, Donald D, Wood K. The specific monocarboxylate transporter (MCT1) inhibitor, A R-C117977, a novel immunosuppressant, prolongs allograft survival in the mouse. *Transplantation.* 2007; 84 (9): 1204-7. doi: 10.1097/01.tp.0000287543.91765.41. PubMed PMID: 17998878.

48. Murray C. Targeting MCT1: Targeting MCT1: Role in immunosuppression. *Nat. Chem Biol.,* 1 (7): 371-6 2009.

49. van Hasselt P M, Ferdinandusse S, Monroe G R, Ruiter J P, Turkenburg M, Geerlings M J, Duran K, Harakalova M, van der Zwaag B, Monavari A A, Okur I, Sharrard M J, Cleary M, O'Connell N, Walker V, Rubio-Gozalbo M E, de Vries M C, Visser G, Houwen R H, van der Smagt J J, Verhoeven-Duif N M, Wanders R J, van Haaften G. Monocarboxylate transporter 1 deficiency and ketone utilization. *The New England Journal of Medicine.* 2014; 371 (20): 1900-7. Epub 2014 Nov. 13. doi: 10.1056/NEJMoa1407778. PubMed PMID: 25390740.

50. Guile S D, Bantick J R, Cheshire D R, Cooper M E, Davis A M, Donald D K, Evans R, Eyssade C, Ferguson D D, Hill S, Hutchinson R, Ingall A H, Kingston L P, Martin I, Martin B P, Mohammed R T, Murray C, Perry M W, Reynolds R H, Thorne P V, Wilkinson D J, Withnall J. Potent blockers of the monocarboxylate transporter MCT1: novel immunomodulatory compounds. *Bioorg Med Chem Lett.* 2006; 16(8):2260-5. doi: 10.1016/j.bmcl.2006.01.024. PubMed PMID: 16455256.

51. Kim Y, Choi J W, Lee J H, Kim Y S. Expression of lactate/H (+) symporters MCT1 and MCT4 and their chaperone CD147 predicts tumor progression in clear cell renal cell carcinoma: immunohistochemical and The Cancer Genome Atlas data analyses. *Human Pathology.* 2015; 46(1):104-12. doi: 10.1016/j.humpath.2014.09.013. PubMed PMID: 25456395.

52. Hong C S, Graham N A, Gu W, Espindola Camacho C, Mah V, Maresh E L, Alavi M, Bagryanova L, Krotee P A, Gardner B K, Behbahan I S, Horvath S, Chia D, Mellinghoff I K, Hurvitz S A, Dubinett S M, Critchlow S E, Kurdistani S K, Goodglick L, Braas D, Graeber T G, Christofk H R. MCT1 Modulates Cancer Cell Pyruvate Export and Growth of Tumors that Co-express MCT1 and MCT4. *Cell Reports.* 2016; 14(7):1590-601. Epub 2016

Feb. 16. doi: 10.1016/j.celrep.2016.01.057. PubMed PMID: 26876179; PMCID: PMC4816454.

53. Yin Y, Choi S C, Xu Z, Perry D J, Seay H, Croker B P, Sobel E S, Brusko T M, Morel L. Normalization of CD4+ T cell metabolism reverses lupus. *Sci Transl Med.* 2015; 7(274):274ra18. Epub 2015 Feb. 13. doi: 10.1126/scitranslmed.aaa0835. PubMed PMID: 25673763; PMCID: PMC5292723.

54. Buck M D, O'Sullivan D, Pearce E L. T cell metabolism drives immunity. *The Journal of Experimental Medicine.* 2015; 212(9):1345-60. Epub 2015 Aug. 12. doi: 10.1084/jem.20151159. PubMed PMID: 26261266; PMCID: PMC4548052.

55. Doherty J R, Yang C, Scott K E, Cameron M D, Fallahi M, Li W, Hall M A, Amelio A L, Mishra J K, Li F, Tortosa M, Genau H M, Rounbehler R J, Lu Y, Dang C V, Kumar K G, Butler A A, Bannister T D, Hooper A T, Unsal-Kacmaz K, Roush W R, Cleveland J L. Blocking lactate export by inhibiting the Myc target MCT1 Disables glycolysis and glutathione synthesis. *Cancer Research.* 2014; 74(3):908-20. Epub 2013 Nov. 29. doi: 10.1158/0008-5472.CAN-13-2034. PubMed PMID: 24285728; PMCID: PMC3946415.

56. Wang R, Dillon C P, Shi L Z, Milasta S, Carter R, Finkelstein D, McCormick L L, Fitzgerald P, Chi H, Munger J, Green D R. The transcription factor Myc controls metabolic reprogramming upon T lymphocyte activation. *Immunity.* 2011; 35(6):871-82. Epub 2011 Dec. 27. doi: 10.1016/j.immuni.2011.09.021. PubMed PMID: 22195744; PMCID: PMC3248798.

57. Cho K S, Yamada T, Wynn C, Behanna H A, Hong I C, Manaves V, Nakanishi T, Hirose J, Abe Y, Jiang H, Tamura K, Saita Y. Mechanism analysis of long-term graft survival by monocarboxylate transporter-1 inhibition. *Transplantation.* 2010; 90 (12): 1299-306. Epub 2010 Nov. 16. doi: 10.1097/TP.0b013e3181ff8818. PubMed PMID: 21076380.

58. Ekberg H, Qi Z, Pahlman C, Veress B, Bundick R V, Craggs R I, Holness E, Edwards S, Murray C M, Ferguson D, Kerry P J, Wilson E, Donald D K. The specific monocarboxylate transporter-1 (MCT-1) inhibitor, A R-C117977, induces donor-specific suppression, reducing acute and chronic allograft rejection in the rat. *Transplantation.* 2007; 84 (9): 1191-9. doi: 10.1097/01.tp.0000287541.53389.be. PubMed PMID: 17998876.

59. Durrbach A, Francois H. Intracellular lactate flux: a new regulator of the allogenic immune response. Transpl Int. 2013; 26 (1): 20-1. Epub 2012 Dec. 15. doi: 10.1111/tri.12035. PubMed PMID: 23237578.

60. Rubtsov Y P, Niec R E, Josefowicz S, Li L, Darce J, Mathis D, Benoist C, Rudensky A Y. Stability of the regulatory T cell lineage in vivo. *Science.* 2010; 329 (5999):1667-71. Epub 2010 Oct. 12. doi: 10.1126/science.1191996. PubMed PMID: 20929851; PMCID: PMC4262151.

61. Sakaguchi S, Vignali D A, Rudensky A Y, Niec R E, Waldmann H. The plasticity and stability of regulatory T cells. *Nature Reviews Immunology.* 2013; 13(6):461-7. Epub 2013 May 18. doi: 10.1038/nri3464. PubMed PMID: 23681097.

62. Hoeppli R E, Wu D, Cook L, Levings M K. The environment of regulatory T cell biology: cytokines, metabolites, and the microbiome. *Frontiers in Immunology.* 2015; 6:61. Epub 2015 Mar. 6. doi: 10.3389/fimmu.2015.00061. PubMed PMID: 25741338; PMCID: PMC4332351.

63. Vetter I. Development and optimization of FLIPR high throughput calcium assays for ion channels and GPCRs. *Advances in Experimental Medicine and Biology.* 2012; 740:45-82. Epub 2012 Mar. 29. doi: 10.1007/978-94-007-2888-2_3. PubMed PMID: 22453938.

64. Manning Fox J E, Meredith D, Halestrap A P. Characterisation of human monocarboxylate transporter 4 substantiates its role in lactic acid efflux from skeletal muscle. *The Journal of Physiology.* 2000; 529 Pt 2:285-93. Epub 2000 Dec. 2. PubMed PMID: 11101640; PMCID: PMC2270204.

65. Murray C M, Hutchinson R, Bantick J R, Belfield G P, Benjamin A D, Brazma D, Bundick R V, Cook I D, Craggs R I, Edwards S, Evans L R, Harrison R, Holness E, Jackson A P, Jackson C G, Kingston L P, Perry M W, Ross A R, Rugman P A, Sidhu S S, Sullivan M, Taylor-Fishwick D A, Walker P C, Whitehead Y M, Wilkinson D J, Wright A, Donald D K. Monocarboxylate transporter MCT1 is a target for immunosuppression. *Nat Chem Biol.* 2005; 1(7):371-6. PubMed PMID: 16370372.

66. Birsoy K, Wang T, Possemato R, Yilmaz O H, Koch C E, Chen W W, Hutchins A W, Gultekin Y, Peterson T R, Carette J E, Brummelkamp T R, Clish C B, Sabatini D M. MCT1-mediated transport of a toxic molecule is an effective strategy for targeting glycolytic tumors. *Nature Genetics.* 2013; 45(1):104-8. doi: 10.1038/ng.2471. PubMed PMID: 23202129; PMCID: 3530647.

67. Youm Y H, Nguyen K Y, Grant R W, Goldberg E L, Bodogai M, Kim D, D'Agostino D, Planavsky N, Lupfer C, Kanneganti T D, Kang S, Horvath T L, Fahmy T M, Crawford P A, Biragyn A, Alnemri E, Dixit V D. The ketone metabolite beta-hydroxybutyrate blocks NLRP3 inflammasome-mediated inflammatory disease. *Nature Medicine.* 2015; 21(3):263-9. Epub 2015 Feb. 17. doi: 10.1038/nm.3804. PubMed PMID: 25686106; PMCID: PMC4352123.

68. Balasubramanian S, Lewis B, Greed L, Meili D, Flier A, Yamamoto R, Bilic K, Till C, Sass J O. Heterozygous Monocarboxylate Transporter 1 (MCT1, SLC16A1) Deficiency as a Cause of Recurrent Ketoacidosis. *JIMD Rep.* 2016; 29:33-8. Epub 2015 Nov. 27. doi: 10.1007/8904_2015_519. PubMed PMID: 26608392; PMCID: PMC5059203.

69. Philp N J, Ochrietor J D, Rudoy C, Muramatsu T, Linser P J. Loss of MCT1, MCT3, and MCT4 expression in the retinal pigment epithelium and neural retina of the 5A11/basigin-null mouse. *Investigative Ophthalmology & Visual Science.* 2003; 44 (3): 1305-11. Epub 2003 Feb. 26. PubMed PMID: 12601063.

70. Vaihkonen L K, Poso A R. Interindividual variation in total and carrier-mediated lactate influx into red blood cells. *The American Journal of Physiology.* 1998; 274 (4 Pt 2):R1025-30. Epub 1998 May 12. PubMed PMID: 9575965.

71. Merezhinskaya N, Fishbein W N, Davis J I, Foellmer J W. Mutations in MCT1 cDNA in patients with symptomatic deficiency in lactate transport. Muscle & Nerve. 2000; 23(1):90-7. Epub 1999 Dec. 11. PubMed PMID: 10590411.

72. Koho N M, Vaihkonen L K, Poso A R. Lactate transport in red blood cells by monocarboxylate transporters. *Equine Veterinary Journal Supplement.* 2002 (34): 555-9. Epub 2002 Oct. 31. doi: 10.1111/j.2042-3306.2002.tb05482.x. PubMed PMID: 12405750.

73. Koho N M, Raekallio M, Kuusela E, Vuolle J, Poso A R. Lactate transport in canine red blood cells. *Am J Vet Res.*

2008; 69(8):1091-6. Epub 2008 Aug. 5. doi: 10.2460/ajvr.69.8.1091. PubMed PMID: 18672976.

74. Koho N M, Hyyppa S, Poso A R. Monocarboxylate transporters (MCT) as lactate carriers in equine muscle and red blood cells. *Equine Veterinary Journal Supplement.* 2006(36):354-8. Epub 2007 Apr. 4. doi: 10.1111/j.2042-3306.2006.tb05568.x. PubMed PMID: 17402447.

75. Deuticke B. Monocarboxylate transport in red blood cells: kinetics and chemical modification. *Methods Enzymol.* 1989; 173:300-29. Epub 1989 Jan. 1. PubMed PMID: 2674614.

76. Dubinsky W P, Racker E. The mechanism of lactate transport in human erythrocytes. The *Journal of Membrane Biology.* 1978; 44(1):25-36. Epub 1978 Dec. 8. PubMed PMID: 32398.

77. Pattillo R E, Gladden L B. Red blood cell lactate transport in sickle disease and sickle cell trait. *Journal of Applied Physiology.* 2005; 99(3):822-7. Epub 2005 May 14. doi: 10.1152/japplphysiol.00235.2005. PubMed PMID: 15890755.

78. Poole R C, Cranmer S L, Holdup D W, Halestrap A P. Inhibition of L-lactate transport and band 3-mediated anion transport in erythrocytes by the novel stilbenedisulphonate N,N,N',N'-tetrabenzyl-4,4'-diaminostilbene-2,2'-disulphonate (TBenzDS). *Biochimica et Biophysica Acta.* 1991; 1070(1):69-76. Epub 1991 Nov. 18. PubMed PMID: 1751540.

79. Lengacher S, Nehiri-Sitayeb T, Steiner N, Carneiro L, Favrod C, Preitner F, Thorens B, Stehle J C, Dix L, Pralong F, Magistretti P J, Pellerin L. Resistance to diet-induced obesity and associated metabolic perturbations in haploinsufficient monocarboxylate transporter 1 mice. *PloS One.* 2013; 8(12):e82505. Epub 2013 Dec. 25. doi: 10.1371/journal.pone.0082505. PubMed PMID: 24367518; PMCID: PMC3867350.

80. Lee Y, Morrison B M, Li Y, Lengacher S, Farah M H, Hoffman P N, Liu Y, Tsingalia A, Jin L, Zhang P W, Pellerin L, Magistretti P J, Rothstein J D. Oligodendroglia metabolically support axons and contribute to neurodegeneration. *Nature.* 2012; 487(7408):443-8. Epub 2012 Jul. 18. doi: 10.1038/nature11314. PubMed PMID: 22801498; PMCID: PMC3408792.

81. Morrison B M, Tsingalia A, Vidensky S, Lee Y, Jin L, Farah M H, Lengacher S, Magistretti P J, Pellerin L, Rothstein J D. Deficiency in monocarboxylate transporter 1 (MCT1) in mice delays regeneration of peripheral nerves following sciatic nerve crush. *Experimental Neurology.* 2015; 263:325-38. doi: 10.1016/j.expneurol.2014.10.018. PubMed PMID: 25447940.

82. Yan W. Male infertility caused by spermatogenic defects: lessons from gene knockouts. *Mol Cell Endocrinol.* 2009; 306(1-2):24-32. Epub 2009 Jun. 2. doi: 10.1016/j.mce.2009.03.003. PubMed PMID: 19481682; PMCID: PMC5438260.

83. Murdoch F, Goldberg E. Male contraception: another Holy Grail. *Bioorg Med Chem Lett* 2014; 24(2):419-24. Epub Epub 2013 Dec. 7. doi: doi: 10.1016/j.bmcl.2013.12.004.

84. Sexton J Z, Danshina P V, Lamson D R, Hughes M, House A J, Yeh L A, O'Brien D A, Williams K P. Development and Implementation of a High Throughput Screen for the Human Sperm-Specific Isoform of Glyceraldehyde 3-Phosphate Dehydrogenase (GAPDHS). *Curr Chem Genomics.* 2011; 5:30-41. Epub 2011 Jul. 16. doi: 10.2174/1875397301105010030. PubMed PMID: 21760877; PMCID: PMC3134944.

85. Halford S E R, Jones P, Wedge S, Hirschberg S, Katugampola S, Veal G, Payne G, Bacon C, Potter S, Griffin M, Chenard-Poirier M, Petrides G, Holder G, Keun H C, Banerji U, Plummer E R. A first-in-human first-in-class (FIC) trial of the monocarboxylate transporter 1 (MCT1) inhibitor AZD3965 in patients with advanced solid tumours. *Journal of Clinical Oncology.* 2017; 35(15_suppl): 2516—. doi: 10.1200/JCO.2017.35.15_suppl.2516.

86. Smith A J. New horizons in therapeutic antibody discovery: opportunities and challenges versus small-molecule therapeutics. *J Biomol Screen.* 2015; 20(4):437-53. Epub 2014 Dec. 17. doi: 10.1177/1087057114562544. PubMed PMID: 25512329.

87. Jones T D, Crompton U J, Carr F J, Baker M P. Deimmunization of Monoclonal Antibodies. In: Dimitrov A S, editor. *Therapeutic Antibodies: Methods and Protocols.* Totowa, NJ: Humana Press; 2009. p. 405-23.

88. Kirk P, Wilson M C, Heddle C, Brown M H, Barclay A N, Halestrap A P. CD147 is tightly associated with lactate transporters MCT1 and MCT4 and facilitates their cell surface expression. *The EMBO Journal.* 2000; 19(15): 3896-904. doi: 10.1093/emboj/19.15.3896. PubMed PMID: 10921872; PMCID: 306613.

89. Toleikis L, Frenzel A. Cloning single-chain antibody fragments (ScFv) from hybridoma cells. *Methods in Molecular Biology.* 2012; 907:59-71. Epub 2012 Aug. 22. doi: 10.1007/978-1-61779-974-7_3. PubMed PMID: 22907345.

90. Gleichmann E, Van Elven E H, Van der Veen J P. A systemic lupus erythematosus (SLE)-like disease in mice induced by abnormal T-B cell cooperation. Preferential formation of autoantibodies characteristic of SLE. *European journal of Immunology.* 1982; 12(2):152-9. Epub 1982 Feb. 1. doi: 10.1002/eji.1830120210. PubMed PMID: 6978818.

91. Chu Y W, Gress R E. Murine models of chronic graft-versus-host disease: insights and unresolved issues. *Biol Blood Marrow Transplant.* 2008; 14(4):365-78. Epub 2008 Mar. 18. doi: 10.1016/j.bbmt.2007.12.002. PubMed PMID: 18342778; PMCID: PMC2376050.

92. Liu J, Wang L, Zhao F, Tseng S, Narayanan C, Shura L, Willingham S, Howard M, Prohaska S, Volkmer J, Chao M, Weissman I L, Majeti R. Pre-Clinical Development of a Humanized Anti-CD47 Antibody with Anti-Cancer Therapeutic Potential. *PloS One.* 2015; 10(9):e0137345. doi: 10.1371/journal.pone.0137345. PubMed PMID: 26390038; PMCID: PMC4577081.

93 Kelley M, Ahene A B, Gorovits B, Kamerud J, King L E, McIntosh T, Yang J. Theoretical considerations and practical approaches to address the effect of anti-drug antibody (ADA) on quantification of biotherapeutics in circulation. *AAPS J.* 2013; 15 (3): 646-58. Epub 2013 Apr. 2. doi: 10.1208/s12248-013-9468-4. PubMed PMID: 23543601; PMCID: PMC3691419.

94. Warburg, O. On the origin of cancer cells. *Science* 1956, 723, 309-314.

95. Koppenol, W. H.; Bounds, P. L; Dang, C. V. Otto Warburg's contributions to current concepts of cancer metabolism. *Nature Rev. Cancer* 2011, 77, 325-327.

96. Doherty, J. R.; Yang, C; Scott, K.; Cameron M. D.; Fallahi, M.; Li, W; Hall, M. A.; Amelio, A. L.; Mishra, J. K.; Li, F; Tortosa, M.; Genau, H. M.; Rounbehler, R. J.; Yungi, L.; Dang, C. V.; Kumar, K. G.; Butler, A. A.; Bannister, T. D.; Hooper, A. T.; Unsal-Kacmaz, K.; Roush, W. R.; and Cleveland, J. L. Blocking lactate export by inhibiting the myc target MCT1 disables glycolysis and glutathione synthesis. *Cancer Res.* 2014, 74, 908-920.

97. Ullah, M. S.; Davies, A. J.; Halestrap, A. P. The plasma membrane lactate transporter MCT4, but not MCT1, is up-regulated by hypoxia through a HIF-1α-dependent mechanism. *J. Biol. Chem.* 2006, 287, 9030-9037.

98. Dang, C. V. The interplay between MYC and HIF in the Warburg effect. *Ernst Schering Found Symp. Proc.* 2007, 35-53.

99. Vaupel, P.; Mayer, A. Hypoxia in cancer: significance and impact on clinical outcome. *Cancer Metastasis Rev.* 2007, 26, 225-239.

100. Kizaka-Kondoh, S.; Inoue, M.; Harada, H.; Hiraoka, M. Tumor hypoxia: a target for selective cancer therapy. *Cancer Sci.* 2003, 94, 1021-1028.

101. Otonkoski, T; Jiao, H; Kaminen-Ahola, N; et al. Physical exercise-induced hypoglycemia caused by failed silencing of monocarboxylate transporter 1 in pancreatic beta cells. *Am J Hum Genet* 2007; 87, 467-474.

102. Zhao, C; Wilson, M. C; Schuit, F; Halestrap, A. P.; Rutter, G. A. Expression and distribution of lactate/monocarboxylate transporter isoforms in pancreatic islets and the exocrine pancreas. *Diabetes* 2001; 50, 361-366.

103. Otonkoski, T.; Kaminen, N; Ustinov, J; et al. Physical exercise-induced hyperinsulinemic hypoglycemia is an autosomal-dominant trait characterized by abnormal pyruvate-induced insulin release. *Diabetes* 2003; 52, 199-204.

104. Pullen T. J; Sylow, L; Sun, G.; Halestrap, A. P.; Richter, E. A.; Rutter, G. A. Overexpression of Monocarboxylate Transporter-1 (Slc16a1) in Mouse Pancreatic beta-Cells Leads to Relative Hyperinsulinism During Exercise. *Diabetes* 2012, 61, 1719-1725.

105. Roncarolo M G, Yssel H, Touraine J L, Betuel H, De Vries J E, Spits H. Autoreactive T cell clones specific for class I and class II HLA antigens isolated from a human chimera. *J Exp Med.* 1988 May 1; 167(5):1523-1534

106. Bacchetta R, Bigler M, Touraine J L, Parkman R, Tovo P A, Abrams J, de Waal Malefyt R, de Vries J E, Roncarolo M G. High levels of interleukin 10 production in vivo are associated with tolerance in SCID patients transplanted with HLA mismatched hematopoietic stem cells. *The Journal of Experimental Medicine.* 1994; 179 (2):493-502.

107. Winfried Barchet, Jeffrey D. Price, Marina Cella, Marco Colonna, Sandra K. MacMillan, J. Perren Cobb, Paul A. Thompson, Kenneth M. Murphy, John P. Atkinson, and Claudia Kemper. Complement-induced regulatory T cells suppress T-cell responses but allow for dendritic-cell maturation. *Blood.* 2006 Feb. 15; 107(4): 1497-1504.

MCT1 AND ANTI-MCT1 ANTIBODY SEQUENCES

Human MCT1 amino acid sequence

SEQ ID NO: 1

```
MPPAVGGPVGYTPPDGGWGWAVVIGAFISIGFSYAFPKSITVFFKEIEGIFHATTSEVSWISSIMLAVMYGGG
PISSILVNKYGSRIVMIVGGCLSGCGLIAASFCNTVQQLYVCIGVIGGLGLAFNLNPALTMIGKYFYKRRPLANG
LAMAGSPVFLCTLAPLNQVFFGIFGWRGSFLILGGLLLNCCVAGALMRPIGPKPTKAGKDKSKASLEKAGKSG
```

-continued

---

MCT1 AND ANTI-MCT1 ANTIBODY SEQUENCES

---

VKKDLHDANTDLIGRHPKQEKRSVFQTINQFLDLTLFTHRGFLLYLSGNVIMFFGLFAPLVFLSSYGKSQHYSSE
KSAFLLSILAFVDMVARPSMGLVANTKPIRPRIQYFFAASVVANGVCHMLAPLSTTYVGFCVYAGFFGFAFG
WLSSV_FETLMDLVGPQRFSSAVGLVTIVECCPV_LGPPLLGRLNDMYGDYKYTYWACGVVLIISGIYLFIGMGI
NYRLLAKEQKANEQKKESKEEETSIDVAGKPNEVTKAAESPDQKDTDGGPKEEESPV

MCT1 Ab1 (INX310) VH

SEQ ID NO: 2

QVQLKATGPGLVQPTQTLSITCTVSGFSLTNYHLQWVRQTPGKGLEWMGFIRSSGNTEYNSEFKSRLSISRD
TSKNQVFLKMNSLKTDDTGVYYCARNSWYHGTYYSPGYYVMDAWGQGASVTVSS

MCT1 Ab1 (INX310) VL

SEQ ID NO: 3

NIHLTQSPSLLSASVGDRVTLSCKGSQNINNYLAWFQQKFGETPKLLIYNRHNLQTGIPSRFSGSGSGTDYTLT
INSLQPEDVATYFCQYSDGYTFGAGTKLELK

MCT1 Ab1 (INX310) VH CDR1

SEQ ID NO: 4

GFSLTNYH

MCT1 Ab1 (INX310) VH CDR2

SEQ ID NO: 5

IRSSGNT

MCT1 Ab1 (INX310) VH CDR3

SEQ ID NO: 6

ARNSWYHGTYYSPGYYVMDAWG

MCT1 Ab1 (INX310) VL CDR1

SEQ ID NO: 7

QNINNY

MCT1 Ab1 (INX310) VL CDR2

SEQ ID NO: 8

NRH

MCT1 Ab1 (INX310) VL CDR3

SEQ ID NO: 9

YQYSDGYT

Ab1 (INX310)
>INX310_VH

SEQ ID NO: 10

QVQLKATGPGLVQPTQTLSITCTVSGFSLTNYHLQWVRQTPGKGLEWMGFIRSSGNTEYN
SEFKSRLSISRDTSKNQVFLKMNSLKTDDTGVYYCARNSWYHGTYYSPGYYVMDAWGQGA
SVTVSS

>INX310_VL

SEQ ID NO: 11

NIHLTQSPSLLSASVGDRVTLSCKGSQNINNYLAWFQQKFGETPKLLIYNRHNLQTGIPS
RFSGSGSGTDYTLTINSLQPEDVATYFCQYSDGYTFGAGTKLELK

Ab2 (INX352)
>INX352_VH

SEQ ID NO: 12

QVQLKESGPGLVKPSQTLSLTCTVSGFSLTNYHLQWVRQPPGKGLEWIGFIRSSGNTEYN
PSLKSRVTISRDTSKNQVSLKLSSVTAADTAVYYCARNSWYHGTYYSPGYYVMDAWGQGT
LVTVSS

>INX352|INX356|INX364_VL

SEQ ID NO: 13

DIQMTQSPSSLSASVGDKVTITCRGSQNINNYLAWFQQKPGKTPALLIYNRHNLQSGVPS
RFRGSGSGTDYTLTISSLQPEDVATYYCQYSDGYTFGPGTKVDIK

Ab3 (INX356)
>INX356_VH

SEQ ID NO: 14

QVQLQESGPGLVKPSETLSLTCTVSGFSLTNYHLQWIRQPPGKGLEWIGFIRSSGNTEYN
PSLKSRVTISRDTSKNQVSLKLSSVTAADTAVYYCARNSWYHGTYYSPGYYVMDAWGQGT
MVTVSS

>INX352|INX356|INX364_VL

SEQ ID NO: 15

DIQMTQSPSSLSASVGDKVTITCRGSQNINNYLAWFQQKPGKTPALLIYNRHNLQSGVPS
RFRGSGSGTDYTLTISSLQPEDVATYYCYQYSDGYTFGPGTKVDIK

Ab4 (INX364)
>INX364_VH

-continued

---

MCT1 AND ANTI-MCT1 ANTIBODY SEQUENCES

SEQ ID NO: 16

QVQLQESGPGLVKPSQTLSLTCTVSGFSLTNYHLQWIRQPPGKGLEWIGIRSSGNTEYN
PSLKSRVTISRDTSKNQVSLKLSSVTAADTAVYYCARNSWYHGTYYSPGYYVMDAWGQGT
LVTVSS

>INX352|INX356|INX364_VL

SEQ ID NO: 17

DIQMTQSPSSLSASVGDKVTITCRGSQNINNYLAWFQQKPGKTPALLIYNRHNLQSGVPS
RFRGSGSGTDYTLTISSLQPEDVATYYCYQYSDGYTFGPGTKVDIK silent IgG1 (constant)
E269R/K322A
>IgG1_INX_Silent

SEQ ID NO: 18

ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCDKTHTCPPCPAPELLGG
PSVFLFPPKPKDTLMISRTPEVTCVVVDVSHRDPEVKFNWYVDGVEVHNAKTKPREEQYN
STYRVVSVLTVLHQDWLNGKEYKCAVSNKALPAPIEKTISKAKGQPREPQVYTLPPSRDE
LTKNQVSLTCLVKGFYPSDIAVEWESNGQPENNYKTTPPVLDSDGSFFLYSKLTVDKSRW
QQGNVFSCSVMHEALHNHYTQKSLSLSPGK

HUMANIZED Ab1 (INX310) VARIABLE HEAVY CHAIN POLYPEPTIDE
SEQ ID NO: 19

QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNSWYHGTYYSPGYYVMDAWGQGT

HUMANIZED Ab1 (INX310) HEAVY CHAIN POLYPEPTIDE
aMCT1_Humanized_VH1_hIgG1_INXsilent_HC
SEQ ID NO: 20

<u>QVQLQESGPGLVKPSETLSLTCTVSGFSLTNYHLQWIRQPPGKGLEWIGFIRSSGNTEYNPSLKSRVTISRDTS</u>
<u>KNQVSLKLSSVTAADTAVYYCARNSWYHGTYYSPGYYVMDAWGQGTM</u>*VTVSSASTKGPSVFPLAPSSKSTS*
*GGTAALGCLVKDYFPEPVTVSWNSGALTSGVHTFPAVLQSSGLYSLSSVVTVPSSSLGTQTYICNVNHKPSNT*
*KVDKKVEPKSCDKTHTCPPCPAPELLGGPSVFLFPPKPKDTLMISRTPEVTCVVVDVSHRDPEVKFNWYVDG*
*VEVHNAKTKPREEQYNSTYRVVSVLTVLHQDWLNGKEYKCAVSNKALPAPIEKTISKAKGQPREPQVYTLPPS*
*RDELTKNQVSLTCLVKGFYPSDIAVEWESNGQPENNYKTTPPVLDSDGSFFLYSKLTVDKSRWQQGNVFSCS*
*VMHEALHNHYTQKSLSLSPGK*

HUMANIZED Ab1 (INX310) VARIABLE HEAVY CHAIN POLYPEPTIDE
SEQ ID NO: 21

QVQLKESGPGLVKPSETLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYVMDAWGQGTMVTVSS

HUMANIZED Ab1 (INX310) HEAVY CHAIN POLYPEPTIDE
aMCT1_Humanized_VH2_hIgG1_INXsilent_HC
SEQ ID NO: 22

<u>QVQLKESGPGLVKPSETLSLTCTVSGFSLTNYHLQWVRQPPGKGLEWIGFIRSSGNTEYN</u>
<u>PSLKSRVTISRDTSKNQVSLKLSSVTAADTAVYYCARNSWYHGTYYSPGYYVMDAWGQGTM</u>*VTVSSASTKG*
*PSVFPLAPSSKSTSGGTAALGCLVKDYFPEPVTVSWNSGALTSGVHTFPAVLQSSGLYSLSSVVTVPSSSLGTQ*
*TYICNVNHKPSNTKVDKKVEPKSCDKTHTCPPCPAPELLGGPSVFLFPPKPKDTLMISRTPEVTCVVVDVSHRD*
*PEVKFNWYVDGVEVHNAKTKPREEQYNSTYRVVSVLTVLHQDWLNGKEYKCAVSNKALPAPIEKTISKAKGQ*
*PREPQVYTLPPSRDELTKNQVSLTCLVKGFYPSDIAVEWESNGQPENNYKTTPPVLDSDGSFFLYSKLTVDKSR*
*WQQGNVFSCSVMHEALHNHYTQKSLSLSPGK*

HUMANIZED Ab1 (INX310) VARIABLE HEAVY CHAIN POLYPEPTIDE
SEQ ID NO: 23

QVQLQESGPGLVKPSQTLSLTCTVSGFSLTNYHLQWIRQPPGKGLEWIGFIRSSGNTEYN
PSLKSRVTISRDTSKNQVSLKLSSVTAADTAVYYCARNSWYHGTYYSPGYYVMDAWGQGTLVTVSS

HUMANIZED Ab1 (INX310) HEAVY CHAIN POLYPEPTIDE
aMCT1_Humanized_VH3_hIgG1_INXsilent_HC
SEQ ID NO: 24

<u>QVQLQESGPGLVKPSQTLSLTCTVSGFSLTNYHLQWIRQPPGKGLEWIGFIRSSGNTEYN</u>
<u>PSLKSRVTISRDTSKNQVSLKLSSVTAADTAVYYCARNSWYHGTYYSPGYYVMDAWGQGTLVTVSSA</u>*STKGP*
*SVFPLAPSSKSTSGGTAALGCLVKDYFPEPVTVSWNSGALTSGVHTFPAVLQSSGLYSLSSVVTVPSSSLGTQT*
*YICNVNHKPSNTKVDKKVEPKSCDKTHTCPPCPAPELLGGPSVFLFPPKPKDTLMISRTPEVTCVVVDVSHRDP*
*EVKFNWYVDGVEVHNAKTKPREEQYNSTYRVVSVLTVLHQDWLNGKEYKCAVSNKALPAPIEKTISKAKGQP*
*REPQVYTL*
*PPSRDELTKNQVSLTCLVKGFYPSDIAVEWESNGQPENNYKTTPPVLDSDGSFFLYSKLT*
*VDKSRWQQGNVFSCSVMHEALHNHYTQKSLSLSPGK*

HUMANIZED Ab1 (INX310) VARIABLE HEAVY CHAIN POLYPEPTIDE
SEQ ID NO: 25

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYVMDAWGQGTLVTVSS

HUMANIZED Ab1 (INX310) HEAVY CHAIN POLYPEPTIDE
aMCT1_Humanized_VH4_hIgG1_INXsilent_HC -continued

---

MCT1 AND ANTI-MCT1 ANTIBODY SEQUENCES

SEQ ID NO: 26
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYVMDAWGQGTLVTVSSASTKGPSVFPLAPSSKSTS
*GGTAALGCLVKDYFPEPVTVSWNSGALTSGVHTFPAVLQSSGLYSLSSVVTVPSSSLGTQTYICNVNHKPSNT*
*KVDKKVEPKSCDKTHTCPPCPAPELLGGPSVFLFPPKPKDTLMISRTPEVTCVVVDVSHRDPEVKFNWYVDG*
*VEVHNAKTKPREEQYNSTYRVVSVLTVLHQDWLNGKEYKCAVSNKALPAPIEKTISKAKGQPREPQVYTL*
*PPSRDELTKNQVSLTCLVKGFYPSDIAVEWESNGQPENNYKTTPPVLDSDGSFFLYSKLT*
*VDKSRWQQGNVFSCSVMHEALHNHYTQKSLSLSPGK*

HUMANIZED Ab1 (INX310) VARIABLE HEAVY CHAIN POLYPEPTIDE

SEQ ID NO: 27
QVQLQESGPGLVQPTQTLSITCTVSGFSLTNYHLQWVRQTPGKGLEWMGFIRSSGNTEYNSEFKSRLSISRDT
SKNQVFLKMNSLKTEDTGVYYCARNSWYHGTYYSPGYYVMDAWGQGTTVTVSS

HUMANIZED Ab1 (INX310) HEAVY CHAIN POLYPEPTIDE
>aMCT1_Humanized_VH_AmbCons_hIgG1_INXsilent_HC SEQ ID NO: 28
QVQLQESGPGLVQPTQTLSITCTVSGFSLTNYHLQWVRQTPGKGLEWMGFIRSSGNTEYNSEFKSRLSISRDT
SKNQVFLKMNSLKTEDTGVYYCARNSWYHGTYYSPGYYVMDAWGQGTTVTVSS*ASTKGPSVFPLAPSSKST*
*SGGTAALGCLVKDYFPEPVTVSWNSGALTSGVHTFPAVLQSSGLYSLSSVVTVPSSSLGTQTYICNVNHKPSN*
*TKVDKKVEPKSCDKTHTCPPCPAPELLGGPSVFLFPPKPKDTLMISRTPEVTCVVVDVSHRDPEVKFNWYVDG*
*VEVHNAKTKPREEQYNSTYRVVSVLTVLHQDWLNGKEYKCAVSNKALPAPIEKTISKAKGQPREPQVYTL*
*PPSRDELTKNQVSLTCLVKGFYPSDIAVEWESNGQPENNYKTTPPVLDSDGSFFLYSKLT*
*VDKSRWQQGNVFSCSVMHEALHNHYTQKSLSLSPGK*

HUMANIZED Ab1 (INX310) VARIABLE HEAVY CHAIN POLYPEPTIDE
SEQ ID NO: 29
QVQLQESGPGLVKPSQTLSLTCTVSGFSLTNYHLQWVRQPPGKGLEWMGFIRSSGNTEYNSEFKSRLSISRD
TSKNQVYLQMNSLKTEDTAVYYCARNSWYHGTYYSPGYYVMDAWGQGTTVTVSS

HUMANIZED Ab1 (INX310) HEAVY CHAIN POLYPEPTIDE
aMCT1_Humanized_VH_AmbMod_hIgG1_INXsilent_HC SEQ ID NO: 30
QVQLQESGPGLVKPSQTLSLTCTVSGFSLTNYHLQWVRQPPGKGLEWMGFIRSSGNTEYNSEFKSRLSISRD
TSKNQVYLQMNSLKTEDTAVYYCARNSWYHGTYYSPGYYVMDAWGQGTTVTVSS*ASTKGPSVFPLAPSSKS*
*TSGGTAALGCLVKDYFPEPVTVSWNSGALTSGVHTFPAVLQSSGLYSLSSVVTVPSSSLGTQTYICNVNHKPS*
*NTKVDKKVEPKSCDKTHTCPPCPAPELLGGPSVFLFPPKPKDTLMISRTPEVTCVVVDVSHRDPEVKFNWYVD*
*GVEVHNAKTKPREEQYNSTYRVVSVLTVLHQDWLNGKEYKCAVSNKALPAPIEKTISKAKGQPREPQVYTL*
*PPSRDELTKNQVSLTCLVKGFYPSDIAVEWESNGQPENNYKTTPPVLDSDGSFFLYSKLT*
*VDKSRWQQGNVFSCSVMHEALHNHYTQKSLSLSPGK*

HUMANIZED Ab1 (INX310) VARIABLE HEAVY CHAIN POLYPEPTIDE

SEQ ID NO: 31
QVQLQESGPGLVKPSQTLSLTCTVSGFSLTNYHLQWVRQPPGKGLEWMGFIRSSGNTEYNSEFKSRLTISKD
TSKNQVYLQMNSLKTEDTAVYYCARNSWYHGTYYSPGYYVMDAWGQGTTVTVSS

HUMANIZED Ab1 (INX310) HEAVY CHAIN POLYPEPTIDE
aMCT1_Humanized_VH_AmbAgg_hIgG1_INXsilent_HC SEQ ID NO: 32
QVQLQESGPGLVKPSQTLSLTCTVSGFSLTNYHLQWVRQPPGKGLEWMGFIRSSGNTEYNSEFKSRLTISKD
TSKNQVYLQMNSLKTEDTAVYYCARNSWYHGTYYSPGYYVMDAWGQGTTVTVSS*ASTKGPSVFPLAPSSKS*
*TSGGTAALGCLVKDYFPEPVTVSWNSGALTSGVHTFPAVLQSSGLYSLSSVVTVPSSSLGTQTYICNVNHKPS*
*NTKVDKKVEPKSCDKTHTCPPCPAPELLGGPSVFLFPPKPKDTLMISRTPEVTCVVVDVSHRDPEVKFNWYVD*
*GVEVHNAKTKPREEQYNSTYRVVSVLTVLHQDWLNGKEYKCAVSNKALPAPIEKTISKAKGQPREPQVYTL*
*PPSRDELTKNQVSLTCLVKGFYPSDIAVEWESNGQPENNYKTTPPVLDSDGSFFLYSKLT*
*VDKSRWQQGNVFSCSVMHEALHNHYTQKSLSLSPGK*

HUMANIZED Ab1 (INX310) VARIABLE LIGHT CHAIN POLYPEPTIDE

SEQ ID NO: 33
DIQMTQSPSSLSASVGDRVTITCRGSQNINNYLAWFQQKPGKTPKLLIYNRHNLQSGVPS
RFSGSGSGTDFTLTISSLQPEDVATYYCYQYSDGYTFGQGTKLEIK

HUMANIZED Ab1 (INX310) LIGHT CHAIN POLYPEPTIDE
aMCT1_Humanized_VL1_hKappa_LC

SEQ ID NO: 34
DIQMTQSPSSLSASVGDRVTITCRGSQNINNYLAWFQQKPGKTPKLLIYNRHNLQSGVPS
RFSGSGSGTDFTLTISSLQPEDVATYYCYQYSDGYTFGQGTKLEIK*RTVAAPSVFIFPPSDEQLKSGTASVVCLL*
*NNFYPREAKVQWKVDNALQSGNSQESVTEQDSKDSTYSLSSTLTLSKADYEKHKVYACEVTHQGLSSPVTKSF*
*NRGEC*

HUMANIZED Ab1 (INX310) VARIABLE LIGHT CHAIN POLYPEPTIDE

SEQ ID NO: 35
DIQMTQSPSSLSASVGDKVTITCRGSQNINNYLAWFQQKPGKTPALLIYNRHNLQSGVPS
RFRGSGSGTDFTLTISSLQPEDVATYYCYQYSDGYTFGPGTKVDIK

HUMANIZED Ab1 (INX310) LIGHT CHAIN POLYPEPTIDE
aMCT1_Humanized_VL3_hKappa_LC

-continued

---
MCT1 AND ANTI-MCT1 ANTIBODY SEQUENCES
---

SEQ ID NO: 36

DIQMTQSPSSLSASVGDKVTITCRGSQNINNYLAWFQQKPGKTPALLIYNRHNLQSGVPS
RFRGSGSGTDFTLTISSLQPEDVATYYCYQYSDGYTFGPGTKVDIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLSSPVTKSF
NRGEC

HUMANIZED Ab1 (INX310) VARIABLE LIGHT CHAIN POLYPEPTIDE

SEQ ID NO: 37

DIQMTQSPSSLSASVGDKVTITCRGSQNINNYLAWFQQKPGKTPALLIYNRHNLQSGVPS
RFRGSGSGTDYTLTISSLQPEDVATYYCYQYSDGYTFGPGTKVDIK

HUMANIZED Ab1 (INX310) LIGHT CHAIN POLYPEPTIDE
>aMCT1_Humanized_VL4_hKappa_LC

SEQ ID NO: 38

DIQMTQSPSSLSASVGDKVTITCRGSQNINNYLAWFQQKPGKTPALLIYNRHNLQSGVPS
RFRGSGSGTDYTLTISSLQPEDVATYYCYQYSDGYTFGPGTKVDIKRTVAAPSVFIFPPS
DEQLKSGTASVVCLLNNFYPREAKVQWKVDNALQSGNSQESVTEQDSKDSTYSLSSTLTL
SKADYEKHKVYACEVTHQGLSSPVTKSFNRGEC

HUMANIZED Ab1 (INX310) VARIABLE LIGHT CHAIN POLYPEPTIDE

SEQ ID NO: 39

NIQMTQSPSLLSASVGDRVTLSCKGSQNINNYLAWFQQKFGETPKLLIYNRHNLQTGIPS
RFSGSGSGTDYTLTINSLQPEDVATYFCYQYSDGYTFGGGTKVEIK

HUMANIZED Ab1 (INX310) LIGHT CHAIN POLYPEPTIDE
aMCT1_Humanized_VL_AmbCons_hKappa_LC

SEQ ID NO: 40

NIQMTQSPSLLSASVGDRVTLSCKGSQNINNYLAWFQQKFGETPKLLIYNRHNLQTGIPS
RFSGSGSGTDYTLTINSLQPEDVATYFCYQYSDGYTFGGGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLSSPVTKSF
NRGEC

HUMANIZED Ab1 (INX310) VARIABLE LIGHT CHAIN POLYPEPTIDE

SEQ ID NO: 41

NIQMTQSPSLLSASVGDRVTISCKGSQNINNYLAWFQQKFGETPKLLIYNRHNLQTGIPS
RFSGSGSGTDYTLTISSLQPEDVATYFCYQYSDGYTFGGGTKVEIK

HUMANIZED Ab1 (INX310) LIGHT CHAIN POLYPEPTIDE
aMCT1_Humanized_VL_AmbMod_hKappa_LC

SEQ ID NO: 42

NIQMTQSPSLLSASVGDRVTISCKGSQNINNYLAWFQQKFGETPKLLIYNRHNLQTGIPS
RFSGSGSGTDYTLTISSLQPEDVATYFCYQYSDGYTFGGGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLSSPVTKSF
NRGEC

HUMANIZED Ab1 (INX310) VARIABLE LIGHT CHAIN POLYPEPTIDE

SEQ ID NO: 43

NIQMTQSPSLLSASVGDRVTISCKGSQNINNYLAWFQQKFGQPPKLLIYNRHNLQTGIPS
RFSGSGSGTDYTLTISSLQPEDVATYYCYQYSDGYTFGGGTKVEIK

HUMANIZED Ab1 (INX310) LIGHT CHAIN POLYPEPTIDE
aMCT1_Humanized_VL_AmbAgg_hKappa_LC

SEQ ID NO: 44

NIQMTQSPSLLSASVGDRVTISCKGSQNINNYLAWFQQKFGQPPKLLIYNRHNLQTGIPS
RFSGSGSGTDYTLTISSLQPEDVATYYCYQYSDGYTFGGGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLSSPVTKSF
NRGEC

Ab5 (INX402)
>VH

SEQ ID NO: 45

QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNSWYHGTYYSPGYYVMDAWGQGTMVTVSS

>LC

SEQ ID NO: 46

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab6 (INX403)
>VH

SEQ ID NO: 47

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYVMDAWGQGTLVTVSS

>VL

SEQ ID NO: 48

-continued

---
MCT1 AND ANTI-MCT1 ANTIBODY SEQUENCES
---

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab7 (INX404)
>VH

SEQ ID NO: 49

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWRHGTWYSPGYYVMDAWGQGTLVTVSS

>VL

SEQ ID NO: 50

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab8 (INX405)
>VH

SEQ ID NO: 51

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRFVHGTWYSPGYYVMDAWGQGTLVTVSS

>VL

SEQ ID NO: 52

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab9 (INX406)
>VH

SEQ ID NO: 53

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNKWIHGTWYSPGYYVMDAWGQGTLVTVSS

>VL

SEQ ID NO: 54

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab10 (INX407)
>VH

SEQ ID NO: 55

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYMMDAWGQGTLVTVSS

>VL

SEQ ID NO: 56

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab11 (INX408)
>VH

SEQ ID NO: 57

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYLMDAWGQGTLVTVSS

>VL

SEQ ID NO: 58

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab12 (INX409)
>VH

SEQ ID NO: 59

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWIHGTWYSPGYYVMDAWGQGTLVTVSS

>VL

SEQ ID NO: 60

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab13 (INX410)
>VH

SEQ ID NO: 61

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYWSPGYYVMDAWGQGTLVTVSS

>VL

SEQ ID NO: 62

MCT1 AND ANTI-MCT1 ANTIBODY SEQUENCES

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab14 (INX411)
>VH
                                                             SEQ ID NO: 63
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVHGTWYSPGYYVMDAWGQGTMVTVSS

VL
                                                             SEQ ID NO: 64
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab15 (INX412)
>VH
                                                             SEQ ID NO: 65
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVQGWWYSPGYYVMDAWGQGTMVTVSS

>VL
                                                             SEQ ID NO: 66
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab16 (INX413)
>VH
                                                             SEQ ID NO: 67
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYFSPGYYLMDAWGQGTLVTVSS

>VL
                                                             SEQ ID NO: 68
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab17 (INX414)
>VH
                                                             SEQ ID NO: 69
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARKRWVHGTWYSPGYYVMDAWGQGTLVTVSS

>VL
                                                             SEQ ID NO: 70
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab18 (INX415)
>VH
                                                             SEQ ID NO: 71
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWMHGTWYSPGYYVMDAWGQGTLVTVSS

>VL
                                                             SEQ ID NO: 72
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab19 (INX416)
>VH
                                                             SEQ ID NO: 73
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARERWVHGTYYSPGYYVMDAWGQGTLVTVSS

>VL
                                                             SEQ ID NO: 74
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab20 (INX417)
>VH
                                                             SEQ ID NO: 75
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWVQGTYYSPGYYVMDAWGQGTLVTVSS

>VL
                                                             SEQ ID NO: 76

-continued

---
MCT1 AND ANTI-MCT1 ANTIBODY SEQUENCES
---

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab21 (INX418)
>VH
                                                              SEQ ID NO: 77
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWVHGTWYSPGYYVMDAWGQGTLVTVSS

>VL
                                                              SEQ ID NO: 78
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab22 (INX419)
>VH
                                                              SEQ ID NO: 79
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVQGSYYSPGYYVMDAWGQGTMVTVSS

>VL
                                                              SEQ ID NO: 80
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab23 (NX420)
>VH
                                                              SEQ ID NO: 81
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRFVHGTWYSPGYYLMDAWGQGTLVTVSS

>VL
                                                              SEQ ID NO: 82
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab24 (INX421)
>VH
                                                              SEQ ID NO: 83
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWIHGTWYSPGYYLMDAWGQGTLVTVSS

>VL
                                                              SEQ ID NO: 84
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab25 (INX422)
>VH
                                                              SEQ ID NO: 85
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVHGTWYSPGYYLMDAWGQGTMVTVSS

>VL
                                                              SEQ ID NO: 86
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab26 (INX423)
>VH
                                                              SEQ ID NO: 87
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVQGWWYSPGYYLMDAWGQGTMVTVSS

>VL
                                                              SEQ ID NO: 88
DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab27 (INX424)
>VH
                                                              SEQ ID NO: 89
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWMHGTWYSPGYYLMDAWGQGTLVTVSS

>VL
                                                              SEQ ID NO: 90

-continued

---

MCT1 AND ANTI-MCT1 ANTIBODY SEQUENCES

---

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab28 (INX425)
>VH
<div align="right">SEQ ID NO: 91</div>

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARERWVHGTYFSPGYYLMDAWGQGTLVTVSS

>VL
<div align="right">SEQ ID NO: 92</div>

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab29 (INX426)
>VH
<div align="right">SEQ ID NO: 93</div>

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWVHGTWYSPGYYLMDAWGQGTLVTVSS

>VL
<div align="right">SEQ ID NO: 94</div>

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab30 (INX427)
>VH
<div align="right">SEQ ID NO: 95</div>

QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVQGSYYSPGYYLMDAWGQGTMVTVSS

>VL
<div align="right">SEQ ID NO: 96</div>

DIQMTQSPSSLSASVGDKVTITCRGSQNINNYLAWFQQKPGKTPALLIYNRHNLQSGVPSRFRGSGSGTDYT
LTISSLQPEDVATYYCYQYSDGYTFGPGTKVDIK

Ab31 (INX428)
>VH
<div align="right">SEQ ID NO: 97</div>

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYVMDAWGQGTLVTVSS

>VL
<div align="right">SEQ ID NO: 98</div>

EIVLTQSPDSLAVSLGERATINCKSSQSVFYNSYNRNYLAWYQQKPGQPPKLLIYWASTRESGVPDRFSGSGS
GTDFTLTISSLQAEDVAVYYCQQYYSTPSFTFGPGTKVDIK

Ab32 (INX429)
>VH
<div align="right">SEQ ID NO: 99</div>

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYVMDAWGQGTLVTVSS

>VL
<div align="right">SEQ ID NO: 100</div>

AIQMTQSPSSLSASVGDRVTITCRASQGISNYLAWFQQKPGKAPKSLIYAASSLQSGVPSRFSGSGSGTDFTLT
ISSLQPEDFATYYCQQSDSPPYTFGLGTKLEIK

Ab33 (INX430)
>VH
<div align="right">SEQ ID NO: 101</div>

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYVMDAWGQGTLVTVSS

>VL
<div align="right">SEQ ID NO: 102</div>

DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab34 (INX431)
>VH
<div align="right">SEQ ID NO: 103</div>

QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYVMDAWGQGTLVTVSS

>VL
<div align="right">SEQ ID NO: 104</div>

MCT1 AND ANTI-MCT1 ANTIBODY SEQUENCES

EIVLTQSPSSLSASVGDRVTITCRASQGISNYLAWFQQKPGKAPKSLIYAASSLQSGVPSKFSGSGSGTDFTLTI
NGLQPEDFATYYCQQTDSLPYTFGQGTKLEIK

Ab35 (INX432)
>VH
                                                                  SEQ ID NO: 105
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNSWYHGTYYSPGYYVMDAWGQGTMVTVSS

>VL
                                                                  SEQ ID NO: 106
NIHLTQSPSLLSASVGDRVTLSCKGSQNINNYLAWFQQKFGETPKLLIYNRHNLQTGIPSRFSGSGSGTDYTLTI
NSLQPEDVATYFCYQYSDGYTFGAGTKLELK

Ab36 (INX433)
>VH
                                                                  SEQ ID NO: 107
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYVMDAWGQGTLVTVSS

>VL
                                                                  SEQ ID NO: 108
NIHLTQSPSLLSASVGDRVTLSCKGSQNINNYLAWFQQKFGETPKLLIYNRHNLQTGIPSRFSGSGSGTDYTLTI
NSLQPEDVATYFCYQYSDGYTFGAGTKLELK

Ab37 (INX434)
>VH
                                                                  SEQ ID NO: 109
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWRHGTWYSPGYYVMDAWGQGTLVTVSS

>VL
                                                                  SEQ ID NO: 110
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab38 (INX435)
>VH
                                                                  SEQ ID NO: 111
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRFVHGTWYSPGYYVMDAWGQGTLVTVSS

>VL
                                                                  SEQ ID NO: 112
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab39 (INX436)
>VH
                                                                  SEQ ID NO: 113
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNKWIHGTWYSPGYYVMDAWGQGTLVTVSS

>VL
                                                                  SEQ ID NO: 114
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab40 (INX437)
>VH
                                                                  SEQ ID NO: 115
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYMMDAWGQGTLVTVSS

>VL
                                                                  SEQ ID NO: 116
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab41 (INX438)
>VH
                                                                  SEQ ID NO: 117
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYYSPGYYLMDAWGQGTLVTVSS

>VL
                                                                  SEQ ID NO: 118

-continued

---

MCT1 AND ANTI-MCT1 ANTIBODY SEQUENCES

---

DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab42 (INX439)
>VH
                                                              SEQ ID NO: 119
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWIHGTWYSPGYYVMDAWGQGTLVTVSS

>VL
                                                              SEQ ID NO: 120
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab43 (INX440)
>VH
                                                              SEQ ID NO: 121
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYWSPGYYVMDAWGQGTLVTVSS

>VL
                                                              SEQ ID NO: 122
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab44 (INX441)
>VH
                                                              SEQ ID NO: 123
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVHGTWYSPGYYVMDAWGQGTMVTVSS

>VL
                                                              SEQ ID NO: 124
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab45 (INX442)
>VH
                                                              SEQ ID NO: 125
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVQGWWYSPGYYVMDAWGQGTMVTVSS

>VL
                                                              SEQ ID NO: 126
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab46 (INX443)
>VH
                                                              SEQ ID NO: 127
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNSWYHGTYFSPGYYLMDAWGQGTLVTVSS

>VL
                                                              SEQ ID NO: 128
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab47 (INX444)
>VH
                                                              SEQ ID NO: 129
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARKRWVHGTWYSPGYYVMDAWGQGTLVTVSS

>VL
                                                              SEQ ID NO: 130
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab48 (INX445)
>VH
                                                              SEQ ID NO: 131
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWMHGTWYSPGYYVMDAWGQGTLVTVSS

>VL
                                                              SEQ ID NO: 132

-continued

---

MCT1 AND ANTI-MCT1 ANTIBODY SEQUENCES
---

DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab49 (INX446)
>VH
SEQ ID NO: 133
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARERWVHGTYYSPGYYVMDAWGQGTLVTVSS

>VL
SEQ ID NO: 134
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab50 (INX447)
>VH
SEQ ID NO: 135
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWVQGTYYSPGYYVMDAWGQGTLVTVSS

>VL
SEQ ID NO: 136
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab51 (INX448)
>VH
SEQ ID NO: 137
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWVHGTWYSPGYYVMDAWGQGTLVTVSS

>VL
SEQ ID NO: 138
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab52 (INX449)
>VH
SEQ ID NO: 139
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVQGSYYSPGYYVMDAWGQGTMVTVSS

>VL
SEQ ID NO: 140
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab53 (INX450)
>VH
SEQ ID NO: 141
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRFVHGTWYSPGYYLMDAWGQGTLVTVSS

>VL
SEQ ID NO: 142
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab54 (INX451)
>VH
SEQ ID NO: 143
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWIHGTWYSPGYYLMDAWGQGTLVTVSS

>VL
SEQ ID NO: 144
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab55 (INX452)
>VH
SEQ ID NO: 145
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVHGTWYSPGYYLMDAWGQGTMVTVSS

>VL
SEQ ID NO: 146

MCT1 AND ANTI-MCT1 ANTIBODY SEQUENCES

DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab56 (INX453)
>VH
                                                                          SEQ ID NO: 147
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVQGWWYSPGYYLMDAWGQGTMVTVSS

>VL
                                                                          SEQ ID NO: 148
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab57 (INX454)
>VH
                                                                          SEQ ID NO: 149
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWMHGTWYSPGYYLMDAWGQGTLVTVSS

>VL
                                                                          SEQ ID NO: 150
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab58 (INX455)
>VH
                                                                          SEQ ID NO: 151
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARERWVHGTYFSPGYYLMDAWGQGTLVTVSS

>VL
                                                                          SEQ ID NO: 152
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab59 (INX456)
>VH
                                                                          SEQ ID NO: 153
QVQLKESGPGLVKPSQTLSLTCTVSGFSLTNYHLQWVRQPPGKGLEWIGFIRSSGNTEYNPSLKSRVTISRDTS
KNQVSLKLSSVTAADTAVYYCARNRWVHGTWYSPGYYLMDAWGQGTLVTVSS

>VL
                                                                          SEQ ID NO: 154
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab60 (INX457)
>VH
                                                                          SEQ ID NO: 155
QVQLQESGPGLVKPSETLSLTCTVSGFSLTNYHLQWIRQPPGKGLEWIGFIRSSGNTEYNPSLKSRVTISRDTS
KNQVSLKLSSVTAADTAVYYCARNRWVQGSYYSPGYYLMDAWGQGTMVTVSS

>VL
                                                                          SEQ ID NO: 156
DIQLTQSPSAMSASVGDRVTITCRASQGISNYLAWYQQKPGKAPKLLIYAASTLQSGVASRFSGRGSGTDFTL
TISSLQPEDFATYYCQQSDILPYTFGQGTKVEIK

Ab61 (MCT1 3303 A07 or LM-183)
CDR1-HC
                                                                          (SEQ ID NO: 161)
GFDFSNY

CDR2-HC
                                                                          (SEQ ID NO: 162)
GDSASY

CDR3-HC
                                                                          (SEQ ID NO: 163)
ASEGSYWYYEAGGIDT

HC Protein
                                                                          (SEQ ID NO: 164)
AVTLDESGGGLQTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS

HC DNA

-continued

---

MCT1 AND ANTI-MCT1 ANTIBODY SEQUENCES

---

(SEQ ID NO: 165)
ACGAATTCGGCCGTGACGTTGGACGAGTCCGGGGGGGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGGTTCCTACTGGTATTATGAAGCTGGTGGT
ATCGACACATGGGGCCACGGGACCGAAGTCATCGTCTCCTCG

CDR1-LC
(SEQ ID NO: 166)
SGGGGSYG

CDR2-LC
(SEQ ID NO: 167)
DNDKRPS

CDR3-LC
(SEQ ID NO: 168)
GSAGNSGA

LC Protein
(SEQ ID NO: 169)
ALTQPSSVSANLGGTVKITCSGGGGSYGWYQQKSPGSAPVTVIYDNDKRPSDIPSRFSGSKSGSTATLTITGV
RAEDEAVYYCGSAGNSGAFGAGTTLTVL LC DNA
(SEQ ID NO: 170)
GCCCTGACTCAGCCGTCCTCGGTGTCAGCAAACCTGGGAGGAACCGTCAAGATCACCTGCTCCGGGGGT
GGTGGCAGCTATGGCTGGTATCAGCAGAAGTCACCTGGCAGTGCCCCTGTCACTGTGATCTATGACAAC
GACAAGAGACCCTCGGACATCCCTTCACGATTCTCCGGTTCCAAGTCCGGCTCCACAGCCACATTAACCA
TCACTGGGGTTCGAGCCGAGGACGAGGCTGTCTATTACTGTGGCAGTGCAGGCAATAGTGGTGCATTTG
GGGCCGGGACAACCCTGACCGTCCTT Ab62 (LM-185 or MCT1 3303 B04-1)
CDR1-HC
(SEQ ID NO: 171)
GFDFSNY

CDR2-HC
(SEQ ID NO: 172)
GDSASY

CDR3-HC
(SEQ ID NO: 173)
ASEGSYWYYEAGGIDT

HC Protein
(SEQ ID NO: 174)
AVTLDESGGGLQTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS HC DNA
(SEQ ID NO: 175)
ACGAATTCGGCCGTGACGTTGGACGAGTCCGGGGGCGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGGTTCCTACTGGTATTATGAAGCTGGTGGT
ATCGACACATGGGGCCACGGGACCGAAGTCATCGTCTCCTCG

CDR1-LC
(SEQ ID NO: 176)
SGGSSYG

CDR2-LC
(SEQ ID NO: 177)
YNDKRPS

CDR3-LC
(SEQ ID NO: 178)
GSRDSSGADL

LC Protein
(SEQ ID NO: 179)
ALTQPSSVSANLGGTVKITCSGGSSYGWFQQKSPGSALVTLIYYNDKRPSNIPSRFSGSKSGSTGILTISGVQAE
DEAVYYCGSRDSSGADLFGAGTTLTVL -continued

---
MCT1 AND ANTI-MCT1 ANTIBODY SEQUENCES
---

LC DNA (SEQ ID NO: 180)

GCCCTGACTCAGCCGTCCTCGGTGTCAGCAAACCTGGGAGGAACCGTCAAGATCACCTGCTCCGGGGGC
AGCAGTTATGGCTGGTTCCAGCAGAAGTCTCCTGGCAGTGCCCTTGTCACTCTGATCTATTACAACGACA
AGAGACCCTCGAACATCCCTTCACGATTCTCCGGTTCCAAATCCGGCTCCACGGGCATTTTGACCATCTCT
GGGGTCCAAGCCGAGGACGAGGCTGTCTATTACTGTGGGAGCAGGGACAGCAGTGGTGCTGATCTATT
TGGGGCCGGGACAACCCTGACCGTCCTT

Ab63 (LM-186 or MCT1 3308 B04-2)
CDR1-HC (SEQ ID NO: 181)

GFSFSSR

CDR2-HC (SEQ ID NO: 182)

DNDGGYP

CDR3-HC (SEQ ID NO: 183)

GAYGGGWYAASSIDA

HC Protein (SEQ ID NO: 184)

AVTLDESGGGLQTPGGGLSLVCKASGFSFSSRGMFWVRQAPGKGLEYVAGIDNDGGYPNYGSAVKGRATIS
RDNRQSTVRLQLNNLRADDTGTYYCAKGAYGGGWYAASSIDAWGHGTEVIVSS

HC DNA (SEQ ID NO: 185)

GTCACGAATTCGGCCGTGACGTTGGACGAGTCCGGGGGCGGCCTCCAGACGCCCGGAGGAGGGCTCA
GCCTCGTCTGCAAGGCCTCCGGGTTCTCCTTCAGCAGCCGGGGCATGTTCTGGGTGCGACAGGCACCTG
GCAAGGGGCTGGAATACGTTGCGGGTATTGATAATGATGGTGGTTACCCAAACTACGGGTCGGCGGTG
AAGGGCCGTGCCACCATCTCGAGGGACAACAGGCAGAGCACAGTGAGGCTGCAGCTGAACAACCTCAG
GGCTGACGACACCGGCACCTACTACTGCGCCAAGGGTGCTTATGGTGGTGGTTGGTATGCCGCTAGTAG
CATCGACGCATGGGGCCACGGGACCGAAGTCATCGTCTCCTCG

CDR1-LC (SEQ ID NO: 186)

SGGVGQWYG

CDR2-LC (SEQ ID NO: 187)

DNTNRPS

CDR3-LC (SEQ ID NO: 188)

ANTYSDGNDAP

LC Protein (SEQ ID NO: 189)

ALTQPSSVSANPGEAVKITCSGGVGQWYGWFQQKAPGSAPVTVIHDNTNRPSDIPSRFSGSKSGSTGTLTIT
GVQAEDEAVYFCANTYSDGNDAPFGAGTTLTVL

LC DNA (SEQ ID NO: 190)

GCCCTGACTCAGCCGTCCTCGGTGTCAGCAAACCCGGGAGAAGCCGTCAAGATCACCTGCAGTGGAGG
TGTCGGCCAGTGGTATGGCTGGTTCCAGCAGAAGGCACCTGGCAGTGCCCCTGTCACTGTGATCCATGA
CAACACCAACAGACCCTCGGACATCCCTTCACGATTCTCCGGTTCCAAATCCGGCTCCACGGGCACATTA
ACCATCACTGGGGTCCAAGCCGAGGACGAGGCTGTCTATTTCTGTGCGAATACATACAGCGACGGTAAT
GATGCTCCATTTGGGGCCGGGACAACCCTGACCGTCCTT

Ab64 (LM-188 or MCT1 3308 E08)
CDR1-HC (SEQ ID NO: 191)

GFTFSSR

CDR2-HC (SEQ ID NO: 192)

DNDGGYP

CDR3-HC (SEQ ID NO: 193)

GAYGGGWYAASSIDA

HC Protein (SEQ ID NO: 194)

AVTLDESGGGLQTPGGGLSLVCKASGFTFSSRGMFWVRRAPGKGLEYVAGIDNDGGYPNYGSAVKGRATIS
RDNRQSTVRLQLNNLRADDTGTYYCAKGAYGGGWYAASSIDAWGHGTEVIVSS

-continued

MCT1 AND ANTI-MCT1 ANTIBODY SEQUENCES

HC DNA (SEQ ID NO: 195)

GTCACGAATTCGGCCGTGACGTTGGACGAGTCCGGGGGCGGCCTCCAGACGCCCGGAGGAGGGCTCA
GCCTCGTCTGCAAGGCCTCCGGGTTCACCTTCAGCAGCCGGGGCATGTTCTGGGTGCGACGGGCACCTG
GCAAGGGGCTGGAATACGTTGCGGGTATTGATAATGATGGTGGTTACCCAAACTACGGGTCGGCGGTG
AAGGGCCGTGCCACCATCTCGAGGGACAACAGGCAGAGCACAGTGAGGCTGCAGCTGAACAACCTCAG
GGCTGACGACACCGGCACCTACTACTGCGCCAAGGGTGCTTATGGTGGTGGTTGGTATGCCGCTAGTAG
CATCGACGCATGGGGCCACGGGACCGAAGTCATCGTCTCCTCG

CDR1-LC (SEQ ID NO: 196)

SGGVGQWYG

CDR2-LC (SEQ ID NO: 197)

DNTNRPS

CDR3-LC (SEQ ID NO: 198)

ANTYSDGNDAP

LC Protein (SEQ ID NO: 199)

ALTQPSSVSANPGEAVKITCSGGVGQWYGWFQQKAPGSAPVTVIYDNTNRPSDIPSRFSGSKSGSTGTLTIT
GVQAEDEAVYFCANTYSDGNDAPFGAGTTLTVL

LC DNA (SEQ ID NO: 200)

GCCCTGACTCAGCCGTCCTCGGTGTCAGCAAACCCGGGAGAAGCCGTCAAGATCACCTGCAGTGGAGG
TGTCGGCCAGTGGTATGGCTGGTTCCAGCAGAAGGCACCTGGCAGTGCCCCTGTCACTGTGATCTATGA
CAACACCAACAGACCCTCGGACATCCCTTCACGATTCTCCGGTTCCAAATCCGGCTCCACGGGCACATTA
ACCATCACTGGGGTCCAAGCCGAGGACGAGGCTGTCTATTTCTGTGCGAATACATACAGCGACGGTAAT
GATGCTCCATTTGGGGCCGGGACAACCCTGACCGTCCTT

Ab65 (LM-189 or MCT1 3308 G12)
CDR1-HC (SEQ ID NO: 201)

GFSFSSR

CDR2-HC (SEQ ID NO: 202)

DNDGGYP

CDR3-HC (SEQ ID NO: 203)

GAYGGGWYAASSIDA

HC Protein (SEQ ID NO: 204)

AVTLDESGGGLQTPGGGLSLVCKASGFSFSSRGMFWVRQAPGKGLEYVAGIDNDGGYPNYGSAVKGRATIS
RDNRQSTVRLQLNNLRADDTGTYYCAKGAYGGGWYAASSIDAWGHGTEVIVSS

HC DNA (SEQ ID NO: 205)

GTCACGAATTCGGCCGTGACGTTGGACGAGTCCGGGGGCGGCCTCCAGACGCCCGGAGGAGGGCTCA
GCCTCGTCTGCAAGGCCTCCGGGTTCTCCTTCAGCAGCCGGGGCATGTTCTGGGTGCGACAGGCACCTG
GCAAGGGGCTGGAATACGTTGCGGGTATTGATAATGATGGTGGTTACCCAAACTACGGGTCGGCGGTG
AAGGGCCGTGCCACCATCTCGAGGGACAACAGGCAGAGCACAGTGAGGCTGCAGCTGAACAACCTCAG
GGCTGACGACACCGGCACCTACTACTGCGCCAAGGGTGCTTATGGTGGTGGTTGGTATGCCGCTAGTAG
CATCGACGCATGGGGCCACGGGACCGAAGTCATCGTCTCCTCG

CDR1-LC (SEQ ID NO: 206)

SGGGGGWYG

CDR2-LC (SEQ ID NO: 207)

DNTNRPS

CDR3-LC (SEQ ID NO: 208)

ANTDSDGNDAP

LC Protein (SEQ ID NO: 209)

ALTQPSSVSANPGETVKITCSGGGGGWYGWYQQKSPGSAPVTVIYDNTNRPSDIPSRFSGSKSGSTGTLTITG

-continued

| MCT1 AND ANTI-MCT1 ANTIBODY SEQUENCES |
| --- |

VQAEDEAVYFCANTDSDGNDAPFGAGTTLTVL

LC DNA (SEQ ID NO: 210)

GCCCTGACTCAGCCGTCCTCGGTGTCAGCGAACCCGGGAGAAACCGTCAAGATCACCTGCTCCGGGGGT
GGTGGCGGCTGGTATGGCTGGTATCAGCAGAAGTCTCCTGGCAGTGCCCCTGTCACTGTGATCTATGAC
AACACCAACAGACCCTCGGACATCCCTTCACGATTCTCCGGTTCCAAATCCGGCTCCACGGGCACATTAA
CCATCACTGGGGTCCAAGCCGAGGACGAGGCTGTCTATTTCTGTGCGAATACAGACAGCGACGGTAATG
ATGCTCCATTTGGGGCCGGGACAACCCTGACCGTCCTT

Ab66 (LM-190 or MCT1 3308 H02)
CDR1-HC (SEQ ID NO: 211)

GFSFSSR

CDR2-HC (SEQ ID NO: 212)

DNDGGYP

CDR3-HC (SEQ ID NO: 213)

GAYGGGWYAASSIDA

HC Protein (SEQ ID NO: 214)

AVTLDESGGGLQTPGGGLSLVCKASGFSFSSRGMFWVRQAPGKGLEYVAGIDNDGGYPNYGSAVKGRATIS
RDNRQSTVRLQLNNLRADDTGTYYCAKGAYGGGWYAASSIDAWGHGTEVIVSS

HC DNA (SEQ ID NO: 215)

TCCGCCGTGACGTTGGACGAGTCCGGGGGCGGCCTCCAGACGCCCGGAGGAGGGCTCAGCCTCGTCTG
CAAGGCCTCCGGGTTCTCCTTCAGCAGCCGGGGCATGTTCTGGGTGCGACAGGCACCTGGCAAGGGGC
TGGAATACGTTGCGGGTATTGATAATGATGGTGGTTACCCAAACTACGGGTCGGCGGTGAAGGGCCGT
GCCACCATCTCGAGGGACAACAGGCAGAGCACAGTGAGGCTGCAGCTGAACAACCTCAGGGCTGACGA
CACCGGCACCTACTACTGCGCCAAGGGTGCTTATGGTGGTGGTTGGTATGCCGCTAGTAGCATCGACGC
ATGGGGCCACGGGACCGAAGTCATCGTCTCCTCG

CDR1-LC (SEQ ID NO: 216)

SGGVGQWYG

CDR2-LC (SEQ ID NO: 217)

DNTKRPS

CDR3-LC (SEQ ID NO: 218)

ANTYSDGNDAP

LC Protein (SEQ ID NO: 219)

ALTQPSSVSANLGEAVKITCSGGVGQWYGWYQQKAPGSAPVTVIYDNTKRPSNIPSRFSGSASGSTATLTITG
VRAEDEAVYFCANTYSDGNDAPFGAGTTLTVL

LC DNA (SEQ ID NO: 220)

GCCCTGACTCAGCCGTCCTCGGTGTCAGCAAACCTGGGAGAAGCCGTCAAGATCACCTGCAGTGGAGGT
GTCGGCCAGTGGTATGGCTGGTACCAGCAGAAGGCACCTGGCAGTGCCCCTGTCACTGTGATCTATGAC
AACACCAAGAGACCCTCAAACATCCCTTCACGATTCTCCGGTTCCGCATCCGGCTCCACAGCCACACTAA
CCATCACTGGAGTCCGAGCCGAGGACGAGGCTGTCTATTTCTGTGCGAATACATACAGCGACGGTAATG
ATGCTCCATTTGGGGCCGGGACAACCCTGACCGTCCTT

Ab67 (LM-193 or MCT1 3310 A07)
CDR1-HC (SEQ ID NO: 221)

GFDFSNY

CDR2-HC (SEQ ID NO: 222)

GDSASY

CDR3-HC (SEQ ID NO: 223)

ASEGSYWYYEAGGIDT

HC Protein (SEQ ID NO: 224)

| MCT1 AND ANTI-MCT1 ANTIBODY SEQUENCES |
| --- |

AVTLDESGGGLQTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS

HC DNA (SEQ ID NO: 225)
ACGAATTCGGCCGTGACGTTGGACGAGTCCGGGGGGGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC (SEQ ID NO: 226)
SGGSGSYG

CDR2-LC (SEQ ID NO: 227)
YNDKRPS

CDR3-LC (SEQ ID NO: 228)
GSAGNSGA

LC Protein (SEQ ID NO: 229)
ALTQPSSVSANLGGTVKITCSGGSGSYGWFRQKSPGSAPVTVIYYNDKRPSDIPSRFSGSKSGSTATLTITGVR
AEDEAVYFCGSAGNSGAFGAGTTLTVL

LC DNA (SEQ ID NO: 230)
GCCCTGACTCAGCCGTCCTCGGTGTCAGCAAACCTGGGAGGAACAGTCAAGATCACCTGCTCCGGGGGT
AGTGGCAGCTATGGCTGGTTCCGGCAGAAGTCTCCTGGCAGTGCCCCTGTCACTGTGATCTATTACAAC
GACAAGAGACCCTCGGACATCCCTTCACGATTCTCCGGTTCCAAATCCGGCTCCACAGCCACATTAACCA
TCACTGGGGTCCGAGCCGAGGACGAGGCTGTCTATTTCTGTGGGAGTGCAGGCAACAGTGGTGCATTT
GGGGCCGGGACAACCCTGACCGTCCTT

Ab68 (LM-194 or MCT1 3310 B07-1)
CDR1-HC (SEQ ID NO: 231)
GFDFSSY

CDR2-HC (SEQ ID NO: 232)
GDGASY

CDR3-HC (SEQ ID NO: 233)
ASEGSYWYYETGGIDT

HC Protein (SEQ ID NO: 234)
AVTLDESGGGLQTPGGTLSLVCKASGFDFSSYEMLWVRQAPGKGLAYVAGIGDGASYSAYGVAVKGRATISR
DNGQSTVRLQLNNLRAEDTGTYYCAKASEGSYWYYETGGIDTWGHGTEVIVSS

HC DNA (SEQ ID NO: 235)
ACGAATTCGGCCGTGACGTTGGACGAGTCCGGGGGGGGCCTCCAGACGCCCGGAGGAACGCTCAGCCT
CGTCTGCAAGGCCTCCGGGTTCGACTTCAGCAGCTACGAAATGCTCTGGGTGCGACAGGCGCCCGGCAA
GGGGCTGGCATACGTCGCTGGTATCGGCGACGGTGCTAGTTACTCAGCATACGGGGTGGCGGTGAAGG
GCCGAGCCACCATCTCGAGGGACAACGGGCAGAGCACAGTGAGGCTGCAGCTGAACAACCTCAGGGCT
GAGGACACCGGCACCTACTACTGCGCCAAAGCTTCCGAGGGTTCCTACTGGTATTATGAAACTGGTGGT
ATCGACACATGGGGCCACGGGACCGAAGTCATCGTCTCCTCG

CDR1-LC (SEQ ID NO: 236)
SGGGGSYG

CDR2-LC (SEQ ID NO: 237)
YNDKRPS

CDR3-LC (SEQ ID NO: 238)
GSAGNSGA

LC Protein

MCT1 AND ANTI-MCT1 ANTIBODY SEQUENCES (SEQ ID NO: 239)
ALTQPSSVSANLGGTVKITCSGGGGSYGWFQQKSPGSAPVTVIYYNDKRPSDIPSRFSGSKSGSTATLTITGVR
AEDEAVYFCGSAGNSGAFGAGTTLTVL

LC DNA
(SEQ ID NO: 240)
GCCCTGACTCAGCCGTCCTCGGTGTCAGCAAACCTGGGAGGAACCGTCAAGATCACCTGCTCCGGGGGT
GGTGGCAGCTATGGCTGGTTCCAGCAGAAGTCTCCTGGCAGTGCCCCTGTCACTGTGATCTATTACAAC
GACAAGAGACCCTCGGACATCCCTTCACGATTCTCCGGTTCCAAATCCGGCTCCACAGCCACATTAACCA
TCACTGGGGTCCGAGCCGAGGACGAGGCTGTCTATTTCTGTGGGAGTGCAGGCAACAGTGGTGCATTT
GGGGCCGGGACAACCCTGACCGTCCTT

Ab69 (LM-195 or MCT1 3310 B07-2)
CDR1-HC
(SEQ ID NO: 241)
GFDFSSY

CDR2-HC
(SEQ ID NO: 242)
GDGASY

CDR3-HC
(SEQ ID NO: 243)
ASEGSYWYYETGGIDT

HC Protein
(SEQ ID NO: 244)
AVTLDESGGGLQTPGGTLSLVCKASGFDFSSYEMLWVRQAPGKGLAYVAGIGDGASYSAYGVAVKGRATISR
DNGQSTLRLQLNGLRAEDTGTYYCAKASEGSYWYYETGGIDTWGHGTEVIVSS HC DNA
(SEQ ID NO: 245)
ACGAATTCGGCCGTGACGTTGGACGAGTCCGGGGGGGGCCTCCAGACGCCCGGAGGAACGCTCAGCCT
CGTCTGCAAGGCCTCCGGGTTCGACTTCAGCAGCTACGAAATGCTCTGGGTGCGACAGGCGCCCGGCAA
GGGGCTGGCATACGTCGCTGGTATCGGCGACGGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCGCCAAAGCTTCCGAGGGTTCCTACTGGTATTATGAAACTGGTGGT
ATCGACACATGGGGCCACGGGACCGAAGTCATCGTCTCCTCG

CDR1-LC
(SEQ ID NO: 246)
SGGGGSYG

CDR2-LC
(SEQ ID NO: 247)
YNDKRPS

CDR3-LC
(SEQ ID NO: 248)
GSAGNSGA

LC Protein
(SEQ ID NO: 249)
ALTQPSSVSANLGGTVKITCSGGGGSYGWFQQKSPGSAPVTVIYYNDKRPSDIPSRFSGSKSGSTATLTITGVR
AEDEAVYFCGSAGNSGAFGAGTTLTVL LC DNA
(SEQ ID NO: 250)
GCCCTGACTCAGCCGTCCTCGGTGTCAGCAAACCTGGGAGGAACCGTCAAGATCACCTGCTCCGGGGGT
GGTGGCAGCTATGGCTGGTTCCAGCAGAAGTCTCCTGGCAGTGCCCCTGTCACTGTGATCTATTACAAC
GACAAGAGACCCTCGGACATCCCTTCACGATTCTCCGGTTCCAAATCCGGCTCCACAGCCACATTAACCA
TCACTGGGGTCCGAGCCGAGGACGAGGCTGTCTATTTCTGTGGGAGTGCAGGCAACAGTGGTGCATTT
GGGGCCGGGACAACCCTGACCGTCCTT Ab70 (LM-197 or MCT1 3310 E01)
CDR1-HC
(SEQ ID NO: 251)
GFDFSSY

CDR2-HC
(SEQ ID NO: 252)
GNSASY

CDR3-HC
(SEQ ID NO: 253)
PSDGSYWYYEAGGIDT

-continued

---

MCT1 AND ANTI-MCT1 ANTIBODY SEQUENCES
---

HC Protein (SEQ ID NO: 254)

AVTLDESGGGLQTPGGTLSLVCKASGFDFSSYEMLWVRQAPGKGLEFVAGIGNSASYSAYGVAVKGRATISR
DNGQSTVRLKLNNLRAEDTGTYYCAKPSDGSYWYYEAGGIDTWGHGTEVIVSS

HC DNA (SEQ ID NO: 255)

ACGAATTCGGCCGTGACGTTGGACGAGTCCGGGGGCGGCCTCCAGACGCCCGGAGGAACGCTCAGCCT
CGTCTGCAAGGCCTCCGGGTTCGACTTCAGCAGCTACGAAATGCTCTGGGTGCGACAGGCGCCCGGCAA
GGGGCTGGAATTCGTCGCTGGTATTGGCAACAGTGCTAGTTACTCAGCATACGGGGTGGCGGTGAAGG
GCCGTGCCACCATCTCGAGGGACAACGGGCAGAGCACAGTGAGGCTGAAGCTGAACAACCTCAGGGCT
GAGGACACCGGCACCTACTACTGCGCCAAACCTTCCGATGGTTCCTACTGGTATTATGAAGCTGGTGGT
ATCGACACATGGGGCCACGGGACCGAAGTCATCGTCTCCTCG

CDR1-LC (SEQ ID NO: 256)

SGGGGSYG

CDR2-LC (SEQ ID NO: 257)

DNDKRPS

CDR3-LC (SEQ ID NO: 258)

GSAGNSGA

LC Protein (SEQ ID NO: 259)

ALTQPSSVSANPGGTVKITCSGGGGSYGWYQQKSPGSAPVTVIYDNDKRPSDIPSRFSGSKSGSTATLTITGV
RAEDEAVYYCGSAGNSGAFGAGTTLTVL

LC DNA (SEQ ID NO: 260)

GCCCTGACTCAGCCGTCCTCGGTGTCAGCAAACCCGGGAGGAACCGTCAAGATCACCTGCTCCGGGGGT
GGTGGCAGCTATGGCTGGTATCAGCAGAAGTCACCTGGCAGTGCCCCTGTCACTGTGATCTATGACAAC
GACAAGAGACCCTCGGACATCCCTTCACGATTCTCCGGTTCCAAGTCCGGCTCCACAGCCACATTAACCA
TCACTGGGGTTCGAGCCGAGGACGAGGCTGTCTATTACTGTGGCAGTGCAGGCAATAGTGGTGCATTTG
GGGCCGGGACAACCCTGACCGTCCTT

Ab71 (LM-198 or MCT1 3310 E03)
CDR1-HC (SEQ ID NO: 261)

GFDFSNY

CDR2-HC (SEQ ID NO: 262)

GDSASY

CDR3-HC (SEQ ID NO: 263)

ASEGSYWYYEAGGIDT

HC Protein (SEQ ID NO: 264)

AVTLDESGGGLQTPGGTLSLVCKASGFDFSNYEMLWVRQAPGKGLEYVAGIGDSASYSAYGVAVKGRATISR
DNGQSALRLQLNGLRAEDTGTYYCTKASEGSYWYYEAGGIDTWGHGTEVIVSS

HC DNA (SEQ ID NO: 265)

ACGAATTCGGCCGTGACGTTGGACGAGTCCGGGGGGGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCGCACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC (SEQ ID NO: 266)

SGGGGSYG

CDR2-LC (SEQ ID NO: 267)

YNDKRPS

CDR3-LC (SEQ ID NO: 268)

GSGDSSGGI

-continued

---

MCT1 AND ANTI-MCT1 ANTIBODY SEQUENCES

---

LC Protein (SEQ ID NO: 269)

ALTQPSSVSANLGGTVKITCSGGGGSYGWFQQKSPGSAPVTVIYYNDKRPSDIPSRFSGSKSGSTATLTITGVQ
VDDEAVYFCGSGDSSGGIFGAGTTLTVL

LC DNA (SEQ ID NO: 270)

GCCCTGACTCAGCCGTCCTCGGTGTCAGCAAACCTGGGAGGAACCGTCAAGATCACCTGCTCCGGGGGT
GGTGGCAGCTATGGCTGGTTCCAGCAGAAGTCTCCTGGCAGTGCCCCTGTCACTGTGATCTATTACAAC
GACAAGAGACCCTCGGACATCCCTTCACGATTCTCCGGCTCCAAATCCGGCTCCACGGCCACATTAACCA
TCACTGGGGTCCAAGTCGACGACGAGGCTGTCTATTTCTGTGGGAGTGGAGACAGCAGTGGTGGTATA
TTTGGGGCCGGGACAACCCTGACCGTCCTT

Ab72 (LM-199 or MCT1 3310 E04)
CDR1-HC (SEQ ID NO: 271)

GFDFSNY

CDR2-HC (SEQ ID NO: 272)

GDSASY

CDR3-HC (SEQ ID NO: 273)

ASEGSYWYYEAGGIDT

HC Protein (SEQ ID NO: 274)

AVTLDESGGGLRTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS

HC DNA (SEQ ID NO: 275)

ACGAATTCGGCCGTGACGTTGGACGAGTCCGGGGGCGGCCTCCGGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC (SEQ ID NO: 276)

SGGGGSYG

CDR2-LC (SEQ ID NO: 277)

YNDKRPS

CDR3-LC (SEQ ID NO: 278)

GSAGNSGA

LC Protein (SEQ ID NO: 279)

ALTQPSSVSANLGGTVKITCSGGGGSYGWFQQKSPGSAPVTVIYYNDKRPSDIPSRFSGSKSGSTGTLTITGVR
AEDEAVYFCGSAGNSGAFGAGTTLTVL

LC DNA (SEQ ID NO: 280)

GCCCTGACTCAGCCGTCCTCGGTGTCAGCAAACCTGGGAGGAACCGTCAAGATCACCTGCTCCGGGGGT
GGTGGCAGCTATGGCTGGTTCCAGCAGAAGTCTCCTGGCAGTGCCCCTGTCACTGTGATCTATTACAAC
GACAAGAGACCCTCAGACATCCCTTCACGATTCTCCGGTTCCAAATCCGGCTCCACGGGCACATTAACCA
TCACTGGGGTCCGAGCCGAGGACGAGGCTGTCTATTTCTGTGGGAGTGCAGGCAACAGTGGTGCATTT
GGGGCCGGGACAACCCTGACCGTCCTT

Ab73 (LM-201 or MCT1 3310 H09)
CDR1-HC (SEQ ID NO: 281)

GFDFSSY

CDR2-HC (SEQ ID NO: 282)

GDGASY

CDR3-HC (SEQ ID NO: 283)

MCT1 AND ANTI-MCT1 ANTIBODY SEQUENCES

ASEGSYWYYETGGIDT

HC Protein
(SEQ ID NO: 284)
AVTLDESGGGLQTPGGTLSLVCKASGFDFSSYEMLWVRQAPGKGLAYVAGIGDGASYSAYGVAVKGRATISR
DNGQSTVRLQLNNLRAEDTGTYYCAKASEGSYWYYETGGIDTWGHGTEVIVSS HC DNA
(SEQ ID NO: 285)
ACGAATTCGGCCGTGACGTTGGACGAGTCCGGGGGCGGCCTCCAGACGCCCGGAGGAACGCTCAGCCT
CGTCTGCAAGGCCTCCGGGTTCGACTTCAGCAGCTACGAAATGCTCTGGGTGCGACAGGCGCCCGGCAA
GGGGCTGGCATACGTCGCTGGTATCGGCGACGGTGCTAGTTACTCAGCATACGGGGTGGCGGTGAAGG
GCCGAGCCACCATCTCGAGGGACAACGGGCAGAGCACAGTGAGGCTGCAGCTGAACAACCTCAGGGCT
GAGGACACCGGCACCTACTACTGCGCCAAAGCTTCCGAGGGTTCCTACTGGTATTATGAAACTGGTGGT
ATCGACACATGGGGCCACGGGACCGAAGTCATCGTCTCCTCG

CDR1-LC
(SEQ ID NO: 286)
SGGGGSYG

CDR2-LC
(SEQ ID NO: 287)
YNDKRPS

CDR3-LC
(SEQ ID NO: 288)
GSAGNSGA

LC Protein
(SEQ ID NO: 289)
ALTQPSSVSANLGETVKITCSGGGGSYGWFQQKSPGSAPVTVIYYNDKRPSDIPSRFSGSKSGSTATLTITGVR
AEDEAVYFCGSAGNSGAFGAGTTLTVL LC DNA
(SEQ ID NO: 290)
GCCCTGACTCAGCCGTCCTCGGTGTCAGCAAACCTAGGAGAAACCGTCAAGATCACCTGCTCCGGGGGT
GGTGGCAGCTATGGCTGGTTCCAGCAGAAGTCTCCTGGCAGTGCCCCTGTCACTGTGATCTATTACAAC
GACAAGAGACCCTCGGACATCCCTTCACGATTCTCCGGTTCCAAATCCGGCTCCACAGCCACATTAACCA
TCACTGGGGTCCGAGCCGAGGACGAGGCTGTCTATTTCTGTGGGAGTGCAGGCAACAGTGGTGCATTT
GGGGCCGGGACAACCCTGACCGTCCTT Ab74 (LM-202 or MCT1 3310 H12)
CDR1-HC
(SEQ ID NO: 291)
GFDFSSY

CDR2-HC
(SEQ ID NO: 292)
GDGASY

CDR3-HC
(SEQ ID NO: 293)
ASEGSYWYYETGGIDT

HC Protein
(SEQ ID NO: 294)
AVTLDESGGGLQTPGGTLSLVCKASGFDFSSYEMLWVRQAPGKGLAYVAGIGDGASYSAYGVAVKGRATISR
DNGQSTVRLQLNNLRAEDTGTYYCAKASEGSYWYYETGGIDTWGHGTEVIVSS HC DNA
(SEQ ID NO: 295)
ACGAATTCGGCCGTGACGTTGGACGAGTCCGGGGGGGGCCTCCAGACGCCCGGAGGAACGCTCAGCCT
CGTCTGCAAGGCCTCCGGGTTCGACTTCAGCAGCTACGAAATGCTCTGGGTGCGACAGGCGCCCGGCAA
GGGGCTGGCATACGTCGCTGGTATCGGCGACGGTGCTAGTTACTCAGCATACGGGGTGGCGGTGAAGG
GCCGAGCCACCATCTCGAGGGACAACGGGCAGAGCACAGTGAGGCTGCAGCTGAACAACCTCAGGGCT
GAGGACACCGGCACCTACTACTGCGCCAAAGCTTCCGAGGGTTCCTACTGGTATTATGAAACTGGTGGT
ATCGACACATGGGGCCACGGGACCGAAGTCATCGTCTCCTCG

CDR1-LC
(SEQ ID NO: 296)
SGGGGSYG

CDR2-LC
(SEQ ID NO: 297)
YNDKRPS

CDR3-LC

-continued

MCT1 AND ANTI-MCT1 ANTIBODY SEQUENCES (SEQ ID NO: 298)
GSAGNSGA

LC Protein
(SEQ ID NO: 299)
ALTQPSSVSANLGGTVKITCSGGGGSYGWFQQKSPGSAPVTVIYYNDKRPSDIPSRFSGSKSGSTATLTITGVR
AEDEAVYFCGSAGNSGAFGAGTTLTVL LC DNA
(SEQ ID NO: 300)
GCCCTGACTCAGCCGTCCTCGGTGTCAGCAAACCTGGGAGGAACCGTCAAGATCACCTGCTCCGGGGGT
GGTGGCAGCTATGGCTGGTTCCAGCAGAAGTCTCCTGGCAGTGCCCCTGTCACTGTGATCTATTACAAC
GACAAGAGACCCTCGGACATCCCTTCACGATTCTCCGGTTCCAAATCCGGCTCCACAGCCACATTAACCA
TCACTGGGGTCCGAGCCGAGGACGAGGCTGTCTATTTCTGTGGGAGTGCAGGCAACAGTGGTGCATTT
GGGGCCGGGACAACCCTGACCGTCCTT Ab75 (LM-203 or MCT1 3311 A07)
CDR1-HC
(SEQ ID NO: 301)
GFDFSNY

CDR2-HC
(SEQ ID NO: 302)
GDSASY

CDR3-HC
(SEQ ID NO: 303)
ASEGSYWYYEAGGIDT

HC Protein
(SEQ ID NO: 304)
AVTLDESGGGLQTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS HC DNA
(SEQ ID NO: 305)
ACGAATTCGGCCGTGACGTTGGACGAGTCCGGGGGCGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC
(SEQ ID NO: 306)
SGGSGSYG

CDR2-LC
(SEQ ID NO: 307)
ANTNRPS

CDR3-LC
(SEQ ID NO: 308)
GSADSTGAGM

LC Protein
(SEQ ID NO: 309)
ALTQPSSVSLNLGGTVKITCSGGSGSYGWFQQKSPGSAPVTLIYANTNRPSDIPSRFSGSKSGSTNTLTITGVQ
AEDEAIYYCGSADSTGAGMFGAGTTLTVL LC DNA
(SEQ ID NO: 310)
GCCCTGACTCAGCCGTCCTCGGTGTCACTAAACCTGGGAGGAACCGTCAAGATCACCTGCTCCGGGGGT
AGTGGCAGCTACGGCTGGTTCCAGCAGAAGTCACCTGGCAGTGCCCCTGTCACTCTGATCTATGCTAATA
CCAACAGACCCTCAGACATCCCTTCACGATTCTCCGGTTCCAAATCTGGCTCCACAAACACATTAACCATC
ACTGGGGTCCAAGCCGAGGACGAGGCTATCTATTACTGTGGGAGTGCAGACAGCACTGGTGCTGGTAT
GTTTGGGGCCGGGACAACCCTGACCGTCCTT Ab76 (LM-204 or MCT1 3311 B11)
CDR1-HC
(SEQ ID NO: 311)
GFDFSNY

CDR2-HC
(SEQ ID NO: 312)
GDSASY

-continued

MCT1 AND ANTI-MCT1 ANTIBODY SEQUENCES

CDR3-HC (SEQ ID NO: 313)

ASEGSYWYYEAGGIDT

HC Protein (SEQ ID NO: 314)

AVTLDESGGGLQTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS

HC DNA (SEQ ID NO: 315)

ACGAATTCGGCCGTGACGTTGGACGAGTCCGGGGGCGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC (SEQ ID NO: 316)

SGGGGSYG

CDR2-LC (SEQ ID NO: 317)

YNDKRPS

CDR3-LC (SEQ ID NO: 318)

GSAGNSGA

LC Protein (SEQ ID NO: 319)

ALTQPSSVSANLGGTVKITCSGGGGSYGWFQQKSPGSAPVTVIYYNDKRPSDIPSRFSGSKSGSTGTLTITGVR
AEDEAVYFCGSAGNSGAFGAGTTLTVL

LC DNA (SEQ ID NO: 320)

GCCCTGACTCAGCCGTCCTCGGTGTCAGCAAACCTGGGAGGAACCGTCAAGATCACCTGCTCCGGGGGT
GGTGGCAGCTATGGCTGGTTCCAGCAGAAGTCTCCTGGCAGTGCCCCTGTCACTGTGATCTATTACAAC
GACAAGAGACCCTCGGACATCCCTTCACGATTCTCCGGTTCCAAATCCGGCTCCACGGGCACATTAACCA
TCACTGGGGTCCGAGCCGAGGACGAGGCTGTCTATTTCTGTGGGAGTGCAGGCAACAGTGGTGCATTT
GGGGCCGGGACAACCCTGACCGTCCTT

Ab77 (LM-205 or MCT1 3311 C05)
CDR1-HC (SEQ ID NO: 321)

GFDFSNY

CDR2-HC (SEQ ID NO: 322)

GDSASY

CDR3-HC (SEQ ID NO: 323)

ASEGSYWYYEAGGIDT

HC Protein (SEQ ID NO: 324)

AVTLDESGGGLRTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS

HC DNA (SEQ ID NO: 325)

ACGAATTCGGCCGTGACGTTGGACGAGTCCGGGGGCGGCCTCCGGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC (SEQ ID NO: 326)

SGGGGSYG

CDR2-LC (SEQ ID NO: 327)

YNDKRPS

-continued

MCT1 AND ANTI-MCT1 ANTIBODY SEQUENCES

CDR3-LC (SEQ ID NO: 328)

GSAGNSGA

LC Protein (SEQ ID NO: 329)

ALTQPSSVSANLGGTVKITCSGGGGSYGWFQQKSPGSAPVTVIYYNDKRPSDIPSRFSGSKSGSTGTLTITGVR
AEDEAVYFCGSAGNSGAFGAGTTLTVL

LC DNA (SEQ ID NO: 330)

GCCCTGACTCAGCCGTCCTCGGTGTCAGCAAACCTGGGAGGAACCGTCAAGATCACCTGCTCCGGGGGT
GGTGGCAGCTATGGCTGGTTCCAGCAGAAGTCTCCTGGCAGTGCCCCTGTCACTGTGATCTATTACAAC
GACAAGAGACCCTCAGACATCCCTTCACGATTCTCCGGTTCAAATCCGGCTCCACGGGCACATTAACCA
TCACTGGGGTCCGAGCCGAGGACGAGGCTGTCTATTTCTGTGGGAGTGCAGGCAACAGTGGTGCATTT
GGGGCCGGGACAACCCTGACCGTCCTT

Ab78 (LM-206 or MCT1 3311 F10)
CDR1-HC (SEQ ID NO: 331)

GFDFSNY

CDR2-HC (SEQ ID NO: 332)

GDSASY

CDR3-HC (SEQ ID NO: 333)

ASEGSYWYYEAGGIDT

HC Protein (SEQ ID NO: 334)

AVTLDESGGGLQTPGGALSLVCKASGFDFSNYEMLWVRQAPGKGLEYVAGIGDSASYSAYGVAVKGRATIS
RDNGQSTLRLQLNGLRAEDTGTYYCTKASEGSYWYYEAGGIDTWGHGTEVIVSS

HC DNA (SEQ ID NO: 335)

ACGAATTCGGCCGTGACGTTGGACGAGTCCGGGGGCGGCCTCCAGACGCCCGGAGGAGCGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCTGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC (SEQ ID NO: 336)

SGGGGSYG

CDR2-LC (SEQ ID NO: 337)

YNDKRPS

CDR3-LC (SEQ ID NO: 338)

GSAGNSGA

LC Protein (SEQ ID NO: 339)

ALTQPSSVSANLGGTVKITCSGGGGSYGWFQQKSPGSAPVTVIYYNDKRPSDIPSRFSGSKSGSTGTLTITGVR
AEDEAVYFCGSAGNSGAFGAGTTLTVL

LC DNA (SEQ ID NO: 340)

GCCCTGACTCAGCCGTCCTCGGTGTCAGCAAACCTGGGAGGAACCGTCAAGATCACCTGCTCCGGGGGT
GGTGGCAGCTATGGCTGGTTCCAGCAGAAGTCTCCTGGCAGTGCCCCTGTCACTGTGATCTATTACAAC
GACAAGAGACCCTCGGACATCCCTTCACGATTCTCCGGTTCAAATCCGGCTCCACGGGCACATTAACCA
TCACTGGGGTCCGAGCCGAGGACGAGGCTGTCTATTTCTGTGGGAGTGCAGGCAACAGTGGTGCATTT
GGGGCCGGGACAACCCTGACCGTCCTT

Ab79 (LM-207 or MCT1 3311 G09)
CDR1-HC (SEQ ID NO: 341)

GFDFSNY

CDR2-HC (SEQ ID NO: 342)

-continued

| MCT1 AND ANTI-MCT1 ANTIBODY SEQUENCES |
| --- |

GDSASY

CDR3-HC (SEQ ID NO: 343)

ASEGSYWYYEAGGIDT

HC Protein (SEQ ID NO: 344)

AVTLDESGGGLQTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS

HC DNA (SEQ ID NO: 345)

ACGAATTCGGCCGTGACGTTGGACGAGTCCGGGGGGGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC (SEQ ID NO: 346)

SGGGGSYG

CDR2-LC (SEQ ID NO: 347)

YNDKRPS

CDR3-LC (SEQ ID NO: 348)

GSAGNSGA

LC Protein (SEQ ID NO: 349)

ALTQPSSVSANLGGTVKITCSGGGGSYGWFQQKSPGSAPVTVIYYNDKRPSDIPSRFSGSKSGSTGTLTITGVR
AEDEAVYFCGSAGNSGAFGAGTTLTVL

LC DNA (SEQ ID NO: 350)

GCCCTGACTCAGCCGTCCTCGGTGTCAGCAAACCTGGGAGGAACCGTCAAGATCACCTGCTCCGGGGGT
GGTGGCAGCTATGGCTGGTTCCAGCAGAAGTCTCCTGGCAGTGCCCCTGTCACTGTGATCTATTACAAC
GACAAGAGACCCTCGGACATCCCTTCACGATTCTCCGGTTCCAAATCCGGCTCCACGGGCACATTAACCA
TCACTGGGGTCCGAGCCGAGGACGAGGCTGTCTATTTCTGTGGGAGTGCAGGCAACAGTGGTGCATTT
GGGGCCGGGACAACCCTGACCGTCCTT

Ab80 (LM-208 or MCT1 3312 H10)
CDR1-HC (SEQ ID NO: 351)

GFSFSSR

CDR2-HC (SEQ ID NO: 352)

DNDGGY

CDR3-HC (SEQ ID NO: 353)

GAYGGGWYAASSIDA

HC Protein (SEQ ID NO: 354)

AVTLDESGGGLQTPGGGLSLVCKASGFSFSSRGMFWVRQAPGKGLEYVAGIDNDGGYPNYGSAVKGRATIS
RDNRQSTVRLQLNNLRADDTGTYYCAKGAYGGGWYAASSIDAWGHGTEVIVSS

HC DNA (SEQ ID NO: 355)

GTCACGAATTCGGCCGTGACGTTGGACGAGTCCGGGGGCGGCCTCCAGACGCCCGGAGGAGGGCTCA
GCCTCGTCTGCAAGGCCTCCGGGTTCTCCTTCAGCAGCCGGGGCATGTTCTGGGTGCGACAGGCACCTG
GCAAGGGGCTGGAATACGTTGCGGGTATTGATAATGATGGTGGTTACCCAAACTACGGGTCGGCGGTG
AAGGGCCGTGCCACCATCTCGAGGGACAACAGGCAGAGCACAGTGAGGCTGCAGCTGAACAACCTCAG
GGCTGACGCACACCGGCACCTACTACTGCGCCAAGGGTGCTTATGGTGGTGGTTGGTATGCCGCTAGTAG
CATCGACGCATGGGGCCACGGGACCGAAGTCATCGTCTCCTCG

CDR1-LC (SEQ ID NO: 356)

SGGGSSSYYG

CDR2-LC

-continued

| MCT1 AND ANTI-MCT1 ANTIBODY SEQUENCES |
|---|

(SEQ ID NO: 357)
DNNKRPS

CDR3-LC (SEQ ID NO: 358)
ANTYSDGNDAP

LC Protein (SEQ ID NO: 359)
ALTQPSSVSAKSGETVKITCSGGGSSSYYGWYQQKSPGSAPVTVIYDNNKRPSNIPSQFSGSKSGSTSTLTITG
VQADDEAVYFCANTYSDGNDAPFGAGTTLTVL

LC DNA (SEQ ID NO: 360)
GCCCTGACTCAGCCGTCCTCGGTGTCAGCAAAGTCAGGAGAAACCGTCAAGATCACCTGCTCCGGGGGT
GGTAGCAGCAGCTACTATGGCTGGTATCAGCAGAAGTCACCTGGCAGTGCCCCTGTCACTGTGATCTAT
GACAACAACAAGAGACCCTCGAACATCCCTTCACAATTCTCCGGTTCCAAATCTGGCTCCACAAGCACAT
TAACCATCACTGGGGTCCAAGCCGACGACGAGGCTGTCTATTTCTGTGCGAATACATACAGCGACGGTA
ATGATGCTCCATTTGGGGCCGGGACAACCCTGACCGTCCTT

Ab81 (LM-209 or MCT1 3313 A11)
CDR1-HC (SEQ ID NO: 361)
GFSFSSR

CDR2-HC (SEQ ID NO: 362)
DNDGGY

CDR3-HC (SEQ ID NO: 363)
GAYGGGWYAASSIDA

HC Protein (SEQ ID NO: 364)
AVTLDESGGGLQTPGGALSLICKASGFSFSSRGMFWVRQAPGKGLEYVAGIDNDGGYPNYGSAVKGRATIS
RDNRQSTVRLQLNNLRADDTGTYYCAKGAYGGGWYAASSIDAWGHGTEVIVSS

HC DNA (SEQ ID NO: 365)
GTCACGAATTCGGCCGTGACGTTGGACGAGTCCGGGGGCGGCCTCCAGACGCCCGGAGGAGCTCTCAG
CCTCATCTGCAAGGCCTCCGGGTTCTCCTTCAGCAGCCGGGGCATGTTCTGGGTGCGACAGGCACCTGG
CAAGGGGCTGGAATACGTTGCGGGTATTGATAATGATGGTGGTTACCCAAACTACGGGTCGGCGGTGA
AGGGCCGTGCCACCATCTCGAGGGACAACAGGCAGAGCACAGTGAGGCTGCAGCTGAACAACCTCAGG
GCTGACGACACCGGCACCTACTACTGCGCCAAGGGTGCTTATGGTGGTGGTTGGTATGCCGCTAGTAGC
ATCGACGCATGGGGCCACGGGACCGAAGTCATCGTCTCCTCG

CDR1-LC (SEQ ID NO: 366)
SGGVGQWYG

CDR2-LC (SEQ ID NO: 367)
DNTNRPS

CDR3-LC (SEQ ID NO: 368)
ANTYSDGNDAP

LC Protein (SEQ ID NO: 369)
ALTQPSSVSANPGEAVKITCSGGVGQWYGWYQQKAPGSAPVTVIYDNTNRPSDIPSRFSGSKSGSTNTLTIT
GVQAEDEAVYFCANTYSDGNDAPFGAGTTLTVL

LC DNA (SEQ ID NO: 370)
GCCCTGACTCAGCCGTCCTCGGTGTCAGCAAACCCGGGAGAAGCCGTCAAGATCACCTGCAGTGGAGG
TGTCGGCCAGTGGTATGGCTGGTACCAGCAGAAGGCACCTGGCAGTGCCCCTGTCACTGTGATCTATGA
CAACACCAACAGACCCTCGGACATCCCTTCACGATTCTCCGGTTCCAAATCCGGCTCCACAAACACATTA
ACCATCACTGGGGTCCAAGCCGAGGACGAGGCTGTCTATTTCTGTGCGAATACATACAGCGACGGTAAT
GATGCTCCATTTGGGGCCGGGACAACCCTGACCGTCCTT

Ab82 (LM-210 or MCT1 3313 B10)
CDR1-HC (SEQ ID NO: 371)
GFSFSSR

MCT1 AND ANTI-MCT1 ANTIBODY SEQUENCES

CDR2-HC
(SEQ ID NO: 372)
DNDGGY

CDR3-HC
(SEQ ID NO: 373)
GAYGGGWYAASSIDA

HC Protein
(SEQ ID NO: 374)
AVTLDESGGGLQTPGGGLSLVCKASGFSFSSRGMFWVRQAPGKGLEYVAGIDNDGGYPNYGSAVKGRATIS
RDNRQSTVRLQLNNLRADDTGTYYCAKGAYGGGWYAASSIDAWGHGTEVIVSS HC DNA
(SEQ ID NO: 375)
GTCACGAATTCGGCCGTGACGTTGGACGAGTCCGGGGGGGGGCCTCCAGACGCCCGGAGGAGGGCTCA
GCCTCGTCTGCAAGGCCTCCGGGTTCTCCTTCAGCAGCCGGGGCATGTTCTGGGTGCGACAGGCACCTG
GCAAGGGGCTGGAATACGTTGCGGGTATTGATAATGATGGTGGTTACCCAAACTACGGGTCGGCGGTG
AAGGGCCGTGCCACCATCTCGAGGGACAACAGGCAGAGCACAGTGAGGCTGCAGCTGAATAACCTCAG
GGCTGACGACACCGGCACCTACTACTGCGCCAAGGGTGCTTATGGTGGTGGTTGGTATGCCGCTAGTAG
CATCGACGCATGGGGCCACGGGACCGAAGTCATCGTCTCCTCG

CDR1-LC
(SEQ ID NO: 376)
SGGVGQWYG

CDR2-LC
(SEQ ID NO: 377)
DNANRPS

CDR3-LC
(SEQ ID NO: 378)
ANTYSDGNDAP

LC Protein
(SEQ ID NO: 379)
ALTQPSSVSANPGEAVKITCSGGVGQWYGWYQQKAPGSAPVTVIYDNANRPSDIPSRFSGSKSGSTGTLTIT
GVQAEDEAVYFCANTYSDGNDAPFGAGTTLTVL LC DNA
(SEQ ID NO: 380)
GCCCTGACTCAGCCGTCCTCGGTGTCAGCAAACCCGGGAGAAGCCGTCAAGATCACCTGCAGTGGAGG
TGTCGGCCAGTGGTATGGCTGGTACCAGCAGAAGGCACCTGGCAGTGCCCCTGTCACTGTGATCTATGA
CAACGCCAACAGACCCTCGGACATCCCTTCACGATTCTCCGGTTCCAAATCCGGCTCCACGGGCACATTA
ACCATCACTGGGGTCCAAGCCGAGGACGAGGCTGTCTATTTCTGTGCGAATACATACAGCGACGGTAAT
GATGCTCCATTTGGGGCCGGGACAACCCTGACCGTCCTT Ab83 (LM-211 or MCT1 3309 B01)
CDR1-HC
(SEQ ID NO: 381)
GFSFSSR

CDR2-HC
(SEQ ID NO: 382)
DNDGGY

CDR3-HC
(SEQ ID NO: 383)
GAYGGGWYAASSIDA

HC Protein
(SEQ ID NO: 384)
AVTLDESGGGLQTPGGALSLICKASGFSFSSRGMFWVRQAPGKGLEYVAGIDNDGGYPNYGSAVKGRATIS
RDNRQSTVRLQLNNLRADDTGTYYCAKGAYGGGWYAASSIDAWGHGTEVIVSS HC DNA
(SEQ ID NO: 385)
GTCACGAATTCGGCCGTGACGTTGGACGAGTCCGGGGGCGGCCTCCAGACGCCCGGAGGAGCTCTCAG
CCTCATCTGCAAGGCCTCCGGGTTCTCCTTCAGCAGCCGGGGCATGTTCTGGGTGCGACAGGCACCTGG
CAAGGGGCTGGAATACGTTGCGGGTATTGATAATGATGGTGGTTACCCAAACTACGGGTCGGCGGTGA
AGGGCCGTGCCACCATCTCGAGGGACAACAGGCAGAGCACAGTGAGGCTGCAGCTGAACAACCTCAGG
GCTGACGACACCGGCACCTACTACTGCGCCAAGGGTGCTTATGGTGGTGGTTGGTATGCCGCTAGTAGC
ATCGACGCATGGGGCCACGGGACCGAAGTCATCGTCTCCTCG

CDR1-LC
(SEQ ID NO: 386)
SGGVGQWYG

-continued

---

MCT1 AND ANTI-MCT1 ANTIBODY SEQUENCES

---

CDR2-LC (SEQ ID NO: 387)

DNTNRPS

CDR3-LC (SEQ ID NO: 388)

ANTYSDGNDAP

LC Protein (SEQ ID NO: 389)

ALTQPSSVSANPGEAVKITCSGGVGQWYGWYQQKAPGSAPVTVIYDNTNRPSDIPSRFSGSKSGSTNTLTIT
GVQAEDEAVYFCANTYSDGNDAPFGAGTTLTVL

LC DNA (SEQ ID NO: 390)

GCCCTGACTCAGCCGTCCTCGGTGTCAGCAAACCCGGGAGAAGCCGTCAAGATCACCTGCAGTGGAGG
TGTCGGCCAGTGGTATGGCTGGTACCAGCAGAAGGCACCTGGCAGTGCCCCTGTCACTGTGATCTATGA
CAACACCAACAGACCCTCGGACATCCCTTCACGATTCTCCGGTTCCAAATCCGGCTCCACAAACACATTA
ACCATCACTGGGGTCCAAGCCGAGGACGAGGCTGTCTATTTCTGTGCGAATACATACAGCGACGGTAAT
GATGCTCCATTTGGGGCCGGGACAACCCTGACCGTCCTT

Ab84 (LM-184 or MCT1 3303 C03)
CDR1-HC (SEQ ID NO: 391)

GFDFSNY

CDR2-HC (SEQ ID NO: 392)

GDSASY

CDR3-HC (SEQ ID NO: 393)

ASEGSYWYYEAGGIDT

HC Protein (SEQ ID NO: 394)

AVTLDESGGGLQTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS

HC DNA (SEQ ID NO: 395)

ACGAATTCGGCCGTGACGTTGGACGAGTCCGGGGGCGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC (SEQ ID NO: 396)

SGGTYSYG

CDR2-LC (SEQ ID NO: 397)

QNDKRPS

CDR3-LC (SEQ ID NO: 398)

GSGDTTGGI

LC Protein (SEQ ID NO: 399)

ALTQPSSVSANPGETVKITCSGGTYSYGWFQQKSPGSAPVTVIYQNDKRPSDIPSRFSGSKSGSTGTLTITGVQ
AEDEAVYFCGSGDTTGGIFGAGTTLTVL

LC DNA (SEQ ID NO: 400)

GCCCTGACTCAGCCGTCCTCGGTGTCAGCAAACCCAGGAGAAACCGTCAAGATCACCTGCTCTGGGGGC
ACCTATAGTTATGGCTGGTTCCAGCAGAAGTCTCCTGGCAGTGCCCCTGTCACTGTGATCTATCAAAACG
ACAAGAGACCCTCGGACATCCCTTCACGATTCTCCGGTTCCAAATCCGGCTCCACGGGCACATTAACCAT
CACTGGGGTCCAAGCCGAGGACGAGGCTGTCTATTTCTGTGGGAGTGGAGACACCACCGGTGGTATAT
TTGGGGCCGGGACAACCCTGACCGTCCTT

Ab85 (LM-187 or MCT1 3308 B07)
CDR1-HC (SEQ ID NO: 401)

-continued

| MCT1 AND ANTI-MCT1 ANTIBODY SEQUENCES |
| --- |

GFGFTNY

CDR2-HC (SEQ ID NO: 402)

SSGGAY

CDR3-HC (SEQ ID NO: 403)

APCGSWCGWGYTGVDNIDA

HC Protein (SEQ ID NO: 404)

AVTLDESGGGLQTPGGLVSLVCKASGFGFTNYEIHWVRQAPGKGLEWVGFVSSGGAYADYAPAVKGRATIT
RDNGQSTVRLQLVNLRAEDTGTYYCTRAPCGSWCGWGYTGVDNIDAWGHGTEVIVSS

HC DNA (SEQ ID NO: 405)

GCCGTGACGTTGGACGAGTCCGGGGGCGGCCTCCAGACGCCCGGAGGACTGGTCAGTCTCGTCTGCAA
GGCCTCCGGGTTCGGCTTCACCAATTATGAGATCCACTGGGTGCGACAGGCGCCCGGCAAGGGGCTGG
AGTGGGTCGGTTTTGTTAGTAGTGGTGGTGCTTACGCAGATTACGCGCCGGCGGTGAAGGGCCGTGCC
ACCATCACGAGGGACAACGGGCAGAGCACAGTGAGGCTGCAGCTGGTCAACCTCAGGGCGGAGGACA
CCGGCACCTACTACTGCACCAGAGCTCCTTGTGGTAGTTGGTGTGGTTGGGGTTATACTGGTGTCGATA
ACATCGACGCGTGGGGCCACGGGACCGAAGTCATCGTCTCCTCG

CDR1-LC (SEQ ID NO: 406)

SGGGRGSHYG

CDR2-LC (SEQ ID NO: 407)

ANNQRPS

CDR3-LC (SEQ ID NO: 408)

GGYDSGAT

LC Protein (SEQ ID NO: 409)

ALTQPSSVSANPGGIVKITCSGGGRGSHYGWYQQKSPGSAPVTLIYANNQRPSDIPSRFSGSESGSTATLTITG
VQAEDEAVYFCGGYDSGATFGAGTTLTVL

LC DNA (SEQ ID NO: 410)

GCCCTGACTCAGCCGTCCTCGGTGTCAGCGAACCCAGGAGGAATCGTCAAGATCACCTGCTCCGGGGGT
GGTCGCGGCAGCCACTATGGCTGGTATCAGCAGAAGTCTCCTGGCAGTGCCCCTGTCACTCTGATCTAT
GCTAACAACCAGAGACCCTCGGACATCCCTTCGCGATTCTCCGGTTCCGAATCCGGCTCCACGGCCACAT
TAACCATCACTGGGGTCCAAGCCGAGGACGAGGCTGTCTATTTCTGTGGTGGCTACGACAGCGGTGCTA
CATTTGGGGCCGGGACAACCCTGACCGTCCTT

Ab86 (LM-191 or MCT1 3310 A01)
CDR1-HC (SEQ ID NO: 411)

GFDFSNY

CDR2-HC (SEQ ID NO: 412)

GDSASY

CDR3-HC (SEQ ID NO: 413)

ASEGSYWYYEAGGIDT

HC Protein (SEQ ID NO: 414)

AVTLDESGGGLQTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS

HC DNA (SEQ ID NO: 415)

ACGAATTCGGCCGTGACGTTGGACGAGTCCGGGGGCGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC

-continued

---

MCT1 AND ANTI-MCT1 ANTIBODY SEQUENCES

---

(SEQ ID NO: 416)

SGSSGSYG

CDR2-LC (SEQ ID NO: 417)

YNDKRPS

CDR3-LC (SEQ ID NO: 418)

GSYGSTDAAI

LC Protein (SEQ ID NO: 419)

ALTQPSSVSASPGGTVKITCSGSSGSYGWYQQKSPGSAPVTVIYYNDKRPSDIPSRFSGSKSGSTGTLTITGVQ
AEDEAVYFCGSYGSTDAAIFGAGTTLTVL

LC DNA (SEQ ID NO: 420)

GCCCTGACTCAGCCGTCCTCGGTGTCCGCGAGCCCAGGAGGAACCGTCAAGATCACCTGCTCCGGGAGT
AGTGGCAGCTATGGCTGGTATCAGCAGAAGTCACCTGGCAGTGCCCCTGTCACTGTGATCTATTACAAC
GACAAGAGACCCTCGGACATCCCTTCACGATTCTCCGGTTCCAAATCCGGCTCCACGGGCACATTAACCA
TCACTGGGGTCCAAGCCGAGGACGAGGCTGTCTATTTCTGTGGGAGCTACGGCAGCACTGATGCTGCTA
TATTTGGGGCCGGGACAACCCTGACCGTCCTT

Ab87 (LM-192 or MCT1 3310 A02-1)
CDR1-HC (SEQ ID NO: 421)

GFDFSNY

CDR2-HC (SEQ ID NO: 422)

GDSASY

CDR3-HC (SEQ ID NO: 423)

ASEGSYWYYEAGGIDT

HC Protein (SEQ ID NO: 424)

AVTLDESGGGLQTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS

HC DNA (SEQ ID NO: 425)

ACGAATTCGGCCGTGACGTTGGACGAGTCCGGGGGGGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

CDR1-LC (SEQ ID NO: 426)

SGGYSSYG

CDR2-LC (SEQ ID NO: 427)

YNAKRPS

CDR3-LC (SEQ ID NO: 428)

GTADRSSTAL

LC Protein (SEQ ID NO: 429)

ALTQPSSVSANLGGTVKITCSGGYSSYGWYQQKSPGSAPVTLIYYNAKRPSNIPSRFSGSKSGSTATLTITGVQ
AEDEAVYFCGTADRSSTALFGAGTTLTVL

LC DNA (SEQ ID NO: 430)

GCCCTGACTCAGCCGTCCTCGGTGTCAGCAAACCTGGGAGGAACCGTCAAGATCACCTGCTCCGGGGGT
TACAGCAGCTATGGCTGGTATCAGCAGAAGTCTCCTGGCAGTGCTCCTGTCACTCTGATCTATTACAACG
CCAAGAGACCCTCGAACATCCCTTCACGATTCTCCGGTTCCAAATCCGGCTCCACAGCCACATTAACCATC
ACTGGGGTCCAAGCCGAGGACGAGGCTGTCTATTTCTGTGGGACTGCAGACAGGAGCAGTACTGCTTTA
TTTGGGGCCGGGACAACCCTGACCGTCCTT

Ab88 (LM-196 or MCT1 3310 C01)

MCT1 AND ANTI-MCT1 ANTIBODY SEQUENCES

CDR1-HC (SEQ ID NO: 431)

GFDFSSY

CDR2-HC (SEQ ID NO: 432)

GDGASY

CDR3-HC (SEQ ID NO: 433)

ASEGSYWYYETGGIDT

HC Protein (SEQ ID NO: 434)

AVTLDESGGGLQTPGGTLSLVCKASGFDFSSYEMLWVRQAPGKGLAYVAGIGDGASYSAYGVAVKGRATISR
DNGQSTVRLQLNNLRAEDTGTYYCAKASEGSYWYYETGGIDTWGHGTEVIVSS

HC DNA (SEQ ID NO: 435)

ACGAATTCGGCCGTGACGTTGGACGAGTCCGGGGGGGGCCTCCAGACGCCCGGAGGAACGCTCAGCCT
CGTCTGCAAGGCCTCCGGGTTCGACTTCAGCAGCTACGAAATGCTCTGGGTGCGACAGGCGCCCGGCAA
GGGGCTGGCATACGTCGCTGGTATCGGCGACGGTGCTAGTTACTCAGCATACGGGGTGGCGGTGAAGG
GCCGAGCCACCATCTCGAGGGACAACGGGCAGAGCACAGTGAGGCTGCAGCTGAACAACCTCAGGGCT
GAGGACACCGGCACCTACTACTGCGCCAAAGCTTCCGAGGGTTCCTACTGGTATTATGAAACTGGTGGT
ATCGACACATGGGGCCACGGGACCGAAGTCATCGTCTCCTCG

CDR1-LC (SEQ ID NO: 436)

SGGSGSYG

CDR2-LC (SEQ ID NO: 437)

YNDKRPS

CDR3-LC (SEQ ID NO: 438)

GSGDRSYDGM

LC Protein (SEQ ID NO: 439)

ALTQPSSVSANPGETVEITCSGGSGSYGWYQQKSPGSAPVTVIHYNDKRPSDIPSRFSGSASGSTATLTITGVQ
VEDEAVYFCGSGDRSYDGMFGAGTTLTVL

LC DNA (SEQ ID NO: 440)

GCCCTGACTCAGCCGTCCTCGGTGTCAGCAAACCCGGGAGAAACCGTCGAGATCACCTGCTCCGGGGGT
AGTGGCAGCTACGGCTGGTACCAGCAGAAGTCTCCTGGCAGTGCCCCTGTCACTGTGATCCATTACAAC
GACAAGAGACCCTCGGACATCCCTTCACGATTCTCCGGTTCCGCATCCGGCTCCACAGCCACATTAACCA
TCACTGGGGTCCAAGTCGAGGACGAGGCTGTCTATTTCTGTGGGAGTGGAGACAGGAGTTATGATGGT
ATGTTCGGGGCCGGGACAACCCTGACCGTCCTT

Ab89 (LM-200 or MCT1 3310 F12)
CDR1-HC (SEQ ID NO: 441)

GFDFSNY

CDR2-HC (SEQ ID NO: 442)

GDSASY

CDR3-HC (SEQ ID NO: 443)

ASEGSYWYYEAGGIDT

HC Protein (SEQ ID NO: 444)

AVTLDESGGGLQTPGGTLSLVCKASGFDFSNYEMLWVRQAPGKGLEYVAGIGDSASYSAYGVAVKGRATISR
DNGQSTLRLQLNGLRAEDTGTYYCTKASEGSYWYYEAGGIDTWGHGTEVIVSS

HC DNA (SEQ ID NO: 445)

ACGAATTCGGCCGTGACGTTGGACGAGTCCGGGGGCGGCCTCCAGACGCCCGGAGGAACGCTCAGCCT
CGTCTGCAAGGCCTCCGGGTTCGACTTCAGCAACTACGAAATGCTCTGGGTGCGACAGGCGCCCGGCAA
GGGGCTGGAATACGTCGCTGGTATTGGCGACAGTGCTAGTTACTCAGCATACGGGGTGGCGGTGAAGG
GCCGTGCCACCATCTCGAGGGACAACGGGCAGAGCACACTGAGGCTGCAGCTGAACGGCCTCAGGGCT
GAGGACACCGGCACCTACTACTGCACCAAAGCTTCCGAGGGTTCCTACTGGTATTATGAAGCTGGTGGT
ATCGACACATGGGGCCACGGGACCGAAGTCATCGTCTCCTCG

-continued

---
MCT1 AND ANTI-MCT1 ANTIBODY SEQUENCES
---

CDR1-LC (SEQ ID NO: 446)

SGGSSTYG

CDR2-LC (SEQ ID NO: 447)

RNDNRPS

CDR3-LC (SEQ ID NO: 448)

GSADSSGAI

LC Protein (SFO ID NO: 449)

ALTQPSSVSANLGGTVEITCSGGSSTYGWYQQKSPGSAPVTVIYRNDNRPSNIPSRFSGSKYGSTGTLTITGVQ
AEDEAVYLCGSADSSGAIFGAGTTLTVL

LC DNA (SEQ ID NO: 450)

GCCCTGACTCAGCCGTCCTCGGTGTCAGCAAACCTGGGAGGAACCGTCGAGATCACCTGCTCCGGGGGT
AGCAGCACCTATGGCTGGTACCAGCAGAAGTCTCCTGGCAGTGCCCCTGTCACTGTGATCTATAGGAAC
GACAACAGACCCTCAAACATCCCTTCACGATTCTCCGGTTCCAAATACGGCTCCACGGGCACATTAACCA
TCACTGGGGTCCAAGCCGAGGACGAGGCTGTCTATTTATGTGGGAGTGCAGACAGCAGTGGTGCTATA
TTTGGGGCCGGGACAACCCTGACCGTCCTT

Ab90 (MCT1 3308 A05)
CDR1-HC (SEQ ID NO: 451)

GFSFSGF

CDR2-HC (SEQ ID NO: 452)

DDGGSS

CDR3-HC (SEQ ID NO: 453)

DTAACTYPCGSYVHTIDT

HC Protein (SEQ ID NO: 454)

AVTLDESGGGLQTPGGALSLVCKASGFSFSGFSMGWVRQTPGKGLEWVAGIDDGGSSTYYGAAVKGRATIS
RDNGQSTVRLQLSNLRAEDTGIYYCARDTAACTYPCGSYVHTIDTWGHGTEVIVSS

HC DNA (SEQ ID NO: 455)

TCGGCCGTGACGTTGGACGAGTCCGGGGGCGGCCTCCAGACGCCCGGAGGAGCGCTCAGTCTCGTCTG
CAAGGCCTCCGGGTTCTCCTTCAGTGGTTTCAGCATGGGTTGGGTGCGCCAGACGCCCGGCAAAGGGCT
GGAATGGGTCGCTGGTATTGATGATGGTGGCAGTAGCACCTACTACGGGGCGGCGGTGAAGGGCCGT
GCCACCATCTCGAGGGACAACGGGCAGAGCACAGTGAGGCTGCAGCTGAGCAACCTCAGGGCTGAGG
ACACCGGCATCTACTACTGCGCCAGAGATACTGCTGCTTGTACTTATCCTTGTGGTTCTTATGTGCATACG
ATAGACACATGGGGCCACGGGACCGAAGTCATCGTCTCCTCG

CDR1-LC (SEQ ID NO: 456)

SGGGGDYG

CDR2-LC (SEQ ID NO: 457)

YSDKRPP

CDR3-LC (SEQ ID NO: 458)

GGWDDTNGGI

LC Protein (SEQ ID NO: 459)

ALTQPSSVSANLGGTVKITCSGGGGDYGWFQQKSPGSAPVTVIYYSDKRPPNIPSRFSGSLSGSTATLTITGVQ
AEDEAVYYCGGWDDTNGGIFGAGTTLTVL

LC DNA (SEQ ID NO: 460)

GCCCTGACTCAGCCGTCCTCGGTGTCAGCAAACCTGGGAGGAACCGTCAAGATCACCTGCTCCGGGGGT
GGTGGCGACTATGGCTGGTTCCAGCAGAAGTCTCCTGGCAGTGCCCCTGTCACTGTGATCTATTACAGC
GACAAGAGACCCCCGAACATCCCTTCACGATTCTCCGGTTCCCTATCCGGCTCCACAGCCACATTAACCA
TCACTGGGGTCCAAGCCGAGGACGAGGCTGTCTATTACTGTGGTGGCTGGGACGATACTAATGGTGGT
ATATTTGGGGCCGGGACAACCCTGACCGTCCTT

-continued

---

MCT1 AND ANTI-MCT1 ANTIBODY SEQUENCES

---

Ab91 (MCT1 3309 D07)
CDR1-HC (SEQ ID NO: 461)

GFSFSSY

CDR2-HC (SEQ ID NO: 462)

RSSGSS

CDR3-HC (SEQ ID NO: 463)

AGCSDCWRSTPGRIDA

HC Protein (SEQ ID NO: 464)

AVTLDESGGGLQTPGGGLSLVCKASGFSFSSYGMGWVRQAPGKGLEFIAGIRSSGSSTYYGAAVKGRATITR
DNGQSTVRLQLNNLRAEDTATYYCAKAGCSDCWRSTPGRIDAWGHGTEVIVSS

HC DNA (SEQ ID NO: 465)

ACGAATTCGGCCGTGACGTTGGACGAGTCTGGGGGCGGCCTCCAGACGCCCGGAGGAGGGCTCAGCCT
CGTCTGCAAGGCCTCCGGGTTCTCCTTCAGCAGTTATGGCATGGGCTGGGTGCGACAGGCGCCCGGCAA
GGGGCTGGAATTCATCGCGGGTATTAGAAGCAGTGGTAGTAGCACATACTACGGGGCGGCGGTGAAG
GGCCGTGCCACCATCACGAGGGACAACGGGCAGAGCACAGTGAGGCTGCAGCTGAACAACCTCAGGG
CTGAGGACACCGCCACCTACTACTGCGCCAAAGCTGGTTGTAGTGATTGTTGGCGTAGTACTCCTGGTA
GGATCGACGCATGGGGCCACGGGACCGAAGTCATCGTCTCCTCG

CDR1-LC (SEQ ID NO: 466)

SGSSSGYGYG

CDR2-LC (SEQ ID NO: 467)

TNTNRPS

CDR3-LC (SEQ ID NO: 468)

GSYDSNTYLGL

LC Protein (SEQ ID NO: 469)

ALTQPSSVSANLGGTVEITCSGSSSGYGYGWYQQKSPGSAPVTLIYTNTNRPSDIPSRFSGSTSGSTNTLTIAG
VQAEDEAVYYCGSYDSNTYLGLFGAGTTLTVL
LC DNA (SEQ ID NO: 470)

GCCCTGACTCAGCCGTCCTCGGTGTCAGCAAACCTGGGAGGAACCGTCGAGATCACCTGCTCCGGGAGT
AGCAGTGGCTATGGTTATGGCTGGTATCAGCAGAAGTCACCTGGCAGTGCCCCTGTCACTCTGATCTATA
CTAACACCAACAGACCCTCGGACATCCCTTCGCGATTCTCCGGTTCCACATCCGGCTCCACAAACACATTA
ACGATCGCTGGGGTCCAAGCCGAGGACGAGGCTGTCTATTATTGTGGGAGCTACGACAGCAACACTTAT
CTTGGTCTATTTGGGGCCGGGACAACCCTGACCGTCCTT

Ab92 (MCT1 3310 A05)
CDR1-HC (SEQ ID NO: 471)

GFTFSSY

CDR2-HC (SEQ ID NO: 472)

SKDGGSD

CDR3-HC (SEQ ID NO: 473)

GIGVGNIDA

HC Protein (SEQ ID NO: 474)

AVTLDESEGGLHTPGGGLSLVCKASGFTFSSYAMYWIRQAPGKGLEWVAYISKDGGSDTAYETAVKGRATIS
RDDGQSTVRLQLNNLRAEDTATYYCARGIGVGNIDAWGHGTEVIVSS

HC DNA (SEQ ID NO: 475)

GCCGTGACGTTGGACGAGTCCGAGGGCGGCCTCCATACACCCGGAGGAGGGCTCAGCCTCGTCTGCAA
GGCCTCCGGGTTCACCTTCAGCAGTTATGCCATGTACTGGATCCGACAGGCGCCCGGCAAGGGGCTGGA
GTGGGTCGCCTATATTAGCAAGGATGGTGGTAGTGACACAGCATACGAGACAGCGGTGAAGGGCCGTG
CCACCATCTCGAGGGACGACGGGCAGAGCACAGTGAGGCTGCAGCTGAACAACCTCAGGGCTGAGGAC
ACCGCCACCTACTACTGCGCCAGAGGTATTGGTGTTGGTAACATCGACGCATGGGGCCACGGGACCGA

-continued

| MCT1 AND ANTI-MCT1 ANTIBODY SEQUENCES |
| --- |

AGTCATCGTCTCCTCC

CDR1-LC
(SEQ ID NO: 476)

SGSSSGYGYG

CDR2-LC
(SEQ ID NO: 477)

TNTNRPS

CDR3-LC
(SEQ ID NO: 478)

GSYDSNTYLGL

LC Protein
(SEQ ID NO: 479)

ALTQPSSVSANLGETVKITCSGTSDNNYFGWYQQKSPGSAPVTVIYGNDKRPSDIPSRFSGSKSGSTATLTITG
VQADDEAVYFCGSYDTYVNDDIFGAGTTLTVL

LC DNA
(SEQ ID NO: 480)

GCCCTGACTCAGCCGTCCTCGGTGTCAGCAAACCTGGGAGAAACCGTCAAGATCACCTGCTCCGGGACT
AGTGACAATAACTACTTTGGTTGGTATCAGCAGAAGTCTCCTGGCAGTGCCCCTGTCACGGTGATCTATG
GCAACGACAAGAGACCCTCGGACATCCCTTCACGATTCTCCGGTTCCAAATCCGGCTCCACGGCCACATT
AACCATCACTGGGGTCAAGCCGACGACGAGGCTGTCTATTTCTGTGGGAGCTATGACACCTATGTTAA
TGATGATATATTTGGGGCCGGGACAACCCTGACCGTCCTA

Ab93 (MCT1 3310 A12)
CDR1-HC
(SEQ ID NO: 481)

GFDFSSY

CDR2-HC
(SEQ ID NO: 482)

YKDGGSD

CDR3-HC
(SEQ ID NO: 483)

GIGIGNIDA

HC Protein
(SEQ ID NO: 484)

AVTLDESGGGLQTPGGGLSLVCKASGFDFSSYAMYWIRQAPGKGLEWVAYIYKDGGSDTAYETAVKGRATIS
RDDGQSTMRLQLNNLRAEDTATYYCARGIGIGNIDAWGHGTEVIVSS

HC DNA
(SEQ ID NO: 485)

GCCGTGACGTTGGACGAGTCCGGGGGCGGCCTCCAGACGCCCGGAGGAGGGCTCAGCCTCGTCTGCAA
GGCCTCCGGGTTTGACTTCAGCAGTTACGCCATGTACTGGATCCGACAGGCGCCCGGCAAGGGGCTGG
AGTGGGTCGCCTATATTTACAAGGATGGTGGTAGTGACACAGCATACGAGACAGCGGTGAAGGGCCGT
GCCACCATCTCGAGGGACGACGGGCAGAGTACGATGAGGCTGCAGCTGAACAACCTCAGGGCTGAGG
ACACCGCCACCTACTACTGTGCCAGAGGTATTGGTATTGGTAACATCGACGCATGGGGCCACGGGACCG
AAGTCATCGTCTCCTCC

CDR1-LC
(SEQ ID NO: 486)

SGNSDNNYFG

CDR2-LC
(SEQ ID NO: 487)

GNDKRPS

CDR3-LC
(SEQ ID NO: 488)

GSYDTYVNDDM

LC Protein
(SEQ ID NO: 489)

ALTQPSSVSANPGGTVEITCSGNSDNNYFGWFQQKSPGSAPVTVIYGNDKRPSDIPSRFSGSKSGSTATLTIT
GVQADDEAVYFCGSYDTYVNDDMFGAGTTLTVL

LC DNA
(SEQ ID NO: 490)

GCCCTGACTCAGCCGTCCTCGGTGTCAGCAAACCCGGGAGGAACCGTCGAGATCACCTGCTCCGGGAAT
AGTGACAATAACTACTTTGGCTGGTTCCAGCAGAAGTCTCCTGGCAGTGCCCCAGTCACTGTGATCTATG
GCAACGACAAGAGACCCTCGGACATCCCTTCACGATTCTCCGGTTCCAAATCCGGCTCCACGGCCACATT
AACCATCACTGGGGTCCAAGCCGACGACGAGGCTGTCTATTTCTGTGGGAGCTACGACACCTATGTCAA

-continued

<div style="text-align:center">MCT1 AND ANTI-MCT1 ANTIBODY SEQUENCES</div>

TGATGACATGTTTGGGGCCGGGACAACCCTGACCGTCCTT

Ab94 (MCT1 3311 B04)
CDR1-HC (SEQ ID NO: 491)

GFTFSSF

CDR2-HC (SEQ ID NO: 492)

SNDGGG

CDR3-HC (SEQ ID NO: 493)

GGGASSIDA

HC Protein (SEQ ID NO: 494)

AVTLDESEGGLQTPGGTLSLVCKGSGFTFSSFNMFWVRQAPGKGLEFVAAVSNDGGGTWYATAVKGRATIS
KDNGQSTVRLQLNNLRAEDTGTYYCARGGGASSIDAWGHGTEVIVSS

HC DNA (SEQ ID NO: 495)

GCCGTGACGTTGGACGAGTCCGAGGGCGGCCTCCAGACGCCCGGAGGAACGCTCAGCCTCGTCTGCAA
GGGCTCCGGGTTCACCTTCAGCAGCTTCAACATGTTCTGGGTGCGACAGGCGCCCGGCAAGGGGCTGG
AATTCGTCGCTGCTGTTAGCAATGATGGTGGTGGCACATGGTACGCGACGGCGGTGAAGGGCCGTGCC
ACCATCTCGAAGGACAACGGGCAGAGCACAGTGAGGCTGCAGCTGAACAACCTCAGGGCTGAGGACAC
CGGCACCTACTACTGCGCCAGAGGTGGTGGTGCCAGTAGTATCGACGCATGGGGCCACGGGACCGAAG
TCATCGTCTCCTCC

CDR1-LC (SEQ ID NO: 496)

SGGSGRYG

CDR2-LC (SEQ ID NO: 497)

ANTKRPS

CDR3-LC (SEQ ID NO: 498)

GSIDNNYVGI

LC Protein (SEQ ID NO: 499)

ALTQPSSVSANPGETVKITCSGGSGRYGWYQQKSPGSAPVTVIRANTKRPSDIPSRFSGSKSGSTGTLTITGVQ
VEDEAVYFCGSIDNNYVGIFGAGTTLTVL

LC DNA (SEQ ID NO: 500)

GCCCTGACTCAGCCGTCCTCGGTGTCAGCAAACCCAGGAGAAACCGTCAAGATCACCTGCTCCGGGGGT
AGTGGCAGGTACGGCTGGTATCAGCAGAAGTCACCTGGCAGTGCCCCTGTCACTGTGATCAGGGCTAAC
ACCAAGAGACCCTCGGACATCCCTTCACGATTCTCCGGTTCCAAATCCGGCTCCACGGGCACATTAACCA
TCACTGGGGTCCAAGTCGAGGACGAGGCTGTCTATTTCTGTGGGAGCATAGACAACAACTATGTTGGTA
TATTTGGGGCCGGGACAACCCTGACCGTCCTA

Ab95 (MCT1 3311 B07)
CDR1-HC (SEQ ID NO: 501)

GFTISSY

CDR2-HC (SEQ ID NO: 502)

SGSGRY

CDR3-HC (SEQ ID NO: 503)

DGGGNYWNAAGGIDA

HC Protein (SEQ ID NO: 504)

AVTLDESGGGLQTPGGTLSLVCKGSGFTISSYTMQWVRQAPDKGLEYVASISGSGRYTGYGAAVKGRATISR
DNGQSTVRLQLNNLRAEDTGTYYCAKDGGGNYWNAAGGIDAWGHGTEVIVSS

HC DNA (SEQ ID NO: 505)

GCCGTGACGTTGGACGAGTCCGGGGGGGGCCTCCAGACGCCCGGAGGAACGCTCAGCCTCGTCTGCAA
GGGCTCCGGGTTCACCATCAGCAGTTACACCATGCAGTGGGTGCGACAGGCGCCCGACAAGGGGTTGG
AATATGTCGCCAGTATTAGCGGCAGTGGTAGATACACAGGCTACGGGGCGGCGGTGAAGGGCCGTGCC

-continued

| MCT1 AND ANTI-MCT1 ANTIBODY SEQUENCES |
| --- |

ACCATCTCGAGGGACAACGGGCAGAGCACAGTGAGGCTGCAGCTGAACAACCTCAGGGCTGAGGACAC
CGGCACCTACTACTGCGCCAAAGATGGTGGTGGTAATTACTGGAATGCTGCTGGTGGTATCGACGCATG
GGGCCACGGGACCGAAGTCATCGTCTCCTCC

CDR1-LC
(SEQ ID NO: 506)

SGGSSTYG

CDR2-LC
(SEQ ID NO: 507)

NDDERPS

CDR3-LC
(SEQ ID NO: 508)

GNEDSSAGKGGI

LC Protein
(SEQ ID NO: 509)

ALTQPSSVSANLGGTVEITCSGGSSTYGWYQQKSPGSAPVTLIYNDDERPSNIPSRFSGSTSDFTGTLTITGVQ
ADDEAVYFCGNEDSSAGKGGIFGAGTTLTVL

LC DNA
(SEQ ID NO: 510)

GCCCTGACTCAGCCGTCCTCGGTGTCAGCGAACCTGGGAGGAACCGTCGAGATCACCTGCTCCGGGGGT
AGCAGCACCTATGGCTGGTACCAGCAGAAGTCTCCTGGCAGTGCCCCTGTCACTCTGATTTATAATGATG
ATGAGAGACCCTCGAACATCCCTTCACGATTCTCCGGTTCCACATCCGACTTCACGGGCACATTAACCAT
CACTGGGGTCCAAGCCGACGACGAGGCTGTCTATTTCTGTGGGAATGAAGACAGCAGTGCTGGTAAAG
GTGGCATATTTGGGGCCGGGACAACCCTGACCGTCCTA

What is claimed is:

1. An antibody that binds human MCT1, wherein the antibody comprises a heavy chain variable region (VH) and a light chain variable region (VL), wherein the VH comprises heavy chain complementarity determining regions HCDR1, HCDR2, and HCDR3 comprising the amino acid sequence of SEQ ID NO: 4, SEQ ID NO: 5, and SEQ ID NO: 6, respectively, and wherein the VL comprises light chain complementarity determining regions LCDR1, LCDR2, and LCDR3 comprising the amino acid sequence of SEQ ID NO: 7, SEQ ID NO: 8, and SEQ ID NO: 9, respectively.

2. The antibody of claim 1, wherein the antibody is a humanized MCT1 antibody.

3. The antibody of claim 2, further comprising a human IgG1 constant region that is modified to decrease FcR binding or complement binding.

4. The antibody of claim 1, wherein the antibody comprises:
   a. a VL comprising SEQ ID NO: 39 and a VH comprising SEQ ID NO: 19;
   b. a VL comprising SEQ ID NO: 13 and a VH comprising SEQ ID NO: 12;
   c. a VL comprising SEQ ID NO: 15 and a VH comprising SEQ ID NO: 14;
   d. a VL comprising SEQ ID NO: 17 and a VH comprising SEQ ID NO: 16;
   e. a VL comprising SEQ ID NO: 122 and a VH comprising SEQ ID NO: 121; or
   f. a VL comprising SEQ ID NO: 130 and a VH comprising SEQ ID NO: 129.

5. A pharmaceutical composition comprising the antibody of claim 2 and a pharmaceutically acceptable excipient, diluent or carrier.

* * * * *